(12) United States Patent
Oshima et al.

(10) Patent No.: US 9,212,187 B2
(45) Date of Patent: Dec. 15, 2015

(54) NITROGEN-CONTAINING COMPOUNDS AND PHARMACEUTICAL COMPOSITIONS THEREOF FOR THE TREATMENT OF ATRIAL FIBRILLATION

(71) Applicant: OTSUKA PHARMACEUTICAL CO., LTD., Tokyo (JP)

(72) Inventors: Kunio Oshima, Osaka (JP); Shuuji Matsumura, Osaka (JP); Hokuto Yamabe, Osaka (JP)

(73) Assignee: OTSUKA PHARMACEUTICAL CO., LTD., Tokyo (JP)

( * ) Notice: Subject to any disclaimer, the term of this patent is extended or adjusted under 35 U.S.C. 154(b) by 0 days.

(21) Appl. No.: 14/314,189

(22) Filed: Jun. 25, 2014

(65) Prior Publication Data

US 2014/0343278 A1 Nov. 20, 2014

Related U.S. Application Data

(62) Division of application No. 13/388,442, filed as application No. PCT/JP2010/064545 on Aug. 20, 2010, now Pat. No. 8,822,453.

(60) Provisional application No. 61/235,973, filed on Aug. 21, 2009, provisional application No. 61/359,686, filed on Jun. 29, 2010, provisional application No. 61/235,983, filed on Aug. 21, 2009, provisional application No. 61/235,981, filed on Aug. 21, 2009.

(51) Int. Cl.
*C07D 401/12* (2006.01)
*C07D 401/14* (2006.01)
*C07D 491/048* (2006.01)
(Continued)

(52) U.S. Cl.
CPC .......... *C07D 491/048* (2013.01); *C07D 213/38* (2013.01); *C07D 215/227* (2013.01); *C07D 243/12* (2013.01); *C07D 401/12* (2013.01); *C07D 401/14* (2013.01); *C07D 403/12* (2013.01); *C07D 405/14* (2013.01); *C07D 409/14* (2013.01); *C07D 413/14* (2013.01); *C07D 417/12* (2013.01); (Continued)

(58) Field of Classification Search
CPC ............................ C07D 401/12; C07D 401/14
USPC ........................................................ 540/518
See application file for complete search history.

(56) References Cited

U.S. PATENT DOCUMENTS 3,133,056 A 5/1964 Ash et al.
3,984,398 A 10/1976 Rossi
(Continued)

FOREIGN PATENT DOCUMENTS

EG 1995040308 A1 4/1995
EG 2003020125 A1 2/2003
(Continued)

OTHER PUBLICATIONS

Alan S. Go, et al., "Prevalence of Diagnosed Atrial Fibrillation in Adults: National Implications for Rhythm Management and Stroke Prevention: the Anticoagulation and Risk Factors in Atrial Fibrillation (ATRIA) Study", The Journal of American Medical Association, May 2001, pp. 2370-2375, vol. 285, No. 18.

(Continued)

*Primary Examiner* — Bruck Kifle
(74) *Attorney, Agent, or Firm* — Sughrue Mion, PLLC

(57) ABSTRACT

The present invention provides a novel diazepine compound that blocks the $I_{Kur}$ current or the Kv1.5 channel potently and more selectively than other $K^+$ channels. The present invention relates to a diazepine compound represented by General Formula (1)

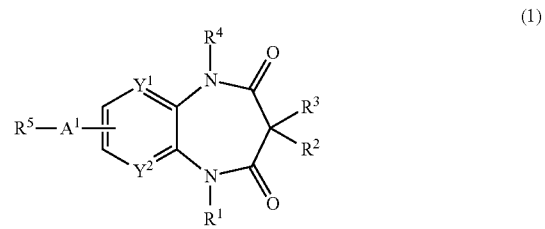

or a salt thereof,
wherein $R^1$, $R^2$, $R^3$, and $R^4$ are each independently hydrogen, lower alkyl, cyclo lower alkyl or lower alkoxy lower alkyl;
$R^2$ and $R^3$ may be linked to form lower alkylene;
$A^1$ is lower alkylene optionally substituted with one or more substituents selected from the group consisting of hydroxyl and oxo;
$Y^1$ and $Y^2$ are each independently —N= or —CH=;
and
$R^5$ is group represented by

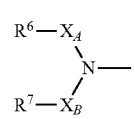

wherein $R^6$ and $R^7$ are each independently hydrogen or organic group;
$R^6$ and $R^7$ may be linked to form a ring together with the neighboring group —$X_A$—N—$X_B$—;
$X_A$ and $X_B$ are each independently a bond, lower alkylene, etc.

4 Claims, No Drawings

(51) Int. Cl.

| | |
|---|---|
| C07D 405/14 | (2006.01) |
| C07D 409/14 | (2006.01) |
| C07D 417/14 | (2006.01) |
| C07D 413/14 | (2006.01) |
| C07D 243/12 | (2006.01) |
| C07D 417/12 | (2006.01) |
| C07D 403/12 | (2006.01) |
| C07D 213/38 | (2006.01) |
| C07D 215/227 | (2006.01) |
| C07D 471/04 | (2006.01) |
| C07D 495/04 | (2006.01) |

(52) U.S. Cl.
CPC .......... C07D 417/14 (2013.01); C07D 471/04 (2013.01); C07D 495/04 (2013.01)

(56) References Cited

U.S. PATENT DOCUMENTS

| | | | |
|---|---|---|---|
| 4,001,408 | A | 1/1977 | Rossi |
| 4,298,739 | A | 11/1981 | Nishi et al. |
| 4,435,404 | A | 3/1984 | Nishi et al. |
| 5,216,148 | A | 6/1993 | Klaus et al. |
| 5,506,239 | A | 4/1996 | Sato et al. |
| 7,321,001 | B2 | 1/2008 | Fu et al. |
| 2003/0158082 | A1 | 8/2003 | Colclough et al. |
| 2008/0057068 | A1 | 3/2008 | Dalton et al. |
| 2009/0264404 | A1 | 10/2009 | Yamashita et al. |

FOREIGN PATENT DOCUMENTS

| | | |
|---|---|---|
| EP | 0 450 066 A1 | 10/1991 |
| EP | 0 504 695 A1 | 9/1992 |
| EP | 0 569 592 A1 | 11/1993 |
| GB | 1 210 809 | 11/1970 |
| GB | 1 460 936 | 1/1977 |
| JP | 2-96133 A | 4/1990 |
| JP | 2008-239617 A | 10/2008 |
| WO | 9528391 A1 | 10/1995 |
| WO | 96/40655 A1 | 12/1996 |
| WO | 9640654 A1 | 12/1996 |
| WO | 97/12869 A1 | 4/1997 |
| WO | 01/10216 A1 | 2/2001 |
| WO | 01/77143 A2 | 10/2001 |
| WO | 03066623 A1 | 8/2003 |
| WO | 2007/026959 A2 | 3/2007 |
| WO | 2009/104819 A1 | 8/2009 |

OTHER PUBLICATIONS

Dan M. Roden, et al., "Current Status of Class III Antiarrhythmic Drug Therapy", The American Journal of Cardiology, Aug. 1993, pp. 44B-49B, vol. 72.

G. Krapivinsky, et al., "The G-Protein-Gated Atrial K+ Channel IKACh is a Heteromultimer of two Inwardly Rectifying K+– Channel Proteins", Nature, Mar. 1995, pp. 135-141, vol. 374.

Gregory J. Amos, et al., "Differences Between Outward Currents of Human Atrial and Subepicardial Ventricular Myocytes", Journal of Physiology, 1996, pp. 31-50, vol. 491.1.

Jamie I. Vandenberg, et al., "HERG K+ Channels: Friend and Foe", Trends in Pharmacological Sciences, May 2001, pp. 240-246, vol. 22, No. 5.

Jianlin Feng, et al., "Antisense Oligodeoxynucleotides Directed Against Kv1.5 mRNA Specifically Inhibit Ultrarapid Delayed Rectifier K+ Current in Cultured Adult Human Atrial Myocytes", Circulation Research, Apr. 1997, pp. 572-579, vol. 80, No. 4.

Richard L. Page., et al. "Drug Therapy for Atrial Fibrillation: Where Do We Go From Here?", Nature Reviews Drug Discovery, Nov. 2005, pp. 899-910, vol. 4.

Stanley Nattel, et al., "Innovative Approaches to Anti-Arrhythmic Drug Therapy", Nature Reviews Drug Discovery, Dec. 2006, pp. 1034-1049, vol. 5.

Yoko Miyasaka, et al., "Secular Trends in Incidence of Atrial Fibrillation in Olmsted County, Minnesota, 1980 to 2000, and Implications on the Projections for Future Prevalence", Circulation, Journal of the American Heart Association, Jul. 2006, pp. 119-125, vol. 114.

Z. Wang, et al., "Sustained Depolarization-Induced Outward Current in Human Atrial Myocytes. Evidence for a Novel Delayed Rectifier K+ Current Similar to Kv1.5 Cloned Channel Currents", Circulation Research, Dec. 1993, pp. 1061-1076, vol. 73, No. 6.

Office Action dated May 22, 2012, issued in U.S. Appl. No. 12/918,226.

Supplementary European Search Report dated Jan. 8, 2013 for European Patent Application No. 10810017.3.

Office Action dated Dec. 27, 2012 for U.S. Appl. No. 13/591,361.

Office Action dated May 20, 2013 in U.S. Appl. No. 13/391,468.

Supplementary European Search Report dated Dec. 19, 2012 in European Application No. 10 81 0017.

Office Action dated Jun. 14, 2013 in U.S. Appl. No. 13/591,361.

Office Action dated Oct. 9, 2013 issued in U.S. Appl. No. 13/391,468.

Extended European Search Report dated May 22, 2014 for European Patent Application No. 14153418.0.

Bonsignore et al., (European Journal of Medicinal Chemistry (1994), 29(6), 479-85). Abstract.

Lugnier, C. et al., "Analysis of the specificity of inhibitors against some cyclic phosphodiesterases by multiparametric techniques", Die Pharmazie, vol. 47, No. 1, Jan. 1, 1992, pp. 46-49.

Koga Y. et al., "2(1H)-Quinolinone derivatives as novel anti-arteriostenotic agents showing anti-thrombotic and anti-hyperplastic activities", Bioorganic & Medicinal Chemistry Letters, vol. 8, No. 12, Jun. 16, 1998, pp. 1471-1476.

R. Kumar et al., "Synthesis, spectral studies and biological activity of novel 3H-1, 5-benzodiazepine derivatives", Indian Journal of Chemistry, vol. 46B, Dec. 2007, pp. 2021-2025.

T. Kajitani, et al., "Spontaneous Chiral Induction in a Cubic Phase", Chemistry of Materials, 17(15), 2005, pp. 3812-3819.

X. Huang et al., "Modulation of Recombinant Human Prostate-Specific Antigen: Activation by Hofmeister Salts and Inhibition by Azapeptides", Biochemistry, 40(39), 2001, pp. 11734-11741.

Office Action dated Feb. 10, 2015, issued by the U.S. Patent and Trademark Office in U.S. Appl. No. 14/314,142.

SEQUENCE LISTING

```
<160> NUMBER OF SEQ ID NOS: 9

<210> SEQ ID NO 1
<211> LENGTH: 25
<212> TYPE: DNA
<213> ORGANISM: Artificial Sequence
<220> FEATURE:
<223> OTHER INFORMATION: Synthetic oligonucleotide primer

<400> SEQUENCE: 1
atgtctgcac tccgaaggaa atttg                                          25

<210> SEQ ID NO 2
<211> LENGTH: 22
<212> TYPE: DNA
<213> ORGANISM: Artificial Sequence
<220> FEATURE:
<223> OTHER INFORMATION: Synthetic oligonucleotide primer

<400> SEQUENCE: 2
ttatgtgaag cgatcagagt tc                                             22

<210> SEQ ID NO 3
<211> LENGTH: 33
<212> TYPE: DNA
<213> ORGANISM: Artificial Sequence
<220> FEATURE:
<223> OTHER INFORMATION: Synthetic oligonucleotide primer

<400> SEQUENCE: 3
gcagggtacc ccttcgtatt atgtctgcac tcc                                 33

<210> SEQ ID NO 4
<211> LENGTH: 19
<212> TYPE: DNA
<213> ORGANISM: Artificial Sequence
```

```
<220> FEATURE:
<223> OTHER INFORMATION: Synthetic oligonucleotide primer

<400> SEQUENCE: 4
ggtgtctgcc gagatttga                                              19

<210> SEQ ID NO 5
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 5
ccgagtgtag gcgatcaccc                                             20

<210> SEQ ID NO 6
<211> LENGTH: 24
<212> TYPE: DNA
<213> ORGANISM: Artificial Sequence
<220> FEATURE:
<223> OTHER INFORMATION: Synthetic oligonucleotide primer

<400> SEQUENCE: 6
atggctggcg attctaggaa tgcc                                        24

<210> SEQ ID NO 7
<211> LENGTH: 23
<212> TYPE: DNA
<213> ORGANISM: Artificial Sequence
<220> FEATURE:
<223> OTHER INFORMATION: Synthetic oligonucleotide primer

<400> SEQUENCE: 7
tctcaccgag cccctggcct ccc                                         23

<210> SEQ ID NO 8
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 8
aaccaggaca tggagattgg                                             20

<210> SEQ ID NO 9
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 9
gagaacagga aagcggacac                                             20
```

NITROGEN-CONTAINING COMPOUNDS AND PHARMACEUTICAL COMPOSITIONS THEREOF FOR THE TREATMENT OF ATRIAL FIBRILLATION

CROSS REFERENCE TO RELATED APPLICATIONS

This application is a Divisional application of U.S. application Ser. No. 13/388,442, filed on Apr. 23, 2012, which is a National Stage of International Application No. PCT/JP2010/064545, filed on Aug. 20, 2010, which claims priorities from U.S. Patent Application Nos. 61/235,973 filed on Aug. 21, 2009, 61/235,981 filed on Aug. 21, 2009, 61/235,983 filed on Aug. 21, 2009 and 61/359,686 filed on Jun. 29, 2010, the contents of all of which are incorporated herein by reference in their entirety.

TECHNICAL FIELD

The present invention relates to a nitrogen-containing compound and a pharmaceutical composition containing the same.

BACKGROUND ART

Atrial fibrillation (hereinafter referred to as "AF") is the most frequently observed type of arrhythmia in clinical examinations. Although not a lethal arrhythmia, AF causes cardiogenic cerebral embolism, and is therefore recognized as an arrhythmia that greatly affects vital prognoses and QOL. It is known that the onset of AF increases with age, and that repeated AF strokes lead to chronic (serious) AF (The Journal of American Medical Association, 285, 2370-2375 (2001) and Circulation, 114, 119-123 (2006)).

To prevent chronic AF, which causes difficulty in restoring sinus rhythm and increases the risk of cardiogenic cerebral embolism, early defibrillation and subsequent prevention of recurrence (maintenance of the sinus rhythm) are required. Antiarrhythmic drugs (classes I and III) are most commonly used as pharmacotherapy, but these drugs achieve insufficient therapeutic effects, while causing serious side effects such as a proarrhythmic effect (Am. J. Cardiol., 72, B44-B49 (1993)).

The onset of AF is triggered by atrial premature contraction with underlining causes such as intra-atrial conduction delay, shortening and heterogeneity of the atrial refractory period (Nature Reviews DRUG DISCOVERY 4, 899-910 (2005)). It is known that the prolongation of refractory period of atrial muscle can terminate AF (defibrillation) or prevent the occurrence of AF. The action potential duration of the mammalian cardiac muscle is predominantly determined by voltage-dependent $K^+$ channels. Inhibition of the $K^+$ channel prolongs myocardial action potential duration, which results in prolongation of the refractory period (Nature Reviews DRUG DISCOVERY 5, 1034-49 (2006)). The action mechanism of class III antiarrhythmic drugs (e.g., Dofetilide) is to inhibit rapid delayed rectifier $K^+$ current ($I_{Kr}$), $K^+$ current encoded by HERG. However, since $I_{Kr}$ is present in both the atria and ventricles, such drugs might cause ventricular arrhythmias, such as torsades de pointes (Trends Pharmacol. soc., 22, 240-246 (2001)).

Ultra-rapid delayed rectifier $K^+$ current ($I_{Kur}$), $K^+$ current encoded by Kv1.5, has been identified as $K^+$ channel that is specifically expressed only in human atria (Cric. Res., 73, 1061-1076 (1993), J. Physiol., 491, 31-50 (1996) and Cric. Res., 80, 572-579 (1997)). Muscarine potassium current ($I_{KACh}$) encoded by two genes called GIRK1 and GIRK4 is known as a $K^+$ channel specifically expressed in human atria (Nature 374, 135-141 (1995)). Accordingly, a pharmacologically acceptable substance that selectively blocks the $I_{Kur}$ current (the Kv1.5 channel) or the $I_{KACh}$ current (GIRK1/4 channel) can act selectively on the atrial muscle and is considered effective to exclude the proarrhythmic effect caused by prolonged action potential duration of the ventricular muscle.

SUMMARY OF INVENTION

The present specification discloses three inventions (three nitrogen-containing compounds each having a different structure). The inventions are respectively expressed as a "First Invention", "Second Invention", and "Third Invention", which are described in detail below.

1. First Invention (Diazepine Compound)

The present inventors conducted extensive research to develop a compound that blocks the $I_{Kur}$ current (Kv1.5 channel) and/or the $I_{KACh}$ current (GIRK1/4 channel) potently and more selectively than other $K^+$ channels. As a result, the inventors found that a novel diazepine compound represented by General Formula (1) below could be the desired compound. The present invention has been accomplished based on the above findings.

The present invention provides diazepine compounds, and pharmaceutical compositions comprising the diazepine compounds as summarized in items 1 to 16 below.

Item 1. A diazepine compound represented by General Formula (1)

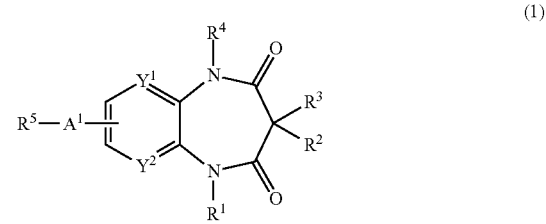

(1)

or a salt thereof,
wherein $R^1$, $R^2$, $R^3$, and $R^4$ are each independently hydrogen, lower alkyl, cyclo lower alkyl or lower alkoxy lower alkyl;
$R^2$ and $R^3$ may be linked to form lower alkylene;
$A^1$ is lower alkylene optionally substituted with one or more substituents selected from the group consisting of hydroxyl and oxo;
$Y^1$ and $Y^2$ are each independently —N= or —CH=;
$R^5$ is group represented by

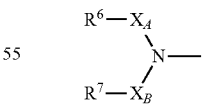

wherein $R^6$ and $R^7$ are each independently hydrogen or an organic group;
$R^6$ and $R^7$ may be linked to form a ring together with the neighboring group —$X_A$—N—$X_B$—;
$X_A$ and $X_B$ are each independently a bond, alkylene, alkenylene, —CO—, —$SO_2$—, or —CONH—, wherein each of the alkylene and alkenylene chains can optionally contain one or more substituents selected from the group consisting of —S—, —C(=S)—, —$SO_2$—, —CO—, —O—, —NH—, —CONH— and —SO$_2$NH—, and the hydrogen atom (H) bonded to the nitrogen atom (N) in X$_A$ and X$_B$ is optionally substituted with a substituent selected from the group consisting of lower alkyl, phenyl lower alkyl and phenyl.

Item 2. A diazepine compound or a salt thereof according to Item 1, wherein R$^6$ and R$^7$ are each independently hydrogen, lower alkyl, cyclo lower alkyl, aryl or heterocyclic group, each of which is optionally substituted, and X$_A$ and X$_B$ are each independently a bond, lower alkylene, lower alkenylene, —CO—, —SO$_2$—, -lower alkylene-SO$_2$—, -lower alkylene-CO—, -lower alkenylene-CO—, -lower alkylene-CO—N(lower alkyl)-lower alkylene-, —N(lower alkyl)-lower alkylene-, —CO—N(lower alkyl)-lower alkylene-, —O-lower alkylene-, —N(phenyl lower alkyl)-lower alkylene-, —CO-lower alkylene-CO—, —CO—NH-lower alkylene-, -lower alkylene-N(lower alkyl)-lower alkylene-, -lower alkylene-N(lower alkyl)-lower alkylene-O—, -lower alkylene-NH-lower alkylene-, -lower alkylene-SO$_2$—NH-lower alkylene-, —N(lower alkyl)-CO-lower alkylene-, —N(lower alkyl)-lower alkylene-CO—, —N(lower alkyl)-lower alkylene-N(lower alkyl)-lower alkylene-, —N(phenyl)-lower alkylene-CO—, —N(phenyl)-lower alkylene-CO—, —NH—CO—, —NH—CO-lower alkylene-, —NH-lower alkylene-, —O-lower alkylene-CO—N(lower alkyl)-lower alkylene-, —O-lower alkylene-CO—, —NH-lower alkylene-CO—N(lower alkyl)-lower alkylene-, —S-lower alkylene-CO—N(lower alkyl)-lower alkylene-, —SO$_2$—N(lower alkyl)-lower alkylene-, —SO$_2$—NH-lower alkylene-, -lower alkenylene-CO—N(lower alkyl)-lower alkylene-, lower alkylene-N(phenyl lower alkyl)-lower alkylene-, —N(phenyl lower alkyl)-lower alkylene-, —N(phenyl)-lower alkylene-CO—N(lower alkyl)-lower alkylene-, or —CO-lower alkylene-O—CO-lower alkylene-O—.

Item 3. A diazepine compound or a salt thereof according to Item 2, wherein R$^6$ and R$^7$ are each independently hydrogen, lower alkyl, cyclo lower alkyl, aryl or saturated or unsaturated monocyclic or polycyclic heterocyclic groups containing at least one hetero atom selected from the group consisting of oxygen, sulfur and nitrogen, each of which is optionally substituted.

Item 4. A diazepine compound or a salt thereof according to Item 3, wherein R$^6$ and R$^7$ are each independently hydrogen, lower alkyl, cyclo lower alkyl, phenyl, naphthyl, piperidyl, piperazinyl, pyrrolidinyl, morpholinyl, furyl, thienyl, pyrazolyl, oxazolyl, isoxazolyl, thiazolyl, isothiazolyl, pyrrolyl, triazolyl, imidazolyl, pyridyl, pyrimidinyl, pyridazinyl, pyrazinyl, imidazo[2,1-b]thiazolyl, thieno[2,3-b]pyrazinyl, 2,3-dihydroimidazo[2,1-b]thiazolyl, benzothiazolyl, indolyl, imidazo[1,2-a]pyridyl, imidazo[1,5-a]pyridyl, benzothienyl, benzimidazolyl, 2,3-dihydrobenzimidazolyl, 2,3-dihydrobenzo[b]furyl, benzofuryl, indazolyl, furo[2,3-c]pyridyl, 6,7-dihydrofuro[2,3-c]pyridyl, furo[3,2-c]pyridyl, 4,5-dihydrofuro[3,2-c]pyridyl, furo[2,3-b]pyridyl, 6,7-dihydrofuro[2,3-b]pyridyl, thieno[2,3-c]pyridyl, 6,7-dihydrothieno[2,3-c]pyridyl, thieno[3,2-c]pyridyl, 4,5-dihydrothieno[3,2-c]pyridyl, thieno[2,3-b]pyridyl, 6,7-dihydrothieno[2,3-b]pyridyl, benzo[1,3]dioxolyl, benzisoxazolyl, pyrazolo[2,3-a]pyridyl, indolizinyl, 2,3-dihydroindolyl, isoquinolyl, 1,2-dihydroisoquinolyl, 1,2,3,4-tetrahydro-1H-isoquinolyl, carbostyril, 3,4-dihydrocarbostyril, quinolyl, 1,4-dihydroquinolyl, 1,2-dihydroquinolyl, 3,4-dihydroquinolyl, 1,2,3,4-tetrahydroquinolyl, pyrido[3,4-d]imidazolyl, pyrido[2,3-d]imidazolyl, chromanyl, 5,6,7,8-tetrahydroisoquinolyl, 3,4-dihydro-1H-isoquinolyl, 3,4-dihydroisoquinolyl, naphthyridinyl, 1,4-benzodioxanyl, cinnolinyl, quinoxalinyl, 2,3-dihydrobenz-1,4-oxazinyl, azetidinyl, 1,2,4-oxadiazolyl and azepanyl, each of which is optionally substituted.

Item 5. A diazepine compound or a salt thereof according to Item 4, wherein R$^6$ and R$^7$ are each independently selected from the group consisting of the following substituents (1) to (54):

(1) hydrogen;
(2) lower alkyl;
(3) cyclo lower alkyl optionally substituted with one or more phenyl lower alkoxys;
(4) phenyl optionally substituted with one or more substituents selected from the group consisting of the following (4-1) to (4-27):
  (4-1) cyano;
  (4-2) hydroxyl;
  (4-3) halogen;
  (4-4) lower alkyl optionally substituted with one or more substituents selected from the group consisting of halogen, hydroxyl, lower alkoxy, imidazolyl, 2-oxo-1,2,3,4-tetrahydroquinolyl and morpholinyl;
  (4-5) lower alkoxy optionally substituted with one or more substituents selected from the group consisting of amino and lower alkyl amino;
  (4-6) pyridyl;
  (4-7) thienyl;
  (4-8) piperazinyl optionally substituted with one or more lower alkyls;
  (4-9) phenyl;
  (4-10) pyrazolyl optionally substituted with one or more lower alkyls;
  (4-11) pyrimidinyl optionally substituted with one or more lower alkyls;
  (4-12) piperidyl optionally substituted with one or more lower alkyls;
  (4-13) furyl;
  (4-14) carboxy;
  (4-15) lower alkoxycarbonyl;
  (4-16) amino optionally substituted with one or more substituents selected from the group consisting of lower alkyl, lower alkanoyl and lower alkylsulfonyl;
  (4-17) lower alkylthio;
  (4-18) triazolyl;
  (4-19) imidazolyl;
  (4-20) pyrrolidinyl optionally substituted with one or more oxos;
  (4-21) lower alkylsulfonyl;
  (4-22) lower alkylenedioxy optionally substituted with one or more halogens;
  (4-23) nitro;
  (4-24) oxazolyl;
  (4-25) thiazolyl optionally substituted with one or more lower alkyls;
  (4-26) lower alkanoyl; and
  (4-27) morpholinyl;
(5) naphthyl;
(6) furyl optionally substituted with one or more substituents selected from the group consisting of lower alkyl optionally substituted with halogen, carboxy, sulfo, pyridyloxy, lower alkoxycarbonyl and phenyl;
(7) thienyl optionally substituted with one or more substituents selected from the group consisting of lower alkyl, lower alkylenedioxy, carboxy, halogen, pyridyl, lower alkoxy, lower alkoxycarbonyl, oxazolyl and furyl;
(8) imidazolyl optionally substituted with one or more substituents selected from the group consisting of phenyl, lower alkyl and halogen;

(9) pyrazolyl optionally substituted with one or more substituents selected from the group consisting of lower alkyl optionally substituted with halogen or lower alkoxy; cyclo lower alkyl; halogen; phenyl optionally substituted with lower alkoxy; furyl and thienyl;

(10) oxazolyl optionally substituted with one or more substituents selected from the group consisting of lower alkyl and phenyl;

(11) isoxazolyl optionally substituted with one or more substituents selected from the group consisting of phenyl, lower alkyl, thienyl and furyl;

(12) thiazolyl optionally substituted with one or more substituents selected from the group consisting of lower alkyl optionally substituted with halogen or lower alkoxy; phenyl; phenoxy and lower alkanoylamino;

(13) pyrrolyl optionally substituted with one or more substituents selected from the group consisting of lower alkyl and lower alkoxycarbonyl;

(14) triazolyl optionally substituted with one or more lower alkyls;

(15) pyridyl optionally substituted with one or more substituents selected from the group consisting of the following (15-1) to (15-14):
 (15-1) halogen;
 (15-2) cyano;
 (15-3) amino optionally substituted with one or more substituents selected from the group consisting of lower alkanoyl and lower alkylsulfonyl;
 (15-4) lower alkyl optionally substituted with one or more substituents selected from the group consisting of halogen, lower alkoxy, lower alkanoyloxy, cyclo lower alkyl amino, lower alkyl amino, lower alkanoyl amino, hydroxyl and pyrrolidinyl optionally substituted with one or more hydroxyls;
 (15-5) oxo;
 (15-6) hydroxyl;
 (15-7) lower alkoxy optionally substituted with one or more phenyls;
 (15-8) pyrrolidinyl;
 (15-9) lower alkanoyl;
 (15-10) morpholinyl;
 (15-11) phenoxy;
 (15-12) pyrazolyl;
 (15-13) thienyl; and
 (15-14) N-oxide

(16) pyrimidinyl optionally substituted with one or more substituents selected from the group consisting of lower alkyl and phenyl;

(17) pyridazinyl;

(18) pyrazinyl optionally substituted with one or more phenyl lower alkoxys;

(19) imidazo[2,1-b]thiazolyl optionally substituted with one or more halogens;

(20) thieno[2,3-b]pyrazinyl;

(21) 2,3-dihydroimidazo[2,1-b]thiazolyl optionally substituted with one or more phenyls;

(22) benzothiazolyl optionally substituted with one or more lower alkyls;

(23) indolyl optionally substituted with one or more substituents selected from the group consisting of lower alkyl, lower alkanoyl and halogen;

(24) imidazo[1,2-a]pyridyl or imidazo[1,5-a]pyridyl, each of which is optionally substituted with one or more lower alkyls;

(25) benzothienyl optionally substituted with one or more lower alkyls;

(26) benzimidazolyl optionally substituted with one or more lower alkyls;

(27) 2,3-dihydrobenzo[b]furyl;

(28) benzofuryl optionally substituted with one or more halogens;

(29) indazolyl optionally substituted with one or more lower alkyls;

(30) furo[2,3-c]pyridyl or 6,7-dihydrofuro[2,3-c]pyridyl, each of which is optionally substituted with one or more substituents selected from the group consisting of oxo and lower alkyl optionally substituted with lower alkoxy;

(31) furo[3,2-c]pyridyl or 4,5-dihydrofuro[3,2-c]pyridyl, each of which is optionally substituted with one or more substituents selected from the group consisting of oxo, lower alkyl optionally substituted with halogen or lower alkoxy, halogen, furyl, pyridyl and phenyl optionally substituted with one or more substituents selected from the group consisting of amino and lower alkoxy;

(32) thieno[2,3-c]pyridyl or 6,7-dihydrothieno[2,3-c]pyridyl, each of which is optionally substituted with one or more substituents selected from the group consisting of oxo group and lower alkyl;

(33) thieno[3,2-c]pyridyl or 4,5-dihydrothieno[3,2-c]pyridyl, each of which is optionally substituted with one or more substituents selected from the group consisting of oxo and lower alkyl;

(34) thieno[2,3-b]pyridyl;

(35) benzo[1,3]dioxolyl optionally substituted with one or more halogens;

(36) benzisoxazolyl;

(37) pyrazolo[2,3-a]pyridyl;

(38) indolizinyl;

(39) 2,3-dihydroindolyl optionally substituted with one or more substituents selected from the group consisting of oxo, lower alkyl and lower alkanoyl;

(40) isoquinolyl or 1,2-dihydroisoquinolyl, each of which is optionally substituted with one or more substituents selected from the group consisting of lower alkyl, halogen and oxo;

(41) 1,2,3,4-tetrahydroisoquinolyl optionally substituted with one or more oxos;

(42) quinolyl optionally substituted with one or more substituents selected from the group consisting of amino optionally substituted with one or two lower alkyls, lower alkoxy, lower alkyl and oxo

(43) 1,2,3,4-tetrahydroquinolyl optionally substituted with one or more substituents selected from the group consisting of lower alkyl, pyridyl lower alkyl, aralkyl, lower alkoxy and oxo;

(44) 1,2-dihydroquinolyl optionally substituted with one or more substituents selected from the group consisting of amino optionally substituted with one or two lower alkyls, lower alkoxy, lower alkyl and oxo;

(45) chromanyl optionally substituted with one or more lower alkyls;

(46) 5,6,7,8-tetrahydroisoquinolyl optionally substituted with one or more oxos;

(47) 3,4-dihydroisoquinolyl optionally substituted with one or more oxos;

(48) naphthyridinyl;

(49) 1,4-benzodioxanyl;

(50) cinnolinyl;

(51) quinoxalinyl;

(52) 2,3-dihydrobenz-1,4-oxazinyl optionally substituted with one or more substituents selected from the group consisting of lower alkyl and oxo;

(53) 2,3-dihydro-1H-benzo[d]imidazolyl optionally substituted with one or more substituents selected from the group consisting of lower alkyl and oxo; and
(54) piperidyl optionally substituted with one or more aryl carbonyls.

Item 6. A diazepine compound or a salt thereof according to Item 5, wherein $R^6$ and $R^7$ are each independently (1), (4a), (6a), (7a), (8a), (9a), (10a), (11a), (12a), (15a), (16a), (17), (18), (23a), (24a), (24b), (26), (29), (30a), (30b), (31a), (31b), (32a), (32b), (33a), (33b), (35), (40a), (40b), (42a), (43a), (44a), and (53):
(1) hydrogen;
(4a) phenyl optionally substituted with one or more substituents selected from the group consisting of the following (4-1), (4-2), (4-4), (4a-5), (4-10), (4a-16), (4-18), (4-19), (4-23), (4-26), and (4-27):
  (4-1) cyano;
  (4-2) hydroxyl;
  (4-4) lower alkyl optionally substituted with one or more substituents selected from the group consisting of halogens, hydroxyl, 2-oxo-1,2,3,4-tetrahydroquinolyl, lower alkoxy, imidazolyl, and morpholinyl;
  (4a-5) lower alkoxy;
  (4-10) pyrazolyl optionally substituted with one or more lower alkyls;
  (4a-16) amino optionally substituted with one or more lower alkylsulfonyls;
  (4-18) triazolyl;
  (4-19) imidazolyl;
  (4-23) nitro;
  (4-26) lower alkanoyl; and
  (4-27) morpholinyl;
(6a) furyl optionally substituted with one or more lower alkyls optionally substituted with halogen;
(7a) thienyl optionally substituted with one or more lower alkyls;
(8a) imidazolyl optionally substituted with one or more lower alkyls;
(9a) pyrazolyl optionally substituted with one or more lower alkyls optionally substituted with lower alkoxy;
(10a) oxazolyl optionally substituted with one or more lower alkyls;
(11a) isoxazolyl optionally substituted with one or more lower alkyls;
(12a) thiazolyl optionally substituted with one or more lower alkyls optionally substituted with halogen;
(15a) pyridyl optionally substituted with one or more substituents selected from the group consisting of the following (15-1) to (15-5), (15a-7), (15-9), (15-11), (15-12) and (15-14):
  (15-1) halogen;
  (15-2) cyano;
  (15-3) amino optionally substituted with one or more substituents selected from the group consisting of lower alkanoyl and lower alkylsulfonyl;
  (15-4) lower alkyl optionally substituted with one or more substituents selected from the group consisting of halogen, lower alkoxy, lower alkanoyloxy, cyclo lower alkyl amino, lower alkyl amino, lower alkanoyl amino, hydroxyl and pyrrolidinyl optionally substituted with one or more hydroxyls;
  (15-5) oxo;
  (15a-7) lower alkoxy;
  (15-9) lower alkanoyl;
  (15-11) phenoxy;
  (15-12) pyrazolyl; and
  (15-14) N-oxide
(16a) pyrimidinyl optionally substituted with one or more lower alkyls;
(17) pyridazinyl
(18) pyrazinyl optionally substituted with one or more phenyl lower alkoxys;
(23a) indolyl optionally substituted with one or more lower alkyls;
(24a) imidazo[1,2-a]pyridyl;
(24b) imidazo[1,5-a]pyridyl optionally substituted with one or more lower alkyls;
(26) benzimidazolyl optionally substituted with one or more lower alkyls;
(29) indazolyl optionally substituted with one or more lower alkyls;
(30a) furo[2,3-c]pyridyl optionally substituted with one or more substituents selected from the group consisting of oxo and lower alkyl;
(30b) 6,7-dihydrofuro[2,3-c]pyridyl optionally substituted with one or more substituents selected from the group consisting of oxo and lower alkyl;
(31a) furo[3,2-c]pyridyl optionally substituted with one or more substituents selected from the group consisting of oxo and lower alkyl;
(31b) 4,5-dihydrofuro[3,2-c]pyridyl optionally substituted with one or more substituents selected from the group consisting of oxo and lower alkyl optionally substituted with halogen or lower alkoxy;
(32a) thieno[2,3-c]pyridyl optionally substituted with one or more substituents selected from the group consisting of oxo and lower alkyl;
(32b) 6,7-dihydrothieno[2,3-c]pyridyl optionally substituted with one or more substituents selected from the group consisting of oxo group and lower alkyl;
(33a) thieno[3,2-c]pyridyl optionally substituted with one or more substituents selected from the group consisting of oxo and lower alkyl;
(33b) 4,5-dihydrothieno[3,2-c]pyridyl optionally substituted with one or more substituents selected from the group consisting of oxo and lower alkyl;
(35a) benzo[1,3]dioxolyl;
(40a) isoquinolyl optionally substituted with one or more oxos;
(40b) 1,2-dihydroisoquinolyl optionally substituted with one or more substituents selected from the group consisting of oxo and lower alkyl;
(42a) quinolyl optionally substituted with one or more oxos;
(43a) 1,2,3,4-tetrahydroquinolyl optionally substituted with one or more substituents selected from the group consisting of aralkyl (e.g., phenyl lower alkyl, etc.), pyridyl lower alkyl and oxo;
(44) 1,2-dihydroquinolyl optionally substituted with one or more oxos; and
(53) 2,3-dihydrobenzo[d]imidazolyl optionally substituted with one or more substituents selected from the group consisting of lower alkyl and oxo.

Item 7. A diazepine compound or a salt thereof according to Item 6, wherein $R^6$ and $R^7$ are each independently phenyl, pyridyl, pyrazolyl, indolyl, 4,5-dihydrofuro[3,2-c]pyridyl, and 1,2-dihydroisoquinolyl, each of which is optionally substituted with one or two substituents selected from the group consisting of oxo, lower alkyl, lower alkoxy lower alkyl, and lower alkylsulfonylamino.

Item 8. A diazepine compound or a salt thereof according to Item 7, which is selected from the group consisting of the following compounds:

1-ethyl-3,3,5-trimethyl-7-(3-{N-[2-(2-methyl-4-oxo-4H-furo[3,2-c]pyridin-5-yl)ethyl]-N-(pyridin-4-ylmethyl)amino}propyl)-1,5-dihydrobenzo[b][1,4]diazepine-2,4-dione, 1-ethyl-3,3,5-trimethyl-7-(2-{N-[2-(2-methyl-4-oxo-4H-furo[3,2-c]pyridin-5-yl)ethyl]-N-(pyridin-4-ylmethyl)amino}ethyl)-1,5-dihydrobenzo[b][1,4]diazepine-2,4-dione, 1-ethyl-3,3,5-trimethyl-7-(2-{N-(2-methylpyridin-3-ylmethyl)-N-[2-(4-oxo-4H-furo[3,2-c]pyridin-5-yl)ethyl]amino}ethyl)-1,5-dihydrobenzo[b][1,4]diazepine-2,4-dione, 1-ethyl-3,3,5-trimethyl-7-{2-[N-[2-(2-methyl-4-oxo-4H-furo[3,2-c]pyridin-5-yl)ethyl]-N-(4-methylpyridin-3-ylmethyl)amino]ethyl}-1,5-dihydrobenzo[b][1,4]diazepine-2,4-dione, 1-ethyl-3,3,5-trimethyl-7-({N-(2-methylpyridin-3-ylmethyl)-N-[2-(1-oxo-1H-isoquinolin-2-yl)ethyl]amino}methyl)-1,5-dihydrobenzo[b][1,4]diazepine-2,4-dione, N-(1-ethyl-3,3,5-trimethyl-2,4-dioxo-2,3,4,5-tetrahydro-1H-benzo[b][1,4]diazepin-7-ylmethyl)-4-methyl-N-(2-pyridin-3-ylethyl)benzamide, N-(1-ethyl-3,3,5-trimethyl-2,4-dioxo-2,3,4,5-tetrahydro-1H-benzo[b][1,4]diazepin-7-ylmethyl)-N-(2-pyridin-3-ylethyl)benzenesulfonamide, 7-{[N-benzyl-N-(2-pyridin-3-ylethyl)amino]methyl}-1-ethyl-3,3,5-trimethyl-1,5-dihydrobenzo[b][1,4]diazepine-2,4-dione, N-(2-{[(1-ethyl-3,3,5-trimethyl-2,4-dioxo-2,3,4,5-tetrahydro-1H-benzo[b][1,4]diazepin-7-ylmethyl)(2-pyridin-3-ylethyl)amino]methyl}phenyl)methanesulfonamide, 7-{[N-[2-(2,7-dimethyl-4-oxo-4H-furo[3,2-c]pyridin-5-yl)ethyl]-N-(2,5-dimethyl-2H-pyrazol-3-ylmethyl)amino]methyl}-1-ethyl-3,3,5-trimethyl-1,5-dihydrobenzo[b][1,4]diazepine-2,4-dione, 1-Ethyl-7-({N-(2-methoxymethylpyridin-3-ylmethyl)-N-[2-(2-methyl-4-oxo-4H-furo[3,2-c]pyridin-5-yl)ethyl]amino}methyl)-3,3,5-trimethyl-1,5-dihydrobenzo[b][1,4]diazepine-2,4-dione, 1-Ethyl-7-({N-(2-methoxymethylpyridin-3-ylmethyl)-N-[2-(7-methyl-4-oxo-4H-furo[3,2-c]pyridin-5-yl)ethyl]amino}methyl)-3,3,5-trimethyl-1,5-dihydrobenzo[b][1,4]diazepine-2,4-dione, N-(1-Ethyl-3,3,5-trimethyl-2,4-dioxo-2,3,4,5-tetrahydro-1H-benzo[b][1,4]diazepin-7-ylmethyl)-2-(1-methyl-1H-indol-3-yl)-N-(2-pyridin-3-ylethyl)acetamide.

Item 9. A diazepine compound according to Item 8, which is selected from the group consisting of the following compounds:

1-ethyl-3,3,5-trimethyl-7-(3-{N-[2-(2-methyl-4-oxo-4H-furo[3,2-c]pyridin-5-yl)ethyl]-N-(pyridin-4-ylmethyl)amino}propyl)-1,5-dihydrobenzo[b][1,4]diazepine-2,4-dione dihydrochloride, 1-ethyl-3,3,5-trimethyl-7-(2-{N-[2-(2-methyl-4-oxo-4H-furo[3,2-c]pyridin-5-yl)ethyl]-N-(pyridin-4-ylmethyl)amino}ethyl)-1,5-dihydrobenzo[b][1,4]diazepine-2,4-dione dihydrochloride, 1-ethyl-3,3,5-trimethyl-7-(2-{N-(2-methylpyridin-3-ylmethyl)-N-[2-(4-oxo-4H-furo[3,2-c]pyridin-5-yl)ethyl]amino}ethyl)-1,5-dihydrobenzo[b][1,4]diazepine-2,4-dione dihydrochloride, 1-ethyl-3,3,5-trimethyl-7-{2-[N-[2-(2-methyl-4-oxo-4H-furo[3,2-c]pyridin-5-yl)ethyl]-N-(4-methylpyridin-3-ylmethyl)amino]ethyl}-1,5-dihydrobenzo[b][1,4]diazepine-2,4-dione dihydrochloride, 1-ethyl-3,3,5-trimethyl-7-({N-(2-methylpyridin-3-ylmethyl)-N-[2-(1-oxo-1H-isoquinolin-2-yl)ethyl]amino}methyl)-1,5-dihydrobenzo[b][1,4]diazepine-2,4-dione dihydrochloride, N-(1-ethyl-3,3,5-trimethyl-2,4-dioxo-2,3,4,5-tetrahydro-1H-benzo[b][1,4]diazepin-7-ylmethyl)-4-methyl-N-(2-pyridin-3-ylethyl)benzamide hydrochloride, N-(1-ethyl-3,3,5-trimethyl-2,4-dioxo-2,3,4,5-tetrahydro-1H-benzo[b][1,4]diazepin-7-ylmethyl)-N-(2-pyridin-3-ylethyl)benzenesulfonamide, 7-{[N-benzyl-N-(2-pyridin-3-ylethyl)amino]methyl}-1-ethyl-3,3,5-trimethyl-1,5-dihydrobenzo[b][1,4]diazepine-2,4-dione hydrochloride, N-(2-{[(1-ethyl-3,3,5-trimethyl-2,4-dioxo-2,3,4,5-tetrahydro-1H-benzo[b][1,4]diazepin-7-ylmethyl)(2-pyridin-3-ylethyl)amino]methyl}phenyl)methanesulfonamide dihydrochloride, 7-{[N-[2-(2,7-dimethyl-4-oxo-4H-furo[3,2-c]pyridin-5-yl)ethyl]-N-(2,5-dimethyl-2H-pyrazol-3-ylmethyl)amino]methyl}-1-ethyl-3,3,5-trimethyl-1,5-dihydrobenzo[b][1,4]diazepine-2,4-dione, 1-Ethyl-7-({N-(2-methoxymethylpyridin-3-ylmethyl)-N-[2-(2-methyl-4-oxo-4H-furo[3,2-c]pyridin-5-yl)ethyl]amino}methyl)-3,3,5-trimethyl-1,5-dihydrobenzo[b][1,4]diazepine-2,4-dione, 1-Ethyl-7-({N-(2-methoxymethylpyridin-3-ylmethyl)-N-[2-(7-methyl-4-oxo-4H-furo[3,2-c]pyridin-5-yl)ethyl]amino}methyl)-3,3,5-trimethyl-1,5-dihydrobenzo[b][1,4]diazepine-2,4-dione, and N-(1-Ethyl-3,3,5-trimethyl-2,4-dioxo-2,3,4,5-tetrahydro-1H-benzo[b][1,4]diazepin-7-ylmethyl)-2-(1-methyl-1H-indol-3-yl)-N-(2-pyridin-3-ylethyl)acetamide hydrochloride.

Item 10. A diazepine compound or a salt thereof according to Item 1, wherein $Y^1$ and $Y^2$ are each —CH=.

Item 11. A pharmaceutical composition comprising a diazepine compound or a salt thereof according to Item 1, and a pharmacologically acceptable carrier.

Item 12. A pharmaceutical composition according to Item 11 for preventing and/or treating arrhythmia.

Item 13. A diazepine compound or a salt thereof according to Item 1 for use in the pharmaceutical composition.

Item 14. Use of a diazepine compound or a salt thereof according to Item 1 as a pharmaceutical composition.

Item 15. Use of a diazepine compound or a salt thereof according to Item 1 for the production of a pharmaceutical composition.

Item 16. A method of preventing and/or treating arrhythmia, comprising administering to a patient a diazepine compound or a salt thereof according to Item 1.

The groups represented by, or substituents of, $R^1$, $R^2$, $R^3$, $R^4$, $R^5$, $R^6$, $R^7$, $A^1$, $X_A$, $X_B$, $Y^1$ and $Y^2$ in the specification are described below.

The term "one or more" may be preferably 1 to 6, more preferably 1 to 3.

Examples of "lower alkyl" include linear or branched alkyl groups having 1 to 6 carbon atoms, such as methyl, ethyl, n-propyl, isopropyl, n-butyl, isobutyl, tert-butyl, sec-butyl, n-pentyl, neopentyl, n-hexyl, isohexyl, and 3-methylpentyl.

Examples of "alkylene" include linear or branched alkylene groups having 1 to 12 carbon atoms, such as the following "lower alkylene", heptamethylene, octamethylene, decamethylene, and dodecamethylene.

Examples of "lower alkylene" include linear or branched alkylene groups having 1 to 6 carbon atoms, such as methylene, ethylene, trimethylene, 2-methyltrimethylene, 2,2-dimethyltrimethylene, 1-methyltrimethylene, methylmethylene, ethylmethylene, dimethylmethylene, tetramethylene, pentamethylene, and hexamethylene.

Examples of "alkenylene" include linear or branched alkenylene groups having 2 to 12 carbon atoms, such as the following "lower alkenylene", heptenylene, octenylene, decenylene, and dodecenylene.

Examples of "lower alkenylene" include linear or branched alkenylene groups having 2 to 6 carbon atoms, such as, ethenylene, propenylene, butenylene, pentenylene, and hexenylene.

Examples of "cyclo lower alkyl" include linear or branched cyclo alkyl having 3 to 8 carbon atoms, preferably 3 to 7 carbon atoms, such as cyclopropyl, cyclobutyl, cyclopentyl, cyclohexyl, cyclopropylmethyl and cyclohexylmethyl.

Examples of "lower alkoxy" include linear or branched alkoxy groups having 1 to 6 carbon atoms, such as methoxy, ethoxy, n-propoxy, isopropoxy, n-butoxy, isobutoxy, tert-butoxy, sec-butoxy, n-pentyloxy, neopentyloxy, n-hexyloxy, isohexyloxy, and 3-methylpentyloxy.

Examples of "halogen" are fluorine, chlorine, bromine, and iodine.

Examples of "lower alkylenedioxy" include linear or branched alkylenedioxy groups having 1 to 4 carbon atoms, such as methylenedioxy, ethylenedioxy, trimethylenedioxy, and tetramethylenedioxy.

Examples of "lower alkanoyl" include linear or branched alkanoyl groups having 1 to 6 carbon atoms, such as formyl, acetyl, propionyl, butyryl, isobutyryl, pentanoyl, tert-butylcarbonyl, and hexanoyl.

Examples of "lower alkoxycarbonyl" include (linear or branched alkoxy having 1 to 6 carbon atoms)carbonyls, such as methoxycarbonyl, ethoxycarbonyl, propoxycarbonyl, butoxycarbonyl, isobutoxycarbonyl, and tert-butoxycarbonyl.

Examples of "aralkyl group" include lower alkyl group substituted with one or more aryl groups, such as benzyl and phenethyl.

Examples of "organic group" include lower alkyl, cyclo lower alkyl, aryl, and heterocyclic group, each of which is optionally substituted.

Examples of "aryl group" include monocyclic or polycyclic aryl groups, such as phenyl, tolyl, xylyl, and naphthyl.

Examples of "aroyl group" include benzoyl and naphthoyl.

Examples of "heterocyclic group" include saturated or unsaturated monocyclic or polycyclic heterocyclic groups containing at least one hetero atom selected from the group consisting of oxygen, sulfur and nitrogen. Examples of preferable heterocyclic groups include the following (a) to (n):

(a) unsaturated 3 to 8-membered, preferably 5 or 6-membered heteromonocyclic groups containing 1 to 4 nitrogen atom(s), for example, pyrrolyl, pyrrolinyl, imidazolyl, pyrazolyl, pyridyl, and its N-oxide, tetrahydropyridyl (e.g., 1,2,3,6-tetrahydropyridyl), pyrimidinyl, pyrazinyl, pyridazinyl, triazolyl (e.g., 4H-1,2,4-triazolyl, 1H-1,2,3-triazolyl, 2H-1,2,3-triazolyl, etc.), tetrazolyl (e.g., 1H-tetrazolyl, 2H-tetrazolyl, etc.), dihydrotriazinyl (e.g., 4,5-dihydro-1,2,4-triazinyl, 2,5-dihydro-1,2,4-triazinyl, etc.), etc.;

(b) saturated 3 to 8-membered, preferably 5 or 7-membered heteromonocyclic groups containing 1 to 4 nitrogen atom(s), for example, azetidinyl, pyrrolidinyl, imidazolidinyl, piperidyl, pyrazolidinyl, piperazinyl, azepanyl, 1,4-diazepanyl, etc.;

(c) saturated or unsaturated condensed 7 to 12-membered heterocyclic groups containing 1 to 5 nitrogen atom(s), for example, decahydroquinolyl, indolyl, dihydroindolyl (e.g., 2,3-dihydroindolyl, etc.), isoindolyl, indolizinyl, benzimidazolyl, dihydrobenzimidazolyl (e.g., 2,3-dihydro-1H-benzo[d]imidazolyl, etc.), quinolyl, dihydroquinolyl (e.g. 1,4-dihydroquinolyl, 1,2-dihydroquinolyl, etc.), tetrahydroquinolyl (1,2,3,4-tetrahydroquinolyl, etc.), isoquinolyl, dihydroisoquinolyl (e.g., 3,4-dihydro-1H-isoquinolyl, 1,2-dihydroisoquinolyl, etc.), tetrahydroisoquinolyl (e.g., 1,2,3,4-tetrahydro-1H-isoquinolyl, 5,6,7,8-tetrahydroisoquinolyl, etc.), carbostyril, dihydrocarbostyril (e.g., 3,4-dihydrocarbostyril, etc.), indazolyl, benzotriazolyl (e.g. benzo[d][1,2,3]triazolyl, etc.), tetrazolopyridyl, tetrazolopyridazinyl (e.g., tetrazolo[1,5-b]pyridazinyl, etc.), dihydrotriazolopyridazinyl, imidazopyridyl (e.g., imidazo[1,2-a]pyridyl, imidazo[4,5-c]pyridyl, imidazo[1,5-a]pyridyl, etc.), naphthyridinyl, cinnolinyl, quinoxalinyl, quinazolinyl, pyrazolopyridyl (e.g., pyrazolo[2,3-a]pyridyl, etc.), tetrahydropyridoindolyl (e.g., 2,3,4,9-tetrahydro-1H-pyrido[3,4-b]indolyl, etc.), azabicyclooctanyl (e.g., (1R,5S)-8-azabicyclo[3.2.1]octanyl), etc.;

(d) saturated or unsaturated 3 to 8-membered, preferably 5 or 6-membered heteromonocyclic groups containing 1 to 2 oxygen atom(s), for example, furyl, tetrahydropyranyl (e.g., tetrahydro-2H-pyranyl, etc.), tetrahydrofuryl, etc.;

(e) unsaturated condensed 7 to 12-membered heterocyclic groups containing 1 to 3 oxygen atom(s), for example, benzofuryl, dihydrobenzofuryl (e.g. 2,3-dihydrobenzo[b]furyl, etc.), chromanyl, benzodioxanyl (e.g., 1,4-benzodioxanyl, etc.), benzodioxolyl (benzo[1,3]dioxolyl, etc.), etc.;

(f) unsaturated 3 to 8-membered, preferably 5 or 6-membered heteromonocyclic groups containing 1 to 2 oxygen atom(s) and 1 to 3 nitrogen atom(s), for example, oxazolyl, isoxazolyl, oxadiazolyl (e.g., 1,2,4-oxadiazolyl, 1,3,4-oxadiazolyl, 1,2,5-oxadiazolyl, etc.), etc.;

(g) saturated 3 to 8-membered, preferably 5 or 6-membered heteromonocyclic groups containing 1 to 2 oxygen atom(s) and 1 to 3 nitrogen atom(s), for example, morpholinyl, etc.;

(h) unsaturated condensed 7 to 12-membered heterocyclic groups containing 1 to 2 oxygen atom(s) and 1 to 3 nitrogen atom(s), for example, benzoxazolyl, benzoxadiazolyl, benzisoxazolyl, dihydrobenzoxazinyl (e.g., 2,3-dihydrobenz-1,4-oxazinyl, etc.), furopyridyl (e.g., furo[2,3-c]pyridyl, 6,7-dihydrofuro[2,3-c]pyridyl, furo[3,2-c]pyridyl, 4,5-dihydrofuro[3,2-c]pyridyl, furo[2,3-b]pyridyl, 6,7-dihydrofuro[2,3-b]pyridyl, etc.), furopyrrolyl (e.g., furo[3,2-b]pyrrolyl etc.), etc.;

(i) unsaturated 3 to 8-membered, preferably 5 or 6-membered heteromonocyclic groups containing 1 to 2 sulfur atom(s) and 1 to 3 nitrogen atom(s), for example, thiazolyl, thiazolinyl, thiadiazolyl (e.g., 1,2,4-thiadiazolyl, 1,3,4-thiadiazolyl, 1,2,5-thiadiazolyl, 1,2,3-thiadiazolyl, etc.), isothiazolyl, etc.;

(j) saturated 3 to 8-membered, preferably 5 or 6-membered heteromonocyclic groups containing 1 to 2 sulfur atom(s) and 1 to 3 nitrogen atom(s), for example, thiazolidinyl, etc.;

(k) unsaturated 3 to 8-membered, preferably 5 or 6-membered heteromonocyclic groups containing a sulfur atom, for example, thienyl, etc.;

(l) unsaturated condensed 7 to 12-membered heterocyclic groups containing 1 to 3 sulfur atom(s), for example, benzothienyl (e.g. benzo[b]thienyl, etc.);

(m) unsaturated condensed 7 to 12-membered heterocyclic groups containing 1 to 2 sulfur atom(s) and 1 to 3 nitrogen atom(s), for example, benzothiazolyl, benzothiadiazolyl, thienopyridyl (e.g., thieno[2,3-c]pyridyl, 6,7-dihydrothieno[2,3-c]pyridyl, thieno[3,2-c]pyridyl, 4,5-dihydrothieno[3,2-c]pyridyl, thieno[2,3-b]pyridyl, 6,7-dihydrothieno[2,3-b]pyridyl, 4,5,6,7-tetrahydrothieno[2,3-c]pyridyl, etc.), imidazothiazolyl (e.g., imidazo[2,1-b]thiazolyl, etc.), dihydroimidazothiazolyl (e.g., 2,3-dihydroimidazo[2,1-b]thiazolyl, etc.), thienopyrazinyl (e.g., thieno[2,3-b]pyrazinyl, etc.), etc.; and (n) saturated or unsaturated 7-to 12-membered heterocyclic spiro groups containing 1 to 2 nitrogen atom(s), for example, azaspiroundecanyl (e.g., 3-azaspiro[5.5]undecanyl), etc.; and the like;

wherein said heterocyclic groups may be substituted with one or more suitable substituents.

Examples of more preferable heterocyclic groups include piperidyl, piperazinyl, pyrrolidinyl, morpholinyl, furyl, thienyl, pyrazolyl, oxazolyl, isoxazolyl, thiazolyl, isothiazolyl, pyrrolyl, triazolyl, imidazolyl, pyridyl, pyrimidinyl, pyridazinyl, pyrazinyl, imidazo[2,1-b]thiazolyl, thieno[2,3-b]pyrazinyl, 2,3-dihydroimidazo[2,1-b]thiazolyl, benzothiazolyl, indolyl, imidazo[1,2-a]pyridyl, imidazo[1,5-a]pyridyl, benzothienyl, benzimidazolyl, 2,3-dihydrobenzimidazolyl, 2,3-dihydrobenzo[b]furyl, benzofuryl, indazolyl, furo[2,3-c]pyridyl, 6,7-dihydrofuro[2,3-c]pyridyl, furo[3,2-c]pyridyl, 4,5-dihydrofuro[3,2-c]pyridyl, furo[2,3-b]pyridyl, 6,7-dihydrofuro[2,3-b]pyridyl, thieno[2,3-c]pyridyl, 6,7-dihydrothieno[2,3-c]pyridyl, thieno[3,2-c]pyridyl, 4,5-dihydrothieno[3,2-c]pyridyl, thieno[2,3-b]pyridyl, 6,7-dihydrothieno[2,3-b]pyridyl, benzo[1,3]dioxolyl, benzisoxazolyl, pyrazolo[2,3-a]pyridyl, indolizinyl, 2,3-dihydroindolyl, isoquinolyl, 1,2-dihydroisoquinolyl, 1,2,3,4-tetrahydro-1H-isoquinolyl, carbostyril, 3,4-dihydrocarbostyril, quinolyl, 1,4-dihydroquinolyl, 1,2-dihydroquinolyl, 3,4-dihydroquinolyl, 1,2,3,4-tetrahydroquinolyl, pyrido[3,4-d]imidazolyl, pyrido[2,3-d]imidazolyl, chromanyl, 5,6,7,8-tetrahydroisoquinolyl, 3,4-dihydro-1H-isoquinolyl, 3,4-dihydroisoquinolyl, naphthyridinyl, 1,4-benzodioxanyl, cinnolinyl, quinoxalinyl, 2,3-dihydrobenz-1,4-oxazinyl, azetidinyl, 1,2,4-oxadiazolyl, and azepanyl, each of which is optionally substituted.

Substituents of "aryl group which is optionally substituted" represented by $R^6$ and $R^7$ are independently one or more substituents selected from the group consisting of:

(a1) cyano;
(a2) hydroxyl;
(a3) halogen;
(a4) lower alkyl optionally substituted with one or more substituents selected from the group consisting of halogen, hydroxyl, lower alkoxy, imidazolyl, 2-oxo-1,2,3,4-tetrahydroquinolyl and morpholinyl;
(a5) lower alkoxy optionally substituted with one or more substituents selected from the group consisting of amino and lower alkyl amino;
(a6) pyridyl;
(a7) thienyl;
(a8) piperazinyl optionally substituted with one or more lower alkyls;
(a9) phenyl;
(a10) pyrazolyl optionally substituted with one or more lower alkyls;
(a11) pyrimidinyl optionally substituted with one or more lower alkyls;
(a12) piperidyl optionally substituted with one or more lower alkyls;
(a13) furyl;
(a14) carboxy;
(a15) lower alkoxycarbonyl;
(a16) amino optionally substituted with one or more substituents selected from the group consisting of lower alkanoyl and lower alkylsulfonyl;
(a17) lower alkylthio;
(a18) triazolyl;
(a19) imidazolyl;
(a20) pyrrolidinyl optionally substituted with one or more oxos;
(a21) lower alkylsulfonyl;
(a22) lower alkylenedioxy optionally substituted with one or more halogens;
(a23) nitro;
(a24) oxazolyl;
(a25) thiazolyl optionally substituted with one or more lower alkyls;
(a26) lower alkanoyl;
(a27) sulfo; and
(a28) morpholinyl.

Substituents of "heterocyclic group which is optionally substituted" represented by $R^6$ and $R^7$ are independently one or more substituents selected from the group consisting of:

(h1) oxo;
(h2) lower alkyl optionally substituted with one or more substituents selected from the group consisting of the following (h2-1) to (h2-10):
  (h2-1) halogen;
  (h2-2) hydroxyl;
  (h2-3) amino optionally substituted with one or more substituents selected from the group consisting of lower alkyl, cyclo lower alkyl and lower alkanoyl;
  (h2-4) pyridyl;
  (h2-5) lower alkanoyloxy;
  (h2-6) lower alkoxy;
  (h2-7) aryloxy;
  (h2-8) pyrimidinyl;
  (h2-9) pyrrolidinyl optionally substituted with one or more hydroxyls; and
  (h2-10) imidazolyl optionally substituted with one or more lower alkyls;
(h3) cyclo lower alkyl;
(h4) lower alkoxy optionally substituted with one or more substitutents selected from the group consisting of pyridyl and aryl;
(h5) aryl optionally substituted with one or more substituents selected from the group consisting of lower alkyl optionally substituted with one or more halogens; lower alkoxy; lower alkanoyl; hydroxyl; halogen; carboxy; lower alkoxycarbonyl; amino; lower alkyl amino, aryl and cyano;
(h6) aralkyl optionally substituted with one or more substituents selected from the group consisting of lower alkyl, lower alkoxy, lower alkanoyl, hydroxyl, halogen, carboxy, lower alkoxycarbonyl, amino, lower alkyl amino, cyano and oxo;
(h7) heterocyclic group optionally substituted with one or more substituents selected from the group consisting of lower alkyl, lower alkoxy, lower alkanoyl, hydroxyl, halogen, carboxy, lower alkoxycarbonyl, amino, lower alkyl amino, cyano and oxo;
(h8) hydroxyl;
(h9) halogen;
(h10) carboxy;
(h11) lower alkanoyl;
(h12) lower alkoxycarbonyl;
(h13) lower alkylenedioxy;
(h14) cyano;
(h15) nitro;
(h16) sulfo;
(h17) amino optionally substituted with one or more substituents selected from the group consisting of lower alkyl, aryl, aroyl, lower alkylsulfonyl and lower alkanoyl;
(h18) lower alkylthio;
(h19) lower alkylsulfonyl; and
(h20) aryloxy.

Preferable substituents represented by $R^6$ and $R^7$ are each independently selected from the group consisting of the following substituents (1) to (54):

(1) hydrogen;
(2) lower alkyl;
(3) cyclo lower alkyl optionally substituted with one or more phenyl lower alkoxys;
(4) phenyl optionally substituted with one or more substituents selected from the group consisting of the following (4-1) to (4-27):
 (4-1) cyano;
 (4-2) hydroxyl;
 (4-3) halogen;
 (4-4) lower alkyl optionally substituted with one or more substituents selected from the group consisting of halogen, hydroxyl, lower alkoxy, imidazolyl, 2-oxo-1,2,3,4-tetrahydroquinolyl and morpholinyl;
 (4-5) lower alkoxy optionally substituted with one or more substituents selected from the group consisting of amino and lower alkyl amino;
 (4-6) pyridyl;
 (4-7) thienyl;
 (4-8) piperazinyl optionally substituted with one or more lower alkyls;
 (4-9) phenyl;
 (4-10) pyrazolyl optionally substituted with one or more lower alkyls;
 (4-11) pyrimidinyl optionally substituted with one or more lower alkyls;
 (4-12) piperidyl optionally substituted with one or more lower alkyls;
 (4-13) furyl;
 (4-14) carboxy;
 (4-15) lower alkoxycarbonyl;
 (4-16) amino optionally substituted with one or more substituents selected from the group consisting of lower alkyl, lower alkanoyl and lower alkylsulfonyl;
 (4-17) lower alkylthio;
 (4-18) triazolyl;
 (4-19) imidazolyl;
 (4-20) pyrrolidinyl optionally substituted with one or more oxos;
 (4-21) lower alkylsulfonyl;
 (4-22) lower alkylenedioxy optionally substituted with one or more halogens;
 (4-23) nitro;
 (4-24) oxazolyl;
 (4-25) thiazolyl optionally substituted with one or more lower alkyls;
 (4-26) lower alkanoyl; and
 (4-27) morpholinyl;
(5) naphthyl;
(6) furyl optionally substituted with one or more substituents selected from the group consisting of lower alkyl optionally substituted with halogen, carboxy, sulfo, pyridyloxy, lower alkoxycarbonyl and phenyl;
(7) thienyl optionally substituted with one or more substituents selected from the group consisting of lower alkyl, lower alkylenedioxy, carboxy, halogen, pyridyl, lower alkoxy, lower alkoxycarbonyl, oxazolyl and furyl;
(8) imidazolyl optionally substituted with one or more substituents selected from the group consisting of phenyl, lower alkyl and halogen;
(9) pyrazolyl optionally substituted with one or more substituents selected from the group consisting of lower alkyl optionally substituted with halogen or lower alkoxy; cyclo lower alkyl; halogen; phenyl optionally substituted with lower alkoxy; furyl and thienyl;
(10) oxazolyl optionally substituted with one or more substituents selected from the group consisting of lower alkyl and phenyl;
(11) isoxazolyl optionally substituted with one or more substituents selected from the group consisting of phenyl, lower alkyl, thienyl and furyl;
(12) thiazolyl optionally substituted with one or more substituents selected from the group consisting of lower alkyl optionally substituted with halogen or lower alkoxy; phenyl; phenoxy and lower alkanoylamino;
(13) pyrrolyl optionally substituted with one or more substituents selected from the group consisting of lower alkyl and lower alkoxycarbonyl;
(14) triazolyl optionally substituted with one or more lower alkyls;
(15) pyridyl optionally substituted with one or more substituents selected from the group consisting of the following (15-1) to (15-14):
 (15-1) halogen;
 (15-2) cyano;
 (15-3) amino optionally substituted with one or more substituents selected from the group consisting of lower alkanoyl and lower alkylsulfonyl;
 (15-4) lower alkyl optionally substituted with one or more substituents selected from the group consisting of halogen, lower alkoxy, lower alkanoyloxy, cyclo lower alkyl amino, lower alkyl amino, lower alkanoyl amino, hydroxyl and pyrrolidinyl optionally substituted with one or more hydroxyls;
 (15-5) oxo;
 (15-6) hydroxyl;
 (15-7) lower alkoxy optionally substituted with one or more phenyls;
 (15-8) pyrrolidinyl;
 (15-9) lower alkanoyl;
 (15-10) morpholinyl;
 (15-11) phenoxy;
 (15-12) pyrazolyl;
 (15-13) thienyl; and
 (15-14) N-oxide;
(16) pyrimidinyl optionally substituted with one or more substituents selected from the group consisting of lower alkyl and phenyl;
(17) pyridazinyl;
(18) pyrazinyl optionally substituted with one or more phenyl lower alkoxys;
(19) imidazo[2,1-b]thiazolyl optionally substituted with one or more halogens;
(20) thieno[2,3-b]pyrazinyl;
(21) 2,3-dihydroimidazo[2,1-b]thiazolyl optionally substituted with one or more phenyls;
(22) benzothiazolyl optionally substituted with one or more lower alkyls;
(23) indolyl optionally substituted with one or more substituents selected from the group consisting of lower alkyl, lower alkanoyl and halogen;
(24) imidazo[1,2-a]pyridyl or imidazo[1,5-a]pyridyl, each of which is optionally substituted with one or more lower alkyls;
(25) benzothienyl optionally substituted with one or more lower alkyls;
(26) benzimidazolyl optionally substituted with one or more lower alkyls;
(27) 2,3-dihydrobenzo[b]furyl;

(28) benzofuryl optionally substituted with one or more halogens;
(29) indazolyl optionally substituted with one or more lower alkyls;
(30) furo[2,3-c]pyridyl or 6,7-dihydrofuro[2,3-c]pyridyl, each of which is optionally substituted with one or more substituents selected from the group consisting of oxo and lower alkyl optionally substituted with lower alkoxy;
(31) furo[3,2-c]pyridyl or 4,5-dihydrofuro[3,2-c]pyridyl, each of which is optionally substituted with one or more substituents selected from the group consisting of oxo, lower alkyl optionally substituted with halogen or lower alkoxy, halogen, furyl, pyridyl and phenyl optionally substituted with one or more substituents selected from the group consisting of amino and lower alkoxy;
(32) thieno[2,3-c]pyridyl or 6,7-dihydrothieno[2,3-c]pyridyl, each of which is optionally substituted with one or more substituents selected from the group consisting of oxo group and lower alkyl;
(33) thieno[3,2-c]pyridyl or 4,5-dihydrothieno[3,2-c]pyridyl, each of which is optionally substituted with one or more substituents selected from the group consisting of oxo and lower alkyl;
(34) thieno[2,3-b]pyridyl;
(35) benzo[1,3]dioxolyl optionally substituted with one or more halogens;
(36) benzisoxazolyl;
(37) pyrazolo[2,3-a]pyridyl;
(38) indolizinyl;
(39) 2,3-dihydroindolyl optionally substituted with one or more substituents selected from the group consisting of oxo, lower alkyl and lower alkanoyl;
(40) isoquinolyl or 1,2-dihydroisoquinolyl, each of which is optionally substituted with one or more substituents selected from the group consisting of lower alkyl, halogen and oxo;
(41) 1,2,3,4-tetrahydroisoquinolyl optionally substituted with one or more oxos;
(42) quinolyl optionally substituted with one or more substituents selected from the group consisting of amino optionally substituted with one or two lower alkyls, lower alkoxy, lower alkyl and oxo;
(43) 1,2,3,4-tetrahydroquinolyl optionally substituted with one or more substituents selected from the group consisting of lower alkyl, pyridyl lower alkyl, aralkyl (e.g., phenyl lower alkyl), lower alkoxy and oxo;
(44) 1,2-dihydroquinolyl optionally substituted with one or more substituents selected from the group consisting of amino optionally substituted with one or two lower alkyls, lower alkoxy, lower alkyl and oxo;
(45) chromanyl optionally substituted with one or more lower alkyls;
(46) 5,6,7,8-tetrahydroisoquinolyl optionally substituted with one or more oxos;
(47) 3,4-dihydroisoquinolyl optionally substituted with one or more oxos;
(48) naphthyridinyl;
(49) 1,4-benzodioxanyl;
(50) cinnolinyl;
(51) quinoxalinyl;
(52) 2,3-dihydrobenz-1,4-oxazinyl optionally substituted with one or more substituents selected from the group consisting of lower alkyl and oxo;
(53) 2,3-dihydro-1H-benzo[d]imidazolyl optionally substituted with one or more substituents selected from the group consisting of lower alkyl and oxo; and
(54) piperidyl optionally substituted with one or more aryl carbonyls (e.g., phenyl carbonyl).

Examples of more preferable substituents represented by $R^6$ and $R^7$ include the following substituents (1), (4a), (6a), (7a), (8a), (9a), (10a), (11a), (12a), (15a), (16a), (17), (18), (23a), (24a), (24b), (26), (29), (30a), (30b), (31a), (31b), (32a), (32b), (33a), (33b), (35a), (40a), (40b), (42a), (43a), (44a), and (53):
(1) hydrogen;
(4a) phenyl optionally substituted with one or more substituents selected from the group consisting of the following (4-1), (4-2), (4a-4), (4a-5), (4-10), (4a-16), (4-18), (4-19), (4-23), (4-26) and (4-27):
(4-1) cyano;
(4-2) hydroxyl;
(4a-4) lower alkyl optionally substituted with one or more substituents selected from the group consisting of halogen, hydroxyl, 2-oxo-1,2,3,4-tetrahydroquinolyl, lower alkoxy, imidazolyl and morpholinyl;
(4a-5) lower alkoxy;
(4-10) pyrazolyl optionally substituted with one or more lower alkyls;
(4a-16) amino optionally substituted with one or more lower alkylsulfonyls;
(4-18) triazolyl
(4-19) imidazolyl;
(4-23) nitro;
(4-26) lower alkanoyl; and
(4-27) morpholinyl;
(6a) furyl optionally substituted with one or more lower alkyls optionally substituted with halogen;
(7a) thienyl optionally substituted with one or more lower alkyls;
(8a) imidazolyl optionally substituted with one or more lower alkyls;
(9a) pyrazolyl optionally substituted with one or more lower alkyls optionally substituted with lower alkoxy;
(10a) oxazolyl optionally substituted with one or more lower alkyls;
(11a) isoxazolyl optionally substituted with one or more lower alkyls;
(12a) thiazolyl optionally substituted with one or more lower alkyls optionally substituted with halogen;
(15a) pyridyl optionally substituted with one or more substituents selected from the group consisting of the following (15-1) to (15-5), (15a-7), (15-9), (15-11), (15-12) and (15-14):
(15-1) halogen;
(15-2) cyano;
(15-3) amino optionally substituted with one or more substituents selected from the group consisting of lower alkanoyl and lower alkylsulfonyl;
(15-4) lower alkyl optionally substituted with one or more substituents selected from the group consisting of halogen, lower alkoxy, lower alkanoyloxy, cyclo lower alkyl amino, lower alkyl amino, lower alkanoyl amino, hydroxyl and pyrrolidinyl optionally substituted with one or more hydroxyls;
(15-5) oxo;
(15a-7) lower alkoxy;
(15-9) lower alkanoyl;
(15-11) phenoxy;
(15-12) pyrazolyl; and
(15-14) N-oxide;

(16a) pyrimidinyl optionally substituted with one or more lower alkyls;
(17) pyridazinyl;
(18) pyrazinyl optionally substituted with one or more phenyl lower alkoxys;
(23a) indolyl optionally substituted with one or more lower alkyls;
(24a) imidazo[1,2-a]pyridyl;
(24b) imidazo[1,5-a]pyridyl optionally substituted with one or more lower alkyls;
(26) benzimidazolyl optionally substituted with one or more lower alkyls;
(29) indazolyl optionally substituted with one or more lower alkyls;
(30a) furo[2,3-c]pyridyl optionally substituted with one or more substituents selected from the group consisting of oxo and lower alkyl;
(30b) 6,7-dihydrofuro[2,3-c]pyridyl optionally substituted with one or more substituents selected from the group consisting of oxo and lower alkyl;
(31a) furo[3,2-c]pyridyl optionally substituted with one or more substituents selected from the group consisting of oxo and lower alkyl;
(31b) 4,5-dihydrofuro[3,2-c]pyridyl optionally substituted with one or more substituents selected from the group consisting of oxo and lower alkyl optionally substituted with halogen or lower alkoxy;
(32a) thieno[2,3-c]pyridyl optionally substituted with one or more substituents selected from the group consisting of oxo and lower alkyl;
(32b) 6,7-dihydrothieno[2,3-c]pyridyl optionally substituted with one or more substituents selected from the group consisting of oxo group and lower alkyl;
(33a) thieno[3,2-c]pyridyl optionally substituted with one or more substituents selected from the group consisting of oxo and lower alkyl;
(33b) 4,5-dihydrothieno[3,2-c]pyridyl optionally substituted with one or more substituents selected from the group consisting of oxo and lower alkyl;
(35a) benzo[1,3]dioxolyl;
(40a) isoquinolyl optionally substituted with one or more oxos;
(40b) 1,2-dihydroisoquinolyl optionally substituted with one or more substituents selected from the group consisting of oxo and lower alkyl;
(42a) quinolyl optionally substituted with one or more oxos;
(43a) 1,2,3,4-tetrahydroquinolyl optionally substituted with one or more substituents selected from the group consisting of aralkyl (e.g., phenyl lower alkyl), pyridyl lower alkyl and oxo;
(44a) 1,2-dihydroquinolyl optionally substituted with one or more oxos; and
(53) 2,3-dihydrobenzo[d]imidazolyl optionally substituted with one or more substituents selected from the group consisting of lower alkyl and oxo.

Preferred embodiments of the diazepine compound of Formula (1) are described below.

$R^1$, $R^2$, $R^3$ and $R^4$ are each independently hydrogen, lower alkyl, cyclo lower alkyl or lower alkoxy lower alkyl, and preferably hydrogen, $C_{1-6}$ alkyl (e.g., methyl, ethyl, n-propyl, iso-propyl, n-butyl, iso-butyl and sec-butyl), $C_{1-6}$ cyclo alkyl (e.g., cyclopropyl, cyclopropylmethyl, cyclopentyl and cyclohexyl), or $C_{1-6}$ alkoxy $C_{1-6}$ alkyl (e.g., 2-methoxyethyl and 2-ethoxyethyl).

Both $Y^1$ and $Y^2$ are —C=.

$A^1$ is lower alkylene, and preferably $C_{1-6}$ alkylene such as methylene, ethylene, trimethylene, or tetramethylene. $X_A$ and $X_B$ are each independently lower alkylene, which is preferably $C_{1-6}$ alkylene such as methylene, ethylene, trimethylene, or tetramethylene; a bond; —CO—; or —SO$_2$—.

$R^6$ and $R^7$ are each independently a group selected from (1), (4a), (6a), (7a), (8a), (9a), (10a), (11a), (12a), (15a), (16a), (17), (18), (23a), (24a), (24b), (26), (29), (30b), (31b), (32b), (33b), (35a), (40b), (42a), (43a), (44a), and (53):

Examples of $X_A$ and $X_B$ include a bond, lower alkylene, lower alkenylene, —CO—, —SO$_2$—, -lower alkylene-SO$_2$—, -lower alkylene-CO—, -lower alkenylene-CO—, -lower alkylene-CO—N(lower alkyl)-lower alkylene-, —N(lower alkyl)-lower alkylene-, —CO—N(lower alkyl)-lower alkylene-, —O-lower alkylene-, —N(phenyl lower alkyl)-lower alkylene-, —CO-lower alkylene-CO—, —CO—NH-lower alkylene-, -lower alkylene-N(lower alkyl)-lower alkylene-, -lower alkylene-N(lower alkyl)-lower alkylene-O—, -lower alkylene-NH-lower alkylene-, -lower alkylene-SO$_2$—NH-lower alkylene-, —N(lower alkyl)-CO-lower alkylene-, —N(lower alkyl)-lower alkylene-CO—, —N(lower alkyl)-lower alkylene-N(lower alkyl)-lower alkylene-, —N(phenyl)-lower alkylene-CO—, —N(phenyl)-lower alkylene-CO—, —NH—CO—, —NH—CO-lower alkylene-, —NH-lower alkylene-, —O-lower alkylene-CO—N(lower alkyl)-lower alkylene-, —O-lower alkylene-CO—, —NH-lower alkylene-CO—N(lower alkyl)-lower alkylene-, —S-lower alkylene-CO—N(lower alkyl)-lower alkylene-, —SO$_2$—N(lower alkyl)-lower alkylene-, —SO$_2$—NH-lower alkylene-, -lower alkenylene-CO—N(lower alkyl)-lower alkylene-, lower alkylene-N(phenyl lower alkyl)-lower alkylene-, —N(phenyl lower alkyl)-lower alkylene-, —N(phenyl)-lower alkylene-CO—N(lower alkyl)-lower alkylene-, and —CO-lower alkylene-O—CO-lower alkylene-O—.

Preferred examples of $X_A$ and $X_B$ include a bond, lower alkylene, lower alkenylene, —CO—, —SO$_2$—, -lower alkylene-SO$_2$—, -lower alkylene-CO—, -lower alkenylene-CO—, -lower alkylene-CO—N(lower alkyl)-lower alkylene-, —N(lower alkyl)-lower alkylene-, —CO—N(lower alkyl)-lower alkylene-, and —O-lower alkylene-.

Either of the two bonds in $X_A$ may be bonded to $R^1$ or N, and either of the two bonds in $X_B$ may be bonded to $R^2$ or N.

The ring formed when $R^6$ and $R^7$ are linked together with the neighboring group —$X_A$—N—$X_B$— is a nitrogen-containing heterocyclic group optionally having one or more substituents. Examples of the nitrogen-containing heterocyclic group include the above-mentioned heterocyclic groups (a) to (c), (f) to (j), and (m) to (n). Examples of substituents of the nitrogen-containing heterocyclic group optionally having one or more substituents include the above-mentioned substituents (h1) to (h20).

The diazepine compound of the present invention represented by Formula (1) or its salt can be readily produced by persons skilled in the art using technical knowledge, based on the Examples and Reference Examples of the present specification. For example, the diazepine compound or its salt can be produced according to the processes shown in the following reaction formulae.

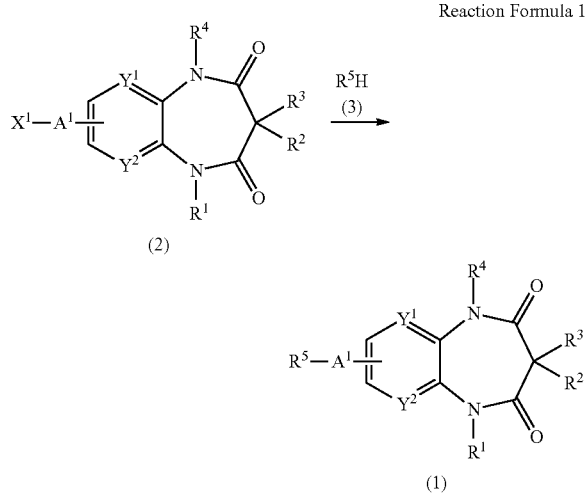

Reaction Formula 1 wherein $R^1$, $R^2$, $R^3$, $R^4$, $R^5$, $A^1$, $Y^1$ and $Y^2$ are the same as above, and $X^1$ is a leaving group.

The reaction of the compound of Formula (2) with the compound of Formula (3) can be performed in a general inert solvent or without using any solvent, in the presence or absence of a basic compound and/or catalyst.

Examples of the leaving groups represented by $X^1$ include halogen atoms (e.g., chlorine, bromine, iodine, and like atoms), lower alkane sulfonyloxy (e.g., methanesulfonyloxy), halo substituted lower alkane sulfonyloxy (e.g., trifluoromethanesulfonyloxy), arylene sulfonyloxy (e.g., p-toluenesulfonyloxy, benzenesulfonyloxy), etc.

Examples of inert solvents include water; ethers such as dioxane, tetrahydrofuran, diethyl ether, diethylene glycol dimethyl ether, and ethylene glycol dimethyl ether; aromatic hydrocarbons such as benzene, toluene, and xylene; halogenated hydrocarbons such as dichloromethane, dichloroethane, chloroform, and carbon tetrachloride; lower ($C_{1-6}$) alcohols such as methanol, ethanol, and isopropanol; ketones such as acetone and methyl ethyl ketone; polar solvents such as dimethylformamide (DMF), dimethyl sulfoxide (DMSO), hexamethylphosphoric triamide, and acetonitrile; and mixtures thereof.

A wide variety of known basic compounds can be used as the basic compound. Examples of such basic compounds include inorganic bases, for example, alkali metal hydroxides such as sodium hydroxide, potassium hydroxide, cesium hydroxide, and lithium hydroxide; alkali metal carbonates such as sodium carbonate, potassium carbonate, cesium carbonate, lithium carbonate, lithium hydrogencarbonate, sodium hydrogencarbonate, and potassium hydrogencarbonate; alkali metals such as sodium and potassium; sodium amide; sodium hydride; and potassium hydride; and organic bases, for example, alkali metal alcoholates such as sodium methoxide, sodium ethoxide, potassium methoxide, and potassium ethoxide; triethylamine; tripropylamine; pyridine; quinoline; 1,5-diazabicyclo[4.3.0]non-5-ene (DBN); 1,8-diazabicyclo[5.4.0]undec-7-ene (DBU); and 1,4-diazabicyclo[2.2.2]octane (DABCO). These basic compounds can be used singly or in a combination of two or more.

Examples of the catalyst include palladium compounds such as palladium acetate, bis(tributyltin)/bis(dibenzylideneacetone)palladium, copper iodide/2,2'-bipyridyl, bis(dibenzylideneacetone)palladium, copper iodide/bis(triphenylphosphine)palladium dichloride, tris(dibenzylideneacetone)dipalladium, R-tris(dibenzylideneacetone)-dipalladium, S-tris(dibenzylideneacetone)dipalladium, palladium(II) acetate, [1,1'-bis(diphenylphosphino)-ferrocene] dichloropalladium (II), and tetrakis(triphenylphosphine)palladium.

Additives (ligands etc.) can be used together with the catalyst. Examples of the additive include compounds such as R-2,2'-bis diphenylphosphino)-1,1'-binaphthyl (R-BINAP), S-2,2'-bis(diphenylphosphino)-1,1'-binaphthyl (S-BINAP), RAC-2,2'-bis(diphenylphosphino)-1,1'-binaphthyl (RAC-BINAP), and 2,2-bis(diphenylimidazolidinyliden), xanthene compounds such as 4,5-bis(diphenylphosphino)-9,9-dimethylxanthene, and borates such as tri-tert-butylphosphine tetrafluoroborate, and a mixture thereof.

The above reaction may be performed by adding to the reaction system, as required, an alkali metal iodide serving as a reaction accelerator, such as potassium iodide or sodium iodide.

The compound of Formula (3) is typically used in an amount of at least 0.5 moles, and preferably about 0.5 to about 10 moles, per mole of the compound of Formula (2).

The amount of basic compound is typically 0.5 to 10 moles, and preferably 0.5 to 6 moles, per mole of the compound of Formula (2).

The catalyst is appropriately used in a typical catalytic amount, preferably 0.0001 to 1 moles, and more preferably 0.001 to 0.5 moles, per mole of the compound (2).

The reaction is typically performed at a temperature of 0 to 250° C., and preferably 0 to 200° C., and is typically completed in about 1 to about 80 hours.

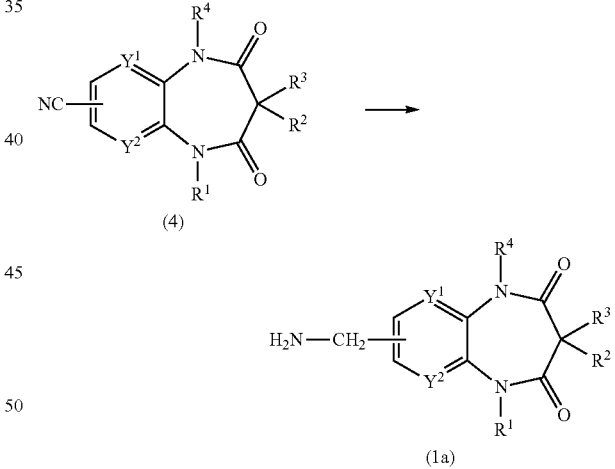

Reaction Formula 2 wherein $R^1$, $R^2$, $R^3$, $R^4$, $Y^1$ and $Y^2$ are the same as above.

The reaction converting the compound of Formula (4) to the compound of Formula (1a) can be performed by catalytic reduction of the compound of Formula (4) in a suitable solvent, in the presence of a catalytic hydrogenation reducing agent.

The solvent is not limited as long as it does not adversely affect the reduction reaction. Examples of such solvents include carboxylic acids such as formic acid and acetic acid; ethers such as dioxane, tetrahydrofuran, diethyl ether, diethylene glycol dimethyl ether, and ethylene glycol dimethyl ether; and lower (e.g., $C_{1-6}$) alcohols such as methanol, ethanol, and isopropanol.

Examples of catalytic hydrogenation reducing agents include palladium black, palladium carbon, platinum oxide, platinum black, and Raney nickel.

The amount of catalytic hydrogenation reducing agent is typically 0.1 to 40 wt %, and preferably 1 to 20 wt %, based on the compound of Formula (4).

The reaction can be typically performed in a hydrogen atmosphere at atmospheric pressure to about 20 atm, and preferably atmospheric pressure to 10 atm; or in the presence of a hydrogen donor such as formic acid, ammonium formate, cyclohexene, or hydrazine hydrate. The reaction temperature may typically be about −30 to about 100° C., and preferably about 0 to about 60° C.

In the reaction, a carboxylic azide is produced from the carboxylic compound of Formula (5) and an azide compound, and the carboxylic azide undergoes subsequent Curtius rearrangement to produce an isocyanate. The isocyanate reacts with a lower ($C_{1-6}$) alcohol ($R^8OH$) to produce a urethane compound of Formula (6).

Next, the reaction converting the compound of Formula (6) to the compound of Formula (1b) can be performed by solvolysis in a suitable solvent, in the presence of an acid or basic compound.

Examples of usable solvents include water; lower ($C_{1-6}$) alcohols such as methanol, ethanol, isopropanol, and tert-butanol; ketones such as acetone and methyl ethyl ketone;

Reaction Formula 3

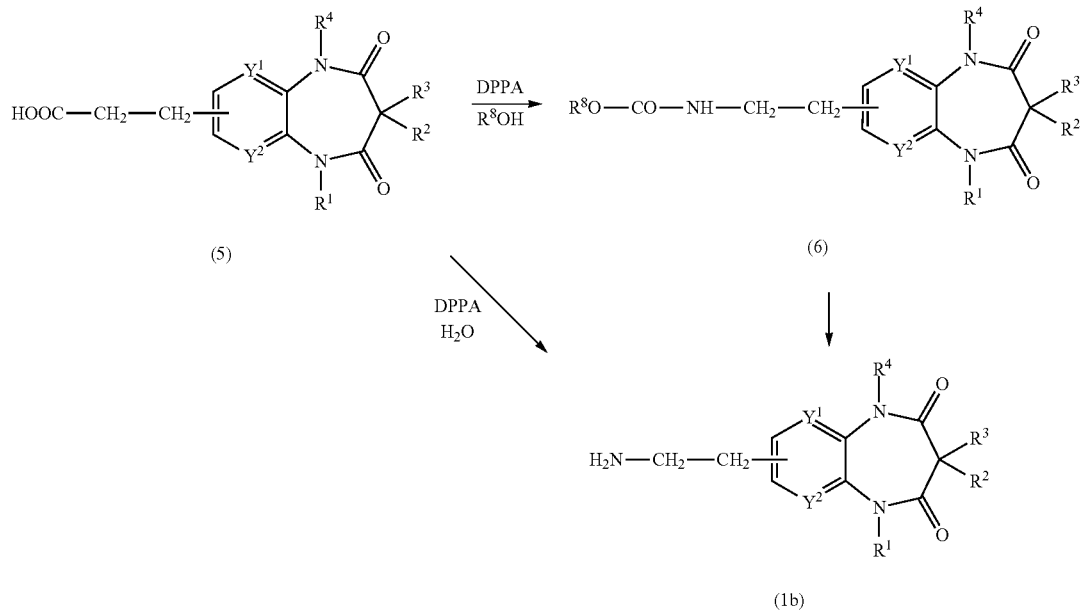

wherein $R^1$, $R^2$, $R^3$, $R^4$, $Y^1$ and $Y^2$ are the same as above; and $R^8$ is lower alkyl.

The reaction converting the compound of Formula (5) to the compound of Formula (6) can be performed in a general inert solvent or without using any solvent, in the presence of an azide compound, a basic compound, and a lower ($C_{1-6}$) alcohol ($R^8OH$).

Examples of "lower alkyl" represented by $R^8$ include linear or branched alkyl groups with 1 to 6 carbon atoms, such as methyl, ethyl, n-propyl, isopropyl, and tert-butyl, with tert-butyl being preferred.

Examples of inert solvents include ethers such as dioxane, tetrahydrofuran, diethylether, diethylene glycol dimethyl ether, and ethylene glycol dimethyl ether; aromatic hydrocarbons such as benzene, toluene, and xylene; halogenated hydrocarbons such as dichloromethane, dichloroethane, chloroform, and carbon tetrachloride; and mixtures thereof.

Examples of azide compounds include sodium azide, lithium azide, and diphenylphosphoryl azide (DPPA).

Examples of usable basic compounds include organic bases such as triethylamine; tripropylamine; diisopropylethylamine; pyridine; quinoline; 1,5-diazabicyclo[4.3.0]non-5-ene (DBN); 1,8-diazabicyclo[5.4.0]undec-7-ene (DBU); and 1,4-diazabicyclo[2.2.2]octane (DABCO).

The reaction temperature is not limited, and the reaction is usually carried out under conventional conditions.

ethers such as diethylether, dioxane, tetrahydrofuran, monoglyme, and diglyme; aliphatic acids such as acetic acid and formic acid; esters such as methyl acetate and ethyl acetate; halogenated hydrocarbons such as chloroform, dichloromethane, dichloroethane, and carbon tetrachloride; dimethyl sulfoxide, N,N-dimethylformamide, hexamethylphosphoric triamide, and mixtures thereof.

Examples of acids include mineral acids such as hydrochloric acid, sulfuric acid, and hydrobromic acid; and organic acids such as formic acid, acetic acid, thioglycolic acid, trifluoroacetic acid, and sulfonic acids such as p-toluenesulfonic acid. These acids may be used singly or in a combination of two or more.

Examples of basic compounds include carbonates such as sodium carbonate, potassium carbonate, sodium hydrogencarbonate, and potassium hydrogencarbonate; and metal hydroxides such as sodium hydroxide, potassium hydroxide, calcium hydroxide, and lithium hydroxide. These basic compounds can be used singly or in a combination of two or more.

The amount of acid or basic compound is typically at least 1 mole, and preferably about 1 to about 10 moles, per mole of the compound of Formula (6).

The solvolysis reaction (particularly the hydrolysis) advantageously proceeds typically at about 0 to about 200° C., and preferably at about 0 to about 150° C., and is typically completed in about 10 minutes to about 80 hours.

Particularly when $R^8$ is tert-butyl, the solvolysis can be easily accomplished using the above-mentioned acids (particularly hydrochloric acid and the like) to produce the compound of Formula (1b).

Alternatively, the compound of Formula (5) can be directly converted to the compound of Formula (1b). This reaction can be performed by reacting the compound (5) with an azide compound in a general inert solvent or without using any solvent, in the presence of a basic compound, followed by treating the product with water. In this reaction, an isocyanate is produced from the above-mentioned carboxylic compound of Formula (5) and azide compound, and the isocyanate is hydrolyzed to produce the amine compound of Formula (1b).

Reaction Formula 4

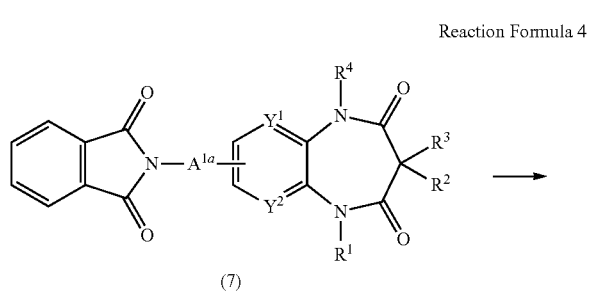

(7)

(1c)

wherein $R^1$, $R^2$, $R^3$, $R^4$, $Y^1$ and $Y^2$ are the same as above; and $A^{1a}$ is lower alkylene with 3 or more carbon atoms.

Examples of "lower alkylene with 3 or more carbon atoms" represented by $A^{1a}$ include alkylene groups with 3 to 6 carbon atoms, such as trimethylene, tetramethylene, pentamethylene, and hexamethylene.

The reaction converting the compound of Formula (7) to the compound of Formula (1c) can be performed by reacting the compound (7) with hydrazine in a suitable solvent, or by hydrolysis. Here, hydrazine hydrate may be used as the hydrazine.

Examples of solvents used in reacting the hydrazine include water; halogenated hydrocarbons such as chloroform, dichloromethane, and dichloroethane; aromatic hydrocarbons such as benzene, toluene, and xylene; ethers such as diethyl ether, diisopropyl ether, tetrahydrofuran, and dimethoxyethane; esters such as methyl acetate and ethyl acetate; aprotic polar solvents such as N,N-dimethylformamide, dimethyl sulfoxide, and hexamethylphosphoric triamide; alcohols such as methanol, ethanol, propanol, butanol, 3-methoxy-1-butanol, ethyl cellosolve, and methyl cellosolve; acetonitrile; pyridine; and mixtures thereof.

The amount of hydrazine is typically at least about 1 mole, and preferably about 1 to about 5 moles, per mole of the compound of Formula (7).

The reaction is performed typically at about 0 to about 120° C., and preferably at about 0 to about 100° C., and is typically completed in about 0.5 to about 5 hours.

Reaction Formula 5

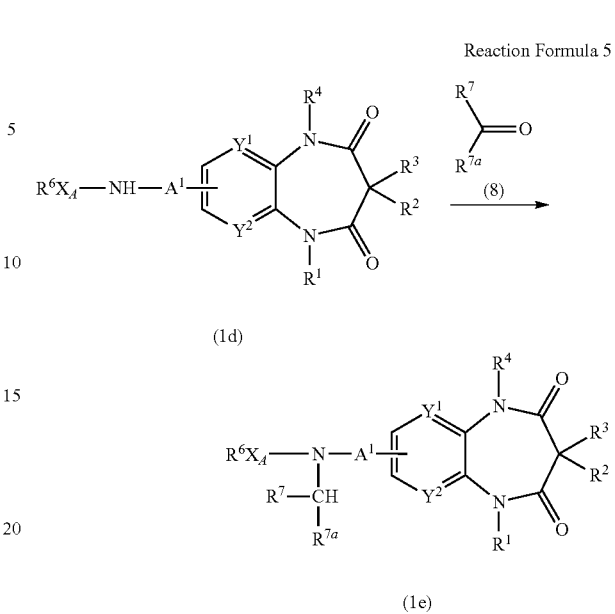

(1d)

(1e)

wherein $R^1$, $R^2$, $R^3$, $R^4$, $R^6$, $R^7$, $X_A$, $A^1$, $Y^1$ and $Y^2$ are the same as above; and $R^{7a}$ is hydrogen or lower alkyl.

Examples of "lower alkyl" represented by $R^{7a}$ include linear or branched alkyl groups with 1 to 6 carbon atoms, such as methyl, ethyl, n-propyl, isopropyl, n-butyl, isobutyl, tert-butyl, sec-butyl, n-pentyl, neopentyl, n-hexyl, isohexyl, and 3-methylpentyl.

The reaction between the compound of Formula (1d) and the compound of Formula (8) is performed, for example, in a suitable solvent or without using any solvent, in the presence of a reducing agent.

Examples of usable solvents include water; lower ($C_{1-6}$) alcohols such as methanol, ethanol, isopropanol, butanol, tert-butanol, and ethylene glycol; aliphatic acids such as formic acid, and acetic acid; ethers such as diethylether, tetrahydrofuran, dioxane, monoglyme, and diglyme; aromatic hydrocarbons such as benzene, toluene, and xylene; halogenated hydrocarbons such as dichloromethane, dichloroethane, chloroform, and carbon tetrachloride; acetonitrile; and mixtures thereof.

Examples of reducing agents include aliphatic acids such as formic acid; aliphatic acid alkali metal salts such as sodium formate; hydride reducing agents such as sodium borohydride, sodium cyanoborohydride, sodium triacetoxyborohydride, sodium trimethoxyborohydride, lithium aluminium hydride, and mixtures thereof, or mixtures of aliphatic acids or aliphatic acid alkali metal salts with hydride reducing agents; and catalytic hydrogenation reducing agents such as palladium black, palladium carbon, platinum oxide, platinum black, and Raney nickel.

When an aliphatic acid such as formic acid, or an aliphatic acid alkali metal salt such as sodium formate is used as a reducing agent, a suitable reaction temperature is typically about room temperature to about 200° C., and preferably about 50 to about 150° C. The reaction is typically completed in about 10 minutes to about 10 hours. Preferably, the aliphatic acid or aliphatic acid alkali metal salt is used in large excess relative to the compound of Formula (1d).

When a hydride reducing agent is used, a suitable reaction temperature is typically about −80 to about 100° C., and preferably about −80 to about 70° C. The reaction is typically completed in about 30 minutes to about 60 hours. The hydride reducing agent is typically used in an amount of about 1 to about 20 moles, and preferably about 1 to about 10 moles, per mole of the compound of Formula (1d). Particularly when lithium aluminium hydride is used as a hydride reducing agent, it is preferable to use as a solvent an ether such as diethyl ether, tetrahydrofuran, dioxane, monoglyme, or diglyme; or an aromatic hydrocarbon such as benzene, toluene, or xylene. To the reaction system may be added an amine such as trimethylamine, triethylamine, or N-ethyldiisopropylamine; or a molecular sieve such as molecular sieve 3A (MS-3A) or molecular sieve 4A (MS-4A).

When a catalytic hydrogenation reducing agent is used, the reaction is typically performed at about −30 to about 100° C., and preferably at about 0 to about 60° C., in a hydrogen atmosphere at typically about atmospheric pressure to about 20 atm, and preferably at about atmospheric pressure to about 10 atm, or in the presence of a hydrogen donor such as formic acid, ammonium formate, cyclohexene, or hydrazine hydrate. The reaction is typically completed in about 1 to about 12 hours. The catalytic hydrogenation reducing agent is typically used in an amount of about 0.1 to about 40 wt %, and preferably about 1 to about 20 wt %, based on the compound of Formula (1d).

In the reaction of the compound of Formula (1d) and the compound of Formula (8), the compound of Formula (8) is typically used in an amount of at least 1 mole, and preferably 1 to 5 moles, per mole of the compound of Formula (1d).

The compound of Formula (8) may also be a hydrated compound wherein a water molecule is attached to a carbonyl group.

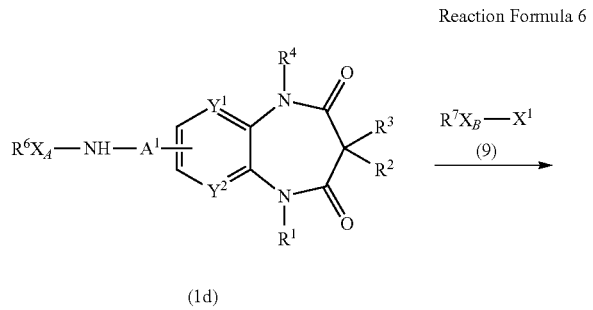

(1d)

(1e-1)

wherein $R^1$, $R^2$, $R^3$, $R^4$, $R^6$, $R^7$, $X_A$, $X_B$, $A^1$, $X^1$, $Y^1$ and $Y^2$ are the same as above.

The reaction of the compound of Formula (1d) with the compound of Formula (9) can be performed under the same reaction conditions as those for the reaction of the compound of Formula (2) with the compound of Formula (3) shown in Reaction Formula 1 above.

Alternatively, the reaction of the compound of Formula (1d) with the compound of Formula (9) can be performed by the known "Ullmann condensation" etc. The reaction can be preferably adopted especially when $X_B$ is a bond and $R^7$ is aryl or heterocyclic (especially unsaturated heterocyclic) group optionally substituted. For example, the reaction can be carried out in a solvent (e.g., toluene, tetrahydrofuran (THF), N,N-dimethylformamide (DMF), N-methylpyrrolidone (NMP) and dimethyl sulfoxide (DMSO)), in the presence of copper compound (e.g., copper oxides, copper halides such as copper iodide), a basic compound (e.g., sodium tert-butoxide, K3PO4 and Cs2CO3), and if necessary a phosphine (e.g., triphenylphosphine, xantphos, tri-tert-butylphosphine, 2,2'-bis(diphenylphosphino)-1,1'-binaphthyl(BINAP), tetrafluoroborate, N,N'-dimethylethylenediamine, and L-proline).

The reaction temperature is not limited, and the reaction is usually carried out at ambient temperature, under warming or under heating.

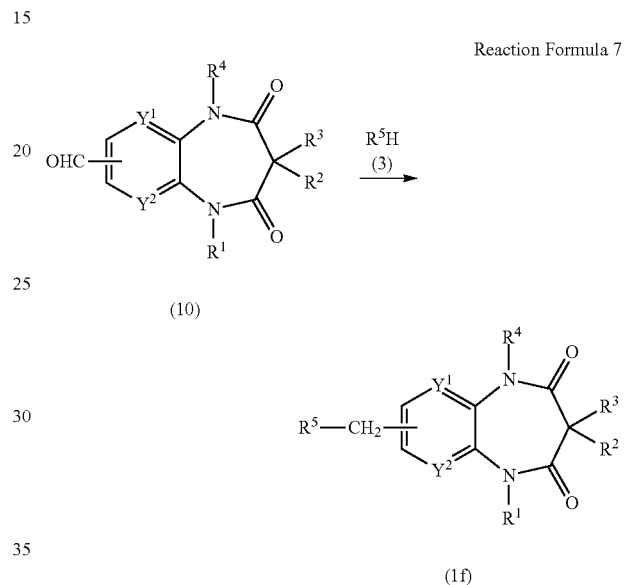

(10)

(1f)

wherein $R^1$, $R^2$, $R^3$, $R^4$, $R^5$, $Y^1$ and $Y^2$ are the same as above.

The reaction of the compound of Formula (10) with the compound of Formula (3) can be performed under the same reaction conditions as those for the reaction of the compound of Formula (1d) with the compound of Formula (8) shown in Reaction Formula 5 above.

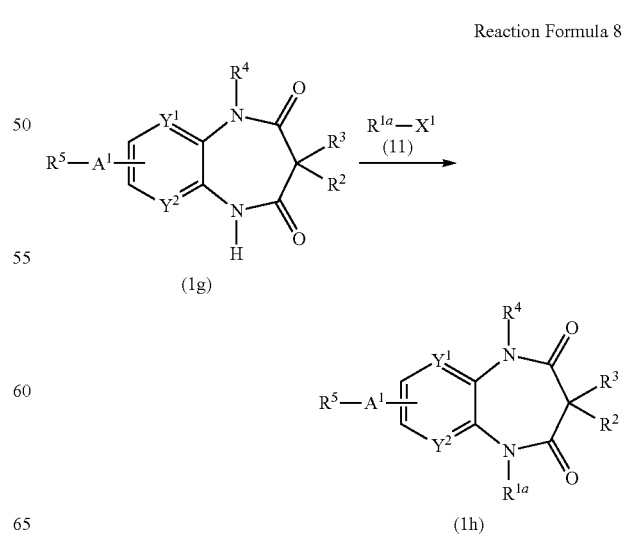

(1g)

(1h)

wherein $R^2$, $R^3$, $R^4$, $R^5$, $A^1$, $X^1$, $Y^1$ and $Y^2$ are the same as above; and $R^{1a}$ is lower alkyl.

Examples of "lower alkyl" represented by $R^{1a}$ include linear or branched alkyl groups with 1 to 6 carbon atoms, such as methyl, ethyl, n-propyl, isopropyl, n-butyl, isobutyl, and sec-butyl.

The reaction of the compound of Formula (1g) with the compound of Formula (11) can be performed under the same reaction conditions as those for the reaction of the compound of Formula (2) with the compound of Formula (3) shown in Reaction Formula 1 above.

In this reaction, when $R^4$ is hydrogen in the compound of Formula (1g), a compound may be obtained wherein the 1- and 5-positions of the benzodiazepine skeleton are simultaneously replaced by the group $R^{1a}$.

Reaction Formula 9

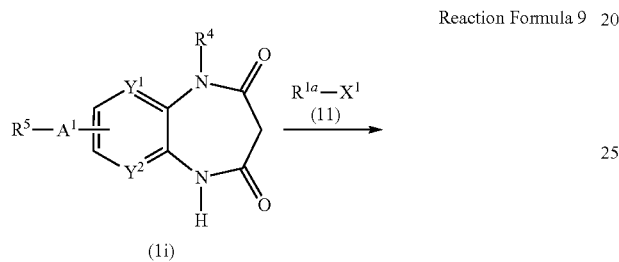

(1i)

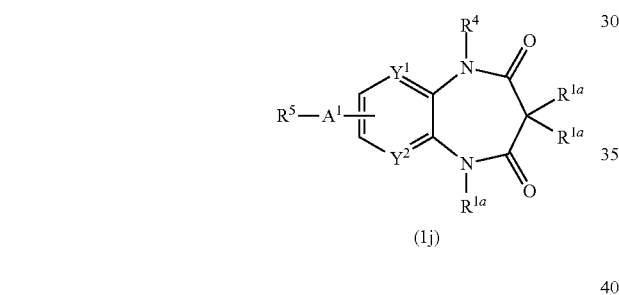

(1j)

wherein $R^{1a}$, $R^4$, $R^5$, $A^1$, $X^1$, $Y^1$ and $Y^2$ are the same as above.

The reaction of the compound of Formula (1i) with the compound of Formula (11) can be performed under the same reaction conditions as those for the reaction of the compound of Formula (2) with the compound of Formula (3) shown in Reaction Formula 1 above.

In this reaction, when $R^4$ is hydrogen in the compound of Formula (1i), a compound may be obtained wherein the 1-, 3-, and 5-positions of the benzodiazepine skeleton are simultaneously replaced by the group $R^{1a}$.

Reaction Formula 10

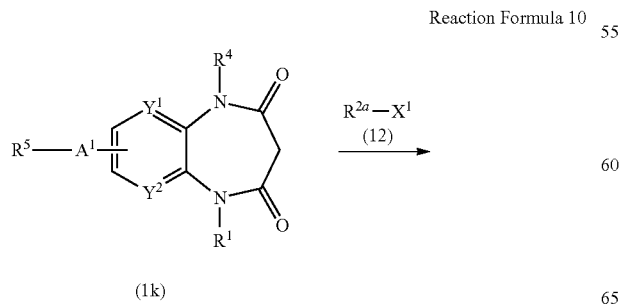

(1k)

-continued

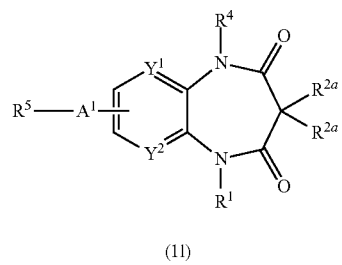

(11)

wherein $R^1$, $R^4$, $R^5$, $A^1$, $X^1$, $Y^1$ and $Y^2$ are the same as above; and $R^{2a}$ is lower alkyl.

Examples of "lower alkyl" represented by $R^{2a}$ include linear or branched alkyl groups with 1 to 6 carbon atoms, such as methyl, ethyl, n-propyl, isopropyl, n-butyl, isobutyl, and sec-butyl.

The reaction of the compound of Formula (1k) with the compound of Formula (11) can be performed under the same reaction conditions as those for the reaction of the compound of Formula (2) with the compound of Formula (3) shown in Reaction Formula 1 above.

In this reaction, when $R^1$ and/or $R^4$ is hydrogen in the compound of Formula (1k), a compound may be obtained wherein the 1-, 3-, and 5-positions of the benzodiazepine skeleton are simultaneously replaced by the group $R^{2a}$.

Reaction Formula 11

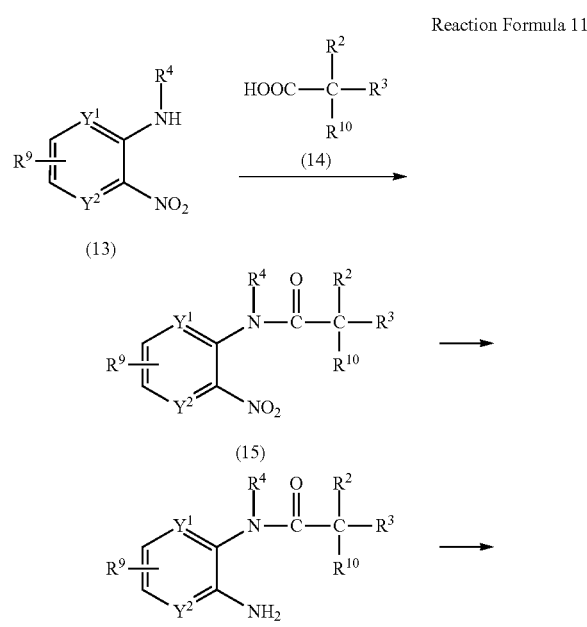

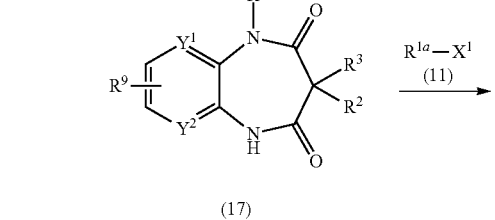

(17)

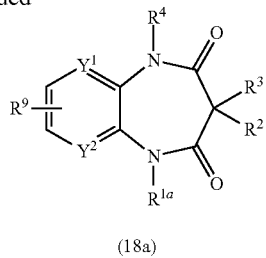

(18a)

wherein $R^2$, $R^3$, $R^4$, $R^{1a}$, $X^1$, $Y^1$ and $Y^2$ are the same as above; $R^9$ is lower alkoxy; and $R^{10}$ is lower alkoxycarbonyl.

Examples of "lower alkoxy" represented by $R^9$ include linear or branched alkoxy groups with 1 to 6 carbon atoms, such as methoxy, and ethoxy. Examples of "lower alkoxycarbonyl" represented by $R^{10}$ include ($C_{1-6}$ alkoxy) carbonyl groups, such as methoxycarbonyl, ethoxycarbonyl.

In the reaction of the compound of Formula (13) with the compound of Formula (14), the compound of Formula (13) is reacted with the carboxylic acid compound of Formula (14) through a general amide bond formation reaction. Conditions for known amide bond formation reactions can be easily employed in this amide formation reaction. For example, the following reaction methods can be employed: (i) a mixed acid anhydride method, in which Carboxylic Acid (14) is reacted with an alkyl halocarboxylate to form a mixed acid anhydride, which is then reacted with Amine (13); (ii) an active ester method, in which Carboxylic Acid (14) is converted to an activated ester such as a phenyl ester, p-nitrophenyl ester, N-hydroxysuccinimide ester, or 1-hydroxybenzotriazole ester, or to an activated amide with benzoxazoline-2-thione, and the activated ester or amide is reacted with Amine (13); (iii) a carbodiimide method, in which Carboxylic Acid (14) is subjected to a condensation reaction with Amine (13) in the presence of an activating agent such as dicyclohexylcarbodiimide, 1-(3-dimethylaminopropyl)-3-ethylcarbodiimide (WSC), or carbonyldiimidazole; and (iv) other methods, for example, a method in which Carboxylic Acid (14) is converted to a carboxylic anhydride using a dehydrating agent such as acetic anhydride, and the carboxylic anhydride is reacted with Amine (13), a method in which an ester of Carboxylic Acid (14) with a lower ($C_{1-6}$) alcohol is reacted with Amine (13) at a high pressure and a high temperature, and a method in which an acid halide of Carboxylic Acid (14), i.e., a carboxylic acid halide, is reacted with Amine (13).

Generally, the mixed acid anhydride method (i) is performed in a solvent, in the presence or absence of a basic compound. Any solvents used for conventional mixed acid anhydride methods are usable. Specific examples of usable solvents include halogenated hydrocarbons such as chloroform, dichloromethane, dichloroethane, and carbon tetrachloride; aromatic hydrocarbons such as benzene, toluene, and xylene; ethers such as diethyl ether, diisopropyl ether, tetrahydrofuran, and dimethoxyethane; esters such as methyl acetate, ethyl acetate, and isopropyl acetate; aprotic polar solvents such as N,N-dimethylformamide, dimethylsulfoxide, and hexamethylphosphoric triamide; and mixtures thereof.

Examples of usable basic compounds include organic bases such as triethylamine, trimethylamine, pyridine, dimethylaniline, N-ethyldiisopropylamine, dimethylaminopyridine, N-methylmorpholine, 1,5-diazabicyclo[4.3.0]non-5-ene (DBN), 1,8-diazabicyclo[5.4.0]undec-7-ene (DBU) and 1,4-diazabicyclo[2.2.2]octane (DABCO); inorganic bases, for example, carbonates such as sodium carbonate, potassium carbonate, sodium hydrogencarbonate, and potassium hydrogencarbonate; metal hydroxides such as sodium hydroxide, potassium hydroxide, and calcium hydroxide; potassium hydride; sodium hydride; potassium; sodium; sodium amide; and metal alcoholates such as sodium methylate and sodium ethylate.

Examples of alkyl halocarboxylates usable in the mixed acid anhydride method include methyl chloroformate, methyl bromoformate, ethyl chloroformate, ethyl bromoformate, and isobutyl chloroformate. In this method, Carboxylic Acid (14), an alkyl halocarboxylate, and Amine (13) are preferably used in equimolar amounts, but each of the alkyl halocarboxylate and Carboxylic Acid (14) can also be used in an amount of about 1 to about 1.5 moles per mole of Amine (13).

The reaction is typically performed at about −20 to about 150° C., and preferably at about 10 to about 50° C., typically for about 5 minutes to about 30 hours, and preferably for about 5 minutes to about 25 hours.

Method (iii), in which a condensation reaction is performed in the presence of an activating agent, can be performed in a suitable solvent in the presence or absence of a basic compound. Solvents and basic compounds usable in this method include those mentioned hereinafter as solvents and basic compounds usable in the method in which a carboxylic acid halide is reacted with Amine (13) mentioned above as one of the other methods (iv). A suitable amount of activating agent is typically at least 1 mole, and preferably 1 to 5 moles per mole of Compound (13). When WSC is used as an activating agent, the addition of 1-hydroxybenzotriazol to the reaction system allows the reaction to proceed advantageously. The reaction is typically performed at about −20 to about 180° C., and preferably at about 0 to about 150° C., and is typically completed in about 5 minutes to about 90 hours.

When the method in which a carboxylic acid halide is reacted with Amine (13), mentioned above as one of the other methods (iv), is employed, the reaction is performed in the presence of a basic compound in a suitable solvent. Examples of usable basic compounds include a wide variety of known basic compounds, such as those for use in the Schotten-Baumann reaction described above. In addition to those usable in the mixed acid anhydride method, usable solvents include alcohols such as methanol, ethanol, isopropanol, propanol, butanol, 3-methoxy-1-butanol, ethyl cellosolve, and methyl cellosolve; acetonitrile; pyridine; acetone; and water. The ratio of the carboxylic acid halide to Amine (13) is not limited, and can be suitably selected from a wide range. It is typically suitable to use, for example, at least about 1 mole, and preferably about 1 to about 5 moles of the carboxylic acid halide per mole of Amine (13). The reaction is typically performed at about −20 to about 180° C., and preferably at about 0 to about 150° C., and is typically completed in about 5 minutes to about 30 hours.

The amide bond formation reaction shown in Reaction Formula 11 can also be performed by reacting Carboxylic Acid (14) with Amine (13) in the presence of a phosphorus compound serving as a condensing agent, such as triphenylphosphine, diphenylphosphinyl chloride, phenyl-N-phenylphosphoramide chloridate, diethyl chlorophosphate, diethyl cyanophosphate, diphenylphosphoric azide, bis(2-oxo-3-oxazolidinyl)phosphinic chloride, or the like.

The reaction is performed in the presence of a solvent and a basic compound usable for the method in which a carboxylic acid halide is reacted with Amine (13), typically at about −20 to about 150° C., and preferably at about 0 to about 100°

C., and is typically completed in about 5 minutes to about 30 hours. It is suitable to use each of the condensing agent and Carboxylic Acid (14) in amounts of at least about 1 mole, and preferably about 1 to about 2 moles, per mole of Amine (13).

The reaction converting the compound of Formula (15) to the compound of Formula (16) can be performed by, for example, [1] reducing the compound of Formula (15) in a suitable solvent using a catalytic hydrogenation reducing agent, or [2] reducing the compound of Formula (15) in a suitable inert solvent using a reducing agent such as a mixture of an acid with a metal or metal salt, a mixture of a metal or metal salt with an alkali metal hydroxide, sulfide, or ammonium salt.

When Method [1] in which a catalytic hydrogenation reducing agent is used, examples of usable solvents are water; acetic acid; alcohols such as methanol, ethanol and isopropanol; hydrocarbons such as n-hexane and cyclohexane; ethers such as dioxane, tetrahydrofuran, diethyl ether and diethylene glycol dimethyl ether; esters such as ethyl acetate and methyl acetate; aprotic polar solvents such as N,N-dimethylformamide; and mixtures thereof. Examples of usable catalytic hydrogenation reducing agents include palladium, palladium black, palladium carbon, platinum carbon, platinum, platinum black, platinum oxide, copper chromite, and Raney nickel. The reducing agent is typically used in an amount of about 0.02 times to about equal to the weight of the compound of Formula (15). The reaction temperature is typically about −20 to about 150° C., and preferably about 0 to about 100° C. The hydrogen pressure is typically about 1 to 10 atm. The reaction is typically completed in about 0.5 to about 100 hours. An acid such as hydrochloric acid may be added to the reaction.

When Method [2] above is used, a mixture of iron, zinc, tin, or tin (II) chloride, with a mineral acid such as hydrochloric acid or sulfuric acid; or a mixture of iron, iron (II) sulfate, zinc, or tin, with an alkali metal hydroxide such as sodium hydroxide, a sulfide such as ammonium sulfide, aqueous ammonia solution, or an ammonium salt such as ammonium chloride, can be used as a reducing agent. Examples of inert solvents are water; acetic acid; alcohols such as methanol and ethanol; ethers such as dioxane; and mixtures thereof. Conditions for the reduction reaction can be suitably selected according to the reducing agent to be used. For example, when a mixture of tin (II) chloride and hydrochloric acid is used as a reducing agent, the reaction is advantageously performed at about 0 to about 150° C. for about 0.5 to about 10 hours. A reducing agent is used in an amount of at least 1 mole, and preferably about 1 to 5 moles, per mole of the compound of Formula (15).

The reaction converting the compound of Formula (16) to the compound of Formula (17) is performed under the same reaction conditions as those for the reaction of the compound of Formula (13) with the compound of Formula (14).

The reaction of the compound of Formula (17) with the compound of Formula (11) is performed under the same reaction conditions as those for the reaction of the compound of Formula (1g) with the compound of Formula (11) in Reaction Formula 8.

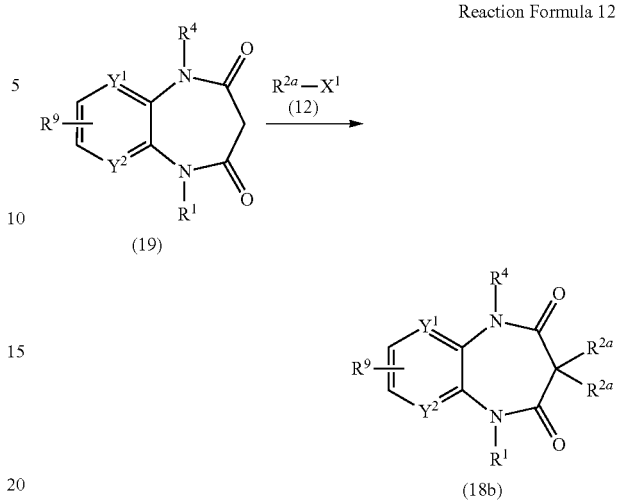

Reaction Formula 12 wherein $R^1$, $R^{2a}$, $R^4$, $R^9$, $X^1$, $Y^1$ and $Y^2$ are the same as above.

The reaction of the compound of Formula (19) with the compound of Formula (12) can be performed under the same reaction conditions as those for the reaction of the compound of Formula (2) with the compound of Formula (3) shown in Reaction Formula 1 above.

When $R^1$ and/or $R^4$ is hydrogen in the reaction of the compound of Formula (19) with the compound of Formula (12), the hydrogen atom may be replaced with $R^{2a}$.

The compound of Formula (18) can also be produced according to the process shown in the following Reaction Formula 13.

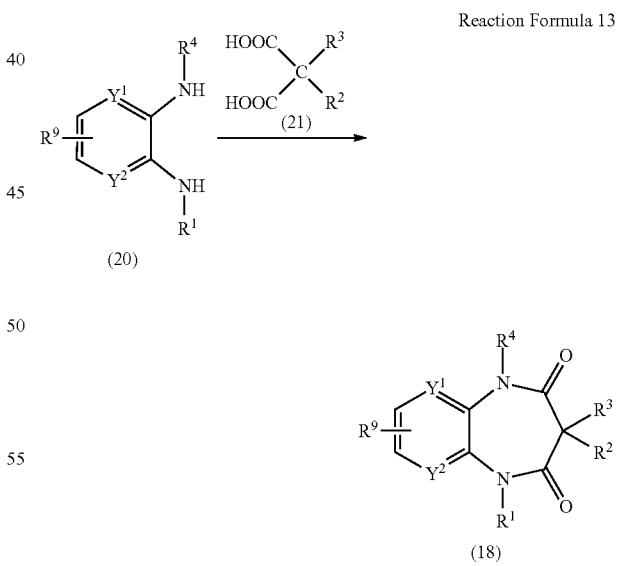

Reaction Formula 13 wherein $R^1$, $R^2$, $R^3$, $R^4$, $R^9$, $Y^1$ and $Y^2$ are the same as above.

The reaction of the compound of Formula (20) with the compound of Formula (21) can be performed under the same reaction conditions as those for the reaction of the compound of Formula (13) with the compound of Formula (14) shown in Reaction Formula 11 above.

Reaction Formula 14

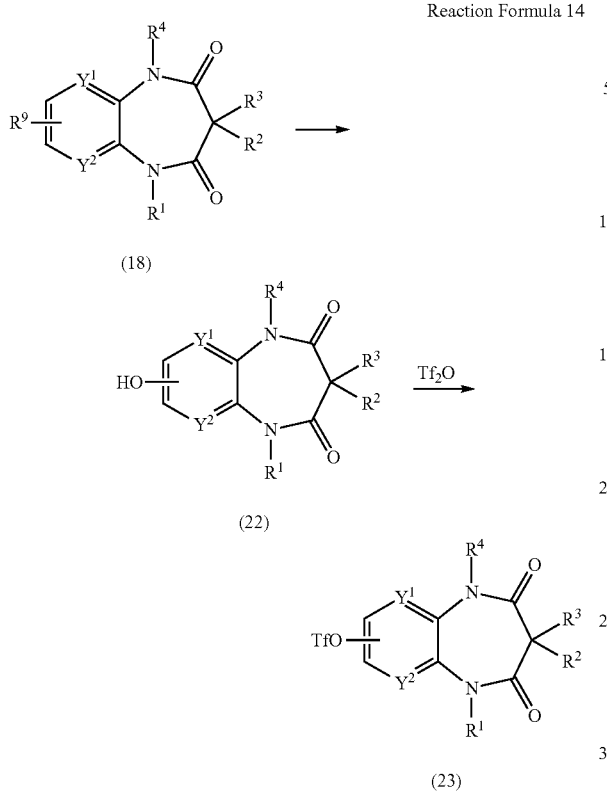

(18)
(22)
(23)

Reaction Formula 15

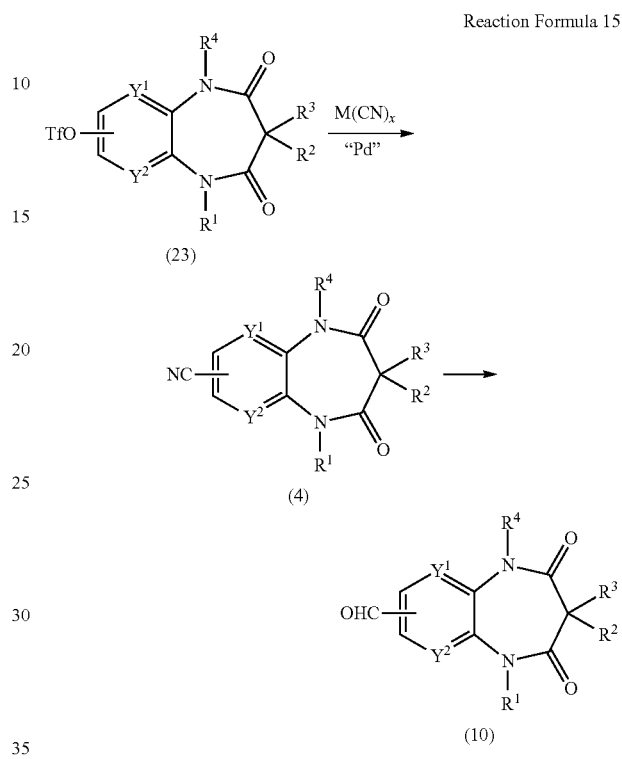

(23)
(4)
(10)

wherein $R^1$, $R^2$, $R^3$, $R^4$, $R^9$, $Y^1$ and $Y^2$ are the same as above; and Tf is trifluoromethanesulfonyl ($CF_3SO_2$—).

The reaction converting the compound of Formula (18) to the compound of Formula (22) can be performed in a suitable solvent in the presence of an acid.

Examples of solvents include water; lower ($C_{1-6}$) alcohols such as methanol, ethanol, and isopropanol; ethers such as dioxane, tetrahydrofuran, and diethylether; halogenated hydrocarbons such as dichloromethane, chloroform, and carbon tetrachloride; polar solvents such as acetonitrile; and mixtures thereof. Examples of acids include mineral acids such as hydrochloric acid, sulfuric acid, and hydrobromic acid; aliphatic acids such as formic acid and acetic acid; sulfonic acids such as p-toluenesulfonic acid; Lewis acids such as boron fluoride, aluminium chloride, and boron tribromide; iodides such as sodium iodide and potassium iodide; and mixtures of these iodides and Lewis acids.

The reaction is performed typically at about 0 to about 200° C., and preferably at about 0 to about 150° C., and is typically completed in about 0.5 to about 25 hours. The amount of acid is typically about 1 to about 10 moles, and preferably about 1 to about 2 moles, per mole of the compound of Formula (18).

The reaction converting the compound of Formula (22) to the compound of Formula (23) is performed by reacting the compound of Formula (22) with trifluoromethanesulfonic anhydride in a suitable solvent, in the presence or absence of a basic compound.

Examples of solvents include ethers such as dioxane, tetrahydrofuran, and diethylether; halogenated hydrocarbons such as dichloromethane, chloroform, and carbon tetrachloride; polar solvents such as acetonitrile; and mixtures thereof. Examples of basic compounds include organic bases such as triethylamine, trimethylamine, pyridine, dimethylaniline, N-ethyldiisopropylamine, dimethylaminopyridine, N-methylmorpholine, 1,5-diazabicyclo[4.3.0]non-5-ene (DBN), 1,8-diazabicyclo[5.4.0]undec-7-ene (DBU), and 1,4-diazabicyclo[2.2.2]octane (DABCO).

The reaction temperature is not limited, and the reaction is usually carried out under conventional conditions.

wherein $R^1$, $R^2$, $R^3$, $R^4$, Tf, $Y^1$ and $Y^2$ are the same as above; M is a metal, for example, Na, K, Ag, Zu, Cu, and the like; and X is a positive number.

The reaction converting the compound of Formula (23) to the compound of Formula (4) can be performed by reacting the compound of Formula (23) with a cyano metal in a suitable solvent, in the presence of a catalyst.

Examples of metal cyanides ($M(CN)_x$) include sodium cyanide, potassium cyanide, silver cyanide, zinc cyanide, and cuprous cyanide.

Examples of solvents usable in this reaction include water; aromatic hydrocarbons such as benzene, toluene, and xylene; ethers such as diethylether, tetrahydrofuran, dioxane, 2-methoxyethanol, monoglyme, and diglyme; halogenated hydrocarbons such as dichloromethane, dichloroethane, chloroform, and carbon tetrachloride; lower ($C_{1-6}$) alcohols such as methanol, ethanol, isopropanol, butanol, tert-butanol, and ethylene glycol; aliphatic acids such as acetic acid; esters such as ethyl acetate and methyl acetate; ketones such as acetone and methyl ethyl ketone; acetonitrile; pyridine; dimethyl sulfoxide; N,N-dimethylformamide; hexamethylphosphoric triamide; and mixtures thereof.

Examples of catalysts include palladium compounds such as tetrakis(triphenylphosphine)palladium (0); dichlorobis (triphenylphosphine)palladium (II); and tris(dibenzylideneacetone)dipalladium (0).

A ligand such as 1,1'-bis(diphenylphosphino)ferrocene or zinc dust may be added, as required, in order to promote the reaction.

The catalyst can be typically used in an amount of 0.01 to 1 mole, and preferably 0.01 to 0.5 moles, per mole of the compound of Formula (23).

The metal cyanide can be typically used in an amount of at least 1 mole, and preferably 1 to 3 moles, per mole of the compound of Formula (23).

The reaction is typically performed at room temperature to 200° C., and preferably at about room temperature to about 150° C. The reaction is typically completed in about 1 hour to about 1 week.

The reaction converting the compound of Formula (4) to the compound of Formula (10) is performed in a suitable solvent, in the presence of a reducing agent.

Examples of solvents include aliphatic acids such as formic acid; ethers such as dioxane, tetrahydrofuran, diethylether, and diethylene glycol dimethyl ether; aromatic hydrocarbons such as benzene, toluene, and xylene; halogenated hydrocarbons such as dichloromethane, dichloroethane, chloroform, and carbon tetrachloride; and mixtures thereof.

Examples of reducing agents include alkylaluminum hydrides such as diisobutylaluminum hydride; and Raney nickel. The reducing agent is typically used in an amount at least equal to, and preferably from an equal weight to 5 times the weight of the compound of Formula (4).

The reaction is typically performed at room temperature to 200° C., and preferably at about room temperature to about 150° C. The reaction is typically completed in about 0.5 to about 20 hours.

Reaction Formula 16

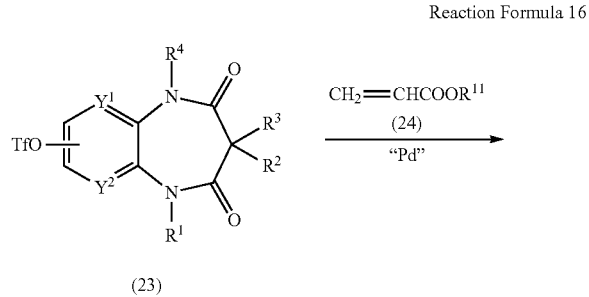

(23)

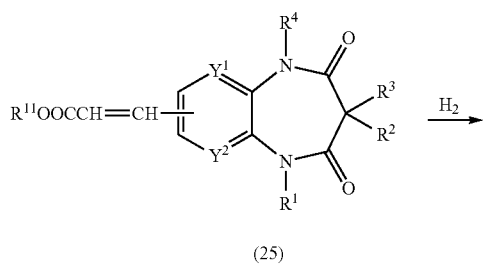

(25)

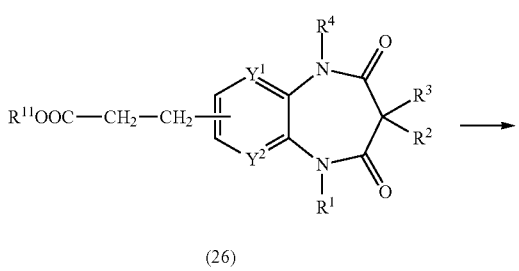

(26)

-continued

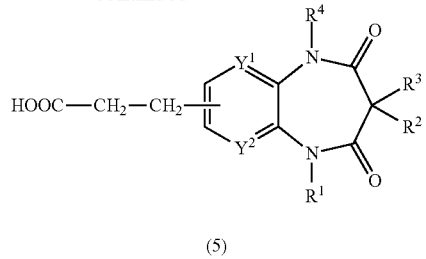

(5)

wherein $R^1$, $R^2$, $R^3$, $R^4$, Tf, $Y^1$ and $Y^2$ are the same as above; and $R^{11}$ is lower alkyl.

Examples of "lower alkyl" represented by $R^{11}$ include linear or branched alkyl groups with 1 to 6 carbon atoms, such as methyl, and ethyl.

The reaction converting the compound of Formula (23) and the compound of Formula (24) to the compound of Formula (25) can be performed in a suitable solvent, in the presence of a catalyst.

Examples of usable solvents include water; aromatic hydrocarbons such as benzene, toluene, and xylene; ethers such as diethylether, tetrahydrofuran, dioxane, 2-methoxyethanol, monoglyme, and diglyme; halogenated hydrocarbons such as dichloromethane, dichloroethane, chloroform, and carbon tetrachloride; lower ($C_{1-6}$) alcohols such as methanol, ethanol, isopropanol, butanol, tert-butanol, and ethylene glycol; aliphatic acids such as acetic acid; esters such as ethyl acetate and methyl acetate; ketones such as acetone and methyl ethyl ketone; acetonitrile; pyridine; dimethyl sulfoxide; N,N-dimethylformamide; hexamethylphosphorictriamide; and mixtures thereof.

Preferable as the catalyst are palladium compounds, for example, tetrakis(triphenylphosphine)palladium (0); dichlorobis(triphenylphosphine)palladium (II); and the like. The catalyst is typically used in an amount of about 0.01 to about 1 mole, and preferably about 0.01 to about 0.5 moles, per mole of the compound of Formula (23).

Further, a basic compound such as triethylamine, pyridine, may be added, as required.

The reaction temperature is not limited, and the reaction is usually carried out under conventional conditions.

The reaction converting the compound of Formula (25) to the compound of Formula (26) can be performed by catalytic reduction of the compound of Formula (25) in a suitable solvent in a hydrogen atmosphere.

Known hydrogenolysis methods can be widely employed in hydrogenolysis. Examples of such hydrogenolysis methods include chemical reduction and catalytic reduction.

Catalysts suitable for use in catalytic reduction include platinum catalysts, such as platinum plates, spongy platinum, platinum black, colloid platinum, platinum oxide, and platinum wires; palladium catalysts, such as spongy palladium, palladium black, palladium oxide, palladium carbon, palladium/barium sulfate, and palladium/barium carbonate; nickel catalysts, such as reduced nickel, nickel oxide, and Raney nickel; cobalt catalysts, such as reduced cobalt and Raney cobalt; and iron catalysts, such as reduced iron.

The amount of the catalyst used for catalytic reduction is not limited, and may be an amount generally used.

The reaction temperature is typically 0 to 120° C., preferably room temperature to about 100° C., and more preferably room temperature to 80° C. The reaction time is typically 30 minutes to 24 hours, preferably 30 minutes to 10 hours, and more preferably 30 minutes to 4 hours.

The reaction converting the compound of Formula (26) to the compound of Formula (5) can be performed by hydrolysis of the compound (26).

This hydrolytic reaction is performed in a suitable solvent or without any solvent, in the presence of an acid or basic compound.

Examples of solvents include water; lower ($C_{1-6}$) alcohols such as methanol, ethanol, isopropanol, and tert-butanol; ketones such as acetone and methyl ethyl ketone; ethers such as diethylether, dioxane, tetrahydrofuran, monoglyme, and diglyme; aliphatic acids such as acetic acid and formic acid; esters such as methyl acetate and ethyl acetate; halogenated hydrocarbons such as chloroform, dichloromethane, dichloroethane, and carbon tetrachloride; dimethyl sulfoxide; N,N-dimethylformamide; hexamethylphosphoric triamide; and mixtures thereof.

Examples of acids include mineral acids such as hydrochloric acid, sulfuric acid, and hydrobromic acid; and organic acids such as formic acid, acetic acid, trifluoroacetic acid, p-toluenesulfonic acid, and like sulfonic acids. These acids may be used singly or in a combination of two or more.

Examples of basic compounds include carbonates such as sodium carbonate, potassium carbonate, sodium hydrogencarbonate, and potassium hydrogencarbonate; and metal hydroxides such as sodium hydroxide, potassium hydroxide, calcium hydroxide, and lithium hydroxide. These basic compounds can be used singly or in a combination of two or more.

The hydrolytic reaction advantageously proceeds typically at about 0 to about 200° C., and preferably at about 0 to about 150° C. The reaction is typically completed in about 10 minutes to about 30 hours.

Reaction Formula 17

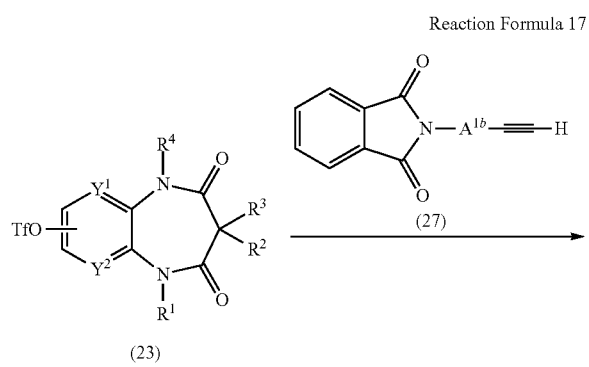

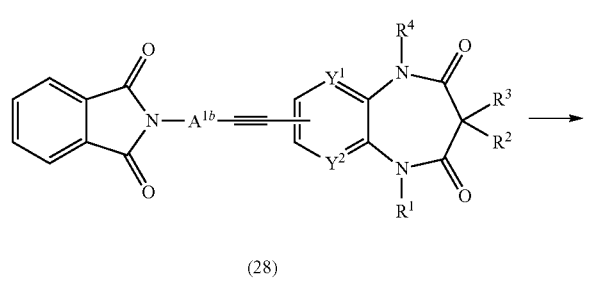

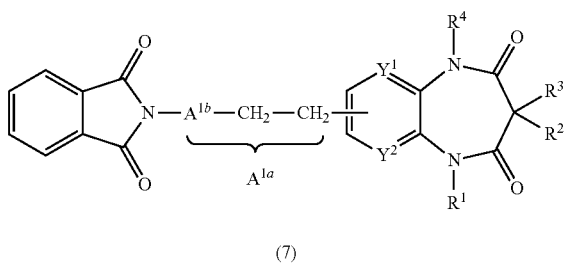

wherein $R^1$, $R^2$, $R^3$, $R^4$, Tf, $Y^1$ and $Y^2$ are the same as above; and $A^{1b}$ is lower alkylene.

Examples of "lower alkylene" represented by $A^{1b}$ include alkylene groups with 1 to 4 carbon atoms, such as methylene, ethylene, trimethylene, and tetramethylene.

The reaction converting the compound of Formula (23) and the compound of Formula (27) to the compound of Formula (28) can be performed in a suitable solvent, in the presence of a copper halide and a palladium catalyst.

Examples of solvents include ketones such as acetone and methyl ethyl ketone; ethers such as diethylether, dioxane, tetrahydrofuran, monoglyme, and diglyme; aliphatic acids such as acetic acid and formic acid; esters such as methyl acetate and ethyl acetate; halogenated hydrocarbons such as chloroform, dichloromethane, dichloroethane, and carbon tetrachloride; dimethyl sulfoxide; N,N-dimethylformamide; hexamethylphosphoric triamide; and mixtures thereof.

Examples of copper halides include copper (I) chloride, copper (I) bromide, and copper (I) iodide.

Examples of palladium catalysts include palladium compounds such as tetrakis(triphenylphosphine)palladium (0); and dichlorobis(triphenylphosphine)palladium (II).

A basic compound may be added, as required. Examples of basic compounds include triethylamine, diisopropylethylamine, pyridine, and diethylamine. The basic compound can be typically used in an amount of 0.01 to 10 mole, and preferably 0.01 to 1 moles, per mole of the compound of Formula (23).

The reaction advantageously proceeds typically at about 0 to about 200° C., and preferably at about 0 to about 180° C. The reaction is typically completed in about 10 minutes to about 30 hours.

The reaction converting the compound of Formula (28) to the compound of Formula (7) can be performed under the same reaction conditions as those for the reaction converting the compound of Formula (25) to the compound of Formula (26) shown in Reaction Formula 16 above.

Reaction Formula 18

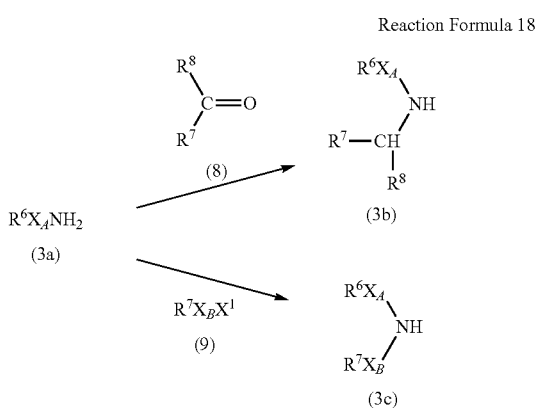

wherein $R^6$, $R^7$, $R^8$, $X_A$, $X_B$, and $X^1$ are the same as above.

The reaction of the compound of Formula (3a) with the compound of Formula (8) can be performed under the same reaction conditions as those for the reaction of the compound of Formula (1d) with the compound of Formula (8) shown in Reaction Formula 5 above.

The reaction of the compound of Formula (3a) with the compound of Formula (9) can be performed under the same reaction conditions as those for the reaction of the compound of Formula (2) with the compound of Formula (3) shown in Reaction Formula 1 above.

The compound of Formula (3), which is used as a starting material, can be easily prepared by the process shown in the following reaction formula.

Reaction Formula 19

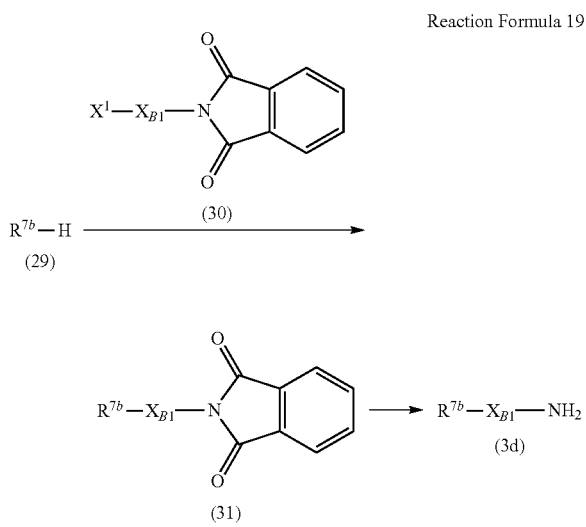

wherein $R^{7b}$ is a nitrogen-containing heterocyclic group optionally having one or more substituents; and $X_{B1}$ is lower alkylene.

Examples of $R^{7b}$ include, among groups represented by the group $R^7$ mentioned above, groups obtained by removing hydrogen from saturated or unsaturated, monocyclic or polycyclic, heterocyclic compounds having an N—H bond, and groups optionally having one or more substituents.

Examples of "lower alkylene" represented by $X_{B1}$ include alkylene groups with 2 to 4 carbon atoms, such as ethylene and trimethylene.

The reaction of the compound of Formula (29) with the compound of Formula (30) can be performed under the same reaction conditions as those for the reaction of the compound of Formula (2) and the compound of Formula (3) shown in Reaction Formula 1 above.

The reaction converting the compound of Formula (31) to the compound of Formula (3d) can be performed under the same reaction conditions as those for the reaction converting the compound of Formula (7) to the compound of Formula (1c) shown in Reaction Formula 4 above.

Reaction Formula 20

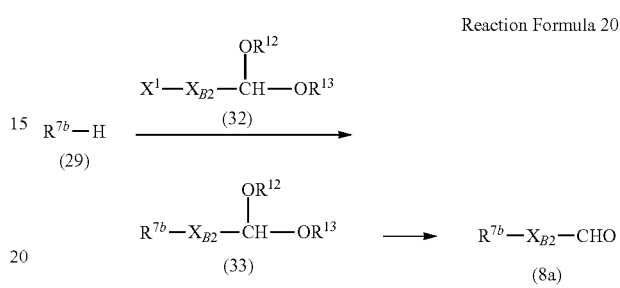

wherein $R^{7b}$ is the same as above; $X_{B2}$ is lower alkylene; and $R^{12}$ and $R^{13}$ are each independently lower alkyl, or $R^{12}$ and $R^{13}$ are linked to form lower alkylene.

Examples of "lower alkyl" represented by $R^{12}$ and $R^{13}$ include linear or branched alkyl groups with 1 to 6 carbon atoms, such as methyl, ethyl, and n-propyl. Examples of "lower alkylene" formed by $R^{12}$ and $R^{13}$ when they are linked include alkylene groups with 1 to 4 carbon atoms, such as methylene, ethylene, trimethylene, and tetramethylene.

Examples of "lower alkylene" represented by $X_{B2}$ include alkylene groups with 1 to 6 carbon atoms, such as methylene, ethylene, trimethylene, and tetramethylene.

The reaction of the compound of Formula (29) with the compound of Formula (32) can be performed under the same reaction conditions as those for the reaction of the compound of Formula (2) and the compound of Formula (3) shown in Reaction Formula 1 above.

The reaction converting the compound of Formula (33) to the compound of Formula (8a) can be performed by hydrolysis of the compound (33).

This hydrolytic reaction is performed in a suitable solvent or without any solvent, in the presence of an acidic compound.

Examples of solvents include water; lower ($C_{1-6}$) alcohols such as methanol, ethanol, isopropanol, and tert-butanol; ketones such as acetone and methyl ethyl ketone; ethers such as diethylether, dioxane, tetrahydrofuran, monoglyme, and diglyme; aliphatic acids such as acetic acid and formic acid; esters such as methyl acetate and ethyl acetate; halogenated hydrocarbons such as chloroform, dichloromethane, dichloroethane, and carbon tetrachloride; dimethyl sulfoxide; N,N-dimethylformamide; hexamethylphosphoric triamide; and mixtures thereof.

Examples of acids include mineral acids such as hydrochloric acid, sulfuric acid, and hydrobromic acid; and organic acids such as formic acid, acetic acid, trifluoroacetic acid, p-toluenesulfonic acid, pyridinium p-toluenesulfonic acid (PPTS), and like sulfonic acids. These acids may be used singly or in a combination of two or more.

The hydrolytic reaction advantageously proceeds typically at about 0 to about 100° C., and preferably at about 0 to about 80° C. The reaction is typically completed in about 10 minutes to about 30 hours.

Reaction Formula 21

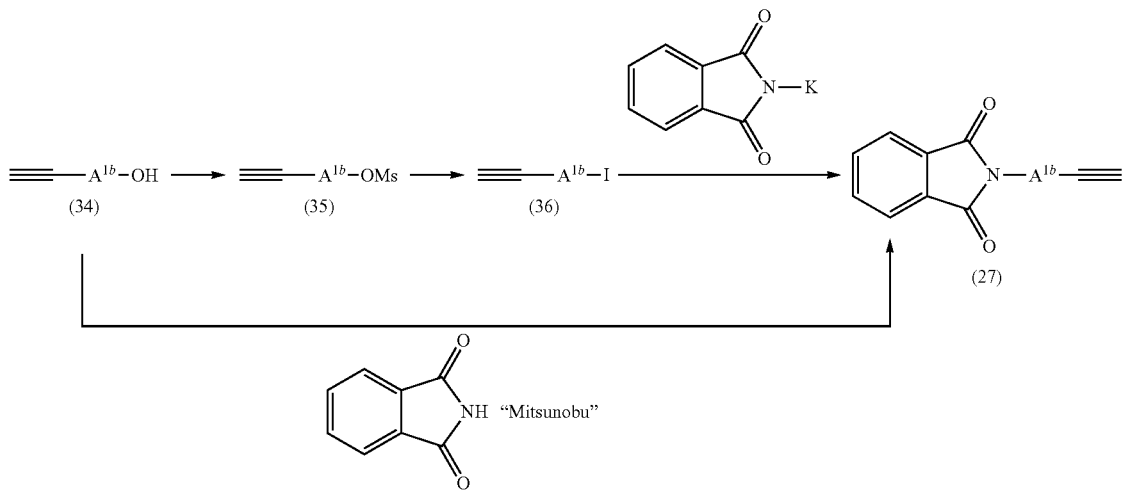

wherein $A^{1b}$ is the same as above; and Ms is methanesulfonyl ($CH_3SO_2-$).

The reaction converting the compound of Formula (34) to the compound of Formula (35) is performed by methanesulfonylation (mesylation) of the compound of Formula (34) using a conventional method. Typically, the compound of Formula (35) can be produced by reacting the compound of Formula (34) with trifluoromethanesulfonic anhydride in a suitable solvent (e.g., dichloromethane), in the presence of a basic compound (e.g., triethylamine).

The reaction converting the compound of Formula (35) to the compound of Formula (36) is performed by iodination of the compound of Formula (35) with an iodinating agent such as sodium iodide, in a suitable solvent (e.g., acetone).

The reaction converting the compound of Formula (36) to the compound of Formula (27) can be performed by reacting the compound of Formula (36) with potassium phthalimide in a suitable solvent (e.g., N,N-dimethylformamide).

Alternatively, the compound of Formula (27) can be directly produced by reacting the compound of Formula (34) with phthalimide under the Mitsunobu reaction conditions (e.g., using diethyl azodicarboxylate (DEAD) and triphenylphosphine).

The compound of Formula (1) according to the present invention and the starting materials thereof can be produced using a known or conventional synthetic method other than the production method described above.

In addition, compounds in the form in which a solvate (for example, a hydrate, ethanolate, etc.) was added to the starting material compounds and object compounds shown in each of the reaction formulae are included in each of the formulae.

The compound of Formula (1) according to the present invention includes stereoisomers and optical isomers.

The starting material compounds and object compounds represented by each of the reaction formulae can be used in an appropriate salt form.

Each of the object compounds obtained according to the above reaction formulae can be isolated and purified from the reaction mixture by, for example, after cooling the reaction mixture, performing an isolation procedure such as filtration, concentration, extraction, etc., to separate a crude reaction product, and then subjecting the crude reaction product to a general purification procedure such as column chromatography, recrystallization, etc.

Among the compounds of the present invention, those having a basic group or groups can easily form salts with common pharmaceutically acceptable acids. Examples of such acids include hydrochloric acid, hydrobromic acid, nitric acid, sulfuric acid, phosphoric acid and other inorganic acids, methansulfonic acid, p-toluenesulfonic acid, acetic acid, citric acid, tartaric acid, maleic acid, fumaric acid, malic acid, lactic acid and other organic acids, etc.

Among the compounds of the present invention, those having an acidic group or groups can easily form salts by reacting with pharmaceutically acceptable basic compounds. Examples of such basic compounds include sodium hydroxide, potassium hydroxide, calcium hydroxide, sodium carbonate, potassium carbonate, sodium hydrogencarbonate, potassium hydrogencarbonate, etc.

In the compound of the present invention, one or more atoms can be substituted with one or more isotopic atoms. Examples of the isotopic atoms include deuterium ($^2H$), tritium ($^3H$), $^{13}C$, $^{14}N$, $^{18}O$, etc.

The following is an explanation of pharmaceutical preparations comprising the compound of the present invention as an active ingredient.

Such pharmaceutical preparations are obtained by formulating the compound of the present invention into general pharmaceutical preparations, using typically employed diluents or excipients such as fillers, extenders, binders, wetting agents, disintegrants, surfactants, lubricants, etc.

The form of such pharmaceutical preparations can be selected from various forms according to the purpose of therapy. Typical examples include tablets, pills, powders, solutions, suspensions, emulsions, granules, capsules, suppositories, injections (solutions, suspensions, etc.) and the like.

To form tablets, any of various known carriers can be used, including, for example, lactose, white sugar, sodium chloride, glucose, urea, starch, calcium carbonate, kaolin, crystalline cellulose and other excipients; water, ethanol, propanol, simple syrup, glucose solutions, starch solutions, gelatin solutions, carboxymethylcellulose, shellac, methylcellulose, potassium phosphate, polyvinylpyrrolidone and other binders; dry starch, sodium alginate, agar powder, laminaran powder, sodium hydrogencarbonate, calcium carbonate, aliphatic acid esters of polyoxyethylenesorbitan, sodium laurylsulfate, stearic acid monoglyceride, starch, lactose and other disintegrants; white sugar, stearin, cacao butter, hydrogenated oils and other disintegration inhibitors; quaternary ammonium base, sodium lauryl sulfate and other absorption promoters; glycerin, starch and other wetting agents; starch, lactose, kaolin, bentonite, colloidal silicic acid and other adsorbents; purified talc, stearates, boric acid powder, polyethylene glycol and other lubricants; etc.

Such tablets may be coated with general coating materials as required, to prepare, for example, sugar-coated tablets, gelatin-coated tablets, enteric-coated tablets, film-coated tablets, double- or multi-layered tablets, etc.

To form pills, any of various known carriers can be used, including, for example, glucose, lactose, starch, cacao butter, hydrogenated vegetable oils, kaolin, talc and other excipients; gum arabic powder, tragacanth powder, gelatin, ethanol and other binders; laminaran, agar and other disintegrants; etc.

To form suppositories, any of various known carriers can be used, including, for example, polyethylene glycol, cacao butter, higher alcohols, esters of higher alcohols, gelatin, semisynthetic glycerides, etc.

To form an injection, a solution, emulsion or suspension is sterilized and preferably made isotonic with blood. Any of various known widely used diluents can be employed to prepare the solution, emulsion or suspension. Examples of such diluents include water, ethanol, propylene glycol, ethoxylated isostearyl alcohol, polyoxylated isostearyl alcohol, aliphatic acid esters of polyoxyethylene sorbitan, etc. In this case, the pharmaceutical preparation may contain sodium chloride, glucose or glycerin in an amount sufficient to prepare an isotonic solution, and may contain general solubilizers, buffers, analgesic agents, etc., and further, if necessary, coloring agents, preservatives, flavors, sweetening agents, etc., and/or other medicines.

The proportion of the compound of the present invention in the pharmaceutical preparation is not limited and can be suitably selected from a wide range. It is typically preferable that the pharmaceutical preparation contain the compound of the present invention in a proportion of 1 to 70 wt. %.

The route of administration of the pharmaceutical preparation according to the present invention is not limited, and the preparation can be administered by a route suitable for the form of the preparation, the patient's age and sex, the conditions of the disease, and other conditions.

For example, tablets, pills, solutions, suspensions, emulsions, granules and capsules are administered orally. Injections are intravenously administered singly or as mixed with general injection transfusions such as glucose solutions, amino acid solutions or the like, or singly administered intramuscularly, intracutaneously, subcutaneously or intraperitoneally, as required. Suppositories are administered intrarectally.

The dosage of the pharmaceutical preparation is suitably selected according to the method of use, the patient's age and sex, the severity of the disease, and other conditions, and is typically about 0.001 to about 100 mg/kg body weight/day, and preferably 0.001 to 50 mg/kg body weight/day, in single or divided doses.

Since the dosage varies depending on various conditions, a dosage smaller than the above range may be sufficient, or a dosage larger than the above range may be required.

When administered to the human body as a pharmaceutical, the compound of the present invention may be used concurrently with, or before or after, antithrombotics such as blood clotting inhibitors and antiplatelet agents (e.g., warfarin, aspirin, etc.). Further, the present compound may be used concurrently with, or before or after, drugs for treating chronic diseases, such as antihypertensive drugs (ACE inhibitors, beta blockers, angiotensin II receptor antagonists), heart failure drugs (cardiotonic agents, diuretics), and diabetes treatment agents.

The compound of the present invention has potent blocking effects on human Kv1.5 and/or GIRK1/4 channels, and weak blocking effects on HERG channels. Thus, the compound of the invention has characteristics as an atrial-selective $K^+$ channel-blocking agent.

Therefore, the compound of the invention can be used as a pharmacologically active substance that is safer and provides a more potent effect on the prolongation of the atrial refractory period than conventional antiarrhythmic agents. The compound of the invention is preferably used as a therapeutic agent for arrhythmia such as atrial fibrillation, atrial flutter, and atrial tachycardia (elimination of arrhythmia and/or prevention of the occurrence of arrhythmia). The compound of the invention is particularly preferably used as a therapeutic agent for atrial fibrillation (defibrillation and maintenance of sinus rhythm). The compound of the invention can also be used as a prophylactic agent for thromboembolism such as cerebral infarction and as a therapeutic agent for heart failure.

The compound having potent blocking effects on both human Kv1.5 and human GIRK1/4 channels has more potent atrial refractory period prolongation effects and is highly safe, compared to compounds inhibiting either one of the channels. Furthermore, this compound has greater therapeutic effects on atrial fibrillation (defibrillation and maintenance of sinus rhythm) than compounds inhibiting either one of the channels. Therefore, the compound having potent blocking effects on both the human Kv1.5 and human GIRK1/4 channels is particularly useful as a therapeutic agent for arrhythmia such as atrial fibrillation, atrial flutter, and atrial tachycardia (termination of arrhythmia and/or prevention of the occurrence of arrhythmia). This compound is particularly useful as a therapeutic agent for atrial fibrillation (defibrillation and maintenance of sinus rhythm).

2. Second Invention (Amino Compound)

The present inventors conducted extensive research to develop a compound that blocks the $I_{Kur}$ current (Kv1.5 channel) and/or the $I_{KACh}$ current (GIRK1/4 channel) potently and more selectively than other $K^+$ channels. As a result, the inventors found that a novel amino compound represented by General Formula (1) below could be the desired compound. The present invention has been accomplished based on the above findings.

The present invention provides amino compounds, and pharmaceutical compositions comprising the amino compounds as summarized in items 1 to 7 below.

Item 1. An amino compound represented by General Formula (1):

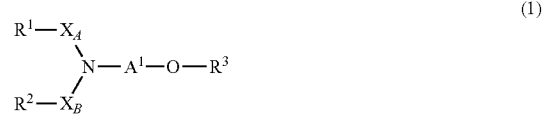

or a salt thereof, wherein $R^1$ and $R^2$ are each independently hydrogen or organic group; $X_A$ and $X_B$ are each independently a bond, alkylene, alkenylene, —CO—, —SO$_2$—, or —CONH—, wherein each of the alkylene and alkenylene chains can optionally contain one or more substituents selected from the group consisting of —S—, —C(=S)—, —SO$_2$—, —CO—, —O—, —NH—, —CONH— and —SO$_2$NH—, and the hydrogen atom (H) bonded to the nitrogen atom (N) in X$_A$ and X$_B$ is optionally substituted with a substituent selected from the group consisting of lower alkyl, phenyl lower alkyl and phenyl;

A$^1$ is lower alkylene optionally substituted with one or more substituents selected from the group consisting of hydroxyl and oxo;

R$^3$ is (i) a heterocyclic group which is optionally substituted with one or more substituents, or (ii) an aryl group substituted with one or more substituents selected from the group consisting of oxo, lower alkyl, carboxyl, halo-lower alkyl, lower alkanoyl lower alkyl, phenyl lower alkyl, cyclo lower alkyl, lower alkoxy, halo lower alkoxy, phenyl lower alkoxy, phenoxy, cyano, hydroxyl, halogen, nitro, lower alkyl thio, lower alkanoyl, lower alkoxy carbonyl, lower alkenyl, phenyl, triazolyl, isoxazolyl, imidazolyl, pyrrolyl, benzo[d]oxazolyl, benzo[d]thiazolyl and the group represented by General Formula (2):

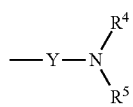

(2)

wherein Y is a bond, lower alkylene, or —CO—; R$^4$ and R$^5$ are each independently hydrogen, lower alkyl, cyclo lower alkyl, phenyl, or lower alkanoyl; or R$^4$ and R$^5$ may be linked to form a ring together with the neighboring nitrogen, and the ring may optionally have one or more substituents.

Item 2. A pharmaceutical composition comprising an amino compound represented by Formula (1) or a salt thereof according to Item 1, and a pharmacologically acceptable carrier.

Item 3. A pharmaceutical composition according to Item 1 for preventing and/or treating arrhythmia.

Item 4. An amino compound represented by Formula (1) or a salt thereof according to Item 1 for use in the pharmaceutical composition.

Item 5. Use of an amino compound represented by Formula (1) or a salt thereof according to Item 1 as a pharmaceutical composition.

Item 6. Use of an amino compound represented by Formula (1) or a salt thereof according to Item 1 for the production of a pharmaceutical composition.

Item 7. A method of preventing and/or treating arrhythmia, comprising administering to a patient an amino compound represented by Formula (1) or a salt thereof according to Item 1.

The groups represented by, or substituents of, R$^1$, R$^2$, R$^3$, R$^4$, R$^5$, A$^1$, X$_A$, X$_B$ and Y in the specification are described below.

The term "one or more" may be preferably 1 to 6, more preferably 1 to 3.

Examples of "lower alkyl" include linear or branched alkyl groups having 1 to 6 carbon atoms, such as methyl, ethyl, n-propyl, isopropyl, n-butyl, isobutyl, tert-butyl, sec-butyl, n-pentyl, neopentyl, n-hexyl, isohexyl, and 3-methylpentyl.

Examples of "alkylene" include linear or branched alkylene groups having 1 to 12 carbon atoms, such as the following "lower alkylene", heptamethylene, octamethylene, decamethylene, and dodecamethylene.

Examples of "lower alkylene" include linear or branched alkylene groups having 1 to 6 carbon atoms, such as methylene, ethylene, trimethylene, 2-methyltrimethylene, 2,2-dimethyltrimethylene, 1-methyltrimethylene, methylmethylene, ethylmethylene, dimethylmethylene, tetramethylene, pentamethylene, and hexamethylene.

Examples of "alkenylene" include linear or branched alkenylene groups having 2 to 12 carbon atoms, such as the following "lower alkenylene", heptenylene, octenylene, decenylene, and dodecenylene.

Examples of "lower alkenylene" include linear or branched alkylene alkenylene groups having 2 to 6 carbon atoms, such as ethenylene, propenylene, butenylene, pentenylene, and hexenylene.

Examples of "lower alkylidene" include linear or branched alkylidene groups having 1 to 6 carbon atoms, such as methylidene, ethylidene, propylidene, and butylidene.

Examples of "cyclo lower alkyl" include linear or branched cyclo alkyl having 3 to 8 carbon atoms, such as cyclopropyl, cyclobutyl, cyclopentyl, cyclohexyl, cycloheptyl, and cyclooctyl.

Examples of "lower alkoxy" include linear or branched alkoxy groups having 1 to 8 carbon atoms, preferably 1 to 6 carbon atoms, such as methoxy, ethoxy, n-propoxy, isopropoxy, n-butoxy, isobutoxy, tert-butoxy, sec-butoxy, n-pentyloxy, neopentyloxy, n-hexyloxy, isohexyloxy, and 3-methylpentyloxy.

Examples of "halogen" include fluorine, chlorine, bromine, and iodine.

Examples of "lower alkylenedioxy" include linear or branched alkylenedioxy groups having 1 to 4 carbon atoms, such as methylenedioxy, ethylenedioxy, trimethylenedioxy, and tetramethylenedioxy.

Examples of "lower alkanoyl" include linear or branched alkanoyl groups having 1 to 6 carbon atoms, such as formyl, acetyl, propionyl, butyryl, isobutyryl, pentanoyl, tert-butylcarbonyl, and hexanoyl.

Examples of "lower alkoxycarbonyl" include (linear or branched alkoxy having 1 to 6 carbon atoms)carbonyls, such as methoxycarbonyl, ethoxycarbonyl, propoxycarbonyl, butoxycarbonyl, isobutoxycarbonyl, and tert-butoxycarbonyl.

Examples of "aralkyl group" include lower alkyl group substituted with one or more aryl groups, such as benzyl and phenethyl.

Examples of "organic group" include lower alkyl, lower alkoxy, cyclo lower alkyl, amino, lower alkyl thio, aryl, and heterocyclic group, each of which is optionally substituted.

Examples of "aryl group" include monocyclic or polycyclic aryl groups, such as phenyl, tolyl, xylyl, naphthyl and tetrahydronaphthyl, indenyl, and dihydroindenyl.

Examples of "heterocyclic group" include saturated or unsaturated monocyclic or polycyclic heterocyclic groups containing at least one hetero atom selected from the group consisting of oxygen, sulfur and nitrogen. More preferable examples of heterocyclic groups include the following (a) to (o):

(a) unsaturated 3- to 8-membered, preferably 5- or 6-membered heteromonocyclic groups containing 1 to 4 nitrogen atom(s), for example, pyrrolyl, pyrrolinyl, imidazolyl, pyrazolyl, pyridyl, and its N-oxide, pyrimidinyl, pyrazinyl, pyridazinyl, triazolyl (e.g., 4H-1,2,4-triazolyl, 1H-1,2,3-triazolyl, 2H-1,2,3-triazolyl, etc.), tetrazolyl (e.g., 1H-tetrazolyl, 2H-tetrazolyl, etc.), dihydrotriazinyl (e.g., 4,5-dihydro-1,2,4-triazinyl, 2,5-dihydro-1,2,4-triazinyl, etc.), etc.;

(b) saturated 3- to 8-membered, preferably 5- or 6-membered heteromonocyclic groups containing 1 to 4 nitrogen atom(s), for example, azetidinyl, pyrrolidinyl, imidazolidinyl, piperidyl, pyrazolidinyl, piperazinyl, 1,4-diazepanyl, etc.;

(c) saturated or unsaturated condensed 7- to 14-membered heterocyclic groups containing 1 to 5 nitrogen atom(s), for example, decahydroquinolyl, indolyl, dihydroindolyl (e.g., 2,3-dihydroindolyl, etc.), isoindolyl, indolizinyl, benzimidazolyl, dihydrobenzimidazolyl (e.g., 2,3-dihydro-1H-benzo[d]imidazolyl, etc.), quinolyl, dihydroquinolyl (e.g. 1,4-dihydroquinolyl, 1,2-dihydroquinolyl, etc.), tetrahydroquinolyl (1,2,3,4-tetrahydroquinolyl, etc.), isoquinolyl, dihydroisoquinolyl (e.g., 3,4-dihydro-1H-isoquinolyl, 1,2-dihydroisoquinolyl, etc.), tetrahydroisoquinolyl (e.g., 1,2,3,4-tetrahydro-1H-isoquinolyl, 5,6,7,8-tetrahydroisoquinolyl, etc.), carbostyril, dihydrocarbostyril (e.g., 3,4-dihydrocarbostyril, etc.), indazolyl, benzotriazolyl (e.g. benzo[d][1,2,3]triazolyl, etc.), tetrazolopyridyl, tetrazolopyridazinyl (e.g., tetrazolo[1,5-b]pyridazinyl, etc.), dihydrotriazolopyridazinyl, imidazopyridyl (e.g., imidazo[1,2-a]pyridyl, imidazo[4,5-c]pyridyl, etc.,), naphthyridinyl, cinnolinyl, quinoxalinyl, quinazolinyl, pyrazolopyridyl (e.g., pyrazolo[2,3-a]pyridyl, etc.) tetrahydropyridoindolyl (e.g., 2,3,4,9-tetrahydro-1H-pyrido[3,4-b]indolyl, etc.), etc.;

(d) saturated or unsaturated 3- to 8-membered, preferably 5- or 6-membered heteromonocyclic groups containing 1 to 2 oxygen atom(s), for example, furyl, tetrahydropyranyl (e.g., tetrahydro-2H-pyranyl, etc.), tetrahydrofuryl, etc.;

(e) unsaturated condensed 7- to 12-membered heterocyclic groups containing 1 to 3 oxygen atom(s), for example, benzofuryl, dihydrobenzofuryl (e.g. 2,3-dihydrobenzo[b]furyl, etc.), chromanyl, benzodioxanyl (e.g., 1,4-benzodioxanyl, etc.), benzodioxolyl(benzo[1,3]dioxolyl, etc.), etc.;

(f) unsaturated 3- to 8-membered, preferably 5- or 6-membered heteromonocyclic groups containing 1 to 2 oxygen atom(s) and 1 to 3 nitrogen atom(s), for example, oxazolyl, isoxazolyl, oxadiazolyl (e.g., 1,2,4-oxadiazolyl, 1,3,4-oxadiazolyl, 1,2,5-oxadiazolyl, etc.), etc.;

(g) saturated 3- to 8-membered, preferably 5- or 6-membered heteromonocyclic groups containing 1 to 2 oxygen atom(s) and 1 to 3 nitrogen atom(s), for example, morpholinyl, etc.;

(h) unsaturated condensed 7- to 12-membered heterocyclic groups containing 1 to 2 oxygen atom(s) and 1 to 3 nitrogen atom(s), for example, benzoxazolyl, benzoxadiazolyl, benzisoxazolyl, dihydrobenzoxazinyl (e.g., 2,3-dihydrobenz-1,4-oxazinyl, etc.), furopyridyl (e.g., furo[2,3-c]pyridyl, 6,7-dihydrofuro[2,3-c]pyridyl, furo[3,2-c]pyridyl, 4,5-dihydrofuro[3,2-c]pyridyl, furo[2,3-b]pyridyl, 6,7-dihydrofuro[2,3-b]pyridyl, etc.), furopyrrolyl (e.g., furo[3,2-b]pyrrolyl etc.) etc.;

(i) unsaturated 3- to 8-membered, preferably 5- or 6-membered heteromonocyclic groups containing 1 to 2 sulfur atom(s) and 1 to 3 nitrogen atom(s), for example, thiazolyl, 1,2-thiazolyl, thiazolinyl, thiadiazolyl (e.g., 1,2,4-thiadiazolyl, 1,3,4-thiadiazolyl, 1,2,5-thiadiazolyl, 1,2,3-thiadiazolyl, etc.), isothiazolyl, etc.;

(j) saturated 3- to 8-membered, preferably 5- or 6-membered heteromonocyclic groups containing 1 to 2 sulfur atom(s) and 1 to 3 nitrogen atom(s), for example, thiazolidinyl, etc.;

(k) unsaturated 3- to 8-membered, preferably 5- or 6-membered heteromonocyclic groups containing a sulfur atom, for example, thienyl, etc.;

(l) unsaturated condensed 7- to 12-membered heterocyclic groups containing 1 to 3 sulfur atom(s), for example, benzothienyl (e.g. benzo[b]thienyl), etc.;

(m) unsaturated condensed 7- to 12-membered heterocyclic groups containing 1 to 2 sulfur atom(s) and 1 to 3 nitrogen atom(s), for example, benzothiazolyl, benzo[d]isothiazolyl, 2,3-dihydrobenzo[d]isothiazolyl, benzothiadiazolyl, thienopyridyl (e.g., thieno[2,3-c]pyridyl, 6,7-dihydrothieno[2,3-c]pyridyl, thieno[3,2-c]pyridyl, 4,5-dihydrothieno[3,2-c]pyridyl, thieno[2,3-b]pyridyl, 6,7-dihydrothieno[2,3-b]pyridyl, 4,5,6,7-tetrahydrothieno[2,3-c]pyridyl, etc.), imidazothiazolyl (e.g., imidazo[2,1-b]thiazolyl, etc.), dihydroimidazothiazolyl (e.g., 2,3-dihydroimidazo[2,1-b]thiazolyl, etc.), thienopyrazinyl (e.g., thieno[2,3-b]pyrazinyl, etc.), etc.;

(n) saturated or unsaturated 7- to 12-membered heterocyclic spiro groups containing 1 to 2 nitrogen atom(s), for example, azaspiroundecanyl (e.g., 3-azaspiro[5.5]undecanyl), etc.; and (o) saturated 7- to 12-membered hetero bicyclic groups containing 1 to 3 nitrogen atom(s), for example, azabicyclooctanyl (e.g., (1R,5S)-8-azabicyclo[3.2.1]octanyl), etc;

wherein said heterocyclic group may be substituted by one or more suitable substituents.

Substituents of "aryl group which is optionally substituted" represented by $R^1$ and $R^2$ are each independently one or more substituents selected from the group consisting of:

(a1) cyano;
(a2) hydroxyl;
(a3) halogen;
(a4) lower alkyl optionally substituted with one or more substituents selected from the group consisting of oxo, halogen, hydroxyl, imidazolyl, morpholinyl, triazolyl and phenyl;
(a5) lower alkoxy optionally substituted with one or more substituents selected from the group consisting of halogen, amino, lower alkyl amino and phenyl;
(a6) pyridyl;
(a7) thienyl;
(a8) piperazinyl optionally substituted with one or more substituents selected from the group consisting of lower alkyl and halo phenyl lower alkyl;
(a9) phenyl;
(a10) pyrazolyl optionally substituted with one or more lower alkyl;
(a11) pyrimidinyl optionally substituted with one or more lower alkyls;
(a12) piperidyl optionally substituted with one or more lower alkyls;
(a13) furyl;
(a14) carboxy;
(a15) lower alkoxycarbonyl;
(a16) amino optionally substituted with one or more substituents selected from the group consisting of lower alkyl, phenyl, lower alkanoyl and lower alkylsulfonyl;
(a17) lower alkylthio;
(a18) triazolyl;
(a19) imidazolyl;
(a20) pyrrolidinyl optionally substituted with one or more oxos;
(a21) lower alkylsulfonyl;
(a22) lower alkylenedioxy optionally substituted with one or more halogens;
(a23) nitro;
(a24) oxazolyl;
(a25) thiazolyl optionally substituted with one or more lower alkyls;
(a26) lower alkanoyl;
(a27) sulfo;

(a28) carbamoyl optionally substituted with one or two lower alkyls;
(a29) phenoxy;
(a30) isoxazolyl;
(a31) pyrrolyl;
(a32) lower alkenyl;
(a33) cyclo lower alkyl;
(a34) benzo[d]oxazolyl; and
(a35) oxo.

Substituents of "heterocyclic group which is optionally substituted" represented by $R^1$ and $R^2$ are each independently one or more substituents selected from the group consisting of:
(h1) oxo;
(h2) lower alkyl optionally substituted with one or more substituents selected from the group consisting of halogen, oxo, phenyl amino, cyclo lower alkyl, lower alkoxy, pyridyl, mono- or di-lower alkyl amino, hydroxyl, lower alkyl substituted isoxazolyl, 1,3-dioxolanyl, lower alkyl substituted piperidinyl, mono or di lower alkyl amino, fulyl, imidazolyl, morpholinyl, lower alkyl substituted 1,4-diazepanyl, phenyl thiazolyl, phenyl lower alkyl tetrazolyl, lower alkyl tetrazolyl, quinolyl, pyrrolyl, imidazolyl, 2,3-dihydrobenzofuryl and benzodioxolyl;
(h3) cyclo lower alkyl;
(h4) lower alkoxy optionally substituted with one or more substituents selected from the group consisting of pyridyl, halo-lower alkoxy phenyl, halo phenyl, phenyl, and halo-lower alkyl phenyl;
(h5) aryl optionally substituted with one or more substituents selected from the group consisting of lower alkyl, halo-lower alkyl, lower alkoxy, halo lower alkoxy, lower alkanoyl, hydroxyl, halogen, carboxy, lower alkoxycarbonyl, amino, lower alkyl amino, and cyano;
(h6) aralkyl optionally substituted with one or more substituents selected from the group consisting of lower alkyl, halo-lower alkyl, lower alkoxy, halo-lower alkoxy, lower alkanoyl, hydroxyl, halogen, carboxy, lower alkoxycarbonyl, amino, lower alkyl amino, cyano, phenyl, and oxo, on the aryl and/or lower alkyl group of aralkyl;
(h7) heterocyclic group optionally substituted with one or more substituents selected from the group consisting of lower alkyl, lower alkoxy, lower alkanoyl, hydroxyl, halogen, carboxy, lower alkoxycarbonyl, amino, lower alkyl amino, cyano, phenyl, and oxo;
(h8) hydroxyl;
(h9) halogen;
(h10) carboxy;
(h11) lower alkanoyl;
(h12) lower alkoxycarbonyl;
(h13) lower alkylenedioxy;
(h14) cyano;
(h15) nitro;
(h16) sulfo;
(h17) amino optionally substituted with one or more substituents selected from the group consisting of lower alkyl, mono- or di-lower alkyl amino lower alkyl, (lower alkyl)(phenyl)amino lower alkyl, lower alkyl substituted phenoxy lower alkyl, phenyl lower alkyl, cyclo lower alkyl lower alkyl, lower alkoxy phenyl lower alkyl, lower alkyl phenyl lower alkyl, triazolyl lower alkyl, halo substituted phenyl, halo-lower alkyl substituted phenyl, halo-lower alkoxy substituted phenyl, piperazinyl lower alkyl carbonyl, phenyl lower alkyl carbonyl and lower alkoxy dihydroindenyl;
(h18) lower alkylthio;
(h19) lower alkylsulfonyl;
(h20) lower alkenyl optionally substituted with one or more phenyls;
(h21) benzo[d][1,3]dioxolyl carbonyl;
(h22) 2,3-dihydroindenyl;
(h23) phenoxy substituted with one or more substituents selected from the group consisting of halo-lower alkoxy and halogen;
(h24) lower alkylidene substituted with one or more lower alkoxy phenyls;

Substituents of "lower alkyl group which is optionally substituted" represented by $R^1$ and $R^2$ are each independently one or more substituents selected from the group consisting of oxo and phenyl.

Substituents of "cyclo lower alkyl group which is optionally substituted" represented by $R^1$ and $R^2$ are each independently one or more substituents selected from the group consisting of lower alkyl phenyl and phenyl.

Substituents of "amino group which is optionally substituted" represented by $R^1$ and $R^2$ are each independently one or more substituents selected from the group consisting of lower alkyl, lower alkanoyl, and phenyl lower alkyl.

Substituents of "dihydroindenyl group which is optionally substituted" represented by $R^1$ and $R^2$ are each independently one or more oxos.

Preferable substituents represented by $R^1$ and $R^2$ are each independently selected from the group consisting of the following substituents (1) to (69):
(1) hydrogen;
(2) lower alkyl optionally substituted with one or more substituents selected from the group consisting of oxo and phenyl;
(3) cyclo lower alkyl optionally substituted with one or more substituents selected from the group consisting of lower alkyl phenyl and phenyl;
(4) phenyl optionally substituted with one or more substituents selected from the group consisting of the following (4-1) to (4-25):
(4-1) cyano;
(4-2) hydroxyl;
(4-3) halogen;
(4-4) lower alkyl optionally substituted with one or more substituents selected from the group consisting of halogen, imidazolyl, hydroxyl, triazolyl (e.g, 1,2,4-triazolyl) and morpholinyl;
(4-5) lower alkoxy optionally substituted with one or more substituents selected from the group consisting of amino and lower alkyl amino;
(4-6) pyridyl;
(4-7) thienyl;
(4-8) piperazinyl optionally substituted with one or more lower alkyls;
(4-9) phenyl;
(4-10) pyrazolyl optionally substituted with one or more lower alkyls;
(4-11) pyrimidinyl optionally substituted with one or more lower alkyls;
(4-12) piperidyl optionally substituted with one or more lower alkyls;
(4-13) furyl;
(4-14) carboxy;
(4-15) lower alkoxycarbonyl;
(4-16) amino optionally substituted with one or more substituents selected from the group consisting of lower alkyl, lower alkanoyl and lower alkylsulfonyl;
(4-17) lower alkylthio;
(4-18) triazolyl;
(4-19) imidazolyl;

(4-20) pyrrolidinyl optionally substituted with one or more oxos;
(4-21) lower alkylsulfonyl;
(4-22) lower alkylenedioxy optionally substituted with one or more halogens;
(4-23) nitro;
(4-24) oxazolyl;
(4-25) thiazolyl optionally substituted with one or more lower alkyls;
(4-26) phenoxy; and
(4-27) carbamoyl optionally substituted with one or two lower alkyls;
(5) naphthyl;
(6) furyl optionally substituted with one or more substituents selected from the group consisting of lower alkyl optionally substituted with halogen, carboxy, sulfo, pyridyloxy, lower alkoxycarbonyl, and phenyl;
(7) thienyl optionally substituted with one or more substituents selected from the group consisting of lower alkyl, lower alkylenedioxy, carboxy, halogen, pyridyl, lower alkoxy, lower alkoxycarbonyl, oxazolyl, and furyl;
(8) imidazolyl optionally substituted with one or more substituents selected from the group consisting of phenyl, lower alkyl, and halogen;
(9) pyrazolyl optionally substituted with one or more substituents selected from the group consisting of lower alkyl optionally substituted with halogen, halogen, phenyl optionally substituted with lower alkoxy, furyl, and thienyl;
(10) oxazolyl optionally substituted with one or more substituents selected from the group consisting of lower alkyl and phenyl;
(11) isoxazolyl optionally substituted with one or more substituents selected from the group consisting of phenyl, lower alkyl, thienyl, and furyl;
(12) thiazolyl optionally substituted with one or more substituents selected from the group consisting of lower alkyl optionally substituted with lower alkoxy, phenyl, and lower alkanoylamino;
(13) pyrrolyl optionally substituted with one or more substituents selected from the group consisting of lower alkyl and lower alkoxycarbonyl;
(14) triazolyl optionally substituted with one or more lower alkyls;
(15) pyridyl optionally substituted with one or more substituents selected from the group consisting of lower alkyl optionally substituted with halogen, oxo, hydroxyl, lower alkoxy, halogen, pyrrolidinyl, morpholinyl, thienyl, piperazinyl lower alkyl carbonyl amino;
(16) pyrimidinyl optionally substituted with one or more substituents selected from the group consisting of lower alkyl and phenyl;
(17) pyridazinyl;
(18) pyrazinyl;
(19) imidazo[2,1-b]thiazolyl optionally substituted with one or more halogens;
(20) thieno[2,3-b]pyrazinyl;
(21) 2,3-dihydroimidazo[2,1-b]thiazolyl optionally substituted with one or more phenyls;
(22) benzothiazolyl optionally substituted with one or more lower alkyls;
(23) indolyl optionally substituted with one or more substituents selected from the group consisting of lower alkyl, lower alkanoyl, and halogen;
(24) imidazo[1,2-a]pyridyl optionally substituted with one or more lower alkyls;
(25) benzothienyl optionally substituted with one or more lower alkyls;
(26) benzimidazolyl optionally substituted with one or more lower alkyls;
(27) 2,3-dihydrobenzo[b]furyl;
(28) benzofuryl optionally substituted with one or more halogens;
(29) indazolyl optionally substituted with one or more lower alkyls;
(30) furo[2,3-c]pyridyl or 6,7-dihydrofuro[2,3-c]pyridyl, each of which is optionally substituted with one or more substituents selected from the group consisting of oxo and lower alkyl;
(31) furo[3,2-c]pyridyl or 4,5-dihydrofuro[3,2-c]pyridyl, each of which is optionally substituted with one or more substituents selected from the group consisting of oxo, lower alkyl optionally substituted with halogen, halogen, furyl, pyridyl, and phenyl optionally substituted with one or more substituents selected from the group consisting of amino and lower alkoxy;
(32) thieno[2,3-c]pyridyl or 6,7-dihydrothieno[2,3-c]pyridyl, each of which is optionally substituted with one or more substituents selected from the group consisting of oxo group and lower alkyl;
(33) thieno[3,2-c]pyridyl or 4,5-dihydrothieno[3,2-c]pyridyl, each of which is optionally substituted with one or more substituents selected from the group consisting of oxo and lower alkyl;
(34) thieno[2,3-b]pyridyl;
(35) benzo[1,3]dioxolyl optionally substituted with one or more halogens;
(36) benzisoxazolyl;
(37) pyrazolo[2,3-a]pyridyl;
(38) indolizinyl;
(39) 2,3-dihydroindolyl optionally substituted with one or more substituents selected from the group consisting of oxo, lower alkyl, and lower alkanoyl;
(40) isoquinolyl or 1,2-dihydroisoquinolyl, each of which is optionally substituted with one or more substituents selected from the group consisting of lower alkyl, halogen, lower alkoxy and oxo;
(41) 1,2,3,4-tetrahydroisoquinolyl optionally substituted with one or more oxos;
(42) 1,2-dihydroquinolyl optionally substituted with one or more substituents selected from the group consisting of lower alkoxy and oxo;
(43) 1,2,3,4-tetrahydroquinolyl optionally substituted with one or more substituents selected from the group consisting of oxo and lower alkoxy;
(44) quinolyl optionally substituted with one or more substituents selected from the group consisting of amino optionally substituted with one or two lower alkyl, lower alkoxy, lower alkyl, and oxo;
(45) chromanyl optionally substituted with one or more lower alkyls;
(46) 5,6,7,8-tetrahydroisoquinolyl optionally substituted with one or more oxos;
(47) 3,4-dihydroisoquinolyl optionally substituted with one or more oxos;
(48) naphthyridinyl;
(49) 1,4-benzodioxanyl;
(50) cinnolinyl;
(51) quinoxalinyl;
(52) 2,3-dihydrobenz-1,4-oxazinyl optionally substituted with one or more substituents selected from the group consisting of lower alkyl and oxo;

(53) 2,3-dihydroindenyl optionally substituted with one or more substituents selected from the group consisting of oxo and lower alkoxy;
(54) amino optionally substituted with one or more substituents selected from the group consisting of lower alkyl, lower alkanoyl and phenyl lower alkyl;
(55) lower alkoxy;
(56) lower alkylthio;
(57) decahydroquinolyl;
(58) piperazinyl optionally substituted with one or more substituents selected from the group consisting of
(58-1) lower alkyl optionally substituted with one or more substituents selected from the group consisting of oxo, lower alkoxy, 1,3-dioxolanyl, lower alkyl-substituted piperidyl, furyl, imidazolyl, phenyl amino, phenyl-substituted thiazolyl, phenyl lower alkyl-substituted tetrazolyl, lower alkyl-substituted tetrazolyl, quinolyl, pyrrolyl, mono- or di-lower alkyl amino, pyridyl and benzo[d][1,3]dioxolyl;
(58-2) oxo;
(58-3) halo-lower alkyl substituted phenyl amino;
(58-4) cyclo lower alkyl;
(58-5) 2,3-dihydroindenyl;
(58-6) phenyl optionally substituted with one or more substituents selected from the group consisting of lower alkyl, lower alkoxy, halo-lower alkyl and halo-lower alkoxy; and
(58-7) phenyl lower alkyl optionally substituted with one or more substituents selected from the group consisting of halogen, halo-lower alkyl, halo-lower alkoxy and pyridyl, on the benzene ring and/or lower alkyl of phenyl lower alkyl;
(59) 1,4-diazepanyl optionally substituted with one or more substituents selected from the group consisting of lower alkyl, pyridyl and morpholinyl lower alkyl;
(60) piperidyl optionally substituted with one or more substituents selected from the group consisting of:
(60-1) lower alkyl optionally substituted with one or more substituents selected from the group consisting of oxo, mono- or di-lower alkylamino, 2,3-dihydrobenzofuryl and imidazolyl;
(60-2) amino optionally substituted with one or two substituents selected from the group consisting of lower alkyl, halo-phenyl, halo-lower alkoxy-substituted phenyl, mono- or di-lower alkyl amino lower alkyl, lower alkyl-substituted phenoxy lower alkyl, phenyl lower alkyl, phenyl lower alkyl carbonyl, cyclo lower alkyl lower alkyl, lower alkoxy phenyl lower alkyl, 1,2,4-triazolyl lower alkyl, pyridyl phenyl, (phenyl)(lower alkyl)amino lower alkyl, lower alkoxy-substituted 2,3-dihydro-1H-indenyl and lower alkyl phenyl lower alkyl;
(60-3) lower alkoxy optionally substituted with one or more substituents selected from the group consisting of phenyl, halo-phenyl, halo-lower alkoxy-substituted phenyl, halo-lower alkyl substituted phenyl and pyridyl;
(60-4) phenoxy optionally substituted with one or more substituents selected from the group consisting of halogen, and halo-lower alkoxy;
(60-5) phenyl lower alkyl optionally substituted with one or more substituents selected from the group consisting of halogen, oxo, lower alkoxy and amino, on the benzene ring and/or lower alkyl of phenyl lower alkyl;
(60-6) lower alkoxy phenyl lower alkylidene;
(60-7) phenyl imidazolyl;
(60-8) phenyl morpholinyl; and
(60-9) phenyl;
(61) morpholinyl optionally substituted with one or more mono- or di-lower alkyl amino-substituted piperidyl lower alkyls;
(62) benzo[d][1,2,3]triazolyl optionally substituted with one or more lower alkyls;
(63) 4,5,6,7-tetrahydrothieno[2,3-c]pyridyl;
(64) 2,3,4,9-tetrahydropyrido[3,4-b]indolyl);
(65) 3-azaspiro[5,5]undecanyl;
(66) 8-azabicyclo[3,2,1]octanyl;
(67) tetrahydro-2H-pyranyl;
(68) furo[3,2-b]pyrrolyl optionally substituted with one or more lower alkyls; and
(69) tetrahydrofuryl.

Preferable examples of "aryl group which is optionally substituted" for $R^1$ and $R^2$ include the substituents (4), (5) and (53).

Preferable examples of "heterocyclic group which is optionally substituted" for $R^1$ and $R^2$ include the substituents (6) to (52) and (57) to (69).

Examples of $X_A$ and $X_B$ include a bond, lower alkylene, lower alkenylene, —CO—, —SO$_2$—, -lower alkylene-SO$_2$—, -lower alkylene-CO—, -lower alkenylene-CO—, -lower alkylene-CO—N(lower alkyl)-lower alkylene-, —N(lower alkyl)-lower alkylene-, —CO—N(lower alkyl)-lower alkylene-, —O-lower alkylene-, —N(phenyl lower alkyl)-lower alkylene-, —CO-lower alkylene-CO—, —CO—NH-lower alkylene-, -lower alkylene-N(lower alkyl)-lower alkylene-, -lower alkylene-N(lower alkyl)-lower alkylene-O—, -lower alkylene-NH-lower alkylene-, -lower alkylene-SO$_2$—NH-lower alkylene-, —N(lower alkyl)-CO-lower alkylene-, —N(lower alkyl)-lower alkylene-CO—, —N(lower alkyl)-lower alkylene-N(lower alkyl)-lower alkylene-, —N(phenyl)-lower alkylene-CO—, —NH—CO—, —NH—CO-lower alkylene-, —NH-lower alkylene-, —O-lower alkylene-CO—N(lower alkyl)-lower alkylene-, —O-lower alkylene-CO—, —NH-lower alkylene-CO—N(lower alkyl)-lower alkylene-, —S-lower alkylene-CO—N(lower alkyl)-lower alkylene-, —SO$_2$—N(lower alkyl)-lower alkylene-, —SO$_2$—NH-lower alkylene-, -lower alkenylene-CO—N(lower alkyl)-lower alkylene-, —N(phenyl)-lower alkylene-CO—N(lower alkyl)-lower alkylene-, and —CO-lower alkylene-O—CO—.

Either of the two bonds in $X_A$ may be bonded to $R^1$ or N, and either of the two bonds in $X_B$ may be bonded to $R^2$ or N.

Examples of "lower alkylene optionally substituted with one or more substituents selected from the group consisting of hydroxyl and oxo" represented by $A^1$ are $C_{1-6}$ alkylene and —CO—$C_{1-6}$ alkylene-.

Examples of heterocyclic groups of "heterocyclic group which is optionally substituted" represented by $R^3$ include pyridyl, pyrazinyl, pyrimidinyl, pyridazinyl, quinolyl, 1,2-dihydroquinolyl, 1,2,3,4-tetrahydroquinolyl, isoquinolyl, 1,2-dihydroisoquinolyl, 1,2,3,4-tetrahydroisoquinolyl, quinazolinyl, 1,2,3,4-tetrahydroquinazolinyl, quinoxalinyl, 1,2,3,4-tetrahydroquinoxalinyl, indolyl, 2,3-dihydroindolyl, isoindolyl, 1,3-dihydroisoindolyl, benzimidazolyl, 2,3-dihydrobenzimidazolyl, benzo[d]isothiazolyl, 2,3-dihydrobenzo[d]isothiazolyl, 2,3,4,5-tetrahydrobenzo[f]1,4-thiazepinyl, 1,7-naphthyridinyl, 1,2,3,4-tetrahydro-1,8-naphthyridinyl, benzo[d][1,3]dioxolyl, benzo[d]thiazolyl, benzo[d][1,3]oxathiolyl, 2H-chromenyl, 2H-pyranyl, benzofuryl, 3,4-dihydro-2H-benzo[b][1,4]thiazinyl, 2,3,4,5-tetrahydrobenzo[e][1,4]diazepinyl, 2,3,4,5-tetrahydrobenzo[b]azepinyl, 2,3-dihydrobenzo[d]thiazolyl, 2,3-dihydrobenzo[d]oxazolyl, 2,3,4,5-tetrahydrobenzo[c]azepinyl, 2,3,4,5-tetrahydrobenzo[b][1,4]thiazepinyl, benzo[d]oxazolyl, benzo[d]isoxazolyl, benzo[c][1,2,5]oxadiazolyl, 2H-pyranyl, 3,4-dihydroisoquinolyl, 2,3,4,5-tetrahydrobenzo[f][1,4]oxazepinyl, 1,2,3,5-tetrahydrobenzo[e][1,4]oxazepinyl, 2,3,4,5-tetrahydrobenzo[b][1,4]oxazepinyl, dibenzo[b,d]furyl, 9H-carbazolyl, benzo[c][1,2,5]oxadiazolyl, 1,2,3,4,5,6-hexahydrobenzo[b]azocinyl, 2,3-dihydrobenzofuryl, 3,4-dihydro-2H-benzo[b][1,4]oxazinyl, 2,4-dihydro-1H-benzo[d][1,3]oxazinyl, and benzo[b]thiophenyl.

Examples of substituents of "substituted heterocyclic group" represented by $R^3$ include the substituents (h1) to (h17) and (h20) to (h24), which are mentioned as substituents of heterocyclic groups represented by $R^1$ and $R^2$. Among these, preferable substituents are (h1), (h2), (h5), (h6), (h8), (h10), (h11), (h12) and (h20), and more preferable substituents are (h1) and/or (h2).

Examples of aryl groups of "aryl group which is substituted" represented by $R^3$ include those as defined above.

When $R^4$ and $R^5$ in General Formula (2) are linked to form a ring together with the neighboring nitrogen, examples of the group —$NR^4R^5$ include the following:

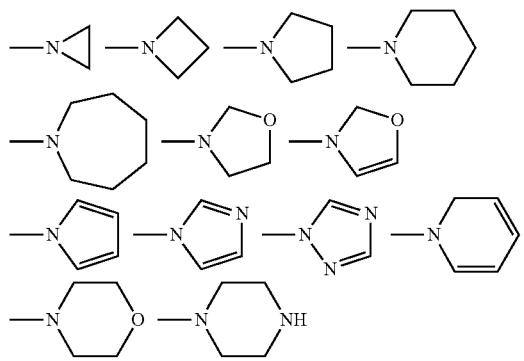

Each of the ring may optionally have one or more substituents selected from the group consisting of oxo; lower alkyl; phenyl lower alkyl; halo-phenyl lower alkyl; and amino optionally substituted with one or more substituents selected from the group consisting of lower alkyl, phenyl and halophenyl.

The amino compound of the present invention represented by General Formula (1) or its salt can be readily produced by persons skilled in the art using technical knowledge, based on the Examples and Reference Examples of the present specification. For example, the amino compound or its salt can be produced according to the processes shown in the following reaction formulae.

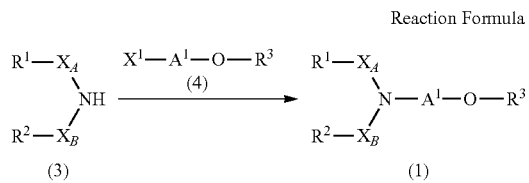

Reaction Formula 1 wherein $R^1$, $R^2$, $R^3$, $X_A$, $X_B$ and $A^1$ are the same as above; and $X^1$ is a leaving group.

The reaction of the compound of Formula (3) with the compound of Formula (4) can be performed in a general inert solvent or without using any solvent, in the presence or absence of a basic compound.

Examples of the leaving groups represented by $X^1$ include halogen atoms (e.g., chlorine, bromine, iodine, and like atoms), lower alkanesulfonyloxy (e.g., methanesulfonyloxy), halo substituted lower alkane sulfonyloxy (e.g., trifluoromethanesulfonyloxy), arylene sulfonyloxy (e.g., p-toluenesulfonyloxy, benzenesulfonyloxy), etc.

Examples of inert solvents include water; ethers such as dioxane, tetrahydrofuran, diethylether, diethylene glycol dimethyl ether, and ethylene glycol dimethyl ether; aromatic hydrocarbons such as benzene, toluene, and xylene; halogenated hydrocarbons such as dichloromethane, dichloroethane, chloroform, and carbon tetrachloride; lower ($C_{1-6}$) alcohols such as methanol, ethanol, and isopropanol; ketones such as acetone and methyl ethyl ketone; polar solvents such as dimethylformamide (DMF), dimethyl sulfoxide (DMSO), hexamethylphosphoric triamide, and acetonitrile; and mixtures thereof.

A wide variety of known basic compounds can be used as the basic compound. Examples of usable basic compounds include inorganic bases, for example, alkali metal hydroxides such as sodium hydroxide, potassium hydroxide, cesium hydroxide, and lithium hydroxide; alkali metal carbonates such as sodium carbonate, potassium carbonate, cesium carbonate, lithium carbonate, lithium hydrogencarbonate, sodium hydrogencarbonate, and potassium hydrogencarbonate; alkali metals such as sodium and potassium; sodium amide; sodium hydride; and potassium hydride; and organic bases, for example, alkali metal alcoholates such as sodium methoxide, sodium ethoxide, potassium methoxide, and potassium ethoxide; triethylamine, tripropylamine, pyridine, quinoline, 1,5-diazabicyclo[4.3.0]nonene-5 (DBN), 1,8-diazabicyclo[5.4.0]undecene-7 (DBU), and 1,4-diazabicyclo[2.2.2]octane (DABCO). These basic compounds can be used singly or in a combination of two or more.

The above reaction may be performed by adding as a reaction accelerator an alkali metal iodide such as potassium iodide or sodium iodide to the reaction system, as required.

The compound of Formula (4) is typically used in an amount of at least 0.5 moles, and preferably about 0.5 to about 10 moles, per mole of the compound of Formula (3).

The amount of basic compound is typically 0.5 to 10 moles, and preferably 0.5 to 6 moles, per mole of the compound of Formula (3).

The reaction is typically performed at a temperature of 0 to 250° C., and preferably 0 to 200° C., and is typically completed in about 1 to about 80 hours.

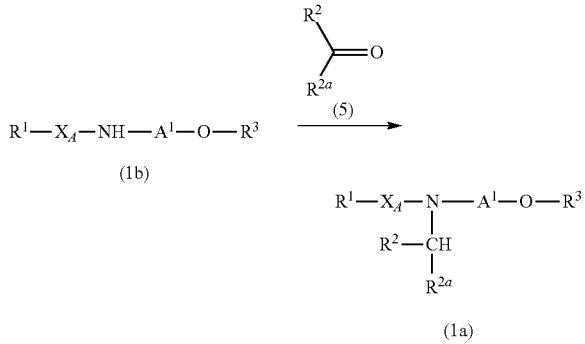

Reaction Formula 2 wherein $R^1$, $R^2$, $R^3$, $X_A$ and $A^1$ are the same as above; and $R^{2a}$ is hydrogen or lower alkyl.

Examples of lower alkyl groups represented by $R^{2a}$ include linear or branched alkyl groups with 1 to 6 carbon atoms, such as methyl, ethyl, n-propyl, and isopropyl.

The reaction between the compound of Formula (1b) and the compound of Formula (5) is performed, for example, in an inert solvent or suitable solvent, in the presence of a reducing agent.

Examples of usable solvents include water; lower ($C_{1-6}$) alcohols such as methanol, ethanol, isopropanol, butanol, tert-butanol, and ethylene glycol; aliphatic acids such as acetonitrile, formic acid, and acetic acid; ethers such as diethylether, tetrahydrofuran, dioxane, monoglyme, and diglyme; aromatic hydrocarbons such as benzene, toluene, and xylene; halogenated hydrocarbons such as dichloromethane, dichloroethane, chloroform, and carbon tetrachloride; and mixtures thereof.

Examples of reducing agents include aliphatic acids such as formic acid; aliphatic acid alkali metal salts such as sodium formate; hydride reducing agents such as sodium borohydride, sodium cyanoborohydride, sodium triacetoxyborohydride, sodium trimethoxyborohydride, and lithium aluminium hydride; and mixtures thereof, or mixtures of aliphatic acids or aliphatic acid alkali metal salts and hydride reducing agents; and catalytic hydrogenation reducing agents such as palladium black, palladium carbon, platinum oxide, platinum black, and Raney nickel.

When an aliphatic acid such as formic acid, or an aliphatic acid alkali metal salt such as sodium formate is used as a reducing agent, a suitable reaction temperature is typically about room temperature to about 200° C., and preferably about 50 to about 150° C. The reaction is typically completed in about 10 minutes to about 10 hours. Preferably, the aliphatic acid or aliphatic acid alkali metal salt is used in large excess relative to the compound of Formula (1b).

When a hydride reducing agent is used, a suitable reaction temperature is typically about −80 to about 100° C., and preferably about −80 to about 70° C. The reaction is typically completed in about 30 minutes to about 60 hours. The hydride reducing agent is typically used in an amount of about 1 to about 20 moles, and preferably about 1 to about 10 moles, per mole of the compound of Formula (1b). Particularly when lithium aluminium hydride is used as a hydride reducing agent, it is preferable to use as a solvent an ether such as diethyl ether, tetrahydrofuran, dioxane, monoglyme, and diglyme; or an aromatic hydrocarbon such as benzene, toluene, or xylene. To the reaction system of the reaction may be added an amine such as trimethylamine, triethylamine, or N-ethyldiisopropylamine; or a molecular sieve such as molecular sieve 3A (MS-3A) or molecular sieve 4A (MS-4A).

When a catalytic hydrogenation reducing agent is used, the reaction is typically performed at about −30 to about 100° C., and preferably about 0 to about 60° C., in a hydrogen atmosphere at typically about atmospheric pressure to about 20 atm, and preferably at about atmospheric pressure to about 10 atm, or in the presence of a hydrogen doner such as formic acid, ammonium formate, cyclohexene, or hydrazine hydrate. The reaction is typically completed in about 1 to about 12 hours. The catalytic hydrogenation reducing agent is typically used in an amount of about 0.1 to about 40 wt %, and preferably about 1 to about 20 wt %, based on the compound of Formula (1b).

In the reaction of the compound of Formula (1b) and the compound of Formula (5), the compound of Formula (5) is typically used in an amount of at least 1 mole, and preferably 1 to 5 moles, per mole of the compound of Formula (1b).

The compound of Formula (5) may also be a hydrated compound wherein a water molecule is attached to a carbonyl group.

Reaction Formula 3

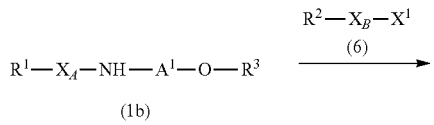

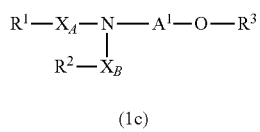

wherein $R^1$, $R^2$, $R^3$, $X_A$, $X_B$, $A^1$ and $X^1$ are the same as above.

The reaction of the compound of Formula (1b) with the compound of Formula (6) can be performed under the same reaction conditions as those for the reaction of the compound of Formula (3) with the compound of Formula (4) shown in Reaction Formula 1 above.

Alternatively, the reaction of the compound of Formula (1b) with the compound of Formula (6) can be performed by the known "Ullmann condensation", "Palladium coupling reaction", etc. The reaction can be preferably adopted especially when $X_B$ is a bond and $R^2$ is aryl or heterocyclic (especially unsaturated heterocyclic) group optionally substituted. For example, the reaction can be carried out in a solvent (e.g., toluene, tetrahydrofuran (THF), N,N-dimethylformamide (DMF), N-methylpyrrolidone (NMP) and dimethyl sulfoxide (DMSO)), in the presence of transition metal compound (e.g., $Pd(OAc)_2$, $Pd_2(dba)_3$ and copper iodide), a basic compound (e.g., sodium tert-butoxide, $K_3PO_4$ and $Cs_2CO_3$), and if necessary a phosphine (e.g., xantphos, tri-tert-butylphosphine, 2,2'-bis(diphenylphosphino)-1,1'-binaphthyl(BINAP), tetrafluoroborate, N,N'-dimethylethylenediamine, and L-proline).

The reaction temperature is not limited, and the reaction is usually carried out at ambient temperature, under warming or under heating.

The compound of Formula (3), which is used as a starting material, can be easily prepared by the process shown in the following reaction formula.

Reaction Formula 4

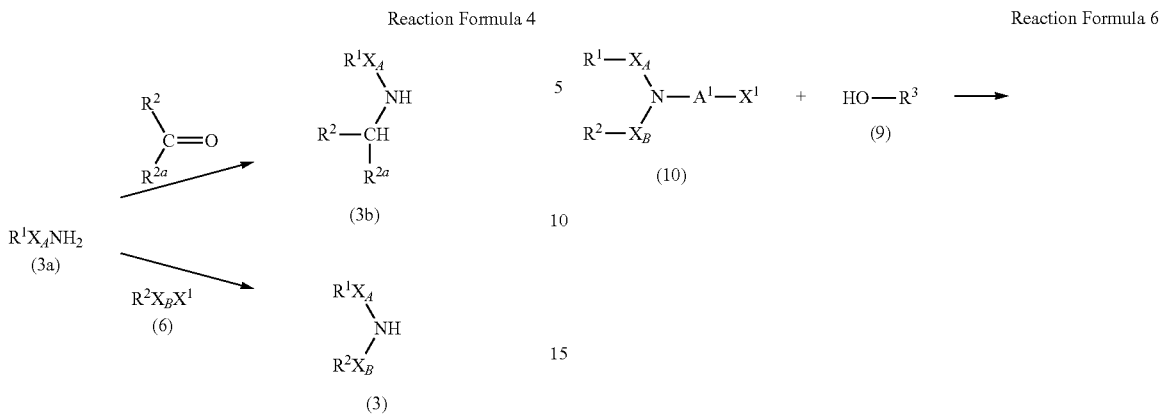

wherein $R^1$, $R^2$, $R^{2a}$, $X_A$, $X_B$ and $X^1$ are the same as above.

The reaction of the compound of Formula (3a) with the compound of Formula (7) can be performed under the same reaction conditions as those for the reaction of the compound of Formula (1b) with the compound of Formula (5) shown in Reaction Formula 2 above.

The reaction of the compound of Formula (3a) with the compound of Formula (6) can be performed under the same reaction conditions as those for the reaction of the compound of Formula (3) with the compound of Formula (4) shown in Reaction Formula 1 above.

Reaction Formula 5

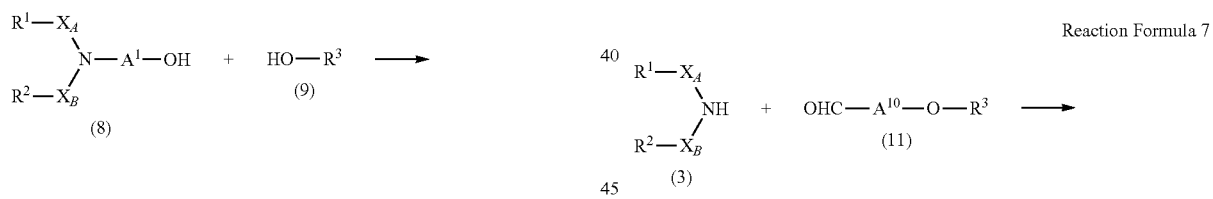

wherein $R^1$, $R^2$, $R^3$, $X_A$, $X_B$ and $A^1$ are the same as above.

The reaction of the compound of Formula (8) with the compound of Formula (9) can be performed by the known "Mitsunobu reaction" conditions (e.g., using diethyl azodicarboxylate (DEAD) and triphenylphosphine).

Reaction Formula 6 wherein $R^1$, $R^2$, $R^3$, $X_A$, $X_B$, $X^1$ and $A^1$ are the same as above.

The reaction of the compound of Formula (10) with the compound of Formula (9) can be performed by the known O-alkylation reaction. For example, The reaction can be performed in the presence of an inert solvent (e.g., DMF, THF, dioxane and acetonitrile) and in the presence of a basic compound (e.g., $K_2CO_3$ and $Cs_2CO_3$).

The reaction temperature is not limited, and the reaction is usually carried out at ambient temperature, under warming or under heating.

Reaction Formula 7 wherein $R^1$, $R^2$, $R^3$, $X_A$ and $X_B$ are the same as above; and $A^{10}$ is a divalent residue which is obtained by removing —$CH_2$— from group $A^1$.

The reaction of the compound of Formula (3) with the compound of Formula (11) can be performed under the same reaction conditions as those for the reaction of the compound of Formula (1b) with the compound of Formula (5) shown in Reaction Formula 2 above, Reaction Formula 8

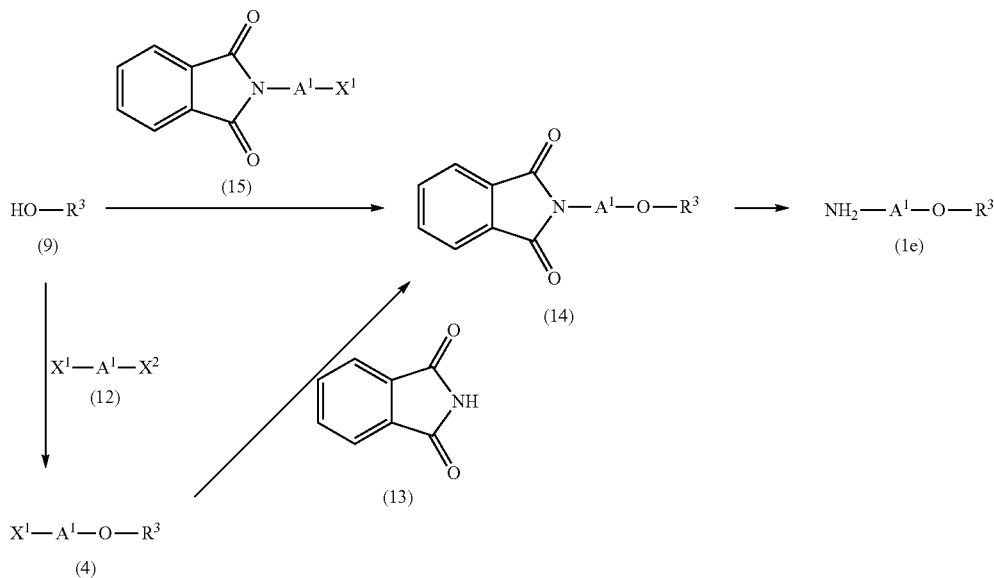

wherein $R^3$, $X^1$, $X^2$ and $A^1$ are the same as above.

The reaction of the compound of Formula (9) with the compound of Formula (15) can be performed under the same reaction conditions as those for the reaction of the compound of Formula (9) with the compound of Formula (10) shown in Reaction Formula 6 above.

The reaction of the compound of Formula (9) with the compound of Formula (12) can be performed under the same reaction conditions as those for the reaction of the compound of Formula (9) with the compound of Formula (10) shown in Reaction Formula 6 above.

The reaction of the compound of Formula (4) with the compound of Formula (13) can be performed by the known N-alkylation reaction. For example, The reaction can be performed in the presence of an inert solvent (e.g., DMF, THF, dioxane and acetonitrile) and in the presence of a basic compound (e.g., $K_2CO_3$ and $Cs_2CO_3$).

The N-alkylation reaction temperature is not limited, and the reaction is usually carried out at ambient temperature, under warming or under heating.

The reaction converting the compound of Formula (14) to the compound of Formula (1e) can be performed by the known method. For example, The reaction can be performed in the presence of hydrazine.

Reaction Formula 9

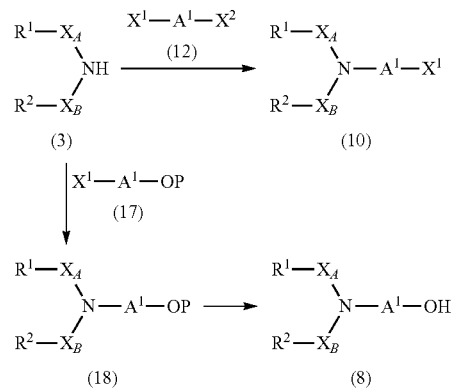

wherein $R^1$, $R^2$, $X_A$, $X_B$, $X^1$ and $A^1$ are the same as above; and P is a hydroxyl-protecting group and $X^2$ is a leaving group.

Examples of hydroxyl-protecting groups represented by P include tetrahydropyran-2-yl, methoxymethyl, benzyl.

Examples of the leaving groups represented by $X^2$ include halogen atoms (e.g., chlorine, bromine, iodine, and like atoms), lower alkanesulfonyloxy (e.g., methanesulfonyloxy), halo substituted lower alkane sulfonyloxy (e.g., trifluoromethanesulfonyloxy), arylene sulfonyloxy (e.g., p-toluenesulfonyloxy, benzenesulfonyloxy), etc.

When $X^1$ and $X^2$ are both halogen atoms, the halogen atom represented by $X^2$ is preferably one having an atomic number equal to or higher than that of the halogen atom represented by $X^1$.

The reaction of the compound of Formula (3) with the compound of Formula (12) can be performed under the same reaction conditions as those for the reaction of the compound of Formula (3) with the compound of Formula (4) shown in Reaction Formula 1 above.

The reaction of the compound of Formula (3) with the compound of Formula (17) can be performed under the same reaction conditions as those for the reaction of the compound of Formula (3) with the compound of Formula (4) shown in Reaction Formula 1 above.

The reaction converting the compound of Formula (18) to the compound of Formula (8) can be performed under the known deprotection method depending on the type of the protecting group (P).

The compound of Formula (1) according to the present invention and the starting materials thereof can be produced using a known or conventional synthetic method other than the production method described above.

In addition, compounds in the form in which a solvate (for example, a hydrate, ethanolate, etc.) was added to the starting material compounds and object compounds shown in each of the reaction formulae are included in each of the formulae.

The compound of Formula (1) according to the present invention includes stereoisomers and optical isomers.

The starting material compounds and object compounds represented by each of the reaction formulae can be used in an appropriate salt form.

Each of the object compounds obtained according to the above reaction formulae can be isolated and purified from the reaction mixture by, for example, after cooling the reaction mixture, performing an isolation procedure such as filtration, concentration, extraction, etc., to separate a crude reaction product, and then subjecting the crude reaction product to a usual purification procedure such as column chromatography, recrystallization, etc.

Among the compounds of the present invention, those having a basic group or groups can easily form salts with common pharmaceutically acceptable acids. Examples of such acids include hydrochloric acid, hydrobromic acid, nitric acid, sulfuric acid, phosphoric acid and other inorganic acids, methansulfonic acid, p-toluenesulfonic acid, acetic acid, citric acid, tartaric acid, maleic acid, fumaric acid, malic acid, lactic acid and other organic acids, etc.

Among the compounds of the present invention, those having an acidic group or groups can easily form salts by reacting with pharmaceutically acceptable basic compounds. Examples of such basic compounds include sodium hydroxide, potassium hydroxide, calcium hydroxide, sodium carbonate, potassium carbonate, sodium hydrogencarbonate, potassium hydrogencarbonate, etc.

In the compound of the present invention, one or more atoms can be substituted with one or more isotopic atoms. Examples of the isotopic atoms include deuterium ($^2H$), tritium ($^3H$), $^{13}C$, $^{14}N$, $^{18}O$, etc.

The following is an explanation of pharmaceutical preparations comprising the compound of the present invention as an active ingredient.

Such pharmaceutical preparations are obtained by formulating the compound of the present invention into usual pharmaceutical preparations, using usually employed diluents or excipients such as fillers, extenders, binders, wetting agents, disintegrants, surfactants, lubricants, etc.

The form of such pharmaceutical preparations can be selected from various forms according to the purpose of therapy. Typical examples include tablets, pills, powders, solutions, suspensions, emulsions, granules, capsules, suppositories, injections (solutions, suspensions, etc.) and the like.

To form tablets, any of various known carriers can be used, including, for example, lactose, white sugar, sodium chloride, glucose, urea, starch, calcium carbonate, kaolin, crystalline cellulose and other excipients; water, ethanol, propanol, simple syrup, glucose solutions, starch solutions, gelatin solutions, carboxymethylcellulose, shellac, methylcellulose, potassium phosphate, polyvinylpyrrolidone and other binders; dry starch, sodium alginate, agar powder, laminaran powder, sodium hydrogencarbonate, calcium carbonate, aliphatic acid esters of polyoxyethylenesorbitan, sodium laurylsulfate, stearic acid monoglyceride, starch, lactose and other disintegrants; white sugar, stearin, cacao butter, hydrogenated oils and other disintegration inhibitors; quaternary ammonium base, sodium lauryl sulfate and other absorption promoters; glycerin, starch and other wetting agents; starch, lactose, kaolin, bentonite, colloidal silicic acid and other adsorbents; purified talc, stearates, boric acid powder, polyethylene glycol and other lubricants; etc.

Such tablets may be coated with usual coating materials as required, to prepare, for example, sugar-coated tablets, gelatin-coated tablets, enteric-coated tablets, film-coated tablets, double- or multi-layered tablets, etc.

To form pills, any of various known carriers can be used, including, for example, glucose, lactose, starch, cacao butter, hydrogenated vegetable oils, kaolin, talc and other excipients; gum arabic powder, tragacanth powder, gelatin, ethanol and other binders; laminaran, agar and other disintegrants; etc.

To form suppositories, any of various known carriers can be used, including, for example, polyethylene glycol, cacao butter, higher alcohols, esters of higher alcohols, gelatin, semisynthetic glycerides, etc.

To form an injection, a solution, emulsion or suspension is sterilized and preferably made isotonic with blood. Any of various known widely used diluents can be employed to prepare the solution, emulsion or suspension. Examples of such diluents include water, ethanol, propylene glycol, ethoxylated isostearyl alcohol, polyoxylated isostearyl alcohol, aliphatic acid esters of polyoxyethylene sorbitan, etc. In this case, the pharmaceutical preparation may contain sodium chloride, glucose or glycerin in an amount sufficient to prepare an isotonic solution, and may contain usual solubilizers, buffers, analgesic agents, etc., and further, if necessary, coloring agents, preservatives, flavors, sweetening agents, etc., and/or other medicines.

The proportion of the compound of the present invention in the pharmaceutical preparation is not limited and can be suitably selected from a wide range. It is usually preferable that the pharmaceutical preparation contain the compound of the present invention in a proportion of 1 to 70 wt. %.

The route of administration of the pharmaceutical preparation according to the present invention is not limited, and the preparation can be administered by a route suitable for the form of the preparation, the patient's age and sex, the conditions of the disease, and other conditions.

For example, tablets, pills, solutions, suspensions, emulsions, granules and capsules are administered orally. Injections are intravenously administered singly or as mixed with usual injection transfusions such as glucose solutions, amino acid solutions or the like, or singly administered intramuscularly, intracutaneously, subcutaneously or intraperitoneally, as required. Suppositories are administered intrarectally.

The dosage of the pharmaceutical preparation is suitably selected according to the method of use, the patient's age and sex, the severity of the disease, and other conditions, and is usually about 0.001 to about 100 mg/kg body weight/day, and preferably 0.001 to 50 mg/kg body weight/day, in single or divided doses.

Since the dosage varies depending on various conditions, a dosage smaller than the above range may be sufficient, or a dosage larger than the above range may be required.

When administered to the human body as a pharmaceutical, the compound of the present invention may be used concurrently with, or before or after, antithrombotics such as blood clotting inhibitors and antiplatelet agents (e.g., warfarin, aspirin, etc.). Further, the present compound may be used concurrently with, or before or after, drugs for treating chronic diseases, such as antihypertensive drugs (ACE inhibitors, beta blockers, angiotensin II receptor antagonists), heart failure drugs (cardiotonic agents, diuretics), and diabetes treatment agents.

The compound of the present invention has potent blocking effects on human Kv1.5 and/or GIRK1/4 channels, and weak blocking effects on HERG channels. Thus, the compound of the invention has characteristics as an atrial-selective $K^+$ channel-blocking agent.

Therefore, the compound of the invention can be used as a pharmacologically active substance that is safer and provides a more potent effect on the prolongation of the atrial refractory period than conventional antiarrhythmic agents. The compound of the invention is preferably used as a therapeutic agent for arrhythmia such as atrial fibrillation, atrial flutter, and atrial tachycardia (elimination of arrhythmia and/or prevention of the occurrence of arrhythmia). The compound of the invention is particularly preferably used as a therapeutic agent for atrial fibrillation (defibrillation and maintenance of sinus rhythm). The compound of the invention can also be used as a prophylactic agent for thromboembolism such as cerebral infarction and as a therapeutic agent for heart failure.

The compound having potent blocking effects on both human Kv1.5 and human GIRK1/4 channels has more potent atrial refractory period prolongation effects and is highly safe, compared to compounds inhibiting either one of the channels. Furthermore, this compound has greater therapeutic effects on atrial fibrillation (defibrillation and maintenance of sinus rhythm) than compounds inhibiting either one of the channels. Therefore, the compound having potent blocking effects on both the human Kv1.5 and human GIRK1/4 channels is particularly useful as a therapeutic agent for arrhythmia such as atrial fibrillation, atrial flutter, and atrial tachycardia (termination of arrhythmia and/or prevention of the occurrence of arrhythmia). This compound is particularly useful as a therapeutic agent for atrial fibrillation (defibrillation and maintenance of sinus rhythm).

3. Third Invention (Benzodiazepine Compound)

The present inventors conducted extensive research to develop a compound that blocks the $I_{Kur}$ current (Kv1.5 channel) and/or the $I_{KACh}$ current (GIRK1/4 channel) potently and more selectively than other $K^+$ channels. As a result, the inventors found that a novel benzodiazepine compound represented by General Formula (1) below could be the desired compound. The present invention has been accomplished based on the above findings.

The present invention provides benzodiazepine compounds, and pharmaceutical compositions comprising the benzodiazepine compounds as summarized in items 1 to 7 below.

Item 1. A benzodiazepine compound represented by General Formula (1):

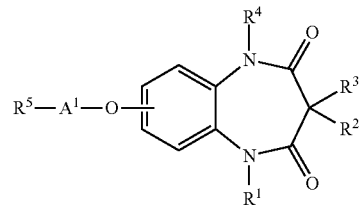

or a salt thereof,
wherein $R^1$, $R^2$, $R^3$, and $R^4$ are each independently hydrogen or lower alkyl; $R^2$ and $R^3$ may be linked to form lower alkylene;
$A^1$ is lower alkylene optionally substituted with one or more hydroxyls; and $R^5$ is an aryl or heterocyclic group, each of which is optionally substituted.

Item 2. A pharmaceutical composition comprising a benzodiazepine compound represented by Formula (1) or a salt thereof according to Item 1, and a pharmacologically acceptable carrier.

Item 3. A pharmaceutical composition according to Item 2 for preventing and/or treating arrhythmia.

Item 4. A benzodiazepine compound represented by Formula (1) or a salt thereof according to Item 1 for use in the pharmaceutical composition.

Item 5. Use of a benzodiazepine compound represented by Formula (1) or a salt thereof according to Item 1 as a pharmaceutical composition.

Item 6. Use of a benzodiazepine compound represented by Formula (1) or a salt thereof according to Item 1 for the production of a pharmaceutical composition.

Item 7. A method of preventing and/or treating arrhythmia, comprising administering to a patient a benzodiazepine compound represented by Formula (1) or a salt thereof according to Item 1.

The groups represented by, or substituents of, $R^1$, $R^2$, $R^3$, $R^4$, $R^5$ and $A^1$ in the specification are described below.

The term "one or more" may be preferably 1 to 6, and more preferably 1 to 3.

Examples of "lower alkyl" include linear or branched alkyl groups having 1 to 6 carbon atoms, such as methyl, ethyl, n-propyl, isopropyl, n-butyl, isobutyl, tert-butyl, sec-butyl, n-pentyl, neopentyl, n-hexyl, isohexyl, and 3-methylpentyl.

Examples of "lower alkylene" include linear or branched alkylene groups having 1 to 6 carbon atoms, such as methylene, ethylene, trimethylene, 2-methyltrimethylene, 2,2-dimethyltrimethylene, 1-methyltrimethylene, methylmethylene, ethylmethylene, tetramethylene, pentamethylene, and hexamethylene.

Examples of "lower alkenylene" include linear or branched alkenylene groups having 2 to 6 carbon atoms, such as, ethenylene, propenylene, butenylene, pentenylene, and hexenylene.

Examples of "cyclo lower alkyl" include linear or branched cyclo alkyl having 3 to 6 carbon atoms, such as cyclopropyl, cyclobutyl, cyclopentyl, and cyclohexyl.

Examples of "lower alkoxy" include linear or branched alkoxy groups having 1 to 6 carbon atoms, such as methoxy, ethoxy, n-propoxy, isopropoxy, n-butoxy, isobutoxy, tert-butoxy, sec-butoxy, n-pentyloxy, neopentyloxy, n-hexyloxy, isohexyloxy, and 3-methylpentyloxy.

Examples of "halogen" are fluorine, chlorine, bromine, and iodine.

Examples of "lower alkylenedioxy" include linear or branched alkylenedioxy groups having 1 to 4 carbon atoms, such as methylenedioxy, ethylenedioxy, trimethylenedioxy, and tetramethylenedioxy.

Examples of "lower alkanoyl" include linear or branched alkanoyl groups having 1 to 6 carbon atoms, such as formyl, acetyl, propionyl, butyryl, isobutyryl, pentanoyl, tert-butylcarbonyl, and hexanoyl.

Examples of "lower alkoxycarbonyl" include (linear or branched alkoxy having 1 to 6 carbon atoms)carbonyls, such as methoxycarbonyl, ethoxycarbonyl, propoxycarbonyl, butoxycarbonyl, isobutoxycarbonyl, and tert-butoxycarbonyl.

Examples of "aralkyl group" include groups wherein aryl groups are substituted on the alkyl groups, such as benzyl and phenethyl.

Examples of "aryl group" include monocyclic or polycyclic aryl groups, such as phenyl, tolyl, xylyl, and naphthyl.

Examples of "heterocyclic group" include saturated or unsaturated monocyclic or polycyclic heterocyclic groups containing at least one hetero atom selected from the group consisting of oxygen, sulfur and nitrogen. Examples of preferable heterocyclic groups include the followings (a) to (m) groups:

(a) unsaturated 3- to 8-membered, preferably 5- or 6-membered heteromonocyclic groups containing 1 to 4 nitrogen atom(s), for example, pyrrolyl, pyrrolinyl, imidazolyl, pyrazolyl, pyridyl, and its N-oxide, pyrimidinyl, pyrazinyl, pyridazinyl, triazolyl (e.g., 4H-1,2,4-triazolyl, 1H-1,2,3-triazolyl, 2H-1,2,3-triazolyl, etc.), tetrazolyl (e.g., 1H-tetrazolyl, 2H-tetrazolyl, etc.), dihydrotriazinyl (e.g., 4,5-dihydro-1,2,4-triazinyl, 2,5-dihydro-1,2,4-triazinyl, etc.), etc.;

(b) saturated 3- to 8-membered, preferably 5- or 6-membered heteromonocyclic groups containing 1 to 4 nitrogen atom(s), for example, azetidinyl, pyrrolidinyl, imidazolidinyl, piperidinyl, pyrazolidinyl, piperazinyl, etc.;

(c) unsaturated condensed 7- to 12-membered heterocyclic groups containing 1 to 5 nitrogen atom(s), for example, indolyl, dihydroindolyl (e.g., 2,3-dihydroindolyl, etc.), isoindolyl, indolizinyl, benzimidazolyl, quinolyl, dihydroquinolyl (e.g. 1,4-dihydroquinolyl, etc.), tetrahydroquinolyl (1,2,3,4-tetrahydroquinolyl, etc.), isoquinolyl, dihydroisoquinolyl (e.g., 3,4-dihydro-1H-isoquinolyl, 1,2-dihydroisoquinolyl, etc.), tetrahydroisoquinolyl (e.g., 1,2,3,4-tetrahydro-1H-isoquinolyl, 5,6,7,8-tetrahydroisoquinolyl, etc.), carbostyril, dihydrocarbostyril (e.g., 3,4-dihydrocarbostyril, etc.), indazolyl, benzotriazolyl, tetrazolopyridyl, tetrazolopyridazinyl (e.g., tetrazolo[1,5-b]pyridazinyl, etc.), dihydrotriazolopyridazinyl, imidazopyridyl (e.g., imidazo[1,2-a]pyridyl, imidazo[4,5-c]pyridyl, etc.,), naphthyridinyl, cinnolinyl, quinoxalinyl, quinazolinyl, pyrazolopyridyl (e.g., pyrazolo[2,3-a]pyridyl, etc.), etc.;

(d) unsaturated 3- to 8-membered, preferably 5- or 6-membered heteromonocyclic groups containing 1 to 2 oxygen atom(s), for example, furyl, etc.;

(e) unsaturated condensed 7- to 12-membered heterocyclic groups containing 1 to 3 oxygen atom(s), for example, benzofuryl, dihydrobenzofuryl (e.g. 2,3-dihydrobenzo[b]furyl, etc.), chromanyl, benzodioxanyl (e.g., 1,4-benzodioxanyl, etc.), dihydrobenzoxazinyl (e.g., 2,3-dihydrobenz-1,4-oxazinyl, etc.), benzodioxolyl(benzo[1,3]dioxolyl, etc.), etc.;

(f) unsaturated 3- to 8-membered, preferably 5- or 6-membered heteromonocyclic groups containing 1 to 2 oxygen atom(s) and 1 to 3 nitrogen atom(s), for example, oxazolyl, isoxazolyl, oxadiazolyl (e.g., 1,2,4-oxadiazolyl, 1,3,4-oxadiazolyl, 1,2,5-oxadiazolyl, etc.), etc.;

(g) saturated 3- to 8-membered, preferably 5- or 6-membered heteromonocyclic groups containing 1 to 2 oxygen atom(s) and 1 to 3 nitrogen atom(s), for example, morpholinyl, etc.;

(h) unsaturated condensed 7 to 12-membered heterocyclic groups containing 1 to 2 oxygen atom(s) and 1 to 3 nitrogen atom(s), for example, benzoxazolyl, benzoxadiazolyl, benzisoxazolyl, furopyridyl (e.g., furo[2,3-c]pyridyl, 6,7-dihydrofuro[2,3-c]pyridyl, furo[3,2-c]pyridyl, 4,5-dihydrofuro[3,2-c]pyridyl, furo[2,3-b]pyridyl, 6,7-dihydrofuro[2,3-b]pyridyl, etc.), etc.;

(i) unsaturated 3- to 8-membered, preferably 5- or 6-membered heteromonocyclic groups containing 1 to 2 sulfur atom(s) and 1 to 3 nitrogen atom(s), for example, thiazolyl, isothiazolyl, thiazolinyl, thiadiazolyl (e.g., 1,2,4-thiadiazolyl, 1,3,4-thiadiazolyl, 1,2,5-thiadiazolyl, 1,2,3-thiadiazolyl, etc.), etc.;

(j) saturated 3- to 8-membered, preferably 5- or 6-membered heteromonocyclic groups containing 1 to 2 sulfur atom(s) and 1 to 3 nitrogen atom(s), for example, thiazolidinyl, etc.;

(k) unsaturated 3- to 8-membered, preferably 5- or 6-membered heteromonocyclic groups containing a sulfur atom, for example, thienyl, etc.;

(l) unsaturated condensed 7- to 12-membered heterocyclic groups containing 1 to 3 sulfur atom(s), for example, benzothienyl (e.g. benzo[b]thienyl, etc.); and (m) unsaturated condensed 7- to 12-membered heterocyclic groups containing 1 to 2 sulfur atom(s) and 1 to 3 nitrogen atom(s), for example, benzothiazolyl, benzothiadiazolyl, thienopyridyl (e.g., thieno[2,3-c]pyridyl, 6,7-dihydrothieno[2,3-c]pyridyl, thieno[3,2-c]pyridyl, 4,5-dihydrothieno[3,2-c]pyridyl, thieno[2,3-b]pyridyl, 6,7-dihydrothieno[2,3-b]pyridyl, etc.), imidazothiazolyl (e.g., imidazo[2,1-b]thiazolyl, etc.), dihydroimidazothiazolyl (e.g., 2,3-dihydroimidazo[2,1-b]thiazolyl, etc.), thienopyrazinyl (e.g., thieno[2,3-b]pyrazinyl, etc.), etc.; wherein said heterocyclic groups may be substituted by one or more suitable substituents.

Substituents of "aryl and heterocyclic group, each of which is optionally substituted" represented by $R^5$ are each independently one or more substituents selected from the group consisting of:

(1) oxo;
(2) lower alkyl optionally substituted with one or more halogens or heterocyclic groups optionally substituted with one or more substituents selected from the group consisting of lower alkyl; lower alkoxy; lower alkanoyl; lower alkylsulfonyl; hydroxyl; halogen; carboxy; lower alkoxycarbonyl; amino optionally substituted with one or more substituents selected from the group consisting of lower alkyl, lower alkanoyl, and lower alkylsulfonyl; lower alkyl thio; cyano; and oxo;
(3) cyclo lower alkyl;
(4) lower alkoxy;
(5) aryl optionally substituted with one or more substituents selected from the group consisting of lower alkyl; lower alkoxy; lower alkanoyl; lower alkylsulfonyl; hydroxyl; halogen; carboxy; lower alkoxycarbonyl; amino optionally substituted with one or more substituents selected from the group consisting of lower alkyl, lower alkanoyl, and lower alkylsulfonyl; lower alkyl thio; and cyano;
(6) aralkyl optionally substituted with one or more substituents selected from the group consisting of lower alkyl; lower alkoxy; lower alkanoyl; lower alkylsulfonyl; hydroxyl; halogen; carboxy; lower alkoxycarbonyl; amino optionally substituted with one or more substituents selected from the group consisting of lower alkyl, lower alkanoyl, and lower alkylsulfonyl; lower alkyl thio; cyano; and oxo;
(7) a heterocyclic group optionally substituted with one or more substituents selected from the group consisting of lower alkyl; lower alkoxy; lower alkanoyl; lower alkylsulfonyl; hydroxyl; halogen; carboxy; lower alkoxycarbonyl; amino optionally substituted with one or more substituents selected from the group consisting of lower alkyl, lower alkanoyl, and lower alkylsulfonyl; lower alkyl thio; cyano; and oxo;
(8) hydroxyl;
(9) halogen;
(10) carboxy;
(11) lower alkanoyl;
(12) lower alkoxycarbonyl;
(13) lower alkylenedioxy;
(14) cyano;
(15) nitro;
(16) sulfo;
(17) amino optionally substituted with one or more substituents selected from the group consisting of lower alkyl, lower alkanoyl, and lower alkylsulfonyl;
(18) lower alkylsulfonyl; and
(19) lower alkyl thio.

The "heterocyclic group" in Item (7) above can be selected from the above-mentioned groups (a) to (m).

Examples of preferable benzodiazepine compounds represented by General Formula (1) include those wherein:
$R^1$, $R^2$, $R^3$, and $R^4$ are each independently lower alkyl;
$A^1$ is lower alkylene; and $R^5$ is piperidyl, piperazinyl, indolyl, benzimidazolyl, 2,3-dihydrobenzimidazolyl, 2,3-dihydroindolyl, furo[2,3-c]pyridyl, 6,7-dihydrofuro[2,3-c]pyridyl, furo[3,2-c]pyridyl, 4,5-dihydrofuro[3,2-c]pyridyl, furo[2,3-b]pyridyl, 6,7-dihydrofuro[2,3-b]pyridyl, thieno[2,3-c]pyridyl, 6,7-dihydrothieno[2,3-c]pyridyl, 1,2,3,4-tetrahydro-1H-isoquinolyl, carbostyril, 3,4-dihydrocarbostyril, quinolyl, 1,4-dihydroquinolyl, 1,2,3,4-tetrahydroquinolyl, pyrido[3,4-d]imidazolyl, or pyrido[2,3-d]imidazolyl; each of which is optionally substituted with one or more substituents selected from the group consisting of:
(1) oxo;
(2a) lower ($C_{1-3}$) alkyl optionally substituted with 6,7-dihydrofuro[2,3-c]pyridyl or 4,5-dihydrofuro[3,2-c]pyridyl, each of which is optionally substituted with one or more substituents selected from the group consisting of oxo and lower alkyl;
(4a) $C_{1-3}$ alkoxy;
(5a) phenyl;
(6a) benzyl;
(7a) pyridyl optionally substituted with one or more substituents selected from the group consisting of lower alkyl and lower alkoxy;
(9) halogen;
(10) carboxy;
(12a) $C_{1-3}$ alkoxycarbonyl; and
(13a) $C_{1-4}$ alkylenedioxy.

The benzodiazepine compound of the present invention represented by Formula (1) or its salt can be readily produced by persons skilled in the art using technical knowledge, based on the Examples and Reference Examples of the present specification. For example, the benzodiazepine compound or its salt can be produced according to the processes shown in the following reaction formulae.

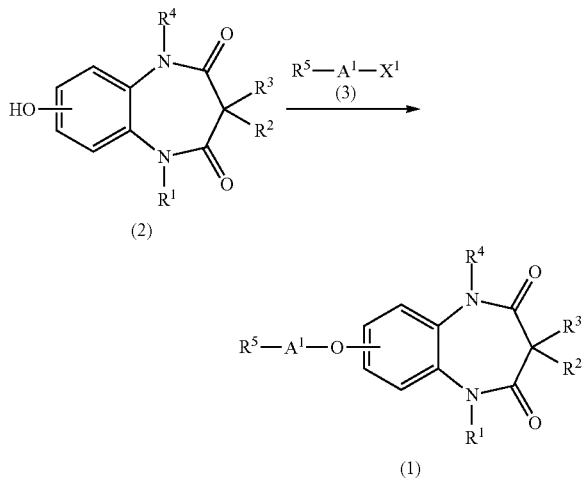

Reaction Formula 1 wherein $R^1$, $R^2$, $R^3$, $R^4$, $R^5$, and $A^1$ are the same as above, and $X^1$ is halogen or hydroxyl.

The reaction of the compound of Formula (2) with the compound of Formula (3) wherein $X^1$ is halogen can be performed in a general inert solvent or without using any solvent in the presence or absence of a basic compound.

Examples of inert solvents include water; ethers such as dioxane, tetrahydrofuran, diethyl ether, diethylene glycol dimethyl ether, and ethylene glycol dimethyl ether; aromatic hydrocarbons such as benzene, toluene, and xylene; halogenated hydrocarbons such as dichloromethane, dichloroethane, chloroform, and carbon tetrachloride; lower ($C_{1-6}$) alcohols such as methanol, ethanol, and isopropanol; ketones such as acetone and methyl ethyl ketone; polar solvents such as dimethylformamide (DMF), dimethyl sulfoxide (DMSO), hexamethylphosphoric triamide, and acetonitrile; and mixed solvents of such solvents.

The basic compound may be selected from various known compounds. Examples of such compounds include inorganic bases, for example, alkali metal hydroxides such as sodium hydroxide, potassium hydroxide, cesium hydroxide, and lithium hydroxide; alkali metal carbonates such as sodium carbonate, potassium carbonate, cesium carbonate, lithium carbonate, lithium hydrogencarbonate, sodium hydrogencarbonate, and potassium hydrogencarbonate; alkali metals such as sodium and potassium; sodium amide; sodium hydride; and potassium hydride; and organic bases, for example, alkali metal alcoholates such as sodium methoxide, sodium ethoxide, potassium methoxide, and potassium ethoxide; triethylamine; tripropylamine; pyridine; quinoline; 1,5-diazabicyclo[4.3.0]nonene-5 (DBN); 1,8-diazabicyclo[5.4.0]undecene-7 (DBU); and 1,4-diazabicyclo[2.2.2]octane (DABCO). These basic compounds can be used singly or in a combination of two or more.

The above reaction may be performed by adding an alkali metal iodide such as potassium iodide or sodium iodide to the reaction system, as required.

The compound of Formula (3) is typically used in an amount of at least 0.5 moles, and preferably 0.5 to 10 moles, per mole of the compound of Formula (2).

The basic compound is typically used in an amount of 0.5 to 10 moles, and preferably 0.5 to 6 moles, per mole of the compound of Formula (2).

The reaction is typically performed at a temperature of 0° C. to 250° C., and preferably 0° C. to 200° C., and is typically completed in about 1 to about 80 hours.

The reaction of the compound of Formula (2) with the compound of Formula (3) wherein $X^1$ is hydroxyl is performed in a suitable solvent in the presence of a condensing agent.

Examples of solvents usable herein include water; halogenated hydrocarbons such as chloroform, dichloromethane, dichloroethane, and carbon tetrachloride; aromatic hydrocarbons such as benzene, toluene, and xylene; ethers such as diethyl ether, diisopropyl ether, tetrahydrofuran, and dimethoxyethane; esters such as methyl acetate, ethyl acetate, and isopropyl acetate; alcohols such as methanol, ethanol, isopropanol, propanol, butanol, 3-methoxy-1-butanol, ethyl cellosolve, and methyl cellosolve; aprotic polar solvents such as acetonitrile, pyridine, acetone, N,N-dimethyl formamide, dimethylsulfoxide, and hexamethylphosphoric triamide; and mixtures of such solvents.

Examples of condensing agents include azocarboxylates such as di-tert-butyl azodicarboxylate, N,N,N',N'-tetramethyl azodicarboxamide, 1,1'-(azodicarbonyl)dipiperidine, diethyl azodicarboxylate; and phosphorus compounds such as triphenylphosphine and tri-n-butylphosphine.

In this reaction, the compound (3) is typically used in an amount of at least 1 mole, and preferably 1 to 2 moles, per mole of the compound (2).

The condensing agent is typically used in an amount of at least 1 mole, and preferably 1 to 2 moles, per mole of the compound (2).

The reaction proceeds typically at 0 to 200° C., and preferably at about 0 to about 150° C., and is completed in about 1 to about 10 hours.

Reaction Formula 2

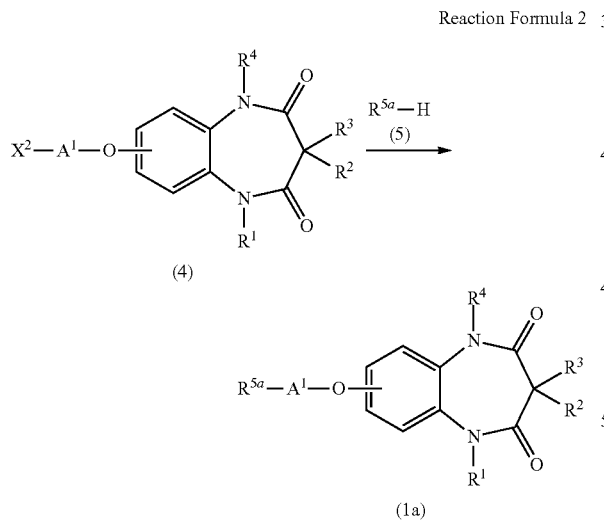

wherein $R^1$, $R^2$, $R^3$, $R^4$, and $A^1$ are the same as above; $R^{5a}$ is a nitrogen-containing heterocyclic group optionally having substituent(s); and $X^2$ is a halogen atom.

Examples of $R^{5a}$ include, among groups represented by the group $R^5$ mentioned above, groups obtained by removing hydrogen from saturated or unsaturated, monocyclic or polycyclic, heterocyclic compounds with an N—H bond, the groups optionally having substituent(s).

The reaction of the compound of Formula (4) with the compound of Formula (5) can be performed in a general inert solvent or without using any solvent, in the presence or absence of a basic compound.

Examples of halogen atoms represented by $X^2$ include chlorine, bromine, iodine, and like atoms.

Examples of inert solvents include water; ethers such as dioxane, tetrahydrofuran, diethylether, diethylene glycol dimethyl ether, and ethylene glycol dimethyl ether; aromatic hydrocarbons such as benzene, toluene, and xylene; halogenated hydrocarbons such as dichloromethane, dichloroethane, chloroform, and carbon tetrachloride; lower alcohols such as methanol, ethanol, and isopropanol; ketones such as acetone and methyl ethyl ketone; polar solvents such as dimethylformamide (DMF), dimethyl sulfoxide (DMSO), hexamethylphosphoric triamide, and acetonitrile; and mixtures thereof.

A wide variety of known basic compounds can be used as the basic compound. Examples of such basic compounds include inorganic bases, for example, alkali metal hydroxides such as sodium hydroxide, potassium hydroxide, cesium hydroxide, and lithium hydroxide; alkali metal carbonates such as sodium carbonate, potassium carbonate, cesium carbonate, lithium carbonate, lithium hydrogencarbonate, sodium hydrogencarbonate, and potassium hydrogencarbonate; alkali metals such as sodium and potassium; sodium amide; sodium hydride; and potassium hydride; and organic bases, for example, alkali metal alcoholates such as sodium methoxide, sodium ethoxide, potassium methoxide, and potassium ethoxide; triethylamine; tripropylamine; pyridine; quinoline; 1,5-diazabicyclo[4.3.0]nonene-5 (DBN); 1,8-diazabicyclo[5.4.0]undecene-7 (DBU); and 1,4-diazabicyclo[2.2.2]octane (DABCO). These basic compounds can be used singly or in a combination of two or more.

The above reaction may be performed by adding as a reaction accelerator an alkali metal iodide such as potassium iodide or sodium iodide to the reaction system, as required.

The compound of Formula (5) is typically used in an amount of at least 0.5 moles, and preferably about 0.5 to about 10 moles, per mole of the compound of Formula (4).

The amount of basic compound is typically 0.5 to 10 moles, and preferably 0.5 to 6 moles, per mole of the compound of Formula (4).

The reaction is typically performed at a temperature of 0 to 250° C., and preferably 0 to 200° C., and is typically completed in about 1 to about 80 hours.

Reaction Formula 3

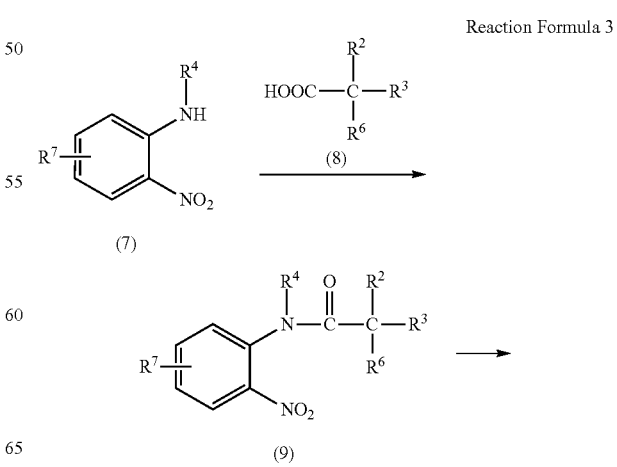

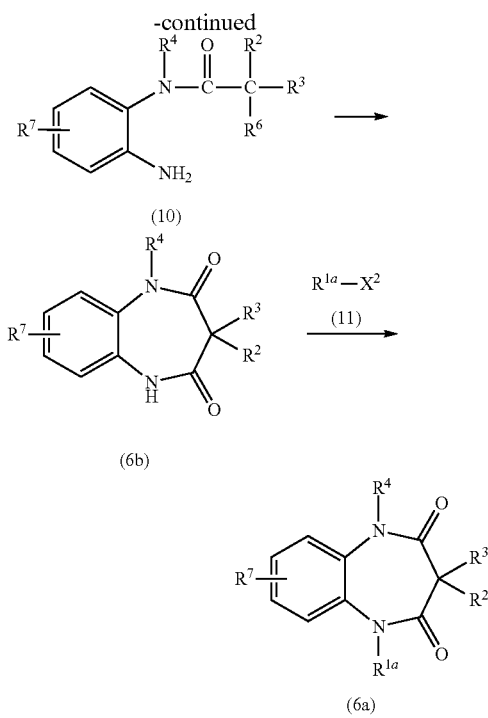

wherein $R^2$, $R^3$, $R^4$, and $X^2$ are as defined above; $R^{1a}$ is lower alkyl; $R^7$ is lower alkoxy; and $R^6$ is lower alkoxycarbonyl.

Examples of lower alkyl groups represented by $R^{1a}$ include alkyl groups with 1 to 6 carbon atoms, such as methyl, ethyl, and propyl groups.

Examples of lower alkoxycarbonyl groups represented by $R^6$ include ($C_{1-6}$ alkoxy)carbonyl groups, such as methoxycarbonyl, and ethoxycarbonyl.

Examples of lower alkoxy groups represented by $R^7$ include linear or branched alkoxy groups with 1 to 6 carbon atoms, such as methoxy, ethoxy, propoxy, and butoxy.

In the reaction of the compound of Formula (7) with the compound of Formula (8), the compound of Formula (7) is reacted with the carboxylic acid compound of Formula (8) through a general amide bond formation reaction. Conditions for known amide bond formation reactions can be easily employed in the amide formation reaction. For example, the following reaction methods can be employed: (i) a mixed acid anhydride method, in which Carboxylic Acid (8) is reacted with an alkyl halocarboxylate to form a mixed acid anhydride, which is then reacted with Amine (7); (ii) an active ester method, in which Carboxylic Acid (8) is converted to an activated ester such as a phenyl ester, p-nitrophenyl ester, N-hydroxysuccinimide ester, 1-hydroxybenzotriazole ester or the like, or an activated amide with benzoxazoline-2-thione, and the activated ester or amide is reacted with Amine (7); (iii) a carbodiimide method, in which Carboxylic Acid (8) is subjected to a condensation reaction with Amine (7) in the presence of an activating agent such as dicyclohexylcarbodiimide, 1-(3-dimethylaminopropyl)-3-ethylcarbodiimide (WSC), carbonyldiimidazole or the like; and (iv) other methods, for example, a method in which Carboxylic Acid (8) is converted to a carboxylic anhydride using a dehydrating agent such as acetic anhydride, and the carboxylic anhydride is reacted with Amine (7), a method in which an ester of Carboxylic Acid (8) with a lower alcohol is reacted with Amine (7) at a high pressure and a high temperature, and a method in which an acid halide of Carboxylic Acid (8), i.e., a carboxylic acid halide, is reacted with Amine (7).

Generally, the mixed acid anhydride method (i) is performed in a solvent, in the presence or absence of a basic compound. Any solvents used for conventional mixed acid anhydride methods are usable. Specific examples of usable solvents include halogenated hydrocarbons such as chloroform, dichloromethane, dichloroethane, and carbon tetrachloride; aromatic hydrocarbons such as benzene, toluene, and xylene; ethers such as diethyl ether, diisopropyl ether, tetrahydrofuran, and dimethoxyethane; esters such as methyl acetate, ethyl acetate, and isopropyl acetate; aprotic polar solvents such as N,N-dimethylformamide, dimethylsulfoxide, and hexamethylphosphoric triamide; and mixtures thereof.

Examples of usable basic compounds include organic bases such as triethylamine, trimethylamine, pyridine, dimethylaniline, N-ethyldiisopropylamine, dimethylaminopyridine, N-methylmorpholine, 1,5-diazabicyclo[4.3.0]non-5-ene (DBN), 1,8-diazabicyclo[5.4.0]undec-7-ene (DBU) and 1,4-diazabicyclo[2.2.2]octane (DABCO); inorganic bases, for example, carbonates such as sodium carbonate, potassium carbonate, sodium hydrogencarbonate, and potassium hydrogencarbonate; metal hydroxides such as sodium hydroxide, potassium hydroxide, and calcium hydroxide; potassium hydride; sodium hydride; potassium; sodium; sodium amide; and metal alcoholates such as sodium methylate and sodium ethylate.

Examples of alkyl halocarboxylates usable in the mixed acid anhydride method include methyl chloroformate, methyl bromoformate, ethyl chloroformate, ethyl bromoformate, and isobutyl chloroformate. In this method, Carboxylic Acid (8), an alkyl halocarboxylate, and Amine (7) are preferably used in equimolar amounts, but each of the alkyl halocarboxylate and Carboxylic Acid (8) can also be used in an amount of about 1 to about 1.5 moles per mole of Amine (7). The reaction is typically performed at about −20 to about 150° C., and preferably at about 10 to about 50° C., typically for about 5 minutes to about 30 hours, and preferably for about 5 minutes to about 25 hours.

Method (iii), in which a condensation reaction is performed in the presence of an activating agent, can be performed in a suitable solvent in the presence or absence of a basic compound. Solvents and basic compounds usable in this method include those mentioned hereinafter as solvents and basic compounds usable in the method in which a carboxylic acid halide is reacted with Amine (7) mentioned above as one of the other methods (iv). A suitable amount of activating agent is typically at least 1 mole, and preferably 1 to 5 moles per mole of Compound (7). When WSC is used as an activating agent, addition of 1-hydroxybenzotriazol to the reaction system allows the reaction to proceed advantageously. The reaction is typically performed at about −20 to about 180° C., and preferably at about 0 to about 150° C., and is typically completed in about 5 minutes to about 90 hours.

When the method in which a carboxylic acid halide is reacted with Amine (7), mentioned above as one of the other methods (iv), is employed, the reaction is performed in the presence of a basic compound in a suitable solvent. Examples of usable basic compounds include a wide variety of known basic compounds, such as those for use in the method (i) above. In addition to those usable in the mixed acid anhydride method, usable solvents include alcohols such as methanol, ethanol, isopropanol, propanol, butanol, 3-methoxy-1-butanol, ethylcellosolve, and methylcellosolve; acetonitrile; pyridine; acetone; and water. The ratio of the carboxylic acid halide to Amine (7) is not limited and can be suitably selected from a wide range. It is typically suitable to use, for example, at least about 1 mole, and preferably about 1 to about 5 moles of the carboxylic acid halide per mole of Amine (7). The reaction is typically performed at about −20 to about 180° C., and preferably at about 0 to about 150° C., and typically completed in about 5 minutes to about 30 hours.

The amide bond formation reaction shown in Reaction Formula 3 above can also be performed by reacting Carboxylic Acid (8) with Amine (7) in the presence of a phosphorus compound serving as a condensing agent, such as triphenylphosphine, diphenylphosphinyl chloride, phenyl-N-phenylphosphoramide chloridate, diethyl chlorophosphate, diethyl cyanophosphate, diphenylphosphoric azide, bis(2-oxo-3-oxazolidinyl)phosphinic chloride, or the like.

The reaction is performed in the presence of a solvent and a basic compound usable for the method in which a carboxylic acid halide is reacted with Amine (7), typically at about −20 to about 150° C., and preferably at about 0 to about 100° C., and is typically completed in about 5 minutes to about 30 hours. It is suitable to use each of the condensing agent and Carboxylic Acid (8) in amounts of at least about 1 mole, and preferably about 1 to about 2 moles, per mole of Amine (7).

The reaction converting the compound of Formula (9) to the compound of Formula (10) can be performed by, for example, [1] reducing the compound of Formula (9) in a suitable solvent using a catalytic hydrogenation reducing agent, or [2] reducing the compound of Formula (9) in a suitable inert solvent using as a reducing agent such as a mixture of an acid with a metal or metal salt, a mixture of a metal or metal salt with an alkali metal hydroxide, sulfide, or ammonium salt.

When Method [1] in which a catalytic hydrogenation reducing agent is used, examples of usable solvents are water; acetic acid; alcohols such as methanol, ethanol and isopropanol; hydrocarbons such as n-hexane and cyclohexane; ethers such as dioxane, tetrahydrofuran, diethyl ether and diethylene glycol dimethyl ether; esters such as ethyl acetate and methyl acetate; aprotic polar solvents such as N,N-dimethylformamide; and mixtures thereof. Examples of usable catalytic hydrogenation reducing agents include palladium, palladium black, palladium carbon, platinum carbon, platinum, platinum black, platinum oxide, copper chromite, and Raney nickel. The reducing agent is typically used in an amount of about 0.02 times to about equal to the weight of the compound of Formula (9). The reaction temperature is typically about −20 to about 150° C., and preferably about 0 to about 100° C. The hydrogen pressure is typically about 1 to 10 atm. The reaction is typically completed in about 0.5 to about 100 hours. An acid such as hydrochloric acid may be added to the reaction.

When Method [2] above is used, a mixture of iron, zinc, tin, or tin (II) chloride with a mineral acid such as hydrochloric acid or sulfuric acid; or a mixture of iron, iron (II) sulfate, zinc, or tin with an alkali metal hydroxide such as sodium hydroxide, a sulfide such as ammonium sulfide, aqueous ammonia solution, or an ammonium salt such as ammonium chloride or the like, can be used as a reducing agent. Examples of inert solvents are water; acetic acid; alcohols such as methanol and ethanol; ethers such as dioxane; and mixtures thereof. Conditions for the reduction reaction can be suitably selected according to the reducing agent to be used. For example, when a mixture of tin (II) chloride and hydrochloric acid is used as a reducing agent, the reaction is advantageously performed at about 0 to about 150° C. for about 0.5 to about 10 hours. A reducing agent is used in an amount of at least 1 mole, and preferably about 1 to 5 moles, per mole of the compound of Formula (9).

The reaction converting the compound of Formula (10) to the compound of Formula (6b) is performed under the same reaction conditions as those for the reaction of the compound of Formula (7) with the compound of Formula (8).

The reaction of the compound of Formula (6b) with the compound of Formula (11) can be performed under the same reaction conditions as those for the reaction of the compound of Formula (2) and the compound of Formula (3) shown in Reaction Formula 1 above.

Reaction Formula 4

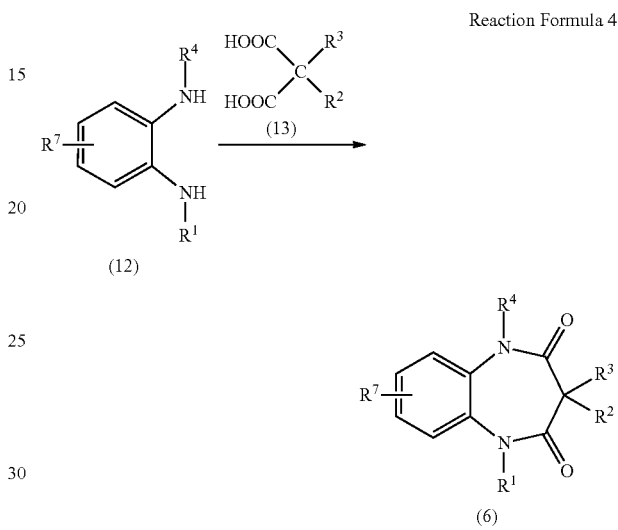

wherein $R^1$, $R^2$, $R^3$, $R^4$, and $R^7$ are the same as above.

The reaction of the compound of Formula (12) with the compound of Formula (13) can be performed under the same reaction conditions as those for the reaction of the compound of Formula (7) with the compound of Formula (8) shown in Reaction Formula 3 above.

Reaction Formula 5

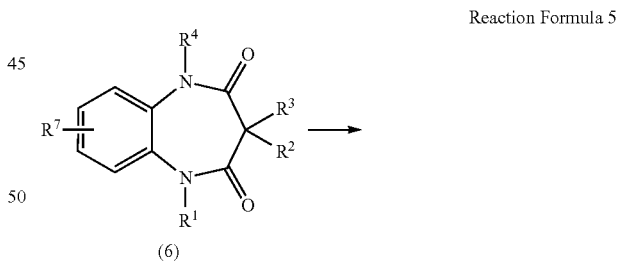

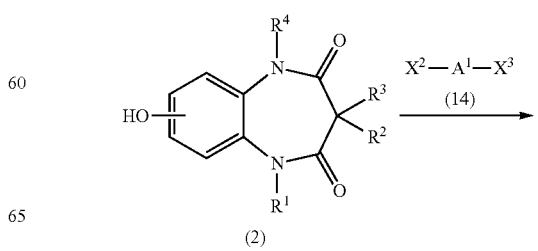

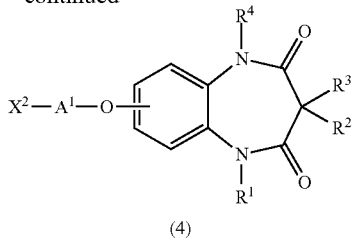

(4)

wherein $R^1$, $R^2$, $R^3$, $R^4$, $R^7$, $A^1$, and $X^2$ are the same as above; and $X^3$ is a halogen atom.

The reaction converting the compound of Formula (6) to the compound of Formula (2) can be performed in a suitable solvent in the presence of an acid.

Examples of solvents include water; lower ($C_{1-6}$) alcohols such as methanol, ethanol, and isopropanol; ethers such as dioxane, tetrahydrofuran, and diethylether; halogenated hydrocarbons such as dichloromethane, chloroform, and carbon tetrachloride; polar solvents such as acetonitrile; and mixtures thereof. Examples of acids include mineral acids such as hydrochloric acid, sulfuric acid, and hydrobromic acid; aliphatic acids such as formic acid and acetic acid; sulfonic acids such as p-toluenesulfonic acid; Lewis acids such as boron fluoride, aluminium chloride, and boron tribromide; iodides such as sodium iodide and potassium iodide; and mixtures of these iodides and Lewis acids.

The reaction is performed typically at about 0 to about 200° C., and preferably at about 0 to about 150° C., and is typically completed in about 0.5 to about 25 hours. The amount of acid is typically about 1 to about 10 moles, and preferably about 1 to about 2 moles, per mole of the compound of Formula (6).

Examples of halogen atoms represented by $X^3$ include chlorine, bromine, iodine, and like atoms. The halogen atom represented by $X^3$ is preferably one having an atomic number equal to or higher than that of the halogen atom represented by $X^2$.

The reaction of the compound of Formula (2) with the compound of Formula (14) can be performed under the same reaction conditions as those for the reaction of the compound of Formula (2) with the compound of Formula (3) shown in Reaction Formula 1 above, wherein $X^1$ is a halogen atom.

The compound of Formula (1) according to the present invention and the starting materials thereof can be produced using a known or conventional synthetic method other than the production method described above.

In addition, compounds in the form in which a solvate (for example, a hydrate, ethanolate, etc.) was added to the starting material compounds and object compounds shown in each of the reaction formulae are included in each of the formulae.

The compound of Formula (1) according to the present invention includes stereoisomers and optical isomers.

The starting material compounds and object compounds represented by each of the reaction formulae can be used in a suitable salt form.

Each of the object compounds obtained according to the above reaction formulae can be isolated and purified from the reaction mixture by, for example, after cooling the reaction mixture, performing an isolation procedure such as filtration, concentration, extraction, etc., to separate a crude reaction product, and then subjecting the crude reaction product to a general purification procedure such as column chromatography, recrystallization, etc.

Among the compounds of the present invention, those having a basic group or groups can easily form salts with common pharmaceutically acceptable acids. Examples of such acids include hydrochloric acid, hydrobromic acid, nitric acid, sulfuric acid, phosphoric acid and other inorganic acids, methansulfonic acid, p-toluenesulfonic acid, acetic acid, citric acid, tartaric acid, maleic acid, fumaric acid, malic acid, lactic acid and other organic acids, etc.

Among the compounds of the present invention, those having an acidic group or groups can easily form salts by reacting with pharmaceutically acceptable basic compounds. Examples of such basic compounds include sodium hydroxide, potassium hydroxide, calcium hydroxide, sodium carbonate, potassium carbonate, sodium hydrogencarbonate, potassium hydrogencarbonate, etc.

In the compound of the present invention, one or more atoms can be substituted with one or more isotopic atoms. Examples of the isotopic atoms include deuterium ($^2H$), tritium ($^3H$), $^{13}C$, $^{14}N$, $^{18}O$, etc.

The following is an explanation of pharmaceutical preparations comprising the compound of the present invention as an active ingredient.

Such pharmaceutical preparations are obtained by formulating the compound of the present invention into general pharmaceutical preparations, using typically employed diluents or excipients such as fillers, extenders, binders, wetting agents, disintegrants, surfactants, lubricants, etc.

The form of such pharmaceutical preparations can be selected from various forms according to the purpose of therapy. Typical examples include tablets, pills, powders, solutions, suspensions, emulsions, granules, capsules, suppositories, injections (solutions, suspensions, etc.) and the like.

To form tablets, any of various known carriers can be used, including, for example, lactose, white sugar, sodium chloride, glucose, urea, starch, calcium carbonate, kaolin, crystalline cellulose and other excipients; water, ethanol, propanol, simple syrup, glucose solutions, starch solutions, gelatin solutions, carboxymethylcellulose, shellac, methylcellulose, potassium phosphate, polyvinylpyrrolidone and other binders; dry starch, sodium alginate, agar powder, laminaran powder, sodium hydrogencarbonate, calcium carbonate, aliphatic acid esters of polyoxyethylenesorbitan, sodium laurylsulfate, stearic acid monoglyceride, starch, lactose and other disintegrants; white sugar, stearin, cacao butter, hydrogenated oils and other disintegration inhibitors; quaternary ammonium base, sodium lauryl sulfate and other absorption promoters; glycerin, starch and other wetting agents; starch, lactose, kaolin, bentonite, colloidal silicic acid and other adsorbents; purified talc, stearates, boric acid powder, polyethylene glycol and other lubricants; etc.

Such tablets may be coated with general coating materials as required, to prepare, for example, sugar-coated tablets, gelatin-coated tablets, enteric-coated tablets, film-coated tablets, double- or multi-layered tablets, etc.

To form pills, any of various known carriers can be used, including, for example, glucose, lactose, starch, cacao butter, hydrogenated vegetable oils, kaolin, talc and other excipients; gum arabic powder, tragacanth powder, gelatin, ethanol and other binders; laminaran, agar and other disintegrants; etc.

To form suppositories, any of various known carriers can be used, including, for example, polyethylene glycol, cacao butter, higher alcohols, esters of higher alcohols, gelatin, semisynthetic glycerides, etc.

To form an injection, a solution, emulsion or suspension is sterilized and preferably made isotonic with blood. Any of various known widely used diluents can be employed to prepare the solution, emulsion or suspension. Examples of such diluents include water, ethanol, propylene glycol, ethoxylated isostearyl alcohol, polyoxylated isostearyl alcohol, aliphatic acid esters of polyoxyethylene sorbitan, etc. In this case, the pharmaceutical preparation may contain sodium chloride, glucose or glycerin in an amount sufficient to prepare an isotonic solution, and may contain general solubilizers, buffers, analgesic agents, etc., and further, if necessary, coloring agents, preservatives, flavors, sweetening agents, etc., and/or other medicines.

The proportion of the compound of the present invention in the pharmaceutical preparation is not limited and can be suitably selected from a wide range. It is typically preferable that the pharmaceutical preparation contain the compound of the present invention in a proportion of 1 to 70 wt. %.

The route of administration of the pharmaceutical preparation according to the present invention is not limited, and the preparation can be administered by a route suitable for the form of the preparation, the patient's age and sex, the conditions of the disease, and other conditions.

For example, tablets, pills, solutions, suspensions, emulsions, granules and capsules are administered orally. Injections are intravenously administered singly or as mixed with general injection transfusions such as glucose solutions, amino acid solutions or the like, or singly administered intramuscularly, intracutaneously, subcutaneously or intraperitoneally, as required. Suppositories are administered intrarectally.

The dosage of the pharmaceutical preparation is suitably selected according to the method of use, the patient's age and sex, the severity of the disease, and other conditions, and is typically about 0.001 to about 100 mg/kg body weight/day, and preferably 0.001 to 50 mg/kg body weight/day, in single or divided doses.

Since the dosage varies depending on various conditions, a dosage smaller than the above range may be sufficient, or a dosage larger than the above range may be required.

When administered to the human body as a pharmaceutical, the compound of the present invention may be used concurrently with, or before or after, antithrombotics such as blood clotting inhibitors and antiplatelet agents (e.g., warfarin, aspirin, etc.). Further, the present compound may be used concurrently with, or before or after, drugs for treating chronic diseases, such as antihypertensive drugs (ACE inhibitors, beta blockers, angiotensin II receptor antagonists), heart failure drugs (cardiotonic agents, diuretics), and diabetes treatment agents.

The compound of the present invention has potent blocking effects on human Kv1.5 and/or GIRK1/4 channels, and weak blocking effects on HERG channels. Thus, the compound of the invention has characteristics as an atrial-selective $K^+$ channel-blocking agent.

Therefore, the compound of the invention can be used as a pharmacologically active substance that is safer and provides a more potent effect on the prolongation of the atrial refractory period than conventional antiarrhythmic agents. The compound of the invention is preferably used as a therapeutic agent for arrhythmia such as atrial fibrillation, atrial flutter, and atrial tachycardia (elimination of arrhythmia and/or prevention of the occurrence of arrhythmia). The compound of the invention is particularly preferably used as a therapeutic agent for atrial fibrillation (defibrillation and maintenance of sinus rhythm). The compound of the invention can also be used as a prophylactic agent for thromboembolism such as cerebral infarction and as a therapeutic agent for heart failure.

The compound having potent blocking effects on both human Kv1.5 and human GIRK1/4 channels has more potent atrial refractory period prolongation effects and is highly safe, compared to compounds inhibiting either one of the channels. Furthermore, this compound has greater therapeutic effects on atrial fibrillation (defibrillation and maintenance of sinus rhythm) than compounds inhibiting either one of the channels. Therefore, the compound having potent blocking effects on both the human Kv1.5 and human GIRK1/4 channels is particularly useful as a therapeutic agent for arrhythmia such as atrial fibrillation, atrial flutter, and atrial tachycardia (termination of arrhythmia and/or prevention of the occurrence of arrhythmia). This compound is particularly useful as a therapeutic agent for atrial fibrillation (defibrillation and maintenance of sinus rhythm).

DESCRIPTION OF EMBODIMENTS

The following Examples are intended to illustrate the present invention in further detail.

1. First Invention

REFERENCE EXAMPLE 1

Synthesis of 8-methoxy-1-methyl-1,5-dihydrobenzo[b][1,4]diazepine-2,4-dione

Sodium ethoxide (204 mg) was added to an ethanol solution (15 ml) of N-(2-amino-5-methoxyphenyl)-N-methylmalonamic acid ethyl ester (266 mg). The mixture was stirred at 65° C. for 2.5 hours. The reaction liquid was cooled to room temperature, and condensed under reduced pressure. The residue was purified by silica gel column chromatography (dichloromethane: methanol=1:0→10:1). The purified product was condensed to dryness under reduced pressure to give the title compound (176.3 mg) as a white powder.

$^1$H-NMR (CDCl$_3$) δppm: 3.36 (2H, s), 3.43 (3H, s), 3.84 (3H, s), 6.79-6.83 (1H, m), 7.06-7.09 (1H, m), and 8.72 (1H, br-s).

REFERENCE EXAMPLE 2

Synthesis of 1-ethyl-7-methoxy-5-methyl-1,5-dihydrobenzo[b][1,4]diazepine-2,4-dione Sodium hydride (60% in oil, 44 mg) was suspended in of DMF (8 ml), and was cooled to 0° C. in an ice water bath. 8-Methoxy-1-methyl-1,5-dihydrobenzo[b][1,4]diazepine-2,4-dione (220 mg) was added thereto at the same temperature, and the mixture was stirred at 0° C. for an hour. Ethyl iodide (187 mg) was added thereto, and the mixture was stirred at room temperature overnight. Water was added to the reaction liquid, followed by extraction by ethyl acetate. The organic layer was dried over sodium sulfate, and condensed under reduced pressure. The residue was purified by silica gel column chromatography (hexane: ethyl acetate=4:1→1:1). The purified product was condensed to dryness to give the title compound (190.2 mg) as a yellow solid.

$^1$H-NMR (CDCl$_3$) δppm: 1.11 (3H, t, J=7.1 Hz), 3.32 (2H, m), 3.59-3.68 (1H, m), 3.85 (3H, s), 4.18-4.30 (1H, m), 6.78 (1H, d, J=2.8 Hz), 6.84 (1H, dd, J=9.0 and 2.8 Hz), 7.26 (1H, d, J=9.0 Hz).

REFERENCE EXAMPLE 3

Synthesis of 1-ethyl-7-methoxy-3,3,5-trimethyl-1,5-dihydrobenzo[b][1,4]diazepine-2,4-dione Sodium hydride (60% in oil, 76 mg) was suspended in of DMF (8 ml). 1-ethyl-7-methoxy-5-methyl-1,5-dihydrobenzo

[b][1,4]diazepine-2,4-dione (190 mg) was added thereto at 0° C. The mixture was stirred at the same temperature for an hour. Methyl iodide (0.19 ml) was added thereto, and the mixture was stirred at room temperature for three days. Water was added to the reaction mixture, followed by extraction by ethyl acetate. The organic layer was dried over sodium sulfate, and condensed under reduced pressure. The residue was purified by silica gel column chromatography (ethyl acetate). The purified product was condensed to dryness to give the title compound (169 mg) as yellow powder.

$^1$H-NMR (CDCl$_3$) δppm: 0.86 (3H, s), 1.15 (3H, t, J=7.1 Hz), 1.53 (3H, s), 3.40 (3H, s), 3.65-3.76 (1H, m), 3.85 (3H, s), 4.12-4.24 (1H, m), 6.73 (1H, d, J=2.8 Hz), 6.83 (1H, dd, J=9.0 and 2.8 Hz), and 7.22 (1H, d, J=9.0 Hz).

REFERENCE EXAMPLE 4

Synthesis of 7-methoxy-1,3,3,5-tetramethyl-1,5-dihydrobenzo[b][1,4]diazepine-2,4-dione Sodium hydride (60% in oil, 128 mg) was suspended in of DMF(10 ml). 8-methoxy-1-methyl-1,5-dihydrobenzo[b][1,4]diazepine-2,4-dione (176 mg) was added thereto at 0° C. The mixture was stirred at the same temperature for an hour. Methyl iodide(0.25 mg) was added thereto, and the mixture was stirred at room temperature overnight. Water was added to the reaction liquid, followed by extraction by ethyl acetate. The organic layer was washed with water, dried over sodium sulfate, and condensed under reduced pressure. The residue was recrystallized from hexane to give the title compound (161.6 mg) as a white powder.

$^1$H-NMR (CDCl$_3$) δppm: 0.87 (3H, s), 1.54 (3H, s), 3.40 (3H, s), 3.42 (3H, s), 3.84 (3H, s), 6.73 (1H, s), 6.84 (1H, d, J=8.9 Hz), 7.14 (1H, d, J=8.9 Hz).

REFERENCE EXAMPLE 5

Synthesis of 1-ethyl-7-hydroxy-3,3,5-trimethyl-1,5-dihydrobenzo[b][1,4]diazepine-2,4-dione 1.0M-boron tribromide/dichloromethane solution (1.22 ml) was added to a dichloromethane solution (3 ml) of 1-ethyl-7-methoxy-3,3,5-trimethyl-1,5-dihydrobenzo[b][1,4]diazepine-2,4-dione (169 mg) at 0° C. The mixture was stirred at room temperature overnight. Water and methanol were added to the reaction mixture, and extraction was performed using a dichloromethane/methanol mixture (dichloromethane:methanol=10:1). The organic layer was dried over anhydrous sodium sulfate, and condensed to dryness under reduced pressure to give the title compound (156.4 mg) as a white powder.

$^1$H-NMR (CDCl$_3$) δppm: 0.90 (3H, s), 1.16 (3H, t, J=7.0 Hz), 1.55 (3H, s), 3.41 (3H, s), 3.66-3.78 (1H, m), 4.12-4.23 (1H, m), 6.79 (1H, d, J=2.7 Hz), 6.84 (1H, dd, J=8.8 and 2.7 Hz), 6.88 (1H, s), 7.18 (1H, d, J=8.8 Hz).

REFERENCE EXAMPLE 6

Synthesis of 7-hydroxy-1,3,3,5-tetramethyl-1,5-dihydrobenzo[b][1,4]diazepine-2,4-dione The synthesis of the title compound was performed in the same manner as in Reference Example 5 using appropriate starting materials.

$^1$H-NMR (CDCl$_3$) δppm: 0.90 (3H, s), 1.49 (3H, s), 3.39 (3H, s), 3.40 (3H, s), 6.73 (1H, d, J=2.7 Hz), 6.80 (1H, dd, J=8.9 and 2.7 Hz), 7.13 (1H, d, J=8.9 Hz).

REFERENCE EXAMPLE 7

Synthesis of trifluoromethanesulfonic acid 1-ethyl-3,3,5-trimethyl-2,4-dioxo-2,3,4,5-tetrahydro-1H-benzo[b][1,4]diazepin-7-yl ester A dichloromethane solution (50 ml) of 1-ethyl-7-hydroxy-3,3,5-trimethyl-1,5-dihydrobenzo[b][1,4]diazepine-2,4-dione(2.6 g) was cooled with ice. After adding of triethylamine (1.5 ml) to the solution, trifluoromethane sulfonic anhydride (1.9 ml) was added, and the mixture was stirred at room temperature for 4 hours. Triethylamine(0.75 ml) and trifluoromethane sulfonic anhydride(0.75 ml) were further added thereto, and the mixture was stirred at room temperature overnight. Water was added to the reaction liquid, followed by extraction by ethyl acetate. The organic layer was condensed under reduced pressure, and the residue was purified by silica gel column chromatography (n-hexane: ethyl acetate=10:1→5:5). The purified product was condensed to dryness under reduced pressure to give the title compound (3.4 g) as a white solid (yield=86%).

$^1$H-NMR (CDCl$_3$) δppm: 0.87 (3H, s), 1.23 (3H, t, J=7.2 Hz), 1.52 (3H, s), 3.42 (3H, s), 3.81-3.91 (1H, m), 4.04-4.14 (1H, m), 7.15-7.22 (2H, m), 7.40 (1H, d, J=8.9 Hz).

REFERENCE EXAMPLE 8

Synthesis of trifluoromethanesulfonic acid 1,5-dimethyl-2,4-dioxo-2,3,4,5-tetrahydro-1H-benzo[b][1,4]diazepin-7-yl ester The synthesis of the title compound was performed in the same manner as in Reference Example 7 using appropriate starting materials.

$^1$H-NMR (CDCl$_3$) δppm: 3.29 (1H, d, J=12.7 Hz), 3.43 (6H, s), 3.48 (1H, d, J=12.7 Hz), 7.21-7.26 (2H, m), 7.38-7.41 (1H, m).

REFERENCE EXAMPLE 9

Synthesis of trifluoromethanesulfonic acid 1,3,3,5-tetramethyl-2,4-dioxo-2,3,4,5-tetrahydro-1H-benzo[b][1,4]diazepin-7-yl ester The synthesis of the title compound was performed in the same manner as in Reference Example 7 using appropriate starting materials.

$^1$H-NMR (CDCl$_3$) δppm: 0.88 (3H, s), 1.56 (3H, s), 3.44 (3H, s), 3.45 (3H, s), 7.16-7.21 (2H, m), 7.33 (1H, d, J=8.9 Hz).

REFERENCE EXAMPLE 10

Synthesis of 1-ethyl-3,3,5-trimethyl-2,4-dioxo-2,3,4,5-tetrahydro-1H-benzo[b][1,4]diazepine-7-carbonitrile Trifluoromethanesulfonic acid 1-ethyl-3,3,5-trimethyl-2,4-dioxo-2,3,4,5-tetrahydro-1H-benzo[b][1,4]diazepine-7-yl ester(0.12 g), zinc cyanide(70 mg), tris(dibenzylideneacetone) dipalladium 7 mg), 1,1'-bis(diphenylphosphino) ferrocene(8 mg), and zinc powder(2 mg) were added to DMF (1 ml), and the mixture was heated for 20 minutes at 170° C. (microwave reactor). The reaction liquid was cooled to room temperature, and subjected to celite filtration. The filtrate was condensed under reduced pressure, and the residue was purified by silica gel column chromatography (hexane: ethyl acetate=50:50→0:100). The purified product was condensed under reduced pressure to give the title compound(77 mg) as a white solid.

$^1$H-NMR (CDCl$_3$) δppm: 0.88 (3H, s), 1.25 (3H, t, J=7.1 Hz), 1.55 (3H, s), 3.44 (3H, s), 3.89-3.95 (1H, m), 4.05-4.11 (1H, m), 7.43 (1H, d, J=9.1 Hz), 7.53-7.56 (2H, m).

REFERENCE EXAMPLE 11

Synthesis of 1,5-dimethyl-2,4-dioxo-2,3,4,5-tetrahydro-1H-benzo[b][1,4]diazepine-7-carbonitrile The synthesis of the title compound was performed in the same manner as in Reference Example 10 using appropriate starting materials.

$^1$H-NMR (CDCl$_3$) δppm: 3.25 (1H, d, J=12.7 Hz), 3.438 (3H, s), 3.444 (3H, s), 3.50 (1H, d, J=12.7 Hz), 7.42 (1H, J=8.4 Hz), 7.57-7.62 (2H, m).

REFERENCE EXAMPLE 12

Synthesis of 1,3,3,5-tetramethyl-2,4-dioxo-2,3,4,5-tetrahydro-1H-benzo[b][1,4]diazepine-7-carbonitrile The synthesis of the title compound was performed in the same manner as in Reference Example 10 using appropriate starting materials.

$^1$H-NMR (CDCl$_3$) δppm: 0.88 (3H, s), 1.56 (3H, s), 3.45 (3H, s), 3.46 (3H, s), 7.34-7.37 (1H, m), 7.53-7.57 (2H, m).

REFERENCE EXAMPLE 13

Synthesis of 1-ethyl-3,3,5-trimethyl-2,4-dioxo-2,3,4,5-tetrahydro-1H-benzo[b][1,4]diazepine-7-carbaldehyde 1-Ethyl-3,3,5-trimethyl-2,4-dioxo-2,3,4,5-tetrahydro-1H-benzo[b][1,4]diazepine-7-carbonitrile(1.0 g) and Raney nickel(3.0 g) were suspended in formic acid(10 ml), and the mixture was stirred at 100° C. for 2 hours. The reaction mixture was filtered to remove insoluble matter, and the filtrate was condensed under reduced pressure. The residue was purified by silica gel column chromatography (hexane: ethyl acetate=50:50→20:80). The purified product was condensed under reduced pressure to give the title compound(0.92 g) as a yellowish-white solid (yield=92%).

$^1$H-NMR (CDCl$_3$) δppm: 0.88 (3H, s), 1.26 (3H, t, J=7.1 Hz), 1.56 (3H, s), 3.48 (3H, s), 3.92-3.99 (1H, m), 4.07-4.15 (1H, m), 7.50 (1H, d, J=8.9 Hz), 7.77-7.80 (2H, m), 10.01 (1H, s).

REFERENCE EXAMPLE 14

Synthesis of 7-[4-(1,3-dioxo-1,3-dihydroisoindol-2-yl)but-1-ynyl]-1-ethyl-3,3,5-trimethyl-1,5-dihydrobenzo[b][1,4]diazepine-2,4-dione Trifluoromethane sulfonic acid 1-ethyl-3,3,5-trimethyl-2,4-dioxo-2,3,4,5-tetrahydro-1H-benzo[b][1,4]diazepine-7-yl ester(0.59 g), 2-(but-3-ynyl)isoindol-1,3-dione(0.3 g), dichlorobis(triphenyl phosphine)palladium (II) (53 mg), copper(I) iodide(29 mg), and triethylamine(0.39 ml) were added to DMF(4 ml). The mixture was heated at 150° C. (microwave reactor) for 10 minutes. The reaction liquid was cooled to room temperature, and subjected to celite filtration. The filtrate was condensed under reduced pressure and the residue was purified by silica gel column chromatography (hexane: ethyl acetate=60:40→30:70). The purified product was condensed under reduced pressure to give the title compound (0.51 g) as a yellowish-white solid.

$^1$H-NMR (CDCl$_3$) δppm: 0.84 (3H, s), 1.17 (3H, t, J=7.1 Hz), 1.52 (3H, s), 2.84 (2H, t, J=6.3 Hz), 3.38 (3H, s), 3.68-3.80 (1H, m), 3.99 (2H, t, J=6.3 Hz), 4.00-4.15 (1H, m), 7.19-7.20 (3H, m), 7.73-7.76 (2H, m), 7.87-7.89 (2H, m).

REFERENCE EXAMPLE 15

Synthesis of 7-[3-(1,3-dioxo-1,3-dihydroisoindol-2-yl)-prop-1-ynyl]-1-ethyl-3,3,5-trimethyl-1,5-dihydrobenzo[b][1,4]diazepine-2,4-dione The synthesis of the title compound was performed in the same manner as in Reference Example 14 using appropriate starting materials.

$^1$H-NMR (CDCl$_3$) δppm: 0.83 (3H, s), 1.17 (3H, t, J=7.1 Hz), 1.52 (3H, s), 3.38 (3H, s), 3.71-3.89 (1H, m), 4.03-4.18 (1H, m) 4.70 (2H, s), 7.20-7.31 (3H, m), 7.75-7.78 (2H, m), 7.90-7.93 (2H, m).

REFERENCE EXAMPLE 16

Synthesis of (E)-3-(1-ethyl-3,3,5-trimethyl-2,4-dioxo-2,3,4,5-tetrahydro-1H-benzo[b][1,4]diazepin-7-yl)acrylic acid ethyl ester Trifluoromethane sulfonic acid 1-ethyl-3,3,5-trimethyl-2,4-dioxo-2,3,4,5-tetrahydro-1H-benzo[b][1,4]diazepin-7-yl ester(0.40 g), ethyl acrylate(0.13 g), dichlorobis(triphenylphosphine) Palladium (II) (35 mg),lithium chloride(64 mg), and triethylamine(0.19 ml) were added to DMF(4 ml). The mixture was heated at 180° C. (microwave reactor) for 20 minutes. The reaction liquid was cooled to room temperature, and subjected to celite filtration. The filtrate was condensed under reduced pressure, and the residue was purified by silica gel column chromatography (hexane: ethyl acetate=70:30→30:70). The purified product was condensed under reduced pressure to give the title compound(0.36 g) as a pale yellow solid.

$^1$H-NMR (CDCl$_3$) δppm: 0.88 (3H, s), 1.22 (3H, t, J=7.2 Hz), 1.35 (3H, t, J=7.1 Hz), 1.55 (3H, s), 3.44 (3H, s), 3.81-3.90 (1H, m), 4.08-4.25(1H, m), 4.13 (2H, q, J=7.1 Hz), 6.45 (1H, d, J=16.0 Hz), 7.25-7.27 (1H, m), 7.32-7.37 (2H, m), 7.65 (1H, d, J=16.0 Hz).

REFERENCE EXAMPLE 17

Synthesis of 3-(1-ethyl-3,3,5-trimethyl-2,4-dioxo-2,3,4,5-tetrahydro-1H-benzo[b][1,4]diazepin-7-yl) propionic acid ethyl ester 10% Palladium on carbon(0.1 g) was added to a methanol solution(10 ml) of (E)-3-(1-ethyl 3,3,5-trimethyl 2,4-dioxo-2,3,4,5-tetrahydro-1H-benzo[b][1,4]diazepin-7-yl) acrylic acid ethyl ester(0.36 g). The mixture was subjected to catalytic reduction at room temperature and under normal pressure. The catalyst was removed by celite filtration, followed by concentration under reduced pressure to give the title compound(0.29 g) as a brown solid.

$^1$H-NMR (CDCl$_3$) δppm: 0.83 (3H, s), 1.18 (3H, t, J=7.2 Hz), 1.23 (3H, t, J=7.1 Hz), 1.53 (3H, s), 2.65 (2H, t, J=7.5 Hz), 2.98 (2H, t, J=7.5 Hz), 3.40 (3H, s), 3.77-3.90 (1H, m), 4.01-4.21 (3H, m), 7.07-7.11 (2H, m), 7.21-7.26 (1H, m).

REFERENCE EXAMPLE 18

Synthesis of 3-(1-ethyl-3,3,5-trimethyl-2,4-dioxo-2,3,4,5-tetrahydro-1H-benzo[b][1,4]diazepin-7-yl)propionic acid 50% Sodium hydroxide aqueous solution(1 ml) was added to a methanol (20 ml) solution of 3-(1-ethyl 3,3,5-trimethyl-2,4-dioxo-2,3,4,5-tetrahydro-1H-benzo[b][1,4]diazepin-7-yl) propionic acid ethyl ester(1.1 g). The mixture was stirred at room temperature overnight. Water was added to the reaction liquid, followed by washing with ether. A hydrochloric acid was added to the aqueous layer, followed by extraction using ethyl acetate and drying using magnesium sulfate. The dried product was condensed under reduced pressure to give the title compound(0.97 g) as a colorless oily matter.
$^1$H-NMR (CDCl$_3$) δppm: 0.82 (3H, s), 1.18 (3H, t, J=7.2 Hz), 1.52 (3H, s), 2.72 (2H, t, J=7.5 Hz), 3.00 (2H, t, J=7.5 Hz), 3.40 (3H, s), 3.72-3.88 (1H, m), 4.03-4.21 (1H, m), 7.09-7.13 (2H, m), 7.23-7.26 (1H, m).

REFERENCE EXAMPLE 19

Synthesis of 2-(1-ethyl-3,3,5-trimethyl-2,4-dioxo-2,3,4,5-tetrahydro-1H-benzo[b][1,4]diazepin-7-yl)ethyl carbamic acid tert-butyl ester Diphenylphosphoryl azide(1.0 ml) and tert-butanol(10 ml) were added to a THF solution (10 ml) of 3-(1-ethyl-3,3,5-trimethyl-2,4-dioxo-2,3,4,5-tetrahydro-1H-benzo[b][1,4]diazepin-7-yl) propionic acid(0.97 g) and triethylamine(0.67 ml). The mixture was stirred at 100° C. overnight. The reaction liquid was cooled to room temperature, and condensed under reduced pressure. The residue was purified by silica gel column chromatography (hexane: ethyl acetate=80:20→50:50). The purified product was condensed under reduced pressure to give the title compound(0.38 g) as a colorless oily matter.
$^1$H-NMR (CDCl$_3$) δppm: 0.83 (3H, s), 1.18 (3H, t, J=7.2 Hz), 1.43 (9H, s), 1.53 (3H, s), 2.83 (2H, t, J=7.1 Hz), 3.38 (2H, t, J=7.1 Hz), 3.41 (3H, s), 3.71-3.85 (1H, m), 4.03-4.19 (1H, m), 4.57 (1H, br), 7.06-7.11 (2H, m), 7.22-7.27 (1H, m).

REFERENCE EXAMPLE 20

Synthesis of 5-(2,2-dihydroxyethyl)-5H-furo[3,2-c]pyridin-4-one

Sodium hydride (60% in oil, 0.36 g) was suspended in DMF(10 ml), and was cooled to 0° C. in an ice water bath. 5H-Furo[3,2-c]pyridin-4-one(1.0 g) was added thereto at the same temperature, and the mixture was stirred at 0° C. for an hour. Bromoacetaldehyde diethylacetal(2.6 ml) was added thereto, and the mixture was stirred at 80° C. for 5 hours. Water was added to the reaction liquid, followed by extraction by ethyl acetate. The organic layer was dried over sodium sulfate, and condensed under reduced pressure. A 3N-hydrochloric acid(5.8 ml) was added to an acetone solution (20 ml) of the residue, and the liquid was stirred at 60° C. for 5 hours. Water was added to the reaction liquid and stirred at room temperature. The precipitated insoluble matter was separated, washed with water, and dried to give the title compound(0.90 g) as a white solid.
$^1$H-NMR (DMSO-d$_6$) δppm: 3.88 (d, J=5.4 Hz, 2H), 4.95-5.03 (m, 1H), 6.08 (d, J=6.4 Hz, 2H), 6.69 (dd, J=7.4, 0.8 Hz, 1H), 6.94 (dd, J=2.1 and 0.8 Hz, 1H), 7.50 (d, J=7.4 Hz, 1H), 7.86 (d, J=2.1 Hz, 1H).

REFERENCE EXAMPLE 21

Synthesis of 5-(2,2-dihydroxy-ethyl)-7-methyl-5H-furo[3,2-c]pyridin-4-one

The synthesis of the title compound was performed in the same manner as in Reference Example 20 using appropriate starting materials.
$^1$H-NMR (DMSO-d$_6$) δppm: 2.28 (3H, d, J=1.0 Hz), 3.85 (2H, d, J=5.4 Hz), 4.95-5.02 (1H, m), 6.06 (2H, d, J=6.3 Hz), 6.95 (1H, d, J=2.1 Hz), 7.33 (1H, d, J=1.0 Hz), 7.90 (1H, d, J=2.1 Hz).

REFERENCE EXAMPLE 22

Synthesis of 5-(2,2-dihydroxyethyl)-2-methyl-5H-furo[3,2-c]pyridin-4-one

The synthesis of the title compound was performed in the same manner as in Reference Example 20 using appropriate starting materials.
$^1$H-NMR (DMSO-d$_6$), δppm: 2.36 (s, 3H), 3.86 (d, J=5.4 Hz, 2H), 4.94-4.98 (m, 1H), 6.04 (d, J=6.4 Hz, 2H), 6.52 (s, 1H), 6.59 (d, J=7.4 Hz, 1H), 7.41 (d, J=7.4 H, 1H).

REFERENCE EXAMPLE 23

Synthesis of 5-(2,2-dihydroxyethyl)-2,3-dimethyl-5H-furo[3,2-c]pyridin-4-one

The synthesis of the title compound was performed in the same manner as in Reference Example 20 using appropriate starting materials.
$^1$H-NMR (DMSO-d$_6$), δppm: 2.18 (3H, s), 2.28 (3H, s), 3.84 (2H, d, J=5.4 Hz), 4.95-5.02 (1H, m), 6.04 (2H, d, J=6.2 Hz), 6.53 (1H, d, J=7.4 Hz), 7.38 (1H, d, J=7.4 Hz).

REFERENCE EXAMPLE 24

Synthesis of 5-(2,2-dihydroxyethyl)-2,7-dimethyl-5H-furo[3,2-c]pyridin-4-one

The synthesis of the title compound was performed in the same manner as in Reference Example 20 using appropriate starting materials.
$^1$H-NMR (DMSO-d$_6$), δppm: 2.14 (3H, s), 2.39 (3H, s), 3.82 (2H, d, J=5.4 Hz), 4.95-5.01 (1H, m), 6.10 (2H, d, J=6.2 Hz), 6.55 (1H, s), 7.24 (1H, s).

REFERENCE EXAMPLE 25

Synthesis of 6-(2,2-dihydroxyethyl)-4-methyl-6H-furo[2,3-c]pyridin-7-one

The synthesis of the title compound was performed in the same manner as in Reference Example 20 using appropriate starting materials.
$^1$H-NMR (DMSO-d$_6$), δppm: 2.17(3H, s), 3.86 (2H, d, J=5.4 Hz), 4.95-5.01 (1H, m), 6.06 (2H, d, J=6.2 Hz), 6.92 (1H, d, J=1.8 Hz), 7.17 (1H, s), 8.10 (1H, d, J=1.8 Hz).

REFERENCE EXAMPLE 26

Synthesis of 5-(2,2-dihydroxyethyl)-5H-thieno[3,2-c]pyridin-4-one

The synthesis of the title compound was performed in the same manner as in Reference Example 20 using appropriate starting materials.

$^1$H-NMR (DMSO-d$_6$), δppm: 3.90 (d, J=6.3 Hz, 2H), 4.99-5.04 (m, 1H), 6.07 (d, J=6.3 Hz, 2H), 6.86 (d, J=7.2 Hz, 1H), 7.41-7.49 (m, 2H), 7.57-7.64 (m, 1H).

REFERENCE EXAMPLE 27

Synthesis of 6-(2,2-dihydroxyethyl)-6H-thieno[2,3-c]pyridin-7-one

The synthesis of the title compound was performed in the same manner as in Reference Example 20 using appropriate starting materials.
$^1$H-NMR (DMSO-d$_6$), δppm: 3.98 (d, J=5.3 Hz, 2H), 5.11-5.16 (m, 1H), 6.04 (d, J=6.4 Hz, 1H), 6.66 (d, J=7.1 Hz, 2H), 7.27 (d, J=5.2 Hz, 1H), 7.41 (d, J=7.1 Hz, 1H), 7.84 (d, J=5.2 H, 1H).

REFERENCE EXAMPLE 28

(1-Ethyl-3,3,5-trimethyl-2,4-dioxo-2,3,4,5-tetrahydro-1H-benzo[b][1,4]diazepin-7-yl)-acetonitrile To a solution of 7-chloromethyl-1-ethyl-3,3,5-trimethyl-1,5-dihydrobenzo[b][1,4]diazepine-2,4-dione (1.11 g) in DMF (15 ml) was added sodium cyanide(0.59 g) at room temperature, the mixture was stirred overnight. Water was added to the reaction mixture, followed by extraction using ethyl acetate. The organic layer was dried with magnesium sulfate, and was condensed under reduced pressure to give the title compound(0.84 g) as a pale yellow oil.
$^1$H NMR (CDCl$_3$), δppm: : 0.85 (3H, s), 1.19 (3H, t, J=7.1 Hz), 1.54 (3H, s), 3.43 (3H, s), 3.77-3.86 (3H, m), 4.09-4.19 (1H, m), 7.21-7.24 (2H, m), 7.34 (1H, d, J=8.3 Hz).

REFERENCE EXAMPLE 29

2-(1-Ethyl-3,3,5-trimethyl-2,4-dioxo-2,3,4,5-tetrahydro-1H-benzo[b][1,4]diazepin-7-yl)-2-methyl-propionitrile (1-Ethyl-3,3,5-trimethyl-2,4-dioxo-2,3,4,5-tetrahydro-1H-benzo[b][1,4]diazepin-7-yl)-acetonitrile (0.84 g) was dissolved in DMF(20 ml), and was cooled to 0° C. in ice water bath. Sodium hydride (60% in oil, 0.259 g) was added thereto at the same temperature, and the mixture was stirred at 0° C. for 0.5 hours. Methyl iodide (0.405 ml) was added thereto, and the mixture was stirred at room temperature overnight. Methanol was added to the reaction mixture, and the mixture was condensed under reduced pressure. The residue was purified by silica gel column chromatography (hexane: ethyl acetate=4:1→1:1). The purified product was condensed to dryness under reduced pressure to give the title compound (0.9 g) as a white powder.
$^1$H NMR (CDCl$_3$), δppm: 0.84 (3H, s), 1.20 (3H, t, J=7.06 Hz), 1.54 (3H, s), 1.77 (6H, s), 3.45 (3H, s), 3.78-3.87 (1H, m), 4.09-4.18 (1H, m), 7.34 (3H, s).

REFERENCE EXAMPLE 30

1-Ethyl-3,3,5-trimethyl-2,4-dioxo-2,3,4,5-tetrahydro-1H-benzo[b][1,4]diazepine-7-carboxylic acid To a t-butanol (20 ml) and H2O (5 ml) solution of 1-ethyl-3,3,5-trimethyl-2,4-dioxo-2,3,4,5-tetrahydro-1H-benzo[b][1,4]diazepine-7-carbaldehyde (2.25 g) and 2-methyl-2-butene(3.25 ml) were added sodium dihydrogenphosphate (0.92 g) and sodium chlorite (2.081 g), and the mixture was stirred at room temperature overnight. Water was added to the reaction mixture, followed by extraction using ethyl acetate. The organic layer was dried with sodium sulfate, and was condensed under reduced pressure to give the title compound (0.98 g) as a white powder.
mp: 296-299° C.

REFERENCE EXAMPLE 31

7-Bromomethyl-1-ethyl-3,3,5-trimethyl-1,5-dihydro-benzo[b][1,4]diazepine-2,4-dione Lithium bromide (0.678 g) was added to an THF solution (2.3 ml) of 7-chloromethyl-1-ethyl-3,3,5-trimethyl-1,5-dihydro-benzo[b][1,4]diazepine-2,4-dione (0.23 g), and the mixture was stirred at room temperature overnight. Water was added to the reaction mixture, followed by extraction using ethyl acetate. The organic layer was dried with magnesium sulfate, and was condensed under reduced pressure to give the title compound(0.24 g) as a white solid.
$^1$H NMR (CDCl$_3$), δppm: 0.85 (3H, s), 1.20 (3H, t, J=7.1 Hz), 1.53 (3H, s), 3.43 (3H, s), 3.77-3.87 (1H, m), 4.08-4.17 (1H, m), 4.49 (2H, s), 7.28-7.29 (3H, m).

REFERENCE EXAMPLE 32

1-Ethyl-7-(3-hydroxy-propyl)-3,3,5-trimethyl-1,5-dihydro-benzo[b][1,4]diazepine-2,4-dione 3-(1-Ethyl-3,3,5-trimethyl-2,4-dioxo-2,3,4,5-tetrahydro-1H-benzo[b][1,4]diazepin-7-yl)propionic acid (1.0 g) was dissolved in THF(20 ml) and was cooled to 0° C. in ice water bath. Triethylamine(0.525 ml) and ethyl chloroformate(0.325 ml) were added to this solution and stirred for 30 minutes at same temperature. Sodium borohydride(0.36 g) was added to the mixture under cooling in ice methanol bath. Methanol (0.64 ml) was added dropwise to the mixture and stirred for 1 hour at same temperature. Water was added to the reaction mixture, followed by extraction using ethyl acetate. The organic layer was dried with magnesium sulfate, and was condensed under reduced pressure. The residue was purified by silica gel column chromatography (hexane: ethyl acetate=1:1→0:1). The purified product was condensed to dryness under reduced pressure to give the title compound (0.71 g) as a colorless oil.
$^1$H NMR (CDCl$_3$), δppm: 0.83 (3H, s), 1.18 (3H, t, J=7.1 Hz), 1.53 (3H, s), 1.88-1.95(2H, m), 2.76 (2H, t, J=7.8 Hz), 3.41 (3H, s), 3.71 (2H, t, J=6.3 Hz), 3.74-3.83 (1H, m), 4.10-4.19 (1H, m), 7.07 (1H, d, J=1.8 Hz), 7.11 (1H, dd, J=8.3 and 1.8 Hz), 7.23 (1H, d, J=8.3 Hz)

REFERENCE EXAMPLE 33

1-(2-Methoxy-ethyl)-3,3-dimethyl-2,4-dioxo-2,3,4,5-tetrahydro-1H-benzo[b][1,4]diazepine-7-carbonitrile The synthesis of the title compound was performed in the same manner as in Reference Example 10 using appropriate starting materials.
mp:184-185° C.

REFERENCE EXAMPLE 34

1-Isobutyl-3,3-dimethyl-2,4-dioxo-2,3,4,5-tetrahydro-1H-benzo[b][1,4]diazepine-7-carbonitrile The synthesis of the title compound was performed in the same manner as in Reference Example 10 using appropriate starting materials.
mp:204-205° C.

REFERENCE EXAMPLE 35

1-(2-Methoxy-ethyl)-3,3-dimethyl-2,4-dioxo-2,3,4,5-tetrahydro-1H-benzo[b][1,4]diazepine-7-carbaldehyde The synthesis of the title compound was performed in the same manner as in Reference Example 13 using appropriate starting materials.
mp:163-166° C.

REFERENCE EXAMPLE 36

1-Isobutyl-3,3-dimethyl-2,4-dioxo-2,3,4,5-tetrahydro-1H-benzo[b][1,4]diazepine-7-carbaldehyde The synthesis of the title compound was performed in the same manner as in Reference Example 13 using appropriate starting materials.
mp:154-155° C.

REFERENCE EXAMPLE 37

1-Cyclopropyl-3,3-dimethyl-2,4-dioxo-2,3,4,5-tetrahydro-1H-benzo[b][1,4]diazepine-7-carbonitrile The synthesis of the title compound was performed in the same manner as in Reference Example 10 using appropriate starting materials.
$^1$H NMR (CDCl$_3$), δppm: 0.43 (2H, br), 1.07 (2H, br), 1.66 (3H, br), 3.17-3.23 (1H, m), 7.35 (1H, br), 7.50-7.56 (2H, m), 8.67 (1H, br).

REFERENCE EXAMPLE 38

1-Cyclopropylmethyl-3,3-dimethyl-2,4-dioxo-2,3,4,5-tetrahydro-1H-benzo[b][1,4]diazepine-7-carbonitrile The synthesis of the title compound was performed in the same manner as in Reference Example 10 using appropriate starting materials.
$^1$H NMR (CDCl$_3$), δppm: 0.22-0.23 (2H, m), 0.46-0.48 (2H, m), 0.98-1.07 (1H, m), 3.90 (1H, br-d), 7.38-7.54 (3H, m), 9.42 (1H, br).

REFERENCE EXAMPLE 39

1-Cyclopropyl-3,3-dimethyl-2,4-dioxo-2,3,4,5-tetrahydro-1H-benzo[b][1,4]diazepine-7-carbaldehyde The synthesis of the title compound was performed in the same manner as in Reference Example 13 using appropriate starting materials.
$^1$H NMR (CDCl$_3$), δppm: 0.44 (2H, br), 1.08 (2H, br), 1.30 (6H, br), 3.20-3.25 (1H, m), 7.49 (1H, d, J=1.8 Hz), 7.58 (1H, d, J=8.4 Hz), 7.78 (1H, dd, J=8.4, 1.8 Hz), 9.98 (1H, s).

REFERENCE EXAMPLE 40

1-Cyclopropylmethyl-3,3-dimethyl-2,4-dioxo-2,3,4,5-tetrahydro-1H-benzo[b][1,4]diazepine-7-carbaldehyde The synthesis of the title compound was performed in the same manner as in Reference Example 13 using appropriate starting materials.
mp:124-125° C.

REFERENCE EXAMPLE 41

1-Cyclopropyl-3,3,5-trimethyl-2,4-dioxo-2,3,4,5-tetrahydro-1H-benzo[b][1,4]diazepine-7-carbonitrile 1-(2-Methoxy-ethyl)-3,3-dimethyl-2,4-dioxo-2,3,4,5-tetrahydro-1H-benzo[b][1,4]diazepine-7-carbonitrile(1.0 g) was dissolved in DMF(10 ml), and was cooled to 0° C. in ice water bath. Sodium hydride (60% in oil, 0.167 g) was added thereto at the same temperature, and the mixture was stirred at 0° C. for 0.5 hours. Methyl iodide (0.261 ml) was added thereto, and the mixture was stirred at room temperature overnight. Water(100 ml) was added to the reaction mixture, and was cooled to 0° C. in ice water bath. The precipitated insoluble matter was separated and dried to give the title compound(0.61 g) as a white powder.
$^1$H NMR (CDCl$_3$), δppm: 0.10-0.17 (1H, m), 0.66-0.73 (1H, m), 0.82-0.92 (1H, m), 0.89 (3H, s), 1.21-1.29 (1H, m), 1.55 (3H, s), 3.16-3.22 (1H, m), 3.41 (3H, s), 7.50-7.57 (3H, m).

REFERENCE EXAMPLE 42

1-Isobutyl-3,3,5-trimethyl-2,4-dioxo-2,3,4,5-tetrahydro-1H-benzo[b][1,4]diazepine-7-carbonitrile The synthesis of the title compound was performed in the same manner as in Reference Example 41 using appropriate starting materials.
$^1$H NMR (CDCl$_3$), δppm: 0.72 (3H, d, J=6.7 Hz), 0.75 (3H, d, J=6.7 Hz), 0.86 (3H, s), 1.55 (3H, s), 1.77-1.88 (1H, m), 3.35 (1H, dd, J=13.7, 6.6 Hz), 3.45 (3H, s), 4.40 (1H, dd, J=13.7, 8.4 Hz), 7.41 (1H, d, J=8.4 Hz), 7.53-7.57 (2H, m).

REFERENCE EXAMPLE 43

1-(2-Methoxy-ethyl)-3,3,5-trimethyl-2,4-dioxo-2,3,4,5-tetrahydro-1H-benzo[b][1,4]diazepine-7-carbonitrile The synthesis of the title compound was performed in the same manner as in Reference Example 41 using appropriate starting materials.
$^1$H NMR (CDCl$_3$), δppm: 0.89 (3H, s), 1.55 (3H, s), 3.32 (3H, s), 3.43 (3H, s), 3.59 (1H, ddd, J=10.4, 5.0, 3.7 Hz), 3.75 (1H, ddd, J=10.4, 7.8, 3.4 Hz), 3.94 (1H, ddd, J=14.4, 7.8, 3.7 Hz), 4.12 (1H, ddd, J=14.4, 5.0, 3.4 Hz), 7.52-7.55 (2H, m), 7.81-7.84 (1H, m).

REFERENCE EXAMPLE 44

5-Cyclopropyl-3,3-dimethyl-2,4-dioxo-2,3,4,5-tetrahydro-1H-benzo[b][1,4]diazepine-7-carbonitrile The synthesis of the title compound was performed in the same manner as in Reference Example 10 using appropriate starting materials.
mp:252-253° C.

REFERENCE EXAMPLE 45

5-Isobutyl-3,3-dimethyl-2,4-dioxo-2,3,4,5-tetrahydro-1H-benzo[b][1,4]diazepine-7-carbonitrile The synthesis of the title compound was performed in the same manner as in Reference Example 10 using appropriate starting materials.
mp:219-220° C.

REFERENCE EXAMPLE 46

5-Cyclopropylmethyl-3,3-dimethyl-2,4-dioxo-2,3,4, 5-tetrahydro-1H-benzo[b][1,4]diazepine-7-carbonitrile The synthesis of the title compound was performed in the same manner as in Reference Example 10 using appropriate starting materials.
mp:234-236° C.

REFERENCE EXAMPLE 47

5-(2-Methoxy-ethyl)-3,3-dimethyl-2,4-dioxo-2,3,4, 5-tetrahydro-1H-benzo[b][1,4]diazepine-7-carbonitrile The synthesis of the title compound was performed in the same manner as in Reference Example 10 using appropriate starting materials.
mp:247-248° C.

REFERENCE EXAMPLE 48

Methanesulfonic acid 3-(1-ethyl-3,3,5-trimethyl-2,4-dioxo-2,3,4,5-tetrahydro-1H-benzo[b][1,4]diazepin-7-yl)-propyl ester The synthesis of the title compound was obtained from 1-ethyl-7-(3-hydroxypropyl)-3,3,5-trimethyl-2,4-dioxo-2,3,4,5-tetrahydro-1H-benzo[b][1,4]diazepine and methanesulfonyl chloride in a conventional matter.
$^1$H NMR (CDCl$_3$), δppm: 0.86 (3H, s), 1.18 (3H, t, J=7.1 Hz), 1.53 (3H, s), 2.05-2.16(2H, m), 2.79 (2H, t, J=7.6 Hz), 3.03 (3H, s), 3.42 (3H, s), 3.74-3.83 (1H, m), 4.10-4.18 (1H, m), 4.26 (2H, t, J=6.2 Hz), 7.07 (1H, dd, J=8.3 and 2.0 Hz), 7.10 (1H, d, J=2.0 Hz), 7.25 (1H, d, J=8.3 Hz).

REFERENCE EXAMPLE 49

1-Cyclopropyl-3,3,5-trimethyl-2,4-dioxo-2,3,4,5-tetrahydro-1H-benzo[b][1,4]diazepine-7-carbaldehyde The synthesis of the title compound was performed in the same manner as in Reference Example 13 using appropriate starting materials.
$^1$H NMR (CDCl$_3$), δppm: 0.10-0.20 (1H, m), 0.66-0.73 (1H, m), 0.73-0.94 (1H, m), 0.89 (3H, s), 1.21-1.28 (1H, m), 1.55 (3H, s), 3.91-3.45 (1H, m), 3.45 (3H, s), 7.57 (1H, d, 8.4 Hz), 7.74 (1H, d, J=1.8 Hz), 7.79 (1H, dd, J=8.4, 1.8 Hz), 10.01 (1H, s).

REFERENCE EXAMPLE 50

1-Isobutyl-3,3,5-trimethyl-2,4-dioxo-2,3,4,5-tetrahydro-1H-benzo[b][1,4]diazepine-7-carbaldehyde The synthesis of the title compound was performed in the same manner as in Reference Example 13 using appropriate starting materials.
$^1$H NMR (CDCl$_3$), δppm: 0.71 (3H, d, J=6.7 Hz), 0.75 (3H, d, J=6.7 Hz), 0.86 (3H, s), 1.53 (3H, s), 1.76-1.90 (1H, m), 3.39 (1H, dd, J=13.6, 6.6 Hz), 3.49 (3H, s), 4.42 (1H, dd, J=13.6, 8.4 Hz), 7.47 (1H, d, J=9.0 Hz), 7.76-7.79 (2H, m), 10.01 (1H, s).

REFERENCE EXAMPLE 51

1-(2-Methoxy-ethyl)-3,3,5-trimethyl-2,4-dioxo-2,3, 4,5-tetrahydro-1H-benzo[b][1,4]diazepine-7-carbaldehyde The synthesis of the title compound was performed in the same manner as in Reference Example 13 using appropriate starting materials.
$^1$H NMR (CDCl$_3$), δppm: 0.88 (3H, s), 1.55 (3H, s), 3.31 (3H, s), 3.48 (3H, s), 3.60 (1H, ddd, J=10.4, 5.2, 4.1 Hz), 3.74 (1H, ddd, J=10.4, 7.1, 4.1 Hz), 4.01-4.15 (2H, m), 7.75-7.78 (2H, m), 7.80-7.83 (1H, m), 10.01 (1H, s).

REFERENCE EXAMPLE 52

5-Isobutyl-3,3-dimethyl-2,4-dioxo-2,3,4,5-tetrahydro-1H-benzo[b][1,4]diazepine-7-carbaldehyde The synthesis of the title compound was performed in the same manner as in Reference Example 13 using appropriate starting materials.
mp:208-211° C.

REFERENCE EXAMPLE 53

5-Cyclopropylmethyl-3,3-dimethyl-2,4-dioxo-2,3,4, 5-tetrahydro-1H-benzo[b][1,4]diazepine-7-carbaldehyde The synthesis of the title compound was performed in the same manner as in Reference Example 13 using appropriate starting materials.
mp:183-188° C.

REFERENCE EXAMPLE 54

1,3,3-Trimethyl-2,4-dioxo-2,3,4,5-tetrahydro-1H-benzo[b][1,4]diazepine-7-carbonitrile The synthesis of the title compound was performed in the same manner as in Reference Example 10 using appropriate starting materials.
mp:289-294° C.

REFERENCE EXAMPLE 55

1-Ethyl-3,3-dimethyl-2,4-dioxo-2,3,4,5-tetrahydro-1H-benzo[b][1,4]diazepine-7-carbonitrile The synthesis of the title compound was performed in the same manner as in Reference Example 10 using appropriate starting materials.
mp:215-218° C.

REFERENCE EXAMPLE 56

3,3,5-Trimethyl-2,4-dioxo-2,3,4,5-tetrahydro-1H-benzo[b][1,4]diazepine-7-carbonitrile The synthesis of the title compound was performed in the same manner as in Reference Example 10 using appropriate starting materials.
mp:250-251° C.

REFERENCE EXAMPLE 57

5-Ethyl-3,3-dimethyl-2,4-dioxo-2,3,4,5-tetrahydro-1H-benzo[b][1,4]diazepine-7-carbonitrile The synthesis of the title compound was performed in the same manner as in Reference Example 10 using appropriate starting materials.
mp:241-247° C.

REFERENCE EXAMPLE 58

1,3,3-Trimethyl-2,4-dioxo-2,3,4,5-tetrahydro-1H-benzo[b][1,4]diazepine-7-carbaldehyde The synthesis of the title compound was performed in the same manner as in Reference Example 13 using appropriate starting materials.
mp:208-210° C.

REFERENCE EXAMPLE 59

1-Ethyl-3,3-dimethyl-2,4-dioxo-2,3,4,5-tetrahydro-1H-benzo[b][1,4]diazepine-7-carbaldehyde The synthesis of the title compound was performed in the same manner as in Reference Example 13 using appropriate starting materials.
$^1$H NMR (CDCl$_3$), δppm: 1.07 (3H, br), 1.29 (3H, t, J=7.1 Hz), 1.57 (3H, br), 4.57 (2H, q, J=7.1 Hz), 7.50 (1H, d, J=8.5 Hz), 7.57 (1H, br), 7.77 (1H, dd, J=8.5, 1.8 Hz), 8.42 (1H, br). 9.99 (1H, s).

REFERENCE EXAMPLE 60

3,3,5-Trimethyl-2,4-dioxo-2,3,4,5-tetrahydro-1H-benzo[b][1,4]diazepine-7-carbaldehyde The synthesis of the title compound was performed in the same manner as in Reference Example 13 using appropriate starting materials.
mp:197-202° C.

REFERENCE EXAMPLE 61

5-Ethyl-3,3-dimethyl-2,4-dioxo-2,3,4,5-tetrahydro-1H-benzo[b][1,4]diazepine-7-carbaldehyde The synthesis of the title compound was performed in the same manner as in Reference Example 13 using appropriate starting materials.
mp:188-191° C.

REFERENCE EXAMPLE 62

5-Cyclopropylmethyl-1-(2-methoxy-ethyl)-3,3-dimethyl-2,4-dioxo-2,3,4,5-tetrahydro-1H-benzo[b][1,4]diazepine-7-carbonitrile The synthesis of the title compound was performed in the same manner as in Reference Example 41 using appropriate starting materials.
$^1$H NMR (CDCl$_3$), δppm: 0.15-0.24 (2H, m), 0.38-0.51 (2H, m), 0.87 (3H, s), 0.93-1.01 (1H, m), 1.55 (3H, s), 3.32 (3H, s), 3.53-3.62 (1H, m), 3.73-3.79 (1H, m), 3.97-4.04 (1H, m), 4.06-4.13 (1H, m), 7.55 (1H, dd, J=8.5, 1.9 Hz), 7.66 (1H, d, J=1.9 Hz), 7.82 (1H, d, J=8.5 Hz).

REFERENCE EXAMPLE 63

1-Cyclopropylmethyl-5-(2-methoxy-ethyl)-3,3-dimethyl-2,4-dioxo-2,3,4,5-tetrahydro-1H-benzo[b][1,4]diazepine-7-carbonitrile The synthesis of the title compound was performed in the same manner as in Reference Example 41 using appropriate starting materials.
$^1$H NMR (CDCl$_3$), δppm: 0.14-0.22 (2H, m), 0.38-0.49 (2H, m), 0.87 (3H, s), 0.93-1.02 (1H, m), 1.55 (3H, s), 3.34 (3H, s), 3.53-3.65 (1H, m), 3.77-3.83 (1H, m), 3.91-3.98 (1H, m), 4.05-4.13 (1H, m), 7.45 (1H, d, J=8.5 Hz), 7.53 (1H, dd, J=8.5, 1.9 Hz), 8.10 (1H, d, J=1.9 Hz).

REFERENCE EXAMPLE 64

5-Cyclopropyl-1-cyclopropylmethyl-3,3-dimethyl-2,4-dioxo-2,3,4,5-tetrahydro-1H-benzo[b][1,4]diazepine-7-carbonitrile The synthesis of the title compound was performed in the same manner as in Reference Example 41 using appropriate starting materials.
$^1$H NMR (CDCl$_3$), δppm: 0.03-0.19 (3H, m), 0.27-0.41 (2H, m), 0.61-0.68 (1H, m), 0.81-0.93 (1H, m), 0.88 (3H, s), 1.21-1.29 (2H, m), 1.54 (3H, s), 3.06-3.26 (1H, m), 3.42 (1H, dd, J=14.3, 6.8 Hz), 4.31 (1H, dd, J=14.3, 7.5 Hz), 7.38 (1H, d, J=8.5. Hz), 7.53 (1H, dd, J=8.5, 1.8 Hz), 7.72 (1H, d, J=1.8 Hz).

REFERENCE EXAMPLE 65

5-Cyclopropylmethyl-1-(2-methoxy-ethyl)-3,3-dimethyl-2,4-dioxo-2,3,4,5-tetrahydro-1H-benzo[b][1,4]diazepine-7-carbaldehyde The synthesis of the title compound was performed in the same manner as in Reference Example 13 using appropriate starting materials.
$^1$H NMR (CDCl$_3$), δppm: 0.13-0.25 (2H, m), 0.37-0.48 (2H, m), 0.87 (3H, s), 0.96-1.03 (1H, m), 1.55 (3H, s), 3.32 (3H, s), 3.54-3.59 (1H, m), 3.66 (1H, dd, J=14.2, 6.4 Hz), 3.75 (1H, ddd, J=10.3, 7.2, 4.7 Hz), 4.04-4.19 (3H, m), 7.78 (1H, dd, J=8.4, 1.7 Hz), 7.82 (1H, d, J=8.4 Hz), 7.88 (1H, d, J=1.7 Hz), 10.0 (1H, s).

REFERENCE EXAMPLE 66

1-Cyclopropylmethyl-5-(2-methoxy-ethyl)-3,3-dimethyl-2,4-dioxo-2,3,4,5-tetrahydro-1H-benzo[b][1,4]diazepine-7-carbaldehyde The synthesis of the title compound was performed in the same manner as in Reference Example 13 using appropriate starting materials.
$^1$H NMR (CDCl$_3$), δppm: 0.14-0.24 (2H, m), 0.38-0.50 (2H, m), 0.87 (3H, s), 0.97-1.07 (1H, m), 1.55 (3H, s), 3.33 (3H, s), 3.53-3.59 (1H, m), 3.65 (1H, dd, J=14.2, 6.4 Hz), 3.73-3.79 (1H, m), 4.03-4.16 (3H, m), 7.51 (1H, d, J=8.4 Hz), 7.79 (1H, dd, J=8.4, 1.9 Hz), 8.19 (1H, d, J=1.9 Hz), 10.0 (1H, s).

REFERENCE EXAMPLE 67

5-Cyclopropyl-1-cyclopropylmethyl-3,3-dimethyl-2,4-dioxo-2,3,4,5-tetrahydro-1H-benzo[b][1,4]diazepine-7-carbaldehyde The synthesis of the title compound was performed in the same manner as in Reference Example 13 using appropriate starting materials.

$^1$H NMR (CDCl$_3$), δppm: 0.09-0.07 (1H, m), 0.09-0.20 (2H, m), 0.27-0.40 (2H, m), 0.62-0.68 (1H, m), 0.83-0.92 (1H, m), 0.88 (3H, s), 1.20-1.28 (2H, m), 1.54 (3H, s), 3.27-3.33 (1H, m), 3.45 (1H, dd, J=14.3, 6.8 Hz), 4.34 (1H, dd, J=14.3, 7.5 Hz), 7.43 (1H, d, J=8.4 Hz), 7.77 (1H, dd, J=8.4, 1.9 Hz), 7.92 (1H, d, J=1.9 Hz), 10.0 (1H, s).

EXAMPLE 1

Synthesis of 7-[4-(1,3-dioxo-1,3-dihydroisoindol-2-yl)butyl]-1-ethyl-3,3,5-trimethyl-1,5-dihydrobenzo[b][1,4]diazepine-2,4-dione 10% Palladium on carbon(0.52 g) was added to a methanol solution (50 ml) of 7-[4-(1,3-dioxo-1,3-dihydroisoindol-2-yl)but-1-ynyl]-1-ethyl-3,3,5-trimethyl-1,5-dihydrobenzo[b][1,4]diazepine-2,4-dione(2.2 g). The mixture was subjected to catalytic reduction at room temperature under normal pressure. The catalyst was removed by celite filtration, followed by concentration under reduced pressure to give the title compound(1.93 g) as a brown solid.

$^1$H-NMR (CDCl$_3$) δppm: 0.81 (3H, s), 1.17 (3H, t, J=7.1 Hz), 1.52 (3H, s), 1.61-1.79 (4H, m), 2.68 (2H, t, J=7.0 Hz), 3.40 (3H, s), 3.71-3.81 (3H, m), 4.01-4.18 (1H, m), 7.02-7.08 (2H, m), 7.20 (1H, d, J=8.3 Hz), 7.70-7.74 (2H, m), 7.83-7.86 (2H, m).

EXAMPLE 2

Synthesis of 7-(4-aminobutyl)-1-ethyl-3,3,5-trimethyl-1,5-dihydrobenzo[b][1,4]diazepine-2,4-dione Hydrazine hydrate(0.5 ml) was added to a methanol solution (60 ml) of 7-[4-(1,3-dioxo-1,3-dihydroisoindol-2-yl)butyl]-1-ethyl-3,3,5-trimethyl-1,5-dihydrobenzo[b][1,4]diazepine 2,4-dione(1.93 g). The mixture was stirred for 5.5 hours while heated under reflux. After cooled to room temperature, a 1N-sodium hydroxide aqueous solution was added to the reaction mixture, followed by extraction using ethyl acetate. The organic layer was dried over anhydrous magnesium sulfate, and condensed under reduced pressure to give the title compound(1.2 g) as a yellow solid.

$^1$H-NMR (CDCl$_3$) δppm: 0.83 (3H, s), 1.18 (3H, t, J=7.1 Hz), 1.47-1.58 (2H, m), 1.52 (3H, s), 1.62-1.73 (4H, m), 2.66 (2H, t, J=7.6 Hz), 2.76 (2H, t, J=7.0 Hz), 3.41 (3H, s), 3.71-3.84 (1H, m), 4.03-4.18 (1H, m), 7.02-7.09 (2H, m), 7.21 (1H, d, J=8.3 Hz).

EXAMPLE 3

Synthesis of 1-ethyl-3,3,5-trimethyl-7-{4-[(pyridin-4-ylmethyl)amino]butyl}-1,5-dihydrobenzo[b][1,4]diazepine-2,4-dione 4-Pyridine carbaldehyde(0.15 ml) was added to a methanol solution (10 ml) of 7-(4-aminobutyl)-1-ethyl-3,3,5-trimethyl-1,5-dihydrobenzo[b][1,4]diazepine-2,4-dione(0.51 g). The mixture was stirred for an hour at room temperature under nitrogen atmosphere. Sodium borohydride (0.2 g) was added to the mixture, and the mixture was stirred at room temperature overnight. The liquid was then condensed under reduced pressure, and the residue was purified by silica gel column chromatography (ethyl acetate: methanol=9:1→3:2). The purified product was condensed under reduced pressure to give the title compound(0.38 g) as a colorless oily matter.

$^1$H-NMR (CDCl$_3$) δppm: 0.82 (3H, s), 1.18 (3H, t, J=7.1 Hz), 1.47-1.58 (2H, m), 1.53 (3H, s), 1.53-1.60 (2H, m), 1.62-1.71 (2H, m), 2.62-2.68 (4H, m), 3.40 (3H, s), 3.69-3.81 (3H, m), 4.03-4.19 (1H, m), 7.01 (1H, d, J=1.9 Hz), 7.06 (1H, dd, J=8.3, 1.9 Hz), 7.21 (1H, d, J=8.3 Hz), 7.25-7.28 (2H, m), 8.53-3.56 (2H, m).

EXAMPLE 4

Synthesis of 1-ethyl-3,3,5-trimethyl-7-(4-{N-[2-(2-methyl-4-oxo-4H-furo[3,2-c]pyridin-5-yl)ethyl]-N-(pyridin-4-ylmethyl)amino}butyl)-1,5-dihydrobenzo[b][1,4]diazepine-2,4-dione dihydrochloride (2-Methyl-4-oxo-4H-furo[3,2-c]pyridin 5-yl)acetaldehyde(0.18 g) and acetic acid(0.1 ml) were added to a 1,2-dichloroethane solution (5 ml) of 1-ethyl-3,3,5-trimethyl-7-{4-[(pyridin-4-ylmethyl)amino]butyl}-1,5-dihydrobenzo[b][1,4]diazepine 2,4-dione(0.38 g). The mixture was stirred for 30 minutes at room temperature. sodium triacetoxyborohydride(0.32 g) was added to the mixture, and the mixture was stirred at room temperature overnight. The reaction mixture was condensed under reduced pressure. The residue was purified by silica gel column chromatography (ethyl acetate: methanol=1:0→9:1). The purified product was condensed under reduced pressure. A 6N-hydrogen chloride ethyl acetate solution(1.0 ml) was added to an ethyl acetate solution (20 ml) of the residue, and the liquid was stirred at room temperature. The precipitated insoluble matter was separated, washed with ethyl acetate, and dried to give the title compound(0.43 g) as a white solid.

$^1$H-NMR (DMSOd$_6$) δppm: 0.69 (3H, s), 1.03 (3H, t, J=7.1 Hz), 1.30 (3H, s), 1.56 (2H, br), 1.76 (2H, br), 2.38 (3H, s), 2.59 (2H, t, J=7.6 Hz), 3.13 (2H, br), 3.31 (3H, s), 3.22-3.38 (2H, m), 3.40-3.55 (1H, m), 3.99-4.08(1H, m), 4.42 (2H, br), 4.64 (2H, br), 6.56 (1H, s), 6.75 (1H, d, J=7.4 Hz), 7.13 (1H, d, J=8.4 Hz), 7.25 (1H, s), 7.38 (1H, d, J=8.4 Hz), 7.63 (1H, br), 8.22 (2H, br), 8.92 (2H, br).

EXAMPLE 5

Synthesis of 1-ethyl-3,3,5-trimethyl-7-{4-[(2-methylpyridin-3-ylmethyl)amino]butyl}-1,5-dihydrobenzo[b][1,4]diazepine-2,4-dione The synthesis of the title compound was performed in the same manner as in Example 3 using appropriate starting materials.

$^1$H-NMR (CDCl$_3$) δppm: 0.82 (3H, s), 1.18 (3H, t, J=7.1 Hz), 1.53 (3H, s), 1.52-1.61 (2H, m), 1.63-1.70 (2H, m), 2.56 (3H, s), 2.62-2.73 (4H, m), 3.40 (3H, s), 3.68-3.81 (3H, m), 4.02-4.19 (1H, m), 7.01-7.11 (3H, m), 7.20 (1H, d, J=8.3 Hz), 7.58-7.61 (1H, m), 8.38-8.40 (1H, m).

EXAMPLE 6

Synthesis of 1-ethyl-3,3,5-trimethyl-7-(4-{N-(2-methylpyridin-3-ylmethyl)-N-[2-(4-oxo-4H-furo[3,2-c]pyridin-5-yl)ethyl]amino}butyl)-1,5-dihydrobenzo[b][1,4]diazepine-2,4-dione dihydrochloride The synthesis of the title compound was performed in the same manner as in Example 4 using appropriate starting materials.

¹H-NMR (DMSO-d₆) δppm: 0.70 (3H, s), 1.04 (3H, t, J=7.1 Hz), 1.31 (3H, s), 1.59 (2H, br), 1.74 (2H, br), 2.50 (3H, s), 2.61 (2H, t, J=7.6 Hz), 2.80 (2H, br), 3.10 (2H, br), 3.31 (3H, s), 3.55-3.70 (1H, m), 3.95-4.08 (1H, m), 4.37 (4H, br), 6.56 (1H, s), 6.82 (1H, br), 6.95 (1H, s), 7.13 (1H, d, J=8.4 Hz), 7.25 (1H, s), 7.39 (1H, d, J=8.4 Hz), 7.68 (1H, br), 7.81 (1H, br), 7.91 (1H, br), 8.71 (2H, br).

EXAMPLE 7

Synthesis of 7-[3-(1,3-dioxo-1,3-dihydroisoindol-2-yl)propyl]-1-ethyl-3,3,5-trimethyl-1,5-dihydro-benzo[b][1,4]diazepine-2,4-dione The synthesis of the title compound was performed in the same manner as in Example 1 using appropriate starting materials.
¹H NMR (CDCl₃) δppm: 0.80 (3H, s), 1.15 (3H, t, J=7.1 Hz), 1.52 (3H, s), 2.00-2.13 (2H, m), 2.72 (2H, t, J=7.7 Hz), 3.42 (3H, s), 3.68-3.73 (3H, m), 3.98-4.11 (1H, m), 7.07-7.10 (2H, m), 7.17-7.20 (1H, m), 7.70-7.75 (2H, m), 7.82-7.85 (2H, m).

EXAMPLE 8

Synthesis of 7-(3-aminopropyl)-1-ethyl-3,3,5-trimethyl-1,5-dihydrobenzo[b][1,4]diazepine-2,4-dione The synthesis of the title compound was performed in the same manner as in Example 2 using appropriate starting materials.
¹H NMR (CDCl₃) δppm: 0.84 (3H, s), 1.19 (3H, t, J=7.1 Hz), 1.54 (3H, s), 1.76 (2H, br), 1.74-1.91 (2H, m), 2.71 (2H, t, J=8.2 Hz), 2.84 (2H, t, J=7.0 Hz), 3.42 (3H, s), 3.81-3.95 (1H, m), 4.08-4.19 (1H, m), 7.09-7.14 (2H, m), 7.22-7.26 (1H, m).

EXAMPLE 9

Synthesis of 1-ethyl-3,3,5-trimethyl-7-{3-[(pyridin-4-ylmethyl)amino]propyl}-1,5-dihydrobenzo[b][1,4]diazepine-2,4-dione The synthesis of the title compound was performed in the same manner as in Example 3 using appropriate starting materials.
¹H NMR (CDCl₃) δppm: 0.81 (3H, s), 1.20 (3H, t, J=7.1 Hz), 1.53 (3H, s), 1.78-1.91 (2H, m), 2.66-2.74 (4H, m), 3.39 (3H, s), 3.71-3.89 (3H, m), 4.05-4.16 (1H, m), 7.02-7.10 (3H, m), 7.19-7.26 (2H, m), 8.52-8.56 (2H, m).

EXAMPLE 10

Synthesis of 1-ethyl-3,3,5-trimethyl-7-(3-{N-[2-(2-methyl-4-oxo-4H-furo[3,2-c]pyridin-5-yl)ethyl]-N-(pyridin-4-ylmethyl)amino}propyl)-1,5-dihydrobenzo[b][1,4]diazepine-2,4-dione dihydrochloride The synthesis of the title compound was performed in the same manner as in Example 4 using appropriate starting materials.
¹H-NMR (DMSO-d₆) δppm: 0.69 (3H, s), 1.03 (3H, t, J=7.1 Hz), 1.32 (3H, s), 2.05 (2H, br), 2.38 (3H, s), 2.60 (2H, br), 3.04 (2H, br), 3.31 (3H, s), 3.25-3.50 (2H, m), 3.40-3.65 (1H, m), 3.91-4.08 (1H, m), 4.38 (2H, br), 4.58 (2H, br), 6.55 (1H, s), 6.75 (1H, d, J=7.4 Hz), 7.13 (1H, d, J=8.4 Hz), 7.25 (1H, s), 7.38 (1H, d, J=8.4 Hz), 7.63 (1H, d, J=7.4 Hz), 8.17 (2H, br), 8.88 (2H, br).

EXAMPLE 11

Synthesis of 7-(2-aminoethyl)-1-ethyl-3,3,5-trimethyl-1,5-dihydrobenzo[b][1,4]diazepine-2,4-dione hydrochloride A 4N-hydrogen chloride ethyl acetate solution(6 ml) was added to an ethyl acetate solution (20 ml) of [2-(1-ethyl-3,3,5-trimethyl-2,4-dioxo-2,3,4,5-tetrahydro-1H-benzo[b][1,4]diazepine-7-yl)ethyl]carbamic acid tert-butyl ester(0.38 g), and the mixture was stirred at room temperature overnight. The reaction mixture was condensed under reduced pressure to give the title compound(0.26 g) as a pale orange amorphous solid.
¹H-NMR (DMSO-d₆) δppm: 0.79 (3H, s), 1.17 (3H, t, J=7.1 Hz), 1.39 (3H, s), 2.91-3.00 (2H, m), 3.02-3.13 (2H, m), 3.38 (3H, s), 3.68-3.83 (1H, m), 3.95-4.11 (1H, m), 7.11-7.16 (1H, m), 7.23 (1H, br), 7.31-7.35 (1H, m), 8.06 (3H, br).

EXAMPLE 12

Synthesis of 1-ethyl-3,3,5-trimethyl-7-{2-[(pyridin-4-ylmethyl)amino]ethyl}-1,5-dihydrobenzo[b][1,4]diazepine-2,4-dione Triethylamine(0.1 ml) and 4-pyridine carbaldehyde(0.094 ml) were added to a methanol solution (10 ml) of 7-(2-aminoethyl)-1-ethyl-3,3,5-trimethyl-1,5-dihydrobenzo[b][1,4]diazepine 2,4-dione hydrochloride(0.26 g). The mixture was stirred at room temperature for 1 hour. Sodium borohydride (0.11 g) was added, and the mixture was further stirred at room temperature overnight. The reaction liquid was condensed under reduced pressure, and the residue was purified by silica gel column chromatography (ethyl acetate: methanol=9:1→3:2). The purified product was condensed under reduced pressure to give the title compound(0.21 g) as a colorless oily matter.
¹H-NMR (CDCl₃) δppm: 0.83 (3H, s), 1.86 (3H, t, J=7.1 Hz), 1.53 (3H, s), 2.82-2.94 (4H, m), 3.40 (3H, s), 3.73-3.85 (1H, m), 3.84 (2H, s), 4.02-4.18 (1H, m), 7.05-7.11 (2H, m), 7.20-7.26 (3H, m), 8.52-8.55 (2H, m).

EXAMPLE 13

Synthesis of 1-ethyl-3,3,5-trimethyl-7-{2-[(2-methylpyridin-3-ylmethyl)amino]ethyl}-1,5-dihydrobenzo[b][1,4]diazepine-2,4-dione The synthesis of the title compound was performed in the same manner as in Example 3 using appropriate starting materials.
¹H-NMR (CDCl₃) δppm: 0.82 (3H, s), 1 18 (3H, t, J=7.1 Hz), 1.53 (3H, s), 2.52 (3H, s), 2.82-2.88 (2H, m), 2.93-2.99 (2H, m), 3.40 (3H, s), 3.75-3.82 (1H, m), 3.81 (3H, s), 4.11-4.18 (1H, m), 7.06-7.12 (2H, m), 7.22-7.26 (2H, m), 7.53-7.57 (1H, m), 8.37-8.40 (1H, m).

EXAMPLE 14

Synthesis of 1-ethyl-3,3,5-trimethyl-7-{2-[(4-methylpyridin-3-ylmethyl)amino]ethyl}-1,5-dihydrobenzo[b][1,4]diazepine-2,4-dione The synthesis of the title compound was performed in the same manner as in Example 3 using appropriate starting materials.

¹H-NMR (CDCl₃) δppm: 0.82 (3H, s), 1 18 (3H, t, J=7.1 Hz), 1.53 (3H, s), 2.33 (3H, s), 2.82-2.87 (2H, m), 2.93-2.99 (2H, m), 3.39 (3H, s), 3.75-3.84 (1H, m), 3.82 (3H, s), 4.10-4.20 (1H, m), 7.06-7.12 (3H, m), 7.21-7.26 (1H, m), 8.38 (1H, d, J=4.9 Hz), 8.41 (1H, s).

EXAMPLE 15

Synthesis of 1-ethyl-3,3,5-trimethyl-7-(2-{N-[2-(2-methyl-4-oxo-4H-furo[3,2-c]pyridin-5-yl)ethyl]-N-(pyridin-4-ylmethyl)amino}ethyl)-1,5-dihydrobenzo[b][1,4]diazepine-2,4-dione dihydrochloride The synthesis of the title compound was performed in the same manner as in Example 4 using appropriate starting materials.

¹H-NMR (DMSO-d₆) δppm: 0.69 (3H, s), 1.02 (3H, t, J=7.1 Hz), 1.31 (3H, s), 2.39 (3H, s), 3.08 (2H, br), 3.29 (3H, s), 3.11-3.42 (2H, m), 3.42-3.70 (3H, m), 3.91-4.10 (1H, m), 4.36 (2H, br), 4.57 (2H, br), 6.54 (1H, s), 6.71 (1H, d, J=7.2 Hz), 7.15-7.20 (1H, m), 7.30 (1H, s), 7.37-7.40 (1H, m), 7.60-7.63 (1H, m), 8.16 (2H, br), 8.86 (2H, br).

EXAMPLE 16

Synthesis of 1-ethyl-3,3,5-trimethyl-7-(2-{N-(2-methylpyridin-3-ylmethyl)-N-[2-(4-oxo-4H-furo[3,2-c]pyridin-5-yl)ethyl]amino}ethyl)-1,5-dihydrobenzo[b][1,4]diazepine-2,4-dione dihydrochloride The synthesis of the title compound was performed in the same manner as in Example 4 using appropriate starting materials.

¹H-NMR (DMSO-d₆) δppm: 0.70 (3H, s), 1.03 (3H, t, J=7.1 Hz), 1.32 (3H, s), 2.50 (3H, s), 2.84 (2H, br), 3.14 (2H, br), 3.34 (3H, s), 3.25-3.45(2H, m), 3.50-3.70 (1H, m), 3.90-4.08 (1H, m), 4.38 (2H, br), 4.47 (2H, br), 6.76 (1H, d, J=7.1 Hz), 6.93 (1H, s), 7.23 (1H, d, J=8.2 Hz), 7.36 (1H, s), 7.40 (1H, d, J=8.2 Hz), 7.69 (1H, br), 7.82 (1H, br), 7.90 (1H, d, J=2.1 Hz),8.71 (2H, br).

EXAMPLE 17

Synthesis of 1-ethyl-3,3,5-trimethyl-7-{2-[N-[2-(2-methyl-4-oxo-4H-furo[3,2-c]pyridin-5-yl)ethyl]-N-(2-methylpyridin-3-ylmethyl)amino]ethyl}-1,5-dihydrobenzo[b][1,4]diazepine-2,4-dione dihydrochloride The synthesis of the title compound was performed in the same manner as in Example 4 using appropriate starting materials.

¹H-NMR (DMSO-d₆) δppm: 0.72 (3H, s), 1.04 (3H, t, J=7.1 Hz), 1.33 (3H, s), 2.40 (3H, s), 2.51 (3H, s), 2.89 (4H, br), 3.31 (3H, s), 3.50 (2H, br), 3.72-3.77 (1H, m), 4.02-4.07 (1H, m), 4.42 (2H, br), 4.61 (2H, br), 6.54 (1H, s), 6.70 (1H, br), 7.23 (1H, br), 7.34 (1H, s), 7.40 (1H, br), 7.64 (1H, br),7.86 (1H, br), 8.73 (2H, br).

EXAMPLE 18

Synthesis of 1-ethyl-3,3,5-trimethyl-7-{2-[N-[2-(2-methyl-4-oxo-4H-furo[3,2-c]pyridin-5-yl)ethyl]-N-(4-methylpyridin-3-ylmethyl)amino]ethyl}-1,5-dihydrobenzo[b][1,4]diazepine-2,4-dione dihydrochloride The synthesis of the title compound was performed in the same manner as in Example 4 using appropriate starting materials.

¹H-NMR (DMSO-d₆) δppm: 0.71 (3H, s), 1.04 (3H, t, J=7.1 Hz), 1.33 (3H, s), 2.39 (3H, s), 2.51 (3H, s), 2.74 (2H, br), 3.15 (2H, br), 3.33 (3H, s), 3.51 (2H, br), 3.72-3.77 (1H, m), 4.02-4.07 (1H, m), 4.42 (2H, br), 4.75 (2H, br), 6.53 (1H, s), 6.70 (1H, br), 7.23-7.26 (1H, m), 7.36 (1H, s), 7.42-7.44 (1H, m), 7.64 (1H, br), 7.86 (1H, br), 8.76 (1H, br), 9.20 (1H, br).

EXAMPLE 19

Synthesis of 7-aminomethyl-1,5-dimethyl-1,5-dihydrobenzo[b][1,4]diazepine-2,4-dione 10% Palladium on carbon(0.1 g) was added to an acetic acid solution (20 ml) of 1,5-dimethyl-2,4-dioxo-2,3,4,5-tetrahydro-1H-benzo[b][1,4]diazepine-7-carbonitrile(0.3 g), and catalytic reduction was carried out at room temperature under 4 atm. The catalyst was removed by celite filtration, followed by concentration under reduced pressure. The residue was purified by silica gel column chromatography (ethyl acetate: methanol=9:1→5:5). The purified product was condensed under reduced pressure to give the title compound (0.17 g) as a yellowish white solid.

¹H NMR (CDCl₃) δppm: 3.28 (1H, d, J=12.4 Hz), 3.42 (3H, s), 3.44 (3H, s), 3.38-3.42 (1H, m), 3.94 (2H, s), 7.26-7.29 (3H, m).

EXAMPLE 20

Synthesis of 7-aminomethyl-1-ethyl-3,3,5-trimethyl-1,5-dihydrobenzo[b][1,4]diazepine-2,4-dione The synthesis of the title compound was performed in the same manner as in Example 19 using appropriate starting materials.

¹H-NMR (CDCl₃) δppm: 0.84 (3H, s), 1.18 (3H, t, J=7.1 Hz), 1.53 (3H, s), 3.43 (3H, s), 3.75-3.82 (1H, m), 3.93 (2H, s), 4.13-4.19 (1H, m), 7.20-7.23 (1H, m), 7.25-7.27 (2H, m).

EXAMPLE 21

Synthesis of 7-aminomethyl-1,3,3,5-tetramethyl-1,5-dihydro-benzo[b][1,4]diazepine-2,4-dione The synthesis of the title compound was performed in the same manner as in Example 19 using appropriate starting materials.

¹H NMR (CDCl₃) δppm: 0.85 (3H, s), 1.54 (3H, s), 3.42 (3H, s), 3.44 (3H, s), 3.93 (2H, s), 7.18-7.26 (3H, m).

EXAMPLE 22

Synthesis of 1-ethyl-3,3,5-trimethyl-7-{[(pyridin-4-ylmethyl)amino]methyl}-1,5-dihydrobenzo[b][1,4]diazepine-2,4-dione The synthesis of the title compound was performed in the same manner as in Example 3 using appropriate starting materials.

¹H-NMR (CDCl₃) δppm: 0.83 (3H, s), 1.18 (3H, t, J=7.1 Hz), 1.53 (3H, s), 3.42 (3H, s), 3.69-3.82 (1H, m), 3.84 (2H, s), 3.87 (2H, s), 4.04-4.20 (1H, m), 7.23-7.26 (3H, m), 7.29-7.32 (2H, m), 8.56-8.58 (2H, m).

EXAMPLE 23

Synthesis of 1-ethyl-3,3,5-trimethyl-7-{[(2-methylpyridin-3-ylmethyl)amino]methyl}-1,5-dihydrobenzo[b][1,4]diazepine-2,4-dione The synthesis of the title compound was performed in the same manner as in Example 3 using appropriate starting materials.

$^1$H-NMR (CDCl$_3$) δppm: 0.84 (3H, s), 1.18 (3H, t, J=7.1 Hz), 1.53 (3H, s), 2.56 (3H, s), 3.42 (3H, s), 3.77-3.88 (1H, m), 3.84 (2H, s), 3.88 (2H, s), 4.09-4.18 (1H, m), 7.11-7.15 (1H, m), 7.24-7.29 (3H, m), 7.63-7.65 (1H, m), 8.41-8.43 (1H, m).

EXAMPLE 24

Synthesis of 1,5-dimethyl-7-{[(2-methylpyridin-3-ylmethyl)amino]methyl}-1,5-dihydrobenzo[b][1,4]diazepine-2,4-dione The synthesis of the title compound was performed in the same manner as in Example 3 using appropriate starting materials.

$^1$H NMR (CDCl$_3$) δppm: 2.59 (3H, s), 3.27 (1H, d, J=12.4 Hz), 3.37-3.43 (7H, m), 3.82 (2H, s), 3.86 (2H, s), 7.10-7.14 (1H, m), 7.23-7.26 (3H, m), 7.61-7.65 (1H, m), 8.39-8.42 (1H, m).

EXAMPLE 25

Synthesis of 1,3,3,5-tetramethyl-7-{[(2-methylpyridin-3-ylmethyl)amino]methyl}-1,5-dihydrobenzo[b][1,4]diazepine-2,4-dione The synthesis of the title compound was performed in the same manner as in Example 3 using appropriate starting materials.

$^1$H NMR (CDCl$_3$) δppm: 0.85 (3H, s), 1.54 (3H, s), 2.56 (3H, s), 3.43 (3H, s), 3.44 (3H, s), 3.82 (2H, s), 3.88 (2H, s), 7.11-7.15 (1H, m), 7.20-7.26 (3H, m), 7.62-7.64 (1H, m), 8.41-8.43 (1H, m).

EXAMPLE 26

Synthesis of 1-ethyl-3,3,5-trimethyl-7-[[[2-(pyridin-3-yl)ethyl]amino]methyl]-1,5-dihydrobenzo[b][1,4]diazepine-2,4-dione Trimethyl orthoformate(9 ml) was added to a methanol solution (50 ml) of 1-ethyl-3,3,5-trimethyl-2,4-dioxo-2,3,4,5-tetrahydro-1H-benzo[b][1,4]diazepine-7-carbaldehyde (2.2 g) and 3-(2-aminoethyl)pyridine(1.0 g). The mixture was stirred at room temperature for 2 hours.
The reaction liquid was condensed under reduced pressure, and a methanol solution (50 ml) of the residue was cooled with ice. Sodium borohydride(0.34 g) was added thereto, and the mixture was stirred at room temperature for 30 minutes. Water was added to the reaction liquid, followed by concentration under reduced pressure. The residue was extracted by ethyl acetate. The organic layer was dried by anhydrous sodium sulfate, and condensed under reduced pressure. The residue was purified by NH silica gel column chromatography (ethyl acetate: methanol=9:1). The purified product was condensed under reduced pressure to give the title compound (2.5 g) as a colorless oily matter.

$^1$H NMR (CDCl$_3$) δppm: 0.82 (3H, s), 1.18 (3H, t, J=7.1 Hz), 1.53 (3H, s), 2.80-2.90 (2H, m), 2.90-2.99 (2H, m), 3.39 (3H, s), 3.72-3.90 (1H, m), 3.83 (2H, s), 4.06-4.22 (1H, m), 7.14-7.20 (2H, m), 7.20-7.28 (2H, m), 7.54 (1H, td, J=2.0, 7.8 Hz), 8.45-8.53 (2H, m).

EXAMPLE 27

Synthesis of 1-ethyl-3,3,5-trimethyl-7-{[2-(2-methyl-4-oxo-4H-furo[3,2-c]pyridin-5-yl)ethylamino]methyl}-1,5-dihydrobenzo[b][1,4]diazepine-2,4-dione Sodium borohydride(0.15 g) was added to a methanol solution (150 ml) of 1-ethyl-3,3,5-trimethyl-2,4-dioxo-2,3,4,5-tetrahydro-1H-benzo[b][1,4]diazepine-7-carbaldehyde(1.1 g) and 5-(2-aminoethyl)-2-methyl-5H-furo[3,2-c]pyridin-4-one(1.0 g), and the mixture was stirred at room temperature overnight. The reaction liquid was filtered to remove insoluble matter, and the filtrate was condensed under reduced pressure.
The residue was purified by silica gel column chromatography (ethyl acetate: methanol=9:1→5:5). The purified product was condensed under reduced pressure to give the title compound(1.1 g) as a colorless amorphous solid.

$^1$H NMR (CDCl$_3$) δppm: 0.79 (3H, s), 1.17 (3H, t, J=7.1 Hz), 1.52 (3H, s), 2.15 (1H, br), 2.42 (3H, s), 3.02-3.10 (2H, m), 3.36 (3H, s), 3.75-3.81 (1H, m), 3.86 (2H, s), 4.09-4.20 (3H, m), 6.49 (1H, d, J=6.7 Hz), 6.53 (1H, d, J=1.9 Hz), 7.15-7.21 (4H, m).

EXAMPLE 28

Synthesis of 1-ethyl-3,3,5-trimethyl-7-{[2-(4-oxo-4H-furo[3,2-c]pyridin-5-yl)ethylamino]methyl}-1,5-dihydrobenzo[b][1,4]diazepine-2,4-dione The synthesis of the title compound was performed in the same manner as in Example 27 using appropriate starting materials.

$^1$H-NMR (CDCl$_3$) δppm: 0.80 (3H, s), 1.17 (3H, t, J=7.1 Hz), 1.52 (3H, s), 2.95 (2H, br), 3.36 (3H, s), 3.74-3.82 (1H, m), 3.86 (2H, br), 4.02-4.14 (1H, m), 4.20 (2H, br), 6.57 (1H, d, J=7.3 Hz), 6.96 (1H, d, J=2.0 Hz), 7.14-7.26 (4H, m), 7.50 (1H, d, J=2.0 Hz).

EXAMPLE 29

Synthesis of 7,7'-azanediylbis(methylene)bis(1-ethyl-3,3,5-trimethyl-1H-benzo[b][1,4]diazepine-2,4-dione)

10% Palladium on carbon(0.3 g) was added to an acetic acid solution (20 ml) of 1-ethyl-3,3,5-trimethyl-2,4-dioxo-2,3,4,5-tetrahydro-1H-benzo[b][1,4]diazepine-7-carbonitrile (1.4 g), and catalytic reduction was carried out at room temperature under 4 atm. The catalyst was removed by celite filtration, followed by concentration under reduced pressure. The residue was purified by silica gel column chromatography (ethyl acetate: methanol=9:1→5:5). The purified product was condensed under reduced pressure to give the title compound(0.19 g) as a colorless oily matter.

$^1$H-NMR (CDCl$_3$) δppm: 0.84 (6H, s), 1.19 (6H, t, J=7.1 Hz), 1.54 (6H, s), 3.43 (6H, s), 3.71-3.92 (2H, m), 3.87 (4H, s), 4.01-4.18 (2H, m), 7.24-7.27 (6H, m).

EXAMPLE 30

Synthesis of 1-ethyl-3,3,5-trimethyl-7-({N-[2-(2-methyl-4-oxo-4H-furo[3,2-c]pyridin-5-yl)ethyl]-N-(pyridin-4-ylmethyl)amino}methyl)-1,5-dihydrobenzo[b][1,4]diazepine-2,4-dione 5-(2,2-Dihydroxyethyl)-2-methyl-5H-furo[3,2-c]pyridine-4-one(0.21 g) and acetic acid(0.1 ml) were added to a 1,2-dichloroethane solution(15 ml) of 1-ethyl-3,3,5-trimethyl-7-{[(pyridin-4-ylmethyl)amino]methyl}-1,5-dihydrobenzo[b][1,4]diazepine-2,4-dione(0.38 g), and the mixture was stirred for 30 minutes at room temperature. Sodium triacetoxy borohydride(0.42 g) was added, and the mixture was stirred at room temperature overnight. The reaction mixture was condensed under reduced pressure. The residue was purified by silica gel column chromatography (ethyl acetate:methanol=1:0→4:1). The purified product was condensed under reduced pressure, and the residue was recrystallized from ether to give the title compound(0.47 g) as a white powder.
mp: 143 to 145° C.

EXAMPLE 31

Synthesis of 1-ethyl-3,3,5-trimethyl-7-({N-(2-methylpyridin-3-ylmethyl)-N-[2-(4-oxo-4H-furo[3,2-c]pyridin-5-yl)ethyl]amino}methyl)-1,5-dihydrobenzo[b][1,4]diazepine-2,4-dione The synthesis of the title compound was performed in the same manner as in Example 30 using appropriate starting materials.
White Powder (Ether)
mp: 153 to 154° C.

EXAMPLE 32

Synthesis of 1-ethyl-3,3,5-trimethyl-7-{[N-[2-(2-methyl-4-oxo-4H-furo[3,2-c]pyridin-5-yl)ethyl]-N-(2-methylpyridin-3-ylmethyl)amino]methyl}-1,5-dihydrobenzo[b][1,4]diazepine-2,4-dione The synthesis of the title compound was performed in the same manner as in Example 30 using appropriate starting materials.
White Powder (ether)
mp: 172 to 173° C.

EXAMPLE 33

Synthesis of 1-ethyl-3,3,5-trimethyl-7-{[N-[3-(2-methyl-4-oxo-4H-furo[3,2-c]pyridin-5-yl)propyl]-N-(2-methylpyridin-3-ylmethyl)amino]methyl}-1,5-dihydrobenzo[b][1,4]diazepine-2,4-dione dihydrochloride The synthesis of the title compound was performed in the same manner as in Example 4 using appropriate starting materials.
$^1$H-NMR (DMSO-$d_6$) δppm: 0.66 (3H, s), 1.04 (3H, br), 1.33 (3H, s), 2.29 (2H, br), 2.41 (3H, s), 2.80 (3H, br). 3.08 (2H, br), 3.33 (3H, s), 3.73-3.79 (1H, m), 3.93-4.01 (3H, m), 4.46 (2H, br), 4.57 (2H, br), 6.56 (1H, s), 6.67(1H, d, J=6.2 Hz), 7.42-7.44 (1H, m), 7.48-7.59 (2H, m), 7.88 (2H, br), 8.76 (1H, br), 8.93 (1H, br).

EXAMPLE 34

Synthesis of 7,7'-(pyridin-4-ylmethylazanediyl)bis(methylene)bis(1-ethyl-3,3,5-trimethyl-1H-benzo[b][1,4]diazepine-2,4-dione) dihydrochloride The synthesis of the title compound was performed in the same manner as in Example 4 using appropriate starting materials.
$^1$H-NMR (DMSO-$d_6$) δppm: 0.69 (6H, s), 1.07 (6H, t, J=7.1 Hz), 1.32 (6H, s), 3.35 (6H, s), 3.74-3.81 (2H, m), 3.94-4.04 (2H, m), 4.52 (2H, br), 4.82 (4H, s), 7.45-7.47 (4H, m), 8.08 (2H, d, J=6.7 Hz), 8.05-8.40 (2H, m), 8.88 (2H, d, J=6.7 Hz).

EXAMPLE 35

Synthesis of 1-ethyl-3,3,5-trimethyl-7-({N-(2-methylpyridin-3-ylmethyl)-N-[2-(1-oxo-1H-isoquinolin-2-yl)ethyl]amino}methyl)-1,5-dihydrobenzo[b][1,4]diazepine-2,4-dione dihydrochloride The synthesis of the title compound was performed in the same manner as in Example 4 using appropriate starting materials.
$^1$H-NMR (DMSO-$d_6$) δppm: 0.67 (3H, s), 1.01 (3H, t, J=7.1 Hz), 1.32 (3H, s), 2.41-2.59 (5H, m), 2.83 (2H, br), 3.25 (3H, s), 3.61-3.83 (3H, m),3.92-3.97 (1H, m), 4.16 (2H, br), 6.58 (1H, br), 7.22 (2H, br), 7.40 (2H, br), 7.48-7.63 (2H, m), 7.67-7.68 (1H, m), 7.71-7.75 (1H, m), 8.10-8.12 (1H, m), 8.24(1H, br), 8.44 (1H, br).

EXAMPLE 36

Synthesis of 1,5-dimethyl-7-{[N-[2-(2-methyl-4-oxo-4H-furo[3,2-c]pyridin-5-yl)ethyl]-N-(2-methylpyridin-3-ylmethyl)amino]methyl}-1,5-dihydrobenzo[b][1,4]diazepine-2,4-dione dihydrochloride The synthesis of the title compound was performed in the same manner as in Example 4 using appropriate starting materials.
$^1$H-NMR (DMSO-$d_6$) δppm: 2.38 (3H, s), 2.51 (3H, s), 2.54 (2H, br), 2.75 (2H, br), 3.05 (1H, d, J=12.4 Hz), 3.26 (6H, s), 3.32 (1H, d, J=12.4 Hz), 3.75 (2H, br), 4.14 (2H, br), 6.45 (1H, br), 6.63 (1H, br), 7.24 (1H, br),7.33 (1H, br), 7.50 (2H, br), 7.68 (1H, br), 8.25 (1H, br), 8.56 (1H, br).

EXAMPLE 37

Synthesis of 1,3,3,5-tetramethyl-7-({N-(2-methylpyridin-3-ylmethyl)-N-[2-(4-oxo-4H-furo[3,2-c]pyridin-5-yl)ethyl]amino}methyl)-1,5-dihydrobenzo[b][1,4]diazepine-2,4-dione dihydrochloride The synthesis of the title compound was performed in the same manner as in Example 4 using appropriate starting materials.
$^1$H-NMR (DMSO-$d_6$) δppm: 0.70 (3H, s), 1.34 (3H, s), 2.51 (3H, s), 2.55 (2H, br), 2.82 (2H, br), 3.30 (6H, s), 3.78

(2H, br), 4.19 (2H, br), 6.73(1H, br), 6.88 (1H, br), 7.31 (3H, br), 7.60 (2H, br), 7.91 (1H, d, J=2.0 Hz),8.26 (1H, br), 8.56 (1H, br).

EXAMPLE 38

Synthesis of 1,3,3,5-tetramethyl-7-{[N-[2-(2-methyl-4-oxo-4H-furo[3,2-c]pyridin-5-yl)ethyl]-N-(2-methylpyridin-3-ylmethyl)amino]methyl}-1,5-dihydrobenzo[b][1,4]diazepine-2,4-dione dihydrochloride The synthesis of the title compound was performed in the same manner as in Example 4 using appropriate starting materials.
$^1$H-NMR (DMSO-$d_6$) δppm: 0.70 (3H, s), 1.34 (3H, s), 2.41 (3H, s), 2.51 (3H, s), 2.56 (2H, br), 2.79 (2H, br), 3.30 (6H, s), 3.77 (2H, br), 4.15 (2H, br), 6.46 (1H, br), 6.63 (1H, br), 7.31 (3H, br), 7.50 (1H, br), 7.68 (1H, br), 8.24 (1H, br), 8.56 (1H, br).

EXAMPLE 39

Synthesis of 1-ethyl-3,3,5-trimethyl-7-{[N-(2-pyridin-3-ylethyl)-N-(pyridin-4-ylmethyl)amino]methyl}-1,5-dihydrobenzo[b][1,4]diazepine-2,4-dione trihydrochloride 1-Ethyl-3,3,5-trimethyl-2,4-dioxo-2,3,4,5-tetrahydro-1H-benzo[b][1,4]diazepine-7-carbaldehyde(0.92 g) and acetic acid(0.1 ml) were added to a 1,2-dichloroethane solution (15 ml) of (2-pyridine 3-ylethyl)pyridin-4-ylmethylamine(0.81 g), and the mixture was stirred for 30 minutes at room temperature. Sodium triacetoxyborohydride(0.90 g) was added, and the mixture was stirred at room temperature overnight. The reaction mixture was condensed under reduced pressure. The residue was purified by silica gel column chromatography (ethyl acetate: methanol=100:0→90:10). The purified product was condensed under reduced pressure. A 4N-hydrogen chloride ethyl acetate solution(1.0 ml) was added to an ethyl acetate solution (20 ml) of the residue, and the liquid was stirred at room temperature. The precipitated insoluble matter was separated, washed with ethyl acetate, and dried to give the title compound(0.83 g) as a white solid
$^1$H-NMR (DMSO-$d_6$) δppm: 0.68 (3H, s), 1.06 (3H, t, J=7.1 Hz), 1.33 (3H, s), 3.00 (2H, br), 3.32 (3H, s), 3.10-3.45 (4H, m), 3.74-3.79 (1H, m), 3.94-4.00 (3H, m), 7.43 (2H, br), 7.98-8.02 (2H, m), 8.45 (1H, d, J=8.0 Hz), 8.82-8.88 (6H, m).

EXAMPLE 40

Synthesis of N-(1-ethyl-3,3,5-trimethyl-2,4-dioxo-2,3,4,5-tetrahydro-1H-benzo[b][1,4]diazepin-7-ylmethyl)-N-(2-pyridin-3-ylethyl)benzamide hydrochloride Benzoyl chloride(0.13 ml) was added to an acetonitrile solution (6 ml) of 1-ethyl-3,3,5-trimethyl-7-[(2-pyridin-3-ylethylamino)methyl]-1,5-dihydrobenzo[b][1,4]diazepine-2,4-dione(0.38 g) and triethylamine(0.17 ml) under ice cooling. The mixture was stirred at room temperature overnight. An aqueous sodium hydrogencarbonate solution was added to the reaction mixture, followed by extraction by ethyl acetate. The organic layer was dried over anhydrous sodium sulfate, and condensed under reduced pressure. The residue was purified by silica gel column chromatography (ethyl acetate: methanol=91:9). The purified product was condensed under reduced pressure. A 1N-hydrogen chloride ethanol solution (0.87 ml) was added to an isopropyl alcohol solution (10 ml) of the residue, and the liquid was condensed under reduced pressure. The residue was recrystallized from the ethanol-ether mixture to give the title compound(0.26 g) as a pale brown white powder.
$^1$H NMR (DMSO-$d_6$) δppm: 0.73 (3H, bs), 0.98-1.14 (3H, m), 1.34 (3H, s), 2.74-3.94 (8H, m), 3.94-4.11 (1H, m), 4.52 and 4.82 (2H, bs), 6.90-7.60(8H, m), 7.60-9.10(4H, m).

EXAMPLE 41

Synthesis of N-(1-ethyl-3,3,5-trimethyl-2,4-dioxo-2,3,4,5-tetrahydro-1H-benzo[b][1,4]diazepin-7-ylmethyl)-4-methyl-N-(2-pyridin-3-ylethyl)benzamide hydrochloride The synthesis of the title compound was performed in the same manner as in Example 40 using appropriate starting materials.
$^1$H NMR (DMSO-$d_6$) δppm: 0.73 (3H, s), 1.09 (3H, t, J=7.0 Hz), 1.34 (3H, s), 2.31 (3H, s), 2.88-3.94 (8H, m), 3.94-4.11 (1H, m), 4.35-5.05 (2H, m), 6.88-7.63(7H, m), 7.63-9.10(4H, m).

EXAMPLE 42

Synthesis of N-(1-ethyl-3,3,5-trimethyl-2,4-dioxo-2,3,4,5-tetrahydro-1H-benzo[b][1,4]diazepin-7-ylmethyl)-N-(2-pyridin-3-ylethyl)benzenesulfonamide Triethylamine(0.15 ml) was added to a acetonitrile solution (6 ml) of 1-ethyl-3,3,5-trimethyl-7-[(2-pyridin-3-ylethylamino)methyl]-1,5-dihydrobenzo[b][1,4]diazepine-2,4-dione(0.35 g). The mixture was cooled with ice. Benzenesulphonyl chloride(0.13 ml) was added, and the mixture was stirred at room temperature overnight. The reaction liquid was condensed under reduced pressure. Water was added to the residue, followed by extraction by ethyl acetate. The organic layer was dried over anhydrous sodium sulfate. After concentration under reduced pressure, the residue was purified by NH silica gel column chromatography (hexane: ethyl acetate=30:70). The purified product was condensed under reduced pressure, and the residue was recrystallized from the ethyl acetate-ether mixture to give the title compound(0.1 g) as a white powder.
mp: 143.2 to 146.4° C.

EXAMPLE 43

Synthesis of 7-{[N-benzyl-N-(2-pyridin-3-ylethyl) amino]methyl}-1-ethyl-3,3,5-trimethyl-1,5-dihydrobenzo[b][1,4]diazepine-2,4-dione hydrochloride The synthesis of the title compound was performed in the same manner as in Example 4 using appropriate starting materials.
$^1$H NMR (DMSO-$d_6$) δppm: 0.72 (3H, s), 1.05 (3H, t, J=7.0 Hz), 1.34 (3H, s), 2.59-3.72 (8H, m), 3.72-3.94 (1H, m), 3.94-4.11 (1H, m), 4.33-4.65 (3H, m), 6.85-8.18(10H, m), 8.30-8.77(2H, m), 11.17 (1H, bs).

EXAMPLE 44

Synthesis of 1-ethyl-3,3,5-trimethyl-7-({N-(4-methylpyridin-3-ylmethyl)-N-[2-(4-oxo-4H-furo[3,2-c]pyridin-5-yl)ethyl]amino}methyl)-1,5-dihydrobenzo[b][1,4]diazepine-2,4-dione The synthesis of the title compound was performed in the same manner as in Example 30 using appropriate starting materials.
White Powder (Ether)
mp: 160 to 161° C.

EXAMPLE 45

Synthesis of 1-ethyl-3,3,5-trimethyl-7-{[N-[2-(2-methyl-4-oxo-4H-furo[3,2-c]pyridin-5-yl)ethyl]-N-(4-methylpyridin-3-ylmethyl)amino]methyl}-1,5-dihydrobenzo[b][1,4]diazepine-2,4-dione The synthesis of the title compound was performed in the same manner as in Example 30 using appropriate starting materials.
White Powder (Ether)
mp: 171 to 174° C.

EXAMPLE 46

Synthesis of 7-({N-(2,6-dimethylpyridin-3-ylmethyl)-N-[2-(2-methyl-4-oxo-4H-furo[3,2-c]pyridin-5-yl)ethyl]amino}methyl)-1-ethyl-3,3,5-trimethyl-1,5-dihydrobenzo[b][1,4]diazepine-2,4-dione The synthesis of the title compound was performed in the same manner as in Example 30 using appropriate starting materials.
White Powder (Ether)
mp: 148 to 149° C.

EXAMPLE 47

Synthesis of 1-ethyl-3,3,5-trimethyl-7-{[N-[2-(2-methyl-4-oxo-4H-furo[3,2-c]pyridin-5-yl)ethyl]-N-(6-methylpyridin-3-ylmethyl)amino]methyl}-1,5-dihydrobenzo[b][1,4]diazepine-2,4-dione The synthesis of the title compound was performed in the same manner as in Example 30 using appropriate starting materials.
White Powder (Ether)
mp: 123 to 125° C.

EXAMPLE 48

Synthesis of N-[2-({[(1-ethyl-3,3,5-trimethyl-2,4-dioxo-2,3,4,5-tetrahydro-1H-1,5-benzodiazepin-7-yl)methyl][2-(pyridin-3-yl)ethyl]amino}methyl)phenyl]methanesulfonamide dihydrochloride The synthesis of the title compound was performed in the same manner as in Example 4 using appropriate starting materials.
$^1$H NMR (DMSO-$d_6$) δppm: 0.71 and 0.73 (3H, s), 0.90-1.20 (3H, m), 1.33 (3H, s), 2.69-2.80 (1H, bs), 2.85 (2H, bs), 2.92-3.10 (4H, m), 3.20-3.70 (3H, m), 3.70-3.96 (3H, m), 3.96-4.10 (1H, m), 4.46-4.73 (2H, m), 7.00-7.70(7H, m), 7.70-8.30(2H, m), 8.52-8.80(2H, m), 9.30-9.59(1H, m),10.90 (1H, bs).

EXAMPLE 49

Synthesis of 7-{[N-(2,4-dimethylthiazol-5-ylmethyl)-N-(2-pyridin-3-ylethyl)amino]methyl}-1-ethyl-3,3,5-trimethyl-1,5-dihydrobenzo[b][1,4]diazepine-2,4-dione dihydrochloride The synthesis of the title compound was performed in the same manner as in Example 4 using appropriate starting materials.
$^1$H NMR (DMSO-$d_6$) δppm: 0.73 (3H, s), 1.09 (3H, t, J=7.0 Hz), 1.34 (3H, s), 2.30 (3H, bs), 2.59 (3H, s), 2.65-5.20 (13H, m), 6.32-8.07(4H, m), 8.16-8.40(1H, m), 8.66-8.90 (2H, m),11.91 (1H, bs).

EXAMPLE 50

Synthesis of N-(1-ethyl-3,3,5-trimethyl-2,4-dioxo-2,3,4,5-tetrahydro-1H-benzo[b][1,4]diazepin-7-ylmethyl)-2-methyl-N-(2-pyridin-3-ylethyl)benzamide hydrochloride The synthesis of the title compound was performed in the same manner as in Example 40 using appropriate starting materials.
$^1$H NMR (DMSO-$d_6$) δppm: 0.71 and 0.75 (3H, s), 1.00-1.12 (3H, m), 1.32 and 1.34(3H, s), 2.03 and 2.04(3H, s), 2.85-5.50 (8H, m), 3.26 and 3.34(3H, s), 6.86(0.4H, d, J=7.8 Hz), 7.05-7.98(8.3H, m), 8.39(0.9H, bs), 8.63(0.4H, bs), 8.74 (0.5H, bs), 8.87(0.5H, bs).

EXAMPLE 51

Synthesis of 1-ethyl-3,3,5-trimethyl-7-{[N-(2-methylpyridin-3-ylmethyl)-N-(2-pyridin-3-ylethyl)amino]methyl}-1,5-dihydrobenzo[b][1,4]diazepine-2,4-dione trihydrochloride The synthesis of the title compound was performed in the same manner as in Example 4 using appropriate starting materials.
$^1$H-NMR (DMSO-$d_6$) δppm: 0.72 (3H, s), 1.06 (3H, t, J=7.1 Hz), 1.34 (3H, s), 2.68 (3H, br), 3.10 (2H, br), 3.34 (3H, s), 3.18-3.60 (4H, m), 3.74-3.90 (3H, m), 3.99-4.05 (1H, m), 7.49 (2H, br), 7.73 (1H, br), 7.87 (1H, br), 7.98-8.01 (1H, br), 8.45 (1H, br), 8.68-8.70 (2H, m), 8.81 (1H, d, J=5.5 Hz), 8.89 (1H, br).

EXAMPLE 52

Synthesis of 1-ethyl-3,3,5-trimethyl-7-({N-[2-(4-oxo-4H-furo[3,2-c]pyridin-5-yl)ethyl]-N-(thiazol-2-ylmethyl)amino}methyl)-1,5-dihydrobenzo[b][1,4]diazepine-2,4-dione The synthesis of the title compound was performed in the same manner as in Example 30 using appropriate starting materials.
White Powder (Ether)
mp: 171 to 172° C.

EXAMPLE 53

Synthesis of 1-ethyl-3,3,5-trimethyl-7-({N-[2-(2-methyl-4-oxo-4H-furo[3,2-c]pyridin-5-yl)ethyl]-N-(thiazol-2-ylmethyl)amino}methyl)-1,5-dihydrobenzo[b][1,4]diazepine-2,4-dione The synthesis of the title compound was performed in the same manner as in Example 30 using appropriate starting materials.
White Powder (Ether)
mp: 146 to 147° C.

EXAMPLE 54

Synthesis of 7-{[N-(2,6-dimethylpyridin-3-ylmethyl)-N-(2-methylpyridin-3-ylmethyl)amino]methyl}-1-ethyl-3,3,5-trimethyl-1,5-dihydrobenzo[b][1,4]diazepine-2,4-dione trihydrochloride The synthesis of the title compound was performed in the same manner as in Example 4 using appropriate starting materials.
$^1$H-NMR (DMSO-$d_6$) δppm: 0.68 (3H, s), 1.02 (3H, t, J=7.1 Hz), 1.32 (3H, s), 3.32 (9H, s), 3.32 (3H, s), 3.67 (2H, br), 3.60-3.82 (1H, m), 3.78 (2H, br), 3.82 (2H, br), 3.97-4.04 (1H, m), 7.28 (1H, br), 7.34 (1H, br), 7.39-7.41 (1H, m), 7.67 (1H, d, J=7.8 Hz), 7.82-7.85 (1H, m), 8.43 (1H, br), 8.56 (1H, br), 8.61 (1H, br).

EXAMPLE 55

Synthesis of 1-ethyl-3,3,5-trimethyl-7-{[N-(2-methylpyridin-3-ylmethyl)-N-(4-methylpyridin-3-ylmethyl)amino]methyl}-1,5-dihydrobenzo[b][1,4]diazepine-2,4-dione trihydrochloride The synthesis of the title compound was performed in the same manner as in Example 4 using appropriate starting materials.
$^1$H-NMR (DMSO-$d_6$) δppm: 0.67 (3H, s), 1.01 (3H, t, J=7.1 Hz), 1.32 (3H, s), 2.48 (3H, s), 2.70 (3H, s), 3.31 (3H, s), 3.63-3.75 (3H, m), 3.87 (4H, br), 3.95-4.08 (1H, m), 7.25 (1H, m), 7.34 (1H, m), 7.38-7.40 (1H, m), 7.81-7.86 (2H, m), 8.55 (1H, br), 8.62 (1H, d, J=5.2 Hz), 8.69 (1H, d, J=5.9 Hz), 8.86 (1H, br).

EXAMPLE 56

Synthesis of 1-ethyl-3,3,5-trimethyl-7-{[N-(4-methylpyridin-3-ylmethyl)-N-(2-pyridin-3-ylethyl)amino]methyl}-1,5-dihydrobenzo[b][1,4]diazepine-2,4-dione trihydrochloride The synthesis of the title compound was performed in the same manner as in Example 39 using appropriate starting materials.
White Powder
$^1$H NMR (DMSO-$d_6$) δppm: 0.70 (3H, s), 1.03 (3H, br), 1.33 (3H, s), 2.33 (3H, br), 2.86 (2H, br), 3.10 (2H, br), 3.32 (3H, s), 3.31-3.41 (1H, m), 3.77 (4H, br), 4.00-4.06 (1H, m), 7.20 (1H, br), 7.43 (2H, br), 7.80 (1H, br), 7.97 (1H, br), 8.41 (1H, br), 8.70 (2H, br), 8.79-8.81 (2H, m).

EXAMPLE 57

Synthesis of 1-ethyl-3,3,5-trimethyl-7-({N-(4-methylthiazol-5-ylmethyl)-N-[2-(4-oxo-4H-furo[3,2-c]pyridin-5-yl)ethyl]amino}methyl)-1,5-dihydrobenzo[b][1,4]diazepine-2,4-dione The synthesis of the title compound was performed in the same manner as in Example 30 using appropriate starting materials.
White Powder (Ether)
mp: 161 to 162° C.

EXAMPLE 58

Synthesis of 1-ethyl-3,3,5-trimethyl-7-{[N-[2-(2-methyl-4-oxo-4H-furo[3,2-c]pyridin-5-yl)ethyl]-N-(4-methylthiazol-5-ylmethyl)amino]methyl}-1,5-dihydrobenzo[b][1,4]diazepine-2,4-dione The synthesis of the title compound was performed in the same manner as in Example 30 using appropriate starting materials.
White Powder (Ether)
mp: 188 to 189° C.

EXAMPLE 59

Synthesis of 2-methyl-2H-pyrazole-3-sulfonic acid N-(1-ethyl-3,3,5-trimethyl-2,4-dioxo-2,3,4,5-tetrahydro-1H-benzo[b][1,4]diazepin-7-ylmethyl)-N-(2-pyridin-3-ylethyl) amide The synthesis of the title compound was performed in the same manner as in Example 42 using appropriate starting materials.
White Powder (Ethyl Acetate)
mp: 123 to 124° C.

EXAMPLE 60

Synthesis of 7-{[N-(2,5-dimethyl-2H-pyrazol-3-ylmethyl)-N-(2-pyridin-3-ylethyl)amino]methyl}-1-ethyl-3,3,5-trimethyl-1,5-dihydrobenzo[b][1,4]diazepine-2,4-dione dihydrochloride The synthesis of the title compound was performed in the same manner as in Example 4 using appropriate starting materials.
White Powder (Diethyl Ether)
mp: 136 to 145° C.

EXAMPLE 61

Synthesis of 1-ethyl-3,3,5-trimethyl-7-{[N-(2-methylpyridin-3-ylmethyl)-N-(2-pyridin-4-ylethyl)amino]methyl}-1,5-dihydrobenzo[b][1,4]diazepine-2,4-dione trihydrochloride The synthesis of the title compound was performed in the same manner as in Example 39 using appropriate starting materials.
$^1$H NMR (DMSO-$d_6$) δppm: 0.71 (3H, s), 1.07 (3H, t, J=7.1 Hz), 1.34 (3H, s), 2.71 (5H, br), 3.20-3.39 (3H, m), 3.37

(3H, s), 3.55 (2H, br), 3.77 (2H, br), 3.99-4.04 (1H, m), 7.31 (1H, br), 7.47 (2H, br), 7.85 (2H, br), 7.95 (2H, br), 8.68 (1H, br), 8.85 (2H, br).

EXAMPLE 62

Synthesis of 1-ethyl-3,3,5-trimethyl-7-{[N-[2-(7-methyl-4-oxo-4H-furo[3,2-c]pyridin-5-yl)ethyl]-N-(2-methylpyridin-3-ylmethyl)amino]methyl}-1,5-dihydrobenzo[b][1,4]diazepine-2,4-dione The synthesis of the title compound was performed in the same manner as in Example 30 using appropriate starting materials.
White Powder
mp: 164 to 165° C.

EXAMPLE 63

Synthesis of 1-ethyl-3,3,5-trimethyl-7-{[N-[2-(7-methyl-4-oxo-4H-furo[3,2-c]pyridin-5-yl)ethyl]-N-(4-methylpyridin-3-ylmethyl)amino]methyl}-1,5-dihydrobenzo[b][1,4]diazepine-2,4-dione The synthesis of the title compound was performed in the same manner as in Example 30 using appropriate starting materials.
White Powder
mp: 181 to 183° C.

EXAMPLE 64

Synthesis of 1-ethyl-3,3,5-trimethyl-7-{[N-[2-(7-methyl-4-oxo-4H-furo[3,2-c]pyridin-5-yl)ethyl]-N-(4-methylthiazol-5-ylmethyl)amino]methyl}-1,5-dihydrobenzo[b][1,4]diazepine-2,4-dione The synthesis of the title compound was performed in the same manner as in Example 30 using appropriate starting materials.
White Powder
mp: 134 to 136° C.

EXAMPLE 65

Synthesis of 1-ethyl-3,3,5-trimethyl-7-{[(thiazol-2-ylmethyl)amino]methyl}-1,5-dihydrobenzo[b][1,4]diazepine-2,4-dione The synthesis of the title compound was performed in the same manner as in Example 3 using appropriate starting materials.
$^1$H NMR (CDCl$_3$) δppm: 0.83 (3H, s), 1.18 (3H, t, J=7.1 Hz), 1.53 (3H, s), 3.43 (3H, s), 3.74-3.84 (1H, m), 3.92 (2H, s), 4.09-4.18 (3H, m), 7.25-7.27 (3H, m), 7.30 (1H, d, J=3.3 Hz), 7.75 (1H, d, J=3.3 Hz).

EXAMPLE 66

Synthesis of 1-ethyl-3,3,5-trimethyl-7-{[(4-methylpyridin-3-ylmethyl)amino]methyl}-1,5-dihydrobenzo[b][1,4]diazepine-2,4-dione The synthesis of the title compound was performed in the same manner as in Example 3 using appropriate starting materials.
$^1$H NMR (CDCl$_3$) δppm: 0.83 (3H, s), 1.18 (3H, t, J=7.1 Hz), 1.53 (3H, s), 2.38 (3H, s), 3.42 (3H, s), 3.74-3.84 (1H, m), 3.83 (2H, s), 3.87 (2H, s), 4.09-4.18 (1H, m), 7.09 (1H, d, J=4.9 Hz), 7.24-7.27 (3H, m), 8.39 (1H, d, J=4.9 Hz), 8.46 (1H, s).

EXAMPLE 67

Synthesis of 1-ethyl-3,3,5-trimethyl-7-{[(4-methylthiazol-5-ylmethyl)amino]methyl}-1,5-dihydrobenzo[b][1,4]diazepine-2,4-dione The synthesis of the title compound was performed in the same manner as in Example 3 using appropriate starting materials.
$^1$H NMR (CDCl$_3$) δppm: 0.83 (3H, s), 1.18 (3H, t, J=7.1 Hz), 1.53 (3H, s), 2.40 (3H, s), 3.43 (3H, s), 3.75-3.84 (1H, m), 3.86 (2H, s), 3.97 (2H, s), 4.09-4.18 (1H, m), 7.22-7.28 (3H, m), 8.65 (1H, s).

EXAMPLE 68

Synthesis of 1-ethyl-3,3,5-trimethyl-7-{[N-[2-(4-methyl-7-oxo-7H-furo[2,3-c]pyridin-6-yl)ethyl]-N-(2-methylpyridin-3-ylmethyl)amino]methyl}-1,5-dihydrobenzo[b][1,4]diazepine-2,4-dione The synthesis of the title compound was performed in the same manner as in Example 30 using appropriate starting materials.
White Powder (Diethyl Ether)
mp: 164-165° C.

EXAMPLE 69

Synthesis of 7-{[N-[2-(2,7-dimethyl-4-oxo-4H-furo[3,2-c]pyridin-5-yl)ethyl]-N-(2-methylpyridin-3-ylmethyl)amino]methyl}-1-ethyl-3,3,5-trimethyl-1,5-dihydrobenzo[b][1,4]diazepine-2,4-dione The synthesis of the title compound was performed in the same manner as in Example 30 using appropriate starting materials.
White Powder (Diethyl Ether)
mp: 193-195° C.

EXAMPLE 70

Synthesis of 1-ethyl-3,3,5-trimethyl-7-{[N-[2-(4-methyl-7-oxo-7H-furo[2,3-c]pyridin-6-yl)ethyl]-N-(4-methylpyridin-3-ylmethyl)amino]methyl}-1,5-dihydrobenzo[b][1,4]diazepine-2,4-dione The synthesis of the title compound was performed in the same manner as in Example 30 using appropriate starting materials.
White Powder (Diethyl Ether)
mp: 203-204° C.

EXAMPLE 71

Synthesis of 7-{[N-[2-(2,7-dimethyl-4-oxo-4H-furo[3,2-c]pyridin-5-yl)ethyl]-N-(4-methylpyridin-3-ylmethyl)amino]methyl}-1-ethyl-3,3,5-trimethyl-1,5-dihydrobenzo[b][1,4]diazepine-2,4-dione The synthesis of the title compound was performed in the same manner as in Example 30 using appropriate starting materials.
White Powder (Diethyl Ether)
mp: 181-182° C.

EXAMPLE 72

Synthesis of 7-({N-[2-(2,7-dimethyl-4-oxo-4H-furo[3,2-c]pyridin-5-yl)ethyl]-N-(thiazol-2-ylmethyl)amino}methyl)-1-ethyl-3,3,5-trimethyl-1,5-dihydrobenzo[b][1,4]diazepine-2,4-dione The synthesis of the title compound was performed in the same manner as in Example 30 using appropriate starting materials.
White Powder (Diethyl Ether)
mp: 157-159° C.

EXAMPLE 73

Synthesis of 1-ethyl-3,3,5-trimethyl-7-{[N-(2-methylpyridin-3-ylmethyl)-N-(4-methylthiazol-5-ylmethyl)amino]methyl}-1,5-dihydrobenzo[b][1,4]diazepine-2,4-dione trihydrochloride The synthesis of the title compound was performed in the same manner as in Example 4 using appropriate starting materials.
$^1$H NMR (DMSO-d$_6$), δppm: 0.68 (3H, s), 1.03 (3H, t, J=7.1 Hz), 1.32 (3H, s), 2.30 (3H, s), 2.70 (3H, s), 3.32 (3H, s), 3.68 (2H, s), 3.67-3.76 (1H, m), 3.84 (4H, br), 3.97-4.06 (1H, m), 7.25-7.27 (1H, m), 7.34 (1H, s), 7.43 (1H, d, J=8.4 Hz), 7.84 (1H, dd, J=6.0, 7.7 Hz), 8.48-8.50 (1H, m), 8.62 (1H, d, J=5.5 Hz), 8.95-8.97 (1H, m).

EXAMPLE 74

Synthesis of 1-ethyl-3,3,5-trimethyl-7-{(N-[(1-methyl-1H-indazol-3-yl)methyl]-N-[2-(pyridin-3-yl)ethyl]amino)methyl}-1,5-dihydro-benzo[b][1,4]diazepine-2,4-dione dihydrochloride The synthesis of the title compound was performed in the same manner as in Example 4 using appropriate starting materials.
$^1$H NMR (D$_2$O), δppm: 0.73 (3H, s), 1.11 (3H, t, J=7.0 Hz), 1.41 (3H, s), 3.15-3.29 (2H, m), 3.30 (3H, s), 3.38-3.58 (2H, m), 3.68-3.88 (1H, m), 4.00-4.20 (1H, m), 4.04 (3H, s), 4.37 (2H, bs), 4.44 (2H, bs), 7.08-7.21(1H, m), 7.35(1H, d, J=7.8 Hz), 7.39-7.60(5H, m), 7.65(1H, dd, J=6.0, 7.5 Hz), 8.10(1H, d, J=7.8 Hz), 8.35-8.49 (2H, m).

EXAMPLE 75

Synthesis of 1-ethyl-3,3,5-trimethyl-7-{[N-(2-methyloxazol-4-ylmethyl)-N-(2-pyridin-3-ylethyl)amino]methyl}-1,5-dihydrobenzo[b][1,4]diazepine-2,4-dione dihydrochloride The synthesis of the title compound was performed in the same manner as in Example 4 using appropriate starting materials.
$^1$H NMR (D$_2$O), δppm: 0.79 (3H, s), 1.14 (3H, t, J=7.0 Hz), 1.43 (3H, s), 2.48 (3H, s), 3.21-3.33 (2H, m), 3.37-3.52 (2H, m), 3.40 (3H, s), 3.77-3.93 (1H, m), 4.07-4.21 (1H, m), 4.36 (2H, s), 4.47 (2H, dd, J=13.6, 22.0 Hz), 7.50(1H, dd, J=1.4, 8.4 Hz), 7.54-7.60(1H, m), 7.63(1H, d, J=8.4 Hz), 7.73(1H, dd, J=5.6, 7.9 Hz), 7.95 (1H, bs), 8.09(1H, d, J=7.9 Hz), 8.54 (1H, bs), 8.58 (1H, d, J=5.6 Hz).

EXAMPLE 76

Synthesis of 7-{[N-[2-(2,3-dimethyl-4-oxo-4H-furo[3,2-c]pyridin-5-yl)ethyl]-N-(2-methylpyridin-3-ylmethyl)amino]methyl}-1-ethyl-3,3,5-trimethyl-1,5-dihydrobenzo[b][1,4]diazepine-2,4-dione dihydrochloride The synthesis of the title compound was performed in the same manner as in Example 4 using appropriate starting materials.
$^1$H NMR (DMSO-d$_6$), δppm: 0.70 (3H, s), 1.04 (3H, t, J=7.1 Hz), 1.33 (3H, s), 2.12 (3H, s), 2.31 (3H, s), 2.45 (3H, br), 2.77 (2H, br), 3.28 (3H, s), 3.71-3.83 (3H, m), 3.94-4.07 (3H, m), 4.08 (2H, br), 6.54 (1H, br), 7.24 (1H, br), 7.35 (2H, br), 7.42 (1H, br), 7.67 (1H, br), 8.26 (1H, br), 8.52 (1H, br).

EXAMPLE 77

Synthesis of 7-{[N-[2-(2,3-dimethyl-4-oxo-4H-furo[3,2-c]pyridin-5-yl)ethyl]-N-(4-methylpyridin-3-ylmethyl)amino]methyl}-1-ethyl-3,3,5-trimethyl-1,5-dihydrobenzo[b][1,4]diazepine-2,4-dione dihydrochloride The synthesis of the title compound was performed in the same manner as in Example 4 using appropriate starting materials.
$^1$H NMR (DMSO-d$_6$), δppm: 0.70 (3H, s), 1.03 (3H, t, J=7.1 Hz), 1.33 (3H, s), 2.11 (3H, s), 2.24 (3H, br), 2.31 (3H, s), 2.80 (2H, br), 3.28 (3H, s), 3.71-3.84 (3H, m), 3.94-4.11 (5H, m), 6.50 (1H, br), 7.24 (1H, br), 7.36 (2H, br), 7.40 (1H, br), 7.59 (1H, br), 8.59 (1H, br), 8.64 (1H, br).

EXAMPLE 78

Synthesis of 1-ethyl-3,3,5-trimethyl-7-{[N-[2-(2-methylpyridin-3-yl)ethyl]-N-(2-methylpyridin-3-ylmethyl)amino]methyl}-1,5-dihydrobenzo[b][1,4]diazepine-2,4-dione trihydrochloride The synthesis of the title compound was performed in the same manner as in Example 39 using appropriate starting materials.
$^1$H NMR (DMSO-d$_6$), δppm: 0.72 (3H, s), 1.05 (3H, t, J=7.1 Hz), 1.34 (3H, s), 2.70 (8H, br), 3.34 (3H, br), 3.78 (3H, br), 4.01-4.20 (5H, m), 7.47 (1H, br), 7.52 (1H, br), 7.85 (2H, br), 8.35 (2H, br), 8.65 (2H, br), 9.00 (1H, br).

EXAMPLE 79

Synthesis of 1-ethyl-3,3,5-trimethyl-7-{[N-[2-(4-methylpyridin-3-yl)ethyl]-N-(4-methylthiazol-5-ylmethyl)amino]methyl}-1,5-dihydrobenzo[b][1,4]diazepine-2,4-dione trihydrochloride The synthesis of the title compound was performed in the same manner as in Example 4 using appropriate starting materials.
$^1$H NMR (DMSO-d$_6$), δppm: 0.73 (3H, s), 1.06 (3H, t, J=7.1 Hz), 1.34 (3H, s), 2.43 (3H, s), 2.46 (3H, s), 3.36 (5H, br), 3.45 (2H, br), 3.77-3.88 (1H, m), 4.00-4.12 (1H, m), 4.45

(2H, br), 4.65 (2H, br), 7.52-7.54 (1H, m), 7.60 (1H, br), 7.88 (1H, d, J=6.0 Hz), 7.90 (1H, br), 7.71 (1H, d, J=6.0 Hz), 8.77 (1H, s), 9.15 (1H, s).

EXAMPLE 80

Synthesis of 7-({N-(2,5-dimethyl-2H-pyrazol-3-ylmethyl)-N-[2-(4-methylpyridin-3-yl)ethyl]amino}methyl)-1-ethyl-3,3,5-trimethyl-1,5-dihydrobenzo[b][1,4]diazepine-2,4-dione trihydrochloride The synthesis of the title compound was performed in the same manner as in Example 4 using appropriate starting materials.

$^1$H NMR (DMSO-d$_6$), δppm: 0.73 (3H, s), 1.07 (3H, t, J=7.1 Hz), 1.34 (3H, s), 2.11 (3H, s), 2.45 (3H, s), 3.36 (5H, br), 3.50 (2H, br), 3.50-3.82 (4H, m), 3.95-4.08 (1H, m), 4.45 (2H, br), 4.53 (2H, br), 6.51 (1H, br), 7.56 (1H, br), 7.61 (1H, br), 7.87-7.89 (1H, m), 8.02 (1H, m), 8.71 (1H, d, J=5.8 Hz), 8.78 (1H, s).

EXAMPLE 81

Synthesis of 1-ethyl-3,3,5-trimethyl-7-{[N-[2-(2-methylpyridin-3-yl)ethyl]-N-(4-methylthiazol-5-ylmethyl)amino]methyl}-1,5-dihydrobenzo[b][1,4]diazepine-2,4-dione trihydrochloride The synthesis of the title compound was performed in the same manner as in Example 4 using appropriate starting materials.

$^1$H NMR (DMSO-d$_6$), δppm: 0.74 (3H, s), 1.06 (3H, t, J=7.1 Hz), 1.34 (3H, s), 2.41 (3H, s), 2.65 (3H, s), 3.36 (7H, br), 3.70-3.79 (1H, m), 3.95-4.08 (1H, m), 4.47 (2H, br), 4.73 (2H, br), 7.54 (1H, br), 7.60 (1H, br), 7.87 (1H, dd, J=7.8, 5.7 Hz), 7.92 (1H, br), 8.33 (1H, d, J=7.8 Hz), 8.66 (1H, d, J=5.7 Hz), 9.12 (1H, s).

EXAMPLE 82

Synthesis of 7-({N-(2,5-dimethyl-2H-pyrazol-3-ylmethyl)-N-[2-(2-methylpyridin-3-yl)ethyl]amino}methyl)-1-ethyl-3,3,5-trimethyl-1,5-dihydrobenzo[b][1,4]diazepine-2,4-dione trihydrochloride The synthesis of the title compound was performed in the same manner as in Example 4 using appropriate starting materials.

$^1$H NMR (DMSO-d$_6$), δppm: 0.75 (3H, s), 1.07 (3H, t, J=7.1 Hz), 1.35 (3H, s), 2.12 (3H, s), 2.67 (3H, s), 3.36 (5H, br), 3.43 (2H, br), 3.70-3.90 (4H, m), 4.00-4.08 (1H, m), 4.45 (2H, br), 4.50 (2H, br), 6.50 (1H, br), 7.55-7.57 (1H, m), 7.61 (1H, br), 7.85-7.88 (1H, m), 7.94 (1H, br), 8.36 (1H, br), 8.67 (1H, d, J=5.6 Hz).

EXAMPLE 83

Synthesis of 7-({N-(2,5-dimethyl-2H-pyrazol-3-ylmethyl)-N-[2-(2-methyl-4-oxo-4H-furo[3,2-c]pyridin-5-yl)ethyl]amino}methyl)-1-ethyl-3,3,5-trimethyl-1,5-dihydrobenzo[b][1,4]diazepine-2,4-dione The synthesis of the title compound was performed in the same manner as in Example 30 using appropriate starting materials.

White Powder (Diethyl Ether)
mp: 152-153° C.

EXAMPLE 84

Synthesis of 1-ethyl-7-({N-(4-methoxypyridin-3-ylmethyl)-N-[2-(2-methyl-4-oxo-4H-furo[3,2-c]pyridin-5-yl)ethyl]amino}methyl)-3,3,5-trimethyl-1,5-dihydrobenzo[b][1,4]diazepine-2,4-dione The synthesis of the title compound was performed in the same manner as in Example 30 using appropriate starting materials.

$^1$H NMR (CDCl$_3$), δppm: 0.79 (3H, s), 1.14 (3H, t, J=7.1 Hz), 1.50 (3H, s), 2.43 (3H, s), 2.77-2.87 (2H, m), 3.29 (3H, s), 3.61 (1H, d, J=14.3 Hz), 3.68-3.74 (2H, m), 3.78 (1H, d, J=14.3 Hz), 3.86 (3H, s), 3.97-4.08 (1H, m), 4.09-4.19 (3H, m), 6.43-6.46 (2H, m), 6.78 (1H, d, J=5.8 Hz), 7.00 (2H, br), 7.05 (1H, s), 7.10 (1H, d, J=7.3 Hz), 8.39-8.40 (2H, m).

EXAMPLE 85

Synthesis of 1-ethyl-3,3,5-trimethyl-7-{[N-[2-(2-methyl-4-oxo-4H-furo[3,2-c]pyridin-5-yl)ethyl]-N-(4-trifluoromethylpyridin-3-ylmethyl)amino]methyl}-1,5-dihydrobenzo[b][1,4]diazepine-2,4-dione The synthesis of the title compound was performed in the same manner as in Example 30 using appropriate starting materials.

White Powder (Diethyl Ether)
mp: 162-164° C.

EXAMPLE 86

Synthesis of 1-ethyl-3,3,5-trimethyl-7-{[N-(4-methylthiazol-5-ylmethyl)-N-(2-pyridin-3-ylethyl)amino]methyl}-1,5-dihydrobenzo[b][1,4]diazepine-2,4-dione 1-Ethyl-3,3,5-trimethyl-2,4-dioxo-2,3,4,5-tetrahydro-1H-benzo[b][1,4]diazepine-7-carbaldehyde(0.423 g) and acetic acid(0.14 g) were added to a 1,2-dichloroethane solution (10 ml) of N-(4-methylthiazol-5-ylmethyl)-N-(2-pyridin-3-ylethyl)amine(0.36 g). The mixture was stirred at room temperature for 30 minutes. Sodium triacetoxyborohydride(0.48 g) was added, and the mixture was stirred at room temperature overnight. The reaction liquid was condensed under reduced pressure. The residue was purified by silica gel column chromatography (ethyl acetate: methanol=100:0→50:50). The purified product was condensed under reduced pressure. The residue was washed with diethyl ether, and dried to give the title compound(0.37 g) as a white powder.
mp: 118-120° C.

EXAMPLE 87

Synthesis of 1-ethyl-3,3,5-trimethyl-7-{[N-[2-(2-methyl-4-oxo-4H-furo[3,2-c]pyridin-5-yl)ethyl]-N-(5-trifluoromethylpyridin-3-ylmethyl)amino]methyl}-1,5-dihydrobenzo[b][1,4]diazepine-2,4-dione The synthesis of the title compound was performed in the same manner as in Example 30 using appropriate starting materials.

White Powder (Diethyl Ether)
mp: 138-140° C.

EXAMPLE 88

Synthesis of 1-ethyl-7-({N-(5-fluoropyridin-3-ylmethyl)-N-[2-(2-methyl-4-oxo-4H-furo[3,2-c]pyridin-5-yl)ethyl]amino}methyl)-3,3,5-trimethyl-1,5-dihydrobenzo[b][1,4]diazepine-2,4-dione The synthesis of the title compound was performed in the same manner as in Example 30 using appropriate starting materials.
White Powder (Diethyl Ether)
mp: 144-146° C.

EXAMPLE 89

Synthesis of 1-ethyl-3,3,5-trimethyl-7-{[N-[2-(2-methyl-4-oxo-4H-furo[3,2-c]pyridin-5-yl)ethyl]-N-(3-methylpyridin-4-ylmethyl)amino]methyl}-1,5-dihydrobenzo[b][1,4]diazepine-2,4-dione The synthesis of the title compound was performed in the same manner as in Example 30 using appropriate starting materials.
White Powder (Diethyl Ether)
mp: 153-154° C.

EXAMPLE 90

Synthesis of 1-Ethyl-7-({N-(3-fluoropyridin-4-ylmethyl)-N-[2-(2-methyl-4-oxo-4H-furo[3,2-c]pyridin-5-yl)ethyl]amino}methyl)-3,3,5-trimethyl-1,5-dihydrobenzo[b][1,4]diazepine-2,4-dione The synthesis of the title compound was performed in the same manner as in Example 30 using appropriate starting materials.
White Powder (Diethyl Ether)
mp: 149-151° C.

EXAMPLE 91

Synthesis of 1-ethyl-3,3,5-trimethyl-7-{[N-(2-methyl-2H-pyrazol-3-ylmethyl)-N-(2-pyridin-3-ylethyl)amino]methyl}-1,5-dihydrobenzo[b][1,4]diazepine-2,4-dione hydrochloride The synthesis of the title compound was performed in the same manner as in Example 4 using appropriate starting materials.
$^1$H NMR (D$_2$O), δppm: 0.79 (3H, s), 1.11 (3H, t, J=7.0 Hz), 1.43 (3H, s), 3.09-3.70 (5H, m), 3.39 (3H, s), 3.45 (2H, s), 3.70-3.94 (1H, m), 3.94-4.59 (5H, m), 6.3-6.57(1H, m), 7.30-7.65(4H, m), 7.82-8.06(1H, m), 8.15-8.47 (1H, m), 8.51 (1H, bs), 8.54-8.74 (1H, m).

EXAMPLE 92

Synthesis of 1-ethyl-7-{[N-(1H-indol-7-ylmethyl)-N-(2-pyridin-3-ylethyl)amino]methyl}-3,3,5-trimethyl-1,5-dihydrobenzo[b][1,4]diazepine-2,4-dione dihydrochloride The synthesis of the title compound was performed in the same manner as in Example 4 using appropriate starting materials.
White Powder (Ethanol)
mp: 155-167.8° C.

EXAMPLE 93

Synthesis of 1-ethyl-3,3,5-trimethyl-7-{[2-(4-methylpyridin-3-yl)ethylamino]methyl}-1,5-dihydrobenzo[b][1,4]diazepine-2,4-dione The synthesis of the title compound was performed in the same manner as in Example 27 using appropriate starting materials.
$^1$H NMR (CDCl$_3$), δppm: 0.82 (3H, s), 1.18 (3H, t, J=7.1 Hz), 1.53 (3H, s), 2.32 (3H, s), 2.94-2.96 (2H, m), 3.00 (2H, br), 3.42 (3H, s), 3.74-3.74 (1H, m), 3.96 (2H, br), 4.04-4.11 (1H, m), 7.07 (1H, d, J=4.9 Hz), 7.26-7.28 (2H, m), 7.34 (1H, br), 8.33 (1H, d, J=4.9 Hz), 8.38 (1H, s).

EXAMPLE 94

Synthesis of 1-ethyl-3,3,5-trimethyl-7-{[2-(2-methylpyridin-3-yl)ethylamino]methyl}-1,5-dihydrobenzo[b][1,4]diazepine-2,4-dione The synthesis of the title compound was performed in the same manner as in Example 27 using appropriate starting materials.
$^1$H NMR (CDCl$_3$), δppm: 0.82 (3H, s), 1.18 (3H, t, J=7.1 Hz), 1.53 (3H, s), 2.55 (3H, s), 2.85-2.93 (4H, m), 3.41 (3H, s), 3.75-3.83 (1H, m), 3.86 (2H, s), 4.11-4.17 (1H, m), 7.08 (1H, dd, J=7.6, 4.8 Hz), 7.19-7.21 (2H, m), 7.24-7.26 (1H, m), 7.44 (1H, dd, J=7.6, 1.6 Hz), 8.37 (1H, dd, 4.8, 1.6 Hz).

EXAMPLE 95

Synthesis of 1-ethyl-3,3,5-trimethyl-7-({N-(2-methyloxazol-4-ylmethyl)-N-[2-(2-methyl-4-oxo-4H-furo[3,2-c]pyridin-5-yl)ethyl]amino}methyl)-1,5-dihydrobenzo[b][1,4]diazepine-2,4-dione dihydrochloride The synthesis of the title compound was performed in the same manner as in Example 4 using appropriate starting materials.
$^1$H NMR (DMSO-d$_6$), δppm: 0.69 (3H, s), 1.06 (3H, t, J=7.1 Hz), 1.33 (3H, s), 2.395 (3H, s), 2.404 (3H, s), 3.32 (3H, s), 3.47 (2H, br), 3.74-3.81 (1H, m), 3.95-4.06 (1H, m), 4.23 (2H, br), 4.37 (4H, br), 6.55 (1H, s), 6.76 (1H, d, J=7.4 Hz), 7.48 (2H, br), 7.57 (1H, d, J=7.4 Hz), 7.67 (1H, br), 8.14 (1H, br).

EXAMPLE 96

Synthesis of 1-ethyl-3,3,5-trimethyl-7-({N-[2-(2-methyl-4-oxo-4H-furo[3,2-c]pyridin-5-yl)ethyl]-N-(oxazol-5-ylmethyl)amino}methyl)-1,5-dihydrobenzo[b][1,4]diazepine-2,4-dione dihydrochloride The synthesis of the title compound was performed in the same manner as in Example 4 using appropriate starting materials.
$^1$H NMR (DMSO-d$_6$), δppm: 0.66 (3H, s), 1.03 (3H, t, J=7.1 Hz), 1.32 (3H, s), 2.39 (3H, s), 3.21 (3H, s), 3.28-3.49 (2H, m), 3.74 (1H, br), 3.91-3.97 (1H, m), 4.20 (6H, br), 6.69 (1H, s), 6.69-6.71 (1H, m), 7.11-7.31 (4H, m), 7.54 (1H, d, J=7.5 Hz), 8.33 (1H, br).

EXAMPLE 97

Synthesis of 7-({N-(2,4-dimethylthiazol-5-ylmethyl)-N-[2-(2-methyl-4-oxo-4H-furo[3,2-c]pyridin-5-yl)ethyl]amino}methyl)-1-ethyl-3,3,5-trimethyl-1,5-dihydrobenzo[b][1,4]diazepine-2,4-dione The synthesis of the title compound was performed in the same manner as in Example 30 using appropriate starting materials.
Pale Yellow Powder
mp: 187-188° C.

EXAMPLE 98

Synthesis of 7-{[N-(2-chloropyridin-3-ylmethyl)-N-(2-pyridin-3-ylethyl)amino]methyl}-1-ethyl-3,3,5-trimethyl-1,5-dihydro-benzo[b][1,4]diazepine-2,4-dione dihydrochloride The synthesis of the title compound was performed in the same manner as in Example 4 using appropriate starting materials.
White Powder
mp: 183-187° C.

EXAMPLE 99

Synthesis of 1-ethyl-3,3,5-trimethyl-7-{[N-(2-pyridin-3-ylethyl)-N-(quinolin-5-ylmethyl)amino]methyl}-1,5-dihydrobenzo[b][1,4]diazepine-2,4-dione dihydrochloride The synthesis of the title compound was performed in the same manner as in Example 4 using appropriate starting materials.
White Powder
mp: 136-141° C.

EXAMPLE 100

Synthesis of 7-{[N-[2-(2,6-dimethylpyridin-3-yl)ethyl]-N-(4-methylthiazol-5-ylmethyl)amino]methyl}-1-ethyl-3,3,5-trimethyl-1,5-dihydrobenzo[b][1,4]diazepine-2,4-dione The synthesis of the title compound was performed in the same manner as in Example 30 using appropriate starting materials.
White Powder
mp: 136-137° C.

EXAMPLE 101

Synthesis of 1-ethyl-3,3,5-trimethyl-7-({N-(2-methylpyridin-3-ylmethyl)-N-[2-(4-oxo-4H-thieno[3,2-c]pyridin-5-yl)ethyl]amino}methyl)-1,5-dihydrobenzo[b][1,4]diazepine-2,4-dione The synthesis of the title compound was performed in the same manner as in Example 30 using appropriate starting materials.
White Powder
mp: 139-140° C.

EXAMPLE 102

Synthesis of 1-ethyl-3,3,5-trimethyl-7-({N-(4-methylpyridin-3-ylmethyl)-N-[2-(4-oxo-4H-thieno[3,2-c]pyridin-5-yl)ethyl]amino}methyl)-1,5-dihydrobenzo[b][1,4]diazepine-2,4-dione The synthesis of the title compound was performed in the same manner as in Example 30 using appropriate starting materials.
White Powder
mp: 145-147° C.

EXAMPLE 103

Synthesis of 1-ethyl-3,3,5-trimethyl-7-({N-(4-methylpyridin-3-ylmethyl)-N-[2-(7-oxo-7H-thieno[2,3-c]pyridin-6-yl)ethyl]amino}methyl)-1,5-dihydrobenzo[b][1,4]diazepine-2,4-dione The synthesis of the title compound was performed in the same manner as in Example 30 using appropriate starting materials.
White Powder
mp: 138-142° C.

EXAMPLE 104

Synthesis of 7-{[N-[2-(2,7-dimethyl-4-oxo-4H-furo[3,2-c]pyridin-5-yl)ethyl]-N-(2,5-dimethyl-2H-pyrazol-3-ylmethyl)amino]methyl}-1-ethyl-3,3,5-trimethyl-1,5-dihydrobenzo[b][1,4]diazepine-2,4-dione The synthesis of the title compound was performed in the same manner as in Example 30 using appropriate starting materials.
White Powder
mp: 144-145° C.

EXAMPLE 105

Synthesis of 7-{[N-[2-(2,3-Dimethyl-4-oxo-4H-furo[3,2-c]pyridin-5-yl)ethyl]-N-(2,5-dimethyl-2H-pyrazol-3-ylmethyl)amino]methyl}-1-ethyl-3,3,5-trimethyl-1,5-dihydrobenzo[b][1,4]diazepine-2,4-dione The synthesis of the title compound was performed in the same manner as in Example 30 using appropriate starting materials.
White Powder
mp: 148-150° C.

EXAMPLE 106

Synthesis of 1-ethyl-3,3,5-trimethyl-7-({N-(2-methylpyridin-3-ylmethyl)-N-[2-(7-oxo-7H-thieno[2,3-c]pyridin-6-yl)ethyl]amino}methyl)-1,5-dihydrobenzo[b][1,4]diazepine-2,4-dione The synthesis of the title compound was performed in the same manner as in Example 30 using appropriate starting materials.
White Powder
mp: 125-127° C.

EXAMPLE 107

Synthesis of 7-({N-(2,5-dimethyl-2H-pyrazol-3-ylmethyl)-N-[2-(7-methyl-4-oxo-4H-furo[3,2-c]pyridin-5-yl)ethyl]amino}methyl)-1-ethyl-3,3,5-trimethyl-1,5-dihydrobenzo[b][1,4]diazepine-2,4-dione The synthesis of the title compound was performed in the same manner as in Example 30 using appropriate starting materials.
White Powder
mp: 193-195° C.

EXAMPLE 108

Synthesis of 7-({N-(2,5-dimethyl-2H-pyrazol-3-ylmethyl)-[2-(2,6-dimethylpyridin-3-yl)ethyl]amino}methyl)-1-ethyl-3,3,5-trimethyl-1,5-dihydrobenzo[b][1,4]diazepine-2,4-dione trihydrochloride The synthesis of the title compound was performed in the same manner as in Example 4 using appropriate starting materials.
White Powder
$^1$H NMR (DMSO-$d_6$), δppm: 0.75 (3H, s), 1.07 (3H, t, J=7.1 Hz), 1.35 (3H, s), 2.11 (3H, s), 2.65 (3H, br), 2.71 (3H, br), 3.36 (5H, br), 3.50 (3H, s), 3.60-3.82 (3H, m), 4.00-4.10 (1H, m), 4.44 (2H, br), 4.53 (2H, br), 6.50 (1H, br), 7.57-7.67 (2H, m), 7.69 (1H, d, J=7.9 Hz), 8.00 (1H, br), 8.23 (1H, br).

The following compounds shown in Examples 109 to 308 can be prepared by the same manner as mentioned above or a conventional manner using appropriate starting materials.

EXAMPLE 109

1-Ethyl-3,3,5-trimethyl-7-{[oxazol-5-ylmethyl-(2-pyridin-3-yl-ethyl)-amino]-methyl}-1,5-dihydro-benzo[b][1,4]diazepine-2,4-dione

EXAMPLE 110

1-Ethyl-3,3,5-trimethyl-7-{[(2-pyridin-3-yl-ethyl)-thiazol-2-ylmethyl-amino]-methyl}-1,5-dihydro-benzo[b][1,4]diazepine-2,4-dione

EXAMPLE 111

1-Ethyl-3,3,5-trimethyl-7-{[(2-pyridin-3-yl-ethyl)-thiazol-5-ylmethyl-amino]-methyl}-1,5-dihydro-benzo[b][1,4]diazepine-2,4-dione

EXAMPLE 112

1-Ethyl-3,3,5-trimethyl-7-{[(2-pyridin-3-yl-ethyl)-thiazol-4-ylmethyl-amino]-methyl}-1,5-dihydro-benzo[b][1,4]diazepine-2,4-dione

EXAMPLE 113

1-Ethyl-3,3,5-trimethyl-7-{[(4-methyl-thiazol-2-ylmethyl)-(2-pyridin-3-yl-ethyl)-amino]-methyl}-1,5-dihydro-benzo[b][1,4]diazepine-2,4-dione

EXAMPLE 114

7-{[(4,5-Dimethyl-thiazol-2-ylmethyl)-(2-pyridin-3-yl-ethyl)-amino]-methyl}-1-ethyl-3,3,5-trimethyl-1,5-dihydro-benzo[b][1,4]diazepine-2,4-dione

EXAMPLE 115

1-Ethyl-3,3,5-trimethyl-7-{[(2-methyl-pyridin-4-ylmethyl)-(2-pyridin-3-yl-ethyl)-amino]-methyl}-1,5-dihydro-benzo[b][1,4]diazepine-2,4-dione

EXAMPLE 116

1-Ethyl-7-{[(3-fluoro-pyridin-4-ylmethyl)-(2-pyridin-3-yl-ethyl)-amino]-methyl}-3,3,5-trimethyl-1,5-dihydro-benzo[b][1,4]diazepine-2,4-dione

EXAMPLE 117

1-Ethyl-3,3,5-trimethyl-7-{[(3-methyl-pyridin-4-ylmethyl)-(2-pyridin-3-yl-ethyl)-amino]-methyl}-1,5-dihydro-benzo[b][1,4]diazepine-2,4-dione

EXAMPLE 118

1-Ethyl-3,3,5-trimethyl-7-{[(2-methyl-pyridin-3-ylmethyl)-(2-pyridin-3-yl-ethyl)-amino]-methyl}-1,5-dihydro-benzo[b][1,4]diazepine-2,4-dione

EXAMPLE 119

7-{[[2-(2,6-Dimethyl-pyridin-3-yl)-ethyl]-(2-methyl-pyridin-3-ylmethyl)-amino]-methyl}-1-ethyl-3,3,5-trimethyl-1,5-dihydro-benzo[b][1,4]diazepine-2,4-dione

EXAMPLE 120

1-Ethyl-3,3,5-trimethyl-7-{[(3-methyl-pyridin-2-ylmethyl)-(2-pyridin-3-yl-ethyl)-amino]-methyl}-1,5-dihydro-benzo[b][1,4]diazepine-2,4-dione

EXAMPLE 121

1-Ethyl-3,3,5-trimethyl-7-{[(2-pyridin-3-yl-ethyl)-(4-trifluoromethyl-pyridin-3-ylmethyl)-amino]-methyl}-1,5-dihydro-benzo[b][1,4]diazepine-2,4-dione

EXAMPLE 122

1-Ethyl-7-{[(2-methoxy-pyridin-3-ylmethyl)-(2-pyridin-3-yl-ethyl)-amino]-methyl}-3,3,5-trimethyl-1,5-dihydro-benzo[b][1,4]diazepine-2,4-dione

EXAMPLE 123

7-{[(2,6-Dimethyl-pyridin-3-ylmethyl)-(2-pyridin-3-yl-ethyl)-amino]-methyl}-1-ethyl-3,3,5-trimethyl-1,5-dihydro-benzo[b][1,4]diazepine-2,4-dione

EXAMPLE 124

1-Ethyl-7-{[(3-hydroxy-benzyl)-(2-pyridin-3-yl-ethyl)-amino]-methyl}-3,3,5-trimethyl-1,5-dihydro-benzo[b][1,4]diazepine-2,4-dione

EXAMPLE 125

1-Ethyl-7-{[furan-2-ylmethyl-(2-pyridin-3-yl-ethyl)-amino]-methyl}-3,3,5-trimethyl-1,5-dihydro-benzo[b][1,4]diazepine-2,4-dione

EXAMPLE 126

1-Ethyl-7-{[furan-3-ylmethyl-(2-pyridin-3-yl-ethyl)-amino]-methyl}-3,3,5-trimethyl-1,5-dihydro-benzo[b][1,4]diazepine-2,4-dione

EXAMPLE 127

1-Ethyl-3,3,5-trimethyl-7-{[(5-methyl-furan-2-ylmethyl)-(2-pyridin-3-yl-ethyl)-amino]-methyl}-1,5-dihydro-benzo[b][1,4]diazepine-2,4-dione

EXAMPLE 128

1-Ethyl-3,3,5-trimethyl-7-{[(2-methyl-furan-3-ylmethyl)-(2-pyridin-3-yl-ethyl)-amino]-methyl}-1,5-dihydro-benzo[b][1,4]diazepine-2,4-dione

EXAMPLE 129

7-{[(4,5-Dimethyl-furan-2-ylmethyl)-(2-pyridin-3-yl-ethyl)-amino]-methyl}-1-ethyl-3,3,5-trimethyl-1,5-dihydro-benzo[b][1,4]diazepine-2,4-dione

EXAMPLE 130

1-Ethyl-3,3,5-trimethyl-7-{[(2-pyridin-3-yl-ethyl)-(5-trifluoromethyl-furan-2-ylmethyl)-amino]-methyl}-1,5-dihydro-benzo[b][1,4]diazepine-2,4-dione

EXAMPLE 131

1-Ethyl-3,3,5-trimethyl-7-{[(3-methyl-thiophen-2-ylmethyl)-(2-pyridin-3-yl-ethyl)-amino]-methyl}-1,5-dihydro-benzo[b][1,4]diazepine-2,4-dione

EXAMPLE 132

1-Ethyl-3,3,5-trimethyl-7-{[(2-pyridin-3-yl-ethyl)-thiophen-2-ylmethyl-amino]-methyl}-1,5-dihydro-benzo[b][1,4]diazepine-2,4-dione

EXAMPLE 133

7-{[(4,5-Dimethyl-thiophen-2-ylmethyl)-(2-pyridin-3-yl-ethyl)-amino]-methyl}-1-ethyl-3,3,5-trimethyl-1,5-dihydro-benzo[b][1,4]diazepine-2,4-dione

EXAMPLE 134

1-Ethyl-3,3,5-trimethyl-7-{2-[(4-methyl-thiazol-2-ylmethyl)-(2-pyridin-3-yl-ethyl)-amino]-ethyl}-1,5-dihydro-benzo[b][1,4]diazepine-2,4-dione

EXAMPLE 135

1-Ethyl-3,3,5-trimethyl-7-{2-[(4-methyl-thiazol-5-ylmethyl)-(2-pyridin-3-yl-ethyl)-amino]-ethyl}-1,5-dihydro-benzo[b][1,4]diazepine-2,4-dione

EXAMPLE 136

1-Ethyl-3,3,5-trimethyl-7-{2-[(2-methyl-pyridin-3-ylmethyl)-(2-pyridin-3-yl-ethyl)-amino]-ethyl}-1,5-dihydro-benzo[b][1,4]diazepine-2,4-dione

EXAMPLE 137

1-Ethyl-3,3,5-trimethyl-7-{2-[(4-methyl-pyridin-3-ylmethyl)-(2-pyridin-3-yl-ethyl)-amino]-ethyl}-1,5-dihydro-benzo[b][1,4]diazepine-2,4-dione

EXAMPLE 138

1-Ethyl-3,3,5-trimethyl-7-{2-[(3-methyl-pyridin-2-ylmethyl)-(2-pyridin-3-yl-ethyl)-amino]-ethyl}-1,5-dihydro-benzo[b][1,4]diazepine-2,4-dione

EXAMPLE 139

7-{2-[(2,6-Dimethyl-pyridin-3-ylmethyl)-(2-pyridin-3-yl-ethyl)-amino]-ethyl}-1-ethyl-3,3,5-trimethyl-1,5-dihydro-benzo[b][1,4]diazepine-2,4-dione

EXAMPLE 140

N-(2-{[[2-(1-Ethyl-3,3,5-trimethyl-2,4-dioxo-2,3,4,5-tetrahydro-1H-benzo[b][1,4]diazepin-7-yl)-ethyl]-(2-pyridin-3-yl-ethyl)-amino]-methyl}-phenyl)-methanesulfonamide

EXAMPLE 141

7-{2-[(2,5-Dimethyl-2H-pyrazol-3-ylmethyl)-(2-pyridin-3-yl-ethyl)-amino]-ethyl}-1-ethyl-3,3,5-trimethyl-1,5-dihydro-benzo[b][1,4]diazepine-2,4-dione

EXAMPLE 142

1-Ethyl-3,3,5-trimethyl-7-{3-[(4-methyl-thiazol-2-ylmethyl)-(2-pyridin-3-yl-ethyl)-amino]-propyl}-1,5-dihydro-benzo[b][1,4]diazepine-2,4-dione

EXAMPLE 143

1-Ethyl-3,3,5-trimethyl-7-{3-[(4-methyl-thiazol-5-ylmethyl)-(2-pyridin-3-yl-ethyl)-amino]-propyl}-1,5-dihydro-benzo[b][1,4]diazepine-2,4-dione

EXAMPLE 144

1-Ethyl-3,3,5-trimethyl-7-{3-[(2-methyl-pyridin-3-ylmethyl)-(2-pyridin-3-yl-ethyl)-amino]-propyl}-1,5-dihydro-benzo[b][1,4]diazepine-2,4-dione

EXAMPLE 145

1-Ethyl-3,3,5-trimethyl-7-{3-[(4-methyl-pyridin-3-ylmethyl)-(2-pyridin-3-yl-ethyl)-amino]-propyl}-1,5-dihydro-benzo[b][1,4]diazepine-2,4-dione

EXAMPLE 146

1-Ethyl-3,3,5-trimethyl-7-{3-[(3-methyl-pyridin-2-ylmethyl)-(2-pyridin-3-yl-ethyl)-amino]-propyl}-1,5-dihydro-benzo[b][1,4]diazepine-2,4-dione

EXAMPLE 147

N-(2-{[[3-(1-Ethyl-3,3,5-trimethyl-2,4-dioxo-2,3,4,5-tetrahydro-1H-benzo[b][1,4]diazepin-7-yl)-propyl]-(2-pyridin-3-yl-ethyl)-amino]-methyl}-phenyl)-methanesulfonamide

EXAMPLE 148

7-{3-[(2,5-Dimethyl-2H-pyrazol-3-ylmethyl)-(2-pyridin-3-yl-ethyl)-amino]-propyl}-1-ethyl-3,3,5-trimethyl-1,5-dihydro-benzo[b][1,4]diazepine-2,4-dione

EXAMPLE 149

1-Ethyl-3,3,5-trimethyl-7-({(2-methyl-pyridin-3-ylmethyl)-[2-(7-oxo-7H-furo[2,3-c]pyridin-6-yl)-ethyl]-amino}-methyl)-1,5-dihydro-benzo[b][1,4]diazepine-2,4-dione

EXAMPLE 150

1-Ethyl-3,3,5-trimethyl-7-({oxazol-5-ylmethyl-[2-(4-oxo-4H-furo[3,2-c]pyridin-5-yl)-ethyl]-amino}-methyl)-1,5-dihydro-benzo[b][1,4]diazepine-2,4-dione

EXAMPLE 151

1-Ethyl-3,3,5-trimethyl-7-({[2-(4-oxo-4H-furo[3,2-c]pyridin-5-yl)-ethyl]-thiazol-2-ylmethyl-amino}-methyl)-1,5-dihydro-benzo[b][1,4]diazepine-2,4-dione

EXAMPLE 152

1-Ethyl-3,3,5-trimethyl-7-({[2-(4-oxo-4H-furo[3,2-c]pyridin-5-yl)-ethyl]-thiazol-4-ylmethyl-amino}-methyl)-1,5-dihydro-benzo[b][1,4]diazepine-2,4-dione

EXAMPLE 153

1-Ethyl-3,3,5-trimethyl-7-({(4-methyl-thiazol-2-ylmethyl)-[2-(4-oxo-4H-furo[3,2-c]pyridin-5-yl)-ethyl]-amino}-methyl)-1,5-dihydro-benzo[b][1,4]diazepine-2,4-dione

EXAMPLE 154

7-({(4,5-Dimethyl-thiazol-2-ylmethyl)-[2-(4-oxo-4H-furo[3,2-c]pyridin-5-yl)-ethyl]-amino}-methyl)-1-ethyl-3,3,5-trimethyl-1,5-dihydro-benzo[b][1,4]diazepine-2,4-dione

EXAMPLE 155

7-({(2,4-Dimethyl-thiazol-5-ylmethyl)-[2-(4-oxo-4H-furo[3,2-c]pyridin-5-yl)-ethyl]-amino}-methyl)-1-ethyl-3,3,5-trimethyl-1,5-dihydro-benzo[b][1,4]diazepine-2,4-dione

EXAMPLE 156

1-Ethyl-3,3,5-trimethyl-7-({[2-(4-oxo-4H-furo[3,2-c]pyridin-5-yl)-ethyl]-pyridin-4-ylmethyl-amino}-methyl)-1,5-dihydro-benzo[b][1,4]diazepine-2,4-dione

EXAMPLE 157

1-Ethyl-3,3,5-trimethyl-7-({(2-methyl-pyridin-4-ylmethyl)-[2-(4-oxo-4H-furo[3,2-c]pyridin-5-yl)-ethyl]-amino}-methyl)-1,5-dihydro-benzo[b][1,4]diazepine-2,4-dione

EXAMPLE 158

1-Ethyl-7-({(3-fluoro-pyridin-4-ylmethyl)-[2-(4-oxo-4H-furo[3,2-c]pyridin-5-yl)-ethyl]-amino}-methyl)-3,3,5-trimethyl-1,5-dihydro-benzo[b][1,4]diazepine-2,4-dione

EXAMPLE 159

1-Ethyl-3,3,5-trimethyl-7-({(3-methyl-pyridin-4-ylmethyl)-[2-(4-oxo-4H-furo[3,2-c]pyridin-5-yl)-ethyl]-amino}-methyl)-1,5-dihydro-benzo[b][1,4]diazepine-2,4-dione

EXAMPLE 160

1-Ethyl-3,3,5-trimethyl-7-({[2-(4-oxo-4H-furo[3,2-c]pyridin-5-yl)-ethyl]-pyridin-3-ylmethyl-amino}-methyl)-1,5-dihydro-benzo[b][1,4]diazepine-2,4-dione

EXAMPLE 161

1-Ethyl-3,3,5-trimethyl-7-({(3-methyl-pyridin-2-ylmethyl)-[2-(4-oxo-4H-furo[3,2-c]pyridin-5-yl)-ethyl]-amino}-methyl)-1,5-dihydro-benzo[b][1,4]diazepine-2,4-dione

EXAMPLE 162

1-Ethyl-3,3,5-trimethyl-7-{[[2-(4-oxo-4H-furo[3,2-c]pyridin-5-yl)-ethyl]-(4-trifluoromethyl-pyridin-3-ylmethyl)-amino]-methyl}-1,5-dihydro-benzo[b][1,4]diazepine-2,4-dione

EXAMPLE 163

1-Ethyl-7-({(2-methoxy-pyridin-3-ylmethyl)-[2-(4-oxo-4H-furo[3,2-c]pyridin-5-yl)-ethyl]-amino}-methyl)-3,3,5-trimethyl-1,5-dihydro-benzo[b][1,4]diazepine-2,4-dione

EXAMPLE 164

7-({(2,6-Dimethyl-pyridin-3-ylmethyl)-[2-(4-oxo-4H-furo[3,2-c]pyridin-5-yl)-ethyl]-amino}-methyl)-1-ethyl-3,3,5-trimethyl-1,5-dihydro-benzo[b][1,4]diazepine-2,4-dione

EXAMPLE 165

N-[2-({(1-Ethyl-3,3,5-trimethyl-2,4-dioxo-2,3,4,5-tetrahydro-1H-benzo[b][1,4]diazepin-7-ylmethyl)-[2-(4-oxo-4H-furo[3,2-c]pyridin-5-yl)-ethyl]-amino}-methyl)-phenyl]-methanesulfonamide

EXAMPLE 166

1-Ethyl-7-({(3-hydroxy-benzyl)-[2-(4-oxo-4H-furo[3,2-c]pyridin-5-yl)-ethyl]-amino}-methyl)-3,3,5-trimethyl-1,5-dihydro-benzo[b][1,4]diazepine-2,4-dione

EXAMPLE 167

1-Ethyl-7-({furan-2-ylmethyl-[2-(4-oxo-4H-furo[3,2-c]pyridin-5-yl)-ethyl]-amino}-methyl)-3,3,5-trimethyl-1,5-dihydro-benzo[b][1,4]diazepine-2,4-dione

EXAMPLE 168

1-Ethyl-7-({furan-3-ylmethyl-[2-(4-oxo-4H-furo[3,2-c]pyridin-5-yl)-ethyl]-amino}-methyl)-3,3,5-trimethyl-1,5-dihydro-benzo[b][1,4]diazepine-2,4-dione

EXAMPLE 169

1-Ethyl-3,3,5-trimethyl-7-({(5-methyl-furan-2-ylmethyl)-[2-(4-oxo-4H-furo[3,2-c]pyridin-5-yl)-ethyl]-amino}-methyl)-1,5-dihydro-benzo[b][1,4]diazepine-2,4-dione

EXAMPLE 170

1-Ethyl-3,3,5-trimethyl-7-({(2-methyl-furan-3-ylmethyl)-[2-(4-oxo-4H-furo[3,2-c]pyridin-5-yl)-ethyl]-amino}-methyl)-1,5-dihydro-benzo[b][1,4]diazepine-2,4-dione

EXAMPLE 171

7-({(4,5-Dimethyl-furan-2-ylmethyl)-[2-(4-oxo-4H-furo[3,2-c]pyridin-5-yl)-ethyl]-amino}-methyl)-1-ethyl-3,3,5-trimethyl-1,5-dihydro-benzo[b][1,4]diazepine-2,4-dione

EXAMPLE 172

1-Ethyl-3,3,5-trimethyl-7-{[[2-(4-oxo-4H-furo[3,2-c]pyridin-5-yl)-ethyl]-(5-trifluoromethyl-furan-2-ylmethyl)-amino]-methyl}-1,5-dihydro-benzo[b][1,4]diazepine-2,4-dione

EXAMPLE 173

7-({(4,5-Dimethyl-thiophen-2-ylmethyl)-[2-(4-oxo-4H-furo[3,2-c]pyridin-5-yl)-ethyl]-amino}-methyl)-1-ethyl-3,3,5-trimethyl-1,5-dihydro-benzo[b][1,4]diazepine-2,4-dione

EXAMPLE 174

1-Ethyl-3,3,5-trimethyl-7-({[2-(4-oxo-4H-furo[3,2-c]pyridin-5-yl)-ethyl]-thiophen-2-ylmethyl-amino}-methyl)-1,5-dihydro-benzo[b][1,4]diazepine-2,4-dione

EXAMPLE 175

1-Ethyl-3,3,5-trimethyl-7-({(3-methyl-thiophen-2-ylmethyl)-[2-(4-oxo-4H-furo[3,2-c]pyridin-5-yl)-ethyl]-amino}-methyl)-1,5-dihydro-benzo[b][1,4]diazepine-2,4-dione

EXAMPLE 176

7-({(2,5-Dimethyl-2H-pyrazol-3-ylmethyl)-[2-(4-oxo-4H-furo[3,2-c]pyridin-5-yl)-ethyl]-amino}-methyl)-1-ethyl-3,3,5-trimethyl-1,5-dihydro-benzo[b][1,4]diazepine-2,4-dione

EXAMPLE 177

1-Ethyl-3,3,5-trimethyl-7-({[2-(2-methyl-4-oxo-4H-furo[3,2-c]pyridin-5-yl)-ethyl]-oxazol-4-ylmethyl-amino}-methyl)-1,5-dihydro-benzo[b][1,4]diazepine-2,4-dione

EXAMPLE 178

1-Ethyl-3,3,5-trimethyl-7-({[2-(2-methyl-4-oxo-4H-furo[3,2-c]pyridin-5-yl)-ethyl]-thiazol-5-ylmethyl-amino}-methyl)-1,5-dihydro-benzo[b][1,4]diazepine-2,4-dione

EXAMPLE 179

1-Ethyl-3,3,5-trimethyl-7-({[2-(2-methyl-4-oxo-4H-furo[3,2-c]pyridin-5-yl)-ethyl]-thiazol-4-ylmethyl-amino}-methyl)-1,5-dihydro-benzo[b][1,4]diazepine-2,4-dione

EXAMPLE 180

1-Ethyl-3,3,5-trimethyl-7-{[[2-(2-methyl-4-oxo-4H-furo[3,2-c]pyridin-5-yl)-ethyl]-(4-methyl-thiazol-2-ylmethyl)-amino]-methyl}-1,5-dihydro-benzo[b][1,4]diazepine-2,4-dione

EXAMPLE 181

7-({(4,5-Dimethyl-thiazol-2-ylmethyl)-[2-(2-methyl-4-oxo-4H-furo[3,2-c]pyridin-5-yl)-ethyl]-amino}-methyl)-1-ethyl-3,3,5-trimethyl-1,5-dihydro-benzo[b][1,4]diazepine-2,4-dione

EXAMPLE 182

1-Ethyl-3,3,5-trimethyl-7-{[[2-(2-methyl-4-oxo-4H-furo[3,2-c]pyridin-5-yl)-ethyl]-(2-methyl-pyridin-4-ylmethyl)-amino]-methyl}-1,5-dihydro-benzo[b][1,4]diazepine-2,4-dione

EXAMPLE 183

1-Ethyl-3,3,5-trimethyl-7-({[2-(2-methyl-4-oxo-4H-furo[3,2-c]pyridin-5-yl)-ethyl]-pyridin-3-ylmethyl-amino}-methyl)-1,5-dihydro-benzo[b][1,4]diazepine-2,4-dione

EXAMPLE 184

1-Ethyl-3,3,5-trimethyl-7-{[[2-(2-methyl-4-oxo-4H-furo[3,2-c]pyridin-5-yl)-ethyl]-(3-methyl-pyridin-2-ylmethyl)-amino]-methyl}-1,5-dihydro-benzo[b][1,4]diazepine-2,4-dione

EXAMPLE 185

1-Ethyl-7-({(2-methoxy-pyridin-3-ylmethyl)-[2-(2-methyl-4-oxo-4H-furo[3,2-c]pyridin-5-yl)-ethyl]-amino}-methyl)-3,3,5-trimethyl-1,5-dihydro-benzo[b][1,4]diazepine-2,4-dione

EXAMPLE 186

N-[2-({(1-Ethyl-3,3,5-trimethyl-2,4-dioxo-2,3,4,5-tetrahydro-1H-benzo[b][1,4]diazepin-7-ylmethyl)-[2-(2-methyl-4-oxo-4H-furo[3,2-c]pyridin-5-yl)-ethyl]-amino}-methyl)-phenyl]-methanesulfonamide

EXAMPLE 187

1-Ethyl-7-({(3-hydroxy-benzyl)-[2-(2-methyl-4-oxo-4H-furo[3,2-c]pyridin-5-yl)-ethyl]-amino}-methyl)-3,3,5-trimethyl-1,5-dihydro-benzo[b][1,4]diazepine-2,4-dione

EXAMPLE 188

1-Ethyl-7-({furan-2-ylmethyl-[2-(2-methyl-4-oxo-4H-furo[3,2-c]pyridin-5-yl)-ethyl]-amino}-methyl)-3,3,5-trimethyl-1,5-dihydro-benzo[b][1,4]diazepine-2,4-dione

EXAMPLE 189

1-Ethyl-7-({furan-3-ylmethyl-[2-(2-methyl-4-oxo-4H-furo[3,2-c]pyridin-5-yl)-ethyl]-amino}-methyl)-3,3,5-trimethyl-1,5-dihydro-benzo[b][1,4]diazepine-2,4-dione

EXAMPLE 190

1-Ethyl-3,3,5-trimethyl-7-({(5-methyl-furan-2-ylmethyl)-[2-(2-methyl-4-oxo-4H-furo[3,2-c]pyridin-5-yl)-ethyl]-amino}-methyl)-1,5-dihydro-benzo[b][1,4]diazepine-2,4-dione

EXAMPLE 191

1-Ethyl-3,3,5-trimethyl-7-({(2-methyl-furan-3-ylmethyl)-[2-(2-methyl-4-oxo-4H-furo[3,2-c]pyridin-5-yl)-ethyl]-amino}-methyl)-1,5-dihydro-benzo[b][1,4]diazepine-2,4-dione

EXAMPLE 192

7-({(4,5-Dimethyl-furan-2-ylmethyl)-[2-(2-methyl-4-oxo-4H-furo[3,2-c]pyridin-5-yl)-ethyl]-amino}-methyl)-1-ethyl-3,3,5-trimethyl-1,5-dihydro-benzo[b][1,4]diazepine-2,4-dione

EXAMPLE 193

1-Ethyl-3,3,5-trimethyl-7-{[[2-(2-methyl-4-oxo-4H-furo[3,2-c]pyridin-5-yl)-ethyl]-(5-trifluoromethyl-furan-2-ylmethyl)-amino]-methyl}-1,5-dihydro-benzo[b][1,4]diazepine-2,4-dione

EXAMPLE 194

1-Ethyl-3,3,5-trimethyl-7-({[2-(2-methyl-4-oxo-4H-furo[3,2-c]pyridin-5-yl)-ethyl]-thiophen-2-ylmethyl-amino}-methyl)-1,5-dihydro-benzo[b][1,4]diazepine-2,4-dione

EXAMPLE 195

1-Ethyl-3,3,5-trimethyl-7-{[[2-(2-methyl-4-oxo-4H-furo[3,2-c]pyridin-5-yl)-ethyl]-(3-methyl-thiophen-2-ylmethyl)-amino]-methyl}-1,5-dihydro-benzo[b][1,4]diazepine-2,4-dione

EXAMPLE 196

7-({(4,5-Dimethyl-thiophen-2-ylmethyl)-[2-(2-methyl-4-oxo-4H-furo[3,2-c]pyridin-5-yl)-ethyl]-amino}-methyl)-1-ethyl-3,3,5-trimethyl-1,5-dihydro-benzo[b][1,4]diazepine-2,4-dione

EXAMPLE 197

1-Ethyl-3,3,5-trimethyl-7-{[[2-(7-methyl-4-oxo-4H-furo[3,2-c]pyridin-5-yl)-ethyl]-(4-methyl-thiazol-2-ylmethyl)-amino]-methyl}-1,5-dihydro-benzo[b][1,4]diazepine-2,4-dione

EXAMPLE 198

1-Ethyl-3,3,5-trimethyl-7-{[[2-(7-methyl-4-oxo-4H-furo[3,2-c]pyridin-5-yl)-ethyl]-(3-methyl-pyridin-2-ylmethyl)-amino]-methyl}-1,5-dihydro-benzo[b][1,4]diazepine-2,4-dione

EXAMPLE 199

N-[2-({(1-Ethyl-3,3,5-trimethyl-2,4-dioxo-2,3,4,5-tetrahydro-1H-benzo[b][1,4]diazepin-7-ylmethyl)-[2-(7-methyl-4-oxo-4H-furo[3,2-c]pyridin-5-yl)-ethyl]-amino}-methyl)-phenyl]-methanesulfonamide

EXAMPLE 200

1-Ethyl-3,3,5-trimethyl-7-{[[2-(3-methyl-4-oxo-4H-furo[3,2-c]pyridin-5-yl)-ethyl]-(2-methyl-pyridin-3-ylmethyl)-amino]-methyl}-1,5-dihydro-benzo[b][1,4]diazepine-2,4-dione

EXAMPLE 201

7-{[[2-(2,7-Dimethyl-4-oxo-4H-furo[3,2-c]pyridin-5-yl)-ethyl]-(4-methyl-thiazol-2-ylmethyl)-amino]-methyl}-1-ethyl-3,3,5-trimethyl-1,5-dihydro-benzo[b][1,4]diazepine-2,4-dione

EXAMPLE 202

7-{[[2-(2,7-Dimethyl-4-oxo-4H-furo[3,2-c]pyridin-5-yl)-ethyl]-(4-methyl-thiazol-5-ylmethyl)-amino]-methyl}-1-ethyl-3,3,5-trimethyl-1,5-dihydro-benzo[b][1,4]diazepine-2,4-dione

EXAMPLE 203

7-{[[2-(2,7-Dimethyl-4-oxo-4H-furo[3,2-c]pyridin-5-yl)-ethyl]-(3-methyl-pyridin-2-ylmethyl)-amino]-methyl}-1-ethyl-3,3,5-trimethyl-1,5-dihydro-benzo[b][1,4]diazepine-2,4-dione

EXAMPLE 204

N-(2-{[[2-(2,7-Dimethyl-4-oxo-4H-furo[3,2-c]pyridin-5-yl)-ethyl]-(1-ethyl-3,3,5-trimethyl-2,4-dioxo-2,3,4,5-tetrahydro-1H-benzo[b][1,4]diazepin-7-ylmethyl)-amino]-methyl}-phenyl)-methanesulfonamide

EXAMPLE 205

1-Ethyl-3,3,5-trimethyl-7-(2-{(4-methyl-thiazol-2-ylmethyl)-[2-(4-oxo-4H-furo[3,2-c]pyridin-5-yl)-ethyl]-amino}-ethyl)-1,5-dihydro-benzo[b][1,4]diazepine-2,4-dione

EXAMPLE 206

1-Ethyl-3,3,5-trimethyl-7-(2-{(4-methyl-thiazol-5-ylmethyl)-[2-(4-oxo-4H-furo[3,2-c]pyridin-5-yl)-ethyl]-amino}-ethyl)-1,5-dihydro-benzo[b][1,4]diazepine-2,4-dione

EXAMPLE 207

1-Ethyl-3,3,5-trimethyl-7-(2-{(4-methyl-pyridin-3-ylmethyl)-[2-(4-oxo-4H-furo[3,2-c]pyridin-5-yl)-ethyl]-amino}-ethyl)-1,5-dihydro-benzo[b][1,4]diazepine-2,4-dione

EXAMPLE 208

1-Ethyl-3,3,5-trimethyl-7-(2-{(3-methyl-pyridin-2-ylmethyl)-[2-(4-oxo-4H-furo[3,2-c]pyridin-5-yl)-ethyl]-amino}-ethyl)-1,5-dihydro-benzo[b][1,4]diazepine-2,4-dione

EXAMPLE 209

N-[2-({[2-(1-Ethyl-3,3,5-trimethyl-2,4-dioxo-2,3,4,5-tetrahydro-1H-benzo[b][1,4]diazepin-7-yl)-ethyl]-[2-(4-oxo-4H-furo[3,2-c]pyridin-5-yl)-ethyl]-amino}-methyl)-phenyl]-methanesulfonamide

EXAMPLE 210

7-(2-{(2,5-Dimethyl-2H-pyrazol-3-ylmethyl)-[2-(4-oxo-4H-furo[3,2-c]pyridin-5-yl)-ethyl]-amino}-ethyl)-1-ethyl-3,3,5-trimethyl-1,5-dihydro-benzo[b][1,4]diazepine-2,4-dione

EXAMPLE 211

1-Ethyl-3,3,5-trimethyl-7-{2-[[2-(2-methyl-4-oxo-4H-furo[3,2-c]pyridin-5-yl)-ethyl]-(4-methyl-thiazol-2-ylmethyl)-amino]-ethyl}-1,5-dihydro-benzo[b][1,4]diazepine-2,4-dione

EXAMPLE 212

1-Ethyl-3,3,5-trimethyl-7-{2-[[2-(2-methyl-4-oxo-4H-furo[3,2-c]pyridin-5-yl)-ethyl]-(4-methyl-thiazol-5-ylmethyl)-amino]-ethyl}-1,5-dihydro-benzo[b][1,4]diazepine-2,4-dione

EXAMPLE 213

1-Ethyl-3,3,5-trimethyl-7-{2-[[2-(2-methyl-4-oxo-4H-furo[3,2-c]pyridin-5-yl)-ethyl]-(3-methyl-pyridin-2-ylmethyl)-amino]-ethyl}-1,5-dihydro-benzo[b][1,4]diazepine-2,4-dione

EXAMPLE 214

7-(2-{(2,6-Dimethyl-pyridin-3-ylmethyl)-[2-(2-methyl-4-oxo-4H-furo[3,2-c]pyridin-5-yl)-ethyl]-amino}-ethyl)-1-ethyl-3,3,5-trimethyl-1,5-dihydro-benzo[b][1,4]diazepine-2,4-dione

EXAMPLE 215

N-[2-({[2-(1-Ethyl-3,3,5-trimethyl-2,4-dioxo-2,3,4,5-tetrahydro-1H-benzo[b][1,4]diazepin-7-yl)-ethyl]-[2-(2-methyl-4-oxo-4H-furo[3,2-c]pyridin-5-yl)-ethyl]-amino}-methyl)-phenyl]-methanesulfonamide

EXAMPLE 216

7-(2-{(2,5-Dimethyl-2H-pyrazol-3-ylmethyl)-[2-(2-methyl-4-oxo-4H-furo[3,2-c]pyridin-5-yl)-ethyl]-amino}-ethyl)-1-ethyl-3,3,5-trimethyl-1,5-dihydro-benzo[b][1,4]diazepine-2,4-dione

EXAMPLE 217

1-Ethyl-3,3,5-trimethyl-7-{2-[[2-(7-methyl-4-oxo-4H-furo[3,2-c]pyridin-5-yl)-ethyl]-(4-methyl-thiazol-2-ylmethyl)-amino]-ethyl}-1,5-dihydro-benzo[b][1,4]diazepine-2,4-dione

EXAMPLE 218

1-Ethyl-3,3,5-trimethyl-7-{2-[[2-(7-methyl-4-oxo-4H-furo[3,2-c]pyridin-5-yl)-ethyl]-(4-methyl-thiazol-5-ylmethyl)-amino]-ethyl}-1,5-dihydro-benzo[b][1,4]diazepine-2,4-dione

EXAMPLE 219

1-Ethyl-3,3,5-trimethyl-7-{2-[[2-(7-methyl-4-oxo-4H-furo[3,2-c]pyridin-5-yl)-ethyl]-(2-methyl-pyridin-3-ylmethyl)-amino]-ethyl}-1,5-dihydro-benzo[b][1,4]diazepine-2,4-dione

EXAMPLE 220

1-Ethyl-3,3,5-trimethyl-7-{2-[[2-(7-methyl-4-oxo-4H-furo[3,2-c]pyridin-5-yl)-ethyl]-(4-methyl-pyridin-3-ylmethyl)-amino]-ethyl}-1,5-dihydro-benzo[b][1,4]diazepine-2,4-dione

EXAMPLE 221

1-Ethyl-3,3,5-trimethyl-7-{2-[[2-(7-methyl-4-oxo-4H-furo[3,2-c]pyridin-5-yl)-ethyl]-(3-methyl-pyridin-2-ylmethyl)-amino]-ethyl}-1,5-dihydro-benzo[b][1,4]diazepine-2,4-dione

EXAMPLE 222

N-[2-({[2-(1-Ethyl-3,3,5-trimethyl-2,4-dioxo-2,3,4,5-tetrahydro-1H-benzo[b][1,4]diazepin-7-yl)-ethyl]-[2-(7-methyl-4-oxo-4H-furo[3,2-c]pyridin-5-yl)-ethyl]-amino}-methyl)-phenyl]-methanesulfonamide

EXAMPLE 223

7-(2-{(2,5-Dimethyl-2H-pyrazol-3-ylmethyl)-[2-(7-methyl-4-oxo-4H-furo[3,2-c]pyridin-5-yl)-ethyl]-amino}-ethyl)-1-ethyl-3,3,5-trimethyl-1,5-dihydro-benzo[b][1,4]diazepine-2,4-dione

EXAMPLE 224

7-{2-[[2-(2,7-Dimethyl-4-oxo-4H-furo[3,2-c]pyridin-5-yl)-ethyl]-(4-methyl-thiazol-2-ylmethyl)-amino]-ethyl}-1-ethyl-3,3,5-trimethyl-1,5-dihydro-benzo[b][1,4]diazepine-2,4-dione

EXAMPLE 225

7-{2-[[2-(2,7-Dimethyl-4-oxo-4H-furo[3,2-c]pyridin-5-yl)-ethyl]-(4-methyl-thiazol-5-ylmethyl)-amino]-ethyl}-1-ethyl-3,3,5-trimethyl-1,5-dihydro-benzo[b][1,4]diazepine-2,4-dione

EXAMPLE 226

7-{2-[[2-(2,7-Dimethyl-4-oxo-4H-furo[3,2-c]pyridin-5-yl)-ethyl]-(2-methyl-pyridin-3-ylmethyl)-amino]-ethyl}-1-ethyl-3,3,5-trimethyl-1,5-dihydro-benzo[b][1,4]diazepine-2,4-dione

EXAMPLE 227

7-{2-[[2-(2,7-Dimethyl-4-oxo-4H-furo[3,2-c]pyridin-5-yl)-ethyl]-(4-methyl-pyridin-3-ylmethyl)-amino]-ethyl}-1-ethyl-3,3,5-trimethyl-1,5-dihydro-benzo[b][1,4]diazepine-2,4-dione

EXAMPLE 228

7-{2-[[2-(2,7-Dimethyl-4-oxo-4H-furo[3,2-c]pyridin-5-yl)-ethyl]-(3-methyl-pyridin-2-ylmethyl)-amino]-ethyl}-1-ethyl-3,3,5-trimethyl-1,5-dihydro-benzo[b][1,4]diazepine-2,4-dione

EXAMPLE 229

N-[2-({[2-(2,7-Dimethyl-4-oxo-4H-furo[3,2-c]pyridin-5-yl)-ethyl]-[2-(1-ethyl-3,3,5-trimethyl-2,4-dioxo-2,3,4,5-tetrahydro-1H-benzo[b][1,4]diazepin-7-yl)-ethyl]-amino}-methyl)-phenyl]-methanesulfonamide

EXAMPLE 230

7-{2-[[2-(2,7-Dimethyl-4-oxo-4H-furo[3,2-c]pyridin-5-yl)-ethyl]-(2,5-dimethyl-2H-pyrazol-3-ylmethyl)-amino]-ethyl}-1-ethyl-3,3,5-trimethyl-1,5-dihydro-benzo[b][1,4]diazepine-2,4-dione

EXAMPLE 231

1-Ethyl-3,3,5-trimethyl-7-(3-{(4-methyl-thiazol-2-ylmethyl)-[2-(4-oxo-4H-furo[3,2-c]pyridin-5-yl)-ethyl]-amino}-propyl)-1,5-dihydro-benzo[b][1,4]diazepine-2,4-dione

EXAMPLE 232

1-Ethyl-3,3,5-trimethyl-7-(3-{(4-methyl-thiazol-5-ylmethyl)-[2-(4-oxo-4H-furo[3,2-c]pyridin-5-yl)-ethyl]-amino}-propyl)-1,5-dihydro-benzo[b][1,4]diazepine-2,4-dione

EXAMPLE 233

1-Ethyl-3,3,5-trimethyl-7-(3-{(2-methyl-pyridin-3-ylmethyl)-[2-(4-oxo-4H-furo[3,2-c]pyridin-5-yl)-ethyl]-amino}-propyl)-1,5-dihydro-benzo[b][1,4]diazepine-2,4-dione

EXAMPLE 234

1-Ethyl-3,3,5-trimethyl-7-(3-{(4-methyl-pyridin-3-ylmethyl)-[2-(4-oxo-4H-furo[3,2-c]pyridin-5-yl)-ethyl]-amino}-propyl)-1,5-dihydro-benzo[b][1,4]diazepine-2,4-dione

EXAMPLE 235

1-Ethyl-3,3,5-trimethyl-7-(3-{(3-methyl-pyridin-2-ylmethyl)-[2-(4-oxo-4H-furo[3,2-c]pyridin-5-yl)-ethyl]-amino}-propyl)-1,5-dihydro-benzo[b][1,4]diazepine-2,4-dione

EXAMPLE 236

N-[2-({[3-(1-Ethyl-3,3,5-trimethyl-2,4-dioxo-2,3,4,5-tetrahydro-1H-benzo[b][1,4]diazepin-7-yl)-propyl]-[2-(4-oxo-4H-furo[3,2-c]pyridin-5-yl)-ethyl]-amino}-methyl)-phenyl]-methanesulfonamide

EXAMPLE 237

7-(3-{(2,5-Dimethyl-2H-pyrazol-3-ylmethyl)-[2-(4-oxo-4H-furo[3,2-c]pyridin-5-yl)-ethyl]-amino}-propyl)-1-ethyl-3,3,5-trimethyl-1,5-dihydro-benzo[b][1,4]diazepine-2,4-dione

EXAMPLE 238

1-Ethyl-3,3,5-trimethyl-7-{3-[[2-(2-methyl-4-oxo-4H-furo[3,2-c]pyridin-5-yl)-ethyl]-(4-methyl-thiazol-2-ylmethyl)-amino]-propyl}-1,5-dihydro-benzo[b][1,4]diazepine-2,4-dione

EXAMPLE 239

1-Ethyl-3,3,5-trimethyl-7-{3-[[2-(2-methyl-4-oxo-4H-furo[3,2-c]pyridin-5-yl)-ethyl]-(4-methyl-thiazol-5-ylmethyl)-amino]-propyl}-1,5-dihydro-benzo[b][1,4]diazepine-2,4-dione

EXAMPLE 240

1-Ethyl-3,3,5-trimethyl-7-{3-[[2-(2-methyl-4-oxo-4H-furo[3,2-c]pyridin-5-yl)-ethyl]-(2-methyl-pyridin-3-ylmethyl)-amino]-propyl}-1,5-dihydro-benzo[b][1,4]diazepine-2,4-dione

EXAMPLE 241

1-Ethyl-3,3,5-trimethyl-7-{3-[[2-(2-methyl-4-oxo-4H-furo[3,2-c]pyridin-5-yl)-ethyl]-(4-methyl-pyridin-3-ylmethyl)-amino]-propyl}-1,5-dihydro-benzo[b][1,4]diazepine-2,4-dione

EXAMPLE 242

1-Ethyl-3,3,5-trimethyl-7-{3-[[2-(2-methyl-4-oxo-4H-furo[3,2-c]pyridin-5-yl)-ethyl]-(3-methyl-pyridin-2-ylmethyl)-amino]-propyl}-1,5-dihydro-benzo[b][1,4]diazepine-2,4-dione

EXAMPLE 243

7-{3-[(2,6-Dimethyl-pyridin-3-ylmethyl)-(2-pyridin-3-yl-ethyl)-amino]-propyl}-1-ethyl-3,3,5-trimethyl-1,5-dihydro-benzo[b][1,4]diazepine-2,4-dione

EXAMPLE 244

7-(3-{(2,6-Dimethyl-pyridin-3-ylmethyl)-[2-(2-methyl-4-oxo-4H-furo[3,2-c]pyridin-5-yl)-ethyl]-amino}-propyl)-1-ethyl-3,3,5-trimethyl-1,5-dihydro-benzo[b][1,4]diazepine-2,4-dione

EXAMPLE 245

N-[2-({[3-(1-Ethyl-3,3,5-trimethyl-2,4-dioxo-2,3,4,5-tetrahydro-1H-benzo[b][1,4]diazepin-7-yl)-propyl]-[2-(2-methyl-4-oxo-4H-furo[3,2-c]pyridin-5-yl)-ethyl]-amino}-methyl)-phenyl]-methanesulfonamide

EXAMPLE 246

7-(3-{(2,5-Dimethyl-2H-pyrazol-3-ylmethyl)-[2-(2-methyl-4-oxo-4H-furo[3,2-c]pyridin-5-yl)-ethyl]-amino}-propyl)-1-ethyl-3,3,5-trimethyl-1,5-dihydro-benzo[b][1,4]diazepine-2,4-dione

EXAMPLE 247

1-Ethyl-3,3,5-trimethyl-7-{3-[[2-(7-methyl-4-oxo-4H-furo[3,2-c]pyridin-5-yl)-ethyl]-(4-methyl-thiazol-2-ylmethyl)-amino]-propyl}-1,5-dihydro-benzo[b][1,4]diazepine-2,4-dione

EXAMPLE 248

1-Ethyl-3,3,5-trimethyl-7-{3-[[2-(7-methyl-4-oxo-4H-furo[3,2-c]pyridin-5-yl)-ethyl]-(4-methyl-thiazol-5-ylmethyl)-amino]-propyl}-1,5-dihydro-benzo[b][1,4]diazepine-2,4-dione

EXAMPLE 249

1-Ethyl-3,3,5-trimethyl-7-{3-[[2-(7-methyl-4-oxo-4H-furo[3,2-c]pyridin-5-yl)-ethyl]-(2-methyl-pyridin-3-ylmethyl)-amino]-propyl}-1,5-dihydro-benzo[b][1,4]diazepine-2,4-dione

EXAMPLE 250

1-Ethyl-3,3,5-trimethyl-7-{3-[[2-(7-methyl-4-oxo-4H-furo[3,2-c]pyridin-5-yl)-ethyl]-(4-methyl-pyridin-3-ylmethyl)-amino]-propyl}-1,5-dihydro-benzo[b][1,4]diazepine-2,4-dione

EXAMPLE 251

1-Ethyl-3,3,5-trimethyl-7-{3-[[2-(7-methyl-4-oxo-4H-furo[3,2-c]pyridin-5-yl)-ethyl]-(3-methyl-pyridin-2-ylmethyl)-amino]-propyl}-1,5-dihydro-benzo[b][1,4]diazepine-2,4-dione

EXAMPLE 252

N-[2-({[3-(1-Ethyl-3,3,5-trimethyl-2,4-dioxo-2,3,4,5-tetrahydro-1H-benzo[b][1,4]diazepin-7-yl)-propyl]-[2-(7-methyl-4-oxo-4H-furo[3,2-c]pyridin-5-yl)-ethyl]-amino}-methyl)-phenyl]-methanesulfonamide

EXAMPLE 253

7-(3-{(2,5-Dimethyl-2H-pyrazol-3-ylmethyl)-[2-(7-methyl-4-oxo-4H-furo[3,2-c]pyridin-5-yl)-ethyl]-amino}-propyl)-1-ethyl-3,3,5-trimethyl-1,5-dihydro-benzo[b][1,4]diazepine-2,4-dione

EXAMPLE 254

7-{3-[[2-(2,7-Dimethyl-4-oxo-4H-furo[3,2-c]pyridin-5-yl)-ethyl]-(4-methyl-thiazol-2-ylmethyl)-amino]-propyl}-1-ethyl-3,3,5-trimethyl-1,5-dihydro-benzo[b][1,4]diazepine-2,4-dione

EXAMPLE 255

7-{3-[[2-(2,7-Dimethyl-4-oxo-4H-furo[3,2-c]pyridin-5-yl)-ethyl]-(4-methyl-thiazol-5-ylmethyl)-amino]-propyl}-1-ethyl-3,3,5-trimethyl-1,5-dihydro-benzo[b][1,4]diazepine-2,4-dione

EXAMPLE 256

7-{3-[[2-(2,7-Dimethyl-4-oxo-4H-furo[3,2-c]pyridin-5-yl)-ethyl]-(2-methyl-pyridin-3-ylmethyl)-amino]-propyl}-1-ethyl-3,3,5-trimethyl-1,5-dihydro-benzo[b][1,4]diazepine-2,4-dione

EXAMPLE 257

7-{3-[[2-(2,7-Dimethyl-4-oxo-4H-furo[3,2-c]pyridin-5-yl)-ethyl]-(4-methyl-pyridin-3-ylmethyl)-amino]-propyl}-1-ethyl-3,3,5-trimethyl-1,5-dihydro-benzo[b][1,4]diazepine-2,4-dione

EXAMPLE 258

7-{3-[[2-(2,7-Dimethyl-4-oxo-4H-furo[3,2-c]pyridin-5-yl)-ethyl]-(3-methyl-pyridin-2-ylmethyl)-amino]-propyl}-1-ethyl-3,3,5-trimethyl-1,5-dihydro-benzo[b][1,4]diazepine-2,4-dione

EXAMPLE 259

N-[2-({[2-(2,7-Dimethyl-4-oxo-4H-furo[3,2-c]pyridin-5-yl)-ethyl]-[3-(1-ethyl-3,3,5-trimethyl-2,4-dioxo-2,3,4,5-tetrahydro-1H-benzo[b][1,4]diazepin-7-yl)-propyl]-amino}-methyl)-phenyl]-methanesulfonamide

EXAMPLE 260

7-{3-[[2-(2,7-Dimethyl-4-oxo-4H-furo[3,2-c]pyridin-5-yl)-ethyl]-(2,5-dimethyl-2H-pyrazol-3-ylmethyl)-amino]-propyl}-1-ethyl-3,3,5-trimethyl-1,5-dihydro-benzo[b][1,4]diazepine-2,4-dione

EXAMPLE 261

1-Ethyl-3,3,5-trimethyl-7-(3-{(2-methyl-pyridin-3-ylmethyl)-[2-(7-oxo-7H-thieno[2,3-c]pyridin-6-yl)-ethyl]-amino}-propyl)-1,5-dihydro-benzo[b][1,4]diazepine-2,4-dione

EXAMPLE 262

1-Ethyl-3,3,5-trimethyl-7-{[[2-(4-methyl-7-oxo-7H-thieno[2,3-c]pyridin-6-yl)-ethyl]-(2-methyl-pyridin-3-ylmethyl)-amino]-methyl}-1,5-dihydro-benzo[b][1,4]diazepine-2,4-dione

EXAMPLE 263

1-Ethyl-3,3,5-trimethyl-7-{[[2-(4-methyl-7-oxo-7H-thieno[2,3-c]pyridin-6-yl)-ethyl]-(4-methyl-pyridin-3-ylmethyl)-amino]-methyl}-1,5-dihydro-benzo[b][1,4]diazepine-2,4-dione

EXAMPLE 264

1-Ethyl-3,3,5-trimethyl-7-(3-{(2-methyl-pyridin-3-ylmethyl)-[2-(4-oxo-4H-thieno[3,2-c]pyridin-5-yl)-ethyl]-amino}-propyl)-1,5-dihydro-benzo[b][1,4]diazepine-2,4-dione

EXAMPLE 265

1-Ethyl-3,3,5-trimethyl-7-{[[2-(7-methyl-4-oxo-4H-thieno[3,2-c]pyridin-5-yl)-ethyl]-(2-methyl-pyridin-3-ylmethyl)-amino]-methyl}-1,5-dihydro-benzo[b][1,4]diazepine-2,4-dione

EXAMPLE 266

1-Ethyl-3,3,5-trimethyl-7-{[[2-(7-methyl-4-oxo-4H-thieno[3,2-c]pyridin-5-yl)-ethyl]-(4-methyl-pyridin-3-ylmethyl)-amino]-methyl}-1,5-dihydro-benzo[b][1,4]diazepine-2,4-dione

EXAMPLE 267

1-Ethyl-3,3,5-trimethyl-7-({oxazol-5-ylmethyl-[2-(1-oxo-2H-isoquinolin-2-yl)-ethyl]-amino}-methyl)-1,5-dihydro-benzo[b][1,4]diazepine-2,4-dione

EXAMPLE 268

1-Ethyl-3,3,5-trimethyl-7-({[2-(1-oxo-2H-isoquinolin-2-yl)-ethyl]-thiazol-2-ylmethyl-amino}-methyl)-1,5-dihydro-benzo[b][1,4]diazepine-2,4-dione

EXAMPLE 269

1-Ethyl-3,3,5-trimethyl-7-({[2-(1-oxo-2H-isoquinolin-2-yl)-ethyl]-thiazol-5-ylmethyl-amino}-methyl)-1,5-dihydro-benzo[b][1,4]diazepine-2,4-dione

EXAMPLE 270

1-Ethyl-3,3,5-trimethyl-7-({[2-(1-oxo-2H-isoquinolin-2-yl)-ethyl]-thiazol-4-ylmethyl-amino}-methyl)-1,5-dihydro-benzo[b][1,4]diazepine-2,4-dione

EXAMPLE 271

1-Ethyl-3,3,5-trimethyl-7-({(4-methyl-thiazol-2-ylmethyl)-[2-(1-oxo-2H-isoquinolin-2-yl)-ethyl]-amino}-methyl)-1,5-dihydro-benzo[b][1,4]diazepine-2,4-dione

EXAMPLE 272

1-Ethyl-3,3,5-trimethyl-7-({(4-methyl-thiazol-5-ylmethyl)-[2-(1-oxo-2H-isoquinolin-2-yl)-ethyl]-amino}-methyl)-1,5-dihydro-benzo[b][1,4]diazepine-2,4-dione

EXAMPLE 273

7-({(4,5-Dimethyl-thiazol-2-ylmethyl)-[2-(1-oxo-2H-isoquinolin-2-yl)-ethyl]-amino}-methyl)-1-ethyl-3,3,5-trimethyl-1,5-dihydro-benzo[b][1,4]diazepine-2,4-dione

EXAMPLE 274

7-({(2,4-Dimethyl-thiazol-5-ylmethyl)-[2-(1-oxo-2H-isoquinolin-2-yl)-ethyl]-amino}-methyl)-1-ethyl-3,3,5-trimethyl-1,5-dihydro-benzo[b][1,4]diazepine-2,4-dione

EXAMPLE 275

1-Ethyl-3,3,5-trimethyl-7-({[2-(1-oxo-2H-isoquinolin-2-yl)-ethyl]-pyridin-4-ylmethyl-amino}-methyl)-1,5-dihydro-benzo[b][1,4]diazepine-2,4-dione

EXAMPLE 276

1-Ethyl-3,3,5-trimethyl-7-({(2-methyl-pyridin-4-ylmethyl)-[2-(1-oxo-2H-isoquinolin-2-yl)-ethyl]-amino}-methyl)-1,5-dihydro-benzo[b][1,4]diazepine-2,4-dione

EXAMPLE 277

1-Ethyl-7-({(3-fluoro-pyridin-4-ylmethyl)-[2-(1-oxo-2H-isoquinolin-2-yl)-ethyl]-amino}-methyl)-3,3,5-trimethyl-1,5-dihydro-benzo[b][1,4]diazepine-2,4-dione

EXAMPLE 278

1-Ethyl-3,3,5-trimethyl-7-({(3-methyl-pyridin-4-ylmethyl)-[2-(1-oxo-2H-isoquinolin-2-yl)-ethyl]-amino}-methyl)-1,5-dihydro-benzo[b][1,4]diazepine-2,4-dione

EXAMPLE 279

1-Ethyl-3,3,5-trimethyl-7-({[2-(1-oxo-2H-isoquinolin-2-yl)-ethyl]-pyridin-3-ylmethyl-amino}-methyl)-1,5-dihydro-benzo[b][1,4]diazepine-2,4-dione

EXAMPLE 280

1-Ethyl-3,3,5-trimethyl-7-({(4-methyl-pyridin-3-ylmethyl)-[2-(1-oxo-2H-isoquinolin-2-yl)-ethyl]-amino}-methyl)-1,5-dihydro-benzo[b][1,4]diazepine-2,4-dione

EXAMPLE 281

1-Ethyl-3,3,5-trimethyl-7-{[[2-(1-oxo-2H-isoquinolin-2-yl)-ethyl]-(4-trifluoromethyl-pyridin-3-ylmethyl)-amino]-methyl}-1,5-dihydro-benzo[b][1,4]diazepine-2,4-dione

EXAMPLE 282

1-Ethyl-7-({(2-methoxy-pyridin-3-ylmethyl)-[2-(1-oxo-2H-isoquinolin-2-yl)-ethyl]-amino}-methyl)-3,3,5-trimethyl-1,5-dihydro-benzo[b][1,4]diazepine-2,4-dione

EXAMPLE 283

7-({(2,6-Dimethyl-pyridin-3-ylmethyl)-[2-(1-oxo-2H-isoquinolin-2-yl)-ethyl]-amino}-methyl)-1-ethyl-3,3,5-trimethyl-1,5-dihydro-benzo[b][1,4]diazepine-2,4-dione

EXAMPLE 284

N-[2-({(1-Ethyl-3,3,5-trimethyl-2,4-dioxo-2,3,4,5-tetrahydro-1H-benzo[b][1,4]diazepin-7-ylmethyl)-[2-(1-oxo-2H-isoquinolin-2-yl)-ethyl]-amino}-methyl)-phenyl]-methanesulfonamide

EXAMPLE 285

1-Ethyl-7-({(3-hydroxybenzyl)-[2-(1-oxo-2H-isoquinolin-2-yl)ethyl]amino}methyl)-3,3,5-trimethyl-1,5-dihydrobenzo[b][1,4]diazepine-2,4-dione

EXAMPLE 286

1-Ethyl-7-({furan-2-ylmethyl-[2-(1-oxo-2H-isoquinolin-2-yl)-ethyl]-amino}-methyl)-3,3,5-trimethyl-1,5-dihydro-benzo[b][1,4]diazepine-2,4-dione

EXAMPLE 287

1-Ethyl-7-({furan-3-ylmethyl-[2-(1-oxo-2H-isoquinolin-2-yl)-ethyl]-amino}-methyl)-3,3,5-trimethyl-1,5-dihydro-benzo[b][1,4]diazepine-2,4-dione

EXAMPLE 288

1-Ethyl-3,3,5-trimethyl-7-({(5-methyl-furan-2-ylmethyl)-[2-(1-oxo-2H-isoquinolin-2-yl)-ethyl]-amino}-methyl)-1,5-dihydro-benzo[b][1,4]diazepine-2,4-dione

EXAMPLE 289

1-Ethyl-3,3,5-trimethyl-7-({(2-methyl-furan-3-ylmethyl)-[2-(2-oxo-3,4-divinyl-2H-pyridin-1-yl)-ethyl]-amino}-methyl)-1,5-dihydro-benzo[b][1,4]diazepine-2,4-dione

EXAMPLE 290

7-({(4,5-Dimethyl-furan-2-ylmethyl)-[2-(1-oxo-2H-isoquinolin-2-yl)-ethyl]-amino}-methyl)-1-ethyl-3,3,5-trimethyl-1,5-dihydro-benzo[b][1,4]diazepine-2,4-dione

EXAMPLE 291

1-Ethyl-3,3,5-trimethyl-7-{[[2-(1-oxo-2H-isoquinolin-2-yl)-ethyl]-(5-trifluoromethyl-furan-2-ylmethyl)-amino]-methyl}-1,5-dihydro-benzo[b][1,4]diazepine-2,4-dione

EXAMPLE 292

1-Ethyl-3,3,5-trimethyl-7-({[2-(1-oxo-2H-isoquinolin-2-yl)-ethyl]-thiophen-2-ylmethyl-amino}-methyl)-1,5-dihydro-benzo[b][1,4]diazepine-2,4-dione

EXAMPLE 293

1-Ethyl-3,3,5-trimethyl-7-({(3-methyl-thiophen-2-ylmethyl)-[2-(1-oxo-2H-isoquinolin-2-yl)-ethyl]-amino}-methyl)-1,5-dihydro-benzo[b][1,4]diazepine-2,4-dione

EXAMPLE 294

7-({(4,5-Dimethyl-thiophen-2-ylmethyl)-[2-(1-oxo-2H-isoquinolin-2-yl)-ethyl]-amino}-methyl)-1-ethyl-3,3,5-trimethyl-1,5-dihydro-benzo[b][1,4]diazepine-2,4-dione

EXAMPLE 295

7-({(2,5-Dimethyl-2H-pyrazol-3-ylmethyl)-[2-(1-oxo-2H-isoquinolin-2-yl)-ethyl]-amino}-methyl)-1-ethyl-3,3,5-trimethyl-1,5-dihydro-benzo[b][1,4]diazepine-2,4-dione

EXAMPLE 296

1-Ethyl-3,3,5-trimethyl-7-(2-{(4-methyl-thiazol-5-ylmethyl)-[2-(1-oxo-2H-isoquinolin-2-yl)-ethyl]-amino}-ethyl)-1,5-dihydro-benzo[b][1,4]diazepine-2,4-dione

EXAMPLE 297

1-Ethyl-3,3,5-trimethyl-7-(2-{(4-methyl-pyridin-3-ylmethyl)-[2-(1-oxo-2H-isoquinolin-2-yl)-ethyl]-amino}-ethyl)-1,5-dihydro-benzo[b][1,4]diazepine-2,4-dione

EXAMPLE 298

1-Ethyl-3,3,5-trimethyl-7-(2-{(2-methyl-pyridin-3-ylmethyl)-[2-(1-oxo-2H-isoquinolin-2-yl)-ethyl]-amino}-ethyl)-1,5-dihydro-benzo[b][1,4]diazepine-2,4-dione

EXAMPLE 299

7-(2-{(2,6-Dimethyl-pyridin-3-ylmethyl)-[2-(1-oxo-2H-isoquinolin-2-yl)-ethyl]-amino}-ethyl)-1-ethyl-3,3,5-trimethyl-1,5-dihydro-benzo[b][1,4]diazepine-2,4-dione

EXAMPLE 300

7-(2-{(2,5-Dimethyl-2H-pyrazol-3-ylmethyl)-[2-(1-oxo-2H-isoquinolin-2-yl)-ethyl]-amino}-ethyl)-1-ethyl-3,3,5-trimethyl-1,5-dihydro-benzo[b][1,4]diazepine-2,4-dione

EXAMPLE 301

1-Ethyl-3,3,5-trimethyl-7-(3-{(4-methyl-thiazol-5-ylmethyl)-[2-(1-oxo-2H-isoquinolin-2-yl)-ethyl]-amino}-propyl)-1,5-dihydro-benzo[b][1,4]diazepine-2,4-dione

EXAMPLE 302

1-Ethyl-3,3,5-trimethyl-7-(3-{(4-methyl-pyridin-3-ylmethyl)-[2-(1-oxo-2H-isoquinolin-2-yl)-ethyl]-amino}-propyl)-1,5-dihydro-benzo[b][1,4]diazepine-2,4-dione

EXAMPLE 303

1-Ethyl-3,3,5-trimethyl-7-(3-{(2-methyl-pyridin-3-ylmethyl)-[2-(1-oxo-2H-isoquinolin-2-yl)-ethyl]-amino}-propyl)-1,5-dihydro-benzo[b][1,4]diazepine-2,4-dione

EXAMPLE 304

7-(3-{(2,6-Dimethyl-pyridin-3-ylmethyl)-[2-(1-oxo-2H-isoquinolin-2-yl)-ethyl]-amino}-propyl)-1-ethyl-3,3,5-trimethyl-1,5-dihydro-benzo[b][1,4]diazepine-2,4-dione

EXAMPLE 305

7-(3-{(2,5-Dimethyl-2H-pyrazol-3-ylmethyl)-[2-(1-oxo-2H-isoquinolin-2-yl)-ethyl]-amino}-propyl)-1-ethyl-3,3,5-trimethyl-1,5-dihydro-benzo[b][1,4]diazepine-2,4-dione

EXAMPLE 306

1-Ethyl-3,3,5-trimethyl-7-({(2-methyl-pyridin-3-ylmethyl)-[2-(2-oxo-2H-quinolin-1-yl)-ethyl]-amino}-methyl)-1,5-dihydro-benzo[b][1,4]diazepine-2,4-dione

EXAMPLE 307

1-Ethyl-3,3,5-trimethyl-7-({(4-methyl-pyridin-3-ylmethyl)-[2-(2-oxo-2H-quinolin-1-yl)-ethyl]-amino}-methyl)-1,5-dihydro-benzo[b][1,4]diazepine-2,4-dione

EXAMPLE 308

7-({(2,6-Dimethyl-pyridin-3-ylmethyl)-[2-(2-oxo-2H-quinolin-1-yl)-ethyl]-amino}-methyl)-1-ethyl-3,3,5-trimethyl-1,5-dihydro-benzo[b][1,4]diazepine-2,4-dione

EXAMPLE 309

7-{[N-(4-Chloropyridin-3-ylmethyl)-N-(2-pyridin-3-ylethyl)amino]methyl}-1-ethyl-3,3,5-trimethyl-1,5-dihydro-benzo[b][1,4]diazepine-2,4-dione trihydrochloride The synthesis of the title compound was performed in the same manner as in EXAMPLE 4 using appropriate starting materials.
White Powder
mp: 200-205° C. (dec.)

EXAMPLE 310

7-({N-(2,5-Dimethyl-2H-pyrazol-3-ylmethyl)-N-[2-(4-oxo-4H-furo[3,2-c]pyridin-5-yl)ethyl]amino}methyl)-1-ethyl-3,3,5-trimethyl-1,5-dihydrobenzo[b][1,4]diazepine-2,4-dione The synthesis of the title compound was performed in the same manner as in EXAMPLE 30 using appropriate starting materials.
White Powder
mp: 161-165° C.

EXAMPLE 311

7-({N-(2,5-Dimethyl-2H-pyrazol-3-ylmethyl)-N-[2-(4-oxo-4H-thieno[3,2-c]pyridin-5-yl)ethyl]amino}methyl)-1-ethyl-3,3,5-trimethyl-1,5-dihydrobenzo[b][1,4]diazepine-2,4-dione The synthesis of the title compound was performed in the same manner as in EXAMPLE 30 using appropriate starting materials.
White Powder
mp: 144-146° C.

EXAMPLE 312

7-({N-(2,5-Dimethyl-2H-pyrazol-3-ylmethyl)-N-[2-(7-oxo-7H-thieno[2,3-c]pyridin-6-yl)ethyl]amino}methyl)-1-ethyl-3,3,5-trimethyl-1,5-dihydrobenzo[b][1,4]diazepine-2,4-dione The synthesis of the title compound was performed in the same manner as in EXAMPLE 30 using appropriate starting materials.
White Powder
mp: 127-128° C.

EXAMPLE 313

7-({N-(2,5-Dimethyl-2H-pyrazol-3-ylmethyl)-N-[2-(7-methyl-4-oxo-4H-thieno[3,2-c]pyridin-5-yl)ethyl]amino}methyl)-1-ethyl-3,3,5-trimethyl-1,5-dihydrobenzo[b][1,4]diazepine-2,4-dione The synthesis of the title compound was performed in the same manner as in EXAMPLE 30 using appropriate starting materials.
White Powder
mp: 197-199° C.

EXAMPLE 314

7-({N-(2,5-Dimethyl-2H-pyrazol-3-ylmethyl)-N-[2-(4-methyl-7-oxo-7H-thieno[2,3-c]pyridin-6-yl)ethyl]amino}methyl)-1-ethyl-3,3,5-trimethyl-1,5-dihydrobenzo[b][1,4]diazepine-2,4-dione The synthesis of the title compound was performed in the same manner as in EXAMPLE 30 using appropriate starting materials.
White Powder
mp: 190-193° C.

EXAMPLE 315

1-Ethyl-3,3,5-trimethyl-7-{[N-(4-methylthiazol-2-ylmethyl)-N-(2-pyridin-3-ylethyl)amino]methyl}-1,5-dihydrobenzo[b][1,4]diazepine-2,4-dione dihydrochloride The synthesis of the title compound was performed in the same manner as in EXAMPLE 4 using appropriate starting materials.
White Amorphous
$^1$H NMR (D$_2$O), δppm: 0.75 (3H, s), 1.10 (3H, t, J=7.2 Hz), 1.42 (3H, s), 2.39 (3H, s), 3.25-3.36 (4H, m), 3.37 (3H, s), 3.73-3.87 (1H, m), 4.07-4.22 (3H, m), 4.41 (2H, s), 7.18 (1H, d, J=1.0 Hz), 7.32-7.38 (1H, m), 7.38-7.43 (1H, m), 7.49 (1H, d, J=8.3 Hz), 7.99 (1H, dd, J=6.0, 8.0 Hz), 8.44 (1H, d, J=8.3 Hz), 8.66-8.73 (2H, m)

EXAMPLE 316

1-Ethyl-7-({N-(2-methoxymethylpyridin-3-ylmethyl)-N-[2-(4-oxo-4H-furo[3,2-c]pyridin-5-yl)ethyl]amino}methyl)-3,3,5-trimethyl-1,5-dihydrobenzo[b][1,4]diazepine-2,4-dione The synthesis of the title compound was performed in the same manner as in EXAMPLE 30 using appropriate starting materials.
White Powder
mp: 123-125° C.

EXAMPLE 317

1-Ethyl-7-({N-(2-methoxymethylpyridin-3-ylmethyl)-N-[2-(2-methyl-4-oxo-4H-furo[3,2-c]pyridin-5-yl)ethyl]amino}methyl)-3,3,5-trimethyl-1,5-dihydrobenzo[b][1,4]diazepine-2,4-dione The synthesis of the title compound was performed in the same manner as in EXAMPLE 30 using appropriate starting materials.
White Powder
mp: 127-129° C.

EXAMPLE 318

1-Ethyl-7-({N-(2-methoxymethylpyridin-3-ylmethyl)-N-[2-(7-methyl-4-oxo-4H-furo[3,2-c]pyridin-5-yl)ethyl]amino}methyl)-3,3,5-trimethyl-1,5-dihydrobenzo[b][1,4]diazepine-2,4-dione The synthesis of the title compound was performed in the same manner as in EXAMPLE 30 using appropriate starting materials.
White Powder
mp: 104-111° C.

EXAMPLE 319

1-Ethyl-7-({N-(2-methoxymethylpyridin-3-ylmethyl)-N-[2-(7-methyl-4-oxo-4H-furo[3,2-c]pyridin-5-yl)ethyl]amino}methyl)-3,3,5-trimethyl-1,5-dihydro-benzo[b][1,4]diazepine-2,4-dione dihydrochloride 4 M HCl/AcOEt (90 μl) was added to an ethyl acetate solution (1 ml) of 1-ethyl-7-({(2-methoxymethylpyridin-3-ylmethyl)-[2-(7-methyl-4-oxo-4H-furo[3,2-c]pyridin-5-yl)ethyl]amino}methyl)-3,3,5-trimethyl-1,5-dihydrobenzo[b][1,4]diazepine-2,4-dione (26 mg) and stirred for 5 minutes at room temperature. The resulting precipitate was collected and washed with ether to give the title compound as a white powder (14 mg).
$^1$H NMR (DMSO-d$_6$), δ ppm: 0.75 (3H, s), 1.05 (3H, t, J=7.1 Hz), 1.35 (3H, s), 2.16 (3H, s), 3.27-3.33 (8H, m), 3.70-4.40 (6H, m), 4.52 (2H, br), 4.65 (2H, br), 6.93 (1H, s), 7.28-7.48 (4H, m), 7.72-7.84 (1H, m), 7.97 (1H, s), 8.35 (1H, br), 8.53-8.65 (1H, m).

EXAMPLE 320

1-Ethyl-3,3,5-trimethyl-7-({N-(2-methylpyridin-3-ylmethyl)-N-[2-(4-oxo-2-trifluoromethyl-4H-furo[3,2-c]pyridin-5-yl)ethyl]amino}methyl)-1,5-dihydrobenzo[b][1,4]diazepine-2,4-dione The synthesis of the title compound was performed in the same manner as in EXAMPLE 30 using appropriate starting materials.
White Powder
mp: 132-134° C.

EXAMPLE 321

1-Ethyl-3,3,5-trimethyl-7-({N-(3-methyl-3H-imidazol-4-ylmethyl)-N-[2-(2-methyl-4-oxo-4H-furo[3,2-c]pyridin-5-yl)ethyl]amino}methyl)-1,5-dihydrobenzo[b][1,4]diazepine-2,4-dione The synthesis of the title compound was performed in the same manner as in EXAMPLE 30 using appropriate starting materials.
White Powder
mp: 106-108° C.

EXAMPLE 322

1-Ethyl-3,3,5-trimethyl-7-({N-(3-methyl-3H-imidazol-4-ylmethyl)-N-[2-(7-methyl-4-oxo-4H-furo[3,2-c]pyridin-5-yl)ethyl]amino}methyl)-1,5-dihydrobenzo[b][1,4]diazepine-2,4-dione The synthesis of the title compound was performed in the same manner as in EXAMPLE 30 using appropriate starting materials.
White Powder
mp: 100-105° C.

EXAMPLE 323

1-Ethyl-7-({N-[2-(2-methoxymethyl-4-oxo-4H-furo[3,2-c]pyridin-5-yl)ethyl]-N-(2-methylpyridin-3-ylmethyl)amino}methyl)-3,3,5-trimethyl-1,5-dihydrobenzo[b][1,4]diazepine-2,4-dione The synthesis of the title compound was performed in the same manner as in EXAMPLE 30 using appropriate starting materials.
Ivory Powder
mp: 123-126° C.

EXAMPLE 324

1-Ethyl-7-({N-[2-(2-methoxymethyl-4-oxo-4H-furo[3,2-c]pyridin-5-yl)ethyl]-N-(4-methylpyridin-3-ylmethyl)amino}methyl)-3,3,5-trimethyl-1,5-dihydrobenzo[b][1,4]diazepine-2,4-dione dihydrochloride The synthesis of the title compound was performed in the same manner as in EXAMPLE 4 using appropriate starting materials.
Pale Yellow Powder
$^1$H NMR (DMSO-d$_6$), δppm: 0.69 (3H, s), 1.01 (3H, t, J=7.1 HZ), 1.33 (3H, s), 2.22 (3H, s), 2.80 (2H, s), 3.27 (3H, s), 3.30 (3H, s), 3.61-4.05 (6H, m), 4.12 (2H, br), 4.48 (2H, s), 6.63 (1H, d, J=7.4 Hz), 6.78 (1H, s), 7.22 (1H, br), 7.32-7.33 (2H, m), 7.54 (1H, d, J=7.0 Hz), 7.61 (1H, d, J=5.7 Hz), 8.61 (1H, d, J=5.7 Hz), 8.63 (1H, s).

EXAMPLE 325

7-({N-(2,5-Dimethyl-2H-pyrazol-3-ylmethyl)-N-[2-(2-methoxymethyl-4-oxo-4H-furo[3,2-c]pyridin-5-yl)ethyl]amino}methyl)-1-ethyl-3,3,5-trimethyl-1,5-dihydrobenzo[b][1,4]diazepine-2,4-dione dihydrochloride The synthesis of the title compound was performed in the same manner as in EXAMPLE 4 using appropriate starting materials.
Ivory Powder
$^1$H NMR (DMSO-d$_6$), δppm: 0.69 (3H, s), 1.03 (3H, t, J=7.1 Hz), 1.32 (3H, s), 2.04 (3H, s), 2.71 (2H, br), 3.27 (3H, s), 3.30 (3H, br), 3.45-4.00 (6H, m), 3.85 (3H, s), 4.39-4.63 (4H, m), 6.44 (1H, br), 6.61-7.02 (2H, m), 7.05-7.95 (4H, m).

EXAMPLE 326

N-(1-Ethyl-3,3,5-trimethyl-2,4-dioxo-2,3,4,5-tetrahydro-1H-benzo[b][1,4]diazepin-7-ylmethyl)-2-phenyl-N-(2-pyridin-3-ylethyl)acetamide hydrochloride The synthesis of the title compound was performed in the same manner as in EXAMPLE 40 using appropriate starting materials.
White Amorphous
$^1$H NMR (DMSO-d$_6$), δppm: 0.70 and 0.73 (3H, s), 0.95-1.13 (3H, m), 1.32 and 1.33 (3H, s), 2.91-3.03 (2H, m), 3.22 and 3.25 (3H, s), 3.50-3.82 (5H, m), 3.96-4.09(1H, m), 4.56-4.74 (2H, m), 7.04-7.34 (7H, m), 7.42-7.52 (1H, m), 7.78 (1H, bs), 8.19 (1H, bs), 8.65-8.77 (2H, m)

EXAMPLE 327

N-[2-({N'-(1-Ethyl-3,3,5-trimethyl-2,4-dioxo-2,3,4,5-tetrahydro-1H-benzo[b][1,4]diazepin-7-ylmethyl)-N'-[2-(2-methyl-4-oxo-4H-furo[3,2-c]pyridin-5-yl)ethyl]amino}methyl)phenyl]methanesulfonamide The synthesis of the title compound was performed in the same manner as in EXAMPLE 30 using appropriate starting materials.
White Powder
mp: 161-163° C.

EXAMPLE 328

7-({N-(2-Chloropyridin-3-ylmethyl)-N-[2-(2-methyl-4-oxo-4H-furo[3,2-c]pyridin-5-yl)ethyl]amino}methyl)-1-ethyl-3,3,5-trimethyl-1,5-dihydrobenzo[b][1,4]diazepine-2,4-dione The synthesis of the title compound was performed in the same manner as in EXAMPLE 30 using appropriate starting materials.
White Powder
mp: 158.7-160.8° C.

EXAMPLE 329

3-({N-(1-Ethyl-3,3,5-trimethyl-2,4-dioxo-2,3,4,5-tetrahydro-1H-benzo[b][1,4]diazepin-7-ylmethyl)-N-[2-(2-methyl-4-oxo-4H-furo[3,2-c]pyridin-5-yl)ethyl]amino}methyl)pyridine-2-carbonitrile 2-Chloro-3-({(1-ethyl-3,3,5-trimethyl-2,4-dioxo-2,3,4,5-tetrahydro-1H-benzo[b][1,4]diazepin-7-ylmethyl)-[2-(2-methyl-4-oxo-4H-furo[3,2-c]pyridin-5-yl)ethyl]amino}methyl)pyridine (0.3 g), zinc cyanide(120 mg), tris(dibenzylideneacetone)dipalladium(24 mg), 1,1'-bis(diphenylphosphino)ferrocene(14 mg), and zinc powder(3.4 mg) were added to DMF(3 ml), and the mixture was heated at 95° C. for 3 hours. The reaction liquid was cooled to room temperature. Water was added to the reaction mixture and subjected to celite filtration. Extraction with ethyl acetate was performed. The organic layer was dried over anhydrous magnesium sulfate, and concentrated under reduced pressure. The residue was purified by silica gel column chromatography (ethyl acetate: methanol=93:7). The purified product was condensed under reduced pressure, and the residue was recrystallized from ether to give the title compound(1.35 g) as a white powder.
mp: 113.5-117.5° C.

EXAMPLE 330

N-(1-Ethyl-3,3,5-trimethyl-2,4-dioxo-2,3,4,5-tetrahydro-1H-benzo[b][1,4]diazepin-7-ylmethyl)-2-(1-methyl-1H-indol-3-yl)-N-(2-pyridin-3-ylethyl)acetamide hydrochloride To a solution of 1-ethyl-3,3,5-trimethyl-7-[(2-pyridine 3-ylethylamino)methyl]-1,5-dihydrobenzo[b][1,4]diazepine-2,4-dione(0.5 g), 1-methyl-3-indoleacetic acid(0.27 g), and 1-hydroxybenzotriazole (HOBT) (0.24 g) in acetonitrile (10 ml), N-(3-dimethylaminopropyl)-N'-ethylcarbodiimide hydrochloride (WSC) (0.30 g) was added and stirred at room temperature for 3 days. The reaction mixture was concentrated under reduced pressure. Ethyl acetate and water were added to the residue and extracted with ethyl acetate. The organic layer was dried over anhydrous sodium sulfate and concentrated under reduced pressure. The residue thus obtained was purified by silica gel column chromatography (hexane:ethyl acetate=1:3→0:1). The purified product was condensed under reduced pressure. A 1N-hydrogen chloride in ethanol solution (1.1 ml) was added to a 2-propanol solution (5 ml) of the residue, and the liquid was stirred at room temperature, and concentrated under reduced pressure. Ethanol and ether were added to the residue. The precipitated insoluble matter was separated, washed with ether, and dried to give the title compound(0.26 g) as a pale orange white amorphous.

$^1$H NMR (DMSO-d$_6$), δppm: 0.65 and 0.69 (3H, s), 0.95-1.13 (3H, m), 1.31 and 1.32 (3H, s), 2.90-3.05 (2H, m), 3.06 and 3.14 (3H, s), 3.20-3.90 (5H, m), 3.70 and 3.73 (3H, s), 3.90-4.08 (1H, m), 4.55-4.79 (2H, m), 6.96 (1H, t, J=7.4 Hz), 7.05-7.24 (4H, m), 7.32-7.42 (2H, m), 7.43-7.55 (1H, m), 7.63-7.79 (1H, m), 8.13 (1H, bs), 8.57-8.72 (2H, m)

EXAMPLE 331

1-Ethyl-3,3,5-trimethyl-7-({N-[2-(2-methyl-4-oxo-4H-furo[3,2-c]pyridin-5-yl)ethyl]-N-(1-pyridin-3-ylethyl)amino}methyl)-1,5-dihydrobenzo[b][1,4]diazepine-2,4-dione The synthesis of the title compound was performed in the same manner as in EXAMPLE 30 using appropriate starting materials.
White Powder
mp: 128-132° C.

EXAMPLE 332

N-(1-Ethyl-3,3,5-trimethyl-2,4-dioxo-2,3,4,5-tetrahydro-1H-benzo[b][1,4]diazepin-7-ylmethyl)-2-phenyl-N-(2-pyridin-3-ylethyl)isobutyramide hydrochloride To a solution of 1-ethyl-3,3,5-trimethyl-7-{[N-(2-pyridin-3-ylethyl)amino]methyl}-1,5-dihydrobenzo[b][1,4]diazepine-2,4-dione(0.5 g), 2-Phenylisobutyric acid(0.24 g), and diisopropylethylamine(0.23 ml) in DMF(10 ml), 2-(7-aza-1H-benzotriazol-1-yl)-1,1,3,3-tetramethyluronium hexafluorophosphate (HATU) (0.50 g) was added and stirred at 40° C. for 10 hours. Water was added to the reaction mixture, and stirred for 1 hour, and extracted with ethyl acetate. The organic layer was dried over anhydrous sodium sulfate and concentrated under reduced pressure. The residue thus obtained was purified by silica gel column chromatography (hexane: ethyl acetate=1:1). The purified product was condensed under reduced pressure. A 1N-hydrogen chloride in ethanol solution was added to a 2-propanol solution (5 ml) of the residue, and the liquid was stirred at room temperature, and concentrated under reduced pressure. Ethanol and ether were added to the residue. The precipitated insoluble matter was separated, washed with ether, and dried to give the title compound(0.35 g) as a white amorphous.

$^1$H NMR (DMSO-d$_6$), δppm: 0.67 and 0.72 (3H, s), 0.90-1.20 (3H, m), 1.20-1.40(3H, m), 1.43 and 1.48 (6H, s), 2.30-2.50 (1H, m), 2.83-3.40 (5H, m), 3.40-4.30 (4H, m), 4.57-4.79 (1H, m), 6.76-7.03 (1H, m), 7.03-7.56 (8H, m), 7.56-8.80 (3H, m)

EXAMPLE 333

N-(1-Ethyl-3,3,5-trimethyl-2,4-dioxo-2,3,4,5-tetrahydro-1H-benzo[b][1,4]diazepin-7-ylmethyl)-3-phenyl-N-(2-pyridin-3-ylethyl)propionamide hydrochloride The synthesis of the title compound was performed in the same manner as in EXAMPLE 40 using appropriate starting materials.
White Amorphous
$^1$H NMR (DMSO-d$_6$), δppm: 0.70 and 0.72 (3H, s), 0.95-1.12 (3H, m), 1.33 (3H, s), 2.53-2.69 (2H, m), 2.69-2.86 (2H, m), 2.90-3.03 (2H, m), 3.25 and 3.28 (3H, s), 3.45-3.68 (2H, m), 3.69-3.81 (1H, m), 3.96-4.10 (1H, m), 4.53-4.69 (2H, m), 7.04-7.29 (7H, m), 7.43 and 7.45 (1H, d, J=4.9 Hz), 7.78-7.86 (1H, m), 8.10-8.27 (1H, m), 8.57-8.77 (2H, m)

EXAMPLE 334

N-(1-Ethyl-3,3,5-trimethyl-2,4-dioxo-2,3,4,5-tetrahydro-1H-benzo[b][1,4]diazepin-7-ylmethyl)-N-(2-pyridin-3-ylethyl)-2-quinolin-6-ylacetamide dihydrochloride The synthesis of the title compound was performed in the same manner as in EXAMPLE 332 using appropriate starting materials.
White Amorphous
$^1$H NMR (DMSO-d$_6$), δppm: 0.68 and 0.70 (3H, s), 1.00-1.08 (3H, m), 1.31 and 1.32 (3H, s), 3.03 (1H, t, J=7.0 Hz), 3.10-3.18 (1H, m), 3.23 and 3.26 (3H, s), 3.40-3.90 (2H, m), 3.95-4.13 (4H, m), 4.60-4.88 (2H, m), 7.18-7.29 (2H, m), 7.42-7.52 (1H, m), 7.66-8.04 (4H, m), 8.07-8.21 (1H, m), 8.28-8.45 (1H, m), 8.65-8.93 (3H, m), 9.06-9.16 (1H, m)

EXAMPLE 335

N-(1-Ethyl-3,3,5-trimethyl-2,4-dioxo-2,3,4,5-tetrahydro-1H-benzo[b][1,4]diazepin-7-ylmethyl)-2-(2-oxo-2,3-dihydrobenzoimidazol-1-yl)-N-(2-pyridin-3-ylethyl)acetamide hydrochloride The synthesis of the title compound was performed in the same manner as in EXAMPLE 332 using appropriate starting materials.
White Powder
$^1$H NMR (DMSO-d$_6$), δppm: 0.71 and 0.76 (3H, s), 1.00-1.13 (3H, m), 1.33 and 1.34 (3H, s), 2.98 (1H, t, J=7.2 Hz), 3.10-3.17 (1H, m), 3.29 and 3.33 (3H, s), 3.50-3.68 (1H, m), 3.68-3.84 (2H, m), 3.97-4.13 (1H, m), 4.55-4.72 (2H, m), 4.76-4.87 (2H, m), 6.63-7.05 (4H, m), 7.15-7.38 (2H, m) 7.41-7.60 (1H, m), 7.75-7.88 (1H, m), 8.17-8.38 (1H, m), 8.56-8.86 (2H, m), 10.84 and 10.89 (1H, s)

EXAMPLE 336

1-Ethyl-3,3,5-trimethyl-7-({N-[2-(2-methyl-4-oxo-4H-furo[3,2-c]pyridin-5-yl)ethyl]N-(pyridin-3-ylmethyl)amino}methyl)-1,5-dihydrobenzo[b][1,4]diazepine-2,4-dione The synthesis of the title compound was performed in the same manner as in EXAMPLE 30 using appropriate starting materials.
White Powder
mp: 124-127° C.

EXAMPLE 337

N-(1-Ethyl-3,3,5-trimethyl-2,4-dioxo-2,3,4,5-tetrahydro-1H-benzo[b][1,4]diazepin-7-ylmethyl)-2-(3-methyl-2-oxo-2,3-dihydrobenzoimidazol-1-yl)-N-(2-pyridin-3-ylethyl)acetamide hydrochloride N-(1-Ethyl-3,3,5-trimethyl-2,4-dioxo-2,3,4,5-tetrahydro-1H-benzo[b][1,4]diazepin-7-ylmethyl)-2-(2-oxo-2,3-dihydrobenzoimidazol-1-yl)-N-(2-pyridin-3-ylethyl)acetamide hydrochloride(0.26 g), cesium carbonate(0.43 g), and methyl iodide(0.04 ml) were added to DMF(5 ml), and the mixture was stirred at room temperature for 1 days. Water was added to the reaction mixture, and stirred for 1 hour, followed by extraction with ethyl acetate. The organic layer was condensed under reduced pressure, and the residue was purified by silica gel column chromatography (ethyl acetate: methanol=85:15). The purified product was condensed under reduced pressure. A 1N-hydrogen chloride in ethanol solution(0.44 ml) was added to a 2-propanol solution (5 ml) of the residue, and the liquid was stirred at room temperature, and concentrated under reduced pressure. Ethanol and ether were added to the residue. The precipitated insoluble matter was separated, washed with ether, and dried to give the title compound(0.20 g) as a white powder.

$^1$H NMR (DMSO-$d_6$), δppm: 0.71 and 0.76 (3H, s), 1.00-1.13 (3H, m), 1.33 and 1.34 (3H, s), 2.92-3.03 (1H, m), 3.10-3.25 (1H, m), 3.30 and 3.30 (3H, s), 3.30-3.50 (3H, m), 3.50-3.81 (3H, m), 3.97-4.14 (1H, m), 4.57-4.91 (4H, m), 6.74-7.11 (3H, m), 7.11-7.40 (3H, m), 7.46 and 7.57 (1H, d, J=8.3 Hz), 7.72-7.85 (1H, m), 8.15-8.37(1H, m), 8.63-8.86 (2H, m)

EXAMPLE 338

N-(1-Ethyl-3,3,5-trimethyl-2,4-dioxo-2,3,4,5-tetrahydro-1H-benzo[b][1,4]diazepin-7-ylmethyl)-N-[2-(2-methyl-4-oxo-4H-furo[3,2-c]pyridin-5-yl)ethyl]benzamide The synthesis of the title compound was performed in the same manner as in EXAMPLE 42 using appropriate starting materials.
White Powder
$^1$H NMR (CDCl3), δppm: 0.79 (3H, bs), 1.15-1.24 (3H, m), 1.52 and 1.54 (3H, s), 2.43 (3H, d, J=0.4 Hz), 3.33-3.42 (3H, m), 3.45-3.83 (3H, m), 3.83-5.04 (5H, m), 6.27-6.77 (2H, m), 6.80-7.14 (2H, m), 7.17-7.44 (7H, m)

EXAMPLE 339

N-(1-Ethyl-3,3,5-trimethyl-2,4-dioxo-2,3,4,5-tetrahydro-1H-benzo[b][1,4]diazepin-7-ylmethyl)-2-(4-methylindol-1-yl)-N-(2-pyridin-3-ylethyl)acetamide hydrochloride The synthesis of the title compound was performed in the same manner as in EXAMPLE 332 using appropriate starting materials.
White Powder
$^1$H NMR (DMSO-$d_6$), δppm: 0.71 and 0.77 (3H, s), 0.90-1.15 (3H, m), 1.33 and 1.35 (3H, s), 2.44 and 2.46 (3H, s), 2.89-3.13 (2H, m), 3.29 and 3.30 (3H, s), 3.58-3.65 (1H, m), 3.66-3.86 (2H, m), 3.96-4.14 (1H, m), 4.56-4.89 (2H, m), 5.10 and 5.20 (2H, s), 6.38-6.50 (1H, m), 6.77-7.03 (3H, m), 7.15-7.36 (3H, m), 7.46 and 7.57 (1H, d, J=8.3 Hz), 7.66-7.78 (1H, m), 8.09-8.23 (1H, m), 8.60-8.79 (2H, m)

EXAMPLE 340

7-({N-[2-(2,7-Dimethyl-4-oxo-4H-furo[3,2-c]pyridin-5-yl)ethyl]-N-(2-methoxymethylpyridin-3-ylmethyl)amino}methyl)-1-ethyl-3,3,5-trimethyl-1,5-dihydrobenzo[b][1,4]diazepine-2,4-dione The synthesis of the title compound was performed in the same manner as in EXAMPLE 30 using appropriate starting materials.
White Powder (Ether)
mp: 103-104° C.

EXAMPLE 341

1-Ethyl-7-({N-(2-methoxymethylpyridin-3-ylmethyl)-N-[2-(4-oxo-4H-thieno[3,2-c]pyridin-5-yl)ethyl]amino}methyl)-3,3,5-trimethyl-1,5-dihydrobenzo[b][1,4]diazepine-2,4-dione The synthesis of the title compound was performed in the same manner as in EXAMPLE 30 using appropriate starting materials.
White Powder
mp: 119-122° C.

EXAMPLE 342

1-Ethyl-3,3,5-trimethyl-7-({N-[2-(2-methyl-4-oxo-4H-furo[3,2-c]pyridin-5-yl)ethyl]-N-(5-methylthiazol-4-ylmethyl)amino}methyl)-1,5-dihydrobenzo[b][1,4]diazepine-2,4-dione The synthesis of the title compound was performed in the same manner as in EXAMPLE 30 using appropriate starting materials.
White Powder
mp: 144-145° C.

EXAMPLE 343

N-(1-Ethyl-3,3,5-trimethyl-2,4-dioxo-2,3,4,5-tetrahydro-1H-benzo[b][1,4]diazepin-7-ylmethyl)-2-(1-methyl-1H-indol-3-yl)-N-[2-(2-methyl-4-oxo-4H-furo[3,2-c]pyridin-5-yl)ethyl]acetamide The synthesis of the title compound was performed in the same manner as in EXAMPLE 330 using appropriate starting materials.
White Amorphous
$^1$H NMR (CDCl$_3$), δppm: 0.74 and 0.78 (3H, s), 1.15-1.24 (3H, m), 1.49 and 1.51 (3H, s), 2.41 (3H, d, J=0.6 Hz), 3.11 and 3.24 (3H, s), 3.60-3.94 (9H, m), 3.94-4.26 (2H, m), 4.33-4.78 (2H, m), 6.09-6.59 (2H, m), 6.77-6.90 (1H, m), 6.90-6.98 (1H, m), 7.03-7.37 (5H, m), 7.57 (1H, d, J=8.0 Hz), 7.66 (1H, d, J=8.0 Hz)

EXAMPLE 344

7-({N-(1,5-Dimethyl-1H-pyrazol-3-ylmethyl)-N-[2-(2-methyl-4-oxo-4H-furo[3,2-c]pyridin-5-yl)ethyl]amino}methyl)-1-ethyl-3,3,5-trimethyl-1,5-dihydrobenzo[b][1,4]diazepine-2,4-dione The synthesis of the title compound was performed in the same manner as in EXAMPLE 30 using appropriate starting materials.

EXAMPLE 345

N-(1-Ethyl-3,3,5-trimethyl-2,4-dioxo-2,3,4,5-tetrahydro-1H-benzo[b][1,4]diazepin-7-ylmethyl)-N-(2-pyridin-3-ylethyl)-2-quinolin-3-ylacetamide dihydrochloride The synthesis of the title compound was performed in the same manner as in EXAMPLE 332 using appropriate starting materials.
White Powder
mp: 189-194° C.

EXAMPLE 346

1-Ethyl-3,3,5-trimethyl-2,4-dioxo-2,3,4,5-tetrahydro-1H-benzo[b][1,4]diazepine-7-carboxylic acid-N-benzyl-N-(2-pyridin-3-yl-ethyl)amide The synthesis of the title compound was performed in the same manner as in EXAMPLE 330 using appropriate starting materials.
White Powder
mp: 181-182° C.

EXAMPLE 347

1-Ethyl-3,3,5-trimethyl-7-({N-(5-methyloxazol-4-ylmethyl)-N-[2-(2-methyl-4-oxo-4H-furo[3,2-c]pyridin-5-yl)ethyl]amino}methyl)-1,5-dihydrobenzo[b][1,4]diazepine-2,4-dione The synthesis of the title compound was performed in the same manner as in EXAMPLE 30 using appropriate starting materials.
White Powder
mp: 129.0-130.5° C.

EXAMPLE 348

1-Ethyl-3,3,5-trimethyl-2,4-dioxo-2,3,4,5-tetrahydro-1H-benzo[b][1,4]diazepine-7-carboxylic acid-N-(4-methoxybenzyl)-N-[2-(2-methyl-4-oxo-4H-furo[3,2-c]pyridin-5-yl)ethyl]amide The synthesis of the title compound was performed in the same manner as in EXAMPLE 330 using appropriate starting materials.
White Powder (Et$_2$O-EtOH)
mp: 151.1-155.1° C.

EXAMPLE 349

7-({N-[2-(2,7-Dimethyl-4-oxo-4H-furo[3,2-c]pyridin-5-yl)ethyl]-N-(1,5-dimethyl-1H-pyrazol-3-ylmethyl)amino}methyl)-1-ethyl-3,3,5-trimethyl-1,5-dihydro-benzo[b][1,4]diazepine-2,4-dione The synthesis of the title compound was performed in the same manner as in EXAMPLE 30 using appropriate starting materials.
White Powder
mp: 113-116° C.

EXAMPLE 350

N-(1-Ethyl-3,3,5-trimethyl-2,4-dioxo-2,3,4,5-tetrahydro-1H-benzo[b][1,4]diazepin-7-ylmethyl)-2-(2-methylbenzoimidazol-1-yl)-N-(2-pyridin-3-yl-ethyl)acetamide The synthesis of the title compound was performed in the same manner as in EXAMPLE 330 using appropriate starting materials.
White Amorphous
$^1$H NMR (CDCl$_3$), δppm: 0.82 and 0.87 (3H, s), 1.15-1.30 (3H, m), 1.53 and 1.55 (3H, s), 2.41 and 2.47 (3H, s), 2.87-3.01 (2H, m), 3.33 and 3.39 (3H, s), 3.60-3.94 (3H, m), 4.05-4.26 (1H, m), 4.50-4.87 (4H, m), 6.89 (1H, t, J=8.0 Hz), 6.98-7.60 (7H, m), 7.68 (1H, t, J=9.1 Hz), 8.44 (1H, s), 8.52 and 8.61 (1H, d, J=3.5 Hz)

EXAMPLE 351

1-Ethyl-3,3,5-trimethyl-7-({[2-(2-methyl-4-oxo-4H-furo[3,2-c]pyridin-5-yl)ethyl]-(3-methylpyridin-2-ylmethyl)amino}methyl)-1,5-dihydrobenzo[b][1,4]diazepine-2,4-dione The synthesis of the title compound was performed in the same manner as in EXAMPLE 30 using appropriate starting materials.
White Powder (AcOEt-Et$_2$O)
mp: 139-143° C.

EXAMPLE 352

1-Ethyl-7-({N-(2-methoxymethylpyridin-3-ylmethyl)-N-[2-(7-oxo-7H-thieno[2,3-c]pyridin-6-yl)ethyl]amino}methyl)-3,3,5-trimethyl-1,5-dihydrobenzo[b][1,4]diazepine-2,4-dione dihydrochloride The synthesis of the title compound was performed in the same manner as in EXAMPLE 4 using appropriate starting materials.
$^1$H NMR (DMSO-d$_6$), δppm: 0.69 (3H, s), 1.04 (3H, t, J=7.1 Hz), 1.31 (3H, s), 2.80-3.20 (2H, m), 3.29 (3H, s), 3.30 (3H, s), 3.39-3.45 (2H, m), 3.70-3.77 (1H, m), 3.92-4.04 (3H, m), 4.36 (2H, br), 4.74 (2H, br), 6.76 (1H, d, J=6.9 Hz), 7.30-7.40 (3H, m), 7.59 (1H, br), 7.83 (2H, br), 8.07 (1H, d, J=5.2 Hz), 8.65 (2H, br).

EXAMPLE 353

7-({N-(1,5-Dimethyl-1H-pyrazol-3-ylmethyl)-N-[2-(4-oxo-4H-furo[3,2-c]pyridin-5-yl)ethyl]amino}methyl)-1-ethyl-3,3,5-trimethyl-1,5-dihydrobenzo[b][1,4]diazepine-2,4-dione dihydrochloride The synthesis of the title compound was performed in the same manner as in EXAMPLE 4 using appropriate starting materials.
White Powder
$^1$H NMR (DMSO-d$_6$), δppm: 0.72 (3H, s), 1.08 (3H, t, J=7.1 Hz), 1.34 (3H, s), 2.24 (3H, s), 3.30-3.43 (5H, m), 3.73 (3H, s), 3.66-3.86 (3H, m), 3.97-4.06 (1H, m), 4.27 (2H, br), 4.43 (2H, br), 6.32-6.35 (1H, m), 6.85 (1H, d, J=7.4 Hz), 6.97 (1H, s), 7.54-7.57 (1H, m), 7.61-7.72 (2H, m), 7.87 (1H, br), 7.94-7.95 (1H, m).

EXAMPLE 354

1-Ethyl-7-({N-(6-methoxymethylpyridin-3-ylmethyl)-N-[2-(2-methyl-4-oxo-4H-furo[3,2-c]pyridin-5-yl)ethyl]amino}methyl)-3,3,5-trimethyl-1,5-dihydrobenzo[b][1,4]diazepine-2,4-dione dihydrochloride The synthesis of the title compound was performed in the same manner as in EXAMPLE 4 using appropriate starting materials.
White Powder
$^1$H NMR (DMSO-$d_6$), δppm: 0.67 (3H, s), 1.04 (3H, t, J=7.0 Hz), 1.33 (3H, s), 2.40 (3H, s), 2.70-3.10 (2H, m), 3.27 (5H, br), 3.41 (3H, s), 3.65-4.10 (6H, m), 4.63 (2H, br), 6.51 (1H, br), 6.70 (1H, br), 7.57 (1H, d, J=7.2 Hz), 7.00-7.70 (4H, m), 8.23 (1H, br), 8.74 (1H, m).

EXAMPLE 355

N-(1-Ethyl-3,3,5-trimethyl-2,4-dioxo-2,3,4,5-tetrahydro-1H-benzo[b][1,4]diazepin-7-ylmethyl)-2-(2-oxo-2,3-dihydrobenzimidazol-1-yl)-N-(2-pyridin-3-ylethyl)isobutyramide The synthesis of the title compound was performed in the same manner as in EXAMPLE 332 using appropriate starting materials.
Pale Brown White Amorphous
$^1$H NMR (CDCl$_3$), δppm: 0.74 and 0.80 (3H, s), 1.08-1.23 (3H, m), 1.50 and 1.52 (3H, s), 1.95-2.07 (6H, m), 2.15-2.35 (1H, m), 2.87 (1H, t, J=7.5 Hz), 3.16 and 3.37 (3H, s), 3.42-3.63 (2H, m), 3.63-3.88 (1H, m), 3.95-4.18 (1H, m), 4.43-4.82 (2H, m), 6.52-6.62 (1H, m), 6.80-7.32 (7H, m), 7.48 (1H, d, J=7.8 Hz), 7.99 and 8.10 (1H, s), 8.30-8.63 (2H, m)

EXAMPLE 356

1-Ethyl-3,3,5-trimethyl-7-({N-[1-(2-methylpyridin-3-yl)ethyl]-N-[2-(4-oxo-4H-furo[3,2-c]pyridin-5-yl)ethyl]amino}methyl)-1,5-dihydrobenzo[b][1,4]diazepine-2,4-dione The synthesis of the title compound was performed in the same manner as in EXAMPLE 30 using appropriate starting materials.
White Powder (Ether)
mp: 164-167° C.

EXAMPLE 357

1-Ethyl-3,3,5-trimethyl-7-({N-[2-(2-methyl-4-oxo-4H-furo[3,2-c]pyridin-5-yl)ethyl]-N-[1-(2-methylpyridin-3-yl)ethyl]amino}methyl)-1,5-dihydrobenzo[b][1,4]diazepine-2,4-dione The synthesis of the title compound was performed in the same manner as in EXAMPLE 30 using appropriate starting materials.
Ivory Powder
mp: 163-164° C.

EXAMPLE 358

7-({N-[2-(2,7-Dimethyl-4-oxo-4H-furo[3,2-c]pyridin-5-yl)ethyl]-N-[1-(2-methylpyridin-3-yl)ethyl]amino}methyl)-1-ethyl-3,3,5-trimethyl-1,5-dihydrobenzo[b][1,4]diazepine-2,4-dione The synthesis of the title compound was performed in the same manner as in EXAMPLE 30 using appropriate starting materials.
White Powder
mp: 169-170° C.

EXAMPLE 359

7-({N-(2-Ethoxymethylpyridin-3-ylmethyl)-N-[2-(2-methyl-4-oxo-4H-furo[3,2-c]pyridin-5-yl)ethyl]amino}methyl)-1-ethyl-3,3,5-trimethyl-1,5-dihydrobenzo[b][1,4]diazepine-2,4-dione The synthesis of the title compound was performed in the same manner as in EXAMPLE 30 using appropriate starting materials.
Ivory Powder
mp: 104-106° C.

EXAMPLE 360

1-Ethyl-3,3,5-trimethyl-7-{[N-(2-pyridin-3-ylethyl)-N-(quinolin-5-yl)amino]methyl}-1,5-dihydrobenzo[b][1,4]diazepine-2,4-dione trihydrochloride 1-Ethyl-3,3,5-trimethyl-7-{[N-(2-pyridin-3-ylethyl)amino]methyl}-1,5-dihydrobenzo[b][1,4]diazepine-2,4-dione (0.45 g), 5-bromoquinoline(0.25 g), tris(dibenzylideneacetone)dipalladium(5.4 mg), xantphos(10 mg), and cesium carbonate (0.46 g) were added to toluene(9 ml), and the mixture was heated at 130° C. for 3 days. The reaction liquid was cooled to room temperature. Water was added to the reaction mixture, and stirred for 1 hour, followed by extraction with ethyl acetate. The organic layer was dried over anhydrous magnesium sulfate. The filtrate was condensed under reduced pressure, and the residue was purified by silica gel column chromatography (ethyl acetate: methanol=85:15). The purified product was condensed under reduced pressure. A 1N-hydrogen chloride in ethanol solution(1 ml) was added to a ethanol solution (5 ml) of the residue, and the liquid was stirred at room temperature, and concentrated under reduced pressure. Ethanol and ether were added to the residue. The precipitated insoluble matter was separated, washed with ether, and dried to give the title compound(0.20 g) as a yellow amorphous.
$^1$H NMR (DMSO-$d_6$), δppm: 0.55 (3H, s), 0.99 (3H, t, J=7.0 Hz), 1.29 (3H, s), 3.03 (2H, t, J=7.1 Hz), 3.14 (3H, s), 3.30-3.80 (3H, m), 3.90-4.03 (1H, m), 4.49 (2H, s), 7.06-7.20 (2H, m), 7.33 (1H, d, J=8.1 Hz), 7.49 (1H, d, J=5.4 Hz), 7.73 (1H, dd, J=4.8 Hz, 8.8 Hz), 7.78-7.90 (3H, m), 8.23 (1H, d, J=8.1 Hz), 8.64 (1H, s), 8.69 (1H, d, J=4.8 Hz), 8.73 (1H, d, J=8.8 Hz), 9.07 (1H, d, J=3.6 Hz),

EXAMPLE 361

N-(1-Ethyl-3,3,5-trimethyl-2,4-dioxo-2,3,4,5-tetrahydro-1H-benzo[b][1,4]diazepin-7-ylmethyl)-2-(1H-indazol-3-yl)-N-(2-pyridin-3-ylethyl)acetamide The synthesis of the title compound was performed in the same manner as in EXAMPLE 330 using appropriate starting materials.

Yellow Amorphous

¹H NMR (CDCl₃), δppm: 0.70 and 0.79 (3H, s), 1.08-1.23 (3H, m), 1.49 and 1.52 (3H, s), 2.77 (1H, t, J=7.7 Hz), 2.85 (1H, t, J=7.3 Hz), 3.06 and 3.21(3H, s), 3.52-3.82 (3H, m), 4.01-4.16 (3H, m), 4.50-4.70 (2H, m), 6.75-7.32 (5H, m), 7.32-7.50 (3H, m), 7.82-7.92 (1H, m), 8.27-8.55 (2H, m), 10.1 and 10.1 (1H, bs)

EXAMPLE 362

7-({N-(4-Chloropyridin-3-ylmethyl)-N-[2-(2-methyl-4-oxo-4H-furo[3,2-c]pyridin-5-yl)ethyl] amino}methyl)-1-ethyl-3,3,5-trimethyl-1,5-dihydrobenzo[b][1,4]diazepine-2,4-dione The synthesis of the title compound was performed in the same manner as in EXAMPLE 30 using appropriate starting materials.

White Powder mp: 114-118° C.

EXAMPLE 363

N-[3-({N-(1-Ethyl-3,3,5-trimethyl-2,4-dioxo-2,3,4, 5-tetrahydro-1H-benzo[b][1,4]diazepin-7-ylmethyl)-N-[2-(2-methyl-4-oxo-4H-furo[3,2-c]pyridin-5-yl) ethyl]amino}methyl)pyridin-2-ylmethyl]formamide 3-({N-(1-Ethyl-3,3,5-trimethyl-2,4-dioxo-2,3,4,5-tetrahydro-1H-benzo[b][1,4]diazepin-7-ylmethyl)-N-[2-(2-methyl-4-oxo-4H-furo[3,2-c]pyridin-5-yl)ethyl] amino}methyl)pyridine-2-carbonitrile(0.40 g) and Raney nickel(1.2 g) were suspended in formic acid(8 ml), and the mixture was stirred at 60° C. for 3 hours. The reaction mixture was filtered to remove insoluble matter, and the filtrate was condensed under reduced pressure. The residue was purified by silica gel column chromatography (ethyl acetate: methanol=75:25→80:20). The purified product was condensed under reduced pressure. Acetone and ether were added to the residue. The precipitated insoluble matter was separated, washed with ether, and dried to give the title compound(33 mg) as a pale brown white amorphous.

¹H NMR (CDCl₃), δppm: 0.77 (3H, s), 1.16 (3H, t, J=7.1 Hz), 1.51 (3H, s), 2.43 (3H, d, J=0.9 Hz), 2.85 (2H, t, J=5.8 Hz), 3.35 (3H, s), 3.58-3.84 (5H, m), 4.00-4.18 (3H, m), 4.54 (2H, d, J=4.4 Hz), 6.41 (1H, dd, J=0.4 Hz, 7.3 Hz), 6.47 (1H, t, J=0.8 Hz), 6.96 (1H, d, J=7.3 Hz), 7.06 (1H, dd, J=4.9, 7.7 Hz), 7.12-7.20 (3H, m), 7.38 (1H, bs), 7.55 (1H, dd, J=1.2, 7.7 Hz), 8.32 (1H, d, J=1.2 Hz), 8.36 (1H, dd, J=1.5, 4.9 Hz)

EXAMPLE 364

1-Ethyl-3,3,5-trimethyl-7-({N-[2-(2-methyl-4-oxo-4H-furo[3,2-c]pyridin-5-yl)ethyl]N-(quinolin-5-yl) amino}methyl)-1,5-dihydrobenzo[b][1,4]diazepine-2,4-dione The synthesis of the title compound was performed in the same manner as in EXAMPLE 30 using appropriate starting materials.

White Powder mp: 166-168° C.

EXAMPLE 365

N-(1-Ethyl-3,3,5-trimethyl-2,4-dioxo-2,3,4,5-tetrahydro-1H-benzo[b][1,4]diazepin-7-ylmethyl)-2-(1-methyl-1H-indazol-3-yl)-N-(2-pyridin-3-ylethyl) propionamide Sodium hydride (55% in oil) (52 mg) was suspended in DMF(7 ml), and cooled to 0° C. in an ice water bath. N-(1-Ethyl-3,3,5-trimethyl-2,4-dioxo-2,3,4,5-tetrahydro-1H-benzo[b][1,4]diazepin-7-ylmethyl)-2-(1H-indazol-3-yl)-N-(2-pyridin-3-ylethyl)acetamide(210 mg) was added thereto at the same temperature, and the mixture was stirred at 0° C. for 30 minutes followed at room temperature for 30 minutes. Methyl iodide(0.03 ml) was added thereto, and the mixture was stirred at room temperature for 3 hours. Water was added to the reaction liquid, followed by extraction with ethyl acetate. The organic layer was dried over sodium sulfate, and condensed under reduced pressure. The residue was purified by silica gel column chromatography (ethyl acetate: methanol=90:10). The purified product was condensed to dryness to give the title compound(20 mg) as a pale yellow white amorphous.

¹H NMR (CDCl₃), δppm: 0.75 and 0.86 (3H, s), 1.17 and 1.21 (3H, t, J=7.1 Hz), 1.51 (3H, s),1.54 (3H, s), 2.94 (1H, t, J=7.7 Hz), 3.06 (1H, t, J=7.2 Hz), 3.40 and 3.48 (3H, s), 3.44-3.54 (2H, m), 3.68 (1H, t, J=6.7 Hz), 3.72-3.90 (1H, m), 3.95-4.22 (2H, m), 4.18 and 4.25 (3H, s), 4.70-4.84 (1H, m), 7.03-7.75 (8H, m), 8.27-8.35 (1H, m), 8.35-8.44 (1H, m), 8.51-8.64 (1H, m)

EXAMPLE 366

N-(1-Ethyl-3,3,5-trimethyl-2,4-dioxo-2,3,4,5-tetrahydro-1H-benzo[b][1,4]diazepin-7-ylmethyl)-N-(2-pyridin-3-ylethyl)formamide Sodium hydride (55% in oil) (52 mg) was suspended in DMF(7 ml), and cooled to 0° C. in an ice water bath. N-(1-Ethyl-3,3,5-trimethyl-2,4-dioxo-2,3,4,5-tetrahydro-1H-benzo[b][1,4]diazepin-7-ylmethyl)-2-(1H-indazol-3-yl)-N-(2-pyridin-3-ylethyl)acetamide(210 mg) was added thereto at the same temperature, and the mixture was stirred at 0° C. for 30 minutes followed at room temperature for 30 minutes. Methyl iodide(0.03 ml) was added thereto, and the mixture was stirred at room temperature for 3 hours. Water was added to the reaction liquid, followed by extraction with ethyl acetate. The organic layer was dried over sodium sulfate, and condensed under reduced pressure. The residue was purified by silica gel column chromatography (ethyl acetate: methanol=85:15). The purified product was condensed to dryness to give the title compound(17 mg) as a pale yellow white amorphous.

Pale Yellow White Amorphous

¹H NMR (CDCl₃), δppm: 0.83 (3H, s), 1.19 and 1.20 (3H, t, J=7.1 Hz), 1.53 (3H, bs),2.85 (2H, t, J=7.7 Hz), 3.39 and 3.39 (3H, s), 3.44-3.54 (2H, m), 3.75-3.88 (1H, m), 4.06-4.20 (1H, m), 4.27-4.65 (2H, m), 6.98-7.10 (1H, m), 7.10-7.18 (1H, m), 7.21-7.35 (2H, m), 7.41 and 7.53 (1H, dt, J=7.9, 2.0 Hz), 8.05 and 8.30 (1H, s), 8.39 and 8.41 (1H, d, J=1.8 Hz), 8.50 and 8.62 (1H, dd, J=1.8, 4.8 Hz)

EXAMPLE 367

1-Ethyl-7-({N-[1-(2-methoxymethylpyridin-3-yl)ethyl]-N-[2-(7-methyl-4-oxo-4H-furo[3,2-c]pyridin-5-yl)ethyl]amino}methyl)-3,3,5-trimethyl-1,5-dihydrobenzo[b][1,4]diazepine-2,4-dione dihydrochloride The synthesis of the title compound was performed in the same manner as in EXAMPLE 4 using appropriate starting materials.
White Powder
$^1$H NMR (DMSO-$d_6$), δppm: 0.75 (3H, s), 1.04 (3H, t, J=7.1 Hz), 1.34 (3H, s), 1.41 (3H, s), 2.09 (3H, s), 2.57-2.84 (2H, m), 3.16 (2H, br), 3.35 (3H, s), 3.40 (3H, s), 3.62-3.70 (2H, m), 4.00-4.13 (1H, m), 4.18 (2H, br), 6.83 (1H, br), 7.09 (1H, br), 7.43-7.63 (3H, m), 7.83 (1H, br), 7.91-7.92 (1H, m), 8.40 (1H, br), 8.46 (1H, br).

EXAMPLE 368

1-Ethyl-7-({N-(2-hydroxymethylpyridin-3-ylmethyl)-N-[2-(7-methyl-4-oxo-4H-furo[3,2-c]pyridin-5-yl)ethyl]amino}methyl)-3,3,5-trimethyl-1,5-dihydrobenzo[b][1,4]diazepine-2,4-dione The synthesis of the title compound was performed in the same manner as in EXAMPLE 30 using appropriate starting materials.
White Powder
mp: 187-190° C.

EXAMPLE 369

7-({N,N-Bis-[2-(2-methyl-4-oxo-4H-furo[3,2-c]pyridin-5-yl)ethyl]amino}methyl)-1-ethyl-3,3,5-trimethyl-1,5-dihydrobenzo[b][1,4]diazepine-2,4-dione The synthesis of the title compound was performed in the same manner as in EXAMPLE 30 using appropriate starting materials.
White Powder
mp: 160-165° C.

EXAMPLE 370

1-Ethyl-7-({N-(5-methoxymethyl-2-methyl-2H-pyrazol-3-ylmethyl)-N-[2-(7-methyl-4-oxo-4H-furo[3,2-c]pyridin-5-yl)ethyl]amino}methyl)-3,3,5-trimethyl-1,5-dihydrobenzo[b][1,4]diazepine-2,4-dione The synthesis of the title compound was performed in the same manner as in EXAMPLE 30 using appropriate starting materials.
White Powder
mp: 169-170° C.

EXAMPLE 371

1-Ethyl-7-({N-(5-methoxymethyl-2-methyl-2H-pyrazol-3-ylmethyl)-N-[2-(2-methyl-4-oxo-4H-furo[3,2-c]pyridin-5-yl)ethyl]amino}methyl)-3,3,5-trimethyl-1,5-dihydrobenzo[b][1,4]diazepine-2,4-dione The synthesis of the title compound was performed in the same manner as in EXAMPLE 30 using appropriate starting materials.
White Powder
mp: 113-115° C.

EXAMPLE 372

1-Isobutyl-7-({N-(2-methoxymethylpyridin-3-ylmethyl)-N-[2-(2-methyl-4-oxo-4H-furo[3,2-c]pyridin-5-yl)ethyl]amino}methyl)-3,3-dimethyl-1,5-dihydrobenzo[b][1,4]diazepine-2,4-dione The synthesis of the title compound was performed in the same manner as in EXAMPLE 30 using appropriate starting materials.
Ivory Powder
mp: 184-186° C.

EXAMPLE 373

1-Isobutyl-7-({N-(2-methoxymethylpyridin-3-ylmethyl)-N-[2-(7-methyl-4-oxo-4H-furo[3,2-c]pyridin-5-yl)ethyl]amino}methyl)-3,3-dimethyl-1,5-dihydrobenzo[b][1,4]diazepine-2,4-dione The synthesis of the title compound was performed in the same manner as in EXAMPLE 30 using appropriate starting materials.
White Powder
mp: 207-210° C.

EXAMPLE 374

1-Isobutyl-3,3-dimethyl-7-({N-[2-(2-methyl-4-oxo-4H-furo[3,2-c]pyridin-5-yl)ethyl]-N-(2-methylpyridin-3-ylmethyl)amino}methyl)-1,5-dihydrobenzo[b][1,4]diazepine-2,4-dione The synthesis of the title compound was performed in the same manner as in EXAMPLE 30 using appropriate starting materials.
White Powder
mp: 180-182° C.

EXAMPLE 375

1-Isobutyl-3,3-dimethyl-7-({N-[2-(7-methyl-4-oxo-4H-furo[3,2-c]pyridin-5-yl)ethyl]-N-(2-methylpyridin-3-ylmethyl)amino}methyl)-1,5-dihydrobenzo[b][1,4]diazepine-2,4-dione The synthesis of the title compound was performed in the same manner as in EXAMPLE 30 using appropriate starting materials.
White Powder
mp: 229-231° C.

EXAMPLE 376

1-(2-Methoxyethyl)-7-({N-(2-methoxymethylpyridin-3-ylmethyl)-N-[2-(2-methyl-4-oxo-4H-furo[3,2-c]pyridin-5-yl)ethyl]amino}methyl)-3,3-dimethyl-1,5-dihydrobenzo[b][1,4]diazepine-2,4-dione The synthesis of the title compound was performed in the same manner as in EXAMPLE 30 using appropriate starting materials.
White Powder
mp: 182-185° C.

EXAMPLE 377

1-(2-Methoxyethyl)-7-({N-(2-methoxymethylpyridin-3-ylmethyl)-N-[2-(7-methyl-4-oxo-4H-furo[3,2-c]pyridin-5-yl)ethyl]amino}methyl)-3,3-dimethyl-1,5-dihydrobenzo[b][1,4]diazepine-2,4-dione The synthesis of the title compound was performed in the same manner as in EXAMPLE 30 using appropriate starting materials.
White Powder
mp: 188-189° C.

EXAMPLE 378

1-Isobutyl-7-({N-(2-methoxymethylpyridin-3-ylmethyl)-N-[2-(4-oxo-4H-furo[3,2-c]pyridin-5-yl)ethyl]amino}methyl)-3,3-dimethyl-1,5-dihydrobenzo[b][1,4]diazepine-2,4-dione The synthesis of the title compound was performed in the same manner as in EXAMPLE 30 using appropriate starting materials.
Ivory Powder
mp: 149-151° C.

EXAMPLE 379

1-(2-Methoxyethyl)-3,3-dimethyl-7-({N-[2-(2-methyl-4-oxo-4H-furo[3,2-c]pyridin-5-yl)ethyl]-N-(2-methylpyridin-3-ylmethyl)amino}methyl)-1,5-dihydrobenzo[b][1,4]diazepine-2,4-dione The synthesis of the title compound was performed in the same manner as in EXAMPLE 30 using appropriate starting materials.
Ivory Powder
mp: 179-181° C.

EXAMPLE 380

1-(2-Methoxyethyl)-3,3-dimethyl-7-({N-[2-(7-methyl-4-oxo-4H-furo[3,2-c]pyridin-5-yl)ethyl]-N-(2-methylpyridin-3-ylmethyl)amino}methyl)-1,5-dihydrobenzo[b][1,4]diazepine-2,4-dione The synthesis of the title compound was performed in the same manner as in EXAMPLE 30 using appropriate starting materials.
White Powder
mp: 205-206° C.

EXAMPLE 381

1-Cyclopropylmethyl-7-({N-(2-methoxymethylpyridin-3-ylmethyl)-N-[2-(2-methyl-4-oxo-4H-furo[3,2-c]pyridin-5-yl)ethyl]amino}methyl)-3,3-dimethyl-1,5-dihydrobenzo[b][1,4]diazepine-2,4-dione The synthesis of the title compound was performed in the same manner as in EXAMPLE 30 using appropriate starting materials.
Ivory Powder
mp:189-191° C.

EXAMPLE 382

1-Cyclopropylmethyl-7-({N-(2-methoxymethylpyridin-3-ylmethyl)-N-[2-(7-methyl-4-oxo-4H-furo[3,2-c]pyridin-5-yl)ethyl]amino}methyl)-3,3-dimethyl-1,5-dihydrobenzo[b][1,4]diazepine-2,4-dione The synthesis of the title compound was performed in the same manner as in EXAMPLE 30 using appropriate starting materials.
White Powder
mp: 192-194° C.

EXAMPLE 383

1-Cyclopropylmethyl-3,3-dimethyl-7-({N-[2-(2-methyl-4-oxo-4H-furo[3,2-c]pyridin-5-yl)ethyl]-N-(2-methylpyridin-3-ylmethyl)amino}methyl)-1,5-dihydrobenzo[b][1,4]diazepine-2,4-dione The synthesis of the title compound was performed in the same manner as in EXAMPLE 30 using appropriate starting materials.
White Powder
mp: 138-143° C.

EXAMPLE 384

1-Cyclopropylmethyl-3,3-dimethyl-7-({N-[2-(7-methyl-4-oxo-4H-furo[3,2-c]pyridin-5-yl)ethyl]-N-(2-methylpyridin-3-ylmethyl)amino}methyl)-1,5-dihydrobenzo[b][1,4]diazepine-2,4-dione The synthesis of the title compound was performed in the same manner as in EXAMPLE 30 using appropriate starting materials.
White Powder
mp: 220-221° C.

EXAMPLE 385

1-Ethyl-3,3,5-trimethyl-7-({N-(2-methylpyridin-3-ylmethyl)-N-[2-(2-oxo-3,4-dihydro-2H-quinolin-1-yl)ethyl]amino}methyl)-1,5-dihydrobenzo[b][1,4]diazepine-2,4-dione The synthesis of the title compound was performed in the same manner as in EXAMPLE 30 using appropriate starting materials.
White Powder
mp: 130-131° C.

EXAMPLE 386

1-Cyclopropyl-7-({N-(2-methoxymethyl-pyridin-3-ylmethyl)-N-[2-(2-methyl-4-oxo-4H-furo[3,2-c]pyridin-5-yl)ethyl]amino}methyl)-3,3-dimethyl-1,5-dihydrobenzo[b][1,4]diazepine-2,4-dione The synthesis of the title compound was performed in the same manner as in EXAMPLE 30 using appropriate starting materials.
Ivory Powder
mp: 213-214° C.

EXAMPLE 387

1-Cyclopropyl-7-({N-(2-methoxymethylpyridin-3-ylmethyl)-N-[2-(7-methyl-4-oxo-4H-furo[3,2-c]pyridin-5-yl)ethyl]amino}methyl)-3,3-dimethyl-1,5-dihydrobenzo[b][1,4]diazepine-2,4-dione The synthesis of the title compound was performed in the same manner as in EXAMPLE 30 using appropriate starting materials.
White Powder
mp: 182-184° C.

EXAMPLE 388

1-Cyclopropyl-3,3-dimethyl-7-({[2-N-(2-methyl-4-oxo-4H-furo[3,2-c]pyridin-5-yl)ethyl]-N-(2-methylpyridin-3-ylmethyl)amino}methyl)-1,5-dihydrobenzo[b][1,4]diazepine-2,4-dione The synthesis of the title compound was performed in the same manner as in EXAMPLE 30 using appropriate starting materials.
Ivory Powder
mp: 172-173° C.

EXAMPLE 389

1-Cyclopropyl-3,3-dimethyl-7-({N-[2-(7-methyl-4-oxo-4H-furo[3,2-c]pyridin-5-yl)ethyl]-N-(2-methylpyridin-3-ylmethyl)amino}methyl)-1,5-dihydrobenzo[b][1,4]diazepine-2,4-dione The synthesis of the title compound was performed in the same manner as in EXAMPLE 30 using appropriate starting materials.
White Powder
mp: 191-193° C.

EXAMPLE 390

1-Ethyl-3,3,5-trimethyl-7-({N-(2-methylpyridin-3-ylmethyl)-N-[2-(2-oxo-2H-quinolin-1-yl)ethyl]amino}methyl)-1,5-dihydrobenzo[b][1,4]diazepine-2,4-dione The synthesis of the title compound was performed in the same manner as in EXAMPLE 30 using appropriate starting materials.
White Powder
mp: 149-150° C.

Examples 391 to 582

The following compounds were obtained in the same manner as in Examples above using appropriate starting materials.

| Example No. | R1 | MS (M + 1) |
|---|---|---|
| 391 | 3-methylfuran | 461 |
| 392 | 3-methylpyridine | 472 |
| 393 | 4-methylpyridine | 472 |
| 394 | 2,5-dimethylfuran | 475 |
| 395 | 2-methylthiophene | 477 |
| 396 | 2-methyl-3-methylthiophene | 491 |
| 397 | 2-methylthiazole | 478 |
| 398 | 2,5-dimethyl-3-methylfuran | 489 |
| 399 | 3-hydroxy-methylphenyl | 487 |
| 400 | 2-methylfuran | 461 |
| 401 | N-(methylsulfonyl)-2-methylaniline | 564 |

169
-continued

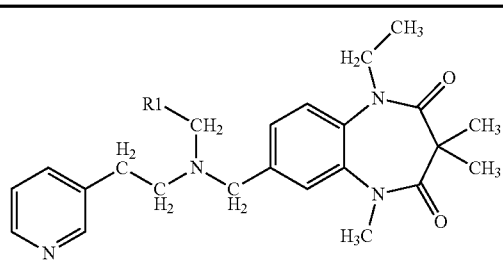

| Example No. | R1 | MS (M + 1) |
|---|---|---|
| 402 | 5-methyl-2-(trifluoromethyl)pyridine | 540 |
| 403 | 1,3,5-trimethylpyrazole | 489 |
| 404 | 4,5-dimethylthiazole | 492 |
| 405 | 5-methyl-2-(trifluoromethyl)furan | 529 |
| 406 | 2,4,5-trimethylthiazole | 506 |
| 407 | 2,4-dimethylthiazole | 492 |
| 408 | 2,3-dimethyl-thiophene (5-methyl) | 505 |
| 409 | 2,4-dimethylthiazole | 492 |
| 410 | 3,4-dimethylpyridine | 486 |

170
-continued

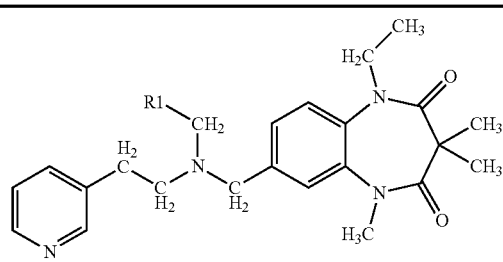

| Example No. | R1 | MS (M + 1) |
|---|---|---|
| 411 | 2,3-dimethylpyridine | 486 |
| 412 | 2,3-dimethylpyridine | 486 |
| 413 | 2,5-dimethylpyridine | 486 |
| 414 | 2,4-dimethylpyridine | 486 |
| 415 | 3-fluoro-4-methylpyridine | 490 |
| 416 | 1,4-dimethylimidazole | 475 |
| 417 | 2,4,5-trimethylthiazole | 506 |
| 418 | 1,3,5-trimethylpyrazole | 489 |
| 419 | 2,3-dimethylfuran | 475 |

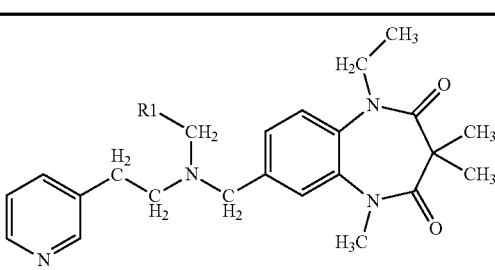

| Example No. | R1 | MS (M + 1) |
|---|---|---|
| 420 | 2,4-dimethylpyridinyl | 486 |
| 421 | 5-fluoro-3-methylpyridinyl | 490 |
| 422 | 3-methyl-4-(trifluoromethyl)pyridinyl | 540 |
| 423 | 2-methoxy-3-methylpyridinyl | 502 |
| 424 | 4-methylthiazolyl | 478 |
| 425 | 5-methylthiazolyl | 478 |
| 426 | methylpyrazinyl | 473 |
| 427 | 5-methyloxazolyl | 462 |
| 428 | 5-methylpyrimidinyl | 473 |
| 429 | 3,4-dimethylpyridinyl | 486 |
| 430 | 5-methyl-3-methoxypyridinyl | 502 |
| 431 | 2,4-dimethyloxazolyl | 476 |
| 432 | 2,5-dimethylpyridinyl | 486 |
| 433 | 4-methyloxazolyl | 462 |
| 434 | 3-methylisoxazolyl | 462 |
| 435 | 3,5-dimethylisoxazolyl | 476 |
| 436 | 2,5-dimethyl-4-(trifluoromethyl)thiazolyl | 560 |
| 437 | 2,5-dimethylpyrimidinyl | 487 |
| 438 | 2,4,6-trimethylpyridinyl | 500 |

173

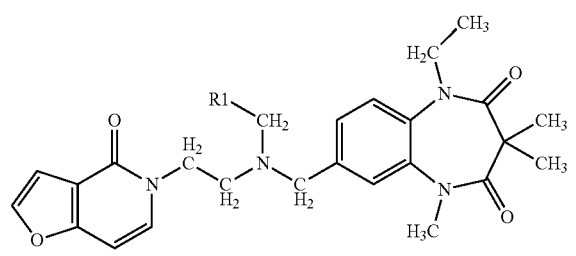

| Example No. | R1 | MS (M + 1) |
|---|---|---|
| 439 | 3-furyl | 517 |
| 440 | 3-pyridyl | 528 |
| 441 | 4-pyridyl | 528 |
| 442 | 2,5-dimethylfuran-3-yl | 531 |
| 443 | 2-methylthien-5-yl | 533 |
| 444 | 2,3-dimethylthien-5-yl | 547 |
| 445 | 2-thiazolyl | 534 |
| 446 | 2,5-dimethyl-3-methylfuran | 545 |
| 447 | 3-hydroxyphenyl (methyl) | 543 |
| 448 | 2-methylfuran | 517 |

174
-continued

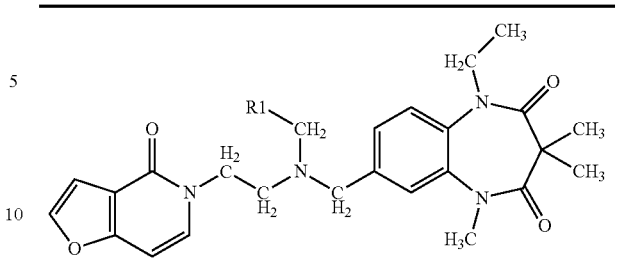

| Example No. | R1 | MS (M + 1) |
|---|---|---|
| 449 | 2-methyl-N-methanesulfonamidophenyl | 620 |
| 450 | 5-methyl-2-(trifluoromethyl)pyridinyl | 596 |
| 451 | 1,3-dimethylpyrazol-5-yl | 545 |
| 452 | 4,5-dimethylthiazol-2-yl | 548 |
| 453 | 5-methyl-2-(trifluoromethyl)furanyl | 585 |
| 454 | 2,4,5-trimethylthiazolyl | 562 |
| 455 | 2,4-dimethylthiazolyl | 548 |
| 456 | 2,5-dimethyl-3-methylthienyl | 561 |

-continued

| Example No. | R1 | MS (M+1) |
|---|---|---|
| 457 | 4-methyl-2-thiazolyl (2-CH3) | 548 |
| 458 | 3-methyl-4-pyridyl | 542 |
| 459 | 2-methyl-3-pyridyl | 542 |
| 460 | 2-methyl-3-pyridyl | 542 |
| 461 | 2,5-dimethylpyridyl | 542 |
| 462 | 2,4-dimethylpyridyl | 542 |
| 463 | 3-fluoro-4-pyridyl | 546 |
| 464 | 4-methyl-1-methylimidazolyl | 531 |
| 465 | 2,4-dimethylthiazolyl | 562 |

-continued

| Example No. | R1 | MS (M+1) |
|---|---|---|
| 466 | 1,5-dimethylpyrazolyl (3-CH3) | 545 |
| 467 | 2,3-dimethylfuryl | 531 |
| 468 | 2,4-dimethylpyridyl | 542 |
| 469 | 5-fluoro-3-methylpyridyl | 546 |
| 470 | 4-trifluoromethyl-3-methylpyridyl | 596 |
| 471 | 2-methoxy-3-methylpyridyl | 558 |
| 472 | 4-methylthiazolyl | 534 |
| 473 | 5-methylthiazolyl | 534 |
| 474 | 3-methylpyrazinyl | 529 |

-continued

[Structure: furopyridinone-CH2CH2-N(R1CH2)-CH2-benzodiazepinedione with N-ethyl, gem-dimethyl, N-methyl]

| Example No. | R1 | MS (M + 1) |
|---|---|---|
| 475 | 5-methyl-oxadiazole | 518 |
| 476 | 5-pyrimidinyl | 529 |
| 477 | 3,4-dimethyl-pyridine | 542 |
| 478 | 5-methyl-3-methoxy-pyridine | 558 |
| 479 | 2-methyl-4-methyl-oxazole | 532 |
| 480 | 2,5-dimethyl-pyridine | 542 |
| 481 | 4-oxazolyl | 518 |
| 482 | 3-methyl-isoxazole | 518 |
| 483 | 3,5-dimethyl-isoxazole | 532 |
| 484 | 2,5-dimethyl-4-(trifluoromethyl)-thiazole | 616 |

-continued

[Same scaffold as above]

| Example No. | R1 | MS (M + 1) |
|---|---|---|
| 485 | 2,5-dimethyl-pyrimidine | 543 |
| 486 | 2,3,6-trimethyl-pyridine | 556 |

[Structure: isoquinolinone-CH2CH2-N(R1CH2)-CH2-benzodiazepinedione with N-ethyl, gem-dimethyl, N-methyl]

| Example No. | R1 | MS (M + 1) |
|---|---|---|
| 487 | 3-methyl-furan | 527 |
| 488 | 3-methyl-pyridine | 538 |
| 489 | 4-methyl-pyridine | 538 |
| 490 | 2,5-dimethyl-furan | 541 |
| 491 | 2-methyl-thiophene | 543 |
| 492 | 2,3-dimethyl-thiophene | 557 |

179
-continued

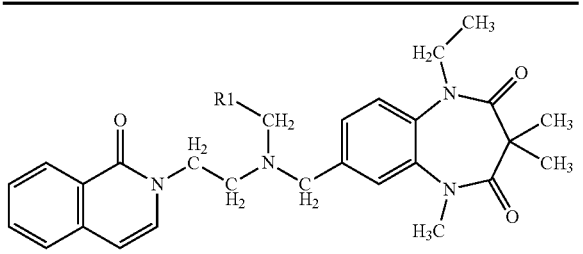

| Example No. | R1 | MS (M + 1) |
|---|---|---|
| 493 | 2-methylthiazol-5-yl | 544 |
| 494 | 2,4-dimethylfuran-3-yl | 555 |
| 495 | 3-hydroxyphenyl | 553 |
| 496 | 5-methylfuran-2-yl | 527 |
| 497 | 2-(methylsulfonamido)phenyl | 630 |
| 498 | 6-(trifluoromethyl)pyridin-3-yl | 606 |
| 499 | 1,3-dimethyl-1H-pyrazol-5-yl | 555 |
| 500 | 4-methylthiazol-5-yl | 558 |
| 501 | 5-(trifluoromethyl)furan-2-yl | 595 |

180
-continued

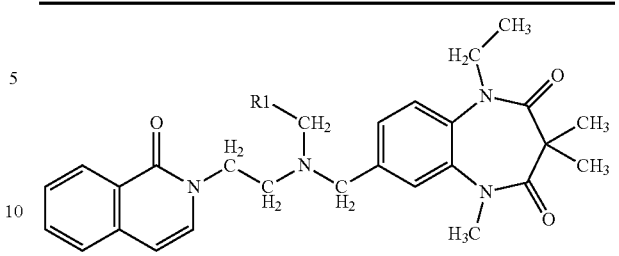

| Example No. | R1 | MS (M + 1) |
|---|---|---|
| 502 | 2,4,5-trimethylthiazol-5-yl | 572 |
| 503 | 2,4-dimethylthiazol-5-yl | 558 |
| 504 | 2,4-dimethylthiophen-5-yl | 571 |
| 505 | 2,4-dimethylthiazol-5-yl | 558 |
| 506 | 3,4-dimethylpyridin-5-yl | 552 |
| 507 | 2,3-dimethylpyridin-5-yl | 552 |
| 508 | 2,3-dimethylpyridin-6-yl | 552 |
| 509 | 2,5-dimethylpyridin-6-yl | 552 |
| 510 | 2,4-dimethylpyridin-6-yl | 552 |

-continued

| Example No. | R1 | MS (M + 1) |
|---|---|---|
| 511 | 3-fluoro-4-methylpyridine | 556 |
| 512 | 1-methyl-1H-imidazol-4-yl | 541 |
| 513 | 2,4-dimethyl-5-methylthiazole | 572 |
| 514 | 1,5-dimethyl-3-methylpyrazole | 555 |
| 515 | 2-methyl-3-methylfuran | 541 |
| 516 | 2,4-dimethylpyridine | 552 |
| 517 | 5-fluoro-3-methylpyridine | 556 |
| 518 | 4-(trifluoromethyl)-3-methylpyridine | 606 |

-continued

| Example No. | R1 | MS (M + 1) |
|---|---|---|
| 519 | 2-methoxy-3-methylpyridine | 568 |
| 520 | 4-methylthiazole | 544 |
| 521 | 5-methylthiazole | 544 |
| 522 | 3-methylpyrazine | 539 |
| 523 | 5-methyloxazole | 528 |
| 524 | 5-methylpyrimidine | 539 |
| 525 | 3,4-dimethylpyridine | 552 |
| 526 | 5-methoxy-3-methylpyridine | 568 |
| 527 | 2,4-dimethyloxazole | 542 |
| 528 | 2,5-dimethylpyridine | 552 |

183
-continued
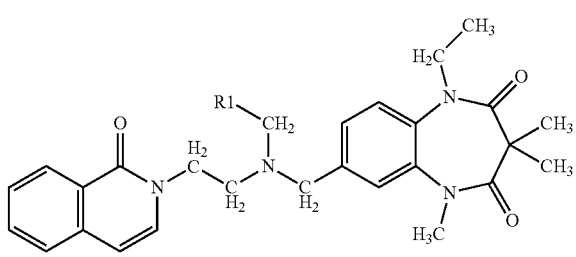
| Example No. | R1 | MS (M + 1) |
|---|---|---|
| 529 | 4-methyloxazole | 528 |
| 530 | 3-methylisoxazole | 528 |
| 531 | 3,5-dimethylisoxazole | 542 |
| 532 | 2,5-dimethyl-4-(trifluoromethyl)thiazole | 626 |
| 533 | 2,5-dimethylpyrimidine | 553 |
| 534 | 2,6-dimethylpyridine | 566 |
184
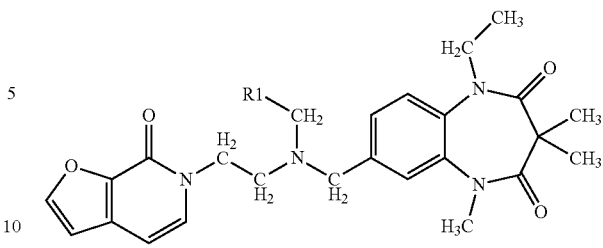
| Example No. | R1 | MS (M + 1) |
|---|---|---|
| 535 | 3-furyl | 517 |
| 536 | 3-pyridyl | 528 |
| 537 | 4-pyridyl | 528 |
| 538 | 2,5-dimethylfuran | 531 |
| 539 | 2-methylthiophene | 533 |
| 540 | 2,3-dimethylthiophene | 547 |
| 541 | 2-methylthiazole | 534 |
| 542 | 2,5-dimethyl-3-methylfuran | 545 |
| 543 | 3-hydroxyphenyl | 543 |
| 544 | 2-methylfuran | 517 |

| Example No. | R1 | MS (M + 1) |
|---|---|---|
| 545 | N-methanesulfonyl-2-methylphenyl | 620 |
| 546 | 5-methyl-2-(trifluoromethyl)pyridinyl | 596 |
| 547 | 1,3,5-trimethyl-1H-pyrazol-4-yl | 545 |
| 548 | 2,4-dimethylthiazol-5-yl | 548 |
| 549 | 5-methyl-2-(trifluoromethyl)furan-3-yl | 585 |
| 550 | 2,4,5-trimethylthiazol-3-yl | 562 |
| 551 | 2,4-dimethylthiazol-5-yl | 548 |
| 552 | 2,5-dimethylthiophen-3-yl | 561 |

| Example No. | R1 | MS (M + 1) |
|---|---|---|
| 553 | 2,4-dimethylthiazol-5-yl | 548 |
| 554 | 3,4-dimethylpyridinyl | 542 |
| 555 | 2,3-dimethylpyridinyl | 542 |
| 556 | 2,3-dimethylpyridinyl | 542 |
| 557 | 2,5-dimethylpyridinyl | 542 |
| 558 | 2,4-dimethylpyridinyl | 542 |
| 559 | 3-fluoro-4-methylpyridinyl | 546 |
| 560 | 1,4-dimethyl-1H-imidazol-5-yl | 531 |
| 561 | 2,4-dimethylthiazol-5-yl | 562 |

| 187 -continued | | | 188 -continued | | |
|---|---|---|---|---|---|
| 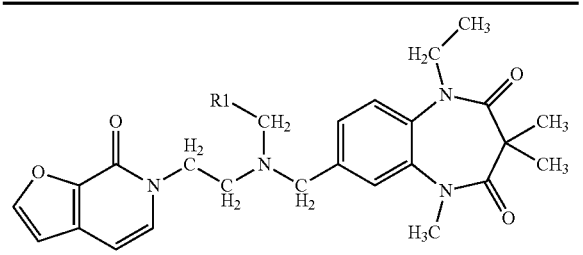 | | | 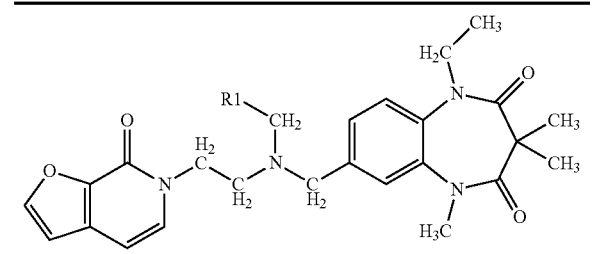 | | |
| Example No. | R1 | MS (M + 1) | Example No. | R1 | MS (M + 1) |
| 562 | 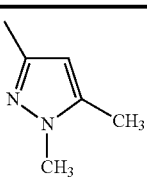 | 545 | 571 | 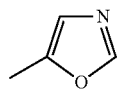 | 518 |
| 563 | 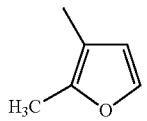 | 531 | 572 | 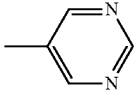 | 529 |
| 564 | 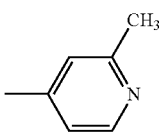 | 542 | 573 | 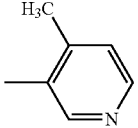 | 542 |
| 565 | 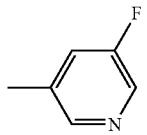 | 546 | 574 | 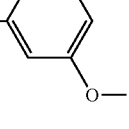 | 558 |
| 566 | 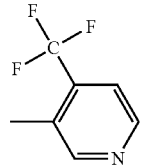 | 596 | 575 | 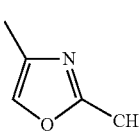 | 532 |
| 567 | 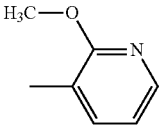 | 558 | 576 | 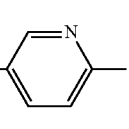 | 542 |
| 568 | 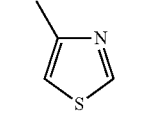 | 534 | 577 | 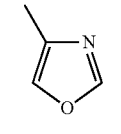 | 518 |
| 569 | 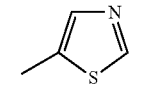 | 534 | 578 | 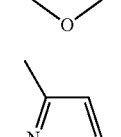 | 518 |
| 570 | 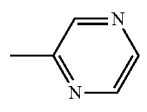 | 529 | 579 | 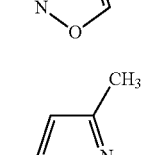 | 532 |
| | | | 580 | 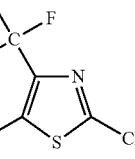 | 616 |

-continued

| Example No. | R1 | MS (M + 1) |
|---|---|---|
| 581 | 5-(pyrimidin-2-yl with CH3) | 543 |
| 582 | (3-methyl-6-methylpyridin-2-yl) | 556 |

EXAMPLE 583

1-Ethyl-3,3,5-trimethyl-7-({N-[2-(2-methyl-4-oxo-4H-furo[3,2-c]pyridin-5-yl)ethyl]-N-(pyrimidin-5-ylmethyl)amino}methyl)-1,5-dihydrobenzo[b][1,4]diazepine-2,4-dione The synthesis of the title compound was performed in the same manner as in EXAMPLE 30 using appropriate starting materials.
White Powder
mp: 146.2-148.2° C.

EXAMPLE 584

1-Ethyl-3,3,5-trimethyl-7-[4-(2-oxo-3,4-dihydro-2H-quinolin-1-yl)piperidin-1-ylmethyl]-1,5-dihydrobenzo[b][1,4]diazepine-2,4-dione 1-Ethyl-3,3,5-trimethyl-2,4-dioxo-2,3,4,5-tetrahydro-1H-benzo[b][1,4]diazepine-7-carbaldehyde(0.203 g) and acetic acid(0.063 ml) were added to a 1,2-dichloroethane solution (5 ml) of 1-(piperidin-4-yl)-3,4-dihydroquinolin-2(1H)-one (0.170 g), and the mixture was stirred at room temperature for 30 minutes. Sodium triacetoxyborohydride(0.235 g) was added, and the mixture was stirred at room temperature overnight. The reaction mixture was condensed under reduced pressure. The residue was purified by silica gel column chromatography (ethyl acetate: methanol=100:0→90:10). The purified product was condensed to dryness to give the title compound(0.205 g) as pale yellow amorphous.

$^1$H NMR (CDCl$_3$), δppm: 0.83 (3H, s), 1.20 (3H, t, J=7.1 Hz), 1.54 (3H, s), 1.68-1.75 (2H, m), 2.13-2.21 (2H, m), 2.55-2.60 (2H, m), 2.64-2.76 (2H, m), 2.80-2.85 (2H, m), 2.95-3.03 (2H, m), 3.44 (3H, s), 3.57(2H, s), 3.77-3.85 (1H, m), 4.10-4.19 (1H, m), 4.25-4.33 (1H, m), 7.01 (1H, dt, J=1.9, 7.4 Hz), 7.14-7.28 (6H, m)

EXAMPLE 585

1-Ethyl-3,3,5-trimethyl-7-[4-(2-oxo-2H-quinolin-1-yl)-piperidin-1-ylmethyl]-1,5-dihydrobenzo[b][1,4]diazepine-2,4-dione The synthesis of the title compound was performed in the same manner as in EXAMPLE 584 using appropriate starting materials.

$^1$H NMR (CDCl$_3$), δppm: 0.85 (3H, s), 1.21 (3H, t, J=7.0 Hz), 1.54 (3H, s), 1.70-1.77 (2H, m), 2.28-2.34 (2H, m), 2.94 (2H, br), 3.05-3.13 (2H, m), 3.46 (3H, s), 3.64 (2H, s), 3.78-3.87 (1H, m), 4.11-4.19 (1H, m), 5.33 (1H, bs), 6.67 (1H, d, J=9.4 Hz), 7.21 (1H, t, J=8.0 Hz), 7.27-7.32 (3H, m), 7.50-7.57 (2H, m), 7.62 (1H, d, J=9.4 Hz), 7.78 (1H, br)

EXAMPLE 586

N-[1-(1-Ethyl-3,3,5-trimethyl-2,4-dioxo-2,3,4,5-tetrahydro-1H-benzo[b][1,4]diazepin-7-ylmethyl)piperidin-4-yl]-N-phenylbenzamide The synthesis of the title compound was performed in the same manner as in EXAMPLE 584 using appropriate starting materials.

$^1$H NMR (CDCl$_3$), δppm: 0.81 (3H, s), 1.17 (3H, t, J=7.1 Hz), 1.52 (3H, s), 1.55-1.63 (2H, m), 1.88-1.95 (2H, m), 2.16-2.26 (2H, m), 2.88-2.94 (2H, m), 3.38 (3H, s), 3.45-3.53 (2H, m), 3.73-3.82 (1H, m), 4.10-4.16 (1H, m), 4.70-4.82 (1H, m), 6.98-7.02 (2H, m), 7.07-7.24 (11H, m)

EXAMPLE 587

1-Ethyl-3,3,5-trimethyl-7-[3-(2-oxo-3,4-dihydro-2H-quinolin-1-yl)-pyrrolidin-1-ylmethyl]-1,5-dihydrobenzo[b][1,4]diazepine-2,4-dione The synthesis of the title compound was performed in the same manner as in EXAMPLE 584 using appropriate starting materials.

$^1$H NMR (CDCl$_3$), δppm: 0.73-0.82 (3H, m), 1.16-1.20 (3H, m), 1.51-1.53 (3H, m), 2.10-2.35 (2H, m), 2.55-3.20 (8H, m), 3.40-3.44 (3H, m), 3.61-4.16 (4H, m), 5.30-5.45 (1H, m), 6.98-7.04 (1H, m), 7.14-7.30 (5H, m), 7.65-7.68 (1H, m)

EXAMPLE 588

1-Ethyl-3,3,5-trimethyl-7-{[N-(2-methylpyridin-3-ylmethyl)-N-(2-oxo-1,2,3,4-tetrahydroquinolin-6-ylmethyl)amino]methyl}-1,5-dihydrobenzo[b][1,4]diazepine-2,4-dione The synthesis of the title compound was performed in the same manner as in EXAMPLE 30 using appropriate starting materials.

$^1$H NMR (CDCl$_3$), δppm: 0.80 (3H, s), 1.18 (3H, t, J=7.0 Hz), 1.52 (3H, s), 2.48 (3H, s), 2.62-2.65 (2H, m), 2.94-2.98 (2H, m), 3.39 (3H, s), 3.46-3.59 (6H, m), 3.76-3.82 (1H, m), 4.09-4.13 (1H, m), 6.71 (1H, d, J=8.0 Hz), 7.09-7.17 (4H, m), 7.21-7.24 (2H, m), 7.68 (1H, dd, J=1.6, 7.7 Hz), 7.91 (1H, br), 8.38 (1H, dd, J=1.7, 4.9 Hz)

EXAMPLE 589

1-Ethyl-3,3,5-trimethyl-7-{[N-(2-methylpyridin-3-ylmethyl)-N-(2-oxo-1,2,3,4-tetrahydroquinolin-7-ylmethyl)amino]methyl}-1,5-dihydrobenzo[b][1,4]diazepine-2,4-dione The synthesis of the title compound was performed in the same manner as in EXAMPLE 30 using appropriate starting materials.
$^1$H NMR (CDCl$_3$), δppm: 0.80 (3H, s), 1.18 (3H, t, J=7.0 Hz), 1.52 (3H, s), 2.50 (3H, s), 2.62-2.65 (2H, m), 2.94-2.97 (2H, m), 3.39 (3H, s), 3.49-3.61 (6H, m), 3.76-3.84 (1H, m), 4.09-4.13 (1H, m), 6.74 (1H, d, J=1.1 Hz), 6.97 (1H, dd, J=1.4, 7.7 Hz), 7.10-7.13 (2H, m), 7.16 (1H, d, J=1.1 Hz), 7.22-7.28 (2H, m), 7.70 (1H, dd, J=1.6, 7.7 Hz), 8.17 (1H, br), 8.38 (1H, dd, J=1.6, 4.9 Hz)

EXAMPLE 590

7-{[N-(1-Benzyl-2-oxo-1,2,3,4-tetrahydroquinolin-6-ylmethyl)amino]methyl}-1-ethyl-3,3,5-trimethyl-1,5-dihydrobenzo[b][1,4]diazepine-2,4-dione 1-Benzyl-2-oxo-1,2,3,4-tetrahydroquinoline-6-carbaldehyde (0.205 g) was added to a methanol solution (10 ml) of 7-(aminomethyl)-1-ethyl-3,3,5-trimethyl-1H-benzo[b][1,4]diazepine-2,4(3H,5H)-dione (0.213 g). The mixture was stirred at room temperature overnight. Sodium borohydride (0.022 g) was added to the mixture, and the mixture was stirred at room temperature overnight. The liquid was then condensed under reduced pressure, and the residue was purified by silica gel column chromatography (ethyl acetate:methanol=9:1). The purified product was condensed under reduced pressure to give the title compound(0.400 g) as a white amorphous.
$^1$H NMR (CDCl$_3$), δppm: 0.82 (3H, s), 1.17 (3H, t, J=7.1 Hz), 1.53 (3H, s), 2.77-2.81 (2H, m), 2.96-3.00 (2H, m), 3.40 (3H, s), 3.73 (2H, s), 3.74-3.83 (1H, m), 3.81 (2H, s), 4.12-4.17 (1H, m), 5.17 (2H, s), 6.83 (1H, d, J=8.3 Hz), 7.05 (1H, dd, J=1.9, 8.3 Hz), 7.16 (1H, d, J=1.6 Hz), 7.19-7.25 (6H, m), 7.27-7.33 (2H, m)

EXAMPLE 591

7-{[N-(1-Benzyl-2-oxo-1,2,3,4-tetrahydroquinolin-7-ylmethyl)amino]methyl}-1-ethyl-3,3,5-trimethyl-1,5-dihydrobenzo[b][1,4]diazepine-2,4-dione The synthesis of the title compound was performed in the same manner as in EXAMPLE 590 using appropriate starting materials.
$^1$H NMR (CDCl$_3$), δppm: 0.81 (3H, s), 1.18 (3H, t, J=7.0 Hz), 1.53 (3H, s), 2.77-2.80 (2H, m), 2.96-3.00 (2H, m), 3.38 (3H, s), 3.67 (2H, s), 3.68 (2H, s), 3.76-3.81 (1H, m), 4.12-4.18 (1H, m), 5.20 (2H, s), 6.90-6.95 (2H, m), 7.09 (1H, dd, J=1.8, 8.4 Hz), 7.12-7.14 (2H, m), 7.17-7.24 (4H, m), 7.25-7.30 (2H, m)

EXAMPLE 592

1-Cyclopropyl-7-({N-(2-methoxymethylpyridin-3-ylmethyl)-N-[2-(2-methyl-4-oxo-4H-furo[3,2-c]pyridin-5-yl)ethyl]amino}methyl)-3,3,5-trimethyl-1,5-dihydrobenzo[b][1,4]diazepine-2,4-dione The synthesis of the title compound was performed in the same manner as in EXAMPLE 30 using appropriate starting materials.
Ivory Powder
mp: 146-148° C.

EXAMPLE 593

1-(2-Methoxyethyl)-3,3,5-trimethyl-7-({N-[2-(7-methyl-4-oxo-4H-furo[3,2-c]pyridin-5-yl)ethyl]-N-(2-methylpyridin-3-ylmethyl)amino}methyl)-1,5-dihydrobenzo[b][1,4]diazepine-2,4-dione The synthesis of the title compound was performed in the same manner as in EXAMPLE 30 using appropriate starting materials.
White Powder
mp: 127-130° C.

EXAMPLE 594

1-Ethyl-3,3,5-trimethyl-7-(2-phenylpiperidin-1-ylmethyl)-1,5-dihydrobenzo[b][1,4]diazepine-2,4-dione The synthesis of the title compound was performed in the same manner as in EXAMPLE 584 using appropriate starting materials.
$^1$H NMR (CDCl$_3$), δppm: 0.78 and 0.81 (3H, s), 1.15-1.20 (3H, m), 1.33-1.47 (1H, m), 1.51-1.53 (3H, m), 1.55-1.84 (5H, m), 1.95-2.05 (1H, m), 2.83-2.97 (2H, m), 3.12-3.17 (1H, m), 3.38 and 3.41 (3H, s), 3.70-3.85 (2H, m), 4.07-4.18 (1H, m), 7.07-7.26 (4H, m), 7.30-7.36 (2H, m), 7.40-7.45 (2H, m)

EXAMPLE 595

1-Cyclopropyl-7-({N-(2-methoxymethylpyridin-3-ylmethyl)-N-[2-(7-methyl-4-oxo-4H-furo[3,2-c]pyridin-5-yl)ethyl]amino}methyl)-3,3,5-trimethyl-1,5-dihydrobenzo[b][1,4]diazepine-2,4-dione dihydrochloride The synthesis of the title compound was performed in the same manner as in EXAMPLE 4 using appropriate starting materials.
White Powder
$^1$H NMR (DMSO-d$_6$), δppm: −0.27-0.01 (1H, m), 0.43-0.46 (1H, m), 0.74 (3H, s), 0.73-0.79 (1H, m), 1.05-1.34 (1H, m), 1.34 (3H, s), 2.16 (3H, s), 2.81 (2H, br), 3.21-3.28 (1H, m), 3.28 (3H, s), 3.28 (3H, s), 3.84 (4H, br), 4.15 (2H, br), 4.55 (2H, br), 6.93 (1H, s), 7.36 (2H, br), 7.43 (2H, br), 7.77 (1H, br), 7.97 (1H, d, J=2.1 Hz), 8.38 (1H, s), 8.60 (1H, br).

EXAMPLE 596

1-(2-Methoxyethyl)-3,3,5-trimethyl-7-{[N-[2-(2-methyl-4-oxo-4H-furo[3,2-c]pyridin-5-yl)ethyl]-N-(2-methylpyridin-3-ylmethyl)amino]methyl}-1,5-dihydro-benzo[b][1,4]diazepine-2,4-dione dihydrochloride The synthesis of the title compound was performed in the same manner as in EXAMPLE 4 using appropriate starting materials.
White Powder
$^1$H NMR (DMSO-d$_6$), δppm: 0.71 (3H, s), 1.35 (3H, s), 2.43 (3H, s), 2.51 (3H, s), 2.80 (2H, br), 3.12 (3H, s), 3.29 (3H, s), 3.41 (2H, t, J=5.2 Hz), 3.83 (2H, br), 3.85-3.88 (2H, m), 4.00-4.60 (4H, m), 6.46 (1H, s), 6.23 (1H, s), 7.10-7.49 (4H, m), 7.71 (1H, br), 8.28 (1H, br), 8.56 (1H, br).

EXAMPLE 597

7-{N-(Benzo[1,3]dioxol-4-ylmethyl)-N-[2-(2-methyl-4-oxo-4H-furo[3,2-c]pyridin-5-yl)ethyl]aminomethyl}-1-ethyl-3,3,5-trimethyl-1,5-dihydrobenzo[b][1,4]diazepine-2,4-dione The synthesis of the title compound was performed in the same manner as in EXAMPLE 30 using appropriate starting materials.
White Powder
mp: 135.9-137.5° C.

EXAMPLE 598

1-Ethyl-3,3,5-trimethyl-7-{N-[3-(2-oxo-3,4-dihydro-2H-quinolin-1-ylmethyl)benzylamino]methyl}-1,5-dihydrobenzo[b][1,4]diazepine-2,4-dione The synthesis of the title compound was performed in the same manner as in EXAMPLE 3 using appropriate starting materials.
White Amorphous
$^1$H NMR (CDCl$_3$), δppm: 0.82 (3H, s), 1.18 (3H, t, J=7.1 Hz), 1.52 (3H, s), 2.77-2.83 (2H, m), 2.97-3.02 (2H, m), 3.41 (3H, s), 3.76-3.83 (5H, m), 4.10-4.18 (1H, m), 5.17 (2H, s), 6.86 (1H, d, J=8.2 Hz), 6.97 (1H, dt, J=1.0 and 7.4 Hz), 7.07-7.14 (2H, m), 7.17-7.29 (7H, m)

EXAMPLE 599

1-Ethyl-7-({N-(1H-indol-7-ylmethyl)-N-[2-(2-methyl-4-oxo-4H-furo[3,2-c]pyridin-5-yl)ethyl]amino}methyl)-3,3,5-trimethyl-1,5-dihydrobenzo[b][1,4]diazepine-2,4-dione The synthesis of the title compound was performed in the same manner as in EXAMPLE 30 using appropriate starting materials.
White Powder
$^1$H NMR (CDCl$_3$), δppm: 0.65 (3H, s), 1.08 (3H, t, J=7.1 Hz), 1.47 (3H, s), 2.48 (3H, d, J=1.0 Hz), 2.86 (2H, t, J=5.1 Hz), 3.13 (3H, s), 3.41 (2H, s), 3.61-3.72(1H, m), 3.91-4.17 (3H, m), 4.22-4.35 (1H, m), 4.35-4.43 (1H, m), 6.24 (1H, dd, J=0.62, 7.4 Hz), 6.47 (1H, dd, J=2.0, 3.0 Hz), 6.67 (1H, d, J=0.84 Hz), 6.73-6.84 (3H, m), 6.89 (1H, d, J=1.4 Hz),6.95-7.03 (2H, m), 7.17 (1H, t, J=2.8 Hz), 7.52-7.59 (1H, m), 10.51 (1H, s).

EXAMPLE 600

7-{N-(Benzo[1,3]dioxol-5-ylmethyl)-N-[2-(2-methyl-4-oxo-4H-furo[3,2-c]pyridin-5-yl)ethyl]aminomethyl}-1-ethyl-3,3,5-trimethyl-1,5-dihydrobenzo[b][1,4]diazepine-2,4-dione The synthesis of the title compound was performed in the same manner as in EXAMPLE 30 using appropriate starting materials.
White Powder
mp: 179.7-181.8° C.

EXAMPLE 601

1-Ethyl-7-({N-(1H-indol-6-ylmethyl)-N-[2-(2-methyl-4-oxo-4H-furo[3,2-c]pyridin-5-yl)ethyl]amino}methyl)-3,3,5-trimethyl-1,5-dihydro-benzo[b][1,4]diazepine-2,4-dione The synthesis of the title compound was performed in the same manner as in EXAMPLE 30 using appropriate starting materials.
White Amorphous
$^1$H NMR (CDCl$_3$), δppm: 0.76 (3H, s), 1.15 (3H, t, J=7.1 Hz), 1.50 (3H, s), 2.44 (3H, d, J=1.0 Hz), 2.86 (2H, dt, J=2.4, 5.9 Hz), 3.31 (3H, s), 3.62-3.83(5H, m), 3.98-4.18 (3H, m), 6.40 (1H, dd, J=0.70, 7.3 Hz), 6.48 (1H, t, J=0.88 Hz), 6.50-6.54(1H, m), 6.95-7.11 (4H, m), 7.15 (1H, bs), 7.19 (1H, dd, J=2.5, 3.1 Hz), 7.53 (1H, d, J=8.1 Hz), 8.10 (1H, bs).

EXAMPLE 602

7-({N-(1H-Benzoimidazol-5-ylmethyl)-N-[2-(2-methyl-4-oxo-4H-furo[3,2-c]pyridin-5-yl)ethyl]amino}methyl)-1-ethyl-3,3,5-trimethyl-1,5-dihydro-benzo[b][1,4]diazepine-2,4-dione The synthesis of the title compound was performed in the same manner as in EXAMPLE 30 using appropriate starting materials.
White Amorphous
$^1$H NMR (CDCl$_3$), δppm: 0.76 (3H, s), 1.16 (3H, t, J=7.0 Hz), 1.51 (3H, s), 2.43 (3H, d, J=0.68 Hz), 2.80-2.92 (2H, m), 3.33 (3H, s), 3.62-3.88 (5.H, m), 3.92-4.25(3H, m), 6.40 (1H, d, J=7.4 Hz), 6.47 (1H, s), 6.82-7.25 (5H, m), 7.26-7.92 (2H, m), 8.02 (1H, s), 9.38 (1H, bs).

EXAMPLE 603

1-Isobutyl-3,3-dimethyl-8-{[N-[2-(2-methyl-4-oxo-4H-furo[3,2-c]pyridin-5-yl)ethyl]-N-(2-methylpyridin-3-ylmethyl)amino]methyl}-1,5-dihydrobenzo[b][1,4]diazepine-2,4-dione The synthesis of the title compound was performed in the same manner as in EXAMPLE 30 using appropriate starting materials.
White Powder (Ethyl Acetate-Hexane-Diisopropyl Ether)
mp: 128-130° C.

EXAMPLE 604

1-Isobutyl-3,3-dimethyl-8-{[N-[2-(7-methyl-4-oxo-4H-furo[3,2-c]pyridin-5-yl)ethyl]-N-(2-methylpyridin-3-ylmethyl)amino]methyl}-1,5-dihydro-benzo[b][1,4]diazepine-2,4-dione The synthesis of the title compound was performed in the same manner as in EXAMPLE 30 using appropriate starting materials.
White Powder
mp: 206-208° C.

EXAMPLE 605

1-Isobutyl-8-({N-(2-methoxymethylpyridin-3-ylmethyl)-N-[2-(7-methyl-4-oxo-4H-furo[3,2-c]pyridin-5-yl)ethyl]amino}methyl)-3,3-dimethyl-1,5-dihydrobenzo[b][1,4]diazepine-2,4-dione The synthesis of the title compound was performed in the same manner as in EXAMPLE 30 using appropriate starting materials.
Pale Pink Powder (Ethyl Acetate-hexane-diisopropyl Ether)
  mp: 155-159° C.

EXAMPLE 606

1-Ethyl-3,3,5-trimethyl-7-({N-(3-methylimidazo[1,5-a]pyridin-1-ylmethyl)-N-[2-(2-methyl-4-oxo-4H-furo[3,2-c]pyridin-5-yl)ethyl]amino}methyl)-1,5-dihydrobenzo[b][1,4]diazepine-2,4-dione The synthesis of the title compound was performed in the same manner as in EXAMPLE 30 using appropriate starting materials.
White Powder
  mp: 104.1-109.4° C.

EXAMPLE 607

1-Cyclopropylmethyl-3,3-dimethyl-8-{[N-[2-(2-methyl-4-oxo-4H-furo[3,2-c]pyridin-5-yl)-ethyl]-N-(2-methylpyridin-3-ylmethyl)amino]methyl}-1,5-dihydrobenzo[b][1,4]diazepine-2,4-dione The synthesis of the title compound was performed in the same manner as in EXAMPLE 30 using appropriate starting materials.
Ivory Powder (Ethyl Acetate-hexane-diisopropyl Ether)
  mp: 153-155° C.

EXAMPLE 608

1-Cyclopropylmethyl-3,3-dimethyl-8-{[N-[2-(7-methyl-4-oxo-4H-furo[3,2-c]pyridin-5-yl)-ethyl]-N-(2-methylpyridin-3-ylmethyl)amino]methyl}-1,5-dihydrobenzo[b][1,4]diazepine-2,4-dione The synthesis of the title compound was performed in the same manner as in EXAMPLE 30 using appropriate starting materials.
Ivory Powder (Ether)
  mp: 207-210° C.

EXAMPLE 609

1-Cyclopropylmethyl-8-({N-(2-methoxymethylpyridin-3-ylmethyl)-N-[2-(7-methyl-4-oxo-4H-furo[3,2-c]pyridin-5-yl)ethyl]amino}methyl)-3,3-dimethyl-1,5-dihydrobenzo[b][1,4]diazepine-2,4-dione The synthesis of the title compound was performed in the same manner as in EXAMPLE 30 using appropriate starting materials.
White Powder (Ether)
  mp: 139-141° C.

EXAMPLE 610

1-Isobutyl-7-({N-(2-methoxymethylpyridin-3-ylmethyl)-N-[2-(2-methyl-4-oxo-4H-furo[3,2-c]pyridin-5-yl)ethyl]amino}methyl)-3,3,5-trimethyl-1,5-dihydrobenzo[b][1,4]diazepine-2,4-dione The synthesis of the title compound was performed in the same manner as in EXAMPLE 30 using appropriate starting materials.
Ivory Powder (Ether)
  mp: 151-152° C.

EXAMPLE 611

1-Ethyl-3,3,5-trimethyl-7-({N-[(1-methyl-1H-benzoimidazol-2-yl)methyl]-N-[2-(2-methyl-4-oxo-4H-furo[3,2-c]pyridin-5-yl)ethyl]amino}methyl)-1,5-dihydrobenzo[b][1,4]diazepine-2,4-dione The synthesis of the title compound was performed in the same manner as in EXAMPLE 30 using appropriate starting materials.
White Powder
  mp: 126.9-132.6° C.

EXAMPLE 612

1-Ethyl-3,3,5-trimethyl-7-{[N-[2-(2-methyl-4-oxo-4H-furo[3,2-c]pyridin-5-yl)ethyl]-N-(3-pyrazol-1-ylbenzyl)amino]methyl}-1,5-dihydrobenzo[b][1,4]diazepine-2,4-dione The synthesis of the title compound was performed in the same manner as in EXAMPLE 30 using appropriate starting materials.
White Amorphous
  $^1$H NMR (CDCl$_3$), δppm: 0.78 (3H, s), 1.17 (3H, t, J=7.1 Hz), 1.51 (3H, s), 2.44 (3H, d, J=1.0 Hz), 2.86 (2H, dt, J=1.8, 5.8 Hz), 3.30 (3H, s), 363-3.84 (5H, m), 3.98-4.23 (3H, m), 6.37 (1H, dd, J=0.68, 7.3 Hz), 6.49 (1H, t, J=0.88 Hz), 6.95 (1H, d, J=7.4 Hz), 7.03-7.15(3H, m), 7.16-7.26 (4H, m), 7.32 (1H, d, J=7.7 Hz), 7.32-7.37 (1H, m), 7.83 (1H, t, J=1.1 Hz).

EXAMPLE 613

1-Ethyl-3,3,5-trimethyl-7-{[N-[2-(2-methyl-4-oxo-4H-furo[3,2-c]pyridin-5-yl)ethyl]-N-(2-pyrazol-1-ylbenzyl)amino]methyl}-1,5-dihydrobenzo[b][1,4]diazepine-2,4-dione The synthesis of the title compound was performed in the same manner as in EXAMPLE 30 using appropriate starting materials.
Pale Yellow White Powder
  mp: 123-130° C.

EXAMPLE 614

1-Ethyl-3,3,5-trimethyl-7-({N-[2-(2-methyl-4-oxo-4H-furo[3,2-c]pyridin-5-yl)ethyl]pyrazin-2-ylmethylamino}methyl)-1,5-dihydro-benzo[b][1,4]diazepine-2,4-dione The synthesis of the title compound was performed in the same manner as in EXAMPLE 30 using appropriate starting materials.
White Powder
  mp: 128.7-130.7° C.

EXAMPLE 615

1-Ethyl-7-({N-(imidazo[1,2-a]pyridin-2-ylmethyl)-N-[2-(2-methyl-4-oxo-4H-furo[3,2-c]pyridin-5-yl)ethyl]amino}methyl)-3,3,5-trimethyl-1,5-dihydrobenzo[b][1,4]diazepine-2,4-dione The synthesis of the title compound was performed in the same manner as in EXAMPLE 30 using appropriate starting materials.

$^1$H NMR (CDCl$_3$), δppm: 0.76 (3H, s), 1.15 (3H, t, J=7.1 Hz), 1.50 (3H, s), 2.43 (3H, d, J=0.72 Hz), 2.91 (2H, t, J=5.5 Hz), 3.32 (3H, s), 3.69-3.85 (3H, m), 3.85-3.95 (2H, m), 3.95-4.22 (3H, m), 6.43 (1H, dd, J=0.68, 7.3 Hz), 6.48 (1H, s), 6.76 (1H, dt, J=1.1, 6.8 Hz), 7.02-7.11 (2H, m), 7.12-7.23 (3H, m), 7.32 (1H, s), 7.53 (1H, q, J=3.2 Hz), 7.95 (1H, td, J=1.1, 6.8 Hz).

EXAMPLE 616

7-{[N-(1-Benzyl-2-oxo-1,2,3,4-tetrahydroquinolin-7-ylmethyl)-N-methylamino]methyl}-1-ethyl-3,3,5-trimethyl-1,5-dihydrobenzo[b][1,4]diazepine-2,4-dione 7-{[N-(1-Benzyl-2-oxo-1,2,3,4-tetrahydroquinolin-7-ylmethyl)amino]methyl}-1-ethyl-3,3,5-trimethyl-1,5-dihydrobenzo[b][1,4]diazepine-2,4-dione (247 mg) was dissolved in DMF(2 ml), and was cooled to 0° C. in ice water bath. Sodium hydride (60% in oil, 13.56 mg) was added thereto at the same temperature, and the mixture was stirred at 0° C. for 0.5 hours. Methyl iodide (73.5 mg) was added thereto, and the mixture was stirred at room temperature for 4 hours. Water was added to the reaction mixture, followed by extraction using ethyl acetate. The organic layer was dried with sodium sulfate, and was condensed under reduced pressure. The residue was purified by silica gel column chromatography (dichloromethane: methanol=10:1). The purified product was condensed to dryness under reduced pressure to give the title compound(169 mg) as a white amorphous.

$^1$H NMR (CDCl$_3$), δppm: 0.80 (3H, s), 1.19 (3H, t, J=7.1 Hz), 1.53 (3H, s), 2.04 (3H, s), 2.75-2.8 (2H, m), 2.95-3.00 (2H, m), 3.38 (3H, s), 3.40-3.44 (4H, m), 3.75-3.85 (1H, m), 4.07-4.19 (1H, m), 5.20 (2H, s), 6.92-6.96 (2H, m), 7.07-7.14 (3H, m), 7.17-7.31 (6H, m)

EXAMPLE 617

1-Ethyl-7-({N-(2-hydroxybenzyl)-N-[2-(2-methyl-4-oxo-4H-furo[3,2-c]pyridin-5-yl)ethyl]amino}methyl)-3,3,5-trimethyl-1,5-dihydrobenzo[b][1,4]diazepine-2,4-dione The synthesis of the title compound was performed in the same manner as in EXAMPLE 30 using appropriate starting materials.

White Powder mp: 166-170° C.

EXAMPLE 618

1-Isobutyl-8-({N-(2-methoxymethylpyridin-3-ylmethyl)-N-[2-(2-methyl-4-oxo-4H-furo[3,2-c]pyridin-5-yl)ethyl]amino}methyl)-3,3-dimethyl-1,5-dihydrobenzo[b][1,4]diazepine-2,4-dione The synthesis of the title compound was performed in the same manner as in EXAMPLE 30 using appropriate starting materials.

White Powder (Ethyl Acetate-hexanes)

mp: 96-100° C.

EXAMPLE 619

1-Cyclopropylmethyl-8-({N-(2-methoxymethylpyridin-3-ylmethyl)-N-[2-(2-methyl-4-oxo-4H-furo[3,2-c]pyridin-5-yl)ethyl]amino}methyl)-3,3-dimethyl-1,5-dihydrobenzo[b][1,4]diazepine-2,4-dione The synthesis of the title compound was performed in the same manner as in EXAMPLE 30 using appropriate starting materials.

White Powder (Ethyl Acetate-hexane)

mp: 95-99° C.

EXAMPLE 620

2-({N-(1-Ethyl-3,3,5-trimethyl-2,4-dioxo-2,3,4,5-tetrahydro-1H-benzo[b][1,4]diazepin-7-ylmethyl)-N-[2-(2-methyl-4-oxo-4H-furo[3,2-c]pyridin-5-yl)ethyl]amino}methyl)benzonitrile The synthesis of the title compound was performed in the same manner as in EXAMPLE 30 using appropriate starting materials.

White Powder mp: 156.7-158.6° C.

EXAMPLE 621

4-({N-(1-Ethyl-3,3,5-trimethyl-2,4-dioxo-2,3,4,5-tetrahydro-1H-benzo[b][1,4]diazepin-7-ylmethyl)-N-[2-(2-methyl-4-oxo-4H-furo[3,2-c]pyridin-5-yl)ethyl]amino}methyl)benzaldehyde A 2N-hydrochloric acid (5 ml) was added to an THF solution (5 ml) of 7-({N-(4-diethoxymethylbenzyl)-N-[2-(2-methyl-4-oxo-4H-furo[3,2-c]pyridin-5-yl)ethyl]amino}methyl)-1-ethyl-3,3,5-trimethyl-1,5-dihydro-benzo[b][1,4]diazepine-2,4-dione (0.52 g), and the mixture was stirred at room temperature for 1 hour. 2N-Sodium hydroxide solution(5 ml) was added to the reaction mixture, followed by extraction using ethyl acetate. The organic layer was dried with sodium sulfate, and was condensed under reduced pressure. The residue was purified by silica gel column chromatography (ethyl acetate). The purified product was condensed under reduced pressure. The residue was recrystallized from ethyl acetate and ether, and dried to give the title compound (0.35 g) as a white powder.

mp: 153-155° C.

EXAMPLE 622

1-Ethyl-7-({N-(2-methoxymethylpyridin-3-ylm-ethyl)-N-[2-(2-oxo-2H-quinolin-1-yl)ethyl]amino}methyl)-3,3,5-trimethyl-1,5-dihydrobenzo[b][1,4]diazepine-2,4-dione The synthesis of the title compound was performed in the same manner as in EXAMPLE 30 using appropriate starting materials.
White Powder
mp: 152-153° C.

EXAMPLE 623

1-Ethyl-7-({N-(6-methoxy-2-methylpyridin-3-ylm-ethyl)-N-[2-(2-oxo-2H-quinolin-1-yl)ethyl]amino}methyl)-3,3,5-trimethyl-1,5-dihydro-benzo[b][1,4]diazepine-2,4-dione The synthesis of the title compound was performed in the same manner as in EXAMPLE 30 using appropriate starting materials.
White Powder
mp: 143-144° C.

EXAMPLE 624

1-Ethyl-7-({N-(2-methoxymethylpyridin-3-ylm-ethyl)-N-[2-(2-oxo-3,4-dihydro-2H-quinolin-1-yl)ethyl]amino}methyl)-3,3,5-trimethyl-1,5-dihy-drobenzo[b][1,4]diazepine-2,4-dione The synthesis of the title compound was performed in the same manner as in EXAMPLE 30 using appropriate starting materials.
White Powder
mp: 112-114° C.

EXAMPLE 625

1,3,3-Trimethyl-8-{[N-[2-(2-methyl-4-oxo-4H-furo[3,2-c]pyridin-5-yl)ethyl]-N-(2-methyl-pyridin-3-ylmethyl)amino]methyl}-1,5-dihydro-benzo[b][1,4]diazepine-2,4-dione The synthesis of the title compound was performed in the same manner as in EXAMPLE 30 using appropriate starting materials.
Ivory Powder (Ether)
mp: 117-122° C.

EXAMPLE 626

1,3,3-Trimethyl-8-{[N-[2-(7-methyl-4-oxo-4H-furo[3,2-c]pyridin-5-yl)ethyl]-N-(2-methylpyridin-3-ylmethyl)amino]methyl}-1,5-dihydrobenzo[b][1,4]diazepine-2,4-dione The synthesis of the title compound was performed in the same manner as in EXAMPLE 30 using appropriate starting materials.
White Powder (Ether)
mp: 154-157° C.

EXAMPLE 627

1-Ethyl-3,3-dimethyl-8-{[N-[2-(2-methyl-4-oxo-4H-furo[3,2-c]pyridin-5-yl)ethyl]-N-(2-methylpyridin-3-ylmethyl)amino]methyl}-1,5-dihydrobenzo[b][1,4]diazepine-2,4-dione The synthesis of the title compound was performed in the same manner as in EXAMPLE 30 using appropriate starting materials.
White Powder (Ether)
mp: 108-114° C.

EXAMPLE 628

1-Ethyl-3,3-dimethyl-8-{[N-[2-(7-methyl-4-oxo-4H-furo[3,2-c]pyridin-5-yl)ethyl]-N-(2-methylpyridin-3-ylmethyl)amino]methyl}-1,5-dihydrobenzo[b][1,4]diazepine-2,4-dione The synthesis of the title compound was performed in the same manner as in EXAMPLE 30 using appropriate starting materials.
White Powder (Ether)
mp: 177-179° C.

EXAMPLE 629

1-Ethyl-7-({N-(6-methoxy-2-methylpyridin-3-ylm-ethyl)-N-[2-(2-methyl-4-oxo-4H-furo[3,2-c]pyridin-5-yl)ethyl]amino}methyl)-3,3,5-trimethyl-1,5-dihy-drobenzo[b][1,4]diazepine-2,4-dione The synthesis of the title compound was performed in the same manner as in EXAMPLE 30 using appropriate starting materials.
White Powder
mp: 155-156° C.

EXAMPLE 630

1,3,3-Trimethyl-7-{[N-[2-(2-methyl-4-oxo-4H-furo[3,2-c]pyridin-5-yl)ethyl]-N-(2-methyl-pyridin-3-ylmethyl)amino]methyl}-1,5-dihydrobenzo[b][1,4]diazepine-2,4-dione The synthesis of the title compound was performed in the same manner as in EXAMPLE 30 using appropriate starting materials.
White Powder (Ether)
mp: 176-178° C.

EXAMPLE 631

1,3,3-Trimethyl-7-{[N-[2-(7-methyl-4-oxo-4H-furo[3,2-c]pyridin-5-yl)ethyl]-N-(2-methylpyridin-3-ylmethyl)amino]methyl}-1,5-dihydrobenzo[b][1,4]diazepine-2,4-dione The synthesis of the title compound was performed in the same manner as in EXAMPLE 30 using appropriate starting materials.
Pale Pink Powder (Ether)
mp: 142-144° C.

EXAMPLE 632

1-Ethyl-3,3-dimethyl-7-{[N-[2-(2-methyl-4-oxo-4H-furo[3,2-c]pyridin-5-yl)ethyl]-N-(2-methylpyridin-3-ylmethyl)amino]methyl}-1,5-dihydrobenzo[b][1,4]diazepine-2,4-dione The synthesis of the title compound was performed in the same manner as in EXAMPLE 30 using appropriate starting materials.
White Powder (Ether)
mp: 213-215° C.

EXAMPLE 633

1-Ethyl-3,3-dimethyl-7-{[N-[2-(7-methyl-4-oxo-4H-furo[3,2-c]pyridin-5-yl)ethyl]-N-(2-methylpyridin-3-ylmethyl)amino]methyl}-1,5-dihydrobenzo[b][1,4]diazepine-2,4-dione The synthesis of the title compound was performed in the same manner as in EXAMPLE 30 using appropriate starting materials.
White Powder (Ether)
mp: 197-199° C.

EXAMPLE 634

1-Ethyl-3,3,5-trimethyl-7-({N-[2-(2-methyl-4-oxo-4H-furo[3,2-c]pyridin-5-yl)ethyl]-N-(pyridazin-4-ylmethyl)amino}methyl)-1,5-dihydrobenzo[b][1,4]diazepine-2,4-dione The synthesis of the title compound was performed in the same manner as in EXAMPLE 30 using appropriate starting materials.
White Powder
mp: 137-141° C.

EXAMPLE 635

1-Ethyl-3,3,5-trimethyl-7-({[N-(1-methyl-1H-indazol-3-yl)methyl]-N-[2-(2-methyl-4-oxo-4H-furo[3,2-c]pyridin-5-yl)ethyl]amino}methyl)-1,5-dihydrobenzo[b][1,4]diazepine-2,4-dione The synthesis of the title compound was performed in the same manner as in EXAMPLE 30 using appropriate starting materials.
White Powder
mp: 96-102° C.

EXAMPLE 636

1-Ethyl-3,3,5-trimethyl-7-({N-(7-methyl-1H-indazol-3-ylmethyl)-N-[2-(2-methyl-4-oxo-4H-furo[3,2-c]pyridin-5-yl)ethyl]amino}methyl)-1,5-dihydrobenzo[b][1,4]diazepine-2,4-dione The synthesis of the title compound was performed in the same manner as in EXAMPLE 30 using appropriate starting materials.
White Powder
mp: 111-118° C.

EXAMPLE 637

1-Ethyl-3,3,5-trimethyl-7-(3-{N-(2-methylpyridin-3-ylmethyl)-N-[2-(1-oxo-1H-isoquinolin-2-yl)ethyl]amino}propyl)-1,5-dihydro-benzo[b][1,4]diazepine-2,4-dione dihydrochloride The synthesis of the title compound was performed in the same manner as in EXAMPLE 4 using appropriate starting materials.
$^1$H NMR (DMSO-$d_6$), δppm: 0.70 (3H, s), 1.04 (3H, t, J=7.0 Hz), 1.32 (3H, s), 2.62-4.68 (20H, m), 6.69-8.75 (12H, m),

EXAMPLE 638

1-Ethyl-3,3,5-trimethyl-7-(3-{N-(2-methylpyridin-3-ylmethyl)-N-[2-(4-oxo-4H-furo[3,2-c]pyridin-5-yl)ethyl]amino}propyl)-1,5-dihydrobenzo[b][1,4]diazepine-2,4-dione The synthesis of the title compound was performed in the same manner as in EXAMPLE 30 using appropriate starting materials.
White Powder
mp: 150.9-154.7° C.

EXAMPLE 639

1-Ethyl-3,3,5-trimethyl-7-{3-[N-(2-methylpyridin-3-ylmethyl)-N-(2-pyridin-3-ylethyl)amino]propyl}-1,5-dihydrobenzo[b][1,4]diazepine-2,4-dione trihydrochloride The synthesis of the title compound was performed in the same manner as in EXAMPLE 4 using appropriate starting materials.
$^1$H NMR (DMSO-$d_6$), δppm: 0.72 (3H, s), 1.04 (3H, t, J=7.0 Hz), 1.33 (3H, s), 2.09-3.79 (18H, m), 4.65 (2H, br-s), 7.22(1H, d, J=8.0 Hz), 7.33 (1H, s), 7.43 (1H, d, J=8.4 Hz), 7.83 (1H, t, J=6.6 Hz), 7.93-7.97 (1H, m), 8.44 (1H, d, J=7.5 Hz), 8.76-8.80 (3H, m), 8.90 (1H, s)

EXAMPLE 640

1-Ethyl-3,3,5-trimethyl-7-(3-{N-(2-methylpyridin-3-ylmethyl)-N-[2-(7-oxo-7H-furo[2,3-c]pyridin-6-yl)ethyl]amino}propyl)-1,5-dihydrobenzo[b][1,4]diazepine-2,4-dione The synthesis of the title compound was performed in the same manner as in EXAMPLE 30 using appropriate starting materials.
White Powder
mp: 106.4-114.6° C.

EXAMPLE 641

1-Ethyl-3,3,5-trimethyl-7-{[N-[2-(2-methyl-4-oxo-4H-furo[3,2-c]pyridin-5-yl)ethyl]-N-(2-methyl-2H-pyrazol-3-ylmethyl)amino]methyl}-1,5-dihydrobenzo[b][1,4]diazepine-2,4-dione The synthesis of the title compound was performed in the same manner as in EXAMPLE 30 using appropriate starting materials.

White Powder
mp: 128.2-130.9° C.

EXAMPLE 642

1-Ethyl-7-({N-(2-methoxymethylpyridin-3-ylmethyl)-N-[2-(2-methyl-4-oxo-4H-furo[3,2-c]pyridin-5-yl)ethyl]amino}methyl)-3,3-dimethyl-1,5-dihydrobenzo[b][1,4]diazepine-2,4-dione The synthesis of the title compound was performed in the same manner as in EXAMPLE 30 using appropriate starting materials.
White Powder (Ether)
mp: 171-173° C.

EXAMPLE 643

1-Ethyl-7-({N-(2-methoxymethylpyridin-3-ylmethyl)-N-[2-(7-methyl-4-oxo-4H-furo[3,2-c]pyridin-5-yl)ethyl]amino}methyl)-3,3-dimethyl-1,5-dihydrobenzo[b][1,4]diazepine-2,4-dione The synthesis of the title compound was performed in the same manner as in EXAMPLE 30 using appropriate starting materials.
White Powder (Ether)
mp: 168-170° C.

EXAMPLE 644

8-({N-(2-Methoxymethylpyridin-3-ylmethyl)-N-[2-(2-methyl-4-oxo-4H-furo[3,2-c]pyridin-5-yl)ethyl]amino}methyl)-1,3,3-trimethyl-1,5-dihydrobenzo[b][1,4]diazepine-2,4-dione The synthesis of the title compound was performed in the same manner as in EXAMPLE 30 using appropriate starting materials.
White Powder (Ether)
mp: 179-182° C.

EXAMPLE 645

8-({N-(2-Methoxymethylpyridin-3-ylmethyl)-N-[2-(7-methyl-4-oxo-4H-furo[3,2-c]pyridin-5-yl)ethyl]amino}methyl)-1,3,3-trimethyl-1,5-dihydrobenzo[b][1,4]diazepine-2,4-dione The synthesis of the title compound was performed in the same manner as in EXAMPLE 30 using appropriate starting materials.
White Powder (Ether)
mp: 123-134° C.

EXAMPLE 646

5-Cyclopropylmethyl-1-(2-methoxyethyl)-3,3-dimethyl-7-{[N-[2-(7-methyl-4-oxo-4H-furo[3,2-c]pyridin-5-yl)ethyl]-N-(2-methylpyridin-3-ylmethyl)amino]methyl}-1,5-dihydrobenzo[b][1,4]diazepine-2,4-dione The synthesis of the title compound was performed in the same manner as in EXAMPLE 30 using appropriate starting materials.
White Powder (Ether)
mp: 159-160° C.

EXAMPLE 647

5-Cyclopropylmethyl-1-(2-methoxyethyl)-7-({N-(2-methoxymethylpyridin-3-ylmethyl)-N-[2-(7-methyl-4-oxo-4H-furo[3,2-c]pyridin-5-yl)ethyl]amino}methyl)-3,3-dimethyl-1,5-dihydrobenzo[b][1,4]diazepine-2,4-dione The synthesis of the title compound was performed in the same manner as in EXAMPLE 30 using appropriate starting materials.
White Powder (Ether)
mp: 131-135° C.

EXAMPLE 648

7-[2-(4-Chlorophenyl)pyrrolidin-1-ylmethyl]-1-ethyl-3,3,5-trimethyl-1,5-dihydrobenzo[b][1,4]diazepine-2,4-dione The synthesis of the title compound was performed in the same manner as in EXAMPLE 584 using appropriate starting materials.
$^1$H NMR (CDCl$_3$), δppm: 0.79 and 0.80 (3H, s), 1.16 (3H, t, J=7.1 Hz), 1.52 (3H, s), 1.65-1.98 (3H, m), 2.15-2.30 (2H, m), 3.05-3.17 (2H, m), 3.35-3.45 (4H, m), 3.70-3.83 (2H, m), 4.08-4.18 (1H, m), 7.06-7.23 (3H, m), 7.27-7.32 (2H, m), 7.34-7.38 (2H, m)

EXAMPLE 649

7-(3-Benzylpiperidin-1-ylmethyl)-1-ethyl-3,3,5-trimethyl-1,5-dihydrobenzo[b][1,4]diazepine-2,4-dione The synthesis of the title compound was performed in the same manner as in EXAMPLE 584 using appropriate starting materials.
$^1$H NMR (CDCl$_3$), δppm: 0.77 and 0.79 (3H, s), 0.97-2.10 (5H, m), 1.18 (3H, t, J=7.1 Hz), 1.52 (3H, s), 2.45-2.55 (2H, m), 2.80-2.90 (2H, m), 3.35 and 3.40 (3H, s), 3.41-3.60 (4H, m), 3.75-3.85 (1H, m), 4.10-4.20 (1H, m), 7.08-7.26 (8H, m)

EXAMPLE 650

1-Ethyl-3,3,5-trimethyl-7-(2-phenylazetidin-1-ylmethyl)-1,5-dihydrobenzo[b][1,4]diazepine-2,4-dione The synthesis of the title compound was performed in the same manner as in EXAMPLE 584 using appropriate starting materials.
$^1$H NMR (CDCl$_3$), δppm: 0.70 and 0.71 (3H, s), 1.10-1.15 (3H, m), 1.50 (3H, s), 2.10-2.20 (1H, m), 2.32-2.40 (1H, m), 2.90-3.01 (1H, m), 3.26 and 3.32 (3H, s), 3.41-3.46 (1H, m), 3.58-3.78 (3H, m), 4.07-4.17 (2H, m), 7.07-7.21 (4H, m), 7.22-7.28 (2H, m), 7.33-7.38 (2H, m)

EXAMPLE 651

1-Ethyl-3,3,5-trimethyl-7-(6-methyl-3',4',5',6'-tetrahydro-2'H-[2,3']bipyridinyl-1'-ylmethyl)-1,5-dihydrobenzo[b][1,4]diazepine-2,4-dione The synthesis of the title compound was performed in the same manner as in EXAMPLE 584 using appropriate starting materials.

¹H NMR (CDCl₃), δppm: 0.81 and 0.82 (3H, s), 1.19 (3H, t, J=7.1 Hz), 1.53 (3H, s), 1.54-1.83 (3H, m), 1.95-2.02 (1H, m), 2.03-2.14 (1H, m), 2.18-2.26 (1H, m), 2.51 (3H, s), 2.81-2.90 (1H, m), 2.95-3.10 (2H, m), 3.41 and 3.42 (3H, s), 3.50-3.60 (2H, m), 3.75-3.85 (1H, m), 4.08-4.17 (1H, m), 6.95-6.98 (2H, m), 7.21-7.24 (3H, m), 7.45-7.50 (1H, m)

EXAMPLE 652

7-(2-Benzylpyrrolidin-1-ylmethyl)-1-ethyl-3,3,5-trimethyl-1,5-dihydrobenzo[b][1,4]diazepine-2,4-dione The synthesis of the title compound was performed in the same manner as in EXAMPLE 584 using appropriate starting materials.
¹H NMR (CDCl₃), δppm: 0.83 (3H, s), 1.18 (3H, t, J=7.1 Hz), 1.53 (3H, s), 1.53-1.83 (4H, m), 2.15-2.25 (1H, m), 2.53-2.63 (1H, m), 2.68-2.76 (1H, m), 2.88-3.06 (2H, m), 3.26-3.35 (1H, m), 3.42 and 3.43 (3H, s), 3.75-3.85 (1H, m), 4.03-4.20 (2H, m), 7.17-7.30 (8H, m)

EXAMPLE 653

1-Ethyl-3,3,5-trimethyl-7-[(2-phenoxypyridin-3-ylamino)methyl]-1,5-dihydrobenzo[b][1,4]diazepine-2,4-dione The synthesis of the title compound was performed in the same manner as in EXAMPLE 584 using appropriate starting materials.
White Amorphous
¹H NMR (CDCl₃), δppm: 0.84 (3H, s), 1.20 (3H, t, J=7.1 Hz), 1.53 (3H, s), 3.39 (3H, s), 3.75-3.85 (1H, m), 4.09-4.19 (1H, m), 4.45 (2H, d, J=5.8 Hz), 4.89 (1H, t, J=5.8 Hz), 6.80 (1H, dd, J=1.7 and 7.8 Hz), 6.85 (1H, dd, J=4.8 and 7.8 Hz), 7.13-7.23 (3H, m), 7.24-7.34 (3H, m), 7.38-7.43 (2H, m), 7.51 (1H, dd, J=1.7 and 4.8 Hz)

EXAMPLE 654

7-[(1-Benzyl-1H-pyrazol-4-ylamino)methyl]-1-ethyl-3,3,5-trimethyl-1,5-dihydrobenzo[b][1,4]diazepine-2,4-dione The synthesis of the title compound was performed in the same manner as in EXAMPLE 584 using appropriate starting materials.
Pale Brown Amorphous
¹H NMR (CDCl₃), δppm: 0.79 (3H, s), 1.17 (3H, t, J=7.0 Hz), 1.51 (3H, s), 3.36 (3H, s), 3.75-3.82 (1H, m), 4.08-4.15 (1H, m), 4.17 (2H, s), 5.18 (2H, s), 6.85 (1H, d, J=0.8 Hz), 7.15-7.20 (3H, m), 7.21-7.35 (6H, m)

EXAMPLE 655

7-[(3-Benzyloxypyrazin-2-ylamino)methyl]-1-ethyl-3,3,5-trimethyl-1,5-dihydrobenzo[b][1,4]diazepine-2,4-dione The synthesis of the title compound was performed in the same manner as in EXAMPLE 584 using appropriate starting materials.
Pale Yellow Amorphous
¹H NMR (CDCl₃), δppm: 0.82 (3H, s), 1.17 (3H, t, J=7.1 Hz), 1.52 (3H, s), 3.37 (3H, s), 3.75-3.83 (1H, m), 4.07-4.15 (1H, m), 4.68 (2H, d, J=6.1 Hz), 5.41 (2H, s), 5.46 (1H, t, J=6.1 Hz), 7.20-7.25 (3H, m), 7.35-7.43 (4H, m), 7.44-7.47 (2H, m), 7.61 (1H, d, J=3.2 Hz)

EXAMPLE 656

1-Ethyl-3,3,5-trimethyl-7-(3-phenethylpiperidin-1-ylmethyl)-1,5-dihydrobenzo[b][1,4]diazepine-2,4-dione The synthesis of the title compound was performed in the same manner as in EXAMPLE 584 using appropriate starting materials.
¹H NMR (CDCl₃), δppm: 0.82 and 0.83 (3H, s), 0.90-1.00 (1H, m), 1.19 (3H, t, J=7.1 Hz), 1.50-1.75 (6H, m), 1.53 (3H, s), 1.80-1.88 (1H, m), 1.90-2.00 (1H, m), 2.50-2.60 (2H, m), 2.71-2.84 (2H, m), 3.40 and 3.41 (3H, s), 3.45-3.52 (2H, m), 3.75-3.85 (1H, m), 4.10-4.20 (1H, m), 7.10-7.30 (8H, m)

EXAMPLE 657

1-Ethyl-3,3,5-trimethyl-7-[(4-phenoxymethylthiazol-2-ylamino)methyl]-1,5-dihydrobenzo[b][1,4]diazepine-2,4-dione The synthesis of the title compound was performed in the same manner as in EXAMPLE 584 using appropriate starting materials.
White Amorphous
¹H NMR (CDCl₃), δppm: 0.83 (3H, s), 1.19 (3H, t, J=7.1 Hz), 1.53 (3H, s), 3.39 (3H, s), 3.76-3.85 (1H, m), 4.09-4.19 (1H, m), 4.53 (2H, d, J=5.0 Hz), 5.04 (2H, s), 5.69 (1H, brs), 6.54 (1H, s), 6.95-7.00 (3H, m), 7.23-7.32 (5H, m)

EXAMPLE 658

1-Ethyl-3,3,5-trimethyl-7-[2-(4-trifluoromethylphenyl)pyrrolidin-1-ylmethyl]-1,5-dihydrobenzo[b][1,4]diazepine-2,4-dione The synthesis of the title compound was performed in the same manner as in EXAMPLE 584 using appropriate starting materials.
¹H NMR (CDCl₃), δppm: 0.79 and 0.80 (3H, s), 1.16 (3H, t, J=7.0 Hz), 1.52 (3H, s), 1.68-2.00 (3H, m), 2.20-2.32 (2H, m), 3.10-3.23 (2H, m), 3.39 (3H, s), 3.47-3.51 (1H, m), 3.70-3.82 (2H, m), 4.09-4.16 (1H, m), 7.07-7.23 (3H, m), 7.53-7.62 (4H, m)

EXAMPLE 659

7-[2-(2-Chlorophenyl)pyrrolidin-1-ylmethyl]-1-ethyl-3,3,5-trimethyl-1,5-dihydrobenzo[b][1,4]diazepine-2,4-dione The synthesis of the title compound was performed in the same manner as in EXAMPLE 584 using appropriate starting materials.
¹H NMR (CDCl₃), δppm: 0.79 and 0.80 (3H, s), 1.16 (3H, t, J=7.1 Hz), 1.52 (3H, s), 1.55-1.70 (1H, m), 1.75-1.95 (2H, m), 2.28-2.45 (2H, m), 3.12-3.18 (1H, m), 3.25-3.30 (1H, m), 3.39 and 3.40 (3H, s), 3.71-3.85 (2H, m), 3.92-4.00 (1H, m), 4.09-4.20 (1H, m), 7.11-7.22 (4H, m), 7.24-7.34 (2H, m), 7.73-7.78 (1H, m)

EXAMPLE 660

7-[2-(3-Chlorophenyl)pyrrolidin-1-ylmethyl]-1-ethyl-3,3,5-trimethyl-1,5-dihydrobenzo[b][1,4]diazepine-2,4-dione The synthesis of the title compound was performed in the same manner as in EXAMPLE 584 using appropriate starting materials.

$^1$H NMR (CDCl$_3$), δppm: 0.80 (3H, s), 1.14-1.19 (3H, m), 1.52 (3H, s), 1.65-2.00 (3H, m), 2.17-2.31 (2H, m), 3.06-3.22 (2H, m), 3.35-3.44 (4H, m), 3.73-3.81 (2H, m), 4.08-4.16 (1H, m), 7.06-7.30 (6H, m), 7.43-7.47 (1H, m)

EXAMPLE 661

5-Cyclopropylmethyl-1-(2-methoxyethyl)-3,3-dimethyl-7-{[N-[2-(2-methyl-4-oxo-4H-furo[3,2-c]pyridin-5-yl)ethyl]-N-(2-methylpyridin-3-ylmethyl)amino]methyl}-1,5-dihydrobenzo[b][1,4]diazepine-2,4-dione The synthesis of the title compound was performed in the same manner as in EXAMPLE 30 using appropriate starting materials.

White Powder (Diisopropyl Ether)

mp: 127-128° C.

EXAMPLE 662

1-Cyclopropylmethyl-5-(2-methoxyethyl)-3,3-dimethyl-7-{[N-[2-(2-methyl-4-oxo-4H-furo[3,2-c]pyridin-5-yl)ethyl]-N-(2-methylpyridin-3-ylmethyl)amino]methyl}-1,5-dihydrobenzo[b][1,4]diazepine-2,4-dione The synthesis of the title compound was performed in the same manner as in EXAMPLE 30 using appropriate starting materials.

White Powder (Ether)

mp: 131° C.

EXAMPLE 663

1-Cyclopropylmethyl-5-(2-methoxyethyl)-3,3-dimethyl-7-{[N-[2-(7-methyl-4-oxo-4H-furo[3,2-c]pyridin-5-yl)ethyl]-N-(2-methylpyridin-3-ylmethyl)amino]methyl}-1,5-dihydrobenzo[b][1,4]diazepine-2,4-dione The synthesis of the title compound was performed in the same manner as in EXAMPLE 30 using appropriate starting materials.

White Powder (Ether)

mp: 146-148° C.

EXAMPLE 664

1-Cyclopropylmethyl-5-(2-methoxyethyl)-7-({N-(2-methoxymethylpyridin-3-ylmethyl)-N-[2-(7-methyl-4-oxo-4H-furo[3,2-c]pyridin-5-yl)ethyl]amino}methyl)-3,3-dimethyl-1,5-dihydrobenzo[b][1,4]diazepine-2,4-dione The synthesis of the title compound was performed in the same manner as in EXAMPLE 30 using appropriate starting materials.

White Powder (Ether)

mp: 128-129° C.

EXAMPLE 665

Acetic acid 3-({N-(1-ethyl-3,3,5-trimethyl-2,4-dioxo-2,3,4,5-tetrahydro-1H-benzo[b][1,4]diazepin-7-ylmethyl)-N-[2-(2-methyl-4-oxo-4H-furo[3,2-c]pyridin-5-yl)ethyl]amino}methyl)pyridin-2-ylmethyl ester The synthesis of the title compound was performed in the same manner as in EXAMPLE 30 using appropriate starting materials.

$^1$H NMR (CDCl$_3$), δppm: 0.78 (3H, s), 1.16 (3H, t, J=7.1 Hz), 1.51 (3H, s), 2.09 (3H, s), 2.43 (1H, d, J=0.96 Hz), 2.84 (2H, t, J=6.4 Hz), 3.35 (3H, s), 3.66-3.80 (5H m), 4.02-4.15 (3H, m), 5.16 (2H, s), 6.40 (1H, d, J=7.3 Hz), 6.50 (1H, br), 6.88 (1H, d, J=7.3 Hz), 7.07-7.19 (4H, m), 7.58 (1H, dd, J=7.8, 1.6 Hz), 8.46 (1H, dd, J=4.8, 1.6 Hz).

EXAMPLE 666

1-Ethyl-7-({N-(2-hydroxymethylpyridin-3-ylmethyl)-N-[2-(2-methyl-4-oxo-4H-furo[3,2-c]pyridin-5-yl)ethyl]amino}methyl)-3,3,5-trimethyl-1,5-dihydrobenzo[b][1,4]diazepine-2,4-dione Potassium carbonate (2.0 g) was added to a methanol solution (30 mL) of (3-((((1-ethyl-3,3,5-trimethyl-2,4-dioxo-2,3,4,5-tetrahydro-1H-benzo[b][1,4]diazepin-7-yl)methyl)(2-(2-methyl-4-oxofuro[3,2-c]pyridin-5(4H)-yl)ethyl)amino)methyl)pyridin-2-yl)methyl acetate (3.0 g) and the mixture was stirred overnight at room temperature. The resulting mixture was filtered and evaporated. The residue was purified by column-chromatography (methanol: ethyl acetate=0:100→1:9) to give the titled compound as ivory powder (1.95 g).

mp: 186-188° C.

EXAMPLE 667

5-Cyclopropyl-1-cyclopropylmethyl-7-({N-(2-methoxymethylpyridin-3-ylmethyl)-N-[2-(7-methyl-4-oxo-4H-furo[3,2-c]pyridin-5-yl)ethyl]amino}methyl)-3,3-dimethyl-1,5-dihydro-benzo[b][1,4]diazepine-2,4-dione The synthesis of the title compound was performed in the same manner as in EXAMPLE 30 using appropriate starting materials.

White Powder (Ethyl Acetate-hexane)

mp: 121-122° C.

EXAMPLE 668

1-Ethyl-3,3,5-trimethyl-7-{3-[N-[2-(2-methyl-4-oxo-4H-furo[3,2-c]pyridin-5-yl)ethyl]-N-(2-methylpyridin-3-ylmethyl)amino]propyl}-1,5-dihydrobenzo[b][1,4]diazepine-2,4-dione The synthesis of the title compound was performed in the same manner as in EXAMPLE 30 using appropriate starting materials.
White Powder
mp: 134.7-134.8° C.

EXAMPLE 669

3-({N-(1-Ethyl-3,3,5-trimethyl-2,4-dioxo-2,3,4,5-tetrahydro-1H-benzo[b][1,4]diazepin-7-ylmethyl)-N-[2-(2-methyl-4-oxo-4H-furo[3,2-c]pyridin-5-yl)ethyl]amino}methyl)pyridine-2-carbaldehyde 2-iodoxybenzoic acid (IBX, 0.235 g) was added to the dimethyl sulfoxide suspension (10 mL) of 1-ethyl-7-((N-((2-(hydroxymethyl)pyridin-3-yl)methyl)-N-(2-(2-methyl-4-oxofuro[3,2-c]pyridin-5(4H)-yl)ethyl)amino)methyl)-3,3,5-trimethyl-1H-benzo[b][1,4]diazepine-2,4(3H,5H)-dione (0.48 g) and the mixture was stirred overnight at room temperature. Water was added to the resulting mixture and then the mixture was extracted with ethyl acetate twice. The combined organic layer was concentrated under reduced pressure, and then the residue was purified by column-chromatography (ethyl acetate: hexanes=50:50→100:0). The purified product was recrystallized from ether to afford the titled compound as ivory powder (0.29 g).
mp: 147-149° C.

EXAMPLE 670

1-Ethyl-3,3,5-trimethyl-7-{[(1-methyl-2-oxo-1,2,3,4-tetrahydro-quinolin-7-ylmethyl)amino]methyl}-1,5-dihydrobenzo[b][1,4]diazepine-2,4-dione Trifluoroacetic acid (43.2 mg) was added to a dichloromethane solution (5 ml) of N-(1-ethyl-3,3,5-trimethyl-2,4-dioxo-2,3,4,5-tetrahydro-1H-benzo[b][1,4]diazepin-7-ylmethyl)-N-(1-methyl-2-oxo-1,2,3,4-tetrahydro-quinolin-7-ylmethyl)carbamic acid tert-butyl ester (208 mg), and the mixture was stirred at room temperature overnight. A saturated sodium bicarbonate solution was added to the reaction mixture, followed by extraction using dichloromethane, and condensed under reduced pressure to give the title compound (148 mg) as a white amorphous.
$^1$H NMR (CDCl$_3$), δppm: 0.83 (3H, s), 1.18 (3H, t, J=7.1 Hz), 1.53 (3H, s), 2.62-2.67 (2H, m), 2.86-2.93 (2H, m), 3.37 (3H, s), 3.42 (3H, s), 3.75-3.86 (5H, m), 4.10-4.17 (1H, m), 6.97-7.02 (2H, m), 7.12-7.15 (1H, m), 7.22-7.29 (3H, m)

EXAMPLE 671

1-Ethyl-3,3,5-trimethyl-7-{[(2-oxo-1-pyridin-4-ylmethyl-1,2,3,4-tetrahydro-quinolin-7-ylmethyl)amino]methyl}-1,5-dihydrobenzo[b][1,4]diazepine-2,4-dione The synthesis of the title compound was performed in the same manner as in EXAMPLE 670 using appropriate starting materials.
$^1$H NMR (CDCl$_3$), δppm: 0.80 (3H, s), 1.18 (3H, t, J=7.1 Hz), 1.52 (3H, s), 2.75-2.81 (2H, m), 2.95-3.02 (2H, m), 3.38 (3H, s), 3.69-3.73 (4H, m), 3.75-3.83 (1H, m), 4.09-4.16 (1H, m), 5.20 (2H, s), 6.78 (1H, brs), 6.96 (1H, dd, J=1.2 and 7.6 Hz), 7.08 (1H, dd, J=1.9 and 8.4 Hz), 7.11-7.18 (4H, m), 7.23 (1H, d, J=8.4 Hz), 8.50-8.53 (2H, m)

EXAMPLE 672

7-({N-(3-Aminopyridin-2-ylmethyl)-N-[2-(2-methyl-4-oxo-4H-furo[3,2-c]pyridin-5-yl)ethyl]amino}methyl)-1-ethyl-3,3,5-trimethyl-1,5-dihydrobenzo[b][1,4]diazepine-2,4-dione The synthesis of the title compound was performed in the same manner as in EXAMPLE 30 using appropriate starting materials.
Ivory Powder
mp: 217-218° C.

EXAMPLE 673

7-({N-(3-Aminopyridin-2-ylmethyl)-N-[2-(7-methyl-4-oxo-4H-furo[3,2-c]pyridin-5-yl)ethyl]amino}methyl)-1-ethyl-3,3,5-trimethyl-1,5-dihydrobenzo[b][1,4]diazepine-2,4-dione The synthesis of the title compound was performed in the same manner as in EXAMPLE 30 using appropriate starting materials.
White Powder
mp: 188-192° C.

EXAMPLE 674

7-({N-(2-Diethoxymethylbenzyl)-N-[2-(2-methyl-4-oxo-4H-furo[3,2-c]pyridin-5-yl)ethyl]amino}methyl)-1-ethyl-3,3,5-trimethyl-1,5-dihydro-benzo[b][1,4]diazepine-2,4-dione The synthesis of the title compound was performed in the same manner as in EXAMPLE 30 using appropriate starting materials.
mp: 138-139° C.

EXAMPLE 675

2-({N-(1-Ethyl-3,3,5-trimethyl-2,4-dioxo-2,3,4,5-tetrahydro-1H-benzo[b][1,4]diazepin-7-ylmethyl)-N-[2-(2-methyl-4-oxo-4H-furo[3,2-c]pyridin-5-yl)ethyl]amino}methyl)benzaldehyde The synthesis of the title compound was performed in the same manner as in EXAMPLE 621 using appropriate starting materials.
mp: 157-158° C.

EXAMPLE 676

1-Cyclopropylmethyl-5-(2-methoxyethyl)-7-({N-(2-methoxymethylpyridin-3-ylmethyl)-N-[2-(2-methyl-4-oxo-4H-furo[3,2-c]pyridin-5-yl)ethyl]amino}methyl)-3,3-dimethyl-1,5-dihydrobenzo[b][1,4]diazepine-2,4-dione dihydrochloride The synthesis of the title compound was performed in the same manner as in EXAMPLE 4 using appropriate starting materials.

¹H NMR (DMSO-d₆), δppm: 0.00 (2H, br), 0.21-0.23 (2H, m), 0.61 (3H, s), 0.75 (1H, br), 1.26 (3H, s), 2.35 (3H, s), 2.68 (2H, br), 3.24 (3H, s), 3.12-3.80 (6H, m), 3.90-4.20 (6H, m), 4.50 (2H, s), 6.41 (1H, s), 6.55 (1H, br), 7.20 (1H, br), 7.25-7.50 (3H, m), 7.60 (1H, br), 8.20 (1H, br), 8.48 (1H, s).

EXAMPLE 677

5-Cyclopropyl-1-cyclopropylmethyl-7-({N-(2-methoxymethylpyridin-3-ylmethyl)-N-[2-(2-methyl-4-oxo-4H-furo[3,2-c]pyridin-5-yl)ethyl]amino}methyl)-3,3-dimethyl-1,5-dihydro-benzo[b][1,4]diazepine-2,4-dione dihydrochloride The synthesis of the title compound was performed in the same manner as in EXAMPLE 4 using appropriate starting materials.
¹H NMR (DMSO-d₆), δppm: −0.09-0.05 (3H, m), 0.12-0.23 (2H, m), 0.35-0.46 (1H, m), 0.63-0.80 (2H, m), 0.72 (3H, s), 1.06-1.13 (1H, m), 1.33 (3H, s), 2.43 (3H, s), 2.81 (2H, br), 3.20 (1H, br), 3.34 (3H, s), 3.37-3.45 (2H, m), 3.80 (2H, br), 4.15-4.20 (3H, m), 4.67 (3H, br), 6.49 (1H, br), 6.66 (1H, br), 7.13-7.60 (4H, m), 7.77-7.80 (1H, br), 8.42 (1H, br), 8.63 (1H, br).

EXAMPLE 678

7-({N-(3-Diethoxymethylbenzyl)-N-[2-(2-methyl-4-oxo-4H-furo[3,2-c]pyridin-5-yl)ethyl]amino}methyl)-1-ethyl-3,3,5-trimethyl-1,5-dihydrobenzo[b][1,4]diazepine-2,4-dione The synthesis of the title compound was performed in the same manner as in EXAMPLE 30 using appropriate starting materials.
mp: 112-114° C.

EXAMPLE 679

3-({N-(1-Ethyl-3,3,5-trimethyl-2,4-dioxo-2,3,4,5-tetrahydro-1H-benzo[b][1,4]diazepin-7-ylmethyl)-N-[2-(2-methyl-4-oxo-4H-furo[3,2-c]pyridin-5-yl)ethyl]amino}methyl)benzaldehyde The synthesis of the title compound was performed in the same manner as in EXAMPLE 621 using appropriate starting materials.
mp: 79-84° C.

EXAMPLE 680

1-Ethyl-7-({N-(2-hydroxymethylbenzyl)-N-[2-(2-methyl-4-oxo-4H-furo[3,2-c]pyridin-5-yl)ethyl]amino}methyl)-3,3,5-trimethyl-1,5-dihydrobenzo[b][1,4]diazepine-2,4-dione Sodium borohydride (47 mg) were added to a methanol solution(10 ml) of 2-({N-(1-Ethyl-3,3,5-trimethyl-2,4-dioxo-2,3,4,5-tetrahydro-1H-benzo[b][1,4]diazepin-7-ylmethyl)-N-[2-(2-methyl-4-oxo-4H-furo[3,2-c]pyridin-5-yl)ethyl]amino}methyl)benzaldehyde (0.59 g) and the mixture was stirred for 3 hours at 0° C. Water was added to the reaction mixture, followed by extraction by ethyl acetate. The organic layer was dried by anhydrous sodium sulfate, and condensed under reduced pressure. The residue was recrystallized from ethyl acetate-ether mixture to give the title compound(0.42 g) as a pale brown white powder.
mp: 159-161° C.

EXAMPLE 681

1-Ethyl-3,3,5-trimethyl-7-{[4-(2-oxo-3,4-dihydro-2H-quinolin-1-ylmethyl)benzylamino]-methyl}-1,5-dihydrobenzo[b][1,4]diazepine-2,4-dione The synthesis of the title compound was performed in the same manner as in EXAMPLE 3 using appropriate starting materials.
¹H NMR (CDCl₃), δppm: 0.82 (3H, s), 1.17 (3H, t, J=7.1 Hz), 1.53 (3H, s), 2.76-2.81 (2H, m), 2.95-3.02 (2H, m), 3.41 (3H, s), 3.74-3.83 (5H, m), 4.10-4.18 (1H, m), 5.17 (2H, s), 6.85-6.90 (1H, m), 6.96-7.00 (1H, m), 7.07-7.13 (1H, m), 7.15-7.35 (8H, m)

EXAMPLE 682

5-Cyclopropylmethyl-1-(2-methoxyethyl)-7-({N-(2-methoxymethylpyridin-3-ylmethyl)-N-[2-(2-methyl-4-oxo-4H-furo[3,2-c]pyridin-5-yl)ethyl]amino}methyl)-3,3-dimethyl-1,5-dihydrobenzo[b][1,4]diazepine-2,4-dione dihydrochloride The synthesis of the title compound was performed in the same manner as in EXAMPLE 4 using appropriate starting materials.
¹H NMR (DMSO-d₆), δppm: 0.03-0.10 (2H, m), 0.25-0.29 (2H, m), 0.66 (3H, s), 0.77-0.85 (1H, m), 1.30 (3H, s), 2.38 (3H, s), 2.95-3.15 (2H, m), 3.07 (3H, s), 3.10-3.42 (4H, m), 3.30 (3H, s), 3.50-3.57 (1H, m), 3.87 (2H, br), 3.97-4.09 (1H, m), 4.33 (4H, br), 4.77 (2H, br), 6.48 (1H, s), 6.64 (1H, d, J=7.3 Hz), 7.47 (2H, br), 7.57-7.60 (1H, m), 7.79-7.82 (2H, m), 8.66-8.67 (2H, m).

EXAMPLE 683

5-Cyclopropyl-1-cyclopropylmethyl-3,3-dimethyl-7-{[N-[2-(2-methyl-4-oxo-4H-furo[3,2-c]pyridin-5-yl)ethyl]-N-(2-methylpyridin-3-ylmethyl)amino]methyl}-1,5-dihydrobenzo[b][1,4]diazepine-2,4-dione dihydrochloride The synthesis of the title compound was performed in the same manner as in EXAMPLE 4 using appropriate starting materials.
¹H NMR (DMSO-d₆), δppm: −0.09-0.03 (3H, m), 0.15-0.27 (2H, m), 0.37-0.44 (1H, m), 0.72 (3H, s), 0.65-0.76 (2H, m), 1.06-1.10 (1H, m), 1.33 (3H, s), 2.43 (3H, br), 2.49 (3H, br), 2.79 (2H, br), 3.17-3.22 (1H, m), 3.38-3.49 (1H, m), 3.77 (2H, br), 3.81 (2H, br), 4.14 (2H, br), 4.16-4.22 (1H, m), 6.45 (1H, s), 6.62 (1H, d, J=7.0 Hz), 7.26 (1H, br), 7.36 (1H, br), 7.45-7.48 (2H, m), 7.68-7.72 (1H, m), 8.29 (1H, br), 8.56 (1H, br).

EXAMPLE 684

1-Ethyl-3,3,5-trimethyl-7-{[N-[2-(2-methyl-4-oxo-4H-furo[3,2-c]pyridin-5-yl)ethyl]-N-(2-morpholin-4-ylmethylbenzyl)amino]methyl}-1,5-dihydrobenzo[b][1,4]diazepine-2,4-dione Morpholine(0.06 ml) and acetic acid(0.1 ml) were added to a 1,2-dichloroethane solution(7 ml) of 2-({N-(1-ethyl-3,3,5-trimethyl-2,4-dioxo-2,3,4,5-tetrahydro-1H-benzo[b][1,4]diazepin-7-ylmethyl)-N-[2-(2-methyl-4-oxo-4H-furo[3,2-c]

pyridin-5-yl)ethyl]amino}methyl)benzaldehyde (0.35 g), and the mixture was stirred for 30 minutes at room temperature. Sodium triacetoxy borohydride(0.20 g) was added, and the mixture was stirred at room temperature overnight. Water was added to the reaction liquid, followed by extraction by dichloromethane. The organic layer was dried by anhydrous sodium sulfate, and condensed under reduced pressure.

The residue was purified by NH silica gel column chromatography (ethyl acetate: hexane=3:2). The purified product was condensed under reduced pressure to give the title compound(0.30 g) as a white amorphous solid.

$^1$H NMR (CDCl$_3$), d ppm: 0.78 (3H, s), 1.16 (3H, t, J=7.0 Hz), 1.51 (3H, s), 2.28-2.38(4H, m), 2.43 (3H, d, J=1.0 Hz), 2.83 (2H, t, J=6.1 Hz), 3.32 (3H, s), 3.43 (2H, s), 3.56-3.88 (9H, m), 3.96-4.07 (2H, m), 4.07-4.18(1H, m), 6.40 (1H, dd, J=0.64, 7.4 Hz), 6.48 (1H, d, J=0.88 Hz), 6.89 (1H, d, J=7.3 Hz), 7.08 (2H, d, J=0.96 Hz), 7.12-7.20 (3H, m), 7.21-7.26 (1H, m), 7.37 (1H, dd, J=2.1, 7.0 Hz).

EXAMPLE 685

1-Ethyl-7-({N-(3-hydroxymethylbenzyl)-N-[2-(2-methyl-4-oxo-4H-furo[3,2-c]pyridin-5-yl)ethyl]amino}methyl)-3,3,5-trimethyl-1,5-dihydrobenzo[b][1,4]diazepine-2,4-dione The synthesis of the title compound was performed in the same manner as in EXAMPLE 680 using appropriate starting materials.

mp: 170-172° C.

EXAMPLE 686

1-Ethyl-3,3,5-trimethyl-7-{[N-[2-(2-methyl-4-oxo-4H-furo[3,2-c]pyridin-5-yl)ethyl]-N-(3-morpholin-4-ylmethylbenzyl)amino]methyl}-1,5-dihydrobenzo[b][1,4]diazepine-2,4-dione $^1$H NMR (CDCl$_3$) 0.77 (3H, s), 1.16 (3H, t, J=7.0 Hz), 1.51 (3H, s), 2.37-2.46 (4H, m), 2.43 (3H, d, J=0.96 Hz), 2.82 (2H, dt, J=2.3, 5.8 Hz), 3.31 (3H, s), 3.41 (2H, s), 3.59-3.82 (9H, m), 3.96-4.19 (3.H, m), 6.44 (1H, dd, J=0.70 7.4 Hz), 6.48 (1H, t, J=0.9 Hz), 6.97-7.09 (3H, m), 7.11-7.26(5H, m).

EXAMPLE 687

1-Ethyl-3,3,5-trimethyl-7-{[N-(2-oxo-1-pyridin-2-ylmethyl-1,2,3,4-tetrahydro-quinolin-7-ylmethyl)amino]methyl}-1,5-dihydrobenzo[b][1,4]diazepine-2,4-dione The synthesis of the title compound was performed in the same manner as in EXAMPLE 670 using appropriate starting materials.

$^1$H NMR (CDCl$_3$), δppm: 0.81 (3H, s), 1.18 (3H, t, J=7.1 Hz), 1.53 (3H, s), 2.75-2.81 (2H, m), 2.95-3.01 (2H, m), 3.39 (3H, s), 3.70-3.73 (4H, m), 3.74-3.84 (1H, m), 4.08-4.14 (1H, m), 5.30 (2H, s), 6.95 (1H, dd, J=1.3 and 7.6 Hz), 7.05 (1H, brs), 7.11-7.25 (6H, m), 7.60 (1H, dt, J=1.8 and 7.7 Hz), 8.50-8.55 (1H, m)

EXAMPLE 688

1-Ethyl-3,3,5-trimethyl-7-{[N-(2-oxo-1-pyridin-3-ylmethyl-1,2,3,4-tetrahydroquinolin-7-ylmethyl)amino]methyl}-1,5-dihydrobenzo[b][1,4]diazepine-2,4-dione The synthesis of the title compound was performed in the same manner as in EXAMPLE 670 using appropriate starting materials.

$^1$H NMR (CDCl$_3$), δppm: 0.81 (3H, s), 1.16 (3H, t, J=7.1 Hz), 1.53 (3H, s), 2.75-2.80 (2H, m), 2.94-2.99 (2H, m), 3.39 (3H, s), 3.70-3.73 (4H, m), 3.75-3.84 (1H, m), 4.08-4.18 (1H, m), 5.22 (2H, s), 6.91 (1H, brs), 6.96 (1H, dd, J=1.2 and 7.6 Hz), 7.10-7.18 (3H, m), 7.20-7.24 (2H, m), 7.55 (1H, dt, J=2.2 and 7.8 Hz), 8.47 (1H, dd, J=1.6 and 4.8 Hz), 8.56 (1H, d, J=1.8 Hz)

EXAMPLE 689

1-Ethyl-3,3,5-trimethyl-7-({N-methyl-N-[3-(2-oxo-3,4-dihydro-2H-quinolin-1-ylmethyl)benzyl]amino}methyl)-1,5-dihydrobenzo[b][1,4]diazepine-2,4-dione The synthesis of the title compound was performed in the same manner as in EXAMPLE 616 using appropriate starting materials.

$^1$H NMR (CDCl$_3$), δppm: 0.82 (3H, s), 1.15-1.21 (3H, m), 1.53 (3H, s), 2.16 (3H, s), 2.76-2.81 (2H, m), 2.95-3.01 (2H, m), 3.40 (3H, s), 3.47-3.54 (4H, m), 3.75-3.82 (1H, m), 4.08-4.16 (1H, m), 5.18 (2H, s), 6.86 (1H, dd, J=0.8 and 8.1 Hz), 6.95 (1H, dt, J=1.0 and 7.4 Hz), 7.04-7.12 (2H, m), 7.15-7.30 (7H, m)

EXAMPLE 690

1-Ethyl-3,3,5-trimethyl-7-({N-methyl-N-[4-(2-oxo-3,4-dihydro-2H-quinolin-1-ylmethyl)-benzyl]amino}methyl)-1,5-dihydrobenzo[b][1,4]diazepine-2,4-dione The synthesis of the title compound was performed in the same manner as in EXAMPLE 616 using appropriate starting materials.

$^1$H NMR (CDCl$_3$), δppm: 0.82 (3H, s), 1.18 (3H, t, J=7.1 Hz), 1.53 (3H, s), 2.18 (3H, s), 2.76-2.81 (2H, m), 2.95-3.01 (2H, m), 3.41 (3H, s), 3.48-3.52 (4H, m), 3.75-3.82 (1H, m), 4.08-4.17 (1H, m), 5.17 (2H, s), 6.85-6.90 (1H, m), 6.95-7.00 (1H, m), 7.06-7.13 (1H, m), 7.15-7.33 (8H, m)

EXAMPLE 691

7-({N-(2-Dimethylaminomethylpyridin-3-ylmethyl)-N-[2-(2-methyl-4-oxo-4H-furo[3,2-c]pyridin-5-yl)ethyl]amino}methyl)-1-ethyl-3,3,5-trimethyl-1,5-dihydro-benzo[b][1,4]diazepine-2,4-dione trihydrochloride To the 1,2-dichloroethan suspension (5 ml) of 3-(((N-(1-ethyl-3,3,5-trimethyl-2,4-dioxo-2,3,4,5-tetrahydro-1H-benzo[b][1,4]diazepin-7-yl)methyl)-N-(2-(2-methyl-4-oxo-furo[3,2-c]pyridin-5(4H)-yl)ethyl)amino)methyl) picolinaldehyde (205 mg), dimethylammonium chloride (59 mg) and triethylamine (0.10 ml) was added sodium triacetoxyborohydride (114 mg) at room temperature, and the mixture was stirred overnight. The mixture was concentrated under reduced pressure, and then the residue was purified by column-chromatography (methanol: ethyl acetate=1:9→50:50). The purified product was dissolved in ethyl acetate (ca. 5 mL) and then 4 M HCl/ethyl acetate was added to the mixture. The precipitate was collected and dried in vacuo to give the titled compound as light brown powder (114 mg).

$^1$H NMR (DMSO-d$_6$), δppm: 0.70 (3H, s), 1.06 (3H, t, J=7.0 Hz), 1.34 (3H, s), 2.40 (3H, br), 2.89 (6H, s), 3.15-3.44

(2H, m), 3.34 (3H, s), 3.70-4.05 (10H, m), 6.55 (1H, s), 6.73 (1H, d, J=7.4 Hz), 7.20-8.00 (5H, m), 8.26 (1H, br), 8.64 (1H, br).

EXAMPLE 692

1-Ethyl-3,3,5-trimethyl-7-({N-(2-methylaminomethylpyridin-3-ylmethyl)-N-[2-(2-methyl-4-oxo-4H-furo[3,2-c]pyridin-5-yl)ethyl]amino}methyl)-1,5-dihydrobenzo[b][1,4]diazepine-2,4-dione trihydrochloride To a methanol solution (5 ml) of 3-({N-(1-ethyl-3,3,5-trimethyl-2,4-dioxo-2,3,4,5-tetrahydro-1H-benzo[b][1,4]diazepin-7-ylmethyl)-N-[2-(2-methyl-4-oxo-4H-furo[3,2-c]pyridin-5-yl)ethyl]amino}methyl)pyridine-2-carbaldehyde (243 mg) was added 9.8 M THF solution of methylamine (87 μl) and the mixture was stirred overnight at room temperature. NaBH$_4$ (16 mg) was added to the mixture, and then the mixture was stirred overnight. The resulting mixture was evaporated and the residue was purified by column chromatography (methanol: ethyl acetate=1:9→50:50). The purified product was dissolved in ethyl acetate (ca. 5 ml) and then 4 M HCl/ethyl acetate was added to the mixture. The precipitate was collected and dried in vacuo to give the titled compound as light brown powder (18 mg).

$^1$H NMR (DMSO-d$_6$), δppm: 0.70 (3H, s), 1.06 (3H, t, J=7.0 Hz), 1.34 (3H, s), 2.40 (3H, br), 2.66 (3H, s), 3.05-3.45 (2H, m), 3.34 (3H, s), 3.70-4.05 (10H, m), 6.56 (1H, s), 6.74 (1H, d, J=7.4 Hz), 7.48 (3H, br), 7.64 (1H, d, J=6.5 Hz), 7.77 (1H, br), 8.23 (1H, br), 8.62 (1H, br), 9.32 (2H, br).

EXAMPLE 693

7-({N-(2-Cyclopropylaminomethylpyridin-3-ylmethyl)-N-[2-(2-methyl-4-oxo-4H-furo[3,2-c]pyridin-5-yl)ethyl]amino}methyl)-1-ethyl-3,3,5-trimethyl-1,5-dihydrobenzo[b][1,4]diazepine-2,4-dione trihydrochloride The synthesis of the title compound was performed in the same manner as in EXAMPLE 692 using appropriate starting materials.

$^1$H NMR (DMSO-d$_6$), δppm: 0.72 (3H, s), 0.70-0.74 (2H, m), 0.98 (2H, br), 1.08 (3H, t, J=7.0 Hz), 1.35 (3H, s), 2.41 (3H, br), 2.75 (2H, br), 3.33 (3H, s), 3.60-3.90 (5H, m), 3.91-4.05 (1H, m), 4.20-4.70 (5H, m), 6.55 (1H, s), 6.73 (1H, d, J=7.3 Hz), 7.45 (3H, br), 7.59-7.61 (2H, m), 8.15 (1H, br), 8.59 (1H, br), 9.54 (2H, br).

EXAMPLE 694

1-Ethyl-3,3,5-trimethyl-7-{[N-[2-(2-methyl-4-oxo-4H-furo[3,2-c]pyridin-5-yl)ethyl]-N-(2-pyrrolidin-1-ylmethylpyridin-3-ylmethyl)amino]methyl}-1,5-dihydrobenzo[b][1,4]diazepine-2,4-dione trihydrochloride The synthesis of the title compound was performed in the same manner as in EXAMPLE 691 using appropriate starting materials.

$^1$H NMR (DMSO-d$_6$), δppm: 0.71 (3H, s), 1.06 (3H, t, J=7.0 Hz), 1.35 (3H, s), 2.00 (4H, br), 2.43 (3H, br), 2.76 (2H, br), 3.28 (7H, br), 3.75 (4H, br), 3.90-4.30 (2H, m), 4.55 (4H, br), 6.52 (1H, br), 6.70 (1H, br), 7.25 (2H, br), 7.32 (1H, br), 7.52 (2H, br), 7.69 (1H, br), 8.47 (1H, br), 10.3 (1H, br).

EXAMPLE 695

1-Ethyl-7-({N-[2-(3-hydroxypyrrolidin-1-ylmethyl)pyridin-3-ylmethyl]-[2-(2-methyl-4-oxo-4H-furo[3,2-c]pyridin-5-yl)ethyl]amino}methyl)-3,3,5-trimethyl-1,5-dihydro-benzo[b][1,4]diazepine-2,4-dione trihydrochloride The synthesis of the title compound was performed in the same manner as in EXAMPLE 691 using appropriate starting materials.

$^1$H NMR (DMSO-d$_6$), δppm: 0.71 (3H, s), 1.07 (3H, t, J=6.9 Hz), 1.35 (3H, s), 1.95 (1H, br), 2.19 (1H, br), 2.42 (3H, br), 2.75 (2H, br), 3.10-3.60 (9H, m), 3.75 (4H, br), 3.90-4.25 (3H, m), 4.47 (2H, br), 6.52 (1H, br), 6.70 (1H, br), 7.27 (3H, br), 7.53 (2H, br), 7.69 (1H, br), 8.49 (1H, br), 10.4 (1H, br).

EXAMPLE 696

1-Ethyl-3,3,5-trimethyl-7-{[2-(2-oxo-3,4-dihydro-2H-quinolin-1-ylmethyl)benzylamino]-methyl}-1,5-dihydrobenzo[b][1,4]diazepine-2,4-dione The synthesis of the title compound was performed in the same manner as in EXAMPLE 3 using appropriate starting materials.

$^1$H NMR (CDCl$_3$), δppm: 0.79 (3H, s), 1.16 (3H, t, J=7.1 Hz), 1.51 (3H, s), 2.78-2.83 (2H, m), 2.99-3.04 (2H, m), 3.32 (3H, s), 3.74-3.81 (1H, m), 3.90-3.93 (4H, m), 4.08-4.14 (1H, m), 5.30-5.34 (2H, m), 6.82 (1H, dd, J=1.0 and 7.9 Hz), 6.91-7.03 (3H, m), 7.13-7.35 (7H, m)

EXAMPLE 697

1-Ethyl-3,3,5-trimethyl-7-({N-(4-methylpyridin-3-ylmethyl)-N-[2-(2-oxo-2H-quinolin-1-yl)ethyl]amino}methyl)-1,5-dihydro-benzo[b][1,4]diazepine-2,4-dione The synthesis of the title compound was performed in the same manner as in EXAMPLE 30 using appropriate starting materials.
White Powder
mp: 120-121° C.

EXAMPLE 698

7-({N-(2,6-Dimethylpyridin-3-ylmethyl)-N-[2-(2-oxo-2H-quinolin-1-yl)ethyl]amino}methyl)-1-ethyl-3,3,5-trimethyl-1,5-dihydro-benzo[b][1,4]diazepine-2,4-dione The synthesis of the title compound was performed in the same manner as in EXAMPLE 30 using appropriate starting materials.
White Powder
mp: 159-160° C.

EXAMPLE 699

1-Ethyl-3,3,5-trimethyl-7-{[N-[2-(7-methyl-4-oxo-4H-thieno[3,2-c]pyridin-5-yl)ethyl]-N-(4-methylpyridin-3-ylmethyl)amino]methyl}-1,5-dihydrobenzo[b][1,4]diazepine-2,4-dione The synthesis of the title compound was performed in the same manner as in EXAMPLE 30 using appropriate starting materials.

White Powder
mp: 174-175° C.

EXAMPLE 700

1-Ethyl-3,3,5-trimethyl-7-{[N-[2-(4-methyl-7-oxo-7H-thieno[2,3-c]pyridin-6-yl)ethyl]-N-(4-methylpyridin-3-ylmethyl)amino]methyl}-1,5-dihydrobenzo[b][1,4]diazepine-2,4-dione The synthesis of the title compound was performed in the same manner as in EXAMPLE 30 using appropriate starting materials.
White Powder
mp: 163-165° C.

EXAMPLE 701

1-Ethyl-3,3,5-trimethyl-7-{[N-[2-(7-methyl-4-oxo-4H-furo[3,2-c]pyridin-5-yl)ethyl]-N-(2-methylpyrimidin-5-ylmethyl)amino]methyl}-1,5-dihydro-benzo[b][1,4]diazepine-2,4-dione The synthesis of the title compound was performed in the same manner as in EXAMPLE 30 using appropriate starting materials.
White Powder
mp: 166-167° C.

EXAMPLE 702

1-Ethyl-3,3,5-trimethyl-7-{[N-[2-(4-methyl-7-oxo-7H-thieno[2,3-c]pyridin-6-yl)ethyl]-N-(2-methylpyridin-3-ylmethyl)amino]methyl}-1,5-dihydro-benzo[b][1,4]diazepine-2,4-dione The synthesis of the title compound was performed in the same manner as in EXAMPLE 30 using appropriate starting materials.
White Powder
mp: 174-177° C.

EXAMPLE 703

1-Ethyl-3,3,5-trimethyl-7-({N-methyl-N-[2-(2-oxo-3,4-dihydro-2H-quinolin-1-ylmethyl)benzyl]amino}methyl)-1,5-dihydro-benzo[b][1,4]diazepine-2,4-dione The synthesis of the title compound was performed in the same manner as in EXAMPLE 616 using appropriate starting materials.
White Powder
mp: 125-127° C.

EXAMPLE 704

1-Ethyl-7-({N-(6-hydroxymethylpyridin-3-ylmethyl)-N-[2-(1-oxo-1H-isoquinolin-2-yl)-ethyl]amino}methyl)-3,3,5-trimethyl-1,5-dihydro-benzo[b][1,4]diazepine-2,4-dione The synthesis of the title compound was performed in the same manner as in EXAMPLE 30 using 6-(((tert-butyldimethylsilyloxy)methyl)nicotinaldehyde and 1-ethyl-3,3,5-trimethyl-7-((2-(1-oxoisoquinolin-2(1H)-yl)ethylamino)methyl)-1H-benzo[b][1,4]diazepine-2,4(3H,5H)-dione, followed by deprotection of TBDMS group with tetrabutylammonium fluoride.
$^1$H NMR (CDCl$_3$), δppm: 0.75 (3H, s), 1.13 (3H, t, J=7.1 Hz), 1.50 (3H, s), 2.85-2.88 (2H, m), 3.27 (3H, s), 3.62-3.75 (5H, m), 3.96-4.02 (1H, m), 4.13 (2H, t, J=7.2 Hz), 4.65 (2H, s), 6.46 (1H, d, J=7.3 Hz), 6.93 (1H, d, J=7.3 Hz), 6.96-6.99 (2H, m), 7.05 (1H, dd, J=1.8, 8.4 Hz), 7.13 (1H, d, J=1.6 Hz), 7.48-7.57 (3H, m), 7.66-7.71 (1H, m), 8.33 (1H, dd, J=0.6, 8.1 Hz), 8.41 (1H, d, J=1.5 Hz).

EXAMPLE 705

1-Ethyl-3,3,5-trimethyl-7-(3-{N-(2-methylpyridin-3-ylmethyl)-N-[2-(7-oxo-7H-thieno[2,3-c]pyridin-6-yl)ethyl]amino}propyl)-1,5-dihydrobenzo[b][1,4]diazepine-2,4-dione dihydrochloride The synthesis of the title compound was performed in the same manner as in EXAMPLE 4 using appropriate starting materials.
$^1$H NMR (DMSO-d$_6$), δppm: 0.71 (3H, s), 1.04 (3H, t, J=7.1 Hz), 1.33 (3H, s), 1.65-2.34 (2H, m), 2.52-2.92 (6H, m), 3.25-4.82 (12H, m), 6.60-6.92 (1H, m), 7.03-7.19 (1H, m), 7.19-7.31 (1H, m), 7.31-7.41 (2H, m), 7.41-7.90 (2H, m), 8.00-8.11 (1H, m), 8.12-8.60 (2H, m).

EXAMPLE 706

1-Ethyl-3,3,5-trimethyl-7-(3-{N-(2-methylpyridin-3-ylmethyl)-N-[2-(4-oxo-4H-thieno[3,2-c]pyridin-5-yl)ethyl]amino}propyl)-1,5-dihydrobenzo[b][1,4]diazepine-2,4-dione dihydrochloride The synthesis of the title compound was performed in the same manner as in EXAMPLE 4 using appropriate starting materials.
$^1$H NMR (DMSO-d$_6$), δppm: 0.71 (3H, s), 1.04 (3H, t, J=7.1 Hz), 1.32 (3H, s), 1.66-2.29 (2H, m), 2.55-2.71 (2H, m), 2.71-2.92 (4H, m), 2.96-4.81 (12H, m), 6.81-7.02 (2H, m), 7.02-7.41 (4H, m), 7.41-7.69 (1H, m), 7.41-7.90 (2H, m), 8.42-8.93 (1H, m).

EXAMPLE 707

7-{[2-(2,6-Dimethylpyridin-3-yl)ethylamino]methyl}-1-ethyl-3,3,5-trimethyl-1,5-dihydro-benzo[b][1,4]diazepine-2,4-dione The synthesis of the title compound was performed in the same manner as in EXAMPLE 590 using appropriate starting materials.
$^1$H NMR (CDCl$_3$), δppm:0.82 (3H, s), 1.18 (3H, t, J=7.1 Hz), 1.53 (3H, s), 2.49 (3H, s), 2.51 (3H, s), 2.78-2.83 (2H, m), 2.85-2.89 (2H, m), 3.40 (3H, s), 3.74-3.84 (1H, m), 3.84 (2H, s), 4.09-4.19 (1H, m), 6.93 (1H, d, J=7.7 Hz), 7.17-7.19 (2H, m), 7.24 (1H, s), 7.32 (1H, d, J=7.7 Hz).

EXAMPLE 708

7-{[N-(2,5-Dimethyl-2H-pyrazol-3-ylmethyl)amino]methyl}-1-ethyl-3,3,5-trimethyl-1,5-dihydrobenzo[b][1,4]diazepine-2,4-dione The synthesis of the title compound was performed in the same manner as in EXAMPLE 3 using appropriate starting materials.

¹H NMR (CDCl₃), δppm: 0.83 (3H, s), 1.18 (3H, t, J=7.1 Hz), 1.53 (3H, s), 2.23 (3H, s), 3.42 (3H, s), 3.75-3.83 (8H, m), 4.09-4.20 (1H, m), 5.94 (1H, s), 7.20-7.28 (3H, m).

EXAMPLE 709

1-Ethyl-7-{[N-(2-methoxymethylpyridin-3-ylmethyl)amino]methyl}-3,3,5-trimethyl-1,5-dihydrobenzo[b][1,4]diazepine-2,4-dione The synthesis of the title compound was performed in the same manner as in EXAMPLE 3 using appropriate starting materials.
¹H NMR (CDCl₃), δppm: 0.83 (3H, s), 1.18 (3H, t, J=7.1 Hz), 1.53 (3H, s), 3.41 (3H, s), 3.42 (3H, s), 3.74-3.85 (1H, s), 3.85 (2H, s), 3.91 (2H, s), 4.10-4.67 (1H, m), 4.67 (2H, s), 7.22-7.28 (4H, m), 7.72-7.74 (1H, m), 8.49-8.51 (1H, m).

EXAMPLE 710

1-Ethyl-3,3,5-trimethyl-7-{[N-(3-methyl-3H-imidazol-4-ylmethyl)amino]methyl}-1,5-dihydrobenzo[b][1,4]diazepine-2,4-dione The synthesis of the title compound was performed in the same manner as in EXAMPLE 3 using appropriate starting materials.
¹H NMR (CDCl₃), δppm: 0.83 (3H, s), 1.18 (3H, t, J=7.1 Hz), 1.53 (3H, s), 3.42 (3H, s), 3.69 (3H, s), 3.75-3.84 (1H, m), 3.80 (2H, s), 3.83 (2H, s), 4.11-4.18 (1H, m), 6.92 (1H, s), 7.20-7.23 (2H, m), 7.25-7.28 (1H, m), 7.42 (1H, s).

EXAMPLE 711

1-Ethyl-3,3,5-trimethyl-7-[(1-pyridin-3-ylethylamino)methyl]-1,5-dihydrobenzo[b][1,4]diazepine-2,4-dione The synthesis of the title compound was performed in the same manner as in EXAMPLE 30 using appropriate starting materials.
¹H NMR (CDCl₃), δppm: 0.81-0.82 (3H, m), 1.17 (3H, t, J=7.1 Hz), 1.42-1.44 (3H, m), 1.53 (3H, s), 3.40-3.41 (3H, m), 3.62-3.70 (2H, m), 3.73-3.83 (1H, m), 3.85-3.91 (1H, m), 4.09-4.19 (1H, m), 7.14-7.19 (2H, m), 7.22-7.31 (2H, m), 7.70-7.74 (1H, m), 8.51-8.53 (1H, m), 8.58 (1H, d, J=2.0 Hz).

EXAMPLE 712

7-{[(1,5-Dimethyl-1H-pyrazol-3-ylmethyl)amino]methyl}-1-ethyl-3,3,5-trimethyl-1,5-dihydrobenzo[b][1,4]diazepine-2,4-dione The synthesis of the title compound was performed in the same manner as in EXAMPLE 3 using appropriate starting materials.
¹H NMR (CDCl₃), δppm: 0.82 (3H, s), 1.17 (3H, t, J=7.1 Hz), 1.53 (3H, s), 1.77 (6H, s), 2.26 (3H, s), 3.42 (3H, s), 3.74-3.85 (1H, m), 3.74 (3H, s), 3.77 (2H, s), 3.86 (2H, s), 5.96 (1H, s), 7.23-7.24 (3H, m).

EXAMPLE 713

N-(1-Ethyl-3,3,5-trimethyl-2,4-dioxo-2,3,4,5-tetrahydro-1H-benzo[b][1,4]diazepin-7-ylmethyl)-2-nitrobenzenesulfonamide Triethylamine(0.6 ml) was added to a dichloromethane solution (6 ml) of 1-ethyl-3,3,5-trimethyl-7-aminomethyl-1,5-dihydrobenzo[b][1,4]diazepine-2,4-dione(1.0 g). The mixture was cooled with ice. 2-Nitrobenzenesulphonyl chloride (0.80 g) was added, and the mixture was stirred at room temperature overnight. A saturated sodium bicarbonate solution was added to the reaction mixture, followed by extraction using dichloromethane.
The organic layer was washed with water and saturated saline, dried with magnecium sulfate. After concentration under reduced pressure, the residue was purified by silica gel column chromatography (hexane: ethyl acetate=1:1→1:4). The purified product was condensed under reduced pressure, and the residue was recrystallized from the ethyl acetate-hexane mixture to give the title compound(1.38 g) as a white solid.
¹H NMR (CDCl₃), δppm: 0.78 (3H, s), 1.16 (3H, t, J=7.1 Hz), 1.51 (3H, s), 3.35 (3H, s), 3.72-3.83 (1H, m), 4.06-4.17 (1H, m), 4.35 (2H, d, J=6.4 Hz), 5.78 (1H, d, J=6.4 Hz), 7.16-7.23 (3H, m), 7.73-7.79 (2H, m), 7.86-7.91 (1H, m), 8.12-8.15 (1H, m)

EXAMPLE 714

1-Ethyl-3,3,5-trimethyl-7-{[(5-methyloxazol-4-ylmethyl)amino]methyl}-1,5-dihydrobenzo[b][1,4]diazepine-2,4-dione The synthesis of the title compound was performed in the same manner as in EXAMPLE 3 using appropriate starting materials.
¹H NMR (CDCl₃), δppm: 0.83 (3H, s), 1.17 (3H, t, J=7.1 Hz), 1.53 (3H, s), 2.29 (3H, s), 3.42 (3H, s), 3.68 (2H, s), 3.72-3.86(3H, m), 4.09-4.23(1H, m), 7.20-7.30 (3H, m), 7.74 (1H, s).

EXAMPLE 715

1-Ethyl-7-{[(6-methoxymethylpyridin-3-ylmethyl)amino]methyl}-3,3,5-trimethyl-1,5-dihydrobenzo[b][1,4]diazepine-2,4-dione The synthesis of the title compound was performed in the same manner as in EXAMPLE 3 using appropriate starting materials.
¹H NMR (CDCl₃), δppm: 0.83 (3H, s), 1.18 (3H, t, J=7.1 Hz), 1.53 (3H, s), 3.42 (3H, s), 3.49 (3H, s), 3.74-3.85 (1H, m), 3.83 (2H, s), 3.85 (2H, s), 4.10-4.20 (1H, m), 4.58 (2H, s), 7.23-7.37 (3H, m), 7.40 (1H, d, J=8.0 Hz), 7.71 (1H, dd, J=8.0, 2.1 Hz), 8.53 (1H, d, J=1.9 Hz).

EXAMPLE 716

1-Ethyl-3,3,5-trimethyl-7-{[N-[2-(2-methyl-4-oxo-4H-furo[3,2-c]pyridin-5-yl)ethyl]-N-(2-methyl-1-oxypyridin-3-ylmethyl)amino]methyl}-1,5-dihydrobenzo[b][1,4]diazepine-2,4-dione To a dichloromethane solution (10 ml) of 1-ethyl-3,3,5-trimethyl-7-{[N-[2-(2-methyl-4-oxo-4H-furo[3,2-c]pyridin-5-yl)ethyl]-N-(2-methylpyridin-3-ylmethyl)amino]methyl}-1,5-dihydrobenzo[b][1,4]diazepine-2,4-dione (2.0 g) was added m-chloroperbenzoic acid (mCPBA, 0.89 g) at 0° C. and the mixture was stirred overnight. The resulting mixture was charged on silica gel and purified by column chromatography (methanol/ethyl acetate 1:9→1:1) to give the titled compound as white amorphous (0.46 g).
¹H NMR (CDCl₃), δppm: 0.79 (3H, s), 1.17 (3H, t, J=7.1 Hz), 1.52 (3H, s), 2.35 (3H, s), 2.44 (3H, d, J=1.0 Hz), 2.84

(2H, t, J=6.1 Hz), 3.35 (3H, s), 3.62 (2H, s), 3.69-3.83 (3H, m), 4.03-4.18 (3H, m), 6.41 (1H, dd, J=7.3, 0.7 Hz), 6.51 (1H, t, J=0.9 Hz), 6.85 (1H, d, J=7.3 Hz), 6.92-6.96 (1H, m), 7.09-7.11 (2H, m), 7.15-7.18 (1H, m), 7.21-7.22 (1H, m), 8.14 (1H, d, J=6.0 Hz).

EXAMPLE 717

1-Ethyl-3,3,5-trimethyl-7-{[(3-methyl-pyridin-2-ylmethyl)amino]methyl}-1,5-dihydrobenzo[b][1,4]diazepine-2,4-dione The synthesis of the title compound was performed in the same manner as in EXAMPLE 3 using appropriate starting materials.
$^1$H NMR (CDCl$_3$), δppm: 0.84 (3H, s), 1.18 (3H, t, J=7.1 Hz), 1.53 (3H, s), 2.28 (3H, s), 3.42 (3H, s), 3.73-3.87(1H, m), 3.91 (2H, s), 3.93 (2H, s), 4.08-4.23 (1H, m), 7.11 (1H, dd, J=4.8, 7.6 Hz), 7.22-7.34 (3H, m), 7.41-7.47 (1H, m), 8.41 (1H, dd, J=1.1, 4.8 Hz).

EXAMPLE 718

1-Ethyl-3,3,5-trimethyl-7-{[1-(2-methylpyridin-3-yl)ethylamino]-methyl}-1,5-dihydrobenzo[b][1,4]diazepine-2,4-dione The synthesis of the title compound was performed in the same manner as in EXAMPLE 584 using appropriate starting materials.
$^1$H NMR (CDCl$_3$), δppm: 0.82-0.83 (3H, m), 1.15-1.89 (3H, m), 1.35-1.37 (3H, m), 1.53 (3H, s), 2.52 (3H, d, J=8.0 Hz), 3.39-3.40 (3H, m), 3.66 (2H, s), 3.73-3.82 (1H, m), 4.05-4.20 (2H, m), 7.18-7.20 (3H, m), 7.23-7.24 (1H, m), 7.85 (1H, dd, J=7.8, 1.6 Hz), 8.40 (1H, d, J=4.7 Hz).

Example 719

7-{[(2-Ethoxymethylpyridin-3-ylmethyl)amino]methyl}-1-ethyl-3,3,5-trimethyl-1,5-dihydrobenzo[b][1,4]diazepine-2,4-dione The synthesis of the title compound was performed in the same manner as in Example 3 using appropriate starting materials.
$^1$H NMR (CDCl$_3$), δppm: 0.83 (3H, s), 1.17 (6H, t, J=7.0 Hz), 1.53 (3H, s), 3.42 (3H, s), 3.57 (2H, q, J=7.0 Hz), 3.74-3.83 (1H, m), 3.84 (2H, s), 3.92 (2H, s), 4.09-4.20 (1H, m), 4.71 (2H, s), 7.22-7.28 (4H, m), 7.71 (1H, dd, J=7.7, 1.6 Hz), 8.49 (1H, dd, J=4.8, 1.6 Hz).

Example 720

1-Ethyl-7-{[1-(2-methoxymethylpyridin-3-yl)ethylamino]methyl}-3,3,5-trimethyl-1,5-dihydro-benzo[b][1,4]diazepine-2,4-dione The synthesis of the title compound was performed in the same manner as in Example 584 using appropriate starting materials.
$^1$H NMR (CDCl$_3$), δppm: : 0.82-0.83 (3H, m), 1.16 (3H, t, J=6.9 Hz), 1.40 (3H, d, J=6.4 Hz), 1.52 (3H, s), 3.37-3.40 (6H, m), 3.60 (1H, d, J=13.6 Hz), 3.68 (1H, d, J=13.6 Hz), 3.72-3.82 (1H, m), 4.09-4.20 (1H, m), 4.23-4.30 (1H, m), 4.57-4.66 (2H, m), 7.15-7.19 (2H, m), 7.22-7.26 (1H, m), 7.27-7.32 (1H, m), 7.96-7.98 (1H, m), 8.49 (1H, dd, J=4.7, 1.7 Hz).

Example 721

1-Ethyl-3,3,5-trimethyl-7-{[2-(1-oxo-1H-isoquinolin-2-yl)ethylamino]methyl}-1,5-dihydrobenzo[b][1,4]diazepine-2,4-dione 2-(2-Aminoethyl)-2H-isoquinolin-1-one (1.0 g) was added to a methanol solution (15 ml) of 1-ethyl-3,3,5-trimethyl-2,4-dioxo-2,3,4,5-tetrahydro-1H-benzo[b][1,4]diazepine-7-carbaldehyde (1.46 g). The mixture was stirred for 0.5 hours at room temperature. Sodium borohydride (0.23 g) was added to the mixture, and the mixture was stirred at room temperature overnight. Water was added to the reaction mixture, followed by extraction using dichloromethane. The organic layer was washed with water and saturated saline, dried with magnesium sulfate, and condensed under reduced pressure. The residue was purified by silica gel column chromatography (ethyl acetate: methanol=9:1→8:2). The purified product was condensed under reduced pressure to give the title compound(1.92 g) as a white solid.
1H NMR (CDCl$_3$), δppm: 0.78 (3H, s), 1.15 (3H, t, J=7.1 Hz), 1.51 (3H, s), 3.01-3.11(2H, m), 3.31 (3H, s), 3.71-3.81 (1H, m), 3.84 (2H, s), 4.04-4.15 (1H, m), 4.16 (2H, t, J=6.0 Hz), 6.51 (1H, d, J=7.3 Hz), 7.12-7.18 (4H, m), 7.48-7.56 (2H, m), 7.63-7.70 (1H, m), 8.41 (1H, d, J=8.1 Hz)

Example 722

1-Ethyl-3,3,5-trimethyl-7-(quinolin-5-ylaminomethyl)-1,5-dihydrobenzo[b][1,4]diazepine-2,4-dione The synthesis of the title compound was performed in the same manner as in Example 721 using appropriate starting materials.
$^1$H NMR (CDCl$_3$), δppm: 0.86 (3H, s), 1.21 (3H, t, J=7.1 Hz), 1.54 (3H, s), 3.38 (3H, s), 3.76-3.89 (1H, m), 4.09-4.22 (1H, m), 4.56 (2H, d, J=4.4 Hz), 4.70-4.88 (1H, m), 6.62 (1H, dd, J=2.6, 6.1 Hz), 7.28-7.35 (3H, m), 7.38 (1H, dd, J=4.2, 8.6 Hz), 7.50-7.58 (2H, m), 8.23 (1H, dd, J=1.4, 8.6 Hz), 8.92 (1H, dd, J=1.6, 4.2 Hz).

Example 723

7-{[(4-Chloro-pyridin-3-ylmethyl)amino]methyl}-1-ethyl-3,3,5-trimethyl-1,5-dihydrobenzo[b][1,4]diazepine-2,4-dione The synthesis of the title compound was performed in the same manner as in Example 3 using appropriate starting materials.
$^1$H NMR (CDCl$_3$), δppm: 0.83 (3H, s), 1.18 (3H, t, J=7.1 Hz), 1.53 (3H, s), 3.42 (3H, s), 3.72-3.90 (3H, m), 3.96 (2H, s), 4.08-4.22 (1H, m), 7.22-7.27(3H, m), 7.33 (1H, d, J=5.3 Hz), 8.44 (1H, d, J=5.3 Hz), 8.60 (1H, s).

Example 724

7-{[(2-Chloropyridin-3-ylmethyl)amino]methyl}-1-ethyl-3,3,5-trimethyl-1,5-dihydrobenzo[b][1,4]diazepine-2,4-dione The synthesis of the title compound was performed in the same manner as in Example 3 using appropriate starting materials.
$^1$H NMR (CDCl$_3$), δppm: 0.84 (3H, s), 1.18 (3H, t, J=7.1 Hz), 1.53 (3H, s), 3.42 (3H, s), 3.74-3.86 (1H, m), 3.86 (2H, s), 3.93 (2H, s), 4.08-4.23 (1H, m), 7.21-7.31 (4H, m), 7.80 (1H, dd, J=1.9, 7.5 Hz), 8.32 (1H, dd, J=1.9, 4.8 Hz).

Example 725

N-(1-Ethyl-3,3,5-trimethyl-2,4-dioxo-2,3,4,5-tetrahydro-1H-benzo[b][1,4]diazepin-7-ylmethyl)-N-(2-methyl-pyridin-3-ylmethyl)carbamic acid tert-butyl ester To a THF solution (15 ml) of 1-ethyl-3,3,5-trimethyl-7-(((2-methylpyridin-3-yl)methylamino)methyl)-1H-benzo[b][1,4]diazepine-2,4(3H,5H)-dione (0.92 g) was added di-tert-butyl dicarbonate (0.58 g) at room temperature, the mixture was stirred overnight. The resulting mixture was concentrated and then purified by column chromatography (ethyl acetate/hexanes 1:4→1:1→7:3) to give the titled compound as colorless oil (0.88 g).

$^1$H NMR (CDCl$_3$), δppm: 0.82 (3H, s), 1.18 (3H, t, J=7.0 Hz), 1.49 (9H, s), 1.53 (3H, s), 2.45 (3H, s), 3.36 (3H, s), 3.75-3.84 (1H, m), 4.09-4.18 (1H, s), 4.43 (4H, br), 6.99-7.12 (3H, m), 7.23-7.25 (1H, m), 7.35-7.38 (1H, m), 8.39-8.41 (1H, m).

Example 726

N-(1-Ethyl-3,3,5-trimethyl-2,4-dioxo-2,3,4,5-tetrahydro-1H-benzo[b][1,4]diazepin-7-ylmethyl)-N-(4-methylthiazol-5-ylmethyl)carbamic acid tert-butyl ester The synthesis of the title compound was performed in the same manner as in Example 725 using appropriate starting materials.

$^1$H NMR (CDCl$_3$), δppm: 0.82 (3H, s), 1.18 (3H, t, J=7.1 Hz), 1.45-1.55 (12H, m), 2.34 (3H, s), 3.36 (3H, s), 3.76-3.84 (1H, m), 4.09-4.16 (1H, m), 4.42 (2H, s), 4.54 (2H, s), 7.00-7.09 (2H, m), 7.24-7.27 (1H, m), 8.62 (1H, s).

Example 727

N-(2,5-Dimethyl-2H-pyrazol-3-ylmethyl)-N-(1-ethyl-3,3,5-trimethyl-2,4-dioxo-2,3,4,5-tetrahydro-1H-benzo[b][1,4]diazepin-7-ylmethyl)carbamic acid tert-butyl ester The synthesis of the title compound was performed in the same manner as in Example 725 using appropriate starting materials.

$^1$H NMR (CDCl$_3$), δppm: 0.83 (3H, s), 1.19 (3H, t, J=7.1 Hz), 1.49 (9H, br), 1.54 (3H, s), 2.21 (3H, s), 3.38 (3H, s), 3.72 (3H, br), 3.75-3.85 (1H, m), 4.09-4.18 (1H, m), 4.35 (2H, br), 4.44 (2H, br), 5.88 (1H, s), 7.00-7.05 (2H, m), 7.24-7.27 (1H, m).

Example 728

N-(1-Ethyl-3,3,5-trimethyl-2,4-dioxo-2,3,4,5-tetrahydro-1H-benzo[b][1,4]diazepin-7-ylmethyl)-N-(2-methyl-1-oxypyridin-3-ylmethyl)carbamic acid tert-butyl ester The synthesis of the title compound was performed in the same manner as in Example 716 using appropriate starting materials.

$^1$H NMR (CDCl$_3$), δppm: 0.83 (3H, s), 1.20 (3H, t, J=7.0 Hz), 1.49 (9H, s), 1.54 (3H, s), 2.45 (3H, s), 3.38 (3H, s), 3.76-3.86 (1H, m), 4.08-4.16 (1H, m), 4.43 (4H, br), 6.99-7.12 (4H, m), 7.25-7.29 (1H, m), 8.21-8.23 (1H, m).

Example 729

N-(1-Ethyl-3,3,5-trimethyl-2,4-dioxo-2,3,4,5-tetrahydro-1H-benzo[b][1,4]diazepin-7-ylmethyl)-N-(2-hydroxymethylpyridin-3-ylmethyl)carbamic acid tert-butyl ester The synthesis of the title compound was performed in the same manner as in Example 666 using appropriate starting materials.

$^1$H NMR (CDCl$_3$), δppm: 0.81 (3H, s), 1.13 (3H, t, J=7.1 Hz), 1.49 (9H, br), 1.53 (3H, s), 3.36 (3H, s), 3.75-3.84 (1H, m), 4.07-4.18 (1H, m), 4.40 (4H, br), 4.62 (2H, s), 7.00-7.08 (2H, m), 7.24-7.27 (2H, m), 7.47-7.49 (1H, m), 8.47-8.49 (1H, m).

Example 730

1-Ethyl-3,3,5-trimethyl-7-{[2-(7-oxo-7H-furo[2,3-c]pyridin-6-yl)ethylamino]methyl}-1,5-dihydrobenzo[b][1,4]diazepine-2,4-dione 1H NMR (CDCl$_3$), δppm: 0.79 (3H, s), 1.17 (3H, t, J=7.1 Hz), 1.52 (3H, s), 3.00-3.10(2H, m), 3.34 (3H, s), 3.72-3.81 (1H, m), 3.84 (2H, s), 4.08-4.17 (1H, m), 4.21 (2H, t, J=6.0 Hz), 6.47 (1H, d, J=7.0 Hz), 6.67 (1H, d, J=2.0 Hz), 7.13-7.22 (4H, m), 7.74 (1H, d, J=2.0 Hz)

Example 731

1-Ethyl-7-{[(2-hydroxymethylpyridin-3-ylmethyl)amino]methyl}-3,3,5-trimethyl-1,5-dihydrobenzo[b][1,4]diazepine-2,4-dione To a ethanol solution (20 ml) of tert-butyl (1-ethyl-3,3,5-trimethyl-2,4-dioxo-2,3,4,5-tetrahydro-1H-benzo[b][1,4]diazepin-7-yl)methyl((2-(hydroxymethyl)pyridin-3-yl)methyl)carbamate (0.82 g) was added 5 M HCl and the mixture was stirred at 50° C. for 7 hours. The resulting mixture was concentrated and then 5 M NaOH was added thereto. Organic materials were extracted with ethyl acetate twice and then dried over MgSO$_4$. After evaporation, the residue was purified by column chromatography (methanol/ethyl acetate 1:9→1:1) to give the titled compound as pale yellow oil (0.37 g).

$^1$H NMR (CDCl$_3$), δppm: 0.82 (3H, s), 1.18 (3H, t, J=7.0 Hz), 1.53 (3H, s), 3.42 (3H, s), 3.74-3.90 (5H, m), 4.09-4.19 (1H, m), 4.80 (2H, s), 7.20-7.29 (4H, m), 7.64-7.67 (1H, m), 8.49-8.51 (1H, m).

Example 732

1-Ethyl-7-{[(5-methoxymethyl-2-methyl-2H-pyrazol-3-ylmethyl)amino]methyl}-3,3,5-trimethyl-1,5-dihydro-benzo[b][1,4]diazepine-2,4-dione The synthesis of the title compound was performed in the same manner as in Example 3 using appropriate starting materials.

$^1$H NMR (CDCl$_3$), δppm: 0.83 (3H, s), 1.18 (3, t, J=7.0 Hz), 1.53 (3H, s), 3.40 (3H, s), 3.42 (3H, s), 3.77-3.87 (5H, m), 4.11-1.18 (1H, m), 4.41 (2H, s), 6.18 (1H, s), 7.21-7.28 (3H, m).

Example 733

1-Isobutyl-3,3-dimethyl-7-{[(2-methylpyridin-3-ylmethyl)amino]methyl}-1,5-dihydrobenzo[b][1,4]diazepine-2,4-dione The synthesis of the title compound was performed in the same manner as in Example 721 using appropriate starting materials.

$^1$H NMR (CDCl$_3$), δppm: 0.75 (3H, s), 0.77 (3H, s), 0.98 (3H, br), 1.53 (3H, br), 1.76-1.84 (1H, m), 2.56 (3H, s), 3.37-3.42 (1H, m), 3.82 (2H, s), 3.85 (2H, s), 4.34-4.40 (1H, m), 7.00-7.02 (1H, m), 7.10-7.14 (1H, m), 7.20-7.23 (1H, m), 7.24-7.27 (1H, m), 7.62 (1H, br), 7.62-7.64 (1H, m), 8.41 (1H, dd, J=4.9, 1.7 Hz).

Example 734

1-Isobutyl-7-{[(2-methoxymethylpyridin-3-ylmethyl)amino]methyl}-3,3-dimethyl-1,5-dihydrobenzo[b][1,4]diazepine-2,4-dione The synthesis of the title compound was performed in the same manner as in Example 721 using appropriate starting materials.

$^1$H NMR (CDCl$_3$), δppm: 0.74 (3H, s), 0.76 (3H, s), 0.98 (3H, br), 1.53 (3H, br), 1.74-1.85 (1H, m), 3.39-3.42 (1H, m), 3.40 (3H, s), 3.82 (2H, s), 3.90 (2H, s), 4.34-4.39 (1H, m), 7.01-7.02 (1H, m), 7.18-7.21 (1H, m), 7.23-7.27 (2H, m), 7.68 (1H, br), 7.74 (1H, dd, J=7.7, 1.6 Hz), 8.50 (1H, dd, J=4.8, 1.6 Hz).

Example 735

1-(2-Methoxyethyl)-3,3-dimethyl-7-{[(2-methylpyridin-3-ylmethyl)amino]methyl}-1,5-dihydrobenzo[b][1,4]diazepine-2,4-dione The synthesis of the title compound was performed in the same manner as in Example 721 using appropriate starting materials.

$^1$H NMR (CDCl$_3$), δppm: 1.01 (3H, br), 1.53 (3H, br), 2.56 (3H, s), 3.34 (3H, s), 3.49 (1H, br), 3.60 (1H, br), 3.81 (2H, s), 3.84 (2H, s), 3.98 (1H, br), 4.11 (1H, br), 7.00 (1H, d, J=1.8 Hz), 7.12 (1H, dd, J=7.6, 4.9 Hz), 7.22 (1H, dd, J=8.4, 1.8 Hz), 7.58 (1H, d, J=8.4 Hz), 7.64 (1H, dd, J=7.6, 1.5 Hz), 7.92 (1H, br), 8.41 (1H, dd, J=4.9, 1.5 Hz).

Example 736

1-(2-Methoxyethyl)-7-{[(2-methoxymethylpyridin-3-ylmethyl)amino]methyl}-3,3-dimethyl-1,5-dihydrobenzo[b][1,4]diazepine-2,4-dione The synthesis of the title compound was performed in the same manner as in Example 721 using appropriate starting materials.

$^1$H NMR (CDCl$_3$), δppm: 1.01 (3H, br), 1.53 (3H, br), 3.34 (3H, s), 3.41 (3H, s), 3.59 (1H, br), 3.72 (1H, br), 3.81 (2H, s), 3.89 (2H, s), 3.98 (1H, br), 4.10 (1H, br), 4.67 (2H, s), 6.98-7.00 (1H, m), 7.21 (1H, dd, J=8.4, 1.9 Hz), 7.24-7.27 (1H, m), 7.57 (1H, d, J=8.4 Hz), 7.66 (1H, br), 7.73 (1H, dd, J=7.7, 1.6 Hz), 8.50 (1H, dd, J=4.8, 1.6 Hz).

Example 737

1-Cyclopropylmethyl-3,3-dimethyl-7-{[(2-methylpyridin-3-ylmethyl)amino]methyl}-1,5-dihydrobenzo[b][1,4]diazepine-2,4-dione The synthesis of the title compound was performed in the same manner as in Example 721 using appropriate starting materials.

$^1$H NMR (CDCl$_3$), δppm: 0.18 (2H, br), 0.41 (2H, d, J=8.0 Hz), 0.96-1.07 (4H, m), 1.54 (3H, br), 3.65 (1H, br), 3.82 (2H, s), 3.85 (2H, s), 4.11 (1H, br), 7.03 (1H, d, J=1.8 Hz), 7.12 (1H, dd, J=7.6, 4.9 Hz), 7.21 (1H, dd, J=8.4, 1.8 Hz), 7.32 (1H, d, J=8.4 Hz), 7.63 (1H, dd, J=7.6, 1.6 Hz), 7.84 (1H, br), 8.41 (1H, dd. J=4.9, 1.6 Hz).

Example 738

1-Cyclopropylmethyl-7-{[(2-methoxymethylpyridin-3-ylmethyl)amino]methyl}-3,3-dimethyl-1,5-dihydrobenzo[b][1,4]diazepine-2,4-dione The synthesis of the title compound was performed in the same manner as in Example 721 using appropriate starting materials.

$^1$H NMR (CDCl$_3$), δppm: 0.19 (2H, br), 0.40 (2H, d, J=8.1 Hz), 0.97-1.07 (4H, m), 1.54 (3H, br), 3.41 (3H, s), 3.66 (1H, br), 3.82 (2H, s), 3.90 (2H, s), 4.10 (1H, br), 4.67 (2H, s), 7.04 (1H, d, J=1.8 Hz), 7.20 (1H, dd, J=8.4, 1.8 Hz), 7.23-7.26 (1H, m), 7.32 (1H, d, J=8.4 Hz), 7.74 (1H, dd, J=7.7, 1.6 Hz), 8.07 (1H, br), 8.50 (1H, dd, J=4.8, 1.6 Hz).

Example 739

1-Cyclopropyl-3,3-dimethyl-7-{[(2-methylpyridin-3-ylmethyl)amino]methyl}-1,5-dihydrobenzo[b][1,4]diazepine-2,4-dione The synthesis of the title compound was performed in the same manner as in Example 721 using appropriate starting materials.

$^1$H NMR (CDCl$_3$), δppm: 0.40 (2H, br), 1.00 (2H, br), 1.54 (6H, br), 2.56 (3H, s), 3.16-3.22 (1H, m), 3.82 (2H, s), 3.85 (2H, s), 6.99 (1H, br), 7.12 (1H, dd, J=7.6, 4.9 Hz), 7.23 (1H, dd, J=8.4, 1.9 Hz), 7.34 (1H, d, J=8.4 Hz), 7.64 (1H, dd, J=7.6, 1.6 Hz), 8.13 (1H, br), 8.41 (1H, dd, J=4.9, 1.6 Hz).

Example 740

1-Cyclopropyl-7-{[(2-methoxymethylpyridin-3-ylmethyl)amino]methyl}-3,3-dimethyl-1,5-dihydrobenzo[b][1,4]diazepine-2,4-dione The synthesis of the title compound was performed in the same manner as in Example 721 using appropriate starting materials.

$^1$H NMR (CDCl$_3$), δppm: 0.40 (2H, br), 1.00 (2H, br), 1.54 (6H, br), 3.16-3.21 (1H, m), 3.41 (3H, s), 3.82 (2H, s), 3.90 (2H, s), 4.67 (2H, s), 6.96 (1H, br), 7.21 (1H, dd, J=8.4, 1.9

Hz), 7.24-7.26 (1H, m), 7.34 (1H, d, J=8.4 Hz), 7.60 (1H, br), 7.74 (1H, dd, J=7.7, 1.6 Hz), 8.50 (1H, dd, J=4.8, 1.6 Hz).

Example 741

N-[3-(1-Ethyl-3,3,5-trimethyl-2,4-dioxo-2,3,4,5-tetrahydro-1H-benzo[b][1,4]diazepin-7-yl)propyl]-2-nitro-N-[2-(1-oxo-1H-isoquinolin-2-yl)ethy[l]benzenesulfonamide Tributyl phosphine(1.2 ml) and 1,1'-(azodicarbonyl)dipiperidine (1.17 g) were added to a toluene solution(100 ml) of 2-nitro-N-[2-(1-oxo-1H-isoquinolin-2-yl)-ethyl]-benzenesulfonamide (1.39 g), and 1-ethyl-7-(3-hydroxy-propyl)-3,3,5-trimethyl-1,5-dihydro-benzo[b][1,4]diazepine-2,4-dione (0.94 g). The mixture was stirred overnight. Water was added to the reaction mixture, followed by extraction using ethyl acetate. The organic layer was washed with water and saturated saline, dried with magnecium sulfate, and condensed under reduced pressure. The residue was purified by silica gel column chromatography (ethyl acetate: hexane=1:1→1:0). The purified product was condensed under reduced pressure to produce the title compound(0.54 g) as a white amorphous.
$^1$H NMR (CDCl$_3$), δppm: 0.81 (3H, s), 1.18 (3H, t, J=7.1 Hz), 1.52 (3H, s), 1.91-2.01(2H, m), 2.61 (2H, t, J=7.7 Hz), 3.31-3.51 (2H, m), 3.40 (3H, s), 3.70 (2H, t, J=6.7 Hz), 3.72-3.81 (1H, m), 4.09-4.17 (1H, m), 4.22 (2H, t, J=6.7 Hz), 6.45 (1H, d, J=7.3 Hz), 6.94 (1H, dd, J=8.4 and 1.9 Hz), 7.02 (1H, d, J=1.9 Hz), 7.12-7.16 (2H, m), 7.46-7.66 (6H, m), 7.90-7.94 (1H, m), 8.34 (1H, d, J=7.5 Hz)

Example 742

1-Ethyl-3,3,5-trimethyl-7-{3-[2-(1-oxo-1H-isoquinolin-2-yl)ethylamino]propyl}-1,5-dihydrobenzo[b][1,4]diazepine-2,4-dione Lithium hydroxide(3.2 g), and thioglycolic acid(2.4 ml) were added to a DMF solution(27.4 ml) of N-[3-(1-ethyl-3,3,5-trimethyl-2,4-dioxo-2,3,4,5-tetrahydro-1H-benzo[b][1,4]diazepin-7-yl)propyl]-2-nitro-N-[2-(1-oxo-1H-isoquinolin-2-yl)ethyl]benzenesulfonamide (4.56 g). The mixture was stirred at room temperature for 1 hour. The reaction mixture was condensed under reduced pressure. Water was added to the residue, followed by extraction using dichloromethane. The organic layer was washed with water and saturated saline, dried with magnesium sulfate, and condensed under reduced pressure. The residue was purified by silica gel column chromatography (ethyl acetate: methanol=10:1). The purified product was condensed under reduced pressure to produce the title compound(2.24 g) as a yellow oil.
1H NMR (CDCl3), δppm: 0.80 (3H, s), 1.17 (3H, t, J=7.1 Hz), 1.52 (3H, s), 1.77-1.88(2H, m), 2.64-2.72 (4H, m), 3.04 (2H, t, J=6.3 Hz), 3.38 (3H, s), 3.69-3.80 (1H, m), 4.08-4.17 (3H, m), 6.51 (1H, d, J=7.3 Hz), 7.00-7.03 (2H, m), 7.11-7.17 (2H, m), 7.46-7.53 (2H, m), 7.61-7.66 (1H, m), 8.42 (1H, dd, J=8.0 and 0.6 Hz)

Example 743

1-Cyclopropyl-7-{[(2-methoxymethylpyridin-3-ylmethyl)amino]methyl}-3,3,5-trimethyl-1,5-dihydrobenzo[b][1,4]diazepine-2,4-dione The synthesis of the title compound was performed in the same manner as in Example 721 using appropriate starting materials.
$^1$H NMR (CDCl$_3$), δppm: 0.12-0.19 (1H, m), 0.60-0.67 (1H, m), 0.75-0.83 (1H, m), 0.85 (3H, s), 1.24-1.28 (1H, m), 1.52 (3H, s), 3.15-3.21 (1H, m), 3.39 (3H, s), 3.40 (3H, s), 3.84 (2H, s), 3.91 (2H, s), 4.67 (2H, s), 7.19-7.20 (1H, m), 7.22-7.29 (2H, m), 7.33 (1H, d, J=4.3 Hz), 7.73 (1H, dd, J=7.7, 1.6 Hz), 8.50 (1H, dd, J=4.8, 1.6 Hz).

Example 744

1-Isobutyl-7-{[(2-methoxymethylpyridin-3-ylmethyl)amino]methyl}-3,3,5-trimethyl-1,5-dihydrobenzo[b][1,4]diazepine-2,4-dione The synthesis of the title compound was performed in the same manner as in Example 721 using appropriate starting materials.
$^1$H NMR (CDCl$_3$), δppm: 0.70 (3H, d, J=6.7 Hz), 0.75 (3H, d, J=6.7 Hz), 0.81 (3H, s), 1.53 (3H, s), 1.75-1.86 (1H, m), 3.31 (1H, dd, J=13.6, 6.4 Hz), 3.85 (2H, s), 3.91 (2H, s), 4.37 (1H, dd, J=13.6, 8.6 Hz), 4.67 (2H, s), 7.23-7.26 (4H, m), 7.72 (1H, dd, J=7.7, 1.6 Hz), 8.50 (1H, dd, J=4.8, 1.6 Hz).

Example 745

1-(2-Methoxyethyl)-3,3,5-trimethyl-7-{[(2-methylpyridin-3-ylmethyl)amino]methyl}-1,5-dihydrobenzo[b][1,4]diazepine-2,4-dione The synthesis of the title compound was performed in the same manner as in Example 721 using appropriate starting materials.
$^1$H NMR (CDCl$_3$), δppm: 0.85 (3H, s), 1.53 (3H, s), 2.56 (3H, s), 3.29 (3H, s), 3.41 (3H, s), 3.53-3.58 (1H, m), 3.69 (1H, ddd, J=10.3, 7.1, 4.4 Hz), 3.82 (2H, s), 3.87 (2H, s), 3.97 (1H, ddd, J=14.1, 5.2, 4.6 Hz), 4.07-4.15 (1H, m), 7.13 (1H, dd, J=7.6, 4.9 Hz), 7.23-7.26 (2H, m), 7.50 (1H, d, J=8.2 Hz), 7.63 (1H, dd, J=7.6, 1.6 Hz), 8.42 (1H, dd, J=4.8, 1.6 Hz).

Example 746

1-Isobutyl-3,3-dimethyl-8-{[(2-methylpyridin-3-ylmethyl)amino]methyl}-1,5-dihydrobenzo[b][1,4]diazepine-2,4-dione The synthesis of the title compound was performed in the same manner as in Example 721 using appropriate starting materials.
$^1$H NMR (CDCl$_3$), δppm: 0.76 (6H, d, J=6.7 Hz), 0.98 (3H, s), 1.53 (3H, s), 1.78-1.89 (1H, m), 2.55 (3H, s), 3.41 (1H, dd, J=13.8, 6.5 Hz), 3.80 (2H, s), 3.87 (2H, s), 4.37 (1H, dd, J=13.8, 8.3 Hz), 6.97 (1H, d, J=8.1 Hz), 7.12 (1H, dd, J=7.6, 4.9 Hz), 7.19 (1H, dd, J=8.1, 1.7 Hz), 7.32 (1H, d, J=1.7 Hz), 7.62 (1H, dd, J=7.6, 1.6 Hz), 7.70 (1H, br), 8.41 (1H, dd, J=4.9, 1.6 Hz).

Example 747

1-Isobutyl-8-{[(2-methoxymethylpyridin-3-ylmethyl)amino]methyl}-3,3-dimethyl-1,5-dihydrobenzo[b][1,4]diazepine-2,4-dione The synthesis of the title compound was performed in the same manner as in Example 721 using appropriate starting materials.
$^1$H NMR (CDCl$_3$), δppm: 0.76 (6H, d, J=6.7 Hz), 0.98 (3H, s), 1.53 (3H, s), 1.78-1.89 (1H, m), 3.39-3.46 (1H, m), 3.40 (3H, s), 3.83 (2H, s), 3.88 (2H, s), 4.33-4.42 (1H, m), 4.66

(2H, s), 6.97 (1H, d, J=8.1 Hz), 7.18 (1H, dd, J=8.1, 1.7 Hz), 7.23-7.26 (1H, m), 7.31 (1H, d, J=1.7 Hz), 7.72 (1H, dd, J=7.6, 1.6 Hz), 7.73 (1H, br), 8.41 (1H, dd, J=4.9, 1.6 Hz).

Example 748

1-Cyclopropylmethyl-3,3-dimethyl-8-{[(2-methylpyridin-3-ylmethyl)amino]methyl}-1,5-dihydrobenzo[b][1,4]diazepine-2,4-dione The synthesis of the title compound was performed in the same manner as in Example 721 using appropriate starting materials.

$^1$H NMR (CDCl$_3$), δppm: 0.18 (2H, br), 0.41 (2H, d, J=7.9 Hz), 0.95-1.08 (4H, m), 1.54 (3H, br), 2.55 (3H, s), 3.70 (1H, br), 3.80 (2H, s), 3.87 (2H, s), 4.14 (1H, br), 6.97 (1H, d, J=8.1 Hz), 7.12 (1H, dd, J=7.6, 4.9 Hz), 7.19 (1H, dd, J=8.1, 1.6 Hz), 7.39 (1H, d, J=1.6 Hz), 7.62 (1H, dd, J=7.6, 1.6 Hz), 7.74 (1H, br), 8.41 (1H, dd, J=4.9, 1.6 Hz).

Example 749

1-Cyclopropylmethyl-8-{[(2-methoxymethylpyridin-3-ylmethyl)amino]methyl}-3,3-dimethyl-1,5-dihydrobenzo[b][1,4]diazepine-2,4-dione The synthesis of the title compound was performed in the same manner as in Example 721 using appropriate starting materials.

$^1$H NMR (CDCl$_3$), δppm: 0.18 (2H, br), 0.41 (2H, d, J=7.9 Hz), 0.95-1.08 (4H, m), 1.54 (3H, br), 3.40 (3H, s), 3.71 (1H, br), 3.84 (2H, s), 3.89 (2H, s), 4.10 (1H, br), 4.66 (2H, s), 6.97 (1H, d, J=8.1 Hz), 7.18 (1H, dd, J=8.1, 1.6 Hz), 7.23-7.26 (1H, m), 7.37 (1H, d, J=1.6 Hz), 7.72 (1H, dd, J=7.7, 1.6 Hz), 7.83 (1H, br), 8.41 (1H, dd, J=4.8, 1.6 Hz).

Example 750

N-(1-Ethyl-3,3,5-trimethyl-2,4-dioxo-2,3,4,5-tetrahydro-1H-benzo[b][1,4]diazepin-7-ylmethyl)-N-(2-methoxymethylpyridin-3-ylmethyl)carbamic acid tert-butyl ester N-(1-Ethyl-3,3,5-trimethyl-2,4-dioxo-2,3,4,5-tetrahydro-1H-benzo[b][1,4]diazepin-7-ylmethyl)-N-(2-methyl-1-oxy-pyridin-3-ylmethyl)carbamic acid tert-butyl ester (188 mg) was dissolved in DMF(20 ml), and was cooled to 0° C. in ice water bath. Sodium hydride (60% in oil, 19.7 mg) was added thereto at the same temperature, and the mixture was stirred at 0° C. for 0.5 hours. Methyl iodide (0.028 ml) was added thereto, and the mixture was stirred at 0° C. for 0.5 hours. Water was added to the reaction mixture, followed by extraction using ethyl acetate. The organic layer was dried with sodium sulfate, and was condensed under reduced pressure. The residue was purified by silica gel column chromatography (ethyl acetate: methanol=10:1). The purified product was condensed to dryness under reduced pressure to give the title compound(162 mg) as a colorless oil.

$^1$H NMR (CDCl$_3$), δppm: 0.82 (3H, s), 1.18 (3H, t, J=7.1 Hz), 1.48 (9H, s), 1.53 (3H, s), 3.33 (3H, s), 3.36 (3H, s), 3.74-3.84 (1H, m), 4.08-4.18 (1H, m), 4.30-4.50 (2H, m), 4.52-4.72 (4H, m), 7.02-7.15 (2H, m), 7.20-7.25 (2H, m), 7.46-7.57 (1H, m), 8.46 (1H, dd, J=1.5 and 4.8 Hz)

Example 751

N-(1-Ethyl-3,3,5-trimethyl-2,4-dioxo-2,3,4,5-tetrahydro-1H-benzo[b][1,4]diazepin-7-ylmethyl)-N-(2-methyl-6-oxo-1,6-dihydropyridin-3-ylmethyl)carbamic acid tert-butyl ester N-(1-Ethyl-3,3,5-trimethyl-2,4-dioxo-2,3,4,5-tetrahydro-1H-benzo[b][1,4]diazepin-7-ylmethyl)-N-(2-methyl-1-oxy-pyridin-3-ylmethyl)carbamic acid tert-butyl ester (2.35 g) was dissolved in acetic anhydride (20 ml). The reaction mixture was stirred at 100° C. for 2 h. The resulting mixture was evaporated, and dissolved in MeOH (15 ml). Potassium carbonate (6.8 g) was added to the mixture, and the reaction mixture was stirred 2 h at room temperature. Water was added to the resulting mixture and then the mixture was extracted with ethyl acetate. The organic layer was dried with sodium sulfate, and was condensed under reduced pressure. The residue was purified by silica gel column chromatography (ethyl acetate: methanol=10:1). The purified product was condensed to dryness under reduced pressure to give the title compound(536 mg) as a pale yellow amorphous.

$^1$H NMR (CDCl$_3$), δppm: 0.82 (3H, s), 1.18 (3H, t, J=7.1 Hz), 1.49 (9H, s), 1.52 (3H, s), 2.37 (3H, s), 3.37 (3H, s), 3.77-3.83 (1H, m), 4.09-4.15 (1H, m), 4.30-4.52 (4H, m), 7.00-7.08 (2H, m), 7.09-7.15 (1H, m), 7.25-7.30 (1H, m), 8.07 (1H, d, J=2.6 Hz)

Example 752

1-Ethyl-3,3,5-trimethyl-7-[3-(2-pyridin-3-yl-ethylamino)propyl]-1,5-dihydro-benzo[b][1,4]diazepine-2,4-dione The synthesis of the title compound was performed in the same manner as in Example 742 using appropriate starting materials.

$^1$H NMR (CDCl$_3$), δppm: 0.82 (3H, s), 1.17 (3H, t, J=7.1 Hz), 1.53 (3H, s), 1.78-1.85 (2H, m), 2.63-2.72 (4H, m), 2.79-2.83 (2H, m), 2.86-2.92 (2H, m), 3.40 (3H, s), 3.73-3.81 (1H, m), 4.09-4.18 (1H, m), 7.01-7.06 (2H, m), 7.19-7.23 (2H, m), 7.52-7.55 (1H, m), 8.47-8.49 (2H, m)

Example 753

1-Ethyl-3,3,5-trimethyl-7-{3-[2-(7-oxo-7H-furo[2,3-c]pyridin-6-yl)ethylamino]propyl}-1,5-dihydrobenzo[b][1,4]diazepine-2,4-dione The synthesis of the title compound was performed in the same manner as in Example 742 using appropriate starting materials.

$^1$H NMR (CDCl$_3$), δppm: 0.84 (3H, s), 1.17 (3H, t, J=7.1 Hz), 1.52 (3H, s), 1.73-1.84 (2H, m), 2.60-2.71 (4H, m), 3.03 (2H, t, J=6.2 Hz), 3.39 (3H, s), 3.73-3.81 (1H, m), 4.09-4.18 (1H, m), 4.17 (2H, t, J=6.2 Hz), 6.47 (1H, d, J=7.0 Hz), 6.66 (1H, d, J=2.0 Hz), 6.98-7.05 (2H, m), 7.14-7.20 (2H, m), 7.74 (1H, d, J=2.0 Hz)

Example 754

Acetic acid 3-{[N-tert-butoxycarbonyl-N-(1-ethyl-3,3,5-trimethyl-2,4-dioxo-2,3,4,5-tetrahydro-1H-benzo[b][1,4]diazepin-7-ylmethyl)amino]methyl}pyridin-2-ylmethyl ester The synthesis of the title compound was performed in the same manner as in Example 751 using appropriate starting materials.

¹H NMR (CDCl₃), δppm: 0.81 (3H, s), 1.19 (3H, t, J=7.1 Hz), 1.48 (9H, br), 1.57 (3H, s), 2.08 (3H, s), 3.36 (3H, s), 3.75-3.84 (1H, m), 4.09-4.18 (1H, m), 4.41 (2H, br), 4.57 (2H, br), 5.15 (2H, s), 7.03-7.12 (2H, m), 7.22-7.26 (2H, m), 7.47-7.50 (1H, m), 8.53 (1H, dd, J=4.8, 1.6 Hz).

Example 755

Acetic acid 3-{[(1-ethyl-3,3,5-trimethyl-2,4-dioxo-2,3,4,5-tetrahydro-1H-benzo[b][1,4]diazepin-7-ylmethyl)amino]methyl}pyridin-2-ylmethyl ester The synthesis of the title compound was performed in the same manner as in Example 731 using appropriate starting materials.

¹H NMR (CDCl₃), δppm: 0.82 (3H, s), 1.17 (3H, t, J=7.1 Hz), 1.52 (3H, s), 2.11 (3H, s), 3.41 (3H, s), 3.74-3.82 (1H, m), 3.86 (2H, s), 3.90 (2H, s), 4.09-4.20 (1H, m), 5.33 (2H, s), 7.23-7.27 (4H, m), 7.72 (1H, d, J=7.7 Hz), 8.52-8.54 (1H, m).

Example 756

1-Ethyl-3,3,5-trimethyl-7-{3-[2-(4-oxo-4H-furo[3,2-c]pyridin-5-yl)ethylamino]propyl}-1,5-dihydrobenzo[b][1,4]diazepine-2,4-dione The synthesis of the title compound was performed in the same manner as in Example 742 using appropriate starting materials.

¹H NMR (CDCl₃), δppm: 0.81 (3H, s), 1.17 (3H, t, J=7.1 Hz), 1.52 (3H, s), 1.76-1.83 (2H, m), 2.63-2.70 (4H, m), 3.01 (2H, t, J=6.2 Hz), 3.39 (3H, s), 3.72-3.81 (1H, m), 4.09-4.18 (3H, m), 6.54 (1H, dd, J=7.4 and 0.8 Hz), 6.96-7.04 (3H, m), 7.19 (1H, d, J=8.6 Hz), 7.23 (1H, d, J=7.4 Hz), 7.49 (1H, d, J=2.1 Hz), Example 757

N-(1-Ethyl-3,3,5-trimethyl-2,4-dioxo-2,3,4,5-tetrahydro-1H-benzo[b][1,4]diazepin-7-ylmethyl)-N-(6-methoxy-2-methylpyridin-3-ylmethyl)carbamic acid tert-butyl ester N-(1-Ethyl-3,3,5-trimethyl-2,4-dioxo-2,3,4,5-tetrahydro-1H-benzo[b][1,4]diazepin-7-ylmethyl)-N-(2-methyl-6-oxo-1,6-dihydropyridin-3-ylmethyl)carbamic acid tert-butyl ester (536 mg) was dissolved in DMF (20 ml), and was cooled to 0° C. in ice water bath. Sodium hydride (60% in oil, 56.1 mg) was added thereto at the same temperature, and the mixture was stirred at 0° C. for 0.5 hours. Methyl iodide (0.081 ml) was added thereto, and the mixture was stirred at 0° C. for 0.5 hours. Water was added to the reaction mixture, followed by extraction using ethyl acetate. The organic layer was dried with sodium sulfate, and was condensed under reduced pressure. The residue was purified by silica gel column chromatography (ethyl acetate: methanol=10:1). The purified product was condensed to dryness under reduced pressure to give the title compound (550 mg) as a yellow oil.

¹H NMR (CDCl₃), δppm: 0.82 (3H, s), 1.18 (3H, t, J=7.1 Hz), 1.50 (9H, s), 1.53 (3H, s), 2.37 (3H, s), 3.36 (3H, s), 3.75-3.85 (4H, m), 4.09-4.20 (1H, m), 4.30-4.50 (4H, m), 6.85-6.98 (1H, m), 7.00-7.12 (2H, m), 7.23-7.28 (1H, m), 8.08 (1H, d, J=2.8 Hz)

Example 758

1-Ethyl-7-{[(6-methoxy-2-methyl-pyridin-3-ylmethyl)amino]methyl}-3,3,5-trimethyl-1,5-dihydrobenzo[b][1,4]diazepine-2,4-dione The synthesis of the title compound was performed in the same manner as in Example 670 using appropriate starting materials.

¹H NMR (CDCl₃), δppm: 0.83 (3H, s), 1.18 (3H, t, J=7.1 Hz), 1.53 (3H, s), 2.47 (3H, s), 3.42 (3H, s), 3.78-3.83 (3H, m), 3.85 (3H, s), 3.88 (2H, s), 4.10-4.17 (1H, m), 7.20-7.30 (4H, m), 8.10 (1H, d, J=2.9 Hz)

Example 759

1,3,3-Trimethyl-8-{[(2-methylpyridin-3-ylmethyl)amino]methyl}-1,5-dihydrobenzo[b][1,4]diazepine-2,4-dione The synthesis of the title compound was performed in the same manner as in Example 721 using appropriate starting materials.

¹H NMR (CDCl₃), δppm: 1.08 (3H, br), 1.63 (3H, br), 2.56 (3H, s), 3.47 (3H, s), 3.81 (2H, s), 3.87 (2H, s), 6.97 (1H, d, J=8.1 Hz), 7.12 (1H, dd, J=7.6, 4.9 Hz), 7.19 (1H, dd, J=8.1, 1.7 Hz), 7.24-7.26 (1H, m), 7.62 (1H, dd, J=7.6, 1.6 Hz), 7.98 (1H, br), 8.41 (1H, dd, J=4.9, 1.6 Hz).

Example 760

1-Ethyl-3,3-dimethyl-8-{[(2-methylpyridin-3-ylmethyl)amino]methyl}-1,5-dihydro-benzo[b][1,4]diazepine-2,4-dione The synthesis of the title compound was performed in the same manner as in Example 721 using appropriate starting materials.

¹H NMR (CDCl₃), δppm: 1.00 (3H, br), 1.26 (3H, t, J=7.1 Hz), 1.55 (3H, br), 2.56 (3H, s), 3.81 (2H, s), 3.87 (2H, s), 3.93 (1H, br), 4.09 (1H, br), 6.93-6.97 (1H, m), 7.12 (1H, dd, J=7.5, 4.9 Hz), 7.19 (1H, dd, J=8.2, 1.8 Hz), 7.24-7.26 (1H, m), 7.35 (1H, br), 7.63 (1H, dd, J=3.5, 1.5 Hz), 8.41 (1H, dd, J=4.8, 1.5 Hz).

Example 761

1,3,3-Trimethyl-7-{[(2-methylpyridin-3-ylmethyl)amino]methyl}-1,5-dihydrobenzo[b][1,4]diazepine-2,4-dione The synthesis of the title compound was performed in the same manner as in Example 721 using appropriate starting materials.

¹H NMR (CDCl₃), δppm: 1.05 (3H, br), 1.55 (3H, br), 2.56 (3H, s), 3.46 (3H, s), 3.82 (2H, s), 3.85 (2H, s), 7.03 (1H, br), 7.12 (1H, dd, J=7.6, 4.9 Hz), 7.20-7.23 (2H, m), 7.63 (1H, dd, J=7.6, 1.6 Hz), 8.03 (1H, br), 8.41 (1H, dd, J=4.9, 1.6 Hz).

Example 762

1-Ethyl-3,3-dimethyl-7-{[(2-methylpyridin-3-ylmethyl)amino]methyl}-1,5-dihydrobenzo[b][1,4]diazepine-2,4-dione The synthesis of the title compound was performed in the same manner as in Example 721 using appropriate starting materials.

¹H NMR (CDCl₃), δppm: 1.00 (3H, br), 1.22 (3H, t, J=7.1 Hz), 1.53 (3H, br), 2.56 (3H, s), 3.82 (2H, s), 3.85 (2H, s), 3.92 (1H, br), 4.12 (1H, br), 7.02 (1H, d, J=1.6 Hz), 7.12 (1H, dd, J=7.6, 4.9 Hz), 7.22 (1H, dd, J=8.4, 1.8 Hz), 7.29, (1H, d, J=8.4 Hz), 7.63 (1H, dd, J=7.6, 1.5 Hz), 7.85 (1H, br), 8.41 (1H, dd, J=4.9, 1.5 Hz).

Example 763

1-Ethyl-7-{[(2-methoxymethylpyridin-3-ylmethyl)amino]methyl}-3,3-dimethyl-1,5-dihydrobenzo[b][1,4]diazepine-2,4-dione The synthesis of the title compound was performed in the same manner as in Example 721 using appropriate starting materials.
¹H NMR (CDCl₃), δppm: 1.00 (3H, br), 1.22 (3H, t, J=7.1 Hz), 1.53 (3H, br), 3.41 (3H, s), 3.82 (2H, s), 3.90 (2H, s), 3.92 (1H, br), 4.08 (1H, br), 4.67 (2H, s), 7.01 (1H, d, J=1.5 Hz), 7.21 (1H, dd, J=8.4, 1.9 Hz), 7.23-7.29 (2H, m), 7.74 (1H, dd, J=7.7, 1.6 Hz), 7.79 (1H, br), 8.50 (1H, dd, J=4.8, 1.6 Hz).

Example 764

8-{[(2-Methoxymethyl-pyridin-3-ylmethyl)amino]methyl}-1,3,3-trimethyl-1,5-dihydrobenzo[b][1,4]diazepine-2,4-dione The synthesis of the title compound was performed in the same manner as in Example 721 using appropriate starting materials.
¹H NMR (CDCl₃), δppm: 1.02 (3H, br), 1.53 (3H, br), 3.40 (3H, s), 3.47 (3H, s), 3.84 (2H, s), 3.90 (2H, s), 4.67 (2H, s), 6.97 (1H, d, J=8.2 Hz), 7.18 (1H, dd, J=8.2, 1.7 Hz), 7.23-7.26 (2H, m), 7.72 (1H, dd, J=7.7, 1.6 Hz), 7.94 (1H, br), 8.50 (1H, dd, J=4.8, 1.6 Hz).

Example 765

5-Cyclopropylmethyl-1-(2-methoxyethyl)-3,3-dimethyl-7-{[(2-methylpyridin-3-ylmethyl)amino]methyl}-1,5-dihydrobenzo[b][1,4]diazepine-2,4-dione The synthesis of the title compound was performed in the same manner as in Example 721 using appropriate starting materials.
¹H NMR (CDCl₃), δppm: 0.12-0.22 (2H, m), 0.34-0.50 (2H, m), 0.82 (3H, s), 0.94-1.03 (1H, m), 1.53 (3H, s), 2.56 (3H, s), 3.31 (3H, s), 3.49-3.60 (2H, m), 3.70 (1H, ddd, J=10.0, 7.1, 5.5 Hz), 3.81 (2H, s), 3.87 (2H, s), 3.94 (1H, dt, J=13.9, 5.3 Hz), 4.12 (1H, dd, J=14.1, 7.4 Hz), 4.15-4.22 (1H, m), 7.12 (1H, dd, J=7.6, 4.9 Hz), 7.24-7.26 (2H, m), 7.33 (1H, br), 7.50 (1H, d, J=8.4 Hz), 7.63 (1H, dd, J=7.6, 1.6 Hz), 8.41 (1H, dd, J=4.9, 1.6 Hz).

Example 766

5-Cyclopropylmethyl-1-(2-methoxyethyl)-7-{[(2-methoxymethylpyridin-3-ylmethyl)amino]-methyl}-3,3-dimethyl-1,5-dihydro-benzo[b][1,4]diazepine-2,4-dione The synthesis of the title compound was performed in the same manner as in Example 721 using appropriate starting materials.
¹H NMR (CDCl₃), δppm: 0.12-0.23 (2H, m), 0.34-0.44 (2H, m), 0.82 (3H, s), 0.96-1.03 (1H, m), 1.53 (3H, s), 3.30 (3H, s), 3.40 (3H, s), 3.49-3.60 (2H, m), 3.69 (1H, ddd, J=10.0, 7.1, 5.5 Hz), 3.84 (2H, s), 3.89 (2H, s), 3.95 (1H, dt, J=13.9, 5.3 Hz), 4.11-4.22 (2H, m), 4.66 (2H, s), 7.23-7.26 (2H, m), 7.32 (1H, br), 7.49 (1H, d, J=8.4 Hz), 7.72 (1H, dd, J=7.6, 1.6 Hz), 8.50 (1H, dd, J=4.8, 1.6 Hz).

Example 767

1-Cyclopropylmethyl-5-(2-methoxyethyl)-3,3-dimethyl-7-{[(2-methylpyridin-3-ylmethyl)-amino]methyl}-1,5-dihydro-benzo[b][1,4]diazepine-2,4-dione The synthesis of the title compound was performed in the same manner as in Example 721 using appropriate starting materials.
¹H NMR (CDCl₃), δppm: 0.11-0.22 (2H, m), 0.34-0.44 (2H, m), 0.82 (3H, s), 0.94-1.03 (1H, m), 1.52 (3H, s), 2.56 (3H, s), 3.29 (3H, s), 3.49-3.57 (2H, m), 3.71 (1H, ddd, J=10.0, 7.1, 5.5 Hz), 3.82 (2H, s), 3.87 (2H, s), 3.97 (1H, dt, J=13.9, 5.2 Hz), 4.11-4.22 (2H, m), 7.12 (1H, dd, J=7.6, 4.9 Hz), 7.23-7.27 (2H, m), 7.55 (1H, d, J=1.3 Hz), 7.64 (1H, dd, J=7.6, 1.6 Hz), 8.40 (1H, dd, J=4.9, 1.6 Hz).

Example 768

1-Cyclopropylmethyl-5-(2-methoxyethyl)-7-{[(2-methoxymethylpyridin-3-ylmethyl)amino]-methyl}-3,3-dimethyl-1,5-dihydrobenzo[b][1,4]diazepine-2,4-dione The synthesis of the title compound was performed in the same manner as in Example 721 using appropriate starting materials.
¹H NMR (CDCl₃), δppm: 0.11-0.22 (2H, m), 0.34-0.44 (2H, m), 0.82 (3H, s), 0.94-1.04 (1H, m), 1.52 (3H, s), 3.29 (3H, s), 3.40 (3H, s), 3.48-3.57 (2H, m), 3.70 (1H, ddd, J=10.0, 7.0, 5.6 Hz), 3.85 (2H, s), 3.90 (2H, s), 3.96 (1H, dt, J=13.9, 5.3 Hz), 4.14 (1H, dd, J=14.1, 7.4 Hz), 4.18-4.25 (1H, m), 4.67 (2H, s), 7.23-7.29 (3H, m), 7.52 (1H, br), 7.75 (1H, dd, J=7.7, 1.6 Hz), 8.50 (1H, dd, J=4.8, 1.6 Hz).

Example 769

5-Cyclopropyl-1-cyclopropylmethyl-7-{[(2-methoxymethylpyridin-3-ylmethyl)amino]methyl}-3,3-dimethyl-1,5-dihydrobenzo[b][1,4]diazepine-2,4-dione The synthesis of the title compound was performed in the same manner as in Example 721 using appropriate starting materials.
¹H NMR (CDCl₃), δppm: 0.00-0.06 (1H, m), 0.07-0.13 (1H, m), 0.18-0.35 (3H, m), 0.58-0.65 (1H, m), 0.75-0.90 (2H, m), 0.84 (3H, s), 1.14-1.22 (1H, m), 1.51 (3H, s), 3.20-3.25 (1H, m), 3.36 (1H, dd, J=14.1, 6.8 Hz), 3.40 (3H, s), 3.86 (2H, s), 3.90 (2H, s), 4.30 (1H, dd, J=14.1, 7.4 Hz), 4.67 (2H, s), 7.18-7.26 (3H, m), 7.36 (1H, br), 7.73 (1H, dd, J=7.7, 1.6 Hz), 8.50 (1H, dd, J=4.8, 1.6 Hz).

Example 770

1-Ethyl-3,3,5-trimethyl-7-{2-[N-[2-(7-methyl-4-oxo-4H-furo[3,2-c]pyridin-5-yl)ethyl]-N-(4-methylpyridin-3-ylmethyl)amino]ethyl}-1,5-dihydro-benzo[b][1,4]diazepine-2,4-dione The synthesis of the title compound was performed in the same manner as in Example 30 using appropriate starting materials.

White Powder
mp: 165.3-166.5° C.

Example 771

7-{2-[N-[2-(2,7-Dimethyl-4-oxo-4H-furo[3,2-c]pyridin-5-yl)ethyl]-N-(4-methylpyridin-3-ylmethyl)amino]ethyl}-1-ethyl-3,3,5-trimethyl-1,5-dihydrobenzo[b][1,4]diazepine-2,4-dione The synthesis of the title compound was performed in the same manner as in Example 30 using appropriate starting materials.
White Powder
mp: 155.1-155.8° C.

Example 772

1-Ethyl-3,3,5-trimethyl-7-{2-[N-[2-(7-methyl-4-oxo-4H-furo[3,2-c]pyridin-5-yl)ethyl]-N-(4-methylthiazol-2-ylmethyl)amino]ethyl}-1,5-dihydrobenzo[b][1,4]diazepine-2,4-dione The synthesis of the title compound was performed in the same manner as in Example 30 using appropriate starting materials.
$^1$H NMR (CDCl$_3$), δppm: 0.78 (3H, s), 1.15 (3H, t, J=7.1 Hz), 1.51 (3H, s), 2.23 (3H, d, J=0.9 Hz), 2.42 (3H, d, J=0.8 Hz), 2.76 (2H, t, J=7.4 Hz), 2.84-2.92 (2H, m), 2.95-3.04 (2H, m), 3.36 (3H, s), 3.71-3.79 (1H, m), 4.01 and 4.02 (2H, s), 4.03-4.16 (3H, m), 6.77 (1H, br), 6.93 (1H, br), 6.97-7.01 (m, 3H), 7.12 (1H, d, J=9.0 Hz), 7.52 (1H, d, J=2.1 Hz).

Example 773

1-Ethyl-3,3,5-trimethyl-7-{2-[N-[2-(2-methyl-4-oxo-4H-furo[3,2-c]pyridin-5-yl)ethyl]-N-(4-methylthiazol-2-ylmethyl)amino]ethyl}-1,5-dihydro-benzo[b][1,4]diazepine-2,4-dione The synthesis of the title compound was performed in the same manner as in Example 30 using appropriate starting materials.
$^1$H NMR (CDCl$_3$), δppm: 0.79 (3H, s), 1.16 (3H, t, J=7.1 Hz), 1.51 (3H, s), 2.41 (3H, s), 2.42 (3H, s), 2.75 (2H, t, J=7.4 Hz), 2.83-2.91 (2H, m), 2.99 (2H, t, J=6.4 Hz), 3.36 (3H, s), 3.72-3.79 (1H, m), 4.01 (2H, s), 4.07 (2H, t, J=6.4 Hz), 4.09-4.16 (1H, m), 6.43 (1H, d, J=7.3 Hz), 6.55 (1H, s), 6.77 (1H, br), 6.98-7.02 (m, 2H), 7.06 (1H, d, J=7.3 Hz), 7.13 (1H, d, J=8.7 Hz).

Example 774

1-Ethyl-3,3,5-trimethyl-7-{2-[N-[2-(2-methyl-4-oxo-4H-furo[3,2-c]pyridin-5-yl)ethyl]-N-(3-methylpyridin-2-ylmethyl)amino]ethyl}-1,5-dihydrobenzo[b][1,4]diazepine-2,4-dione The synthesis of the title compound was performed in the same manner as in Example 30 using appropriate starting materials.
$^1$H NMR (CDCl$_3$), δppm: 0.79 (3H, s), 1.16 (3H, t, J=7.1 Hz), 1.52 (3H, s), 2.24 (3H, s), 2.41 (3H, d, J=0.9 Hz), 2.79-2.85 (2H, m), 2.88-2.93 (2H, m), 2.95 (2H, t, J=6.8 Hz), 3.37 (3H, s), 3.71-3.79 (1H, m), 3.89 (2H, s), 3.94-3.98 (2H, m), 4.10-4.17 (1H, m), 6.34 (1H, d, J=7.4 Hz), 6.53 (1H, br), 6.89 (1H, d, J=7.4 Hz), 7.01 (1H, d, J=1.8 Hz), 7.04 (1H, dd, J=1.8, 8.3 Hz), 7.12 (1H, dd, J=4.8, 7.6 Hz), 7.16 (1H, d, J=8.30 Hz), 7.37 (1H, dd, J=1.1, 7.6 Hz), 8.39 (1H, dd, J=1.1, 4.8 Hz).

Example 775

1-Ethyl-3,3,5-trimethyl-7-{2-[N-[2-(7-methyl-4-oxo-4H-furo[3,2-c]pyridin-5-yl)ethyl]-N-(3-methylpyridin-2-ylmethyl)amino]ethyl}-1,5-dihydro-benzo[b][1,4]diazepine-2,4-dione The synthesis of the title compound was performed in the same manner as in Example 30 using appropriate starting materials.
$^1$H NMR (CDCl$_3$), δppm: 0.80 (3H, s), 1.16 (3H, t, J=7.1 Hz), 1.52 (3H, s), 2.17 (3H, d, J=1.0 Hz), 2.22 (3H, s), 2.81-2.87 (2H, m), 2.89-2.97 (4H, m), 3.38 (3H, s), 3.71-3.80 (1H, m), 3.88 (2H, s), 3.93-4.00 (2H, m), 4.09-4.18 (1H, m), 6.70 (1H, br), 6.96 (1H, d, J=2.1 Hz), 7.03 (1H, d, J=1.8 Hz), 7.06 (1H, dd, J=1.8, 8.3 Hz), 7.11 (1H, dd, J=4.8, 7.6 Hz), 7.17 (1H, d, J=8.3 Hz), 7.34 (1H, dd, J=1.2, 7.6 Hz), 7.50 (1H, d, J=2.1 Hz), 8.39 (1H, dd, J=1.2, 4.8 Hz).

Example 776

7-{2-[N-[2-(2,7-Dimethyl-4-oxo-4H-furo[3,2-c]pyridin-5-yl)ethyl]-N-(3-methylpyridin-2-ylmethyl)amino]ethyl}-1-ethyl-3,3,5-trimethyl-1,5-dihydrobenzo[b][1,4]diazepine-2,4-dione The synthesis of the title compound was performed in the same manner as in Example 30 using appropriate starting materials.
$^1$H NMR (CDCl$_3$), δppm: 0.79 (3H, s), 1.16 (3H, t, J=7.1 Hz), 1.52 (3H, s), 2.14 (3H, d, J=1.0 Hz), 2.23 (3H, s), 2.42 (3H, d, J=1.0 Hz), 2.80-2.86 (2H, m), 2.88-2.96 (4H, m), 3.38 (3H, s), 3.71-3.79 (1H, m), 3.88 (2H, s), 3.91-3.99 (2H, m), 4.10-4.16 (1H, m), 6.54 (1H, br), 6.63 (1H, br), 7.02 (1H, d, J=1.9 Hz), 7.05 (1H, dd, J=1.9, 8.3 Hz), 7.12 (1H, dd, J=4.8, 7.6 Hz), 7.16 (1H, d, J=8.3 Hz), 7.36 (1H, dd, J=1.1, 7.6 Hz), 8.39 (1H, dd, J=1.1, 4.8 Hz).

Example 777

N-[2-({N'-[2-(1-Ethyl-3,3,5-trimethyl-2,4-dioxo-2,3,4,5-tetrahydro-1H-benzo[b][1,4]diazepin-7-yl)ethyl]-N'-[2-(2-methyl-4-oxo-4H-furo[3,2-c]pyridin-5-yl)ethyl]amino}methyl)phenyl]methanesulfonamide The synthesis of the title compound was performed in the same manner as in Example 30 using appropriate starting materials.
$^1$H NMR (CDCl$_3$), δppm: 0.79 (3H, s), 1.17 (3H, t, J=7.1 Hz), 1.52 (3H, s), 2.42 (3H, d, J=1.0 Hz), 2.78-2.98 (6H, m), 3.03 (3H, s), 3.36 (3H, s), 3.70-3.83 (1H, m), 3.88 (2H, s), 4.06-4.22 (3H, m), 6.43-6.45 (1H, m), 6.53 (1H, t, J=0.92 Hz), 6.97 (1H, d, J=1.8 Hz), 6.99-7.03 (1H, m), 7.04 (1H, d, J=7.4 Hz), 7.06-7.11 (1H, m), 7.14-7.18 (1H, m), 7.19 (1H, d, J=8.4 Hz), 7.30-7.35 (1H, m), 7.44 (1H, dd, J=0.96, 8.1 Hz), 9.88 (1H, bs).

Example 778

N-[2-({N'-[2-(1-Ethyl-3,3,5-trimethyl-2,4-dioxo-2,3,4,5-tetrahydro-1H-benzo[b][1,4]diazepin-7-yl)ethyl]-N'-[2-(7-methyl-4-oxo-4H-furo[3,2-c]pyridin-5-yl)ethyl]amino}methyl)phenyl]methanesulfonamide The synthesis of the title compound was performed in the same manner as in Example 30 using appropriate starting materials.

$^1$H NMR (CDCl$_3$), δppm: 0.79 (3H, s), 1.17 (3H, t, J=7.0 Hz), 1.52 (3H, s), 2.24 (3H, s), 2.79-2.97 (6H, m), 3.01 (3H, s), 3.36 (3H, s), 3.71-3.83 (1H, m), 3.87 (2H, s), 4.06-4.20 (3H, m), 6.87 (1H, d, J=1.0 Hz), 6.94-6.99 (2H, m), 7.02 (1H, dd, J=1.9, 8.3 Hz), 7.05-7.13 (1H, m), 7.13-7.18 (1H, m), 7.19 (1H, d, J=8.3 Hz), 7.29-7.36 (1H, m), 7.43 (1H, d, J=8.0 Hz), 7.53 (1H, d, J=2.1 Hz), 9.84 (1H, bs).

Example 779

N-[2-({N'-[2-(2,7-Dimethyl-4-oxo-4H-furo[3,2-c]pyridin-5-yl)ethyl]-N'-[2-(1-ethyl-3,3,5-trimethyl-2,4-dioxo-2,3,4,5-tetrahydro-1H-benzo[b][1,4]diazepin-7-yl)ethyl]amino}methyl)phenyl]methanesulfonamide The synthesis of the title compound was performed in the same manner as in Example 30 using appropriate starting materials.

$^1$H NMR (CDCl$_3$), δppm: 0.79 (3H, s), 1.17 (3H, t, J=7.1 Hz), 1.52 (3H, s), 2.21 (3H, d, J=1.0 Hz), 2.43 (3H, d, J=1.0 Hz), 2.78-2.97 (6H, m), 3.02 (3H, s), 3.36 (3H, s), 3.72-3.85 (1H, m), 3.87 (2H, s), 4.04-4.19 (3H, m), 6.54 (1H, d, J=1.2 Hz), 6.81 (1H, d, J=1.1 Hz), 6.97 (1H, d, J=1.9 Hz), 7.01 (1H, dd, J=1.9, 8.3 Hz), 7.06-7.13 (1H, m), 7.13-7.17 (1H, m), 7.19 (1H, d, J=8.3 Hz), 7.29-7.36 (1H, m,), 7.44 (1H, dd, J=0.92, 8.1 Hz), 9.75 (1H, bs).

Example 780

7-{2-[N-[2-(2,7-Dimethyl-4-oxo-4H-furo[3,2-c]pyridin-5-yl)ethyl]-N-(2,5-dimethyl-2H-pyrazol-3-ylmethyl)amino]ethyl}-1-ethyl-3,3,5-trimethyl-1,5-dihydrobenzo[b][1,4]diazepine-2,4-dione The synthesis of the title compound was performed in the same manner as in Example 30 using appropriate starting materials.
White Powder
mp: 168.5-170.5° C.

Example 781

7-(2-{N-(2,5-Dimethyl-2H-pyrazol-3-ylmethyl)-N-[2-(2-methyl-4-oxo-4H-furo[3,2-c]pyridin-5-yl)ethyl]amino}ethyl)-1-ethyl-3,3,5-trimethyl-1,5-dihydrobenzo[b][1,4]diazepine-2,4-dione The synthesis of the title compound was performed in the same manner as in Example 30 using appropriate starting materials.
White Powder
mp: 133.5-139.7° C.

Example 782

7-(2-{N-(2,5-Dimethyl-2H-pyrazol-3-ylmethyl)-N-[2-(7-methyl-4-oxo-4H-furo[3,2-c]pyridin-5-yl)ethyl]amino}ethyl)-1-ethyl-3,3,5-trimethyl-1,5-dihydrobenzo[b][1,4]diazepine-2,4-dione The synthesis of the title compound was performed in the same manner as in Example 30 using appropriate starting materials.
White Powder
mp: 171-172.9° C.

Example 783

1-Ethyl-3,3,5-trimethyl-7-{2-[N-[2-(2-methyl-4-oxo-4H-furo[3,2-c]pyridin-5-yl)ethyl]-N-(4-methylthiazol-5-ylmethyl)amino]ethyl}-1,5-dihydrobenzo[b][1,4]diazepine-2,4-dione The synthesis of the title compound was performed in the same manner as in Example 30 using appropriate starting materials.

$^1$H NMR (CDCl$_3$), δppm: 0.79 (3H, s), 1.16 (3H, t, J=7.1 Hz), 1.52 (3H, s), 2.39 (3H, s), 2.42 (3H, s), 2.70-2.85 (4H, m), 2.91 (2H, t, J=6.4 Hz), 3.36 (3H, s), 3.71-3.78 (1H, m), 3.83 (2H, s), 4.03 (2H, t, J=6.4 Hz), 4.06-4.16 (1H, m), 6.42 (1H, dd, J=0.8 and 7.4 Hz), 6.55 (1H, t, J=1.0 Hz), 6.95-7.02 (3H, m), 7.13 (1H, d, J=8.8 Hz), 8.58 (1H, s)

Example 784

1-Ethyl-3,3,5-trimethyl-7-{2-[N-[2-(7-methyl-4-oxo-4H-furo[3,2-c]pyridin-5-yl)ethyl]-N-(4-methylthiazol-5-ylmethyl)amino]ethyl}-1,5-dihydrobenzo[b][1,4]diazepine-2,4-dione The synthesis of the title compound was performed in the same manner as in Example 30 using appropriate starting materials.

$^1$H NMR (CDCl$_3$), δppm: 0.79 (3H, s), 1.16 (3H, t, J=7.1 Hz), 1.51 (3H, s), 2.24 (3H, s), 2.39 (3H, s), 2.70-2.85 (4H, m), 2.88-2.95 (2H, m), 3.36 (3H, s), 3.70-3.80 (1H, m), 3.82 (2H, s), 4.00-4.18 (3H, m), 6.86 (1H, d, J=1.0 Hz), 6.95-7.03 (3H, m), 7.12 (1H, d, J=8.2 Hz), 7.52 (1H, d, 2.1 Hz), 8.59 (1H, s)

Example 785

7-{2-[N-[2-(2,7-Dimethyl-4-oxo-4H-furo[3,2-c]pyridin-5-yl)ethyl]-N-(4-methylthiazol-5-ylmethyl)amino]ethyl}-1-ethyl-3,3,5-trimethyl-1,5-dihydrobenzo[b][1,4]diazepine-2,4-dione The synthesis of the title compound was performed in the same manner as in Example 30 using appropriate starting materials.

$^1$H NMR (CDCl$_3$), δppm: 0.79 (3H, s), 1.16 (3H, t, J=7.1 Hz), 1.51 (3H, s), 2.21 (3H, s), 2.39 (3H, s), 2.43 (3H, s), 2.70-2.85 (4H, m), 2.88-2.96 (2H, m), 3.36 (3H, s), 3.70-3.85 (3H, m), 3.96-4.18 (3H, m), 6.56 (1H, d, J=1.1 Hz), 6.79 (1H, d, J=1.1 Hz), 6.95-7.00 (2H, m), 7.12 (1H, d, J=8.6 Hz), 8.60 (1H, s)

The following compounds shown in Examples 786 to 791, Examples 793 and Example 795 to 802 can be prepared by the

Example 786

1-Ethyl-3,3,5-trimethyl-7-{2-[N-(2-methylpyridin-3-ylmethyl)-N-(2-pyridin-3-ylethyl)amino]ethyl}-1,5-dihydro-benzo[b][1,4]diazepine-2,4-dione

Example 787

1-Ethyl-3,3,5-trimethyl-7-{2-[N-[2-(7-methyl-4-oxo-4H-furo[3,2-c]pyridin-5-yl)ethyl]-N-(2-methylpyridin-3-ylmethyl)amino]ethyl}-1,5-dihydrobenzo[b][1,4]diazepine-2,4-dione

Example 788

7-{2-[N-[2-(2,7-Dimethyl-4-oxo-4H-furo[3,2-c]pyridin-5-yl)ethyl]-N-(2-methylpyridin-3-ylmethyl)amino]ethyl}-1-ethyl-3,3,5-trimethyl-1,5-dihydro-benzo[b][1,4]diazepine-2,4-dione

Example 789

1-Ethyl-3,3,5-trimethyl-7-{[N-[2-(2-methyl-4-oxo-4H-furo[3,2-c]pyridin-5-yl)ethyl]-N-(2-methylpyrimidin-5-ylmethyl)amino]methyl}-1,5-dihydrobenzo[b][1,4]diazepine-2,4-dione

Example 790

N-[3-({N'-(1-Ethyl-3,3,5-trimethyl-2,4-dioxo-2,3,4,5-tetrahydro-1H-benzo[b][1,4]diazepin-7-ylmethyl)-N'-[2-(2-methyl-4-oxo-4H-furo[3,2-c]pyridin-5-yl)-ethyl]amino}methyl)pyridin-2-yl]methanesulfonamide

Example 791

N-[3-({N'-(1-Ethyl-3,3,5-trimethyl-2,4-dioxo-2,3,4,5-tetrahydro-1H-benzo[b][1,4]diazepin-7-ylmethyl)-N'-[2-(2-methyl-4-oxo-4H-furo[3,2-c]pyridin-5-yl)ethyl]amino}methyl)pyridin-2-yl]acetamide

Example 792

Acetic acid 3-({N-(1-ethyl-3,3,5-trimethyl-2,4-dioxo-2,3,4,5-tetrahydro-1H-benzo[b][1,4]diazepin-7-ylmethyl)-N-[2-(2-methyl-4-oxo-4H-furo[3,2-c]pyridin-5-yl)ethyl]amino}methyl)pyridin-2-ylmethyl ester dihydrochloride The synthesis of the title compound was performed in the same manner as in Example 4 using appropriate starting materials.

$^1$H NMR (DMSO-d$_6$), δppm: 0.69 (3H, s), 1.04 (3H, t, J=6.9 Hz), 1.34 (3H, s), 2.01-2.04 (3H, m), 2.42 (3H, s), 2.74 (2H, br), 3.26 (3H, s), 3.45-4.30 (8H, m), 5.10 (2H, br), 6.48 (1H, br), 6.64 (1H, br), 7.17 (1H, br), 7.31 (2H, br), 7.48 (2H, br), 7.79 (1H, br), 8.46 (1H, br).

Example 793

1-Ethyl-7-({N-(2-imidazol-1-ylmethylbenzyl)-N-[2-(2-methyl-4-oxo-4H-furo[3,2-c]pyridin-5-yl)ethyl]amino}methyl)-3,3,5-trimethyl-1,5-dihydro-benzo[b][1,4]diazepine-2,4-dione

Example 794

1-Ethyl-7-({N-(3-imidazol-1-ylmethylbenzyl)-N-[2-(2-methyl-4-oxo-4H-furo[3,2-c]pyridin-5-yl)ethyl]amino}methyl)-3,3,5-trimethyl-1,5-dihydro-benzo[b][1,4]diazepine-2,4-dione The synthesis of the title compound was performed in the same manner as in Example 30 using appropriate starting materials.

$^1$H NMR (CDCl$_3$), δppm: 0.77 (3H, s), 1.17 (3H, t, J=7.0 Hz), 1.51 (3H, s), 2.43 (3H, d, J=1.0 Hz), 2.79 (2H, dt, J=2.1, 5.9 Hz), 3.32 (3H, s), 3.55-3.68 (4H, m), 3.71-3.83 (1H, m), 3.99-4.17 (3H, m), 5.02 (2H, s), 6.43 (1H, dd, J=0.74, 7.3 Hz), 6.49 (1H, t, J=1.0 Hz), 6.88 (1H, t, J=1.3 Hz), 6.95 (1H, d, J=7.3 Hz), 6.98-7.07 (3H, m), 7.07-7.15 (3H, m), 7.15-7.25 (2H, m), 7.52 (1H, d, J=1.1 Hz).

Example 795

1-Ethyl-7-({N-(2-imidazol-1-ylbenzyl)-N-[2-(2-methyl-4-oxo-4H-furo[3,2-c]pyridin-5-yl)ethyl]amino}methyl)-3,3,5-trimethyl-1,5-dihydrobenzo[b][1,4]diazepine-2,4-dione

Example 796

1-Ethyl-3,3,5-trimethyl-7-{[N-[2-(2-methyl-4-oxo-4H-furo[3,2-c]pyridin-5-yl)ethyl]-N-(2-morpholin-4-ylbenzyl)amino]methyl}-1,5-dihydro-benzo[b][1,4]diazepine-2,4-dione

Example 797

1-Ethyl-3,3,5-trimethyl-7-{[N-[2-(2-methyl-4-oxo-4H-furo[3,2-c]pyridin-5-yl)ethyl]-N-(2-[1,2,4]triazol-1-yl-benzyl)amino]methyl}-1,5-dihydro-benzo[b][1,4]diazepine-2,4-dione

Example 798

1-Ethyl-7-(N-{imidazo[1,2-a]pyridin-8-ylmethyl-N-[2-(2-methyl-4-oxo-4H-furo[3,2-c]pyridin-5-yl)ethyl]amino}methyl)-3,3,5-trimethyl-1,5-dihydrobenzo[b][1,4]diazepine-2,4-dione

Example 799

1-Ethyl-7-(N-{imidazo[1,2-a]pyridin-6-ylmethyl-N-[2-(2-methyl-4-oxo-4H-furo[3,2-c]pyridin-5-yl)ethyl]amino}methyl)-3,3,5-trimethyl-1,5-dihydrobenzo[b][1,4]diazepine-2,4-dione

Example 800

1-Ethyl-3,3,5-trimethyl-7-{[N-[2-(2-methyl-4-oxo-4H-furo[3,2-c]pyridin-5-yl)ethyl]-N-(2-pyrazol-1-ylpyridin-3-ylmethyl)amino]methyl}-1,5-dihydrobenzo[b][1,4]diazepine-2,4-dione

Example 801

7-({N-(3H-Benzoimidazol-4-ylmethyl)-N-[2-(2-methyl-4-oxo-4H-furo[3,2-c]pyridin-5-yl)ethyl]amino}methyl)-1-ethyl-3,3,5-trimethyl-1,5-dihydrobenzo[b][1,4]diazepine-2,4-dione

Example 802

1-Ethyl-7-({N-(4-methoxymethylpyridin-3-ylmethyl)-N-[2-(2-methyl-4-oxo-4H-furo[3,2-c]pyridin-5-yl)ethyl]amino}methyl)-3,3,5-trimethyl-1,5-dihydrobenzo[b][1,4]diazepine-2,4-dione

Example 802-a

1-Ethyl-3,3,5-trimethyl-7-{2-[N-[2-(2,7-dimethyl-4-oxo-4H-furo[3,2-c]pyridin-5-yl)-ethyl]-N-(4-methylthiazol-2-ylmethyl)-amino]-ethyl}-1,5-dihydrobenzo[b][1,4]diazepine-2,4-dione The synthesis of the title compound was performed in the same manner as in Example 30 using appropriate starting materials.

$^1$H NMR (CDCl$_3$), δppm: 0.78 (3H, s), 1.15 (3H, t, J=7.1 Hz), 1.51 (3H, s), 2.20 (3H, d, J=0.9 Hz), 2.42 (3H, d, J=0.9 Hz), 2.43 (3H, d, J=0.9 Hz), 2.76 (2H, t, J=7.4 Hz), 2.85-2.90 (2H, m), 2.95-3.02 (2H, m), 3.35 (3H, s), 3.71-3.77 (1H, m), 4.01 and 4.02 (2H, s), 4.02-4.16 (3H, m), 6.57 (1H, br), 6.77 (1H, br), 6.86 (1H, br), 6.97-7.01 (m, 2H), 7.12 (1H, d, J=8.9 Hz).

Examples 803 to 1038

The following compounds were obtained in the same manner as in Examples above using appropriate starting materials.

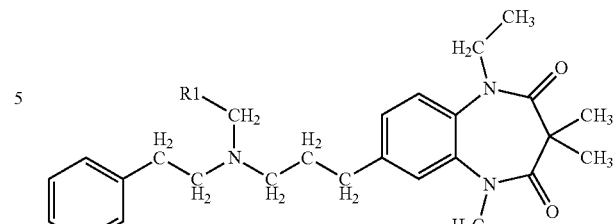

| Example No. | R1 | MS (M + 1) |
|---|---|---|
| 803 |  | 489 |
| 804 | 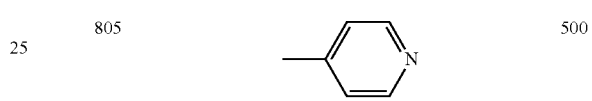 | 500 |
| 805 | 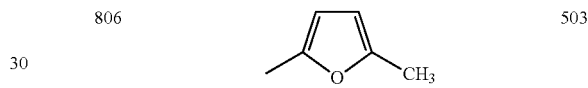 | 500 |
| 806 |  | 503 |
| 807 | 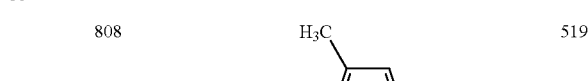 | 505 |
| 808 | 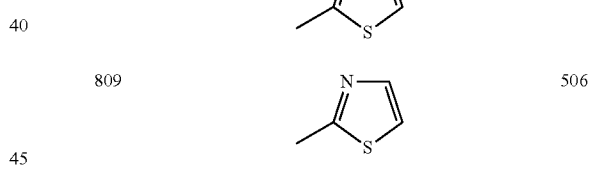 | 519 |
| 809 | 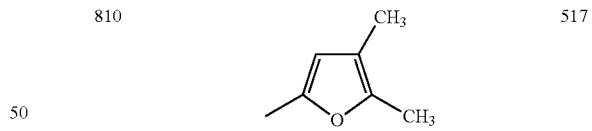 | 506 |
| 810 | 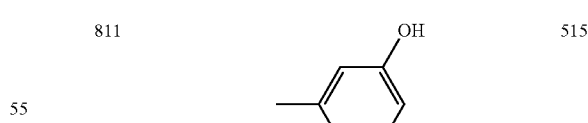 | 517 |
| 811 | 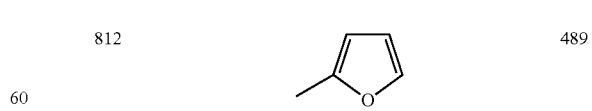 | 515 |
| 812 | 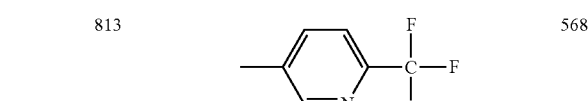 | 489 |
| 813 |  | 568 |

243
-continued

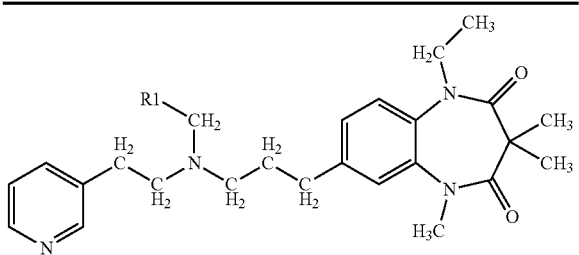

| Example No. | R1 | MS (M + 1) |
|---|---|---|
| 814 | 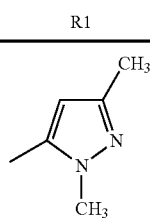 1,3,5-trimethylpyrazol-4-yl | 517 |
| 815 | 4,5-dimethylthiazol-2-yl | 520 |
| 816 | 5-(trifluoromethyl)furan-2-yl | 557 |
| 817 | 2,4,5-trimethylthiazol-3-yl | 534 |
| 818 | 2-methylthiazol-4-yl | 520 |
| 819 | 2,4-dimethylthiophen-5-yl | 533 |
| 820 | 2-methylthiazol-4-yl | 520 |
| 821 | 3,4-dimethylpyridin-2-yl | 514 |
| 822 | 2,3-dimethylpyridin-4-yl | 514 |

244
-continued

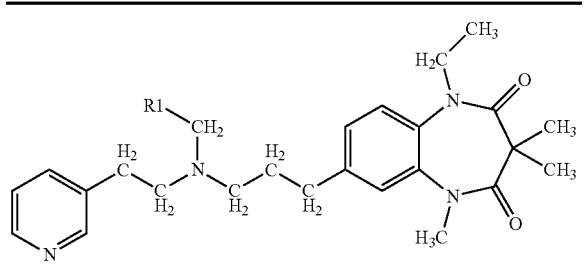

| Example No. | R1 | MS (M + 1) |
|---|---|---|
| 823 | 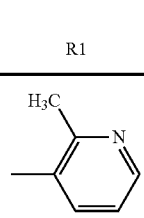 2,3-dimethylpyridin-4-yl | 514 |
| 824 | 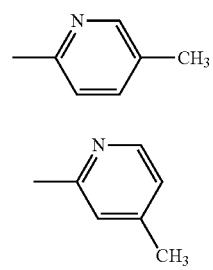 2,5-dimethylpyridin-3-yl | 514 |
| 825 | 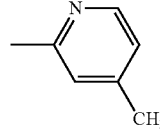 2,4-dimethylpyridin-3-yl | 514 |
| 826 | 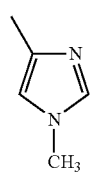 1,4-dimethylimidazol-5-yl | 503 |
| 827 | 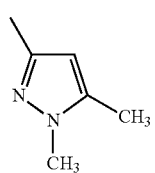 1,3,5-trimethylpyrazol-4-yl | 517 |
| 828 | 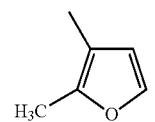 2,3-dimethylfuran-4-yl | 503 |
| 829 | 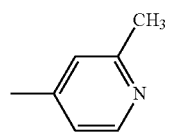 2,4-dimethylpyridin-5-yl | 514 |
| 830 | 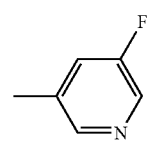 5-fluoro-3-methylpyridin-2-yl | 518 |

-continued
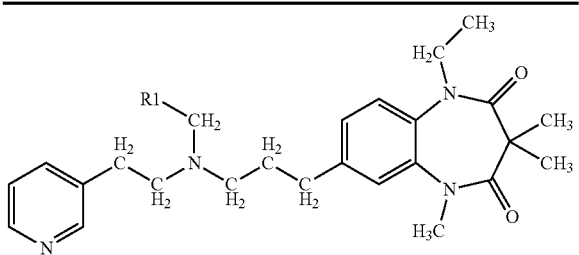
| Example No. | R1 | MS (M + 1) |
|---|---|---|
| 831 | 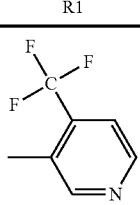 | 568 |
| 832 | 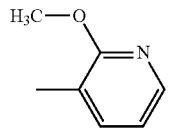 | 530 |
| 833 | 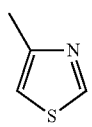 | 506 |
| 834 | 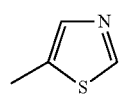 | 506 |
| 835 | 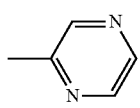 | 501 |
| 836 | 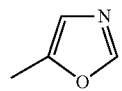 | 490 |
| 837 | 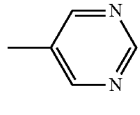 | 501 |
| 838 | 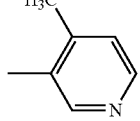 | 514 |
| 839 | 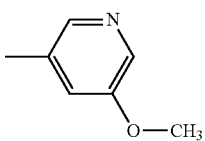 | 530 |
| 840 | 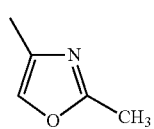 | 504 |
-continued
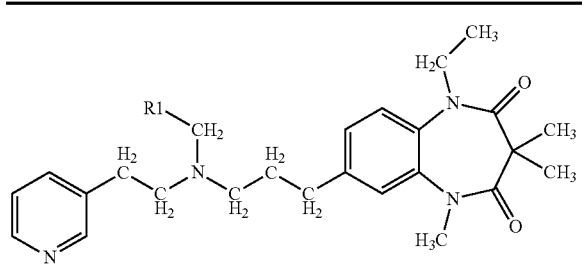
| Example No. | R1 | MS (M + 1) |
|---|---|---|
| 841 | 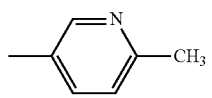 | 514 |
| 842 | 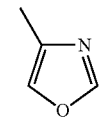 | 490 |
| 843 | 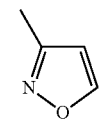 | 490 |
| 844 | 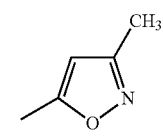 | 504 |
| 845 | 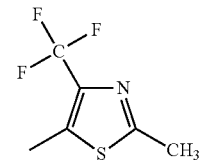 | 588 |
| 846 | 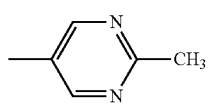 | 515 |
| 847 | 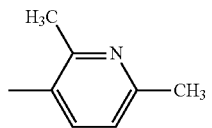 | 528 |

247
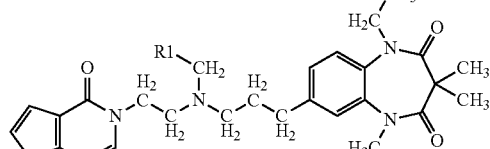
| Example No. | R1 | MS(M + 1) |
|---|---|---|
| 848 | 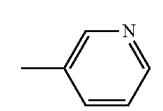 | 545 |
| 849 | 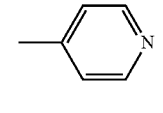 | 556 |
| 850 | 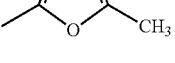 | 556 |
| 851 | 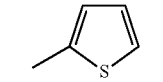 | 559 |
| 852 | 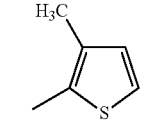 | 561 |
| 853 | 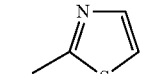 | 575 |
| 854 | 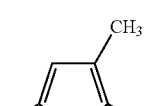 | 562 |
| 855 | 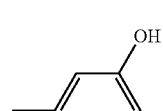 | 573 |
| 856 | 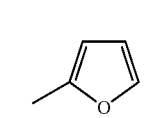 | 571 |
| 857 | 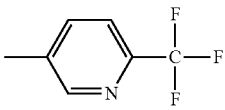 | 545 |
| 858 | 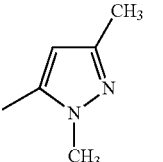 | 624 |
248
-continued
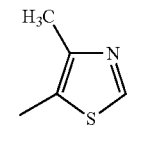
| Example No. | R1 | MS(M + 1) |
|---|---|---|
| 859 | 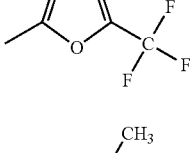 | 573 |
| 860 | 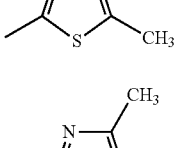 | 576 |
| 861 | 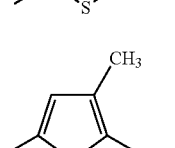 | 613 |
| 862 | 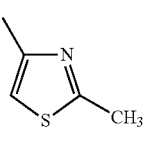 | 590 |
| 863 | 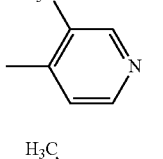 | 576 |
| 864 | 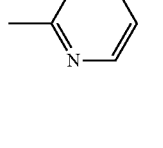 | 589 |
| 865 |  | 576 |
| 866 | H$_3$C <br> (3,4-dimethylpyridine) | 570 |
| 867 | H$_3$C <br> (2,3-dimethylpyridine) | 570 |

249
-continued

| Example No. | R1 | MS(M + 1) |
|---|---|---|
| 868 | 2,3-dimethylpyridine | 570 |
| 869 | 2,5-dimethylpyridine | 570 |
| 870 | 2,4-dimethylpyridine | 570 |
| 871 | 3-fluoro-4-methylpyridine | 574 |
| 872 | 1,4-dimethylimidazole | 559 |
| 873 | 2,4,5-trimethylthiazole | 590 |
| 874 | 1,3-dimethylpyrazole | 573 |
| 875 | 2,3-dimethylfuran | 559 |
| 876 | 2,4-dimethylpyridine | 570 |

250
-continued

| Example No. | R1 | MS(M + 1) |
|---|---|---|
| 877 | 3-fluoro-5-methylpyridine | 574 |
| 878 | 3-methyl-4-trifluoromethylpyridine | 624 |
| 879 | 2-methoxy-3-methylpyridine | 586 |
| 880 | 4-methylthiazole | 562 |
| 881 | 5-methylthiazole | 562 |
| 882 | 2-methylpyrazine | 557 |
| 883 | 5-methyloxazole | 546 |
| 884 | 5-methylpyrimidine | 557 |
| 885 | 3,4-dimethylpyridine | 570 |
| 886 | 3-methyl-5-methoxypyridine | 586 |

-continued
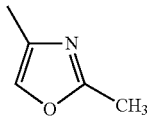
| Example No. | R1 | MS(M + 1) |
|---|---|---|
| 887 | 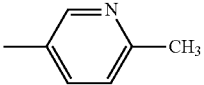 | 560 |
| 888 | 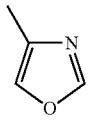 | 570 |
| 889 | 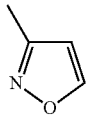 | 546 |
| 890 | 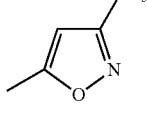 | 546 |
| 891 | 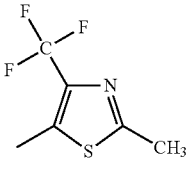 | 560 |
| 892 | 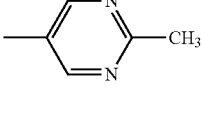 | 644 |
| 893 | 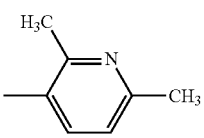 | 571 |
| 894 | 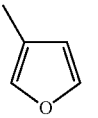 | 584 |
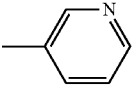
| Example No. | R1 | MS(M + 1) |
|---|---|---|
| 895 | 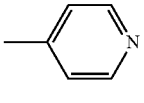 | 555 |
| 896 | 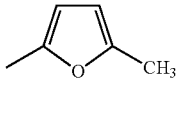 | 566 |
| 897 | 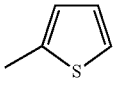 | 566 |
| 898 | 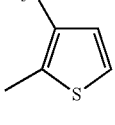 | 569 |
| 899 | 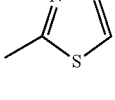 | 571 |
| 900 | 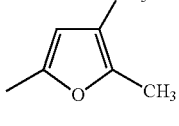 | 585 |
| 901 | 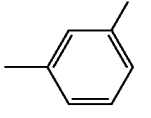 | 572 |
| 902 | 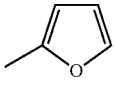 | 583 |
| 903 | 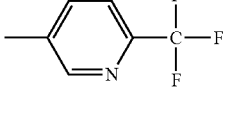 | 581 |
| 904 |  | 555 |
| 905 |  | 634 |

-continued

| Example No. | R1 | MS(M + 1) |
|---|---|---|
| 906 | 3,5-dimethyl-1-methyl-pyrazole | 583 |
| 907 | 4-methyl-5-methyl-thiazole | 586 |
| 908 | 5-methyl-2-(trifluoromethyl)furan | 623 |
| 909 | 2,4-dimethyl-5-methyl-thiazole | 600 |
| 910 | 2-methyl-4-methyl-thiazole | 586 |
| 911 | 2,5-dimethyl-3-methyl-thiophene | 599 |
| 912 | 2-methyl-4-methyl-thiazole | 586 |
| 913 | 3,4-dimethyl-pyridine | 580 |
| 914 | 2,3-dimethyl-pyridine | 580 |

-continued

| Example No. | R1 | MS(M + 1) |
|---|---|---|
| 915 | 2,3-dimethyl-pyridine | 580 |
| 916 | 2,5-dimethyl-pyridine | 580 |
| 917 | 2,4-dimethyl-pyridine | 580 |
| 918 | 3-fluoro-4-methyl-pyridine | 584 |
| 919 | 4-methyl-1-methyl-imidazole | 569 |
| 920 | 2,4-dimethyl-5-methyl-thiazole | 600 |
| 921 | 3,5-dimethyl-1-methyl-pyrazole | 583 |
| 922 | 2,3-dimethyl-furan | 569 |
| 923 | 2,5-dimethyl-pyridine | 580 |

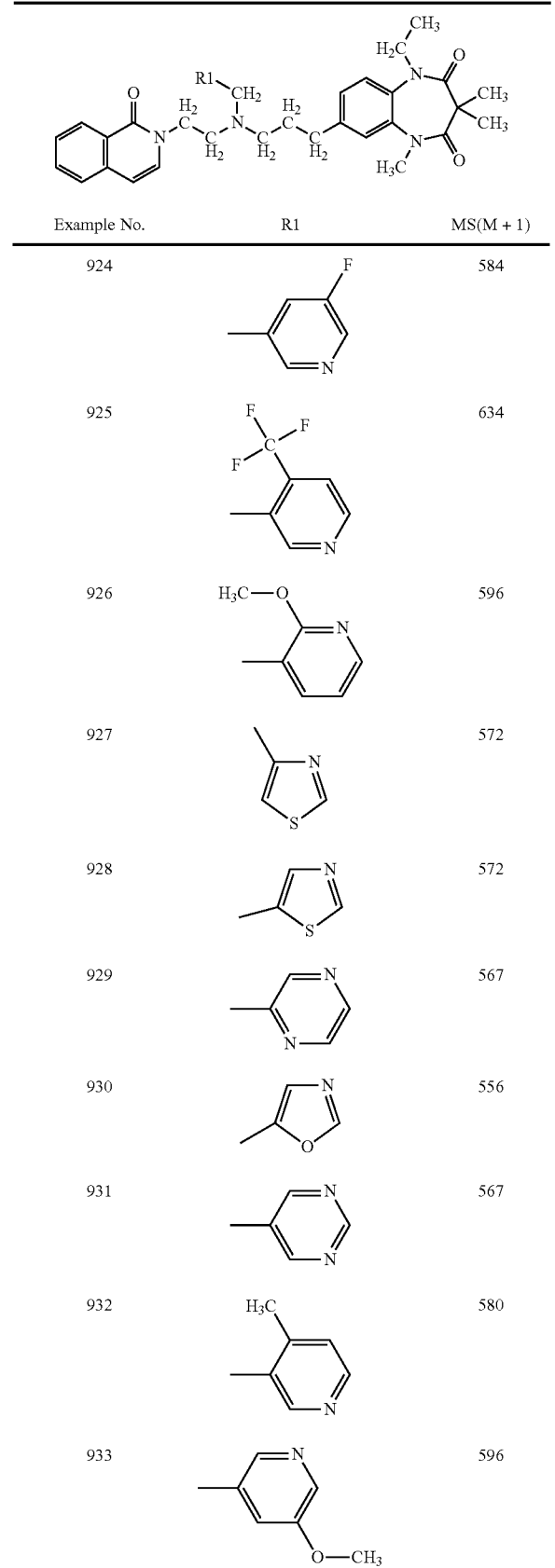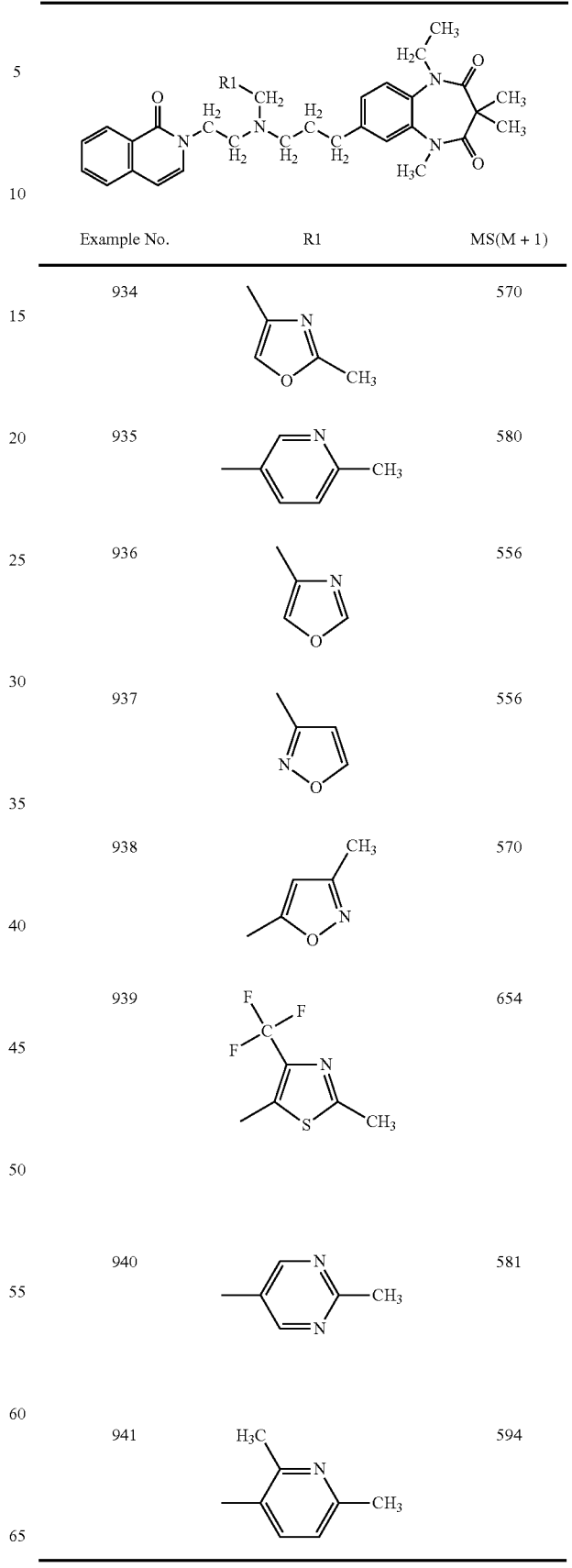

| | 257 | | | 258 -continued | |
|---|---|---|---|---|---|
| Example No. | R1 | MS(M + 1) | Example No. | R1 | MS(M + 1) |
| 942 | 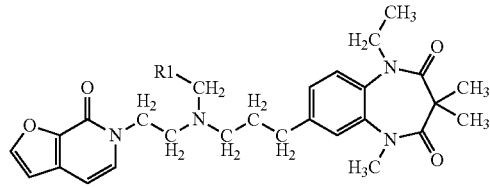 | 545 | 953 | 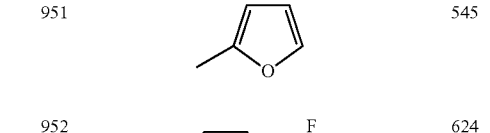 | 573 |
| 943 | 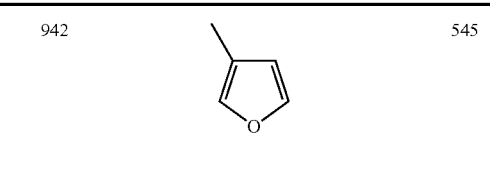 | 556 | 954 | 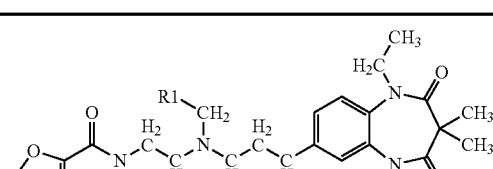 | 576 |
| 944 | 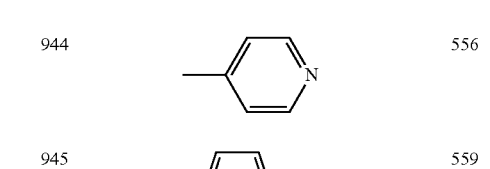 | 556 | 955 | 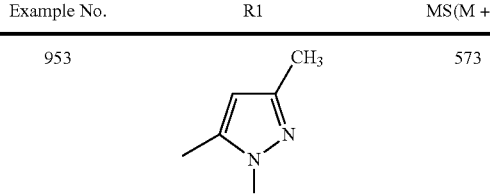 | 613 |
| 945 | 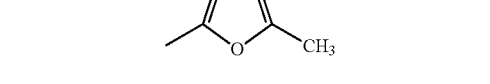 | 559 | 956 | 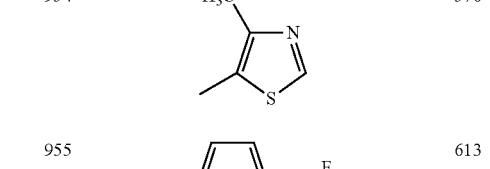 | 590 |
| 946 | 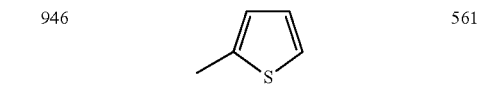 | 561 | 957 | 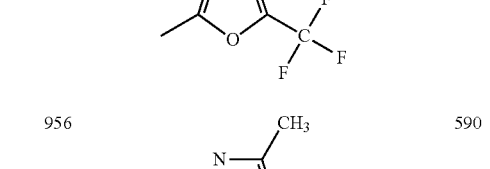 | 576 |
| 947 | 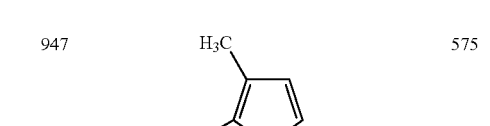 | 575 | 958 | 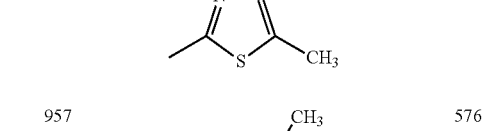 | 589 |
| 948 | 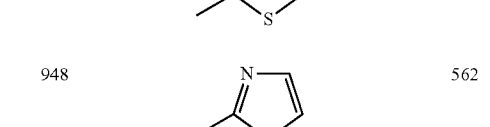 | 562 | 959 | 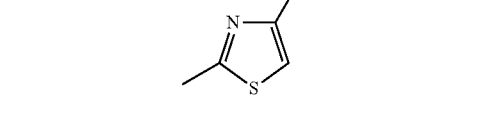 | 576 |
| 949 | 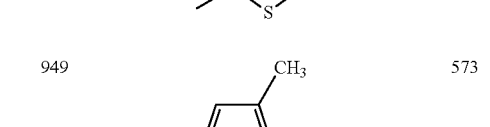 | 573 | 960 | 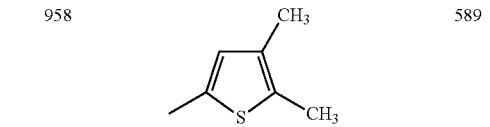 | 570 |
| 950 | 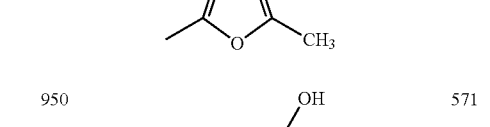 | 571 | 961 | 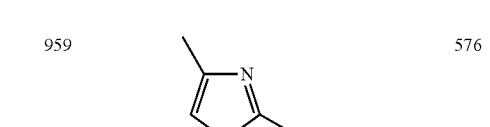 | 570 |
| 951 | 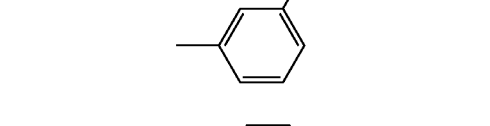 | 545 | | | |
| 952 | 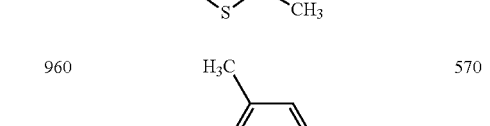 | 624 | | | |

259
-continued
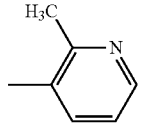
| Example No. | R1 | MS(M + 1) |
|---|---|---|
| 962 | 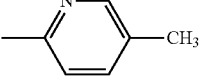 | 570 |
| 963 | 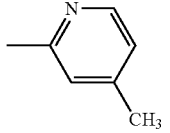 | 570 |
| 964 | 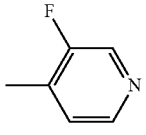 | 570 |
| 965 | 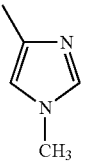 | 574 |
| 966 | 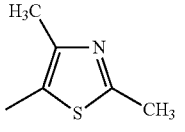 | 559 |
| 967 | 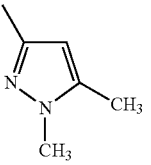 | 590 |
| 968 | 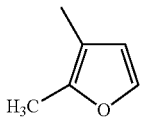 | 573 |
| 969 | 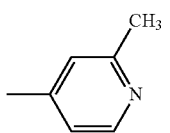 | 559 |
| 970 | 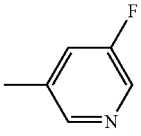 | 570 |
260
-continued
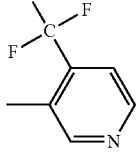
| Example No. | R1 | MS(M + 1) |
|---|---|---|
| 971 | 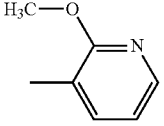 | 574 |
| 972 | 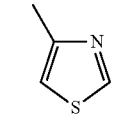 | 624 |
| 973 | 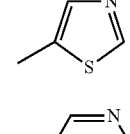 | 586 |
| 974 | 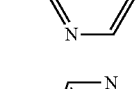 | 562 |
| 975 | 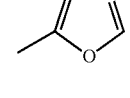 | 562 |
| 976 | 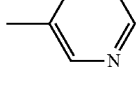 | 557 |
| 977 | 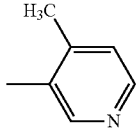 | 546 |
| 978 | 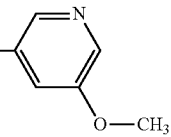 | 557 |
| 979 |  | 570 |
| 980 |  | 586 |

-continued
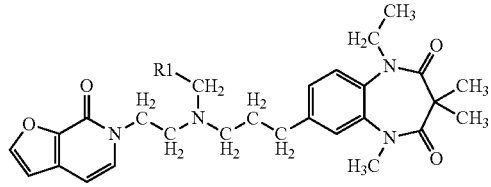
| Example No. | R1 | MS(M + 1) |
|---|---|---|
| 981 | 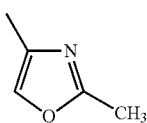 | 560 |
| 982 | 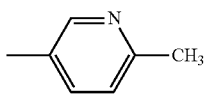 | 570 |
| 983 | 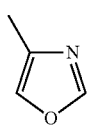 | 546 |
| 984 | 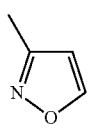 | 546 |
| 985 | 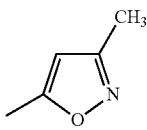 | 560 |
| 986 | 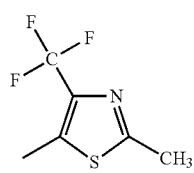 | 644 |
| 987 | 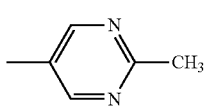 | 571 |
| 988 | 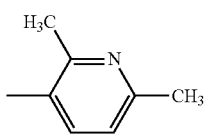 | 584 |
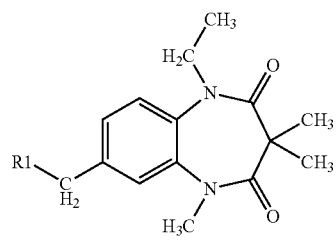
| Example No. | R1 | MS(M + 1) |
|---|---|---|
| 989 | 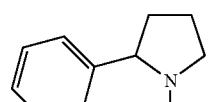 | 406 |
| 990 | 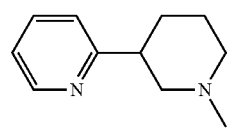 | 421 |
| 991 | 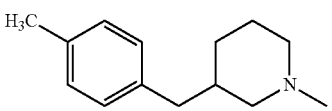 | 448 |
| 992 | 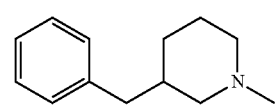 | 434 |
| 993 | 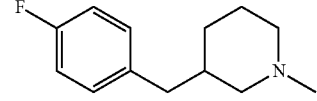 | 452 |
| 994 | 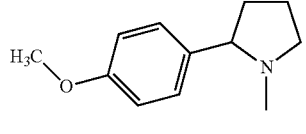 | 436 |
| 995 | 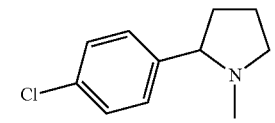 | 440 |
| 996 | 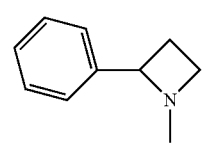 | 392 |
| 997 | 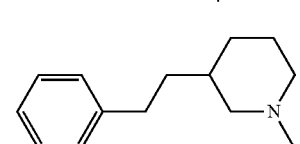 | 448 |
| 998 | 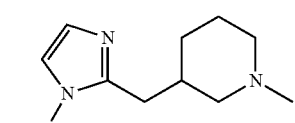 | 438 |

-continued

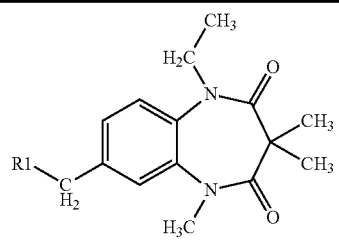

| Example No. | R1 | MS(M + 1) |
|---|---|---|
| 999 | 2-pyridyl-CH2-(1-methylpiperidin-3-yl) | 435 |
| 1000 | 3-pyridyl-CH2-(1-methylpiperidin-3-yl) | 435 |
| 1001 | 2-pyridyl-CH2-(1-methylpyrrolidin-3-yl) | 421 |
| 1002 | 3-pyridyl-CH2-(1-methylpyrrolidin-3-yl) | 421 |
| 1003 | 4-hydroxy-2-methylpyrimidin-6-yl-(1-methylpyrrolidin-2-yl) | 438 |
| 1004 | 6-methyl-2-pyridyl-(1-methylpiperidin-3-yl) | 435 |
| 1005 | phenyl-(1-methylpyrrolidin-3-yl) | 406 |
| 1006 | 2-pyridyl-(1-methylpyrrolidin-3-yl) | 407 |
| 1007 | phenyl-CH2-(1-methylpyrrolidin-2-yl) | 420 |
| 1008 | 2-pyridyl-CH2-(1-methylpyrrolidin-2-yl) | 421 |

-continued

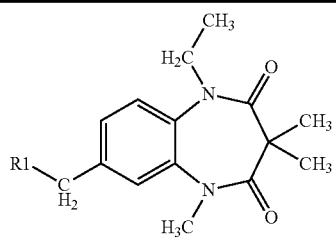

| Example No. | R1 | MS(M + 1) |
|---|---|---|
| 1009 | 2-pyridyl-(1-methyl-1,2,5,6-tetrahydropyridin-3-yl) | 419 |
| 1010 | phenyl-(1-methylpiperidin-3-yl) | 420 |
| 1011 | 4-methoxyphenyl-(1-methylpiperidin-2-yl) | 450 |
| 1012 | 4-chlorophenyl-(1-methylpiperidin-2-yl) | 454 |
| 1013 | 3-methyl-1,2,4-oxadiazol-5-yl-(1-methylpiperidin-3-yl) | 426 |
| 1014 | 4-hydroxy-2-methylpyrimidin-6-yl-(1-methylpiperidin-2-yl) | 452 |
| 1015 | 2-pyridyl-(1-methylpyrrolidin-2-yl) | 407 |
| 1016 | 4-hydroxy-2-methylpyrimidin-6-yl-(1-methylpiperidin-3-yl) | 452 |
| 1017 | 2-pyrimidyl-(1-methylpiperidin-2-yl) | 422 |

265
-continued
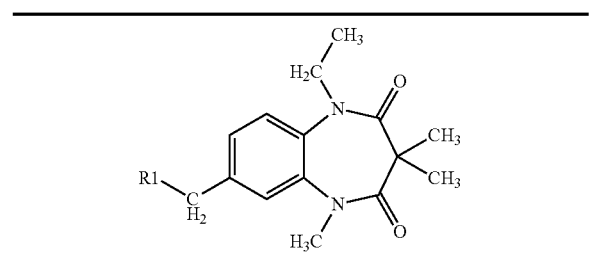
| Example No. | R1 | MS(M + 1) |
|---|---|---|
| 1018 | | 450 |
| 1019 | | 436 |
| 1020 | | 422 |
| 1021 | | 436 |
| 1022 | | 452 |
| 1023 | | 422 |
| 1024 | | 422 |
| 1025 | | 408 |
| 1026 | | 435 |
266
-continued
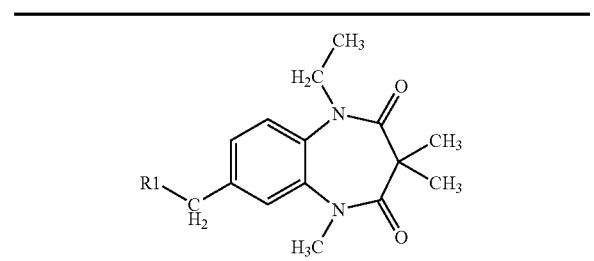
| Example No. | R1 | MS(M + 1) |
|---|---|---|
| 1027 | | 411 |
| 1028 | | 422 |
| 1029 | | 422 |
| 1030 | | 434 |
| 1031 | | 421 |
| 1032 | | 496 |
| 1033 | | 434 |
| 1034 | | 448 |

-continued

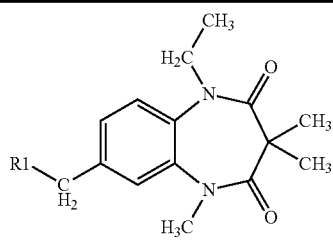

| Example No. | R1 | MS(M + 1) |
|---|---|---|
| 1035 | (phenyl-tetrahydroisoquinoline, N-methyl) | 468 |
| 1036 | (pyridin-2-yl-ethyl-N-methylpiperidine) | 449 |
| 1037 | (pyridin-2-yl-N-methylazepane) | 435 |
| 1038 | (pyridin-4-yl-N-methylazepane) | 435 |

Examples 1039 to 1614

The following compounds can be obtained in the same manner as in Examples above using appropriate starting materials.

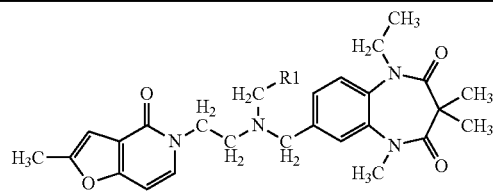

| Example No. | R1 | MS (M + 1) |
|---|---|---|
| 1039 | (3-methylfuran) | |

-continued

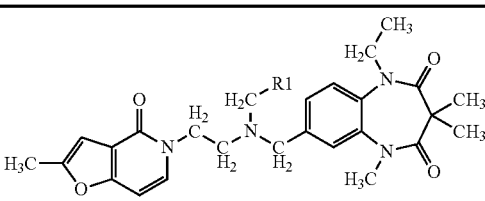

| Example No. | R1 | MS (M + 1) |
|---|---|---|
| 1040 | (3-methylpyridine) | |
| 1041 | (4-methylpyridine) | |
| 1042 | (2,5-dimethylfuran) | |
| 1043 | (2-methylthiophene) | |
| 1044 | (2,3-dimethylthiophene) | |
| 1045 | (2-methylthiazole) | |
| 1046 | (2,4-dimethylfuran) | |
| 1047 | (3-hydroxyphenyl) | |
| 1048 | (2-methylfuran) | |
| 1049 | (2-(methylsulfonylamino)phenyl) | |
| 1050 | (5-methyl-2-(trifluoromethyl)pyridine) | |

| Example No. | R1 | MS (M + 1) |
|---|---|---|
| 1051 | 3,5-dimethyl-1-methyl-pyrazol-4-yl | |
| 1052 | 4-methyl-5-methyl-thiazol-2-yl | |
| 1053 | 5-methyl-2-(trifluoromethyl)furan-... | |
| 1054 | 2,4-dimethyl-5-methyl-thiazol-... | |
| 1055 | 2-methyl-4-methyl-thiazol-5-yl | |
| 1056 | 2,5-dimethyl-3-methyl-thiophen-... | |
| 1057 | 4-methyl-2-methyl-thiazol-5-yl | |
| 1058 | 3,4-dimethyl-pyridin-... | |
| 1059 | 2,3-dimethyl-pyridin-... | |
| 1060 | 2,3-dimethyl-pyridin-... | |
| 1061 | 2,5-dimethyl-pyridin-... | |
| 1062 | 2,4-dimethyl-pyridin-... | |
| 1063 | 3-fluoro-4-methyl-pyridin-... | |
| 1064 | 4-methyl-1-methyl-imidazol-5-yl | |
| 1065 | 2,4-dimethyl-5-methyl-thiazol-... | |
| 1066 | 3,5-dimethyl-1-methyl-pyrazol-4-yl | |
| 1067 | 2,3-dimethyl-furan-... | |
| 1068 | 2,4-dimethyl-pyridin-... | |

-continued
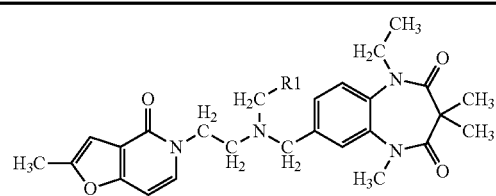
| Example No. | R1 | MS (M + 1) |
|---|---|---|
| 1069 | 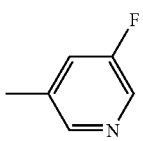 | |
| 1070 | 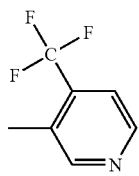 | |
| 1071 | 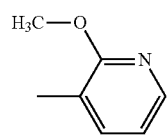 | |
| 1072 | 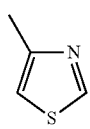 | |
| 1073 | 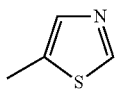 | |
| 1074 | 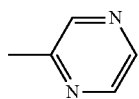 | |
| 1075 | 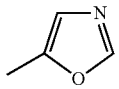 | |
| 1076 | 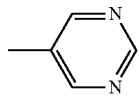 | |
| 1077 | 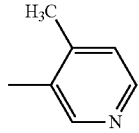 | |
| 1078 | 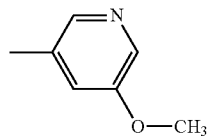 | |
-continued
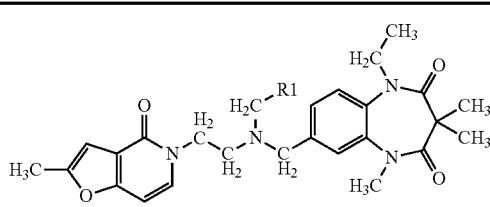
| Example No. | R1 | MS (M + 1) |
|---|---|---|
| 1079 | 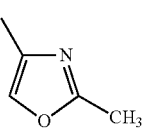 | |
| 1080 | 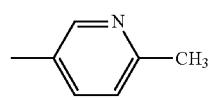 | |
| 1081 | 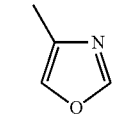 | |
| 1082 | 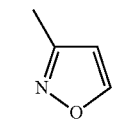 | |
| 1083 | 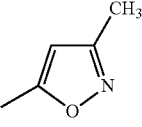 | |
| 1084 | 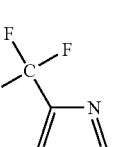 | |
| 1085 | 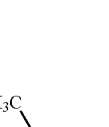 | |
| 1086 | 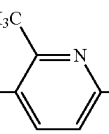 | |

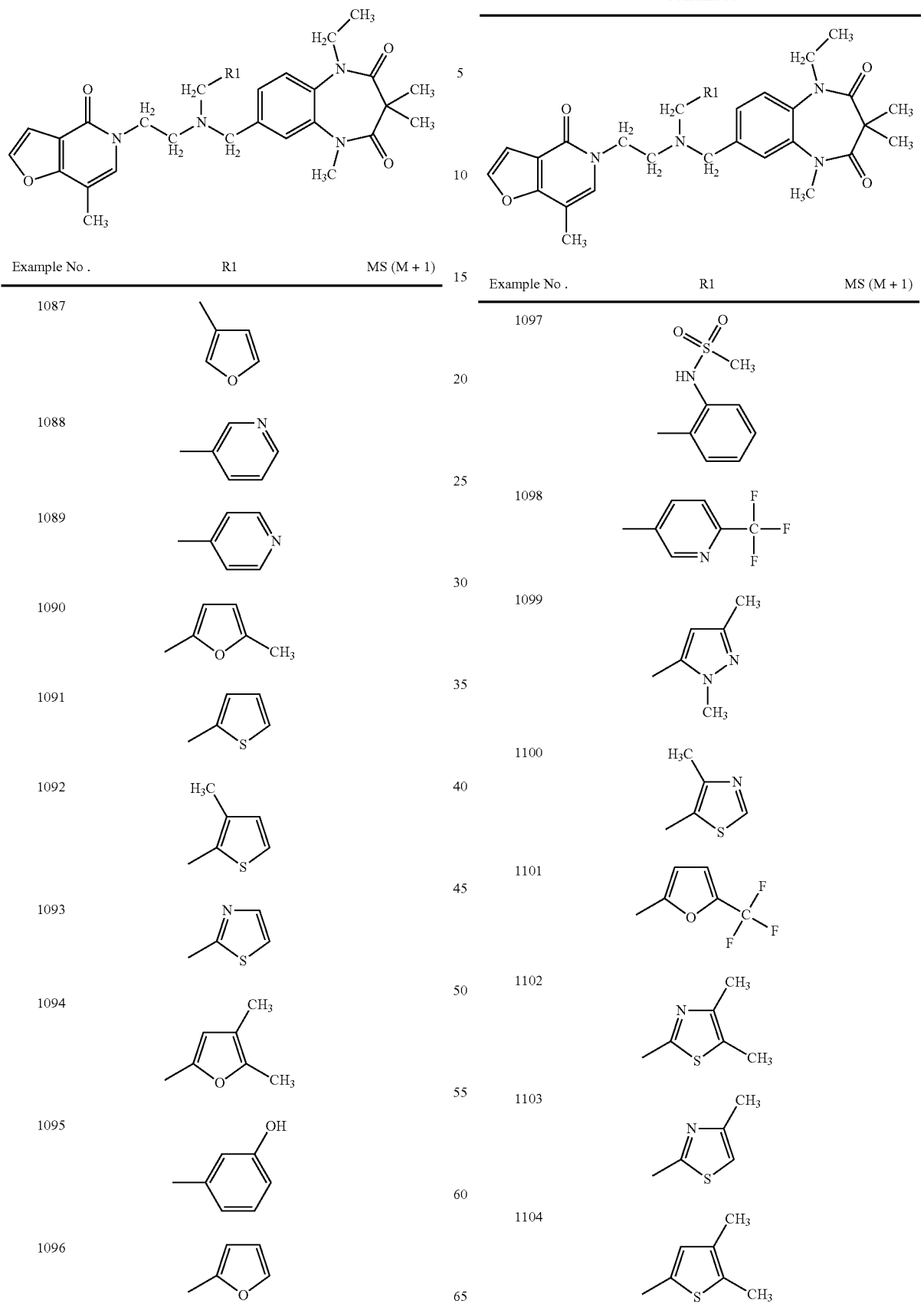

-continued

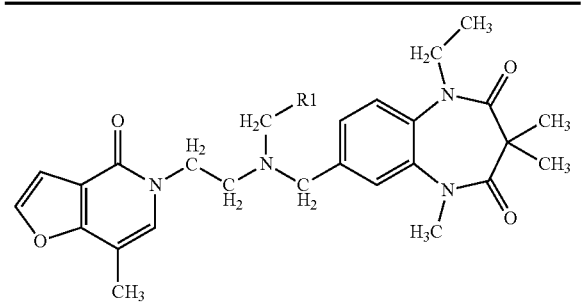

| Example No. | R1 | MS (M + 1) |
|---|---|---|
| 1105 | 2-methyl-4-thiazolyl | |
| 1106 | 3-methyl-4-pyridyl | |
| 1107 | 2-methyl-3-pyridyl | |
| 1108 | 2-methyl-3-pyridyl | |
| 1109 | 2,5-dimethyl-pyridyl | |
| 1110 | 2,4-dimethyl-pyridyl | |
| 1111 | 3-fluoro-4-pyridyl | |
| 1112 | 1-methyl-4-imidazolyl | |
| 1113 | 2,5-dimethyl-4-thiazolyl | |

-continued

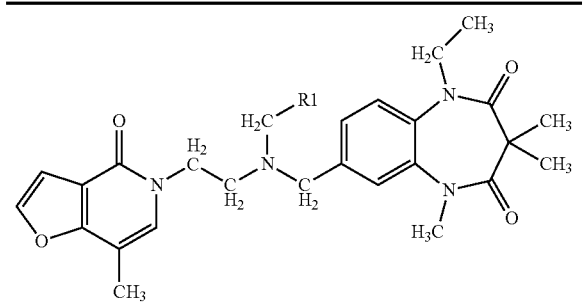

| Example No. | R1 | MS (M + 1) |
|---|---|---|
| 1114 | 1,5-dimethylpyrazol-3-yl | |
| 1115 | 2-methyl-3-furyl | |
| 1116 | 2-methyl-4-pyridyl | |
| 1117 | 2-fluoro-4-pyridyl | |
| 1118 | 4-trifluoromethyl-3-pyridyl | |
| 1119 | 2-methoxy-3-pyridyl | |
| 1120 | 4-thiazolyl | |
| 1121 | 5-methyl-thiazolyl | |
| 1122 | 2-methylpyrazinyl | |

277
-continued
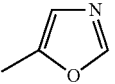
| Example No. | R1 | MS (M + 1) |
|---|---|---|
| 1123 | 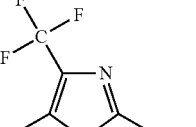 | |
| 1124 | 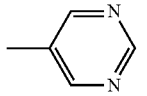 | |
| 1125 | 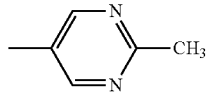 | |
| 1126 | 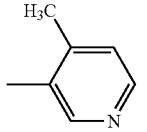 | |
| 1127 | 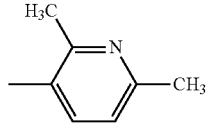 | |
| 1128 | 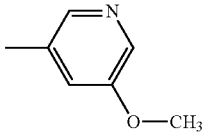 | |
| 1129 | 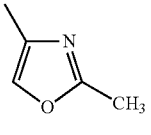 | |
| 1130 | 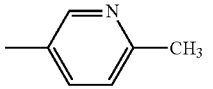 | |
| 1131 | 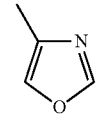 | |
278
-continued
| Example No. | R1 | MS (M + 1) |
|---|---|---|
| 1132 | 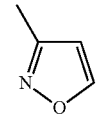 | |
| 1133 | 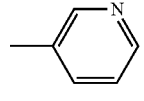 | |
| 1134 | 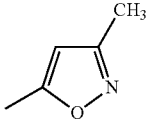 | |
| Example No. | R1 | MS (M + 1) |
|---|---|---|
| 1135 | 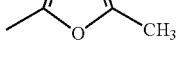 | |
| 1136 | | |
| 1137 | | |
| 1138 | | |

279
-continued
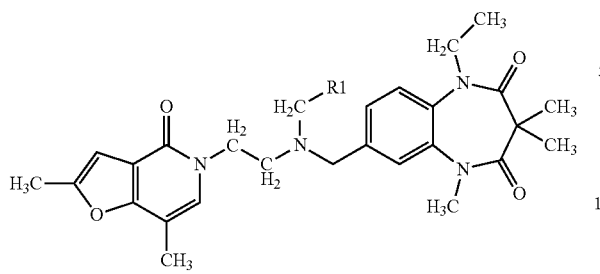
| Example No. | R1 | MS (M + 1) |
|---|---|---|
| 1139 | 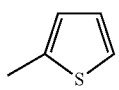 | |
| 1140 | 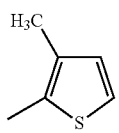 | |
| 1141 | 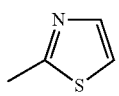 | |
| 1142 | 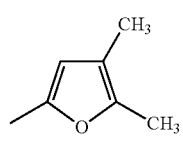 | |
| 1143 | 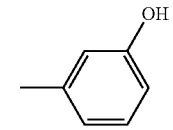 | |
| 1144 | 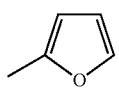 | |
| 1145 | 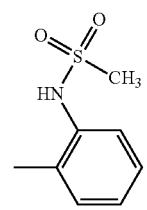 | |
| 1146 | 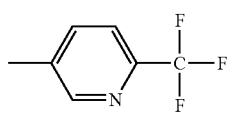 | |
| 1147 | 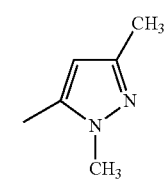 | |
280
-continued
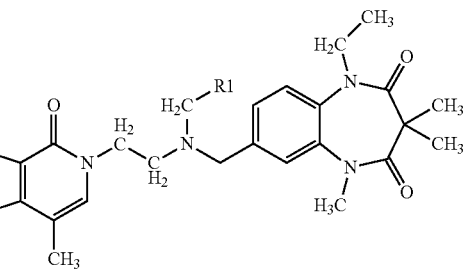
| Example No. | R1 | MS (M + 1) |
|---|---|---|
| 1148 | 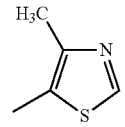 | |
| 1149 | 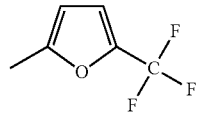 | |
| 1150 | 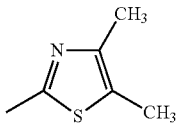 | |
| 1151 | 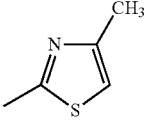 | |
| 1152 | 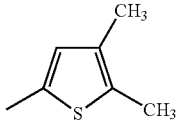 | |
| 1153 | 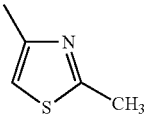 | |
| 1154 | 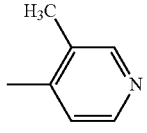 | |
| 1155 | 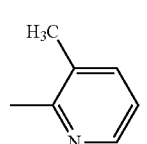 | |
| 1156 | 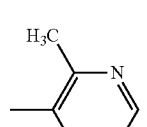 | |

281
-continued
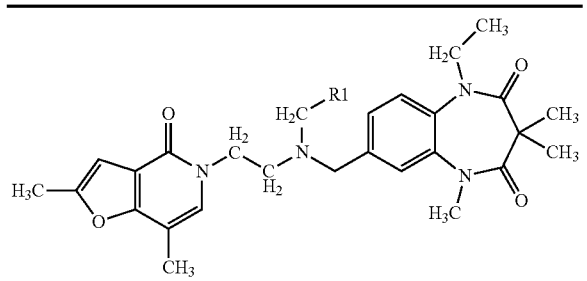
| Example No. | R1 | MS (M + 1) |
|---|---|---|
| 1157 | 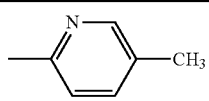 | |
| 1158 | 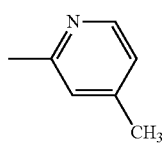 | |
| 1159 | 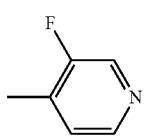 | |
| 1160 | 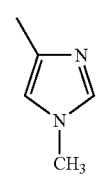 | |
| 1161 | 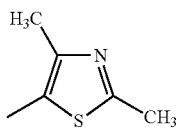 | |
| 1162 | 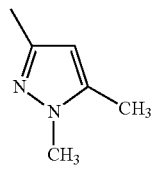 | |
| 1163 | 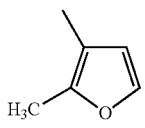 | |
| 1164 | 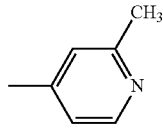 | |
| 1165 | 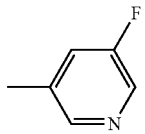 | |
282
-continued
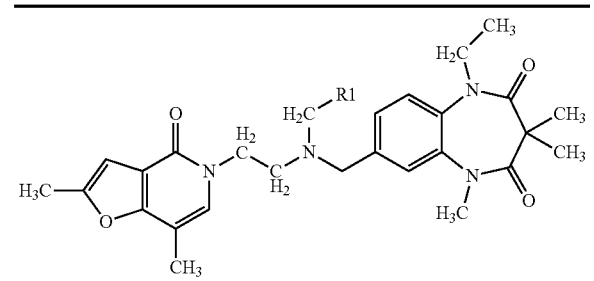
| Example No. | R1 | MS (M + 1) |
|---|---|---|
| 1166 | 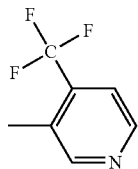 | |
| 1167 | 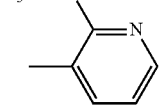 | |
| 1168 | 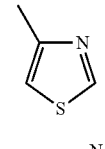 | |
| 1169 | 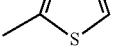 | |
| 1170 | 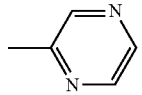 | |
| 1171 | 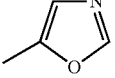 | |
| 1172 | 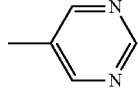 | |
| 1173 | 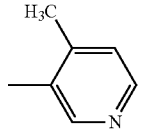 | |
| 1174 | 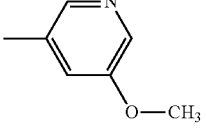 | |
| 1175 | 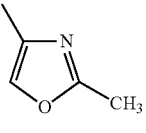 | |

283
-continued
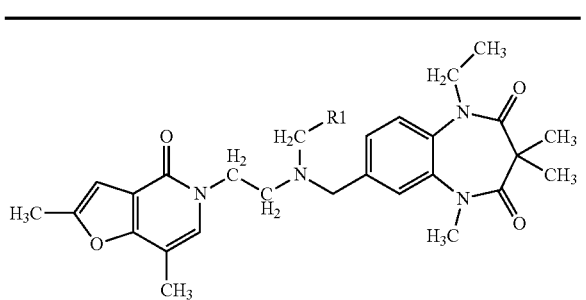
| Example No. | R1 | MS (M + 1) |
|---|---|---|
| 1176 | 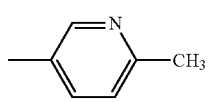 | |
| 1177 | 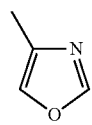 | |
| 1178 | 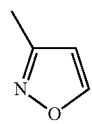 | |
| 1179 | 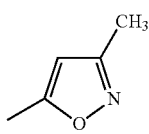 | |
| 1180 | 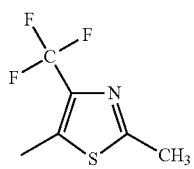 | |
| 1181 | 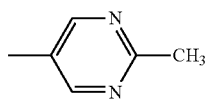 | |
| 1182 | 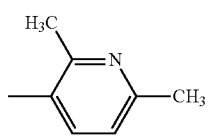 | |
284
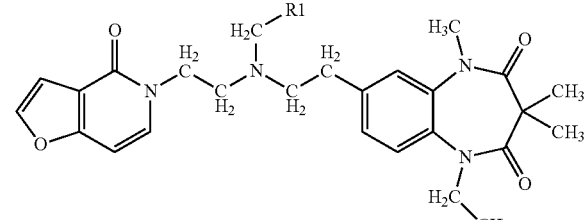
| Example No. | R1 | MS (M + 1) |
|---|---|---|
| 1183 | 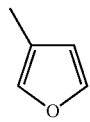 | |
| 1184 | 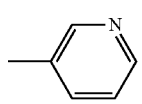 | |
| 1185 | 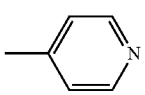 | |
| 1186 | 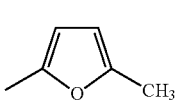 | |
| 1187 | 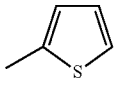 | |
| 1188 | 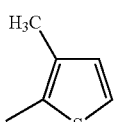 | |
| 1189 | 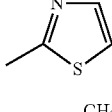 | |
| 1190 | 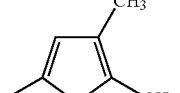 | |
| 1191 | 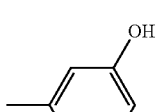 | |
| 1192 | 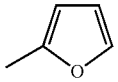 | |
| 1193 | 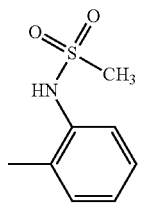 | |

285
-continued

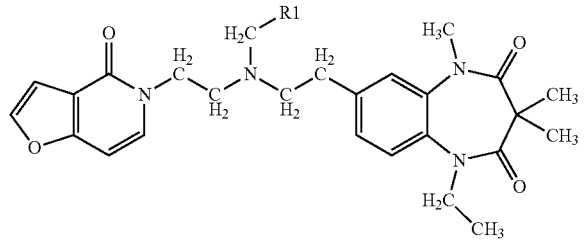

286
-continued

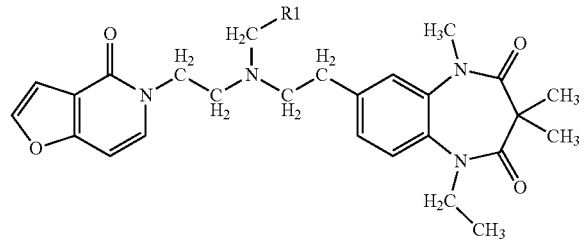

| Example No. | R1 | MS (M + 1) |
|---|---|---|
| 1194 | 5-(trifluoromethyl)pyridin-2-yl | |
| 1195 | 1,3-dimethyl-1H-pyrazol-5-yl | |
| 1196 | 4,5-dimethylthiazol-2-yl | |
| 1197 | 5-(trifluoromethyl)furan-2-yl | |
| 1198 | 2,4,5-trimethylthiazol-? | |
| 1199 | 2,4-dimethylthiazol-5-yl | |
| 1200 | 3,5-dimethylthiophen-2-yl | |
| 1201 | 2-methylthiazol-4-yl | |
| 1202 | 4-methylpyridin-3-yl | |

| Example No. | R1 | MS (M + 1) |
|---|---|---|
| 1203 | 2,3-dimethylpyridin-? | |
| 1204 | 2-methylpyridin-3-yl | |
| 1205 | 5-methylpyridin-2-yl | |
| 1206 | 2,4-dimethylpyridin-? | |
| 1207 | 3-fluoropyridin-4-yl | |
| 1208 | 1-methyl-1H-imidazol-4-yl | |
| 1209 | 2,4-dimethyl-5-? thiazole | |
| 1210 | 1,3,5-trimethyl-1H-pyrazol-4-yl | |
| 1211 | 2-methylfuran-3-yl | |

287
-continued
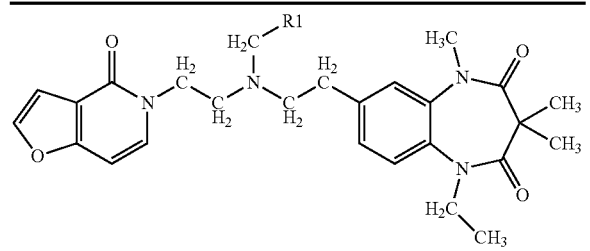
| Example No. | R1 | MS (M + 1) |
|---|---|---|
| 1212 | 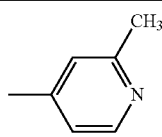 | |
| 1213 | 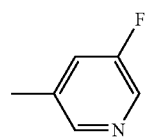 | |
| 1214 | 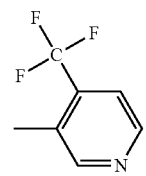 | |
| 1215 | 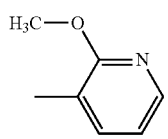 | |
| 1216 | 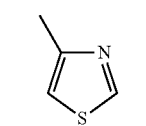 | |
| 1217 | 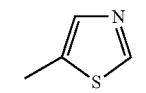 | |
| 1218 | 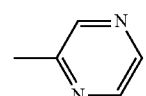 | |
| 1219 | 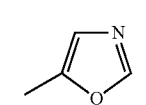 | |
| 1220 | 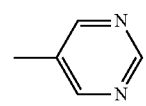 | |
| 1221 | 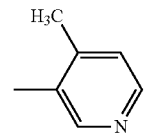 | |
288
-continued
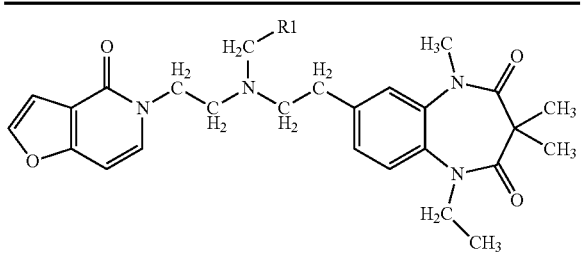
| Example No. | R1 | MS (M + 1) |
|---|---|---|
| 1222 | 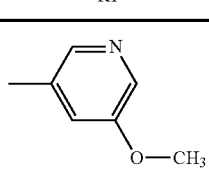 | |
| 1223 | 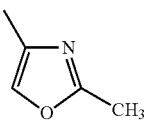 | |
| 1224 | 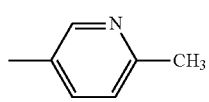 | |
| 1225 | 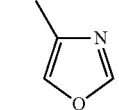 | |
| 1226 | 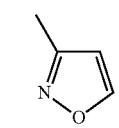 | |
| 1227 | 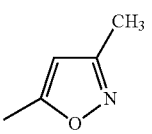 | |
| 1228 | 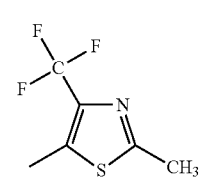 | |
| 1229 | 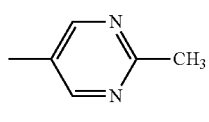 | |
| 1230 | 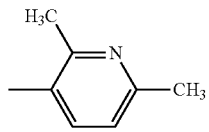 | |

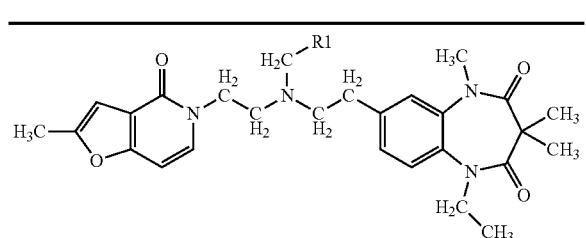
| Example No. | R1 | MS (M + 1) |
|---|---|---|
| 1231 | 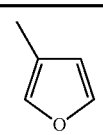 | |
| 1232 | 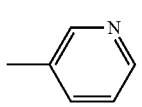 | |
| 1233 | 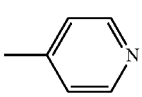 | |
| 1234 | 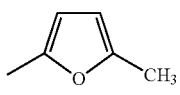 | |
| 1235 | 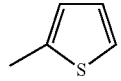 | |
| 1236 | 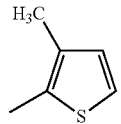 | |
| 1237 | 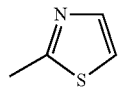 | |
| 1238 | 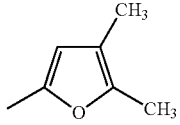 | |
| 1239 | 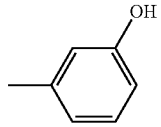 | |
| 1240 | 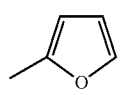 | |
| 1241 | 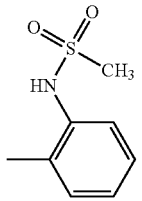 | |
-continued
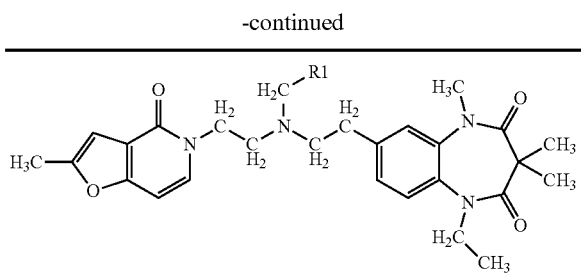
| Example No. | R1 | MS (M + 1) |
|---|---|---|
| 1242 | 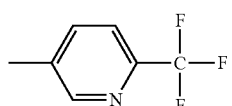 | |
| 1243 | 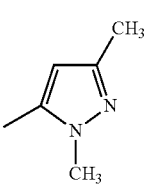 | |
| 1244 | 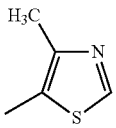 | |
| 1245 | 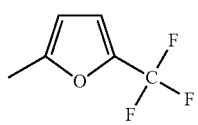 | |
| 1246 | 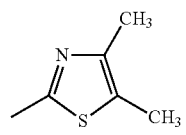 | |
| 1247 | 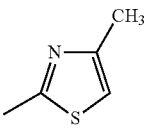 | |
| 1248 | 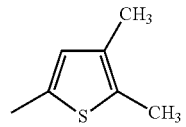 | |
| 1249 | 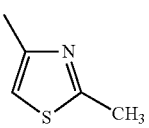 | |
| 1250 | 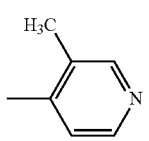 | |

291
-continued
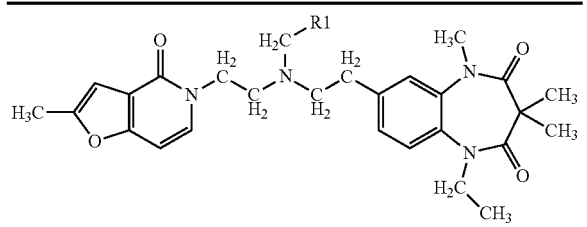
| Example No. | R1 | MS (M + 1) |
|---|---|---|
| 1251 | 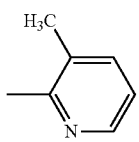 | |
| 1252 | 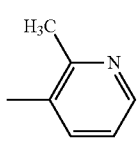 | |
| 1253 | 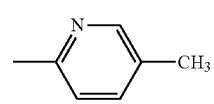 | |
| 1254 | 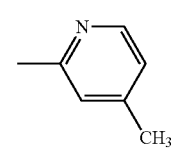 | |
| 1255 | 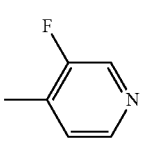 | |
| 1256 | 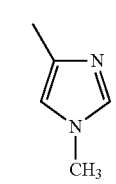 | |
| 1257 | 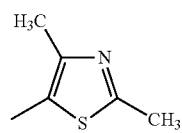 | |
| 1258 | 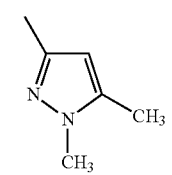 | |
| 1259 | 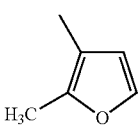 | |
292
-continued
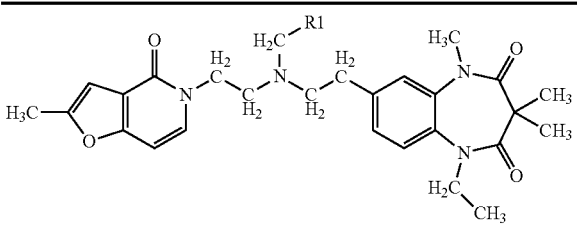
| Example No. | R1 | MS (M + 1) |
|---|---|---|
| 1260 | 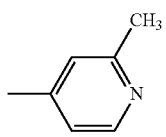 | |
| 1261 | 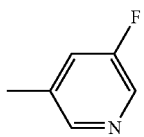 | |
| 1262 | 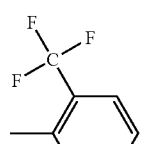 | |
| 1263 | 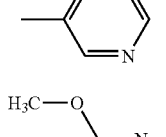 | |
| 1264 | 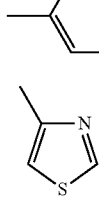 | |
| 1265 | 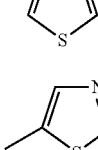 | |
| 1266 | 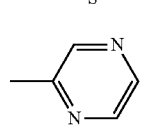 | |
| 1267 | 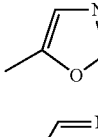 | |
| 1268 | 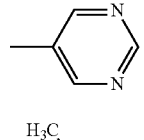 | |
| 1269 | 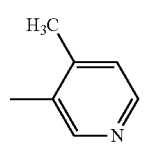 | |

293
-continued

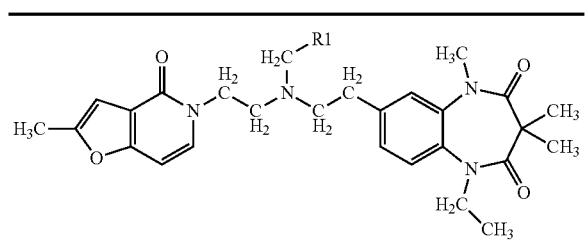

| Example No. | R1 | MS (M + 1) |
|---|---|---|
| 1270 | 5-methoxypyridin-3-yl | |
| 1271 | 2-methyloxazol-4-yl | |
| 1272 | 6-methylpyridin-3-yl | |
| 1273 | oxazol-4-yl | |
| 1274 | isoxazol-3-yl | |
| 1275 | 3,5-dimethylisoxazol-4-yl | |
| 1276 | 2,5-dimethyl-4-(trifluoromethyl)thiazol-... | |
| 1277 | 2-methylpyrimidin-5-yl | |
| 1278 | 2,6-dimethylpyridin-3-yl | |

294

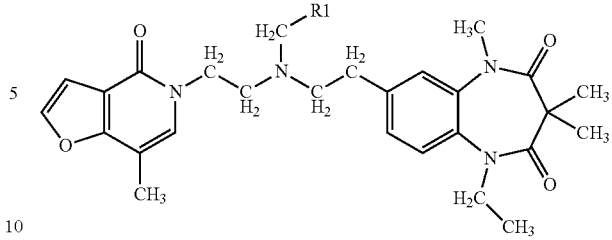

| Example No. | R1 | MS (M + 1) |
|---|---|---|
| 1279 | furan-3-yl | |
| 1280 | pyridin-3-yl | |
| 1281 | pyridin-4-yl | |
| 1282 | 5-methylfuran-2-yl | |
| 1283 | thiophen-2-yl | |
| 1284 | 3-methylthiophen-2-yl | |
| 1285 | thiazol-2-yl | |
| 1286 | 3,4,5-trimethylfuran-2-yl | |
| 1287 | 3-hydroxyphenyl | |
| 1288 | furan-2-yl | |
| 1289 | N-(2-methylphenyl)methanesulfonamide | |

295

-continued

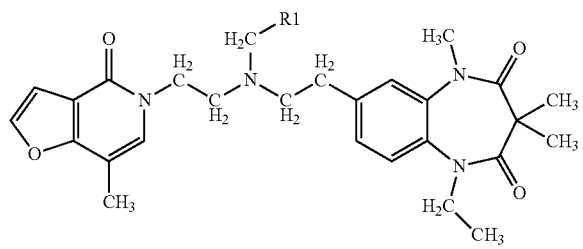

| Example No. | R1 | MS (M + 1) |
|---|---|---|
| 1290 | 5-methyl-2-(trifluoromethyl)pyridine | |
| 1291 | 1,3,5-trimethyl-1H-pyrazole | |
| 1292 | 4,5-dimethylthiazole | |
| 1293 | 5-methyl-2-(trifluoromethyl)furan | |
| 1294 | 2,4,5-trimethylthiazole | |
| 1295 | 2,4-dimethylthiazole | |
| 1296 | 2,3-dimethylthiophene | |
| 1297 | 2,4-dimethylthiazole | |
| 1298 | 3,4-dimethylpyridine | |

296

-continued

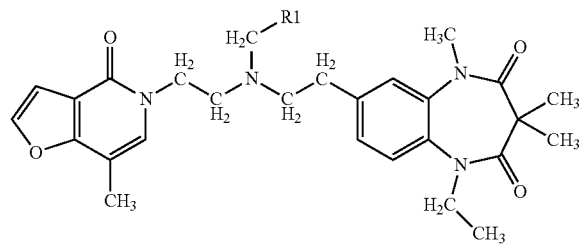

| Example No. | R1 | MS (M + 1) |
|---|---|---|
| 1299 | 2,3-dimethylpyridine | |
| 1300 | 2,3-dimethylpyridine | |
| 1301 | 2,5-dimethylpyridine | |
| 1302 | 2,4-dimethylpyridine | |
| 1303 | 3-fluoro-4-methylpyridine | |
| 1304 | 1,4-dimethylimidazole | |
| 1305 | 2,4,5-trimethylthiazole | |
| 1306 | 1,3,5-trimethyl-1H-pyrazole | |
| 1307 | 2,3-dimethylfuran | |

297
-continued

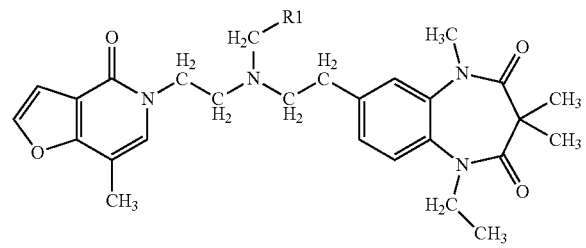

| Example No. | R1 | MS (M + 1) |
|---|---|---|
| 1308 | 2,4-dimethylpyridin-? | |
| 1309 | 5-fluoropyridin-3-yl | |
| 1310 | 3-(trifluoromethyl)pyridin-5-yl | |
| 1311 | 2-methoxy-3-methylpyridin-? | |
| 1312 | 4-methylthiazol-? | |
| 1313 | 5-methylthiazol-? | |
| 1314 | methylpyrazinyl | |
| 1315 | 5-methyloxazol-? | |
| 1316 | 5-methylpyrimidin-? | |
| 1317 | 3,4-dimethylpyridin-? | |

298
-continued

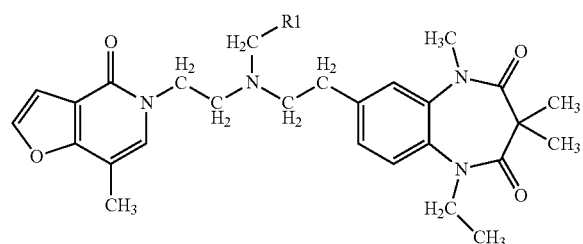

| Example No. | R1 | MS (M + 1) |
|---|---|---|
| 1318 | 5-methoxy-3-methylpyridinyl | |
| 1319 | 2,4-dimethyloxazol-? | |
| 1320 | 2,5-dimethylpyridin-? | |
| 1321 | 4-methyloxazol-? | |
| 1322 | 3-methylisoxazol-? | |
| 1323 | 3,5-dimethylisoxazol-? | |
| 1324 | 2,5-dimethyl-4-(trifluoromethyl)thiazol-? | |
| 1325 | 2,5-dimethylpyrimidin-? | |
| 1326 | 2,4,6-trimethylpyridin-? | |

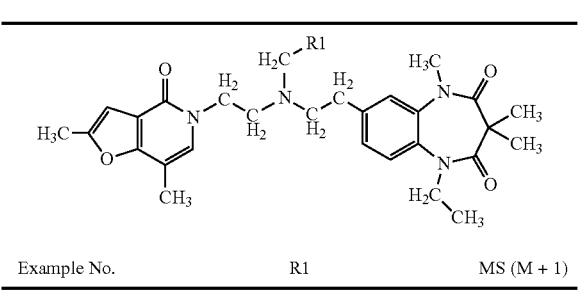

| Example No. | R1 | MS (M + 1) |
|---|---|---|
| 1327 | 3-methylfuran | |
| 1328 | 3-methylpyridine | |
| 1329 | 4-methylpyridine | |
| 1330 | 2,5-dimethylfuran | |
| 1331 | 2-methylthiophene | |
| 1332 | 2,3-dimethylthiophene | |
| 1333 | 2-methylthiazole | |
| 1334 | 2,3,5-trimethylfuran | |
| 1335 | 3-hydroxyphenyl | |
| 1336 | 2-methylfuran | |
| 1337 | N-(2-methylphenyl)methanesulfonamide | |

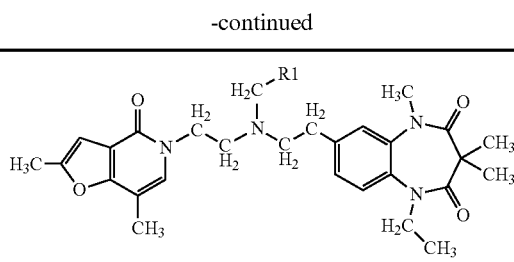

| Example No. | R1 | MS (M + 1) |
|---|---|---|
| 1338 | 2-(trifluoromethyl)-5-methylpyridine | |
| 1339 | 1,3,5-trimethylpyrazole | |
| 1340 | 4,5-dimethylthiazole | |
| 1341 | 5-methyl-2-(trifluoromethyl)furan | |
| 1342 | 2,4,5-trimethylthiazole | |
| 1343 | 2,4-dimethylthiazole | |
| 1344 | 2,3,5-trimethylthiophene | |
| 1345 | 2,4-dimethylthiazole | |
| 1346 | 3,4-dimethylpyridine | |

| | 301 -continued | | | 302 -continued | |
|---|---|---|---|---|---|
| 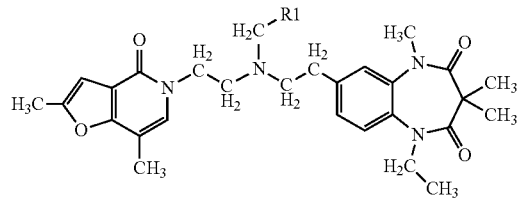 | | | 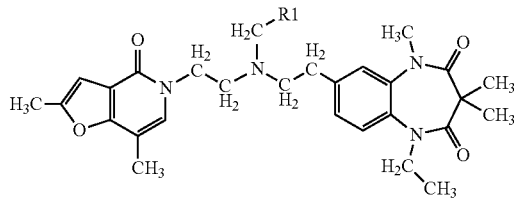 | | |
| Example No. | R1 | MS (M + 1) | Example No. | R1 | MS (M + 1) |
| 1347 | 2,3-dimethylpyridin-4-yl | | 1356 | 2,4-dimethylpyridin-5-yl | |
| 1348 | 2,3-dimethylpyridin-4-yl | | 1357 | 5-fluoro-3-methylpyridin-... | |
| 1349 | 2,5-dimethylpyridin-... | | 1358 | 4-(trifluoromethyl)-3-methylpyridinyl | |
| 1350 | 2,4-dimethylpyridin-... | | 1359 | 2-methoxy-3-methylpyridinyl | |
| 1351 | 3-fluoro-4-methylpyridinyl | | 1360 | 4-methylthiazol-... | |
| 1352 | 1,4-dimethylimidazolyl | | 1361 | 5-methylthiazol-... | |
| 1353 | 2,4,5-trimethylthiazolyl | | 1362 | methylpyrazinyl | |
| 1354 | 1,3,5-trimethylpyrazolyl | | 1363 | methyloxazolyl | |
| 1355 | 2,3-dimethylfuranyl | | 1364 | methylpyrimidinyl | |
| | | | 1365 | 3,4-dimethylpyridin-... | |

303
-continued
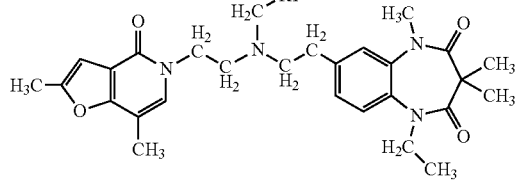
| Example No. | R1 | MS (M + 1) |
|---|---|---|
| 1366 | 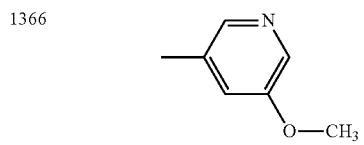 | |
| 1367 | 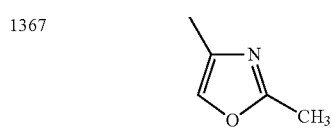 | |
| 1368 | 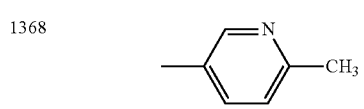 | |
| 1369 | 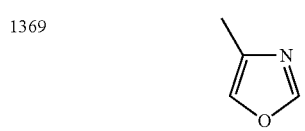 | |
| 1370 |  | |
| 1371 | 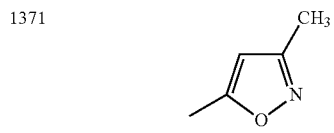 | |
| 1372 | 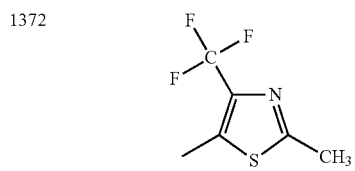 | |
| 1373 | 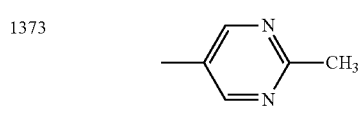 | |
| 1374 | 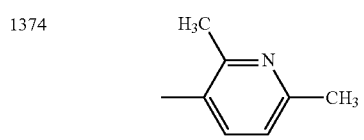 | |
304
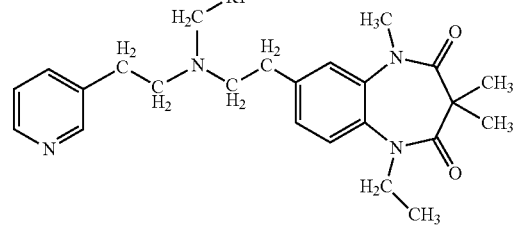
| Example No. | R1 | MS (M + 1) |
|---|---|---|
| 1375 |  | |
| 1376 | 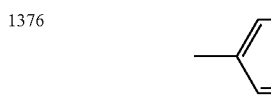 | |
| 1377 | 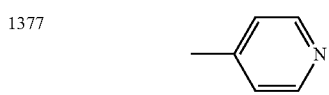 | |
| 1378 | 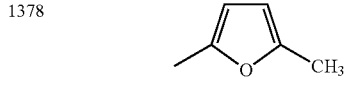 | |
| 1379 |  | |
| 1380 | 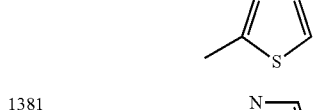 | |
| 1381 |  | |
| 1382 |  | |
| 1383 | 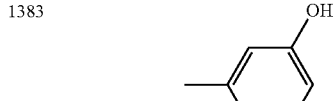 | |
| 1384 |  | |
| 1385 |  | |

305
-continued
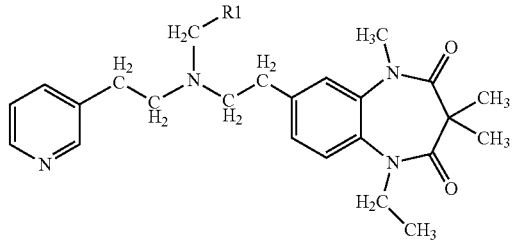
| Example No. | R1 | MS (M + 1) |
|---|---|---|
| 1386 | 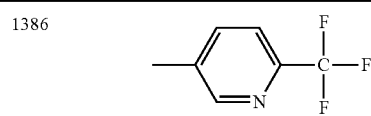 | |
| 1387 | 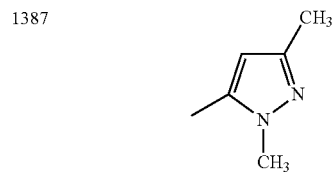 | |
| 1388 | 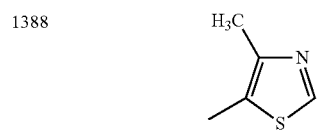 | |
| 1389 | 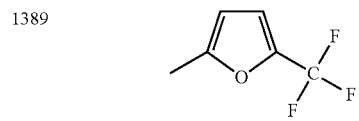 | |
| 1390 | 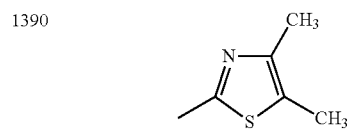 | |
| 1391 | 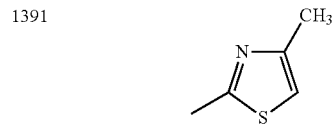 | |
| 1392 | 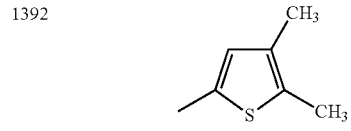 | |
| 1393 | 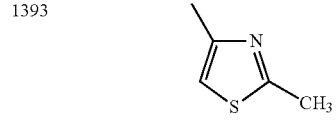 | |
| 1394 | 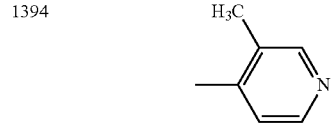 | |
306
-continued
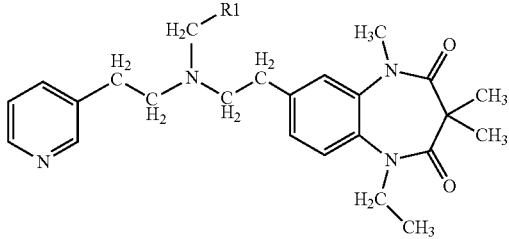
| Example No. | R1 | MS (M + 1) |
|---|---|---|
| 1395 |  | |
| 1396 | 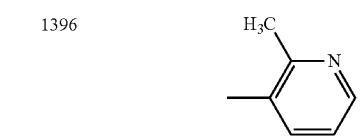 | |
| 1397 | 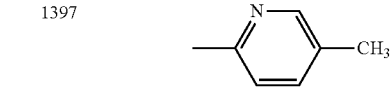 | |
| 1398 | 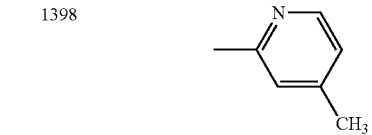 | |
| 1399 |  | |
| 1400 |  | |
| 1401 | 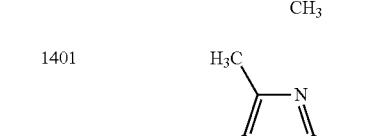 | |
| 1402 | 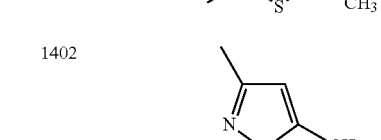 | |
| 1403 |  | |

307
-continued

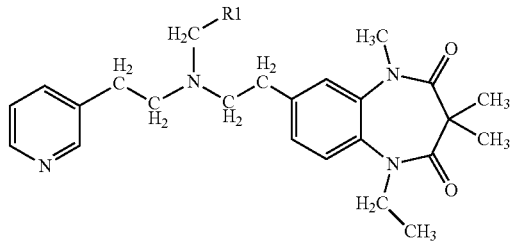

| Example No. | R1 | MS (M + 1) |
|---|---|---|
| 1404 | 2,4-dimethylpyridin-yl | |
| 1405 | 5-fluoro-3-methylpyridin-yl | |
| 1406 | 3-methyl-4-(trifluoromethyl)pyridin-yl | |
| 1407 | 2-methoxy-3-methylpyridin-yl | |
| 1408 | 4-methylthiazol-yl | |
| 1409 | 5-methylthiazol-yl | |
| 1410 | methylpyrazin-yl | |
| 1411 | 5-methyloxazol-yl | |
| 1412 | 5-methylpyrimidin-yl | |
| 1413 | 4,5-dimethylpyridin-yl | |

308
-continued

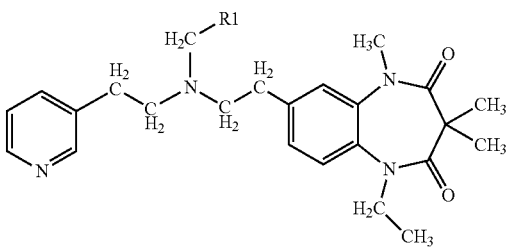

| Example No. | R1 | MS (M + 1) |
|---|---|---|
| 1414 | 5-methoxy-3-methylpyridin-yl | |
| 1415 | 2,4-dimethyloxazol-yl | |
| 1416 | 2,5-dimethylpyridin-yl | |
| 1417 | 4-methyloxazol-yl | |
| 1418 | 3-methylisoxazol-yl | |
| 1419 | 3,5-dimethylisoxazol-yl | |
| 1420 | 2,5-dimethyl-4-(trifluoromethyl)thiazol-yl | |
| 1421 | 2,5-dimethylpyrimidin-yl | |
| 1422 | 2,6-dimethylpyridin-yl | |

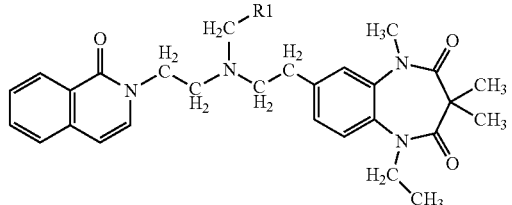

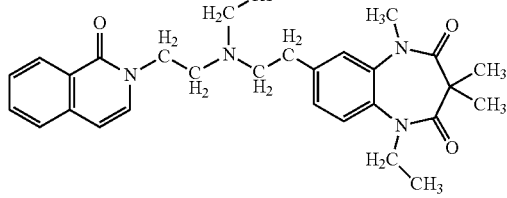

| Example No. | R1 | MS (M + 1) |
|---|---|---|
| 1423 | 3-furyl | |
| 1424 | 3-pyridyl | |
| 1425 | 4-pyridyl | |
| 1426 | 2,5-dimethylfuran-3-yl | |
| 1427 | 2-thienyl | |
| 1428 | 3-methylthiophen-2-yl | |
| 1429 | 2-thiazolyl | |
| 1430 | 3-methyl-2,5-dimethylfuran | |
| 1431 | 3-hydroxyphenyl | |
| 1432 | 2-furyl | |
| 1433 | N-(2-methylphenyl)methanesulfonamide | |

| Example No. | R1 | MS (M + 1) |
|---|---|---|
| 1434 | 5-methyl-2-(trifluoromethyl)pyridin-yl | |
| 1435 | 1,3-dimethyl-5-methylpyrazol-yl | |
| 1436 | 4,5-dimethylthiazol-2-yl | |
| 1437 | 5-methyl-2-(trifluoromethyl)furan | |
| 1438 | 2,4,5-trimethylthiazolyl | |
| 1439 | 2,4-dimethylthiazolyl | |
| 1440 | 2,5-dimethyl-3-methylthiophene | |
| 1441 | 2,4-dimethylthiazolyl | |
| 1442 | 3,4-dimethylpyridyl | |

| 311 -continued | | | 312 -continued | | |
|---|---|---|---|---|---|
| 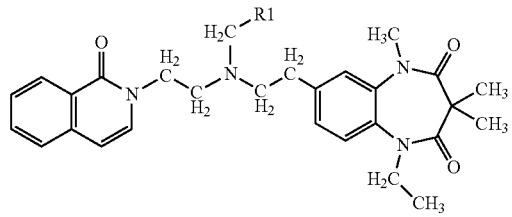 | | | 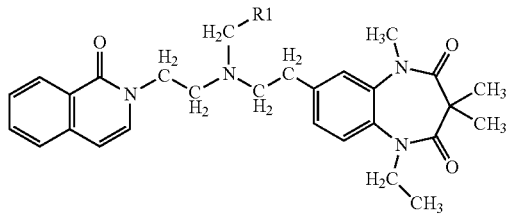 | | |
| Example No. | R1 | MS (M + 1) | Example No. | R1 | MS (M + 1) |
| 1443 | 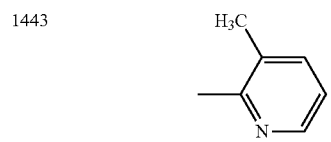 | | 1452 | 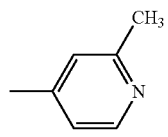 | |
| 1444 | 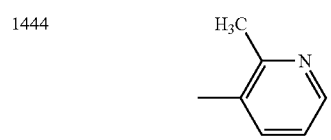 | | 1453 | 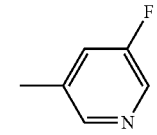 | |
| 1445 | 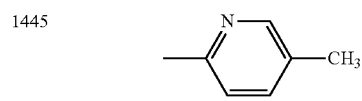 | | 1454 | 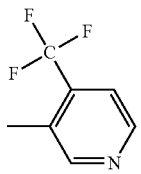 | |
| 1446 | 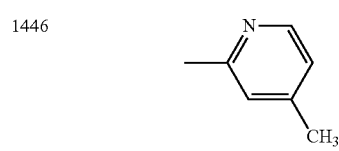 | | 1455 | 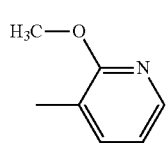 | |
| 1447 |  | | 1456 | 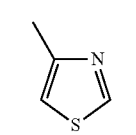 | |
| 1448 | 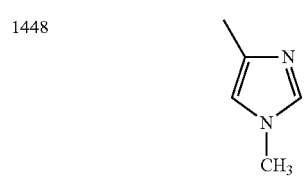 | | 1457 | 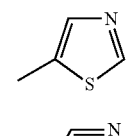 | |
| 1449 | 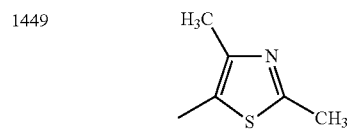 | | 1458 | 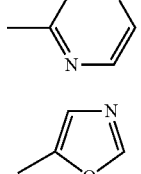 | |
| 1450 | 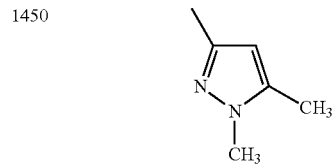 | | 1459 | 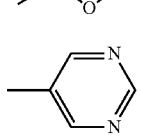 | |
| 1451 | 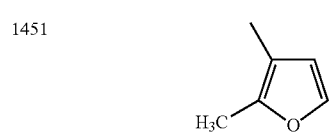 | | 1460 | 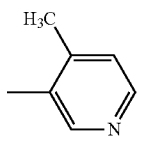 | |
| | | | 1461 | | |

313
-continued

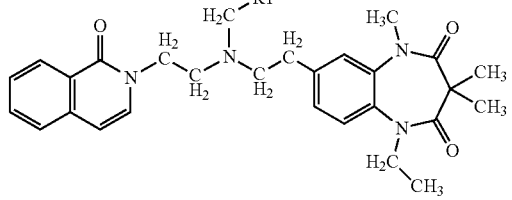

| Example No. | R1 | MS (M + 1) |
|---|---|---|
| 1462 | 5-methoxypyridin-3-yl | |
| 1463 | 2-methyl-1,3-oxazol-4-yl (4-methyl) | |
| 1464 | 6-methylpyridin-3-yl (with 2-CH3) | |
| 1465 | 1,3-oxazol-4-yl | |
| 1466 | isoxazol-3-yl | |
| 1467 | 3,5-dimethylisoxazol-4-yl | |
| 1468 | 2-methyl-4-(trifluoromethyl)-1,3-thiazol-5-yl | |
| 1469 | 2-methylpyrimidin-5-yl | |
| 1470 | 2,6-dimethylpyridin-3-yl | |

314

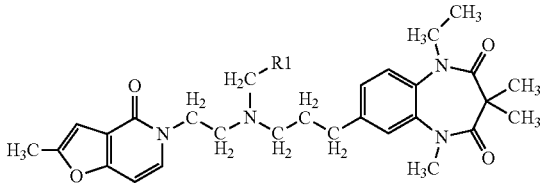

| Example No. | R1 | MS (M + 1) |
|---|---|---|
| 1471 | furan-3-yl | |
| 1472 | pyridin-3-yl | |
| 1473 | pyridin-4-yl | |
| 1474 | 5-methylfuran-2-yl | |
| 1475 | thiophen-2-yl | |
| 1476 | 3-methylthiophen-2-yl | |
| 1477 | 1,3-thiazol-2-yl | |
| 1478 | 2,5-dimethylfuran-3-yl (3-methyl) | |
| 1479 | 3-hydroxyphenyl | |
| 1480 | furan-2-yl | |
| 1481 | 2-(methylsulfonylamino)phenyl | |

| Example No. | R1 | MS (M + 1) |
|---|---|---|
| 1482 | 5-methyl-2-(trifluoromethyl)pyridine | |
| 1483 | 1,3,5-trimethyl-1H-pyrazole | |
| 1484 | 4,5-dimethylthiazole | |
| 1485 | 5-methyl-2-(trifluoromethyl)furan | |
| 1486 | 2,4,5-trimethylthiazole | |
| 1487 | 2,4-dimethylthiazole | |
| 1488 | 2,5-dimethyl-3-methylthiophene | |
| 1489 | 4-methyl-2-methylthiazole | |
| 1490 | 2,4-dimethylpyridine | |
| 1491 | 2,3-dimethylpyridine | |

| Example No. | R1 | MS (M + 1) |
|---|---|---|
| 1492 | 2,3-dimethylpyridine | |
| 1493 | 2,5-dimethylpyridine | |
| 1494 | 2,4-dimethylpyridine | |
| 1495 | 3-fluoro-4-methylpyridine | |
| 1496 | 1,4-dimethylimidazole | |
| 1497 | 2,4,5-trimethylthiazole | |
| 1498 | 1,3,5-trimethyl-1H-pyrazole | |
| 1499 | 2,3-dimethylfuran | |
| 1500 | 2,5-dimethylpyridine | |

317
-continued
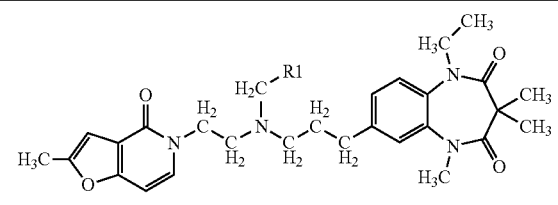
| Example No. | R1 | MS (M + 1) |
|---|---|---|
| 1501 | 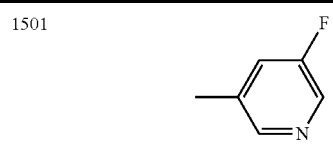 | |
| 1502 | 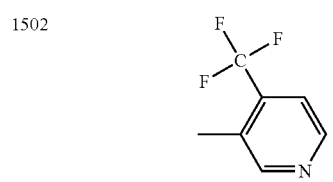 | |
| 1503 | 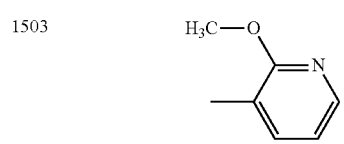 | |
| 1504 |  | |
| 1505 |  | |
| 1506 | 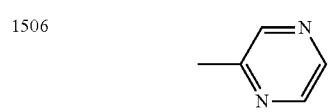 | |
| 1507 |  | |
| 1508 | 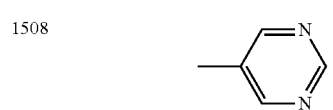 | |
| 1509 | 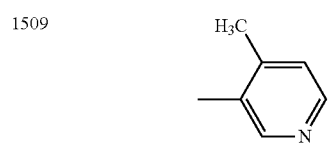 | |
| 1510 | 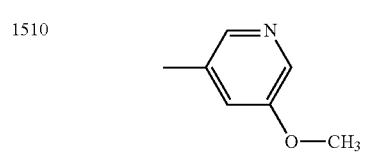 | |
318
-continued
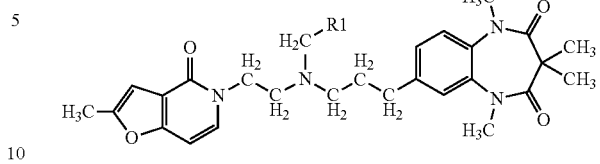
| Example No. | R1 | MS (M + 1) |
|---|---|---|
| 1511 |  | |
| 1512 |  | |
| 1513 |  | |
| 1514 |  | |
| 1515 |  | |
| 1516 | 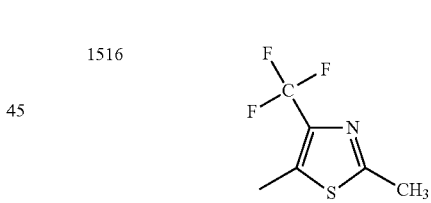 | |
| 1517 | 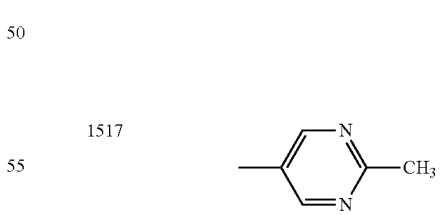 | |
| 1518 | 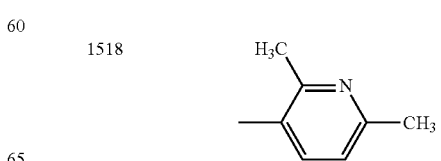 | |

| | 319 | | | 320 -continued | |
|---|---|---|---|---|---|
| 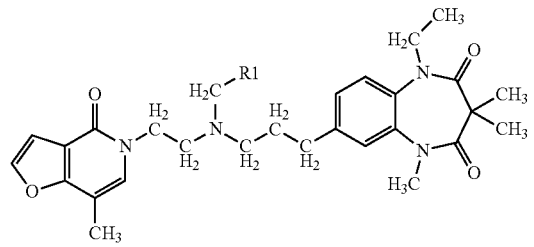 | | | 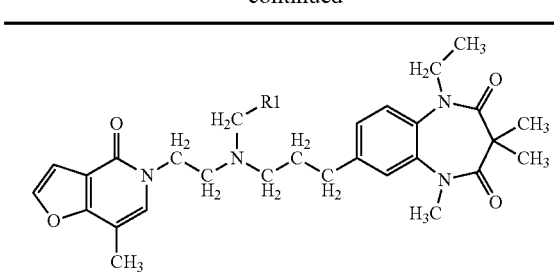 | | |
| Example No. | R1 | MS (M + 1) | Example No. | R1 | MS (M + 1) |
| 1519 | 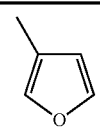 | | 1530 | 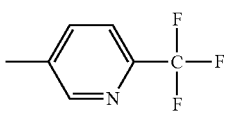 | |
| 1520 | 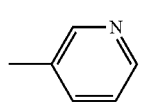 | | 1531 | 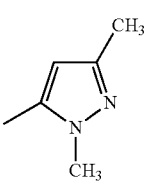 | |
| 1521 | 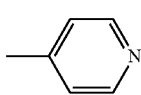 | | | | |
| 1522 | 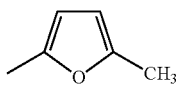 | | 1532 | 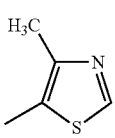 | |
| 1523 | 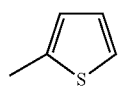 | | | | |
| 1524 | 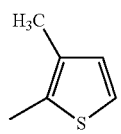 | | 1533 | 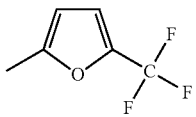 | |
| 1525 | 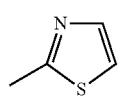 | | 1534 | 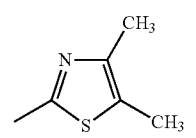 | |
| 1526 | 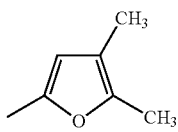 | | 1535 | 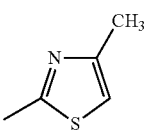 | |
| 1527 | 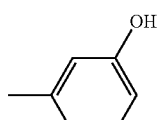 | | 1536 | 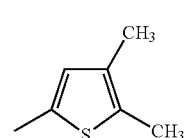 | |
| 1528 | 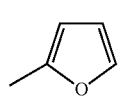 | | 1537 | 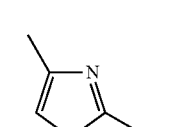 | |
| 1529 | 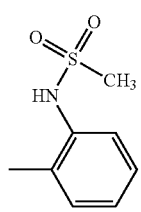 | | 1538 | 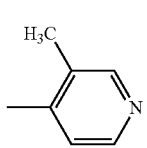 | |

321
-continued
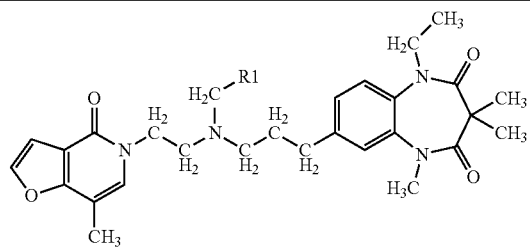
| Example No. | R1 | MS (M + 1) |
|---|---|---|
| 1539 | 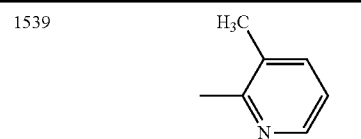 | |
| 1540 | 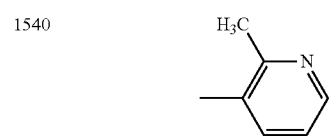 | |
| 1541 | 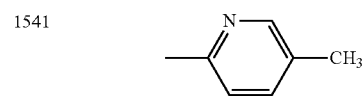 | |
| 1542 | 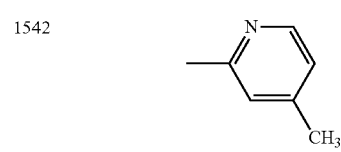 | |
| 1543 |  | |
| 1544 | 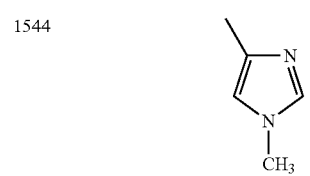 | |
| 1545 | 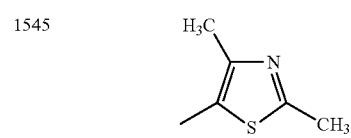 | |
| 1546 | 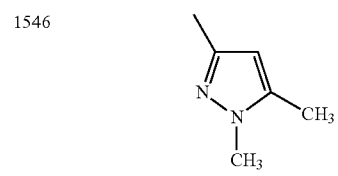 | |
| 1547 | 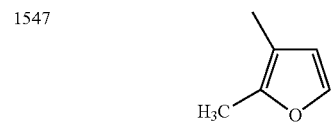 | |
322
-continued
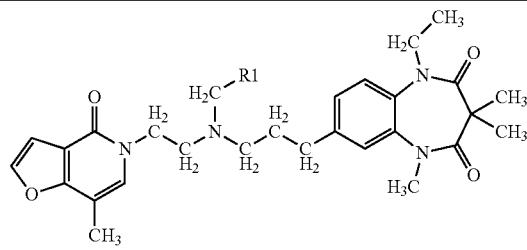
| Example No. | R1 | MS (M + 1) |
|---|---|---|
| 1548 | 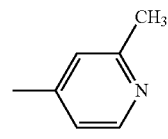 | |
| 1549 | 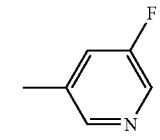 | |
| 1550 | 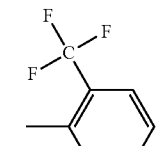 | |
| 1551 | 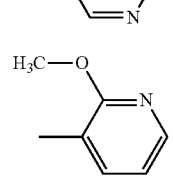 | |
| 1552 | 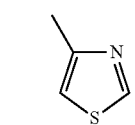 | |
| 1553 | 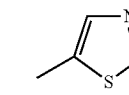 | |
| 1554 | 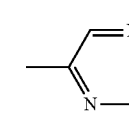 | |
| 1555 | 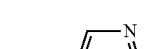 | |
| 1556 | 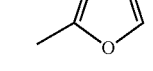 | |
| 1557 | 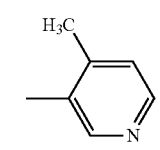 | |

323 -continued
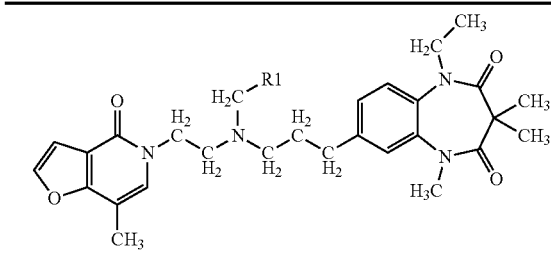
| Example No. | R1 | MS (M + 1) |
|---|---|---|
| 1558 | 5-methoxy-3-pyridyl | |
| 1559 | 4-methyl-2-methyl-oxazolyl | |
| 1560 | 2,5-dimethylpyridyl | |
| 1561 | 4-oxazolyl | |
| 1562 | 3-isoxazolyl | |
324 -continued
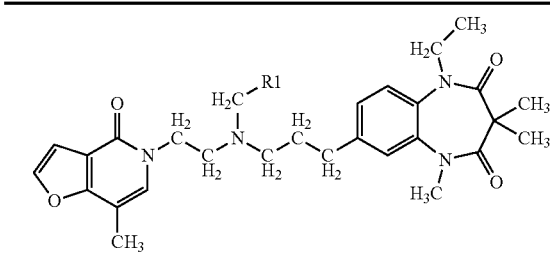
| Example No. | R1 | MS (M + 1) |
|---|---|---|
| 1563 | 3,5-dimethylisoxazolyl | |
| 1564 | 2-methyl-4-trifluoromethyl-5-methylthiazolyl | |
| 1565 | 2-methyl-5-pyrimidinyl | |
| 1566 | 2,3,6-trimethylpyridyl | |
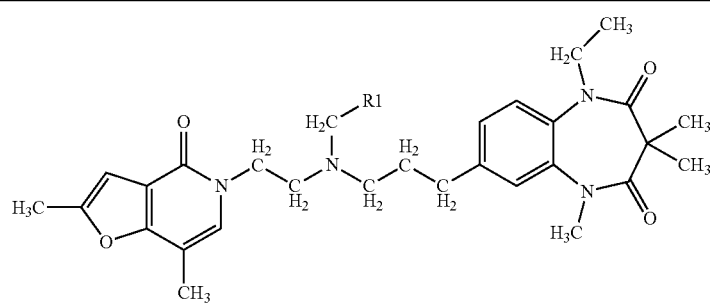
| Example No. | R1 | MS (M + 1) |
|---|---|---|
| 1567 | 3-furyl | |
| 1568 | 3-pyridyl | |

-continued
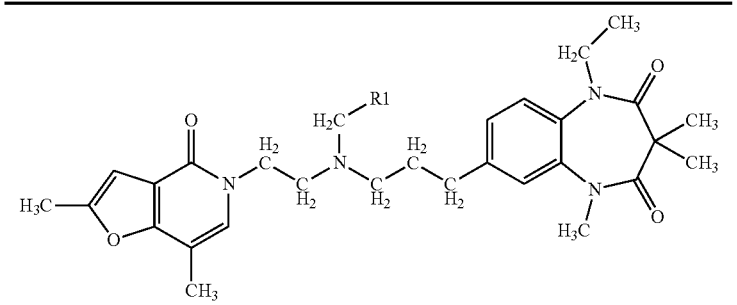
| Example No. | R1 | MS (M + 1) |
|---|---|---|
| 1569 | 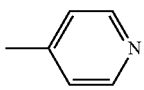 | |
| 1570 | 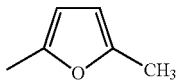 | |
| 1571 | 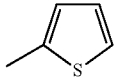 | |
| 1572 | 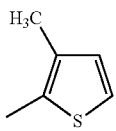 | |
| 1573 | 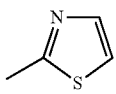 | |
| 1574 | 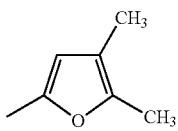 | |
| 1575 | 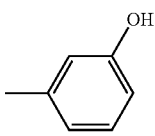 | |
| 1576 | 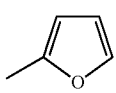 | |
| 1577 | 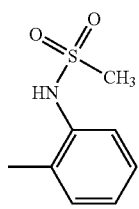 | |
| 1578 | 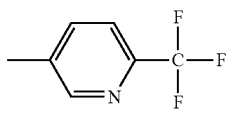 | |

-continued
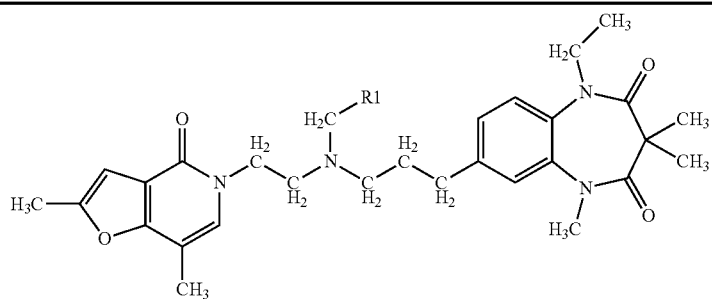
| Example No. | R1 | MS (M + 1) |
|---|---|---|
| 1579 | 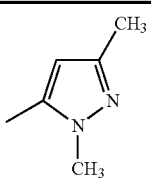 | |
| 1580 | 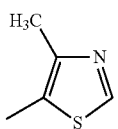 | |
| 1581 | 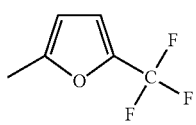 | |
| 1582 | 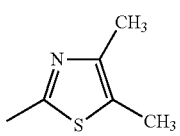 | |
| 1583 | 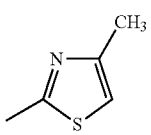 | |
| 1584 | 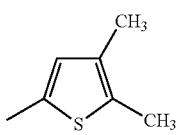 | |
| 1585 | 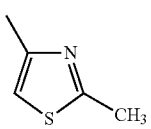 | |
| 1586 | 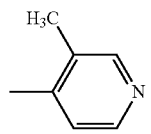 | |
| 1587 | 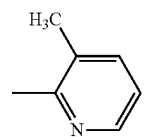 | |

-continued
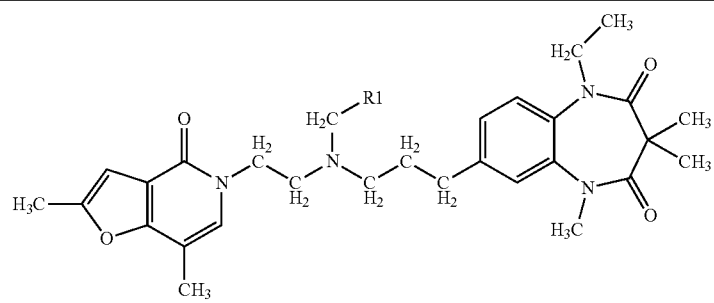
| Example No. | R1 | MS (M + 1) |
|---|---|---|
| 1588 | 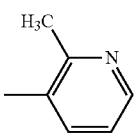 | |
| 1589 | 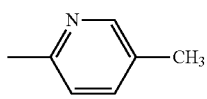 | |
| 1590 | 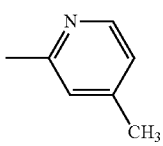 | |
| 1591 | 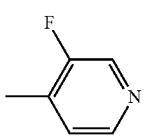 | |
| 1592 | 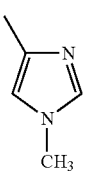 | |
| 1593 | 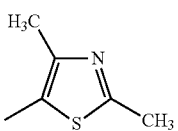 | |
| 1594 | 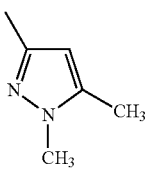 | |
| 1595 | 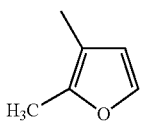 | |

-continued
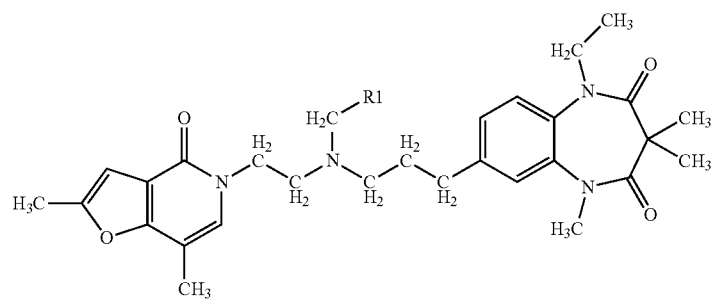
| Example No. | R1 | MS (M + 1) |
|---|---|---|
| 1596 | 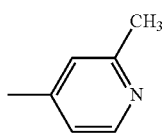 | |
| 1597 | 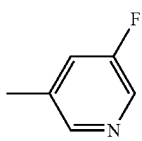 | |
| 1598 | 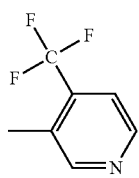 | |
| 1599 | 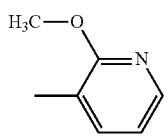 | |
| 1600 | 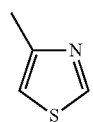 | |
| 1601 | 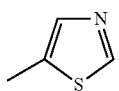 | |
| 1602 | 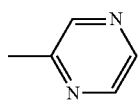 | |
| 1603 | 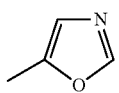 | |
| 1604 | 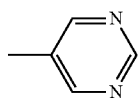 | |

-continued
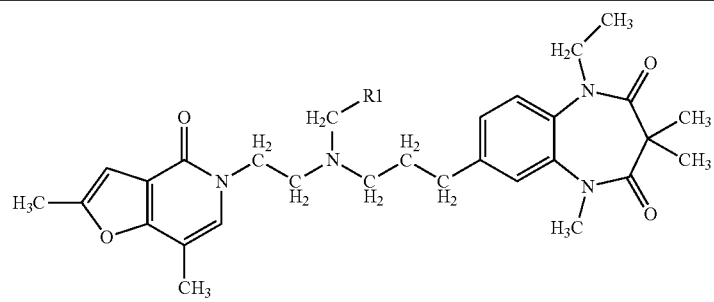
| Example No. | R1 | MS (M + 1) |
|---|---|---|
| 1605 | 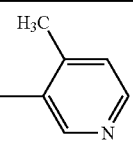 | |
| 1606 | 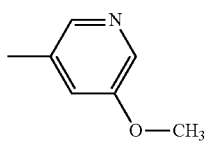 | |
| 1607 | 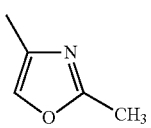 | |
| 1608 | 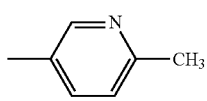 | |
| 1609 | 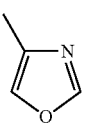 | |
| 1610 | 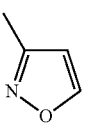 | |
| 1611 | 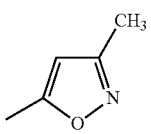 | |
| 1612 | 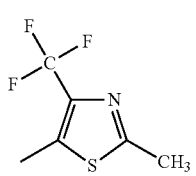 | |
| 1613 | 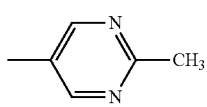 | |

-continued
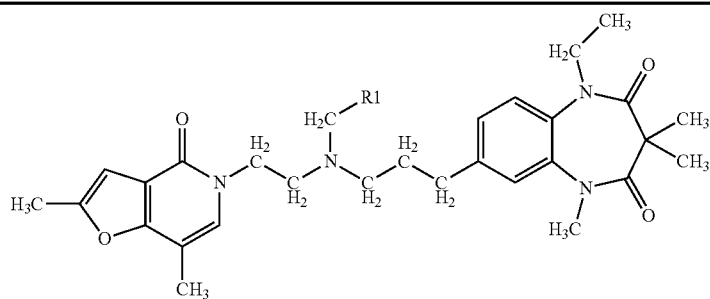
| Example No. | R1 | MS (M + 1) |
|---|---|---|
| 1614 | 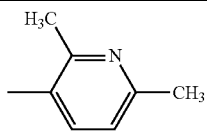 | |
Examples 1615 to 1625
The following compounds were obtained in the same manner as in Examples above using appropriate starting materials.
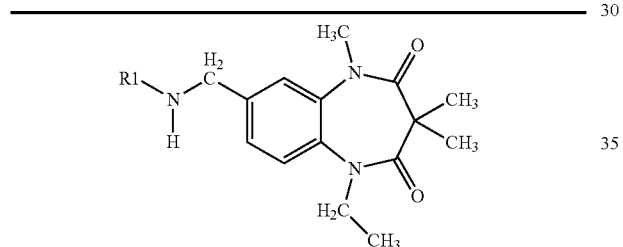
| Example No. | R1 | MS(M + 1) |
|---|---|---|
| 1615 | 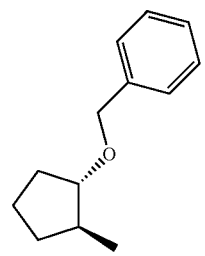 | 450 |
| 1616 | 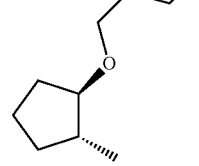 | 450 |
| 1617 | 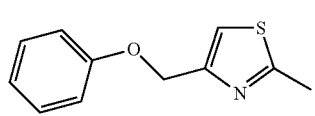 | 465 |
-continued
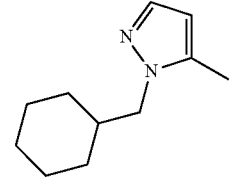
| Example No. | R1 | MS(M + 1) |
|---|---|---|
| 1618 | 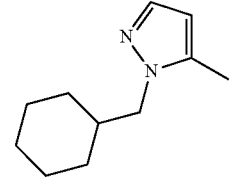 | 438 |
| 1619 | 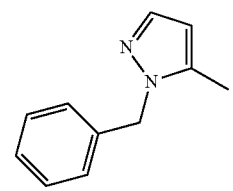 | 432 |
| 1620 | 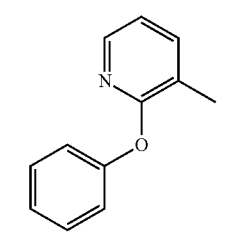 | 445 |

-continued

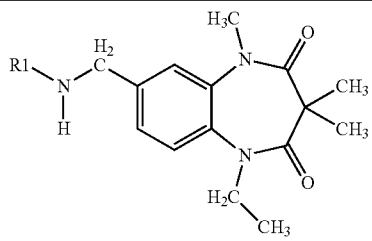

| Example No. | R1 | MS(M + 1) |
|---|---|---|
| 1621 | (N-methylpyrazolyl-CH2-phenyl) | 432 |
| 1622 | (methylpyrazinyl-O-CH2-phenyl) | 460 |
| 1623 | (methylpiperidinyl-C(O)-phenyl) | 463 |
| 1624 | (methylpyridinyl-O-CH2-phenyl) | 459 |
| 1625 | (methylpyrazolyl-CH2-phenyl) | 432 |

Pharmacological Test 1

(1) Production of Human Kv1.5-Expressing CHO-K1 Cell Lines

CHO-K1 cell lines stably expressing human Kv1.5 channels were prepared in the following manner.

Full-length human Kv1.5 cDNA was cloned from a human heart cDNA library (produced by Stratagene). The obtained human Kv1.5 sequence corresponds to the sequence described in FASEB J. 5, 331-337 (1991).

The obtained human Kv1.5 cDNA was inserted into a plasmid encoding a CMV promoter and a G418 resistance marker to produce a Kv1.5 expression vector. The human Kv1.5 expression vector was transfected into CHO-K1 cells by the lipofectamine method. After culturing the cells in an F-12 medium (produced by Invitrogen Corp.) containing 10% FBS (produced by Invitrogen Corp.) for 3 or 4 days, the medium was replaced with a FBS-containing F-12 medium that included 1,000 µg/ml of G418 (produced by Invitrogen Corp.), and single colonies were isolated. The amount of Kv1.5 channel expression in the single colonies was quantified at the mRNA level by RT-PCR and then quantified at the protein level by western blotting. Finally, the expressed current was analyzed by patch clamp method. Cell lines expressing a current of 200 pA or more per cell were selected as channel-expressing cell lines for activity measurement by patch clamp method.

(2) Production of CHO Cell Line Expressing Human GIRK1/4

CHO cell lines stably expressing human GIRK1/4 channels were prepared in the following manner.

Full-length human GIRK1 cDNA was cloned from HuH cell- and HeLa cell-derived cDNA libraries. Full-length GIRK4 cDNA was amplified from a human heart cDNA library (produced by Clontech Laboratories, Inc.) by PCR using synthetic primers shown in Table 1, and cloned into the Eco-RI restriction enzyme site of pCR-Blunt (produced by Invitrogen Corporation) or into the HincII site of pUC118 (produced by Takara Bio, Inc.).

TABLE 1

| Primer | Sequence | |
|---|---|---|
| hGIRK1-S | 5'-ATGTCTGCACTCCGAAGGAAATTTG-3' | SEQ ID No. 1 |
| hGIRK1-A | 5'-TTATGTGAAGCGATCAGAGTTC-3' | SEQ ID No. 2 |
| hGIRK1-F2 | 5'-GCAGGGTACCCCTTCGTATTATGTCTGCACTCC-3' | SEQ ID No. 3 |
| hGIRK1-A3 | 5'-GGTGTCTGCCGAGATTTGA-3' | SEQ ID No. 4 |
| hGIRK1-A4 | 5'-CCGAGTGTAGGCGATCACCC-3' | SEQ ID No. 5 |
| hGIRK4-S | 5'-ATGGCTGGCGATTCTAGGAATGCC-3' | SEQ ID No. 6 |
| hGIRK4-A | 5'-TCTCACCGAGCCCCTGGCCTCCC-3' | SEQ ID No. 7 |
| hGIRK4-S2 | 5'-AACCAGGACATGGAGATTGG-3' | SEQ ID No. 8 |
| hGIRK4-A2 | 5'-GAGAACAGGAAAGCGGACAC-3' | SEQ ID No. 9 |

The obtained human GIRK1 and GIRK4 cDNA sequences correspond to known sequences (NCBI database: GIRK1 (NM_002239) and GIRK4 (NM_000890) respectively). The obtained GIRK1 and GIRK4 cDNA sequences were cloned into the Eco-RI restriction enzyme site of pCR-Blunt (available from Invitrogen Corporation) or into the HincII site of pUC118 (available from Takara Bio, Inc.). A GIRK4 expression vector was constructed by insertion into the BamHI-XhoI site of pcDNA5/FRT. A GIRK1 expression vector was constructed by insertion into the KpnI-XhoI site of pcDNA3.1(+) or pCAG_neo. FLP-IN-CHO cells (produced by Invitrogen Corporation) were transfected with human GIRK1 and GIRK4 expression vectors by using Lipofectamine 2000 (produced by Invitrogen Corporation) according to the protocol enclosed with the reagent or using an electronic induction method ("Nucleofector Kit-T", produced by Amaxa). First, the cells transfected with the GIRK4 expression vector were cultured in a 10% serum-containing F12 medium (produced by Sigma) supplemented with 600 µg/ml of hygromycin in an incubator with 5% carbon dioxide at 37° C. Then the cells expressing GIRK4 were transfected with the GIRK1 expression vector and were cultured in 10% serum-containing F12 medium supplemented with 350 µg/ml of G418 and 600 µg/ml of hygromycin in an incubator with 5% carbon dioxide at 37° C. to select GIRK1/4 expressing cell lines. Cell populations whose growth was observed after about 2 weeks were isolated using cloning rings, and the obtained single colonies were proliferated. RNA was extracted from single colonies, and single-stranded cDNA was synthesized by a cDNA synthesis kit (produced by Invitrogen Corporation), and the amount of expression was quantified at the mRNA level by real-time PCR (Applied Biosystems, Ltd.). Finally, the expressed current was analyzed by patch clamp method described below. The cell lines expressing a current of 500 pA or more per cell were selected as channel-expressing cell lines for activity measurement by patch clamping method.

(3) Measurement of Ion Channel Current by Patch Clamp Method (Human Kv1.5-expressing CHO-K1 Cell Line)

An experiment was carried out using a patch clamp setup at room temperature (20 to 26° C.). A perfusion chamber having a diameter of 20 mm (flow rate: about 5 ml/min) was mounted on the stage of a phase-contrast inverted microscope (produced by Nikon Corporation) placed on a vibration isolated table. A poly-L-lysine (produced by Sigma)-coated coverslip (diameter: 15 mm, produced by Matsunami Glass Ind., Ltd.) on which human Kv1.5-expressing cells were cultured was placed in the perfusion chamber.

Depolarizing stimulation pulses were applied and ionic current was recorded by using a patch clamp amplifier (EPC-7 or EPC-7 PLUS, produced by HEKA) and a personal computer (manufactured by IBM Corp.) in which software for data acquisition and analysis of ion channel current (PULSE 8.77, produced by HEKA) was installed. The current was measured in the whole-cell configuration of the patch-clamp technique. The tip (resistance: 2 to 4 MΩ) of a borosilicate glass pipette (produced by Sutter Instrument Co.) was gently placed on the cell membrane by using a three-dimensional mechanical micromanipulator (produced by Shoshin EM Corporation). Weak suction resulted in giga seal formation (the pipette resistance increased to more than 1 GΩ). Subsequently, stronger suction was applied to break the cell membrane. The capacitative current derived from the cell membrane was corrected using a patch clamp amplifier. Subsequently, the series resistance (Rs) between the pipette and the interior of the cell was measured and corrected.

The composition of the extracellular solution used is shown below. Unless otherwise specified, these components were obtained from Wako Pure Chemical Industries, Ltd.

| NaCl | 140 mM, |
| KCl | 40 mM, |
| $CaCl_2$ | 1.8 mM, |
| $MgCl_2$ | 1 mM, |
| $NaH_2PO_4$ | 0.33 mM, |
| HEPES | 5 mM |
| Glucose | 5.5 mM |
| | (pH = 7.4) |

Each test compound was prepared as a 1000-fold concentrated stock solution that was dissolved in DMSO and then diluted in the extracellular solution.

The composition of the electrode internal solution used is shown below. Unless otherwise specified, these components were obtained from Wako Pure Chemical Industries, Ltd.

| KOH | 100 mM, |
| KCl | 40 mM, |
| Aspartic acid | 70 mM, |
| $MgCl_2$ | 1 mM, |
| MgATP | 5 mM, |
| $K_2$ creatine phosphate | 5 mM, |
| HEPES | 5 mM |
| EGTA | 5 mM |
| | (pH = 7.2) |

(4) Measurement of Ion Channel Current by Patch Clamp Method (Human GIRK1/4-expressing CHO-K1 Cell Line)

An experiment was carried out using a patch clamp setup at room temperature (20 to 26° C.). A perfusion chamber having a diameter of 20 mm (flow rate: about 5 ml/min) was mounted on the stage of a phase-contrast inverted microscope (produced by Nikon Corporation) placed on a vibration isolation table. A poly-L-lysine (produced by Sigma)-coated coverslip (diameter: 15 mm, produced by Matsunami Glass Ind., Ltd.) on which human GIRK1/4-expressing cells were cultured was placed in the perfusion chamber.

Hyperpolarizing stimulation pulses were applied and ionic current was recorded using a patch clamp amplifier (EPC-7 or EPC-7 PLUS, manufactured by HEKA) and a personal computer (manufactured by IBM Corp.) in which software for data acquisition and analysis of ion channel current (PULSE 8.77, manufactured by HEKA) was installed. The current was measured in the whole-cell configuration of the patch-clamp technique. The tip (resistance: 2 to 4 MΩ) of a borosilicate glass pipette (produced by Sutter Instrument Co.) was gently placed on the cell membrane by using a three-dimensional mechanical micromanipulator (produced by Shoshin EM Corporation). Weak suction resulted in giga seal formation (the pipette resistance increased to more than 1 GΩ). Subsequently, stronger suction was applied to break the cell membrane. The capacitative current derived from the cell membrane was corrected using a patch clamp amplifier. Subsequently, the series resistance (Rs) between the pipette and the interior of the cell was measured and corrected.

The composition of the extracellular solution used is shown below. Unless otherwise specified, these components were obtained from Wako Pure Chemical Industries, Ltd.

| NaCl | 140 mM, |
| KCl | 4 mM, |
| $CaCl_2$ | 1.8 mM, |
| $MgCl_2$ | 1 mM, |
| $NaH_2PO_4$ | 0.33 mM, |
| HEPES | 5 mM |
| Glucose | 5.5 mM |
| | (pH = 7.4) |

Each test compound was prepared as a 1000-fold concentrated stock solution that was dissolved in DMSO and then diluted in the extracellular solution.

The composition of the electrode internal solution used is shown below. Unless otherwise specified, these components were obtained from Wako Pure Chemical Industries, Ltd.

| | |
|---|---|
| KOH | 100 mM, |
| KCl | 40 mM, |
| Aspartic acid | 70 mM, |
| $MgCl_2$ | 1 mM, |
| MgATP | 5 mM, |
| $K_2$ creatine phosphate | 5 mM, |
| HEPES | 5 mM |
| EGTA | 5 mM |
| | (pH = 7.2) |

(5) Measurement of Human Kv1.5 Current

While the membrane potential was held at −80 mV, depolarizing pulses (−80 mV for 0.05 seconds→□□+40 mV for 0.2 seconds →□□−40 mV for 0.2 seconds→□□−80 mV for 0.05 seconds) were applied at a stimulation frequency of 1 Hz to measure Kv1.5 channel current. More specifically, first, while perfusing an extracellular solution containing 0.1% DMSO and holding the membrane potential at −80 mV, depolarizing pulses were applied. The current obtained during the pulse application was recorded as a current in the absence of the test compounds. Subsequently, while perfusing an extracellular solution containing 0.1 μM of a test compound and holding the membrane potential at −80 mV, depolarizing pulses were applied. After the inhibitory effect of the test compound had been stabilized, the current was recorded. The same procedure was repeated using an extracellular solution containing 1 μM of the test compound and then using an extracellular solution containing 10 μM of the test compound. The current obtained using the solution containing the test compound at each concentration was recorded.

The data was analyzed by using the step end current recorded during the +40 mV depolarizing stimulation. The "step end current" refers to the average current flowing for a period of 195 to 199 milliseconds from the start of the +40 mV depolarizing pulse stimulation.

Using the step end current in the presence of the test compound and the step end current in the absence of the test compound, the relative current in the solution containing the test compound at each concentration was calculated according to the following formula:

Relative current=(Step end current in the presence of the test compound)/(Step end current in the absence of the test compound)

(6) Measurement of Human GIRK1/4 Current

While the membrane potential was held at −80 mV, hyperpolarizing pulses (−80 mV for 0.05 seconds→□□−120 mV for 0.2 seconds→□□−80 mV for 0.05 seconds) were applied at a stimulation frequency of 1 Hz to measure GIRK1/4 channel current. More specifically, first, while perfusing an extracellular solution containing 0.1% DMSO and maintaining the membrane potential at −80 mV, hyperpolarizing pulses were applied. The current obtained during the pulse application was recorded as the current in the absence of the test compounds. Subsequently, while perfusing an extracellular solution containing 0.1 μM of a test compound and maintaining the membrane potential at −80 mV, hyperpolarizing pulses were applied. After the inhibitory effect of the test compound had been stabilized, the current was recorded. The same procedure was repeated using an extracellular solution containing 1 μM of the test compound and then using an extracellular solution containing 10 μM of the test compound. The current obtained using the solution containing the test compound at each concentration were recorded.

The data was analyzed by using the step end current recorded during the −120 mV depolarizing stimulation. The "step end current" refers to the average current flowing for a period of 195 to 199 milliseconds from the start of the −120 mV depolarizing pulse stimulation.

Using the step end current in the presence of the test compound and the step end current in the absence of the test compound, the relative current in the solution containing the test compound at each concentration was calculated according to the following formula:

Relative current=(Step end current in the presence of the test compound)/(Step end current in the absence of the test compound)

(7) Calculation of Inhibitory Activity on Kv1.5 Channel Ionic Current and GIRK1/4 Channel Current The concentration for 50% inhibition of Kv1.5 channel current or GIRK1/4 channel current ($IC_{50}$ value) was calculated according to the following nonlinear regression equation:

Relative current=1/(1+[Concentration of the compound]/$IC_{50}$)$^{nH}$ wherein nH is the Hill coefficient.

Table 2 shows the test results.

TABLE 2

| Test Compound | KV1.5 $IC_{50}$ (μM) |
|---|---|
| Compound of Example 10 | 0.62 |
| Compound of Example 15 | 0.81 |
| Compound of Example 16 | 0.51 |
| Compound of Example 18 | 0.60 |
| Compound of Example 35 | 0.94 |
| Compound of Example 41 | 6.30 |
| Compound of Example 42 | 1.70 |
| Compound of Example 43 | 0.32 |
| Compound of Example 48 | 0.30 |
| Compound of Example 104 | 1.4 |
| Compound of Example 317 | 0.63 |
| Compound of Example 318 | 2.9 |
| Compound of Example 330 | 0.86 |

2. Second Invention

REFERENCE EXAMPLE 1

Synthesis of 6-hydroxy-2H-isoquinolin-1-one

A 1.0M boron tribromide/dichloromethane solution(8.5 ml) was added at 0° C. to a dichloromethane solution (50 ml) of 6-methoxy-2H-isoquinolin-1-one(1.0 g). The mixture was stirred at room temperature overnight. Water and methanol were added to the reaction mixture and extraction was carried out with a dichloromethane/methanol mixed solvent (dichloromethane:methanol=10:1). The organic layer was dried with anhydrous sodium sulfate, followed by condensation to dryness under reduced pressure, thereby obtaining the title compound(0.4 g) as a pale yellow solid.

$^1$H NMR (DMSO-$d_6$), δ ppm: 6.37 (1H, d, J=7.1 Hz), 6.86-6.94 (2H, m), 7.03-7.08 (1H, m), 8.02 (1H, d, J=8.7 Hz), 10.22 (1H, br), 10.90 (1H, s).

REFERENCE EXAMPLE 2

Synthesis of 6-hydroxy-1,3-dimethyl-3,4-dihydro-1H-quinazolin-2-one

The synthesis of the title compound was performed in the same manner as in Reference Example 1 using appropriate starting materials.

¹H-NMR (DMSO-d₆), δ ppm: 2.87 (3H, s), 3.13 (3H, s), 4.26 (2H, s), 6.57 (1H, d, J=2.7 Hz), 6.65 (1H, dd, J=2.7, 8.7 Hz), 6.73 (1H, d, J=8.7 Hz), 9.13 (1H, s).

REFERENCE EXAMPLE 3

Synthesis of 6-hydroxy-1,3-dimethyl-1H-quinazoline-2,4-dione

The synthesis of the title compound was performed in the same manner as in Reference Example 1 using appropriate starting materials.
¹H-NMR (DMSO-d₆), δ ppm: 3.29 (3H, s), 3.48 (3H, s), 7.20 (1H, dd, J=2.8, 9.0 Hz), 7.31 (1H, d, J=9.0 Hz), 7.40 (1H, d, J=2.8 Hz), 9.76 (1H, s).

REFERENCE EXAMPLE 4

Synthesis of 6-hydroxy-2-methyl-2H-isoquinolin-1-one

The synthesis of the title compound was performed in the same manner as in Reference Example 1 using appropriate starting materials.
¹H-NMR (DMSO-d₆), δ ppm: 3.44 (3H, s), 6.43 (1H, d, J=7.4 Hz), 6.86 (1H, d, J=2.2 Hz), 6.93 (1H, dd, J=8.7, 2.2 Hz), 7.35 (1H, d, J=7.4 Hz), 8.04 (1H, d, J=8.7 Hz).

REFERENCE EXAMPLE 5

Synthesis of 6-hydroxy-2-methyl-3,4-dihydro-2H-isoquinolin-1-one

The synthesis of the title compound was performed in the same manner as in Reference Example 1 using appropriate starting materials.
¹H-NMR (CDCl₃), δ ppm: 2.95 (2H, t, J=6.7 Hz), 3.13 (3H, s), 3.57 (2H, t, J=6.7 Hz), 6.62 (1H, d, J=2.4 Hz), 6.76 (1H, dd, J=8.6, 2.4 Hz), 7.83 (1H, d, J=8.6 Hz).

REFERENCE EXAMPLE 6

Synthesis of 2-methyl-1,1-dioxo-2,3-dihydro-1H-benzo[d]isothiazol-5-ol

The synthesis of the title compound was performed in the same manner as in Reference Example 1 using appropriate starting materials.
¹H-NMR (CDCl₃), δ ppm: 2.92 (3H, s), 4.24 (2H, s), 6.75 (1H, s), 6.92 (1H, d, J=8.5 Hz), 7.60 (1H, d, J=8.5 Hz).

Reference Example 7

Synthesis of 3-hydroxy-7,8-dihydro-6H-5-thia-8-azabenzocyclohepten-9-one

The synthesis of the title compound was performed in the same manner as in Reference Example 1 using appropriate starting materials.
¹H-NMR (CD₃OD), δ ppm: 3.15 (2H, t, J=6.0 Hz), 3.21-3.40 (2H, m), 6.84 (1H, dd, J=8.4, 2.4 Hz), 6.96 (1H, d, J=2.4 Hz), 7.46 (1H, d, J=8.4 Hz).

REFERENCE EXAMPLE 8

Synthesis of 3-hydroxy-1-methyl-1H-quinolin-2-one

The synthesis of the title compound was performed in the same manner as in Reference Example 1 using appropriate starting materials.
¹H-NMR (DMSO-d₆), δ ppm: 3.70 (3H, s), 7.12 (1H, s), 7.17-7.28 (1H, m), 7.35-7.50 (2H, m), 7.56 (1H, d-d, J=1.3, 7.5 Hz), 9.46 (1H, br-s).

REFERENCE EXAMPLE 9

Synthesis of 7-(3-iodopropoxy)-1-methyl-1H-quinolin-2-one 7-(3-Chloropropoxy)-1-methyl-1H-quinolin-2-one(2.5 g) and sodium iodide(3.0 g) were added to 30 ml of acetonitrile. The mixture was stirred for 18 hours while heated under reflux. After cooled to room temperature, water was added to the reaction mixture, followed by extraction using dichloromethane. The organic layer was dried with sodium sulfate and was condensed under reduced pressure to give the title compound(2.4 g) as a pale brown powder.
¹H-NMR (CDCl₃), δ ppm: 2.29-2.37 (2H, m), 3.41 (2H, t, J=6.6 Hz), 3.69 (3H, s), 4.17 (2H, t, J=5.8 Hz), 6.56 (1H, d, J=9.4 Hz), 6.81-6.84 (2H, m), 7.45-7.58 (1H, m), 7.60 (1H, d, J=9.4 Hz).

REFERENCE EXAMPLE 10

Synthesis of 6-(5-bromopentyloxy)-1-methyl-1H-quinolin-2-one

Sodium hydride (60% in oil, 440 mg) was suspended in DMF(20 ml), and was cooled to 0° C. in ice water bath. 6-(5-Bromopentyloxy)-1H-quinolin-2-one(3.1 g) was added thereto at the same temperature, and the mixture was stirred at 0° C. for an hour. Methyl iodide(1.9 ml) was added thereto, and the mixture was stirred at room temperature overnight. Water was added to the reaction mixture, followed by extraction using ethyl acetate. The organic layer was dried with sodium sulfate, and was condensed under reduced pressure. The residue was purified by silica gel column chromatography (hexane: ethyl acetate=4:1→1:1). The purified product was condensed to dryness under reduced pressure to give the title compound(2.68 g) as a yellow powder.
¹H-NMR (CDCl₃), δ ppm: 1.53-1.70 (2H, m), 1.81-1.97 (4H, m), 3.45 (2H, t, J=6.7 Hz), 3.71 (3H, s), 4.00-4.04 (2H, m), 6.71 (1H, d, J=9.5 Hz), 7.00 (1H, d, J=3.0 Hz), 7.16-7.20 (1H, m), 7.27-7.31 (1H, m), 7.59 (1H, d, J=9.5 Hz).

REFERENCE EXAMPLE 11

Synthesis of 6-(8-bromooctyloxy)-2-methoxyquinoline

Sodium hydride (60% in oil, 40 mg) was suspended in DMF(2 ml), and was cooled to 0° C. in ice water bath. 6-Hydroxy-2-methoxyquinoline(171 mg) was added thereto at the same temperature, and the mixture was stirred at 0° C. for an hour. 1,8-Dibromooctane(0.37 ml) was added thereto, and the mixture was stirred at room temperature overnight. Water was added to the reaction mixture, followed by extraction using ethyl acetate. The organic layer was dried with sodium sulfate, and was condensed under reduced pressure. The residue was purified by silica gel column chromatography (hexane: ethyl acetate=10:1). The purified product was condensed to dryness under reduced pressure to give the title compound (225 mg) as a white powder.
¹H-NMR (CDCl₃), δ ppm: 1.37-1.51 (8H, m), 1.81-1.89 (4H, m), 3.41 (2H, t, J=6.8 Hz), 4.04 (3H, s), 4.04 (2H, t, J=6.5

Hz), 6.87 (1H, d, J=8.8 Hz), 7.03 (1H, d, J=2.8 Hz), 7.27 (1H, dd, J=9.1, 2.8 Hz), 7.75 (1H, d, J=9.1 Hz), 7.87 (1H, d J=8.8 Hz).

REFERENCE EXAMPLE 12

Synthesis of
6-(5-bromopentyloxy)-2-methoxyquinoline

The synthesis of the title compound was performed in the same manner as in Reference Example 11 using appropriate starting materials.

$^1$H-NMR (CDCl$_3$), δ ppm: 1.61-1.66 (2H, m), 1.821-1.96 (4H, m), 3.45 (2H, t, J=6.7 Hz), 3.47 (3H, s), 4.00-4.04 (2H, m), 6.70 (1H, d, J=9.5 Hz), 6.99 (1H, d, J=2.8 Hz), 7.17 (1H, dd, J=9.2, 2.8 Hz), 7.29 (1H, d J=9.2 Hz), 7.59 (1H, d, J=9.5 Hz).

REFERENCE EXAMPLE 13

Synthesis of
5-(3-iodopropoxy)-1-methyl-1H-quinolin-2-one

The synthesis of the title compound was performed in the same manner as in Reference Example 9 using appropriate starting materials.

$^1$H-NMR (CDCl$_3$), δ ppm: 2.30-2.44 (2H, m), 3.42 (2H, t, J=6.7 Hz), 3.71 (3H, s), 4.19 (2H, t, J=5.8 Hz), 6.66 (1H, d, J=9.7 Hz), 6.70 (1H, d, J=8.1 Hz), 6.97 (1H, d, J=8.6 Hz), 7.48 (1H, dd, J=8.6, 8.1 Hz), 8.11 (1H, d, J=9.7 Hz).

REFERENCE EXAMPLE 14

Synthesis of
8-(3-iodopropoxy)-1-methyl-1H-quinolin-2-one

The synthesis of the title compound was performed in the same manner as in Reference Example 9 using appropriate starting materials.

$^1$H-NMR (CDCl$_3$), δ ppm: 2.32-2.40 (2H, m), 3.39 (2H, t, J=6.6 Hz), 3.96 (3H, s), 4.15 (2H, t, J=5.9 Hz), 6.70 (1H, d, J=9.4 Hz), 7.08-7.17 (3H, m), 7.60 (1H, d, J=9.4 Hz).

REFERENCE EXAMPLE 15

Synthesis of
(2-pyridin-3-yl-ethyl)-pyridin-4-ylmethyl-amine

4-Pyridine carbaldehyde(5.36 g) and 3-(2-aminoethyl)pyridine (6.5 ml) were added to 100 ml of methanol. The mixture was stirred at room temperature for 7 hours. The mixture was cooled to 0° C., and sodium borohydride(2.8 g) was added thereto. The mixture was further stirred at 0° C. for an hour. Water was added to the reaction mixture and methanol was distilled off under reduced pressure. The residue was subjected to extraction using dichloromethane. The organic layer was washed with saturated saline, dried with anhydrous sodium sulfate, and was condensed under reduced pressure. The residue was purified by basic silica gel column chromatography (ethyl acetate: methanol=95:5→85:5). The purified product was condensed under reduced pressure to give the title compound(10.03 g) as a colorless oily matter.

$^1$H-NMR (CDCl$_3$), δ ppm: 2.79-2.98 (4H, m), 3.82 (2H, s), 7.21 (2H, d, J=5.8 Hz), 7.20-7.27 (1H, m), 7.50-7.56 (1H, m), 8.48 (1H, dd, J=6.7, 1.6 Hz), 8.49 (1H, s), 8.51-8.57 (2H, m).

REFERENCE EXAMPLE 16

Synthesis of (2-pyridin-3-yl-ethyl)-pyridin-4-ylmethyl-[3-(tetrahydro-pyran-2-yloxy)-propyl]-amine Sodium iodide(1.5 g) was added to a DMF solution (20 ml) of 2-(3-bromopropoxy)tetrahydropyran(0.85 ml). The mixture was stirred at 70° C. for 7 hours. The reaction mixture was cooled to room temperature. (2-Pyridin-3-yl-ethyl)-pyridin-4-ylmethyl-amine (1.28 g), and N-ethyldiisopropylamine(1.3 ml) were added thereto. The mixture was stirred at room temperature overnight. Water was added to the reaction mixture, followed by extraction using ethyl acetate. The organic layer was washed with water and then saturated saline, and dried with anhydrous sodium sulfate. After condensation under reduced pressure, the residue was purified by silica gel column chromatography (ethyl acetate: methanol=20:1→4:1). The purified product was condensed under reduced pressure to give the title compound(236 mg) as a colorless oily matter.

$^1$H-NMR (CDCl$_3$), δ ppm: 1.40-1.90 (7H, m), 2.51-2.83 (6H, m), 3.29-3.44 (1H, m), 3.44-3.54 (2H, m), 3.54-3.70 (2H, m), 3.69-3.90 (2H, m), 4.47-4.57 (1H, m), 7.12-7.23 (3H, m), 7.37-7.48 (1H, m), 8.38-8.53 (4H, m).

REFERENCE EXAMPLE 17

Synthesis of 3-[(2-pyridin-3-ylethyl)pyridin-4-ylmethylamino]propan-1-ol

A 2N-hydrogen chloride methanol solution(1.2 ml) was added to a methanol solution (4 ml) of (2-pyridin-3-ylethyl)pyridin-4-ylmethyl-[3-(tetrahydropyran-2-yloxy)propyl]amine(236 mg). The mixture was stirred at room temperature overnight. A 2N-hydrogen chloride methanol solution(0.5 ml) was added thereto, and the mixture was further stirred at 50° C. for 3 hours. Triethylamine(0.64 ml) was added to the reaction mixture, and the mixture was condensed under reduced pressure. The residue was purified by basic silica gel column chromatography (dichloromethane). The purified product was condensed under reduced pressure to give the title compound(186.3 mg) as an orange oily matter.

$^1$H NMR (CDCl$_3$), δ ppm: 1.66-1.88 (2H, m), 2.59-2.77 (4H, m), 2.77-2.88 (2H, m), 3.65 (2H, s), 3.68-3.84 (3H, m), 7.11-7.25 (3H, m), 7.42 (1H, d, J=7.8 Hz), 8.42 (1H, s), 8.43-8.47 (1H, m), 8.50-8.60 (2H, m).

REFERENCE EXAMPLE 18

Synthesis of (3-chloropropyl)-(2-pyridin-3-ylethyl)pyridin-4-ylmethylamine (2-Pyridin-3-yl-ethyl)-pyridin-4-ylmethyl-amine(210 mg) and N-ethyldiisopropylamine(0.34 ml) were added to a DMF solution (2 ml) of 1-chloro-3-iodopropane(0.16 ml). The mixture was stirred at room temperature overnight. Water was added to the reaction mixture, followed by extraction using ethyl acetate. The organic layer was washed with water and then saturated saline, and dried with anhydrous sodium sulfate. After condensation under reduced pressure, the residue was purified by silica gel column chromatography (ethyl acetate: methanol=20:1→4:1). The purified product was condensed under reduced pressure to give the title compound(74 mg) as a colorless oily matter.

¹H-NMR (CDCl₃), δ ppm: 1.82-1.99 (2H, m), 2.61-2.82 (6H, m), 3.52 (2H, t, J=6.3 Hz), 3.61 (2H, s), 7.14 (2H, d, J=5.9 Hz), 7.19 (1H, dd, J=7.7, 4.8 Hz), 7.36-7.49 (1H, m), 8.38-8.56 (4H, m).

REFERENCE EXAMPLE 19

Synthesis of 2-nitro-N-(2-pyridin-3-ylethyl)benzenesulfonamide

2-Nitrobenzene sulfonyl chloride(11.64 g) was added to a dichloromethane solution (100 ml) of 3-(2-aminoethyl)pyridine(6.11 g) and triethylamine(9 ml) at 0° C. The mixture was stirred at room temperature for 2 hours. Water was added to the reaction mixture, followed by extraction with dichloromethane. The organic layer was dried with anhydrous sodium sulfate, and condensed under reduced pressure. The residue was crystallized from ethyl acetate to give the title compound(5.06 g) as a yellow powder.

¹H NMR (DMSO-d₆), δ ppm: 2.76 (2H, t, J=7.1 Hz), 3.19 (2H, t, J=7.1 Hz), 7.26 (1H, dd, J=4.8 Hz, 7.8 Hz), 7.60 (1H, d, J=7.8 Hz), 7.8-8.0 (4H, m), 8.19 (1H, brs), 8.3-8.4 (2H, m).

REFERENCE EXAMPLE 20

Synthesis of (2-methylbenzyl)-(2-pyridin-3-ylethyl)amine

The synthesis of the title compound was performed in the same manner as in Reference Example 15 using appropriate starting materials.

¹H NMR (CDCl₃), δ ppm: 0.95-1.95 (1H, br-s), 2.30 (3H, s), 2.77-2.88 (2H, m), 2.91-3.02 (2H, m), 3.78 (2H, s), 7.06-7.30 (5H, m), 7.53 (1H, br-d, J=7.5 Hz), 8.41-8.53 (2H, m).

REFERENCE EXAMPLE 21

Synthesis of 6-(3-chloropropoxy)-1-methyl-1H-quinolin-2-one

Potassium carbonate (0.829 g) was dissolved in acetonitrile(10 ml) and water(10 ml), and 6-hydroxy-2-methoxyquinoline(0.875 g) and 1-chloro-3-bromopropane(1.48 ml) was added thereto, and the mixture was stirred while heating under reflux for 4 hours. The reaction mixture was condensed under reduced pressure. Water was added to the residue, followed by extraction using ethyl acetate. The organic layer was dried with sodium sulfate, and was condensed under reduced pressure. The residue was purified by silica gel column chromatography (hexane: ethyl acetate=1:1). The purified product was condensed to dryness under reduced pressure to give the title compound(1.107 g) as a white powder.

1H-NMR (CDCl3) δ ppm: 2.18-2.35 (2H, m), 3.71 (3H, s), 3.78 (2H, t, J=6.2 Hz), 4.18 (2H, t, J=5.9 Hz), 6.72 (1H, d, J=9.5 Hz), 7.03 (1H, d, J=2.8 Hz), 7.19 (1H, dd, J=9.2, 2.8 Hz), 7.30 (1H, d, J=9.2 Hz), 7.60 (1H, d, J=9.5 Hz).

REFERENCE EXAMPLE 22

Synthesis of 6-(3-aminopropoxy)-1-methyl-1H-quinolin-2-one

Hydrazine hydrate (6.54 ml) was added to a ethanol solution (250 ml) of 2-[3-(1-methyl-2-oxo-1,2-dihydroquinolin-6-yloxy)propyl]isoindole-1,3-dione (16.28 g), and stirred while heating under reflux for 2 hours. The reaction mixture was concentrated under reduced pressure. A 1N-sodium hydroxide aqueous solution was added to the residue, and stirred for 30 minutes, and extraction with dichloromethane was performed. The organic layer was washed with water and a saturated sodium chloride aqueous solution, in this order. The organic layer was dried over anhydrous magnesium sulfate, and concentrated under reduced pressure to give the title compound(8.04 g) as a colorless oil.

1H-NMR (CDCl3) δ ppm: 1.89-2.06 (2H, m), 2.95 (2H, t, J=6.8 Hz), 3.71 (3H, s), 4.11 (2H, t, J=6.1 Hz), 6.72 (1H, d, J=9.5 Hz), 7.02 (1H, d, J=2.8 Hz), 7.19 (1H, dd, J=9.2, 2.8 Hz), 7.30 (1H, d, J=9.2 Hz), 7.60 (1H, d, J=9.5 Hz).

REFERENCE EXAMPLE 23

Synthesis of 6-(2-iodoethoxy)-1-methyl-1H-quinolin-2-one

The synthesis of the title compound was performed in the same manner as in Reference Example 9 using appropriate starting materials.

1H-NMR (CDCl3) δ ppm: 3.45 (2H, t, J=6.6 Hz), 3.71 (3H, s), 4.31 (2H, t, J=6.6 Hz), 6.73 (1H, d, J=9.5 Hz), 7.02 (1H, d, J=2.8 Hz), 7.21 (1H, dd, J=9.2, 2.8 Hz), 7.31 (1H, d, J=9.2 Hz), 7.60 (1H, d, J=9.5 Hz).

REFERENCE EXAMPLE 24

Synthesis of 6-(2-aminoethoxy)-1-methyl-1H-quinolin-2-one

The synthesis of the title compound was performed in the same manner as in Reference Example 22 using appropriate starting materials.

1H-NMR (CDCl3) δ ppm: 3.13 (2H, t, J=5.1 Hz), 3.71 (3H, s), 4.05 (2H, t, J=5.1 Hz), 6.72 (1H, d, J=9.5 Hz), 7.02 (1H, d, J=2.8 Hz), 7.21 (1H, dd, J=9.2, 2.8 Hz), 7.31 (1H, d, J=9.2 Hz), 7.60 (1H, d, J=9.5 Hz).

REFERENCE EXAMPLE 25

Synthesis of 2-nitro-N-{2-[4-(pyridin-3-ylmethoxy)piperidin-1-yl]ethyl}benzene sulfonamide The synthesis of the title compound was performed in the same manner as in Reference Example 19 using appropriate starting materials.

1H-NMR (CDCl3) δ ppm: 1.42-1.99 (4H, m), 2.13-2.35 (2H, m), 2.43-2.69 (4H, m), 3.21 (2H, t, J=6.0 Hz), 3.39-3.54 (1H, m), 4.52 (2H, s), 7.28 (1H, dd, J=7.9, 4.8 Hz), 7.63-7.70 (1H, m), 7.70-7.79 (2H, m), 7.83-7.89 (1H, m), 8.91-8.98 (1H, m), 8.53 (1H, dd, J=4.8, 1.6 Hz), 8.56 (1H, d, J=1.6 Hz).

REFERENCE EXAMPLE 26

Synthesis of 6-(4-aminobutoxy)-1-methyl-1H-quinolin-2-one

The synthesis of the title compound was performed in the same manner as in Reference Example 22 using appropriate starting materials.

1H-NMR (CDCl3) δ ppm: 1.58-1.72 (2H, m), 1.81-1.98 (2H, m), 2.80 (2H, t, J=6.9 Hz), 3.71 (3H, s), 4.03 (2H, t, J=6.3 Hz), 6.71 (1H, d, J=9.5 Hz), 7.00 (1H, d, J=2.8 Hz), 7.18 (1H, dd, J=9.2, 2.8 Hz), 7.29 (1H, d, J=9.2 Hz), 7.59 (1H, d, J=9.5 Hz).

REFERENCE EXAMPLE 27

Synthesis of 6-(3-iodopropoxy)-1-methyl-3,4-dihydro-1H-quinolin-2-one

The synthesis of the title compound was performed in the same manner as in Reference Example 9 using appropriate starting materials.

1H-NMR (CDCl3) δ ppm: 2.16-2.32 (2H, m), 2.56-2.70 (2H, m), 2.87 (2H, t, J=6.7 Hz), 3.33 (3H, s), 3.31-3.45 (2H, m), 4.02 (2H, t, J=5.8 Hz), 6.75 (1H, d, J=2.8 Hz), 6.78 (1H, dd, J=8.7, 2.8 Hz), 6.89 (1H, d, J=8.7 Hz).

REFERENCE EXAMPLE 28

Synthesis of N-(3-imidazol-1-yl-propyl)-2-nitrobenzenesulfonamide

The synthesis of the title compound was performed in the same manner as in Reference Example 19 using appropriate starting materials.

1H-NMR (CDCl3) δ ppm: 1.71-1.95 (2H, m), 2.85 (2H, t, J=6.8 Hz), 3.97 (2H, t, J=6.9 Hz), 6.86 (1H, s), 7.10 (1H, s), 7.55 (1H, s), 7.83-7.92 (2H, m), 7.92-8.02 (2H, m), 8.16 (1H, s).

REFERENCE EXAMPLE 30

Synthesis of N-(3-Chloropropyl)-N-(2-methylbenzyl)-N-(2-pyridin-3-ylethyl)amine

The synthesis of the title compound was performed in the same manner as in Reference Example 18 using appropriate starting materials.

1H-NMR (CDCl3) δ ppm: 1.78-1.95 (2H, m), 2.26 (3H, s), 2.60-2.79 (6H, m), 3.50 (2H, t, J=6.5 Hz), 3.58 (2H, s), 7.08-7.24 (5H, m), 7.33-7.39 (1H, m), 8.36 (1H, d, J=1.7 Hz), 8.41 (1H, dd, J=4.8, 1.7 Hz).

REFERENCE EXAMPLE 31

Synthesis of 6-(3-iodopropoxy)-3,4-dihydro-2H-isoquinolin-1-one

The synthesis of the title compound was performed in the same manner as in Reference Example 9 using appropriate starting materials.

1H-NMR (CDCl3) δ ppm: 2.19-2.35 (2H, m), 2.97 (2H, t, J=6.6 Hz), 3.37 (2H, t, J=6.7 Hz), 3.50-3.62 (2H, m), 4.09 (2H, t, J=5.8 Hz), 5.98 (1H, s), 6.71 (1H, d, J=2.4 Hz), 6.86 (1H, dd, J=8.6, 2.4 Hz), 8.01 (1H, d, J=8.6 Hz).

REFERENCE EXAMPLE 32

Synthesis of 2-hydroxy-7,8-dihydro-6H-5-thia-8-aza-benzocyclohepten-9-one

The synthesis of the title compound was performed in the same manner as in Reference Example 1 using appropriate starting materials.

1H-NMR (CD3OD) δ ppm: 3.06 (2H, t, J=6.0 Hz), 3.26 (2H, t, J=6.0 Hz), 6.85 (1H, dd, J=8.3, 2.8 Hz), 7.01 (1H, d, J=2.8 Hz), 7.34 (1H, d, J=8.3 Hz).

EXAMPLE 1

Synthesis of 1-methyl-6-{5-[(2-methylbenzyl)-(2-pyridin-3-ylethyl)amino]pentyloxy}-1H-quinolin-2-one dihydrochloride Potassium carbonate(360 mg) and (2-methylbenzyl)-(2-pyridin-3-ylethyl)amine(591 mg) were added to a DMF solution (6.5 ml) of 6-(5-bromopentyloxy)-1-methyl-1H-quinolin-2-one(650 mg). The mixture was stirred at 60° C. for 8 hours. Ice water was added to the reaction mixture, followed by extraction using ethyl acetate. The organic layer was washed with water and then saturated saline, dried with anhydrous sodium sulfate, and condensed under reduced pressure. The residue was purified by silica gel column chromatography (dichloromethane: ethyl acetate: methanol: aqueous ammonia=70:20:10:1). The purified product was condensed under reduced pressure. A 4N-hydrogen chloride ethyl acetate solution(1.0 ml) was added to an ethyl acetate solution (20 ml) of the residue, which was stirred at room temperature. The liquid was condensed to dryness under reduced pressure to give the title compound(270 mg) as a pale yellow amorphous solid.

$^1$H-NMR (DMSO-$d_6$) δ ppm: 1.32-1.50 (2H, m), 1.65-1.99 (4H, m), 2.47 (3H, s), 2.92-3.21 (2H, m), 3.21-3.50 (4H, m), 3.59 (3H, s), 3.88-4.09 (2H, m), 4.30-4.52 (2H, m), 6.61 (1H, d, J=9.4 Hz), 7.05-7.35 (5H, m), 7.46 (1H, d, J=9.2 Hz), 7.73 (1H, d, J=7.2 Hz), 7.84 (1H, d, J=9.6 Hz), 7.89-8.01 (1H, m), 8.40 (1H, br-d, J=7.8 Hz), 8.79 (1H, d, J=4.9 Hz), 8.89 (1H, s).

EXAMPLE 2

Synthesis of N-[5-(1-methyl-2-oxo-1,2-dihydroquinolin-6-yloxy)pentyl]-2-nitro-N-(2-pyridin-3-ylethyl)benzenesulfonamide 2-Nitro-N-(2-pyridin-3-ylethyl)benzenesulfonamide(308 mg), and potassium carbonate(276 mg) were added to a DMF solution(5 ml) of 6-(5-bromopentyloxy)-1-methyl-1H-quinolin-2-one(348 mg). The mixture was stirred at room temperature for 2 hours. Ice water was poured to the reaction mixture, followed by extraction using ethyl acetate. The organic layer was washed with water, dried with anhydrous sodium sulfate, and condensed under reduced pressure. The residue was purified by silica gel column chromatography (ethyl acetate→ethyl acetate: methanol=10:1). The purified product was condensed to dryness under reduced pressure to give 5 the title compound(535 mg) as a yellow amorphous solid.

$^1$H-NMR (CDCl$_3$) δ ppm: 1.4-1.9 (6H, m), 2.88 (2H, t, J=7.5 Hz), 3.40 (2H, t, J=7.5 Hz), 3.52 (2H, t, J=7.7 Hz), 3.71 (3H, s), 3.98 (2H, t, J=6.3 Hz), 6.71 (1H, d, J=9.5 Hz), 6.98 (1H, d, J=2.8 Hz), 7.1-7.3 (2H, m), 7.29 (1H, d, J=9.2 Hz), 7.4-7.7 (5H, m), 7.9-8.1 (1H, m), 8.40 (1H, d, J=1.8 Hz), 8.45 (1H, dd, J=1.8 Hz, 4.8 Hz).

EXAMPLE 3

Synthesis of 1-methyl-6-[5-(2-pyridin-3-ylethylamino)pentyloxy]-1H-quinolin-2-one dihydrochloride Lithium hydroxide(102 mg), and thioglycolic acid(0.141 ml) were added to a DMF solution(5 ml) of N-[5-(1-methyl- 2-oxo-1,2-dihydroquinolin-6-yloxy)pentyl]-2-nitro-N-(2-pyridin-3-ylethyl)benzenesulfonamide(535 mg). The mixture was stirred at room temperature overnight. Ice water was poured to the reaction mixture, followed by extraction using ethyl acetate. The organic layer was washed with water, dried with anhydrous sodium sulfate, and condensed under reduced pressure. A 1N-hydrogen chloride ethanol solution(1.0 ml), and ethyl acetate were added to the residue. The mixture was stirred at room temperature. The precipitated insoluble matter was separated, washed with ethyl acetate, and dried to give the title compound(108 mg) as a white powder.

$^1$H-NMR (DMSO-$d_6$) δ ppm: 1.4-1.6 (2H, m), 1.6-1.8 (4H, m), 2.8-3.0 (2H, m), 3.2-3.4 (4H, m), 3.60 (3H, s), 4.04 (2H, t, J=6.1 Hz), 4.0-4.8 (1H, br), 6.61 (1H, d, J=9.5 Hz), 7.25 (1H, dd, J=2.8 Hz, 9.2 Hz), 7.31 (1H, d, J=2.8 Hz), 7.46 (1H, d, J=9.2 Hz), 7.85 (1H, d, J=9.5 Hz), 8.05 (1H, dd, J=5.6 Hz, 8.1 Hz), 8.57 (1H, d, J=8.1 Hz), 8.84 (1H, d, J=5.6 Hz), 8.94 (1H, s), 9.36 (1H, brs).

EXAMPLE 4

Synthesis of 1-methyl-6-[5-((2-methylbenzyl)-{2-[4-(pyridin-3-ylmethoxy)piperidin-1-yl]ethyl}amino)pentyloxy]-1H-quinolin-2-one trihydrochloride Methane sulfonyl chloride(0.59 ml) was added to a dichloromethane solution(30 ml) of 6-{5-[(2-hydroxyethyl)-(2-methylbenzyl)amino]pentyloxy}-1-methyl-1H-quinolin-2-one (2.83 g) and N-ethyldiisopropylamine(1.81 ml). The mixture was stirred at room temperature for an hour. Water was added to the reaction mixture, followed by extraction using dichloromethane. The organic layer was dried with anhydrous sodium sulfate, and condensed under reduced pressure. The residue was dissolved in acetonitrile(50 ml). Sodium iodide (1.56 g), 3-(piperidin-4-yloxymethyl)pyridine(1.46 g) and N-ethyldiisopropylamine(3.61 ml) were added thereto, and the mixture was stirred at 60° C. for 3 hours. The reaction mixture was condensed under reduced pressure. Water was added to the residue, followed by extraction using dichloromethane. The organic layer was washed with water and then saturated saline, dried with anhydrous sodium sulfate, and condensed under reduced pressure. The residue was purified by silica gel column chromatography (dichloromethane: ethyl acetate: methanol: aqueous ammonia=70:20:10:1). The purified product was condensed under reduced pressure. A 1N-hydrogen chloride ethanol solution(0.41 ml) was added to an isopropyl alcohol solution of the residue. The mixture was stirred at room temperature. The liquid was condensed to dryness under reduced pressure to give the title compound (2.41 g) as a white amorphous solid.

$^1$H-NMR (DMSO-$d_6$) δ ppm: 1.4-1.6 (2H, m), 1.7-2.3 (8H, m), 2.46 (3H, s), 3.0-3.9 (11H, m), 3.60 (3H, s), 4.02 (2H, t, J=6.2 Hz), 4.46 (2H, s), 4.75 (2H, s), 6.62 (1H, d, J=9.5 Hz), 7.2-7.4 (5H, m), 7.47 (1H, d, J=9.2 Hz), 7.73 (1H, d, J=7.5 Hz), 7.86 (1H, d, J=9.5 Hz), 8.04 (1H, dd, J=5.7 Hz, 8.0 Hz), 8.5-8.6 (1H, br), 8.85 (1H, d, J=5.7 Hz), 8.94 (1H, brs), 10.2-11.8 (2H, br).

EXAMPLE 5

Synthesis of 6-{5-[cyclohexylmethyl-(2-pyridin-3-ylethyl)amino]pentyloxy}-1-methyl-1H-quinolin-2-one dihydrochloride Triethylamine(0.15 ml) was added to a 1,2-dichloroethane solution (2.5 ml) of 1-methyl-6-[5-(2-pyridin-3-ylethylamino)pentyloxy]-1H-quinolin-2-one dihydrochloride(219 mg). The mixture was stirred at room temperature for 30 minutes. Cyclohexane carboxaldehyde(0.073 ml) and sodium triacetoxyborohydrate(159 mg) were added thereto, and the mixture was stirred at room temperature overnight. A saturated sodium hydrogencarbonate aqueous solution was added to the reaction mixture, followed by extraction using dichloromethane. The organic layer was dried with anhydrous sodium sulfate, and condensed under reduced pressure. The residue was purified by NH silica gel column chromatography (hexane: ethyl acetate=1:1). The purified product was condensed under reduced pressure. A 1N-hydrogen chloride ethanol solution(1.0 ml) was added to an ethanol solution (20 ml) of the residue, which was stirred at room temperature. The reaction mixture was condensed under reduced pressure and ethyl acetate was added to the residue. The precipitated insoluble matter was separated, washed with ethyl acetate, and dried to give the title compound(100 mg) as a pale yellow powder.

$^1$H-NMR (DMSO-$d_6$) δ ppm: 0.8-1.4 (6H, m), 1.5-2.0 (11H, m), 2.9-3.6 (8H, m), 3.59 (3H, s), 4.0-4.5 (1H, br), 4.06 (2H, t, J=6.1 Hz), 6.61 (1H, d, J=9.5 Hz), 7.25 (1H, dd, J=2.8 Hz, 9.2 Hz), 7.31 (1H, d, J=2.8 Hz), 7.46 (1H, d, J=9.2 Hz), 7.84 (1H, d, J=9.5 Hz), 8.01 (1H, dd, J=5.6 Hz, 8.1 Hz), 8.53 (1H, J=8.1 Hz), 8.83 (1H, d, J=5.6 Hz), 8.95 (1H, s), 10.4 (1H, brs).

EXAMPLE 6

Synthesis of 6-{5-[(2,6-dichlorobenzyl)-(2-pyridin-3-ylethyl)amino]pentyloxy}-1-methyl-1H-quinolin-2-one dihydrochloride The synthesis of the title compound was performed in the same manner as in Example 5 using appropriate starting materials.

$^1$H-NMR (DMSO-$d_6$) δ ppm: 1.3-1.6 (2H, m), 1.7-2.0 (4H, m), 3.0-3.7 (8H, m), 3.58 (3H, s), 4.02 (2H, t, J=6.0 Hz), 4.0-5.0 (1H, br), 6.59 (1H, d, J=9.5 Hz), 7.22 (1H, dd, J=2.8 Hz, 9.1 Hz), 7.27 (1H, d, J=2.8 Hz), 7.44 (1H, d, J=9.1 Hz), 7.4-7.7 (3H, m), 7.82 (1H, d, J=9.5 Hz), 7.8-8.0 (1H, m), 8.38 (1H, d, J=7.7 Hz), 8.76 (1H, d, J=5.3 Hz), 9.02 (1H, s), 9.9-10.2 (1H, br).

EXAMPLE 7

Synthesis of 6-{5-[isobutyl-(2-pyridin-3-ylethyl)amino]pentyloxy}-1-methyl-1H-quinolin-2-one dihydrochloride The synthesis of the title compound was performed in the same manner as in Example 5 using appropriate starting materials.

EXAMPLE 8

Synthesis of 6-{5-[cyclohexyl-(2-pyridin-3-ylethyl)amino]pentyloxy}-1-methyl-1H-quinolin-2-one dihydrochloride The synthesis of the title compound was performed in the same manner as in Example 5 using appropriate starting materials.

EXAMPLE 9

Synthesis of 6-{5-[benzyl-(2-pyridin-3-ylethyl)amino]pentyloxy}-1-methyl-1H-quinolin-2-one dihydrochloride The synthesis of the title compound was performed in the same manner as in Example 5 using appropriate starting materials.

¹H-NMR (DMSO-d₆) δ ppm: 1.3-1.5 (2H, m), 1.7-2.0 (4H, m), 3.0-3.2 (2H, m), 3.3-3.5 (4H, m), 3.59 (3H, s), 4.03 (2H, t, J=6.2 Hz), 4.3-4.6 (2H, m), 4.0-4.5 (1H, br), 6.61 (1H, d, J=9.5 Hz), 7.24 (1H, dd, J=2.8 Hz, 9.1 Hz), 7.29 (1H, d, J=2.8 Hz), 7.4-7.5 (4H, m), 7.6-7.8 (2H, m), 7.83 (1H, d, J=9.5 Hz), 7.90 (1H, dd, J=5.3 Hz, 8.1 Hz), 8.35 (1H, d, J=8.1 Hz), 8.78 (1H, d, J=5.3 Hz), 8.85 (1H, s), 11.22 (1H, brs).

EXAMPLE 10

Synthesis of 1-methyl-6-{5-[(2-pyridin-3-ylethyl)-o-tolylamino]pentyloxy}-1H-quinolin-2-one dihydrochloride 1-Methyl-6-[5-(2-pyridin-3-ylethylamino)pentyloxy]-1H-quinolin-2-one(183 mg), 2-bromotoluene(0.072 ml), palladium acetate (II) (5.6 mg), tri-tert-butylphosphine tetrafluoroborate(8 mg), and sodium t-butoxide(0.19 ml) were added to toluene(1 ml). The mixture was heated under reflux for 8 hours under nitrogen atmosphere. After the reaction, the precipitate was removed from the reaction mixture by celite filtration. Water was added thereto, followed by extraction using dichloromethane. The organic layer was washed with water and then saturated saline, dried with anhydrous sodium sulfate, and condensed under reduced pressure. The residue was purified by silica gel column chromatography (ethyl acetate→ethyl acetate:methanol=20:1). The purified product was condensed under reduced pressure to give the title compound(93 mg) as a yellow oily matter.
¹H-NMR (DMSO-d₆) δ ppm: 1.2-1.5 (2H, m), 1.6-1.9 (2H, m), 2.0-2.2 (2H, m), 2.50 (3H, s), 2.7-3.5 (6H, m), 3.59 (3H, s), 3.96 (2H, t, J=6.3 Hz), 4.0-5.0 (2H, br), 6.59 (1H, d, J=9.5 Hz), 7.0-7.4 (6H, m), 7.44 (1H, d, J=9.1 Hz), 7.82 (1H, d, J=9.5 Hz), 7.9-8.0 (1H, m), 8.3-8.4 (1H, m), 8.7-8.8 (2H, m).

EXAMPLE 11

Synthesis of 1-methyl-6-{5-[(3-phenylpropyl)-(2-pyridin-3-ylethyl)amino]pentyloxy}-1H-quinolin-2-one dihydrochloride The synthesis of the title compound was performed in the same manner as in Example 5 using appropriate starting materials.
¹H-NMR (DMSO-d₆) δ ppm: 1.3-1.5 (2H, m), 1.6-1.9 (4H, m), 2.0-2.2 (2H, m), 2.63 (2H, t, J=7.7 Hz), 3.0-3.5 (8H, m), 3.59 (3H, s), 3.8-4.2 (3H, m), 6.60 (1H, d, J=9.5 Hz), 7.1-7.4 (7H, m), 7.46 (1H, d, J=9.2 Hz), 7.84 (1H, d, J=9.5 Hz), 7.97 (1H, dd, J=5.3 Hz, 8.1 Hz), 8.48 (1H, d, J=8.1 Hz), 8.80 (1H, d, J=5.3 Hz), 8.92 (1H, s), 11.04 (1H, brs).

EXAMPLE 12

Synthesis of 4-{[[5-(1-methyl-2-oxo-1,2-dihydroquinolin-6-yloxy)pentyl]-(2-pyridin-3-ylethyl)amino]methyl}benzoic acid methyl ester dihydrochloride The synthesis of the title compound was performed in the same manner as in Example 5 using appropriate starting materials.
¹H-NMR (DMSO-d₆) δ ppm: 1.3-1.5 (2H, m), 1.6-1.9 (4H, m), 3.0-3.2 (2H, m), 3.2-3.5 (4H, m), 3.58 (3H, s), 3.85 (3H, s), 4.00 (2H, t, J=6.3 Hz), 4.3-4.6 (2H, m), 4.5-5.5 (1H, br), 6.59 (1H, d, J=9.5 Hz), 7.22 (1H, dd, J=2.8 Hz, 9.2 Hz), 7.27 (1H, d, J=2.8 Hz), 7.44 (1H, d, J=9.2 Hz), 7.82 (1H, d, J=9.5 Hz), 7.86 (2H, d, J=8.3 Hz), 7.9-8.0 (1H, m), 7.99 (2H, d, J=8.3 Hz), 8.42 (1H, d, J=8.2 Hz), 8.79 (1H, d, J=5.5 Hz), 8.88 (1H, s), 11.50 (1H, brs).

EXAMPLE 13

Synthesis of 4-{[[5-(1-methyl-2-oxo-1,2-dihydroquinolin-6-yloxy)pentyl]-(2-pyridin-3-ylethyl)amino]methyl}benzoic acid A 1N-sodium hydroxide aqueous solution(0.72 ml) was added to a methanol solution (2 ml) of 4-{[[5-(1-methyl-2-oxo-1,2-dihydroquinolin-6-yloxy)pentyl]-(2-pyridin-3-ylethyl)amino]methyl}benzoic acid methyl ester(153 mg). The mixture was stirred at 50° C. for 3 hours. The reaction mixture was condensed under reduced pressure. Water was added to the residue, and acetic acid was added for neutralization. The mixture was extracted using dichloromethane. The organic layer was dried with anhydrous sodium sulfate, and condensed under reduced pressure. Diisopropyl ether was added to the residue. The generated insoluble matter was separated by filtration and dried to give the title compound(115 mg) as a white powder.
¹H-NMR (DMSO-d₆) δ ppm: 1.2-1.5 (4H, m), 1.6-1.8 (2H, m), 2.3-2.6 (2H, m), 2.6-2.8 (4H, m), 3.59 (3H, s), 3.67 (2H, s), 3.96 (2H, t, J=6.4 Hz), 6.59 (1H, d, J=9.5 Hz), 7.1-7.3 (3H, m), 7.33 (2H, d, J=8.2 Hz), 7.44 (1H, d, J=9.1 Hz), 7.5-7.6 (1H, m), 7.7-7.9 (3H, m), 8.1-8.3 (2H, m), 12.5-13.0 (1H, br).

EXAMPLE 14

Synthesis of 1-methyl-6-{5-[(2-methylbenzyl)pyridin-3-ylmethylamino]pentyloxy}-1H-quinolin-2-one dihydrochloride The synthesis of the title compound was performed in the same manner as in Example 5 using appropriate starting materials.
¹H-NMR (DMSO-d₆) δ ppm: 1.3-1.5 (2H, m), 1.6-1.8 (2H, m), 1.8-2.0 (2H, m), 2.35 (3H, s), 3.0-3.2 (2H, m), 3.60 (3H, s), 3.9-4.1 (2H, m), 4.2-5.7 (5H, m), 6.61 (1H, d, J=9.5 Hz), 7.1-7.4 (5H, m), 7.46 (1H, d, J=9.2 Hz), 7.75 (1H, d, J=7.3 Hz), 7.85 (1H, d, J=9.5 Hz), 7.99 (1H, dd, J=5.4 Hz, 7.9 Hz), 8.85 (1H, d, J=7.9 Hz), 8.91 (1H, d, J=5.4 Hz), 9.21 (1H, s), 11.64 (1H, brs).

EXAMPLE 15

Synthesis of 1-methyl-6-{5-[(3-phenylpropyl)pyridin-3-ylmethylamino]pentyloxy}-1H-quinolin-2-one dihydrochloride The synthesis of the title compound was performed in the same manner as in Example 5 using appropriate starting materials.
¹H-NMR (DMSO-d₆) δ ppm: 1.3-1.5 (2H, m), 1.6-1.9 (4H, m), 1.9-2.2 (2H, m), 2.61 (2H, t, J=7.5 Hz), 2.9-3.2 (4H, m), 3.59 (3H, s), 4.02 (2H, t, J=6.2 Hz), 4.0-5.0 (3H, m), 6.61 (1H, d, J=9.5 Hz), 7.1-7.4 (7H, m), 7.46 (1H, d, J=9.2 Hz), 7.85 (1H, d, J=9.5 Hz), 7.9-8.1 (1H, m), 8.77 (1H, d, J=7.9 Hz), 8.92 (1H, d, J=5.0 Hz), 9.18 (1H, s), 11.71 (1H, brs).

EXAMPLE 16

Synthesis of 6-[5-(bis{pyridin-3-ylmethyl}amino)pentyloxy]-1-methyl-1H-quinolin-2-one Pyridine-3-carbaldehyde(0.076 ml) was added to a 1,2-dichloroethane solution(3 ml) of 1-methyl-6-{5-[(pyridin-3- ylmethyl)-amino]-pentyloxy}-1H-quinolin-2-one(237 mg). The mixture was stirred for 30 minutes at room temperature. Sodium triacetoxyborohydride(0.23 g) was added to the mixture, and the mixture was stirred at room temperature for 3 days. A saturated sodium hydrogencarbonate aqueous solution was added to the reaction mixture, followed by extraction using dichloromethane. The organic layer was dried with anhydrous sodium sulfate, and condensed under reduced pressure. The residue was purified by NH silica gel column chromatography (ethyl acetate: hexane=1:1). The purified product was condensed under reduced pressure to give the title compound(247 mg) as a yellow oil.

$^1$H-NMR (CDCl$_3$) δ ppm: 1.3-1.8 (6H, m), 2.47 (2H, t, J=6.8 Hz), 3.58 (4H, s), 3.71 (3H, s), 3.95 (2H, t, J=6.4 Hz), 6.70 (1H, d, J=9.5 Hz), 6.98 (1H, d, J=2.8 Hz), 7.16 (1H, dd, J=2.8 Hz, 9.2 Hz), 7.2-7.4 (3H, m), 7.60 (1H, d, J=9.5 Hz), 7.6-7.7 (2H, m), 8.49 (2H, dd, J=1.6 Hz, 4.8 Hz), 8.57 (2H, d, J=1.7 Hz).

EXAMPLE 17

Synthesis of 1-methyl-6-{5-[(2-methylbenzyl)pyridin-3-ylamino]pentyloxy}-1H-quinolin-2-one The synthesis of the title compound was performed in the same manner as in Example 16 using appropriate starting materials.

$^1$H-NMR (CDCl$_3$) δ ppm: 1.5-1.7 (2H, m), 1.8-1.9 (4H, m), 2.32 (3H, s), 3.45 (2H, t, J=7.6 Hz), 3.71 (3H, s), 4.01 (2H, t, J=6.3 Hz), 4.46 (2H, s), 6.72 (1H, d, J=9.5 Hz), 6.8-6.9 (1H, m), 6.98 (1H, d, J=2.8 Hz), 7.0-7.3 (6H, m), 7.29 (1H, d, J=9.2 Hz), 7.59 (1H, d, J=9.5 Hz), 7.92 (1H, dd, J=1.2 Hz, 4.6 Hz), 8.09 (1H, d, J=3.0 Hz).

EXAMPLE 18

Synthesis of 1-methyl-6-{5-[(3-phenylpropyl)pyridin-3-ylamino]pentyloxy}-1H-quinolin-2-one The synthesis of the title compound was performed in the same manner as in Example 16 using appropriate starting materials.

$^1$H-NMR (CDCl$_3$) δ ppm: 1.4-1.7 (4H, m), 1.8-2.1 (4H, m), 2.66 (2H, t, J=7.7 Hz), 3.2-3.4 (4H, m), 3.70 (3H, s), 4.00 (2H, t, J=6.3 Hz), 6.71 (1H, d, J=9.5 Hz), 6.8-6.9 (1H, m), 6.98 (1H, d, J=2.8 Hz), 7.05 (1H, dd, J=4.6 Hz, 8.6 Hz), 7.1-7.4 (7H, m), 7.58 (1H, d, J=9.5 Hz), 7.88 (1H, dd, J=1.2 Hz, 4.5 Hz), 8.04 (1H, d, J=3.0 Hz).

EXAMPLE 19

Synthesis of 1-methyl-6-{5-[(2-pyridin-3-ylethyl)pyridin-4-ylmethylamino]pentyloxy}-1H-quinolin-2-one trihydrochloride The synthesis of the title compound was performed in the same manner as in Example 5 using appropriate starting materials.

$^1$H-NMR (DMSO-d$_6$) δ ppm: 0.80-2.02 (6H, m), 3.05-3.25 (2H, m), 3.36-3.52 (4H, m), 3.60 (3H, s), 3.97-4.10 (2H, m), 4.82 (2H, s), 6.61 (1H, d, J=9.5 Hz), 7.25 (1H, dd, J=9.1, 2.8 Hz), 7.32 (1H, d, J=2.8 Hz), 7.46 (1H, d, J=9.1 Hz), 7.86 (1H, d, J=9.5 Hz), 8.06 (1H, dd, J=8.1, 5.7 Hz), 8.53 (1H, d, J=6.3 Hz), 8.59 (1H, d, J=8.1 Hz), 8.86 (1H, d, J=5.7 Hz), 8.88 (1H, s), 9.04 (2H, d, J=6.3 Hz).

EXAMPLE 20

Synthesis of 1-Methyl-6-{2-[(2-pyridin-3-ylethyl)pyridin-3-ylmethylamino]ethoxy}-1H-quinolin-2-one The synthesis of the title compound was performed in the same manner as in Example 16 using appropriate starting materials.

$^1$H-NMR (CDCl$_3$) δ: 2.78-2.91 (4H, m), 3.00 (2H, t, J=5.6 Hz), 3.69 (3H, s), 3.79 (2H, s), 4.04 (2H, t, J=5.6 Hz), 6.70 (1H, d, J=9.5 Hz), 6.63 (1H, d, J=2.8 Hz), 7.15-7.30 (4H, m), 7.41-7.50 (1H, m), 7.57-7.60 (2H, m), 8.42-8.53 (4H, m).

EXAMPLE 21

Synthesis of 1-methyl-6-{2-[(2-pyridin-3-ylethyl)pyridin-4-ylmethylamino]ethoxy}-1H-quinolin-2-one The synthesis of the title compound was performed in the same manner as in Example 5 using appropriate starting materials.

$^1$H-NMR (CDCl$_3$) δ ppm: 2.79-2.91 (4H, m), 3.01 (2H, t, J=5.6 Hz), 3.70 (3H, s), 3.79 (2H, s), 4.05 (2H, t, J=5.6 Hz), 6.71 (1H, d, J=9.5 Hz), 6.93 (1H, d, J=2.8 Hz), 7.11-7.20 (4H, m), 7.27-7.30 (1H, m), 7.41-7.48 (1H, m), 7.58 (1H, d, J=9.5 Hz), 8.43-8.49 (4H, m).

EXAMPLE 22

Synthesis of 1-methyl-6-[3-(pyridin-4-ylmethylpyridin-3-ylmethylamino)propoxy]-1H-quinolin-2-one trihydrochloride The synthesis of the title compound was performed in the same manner as in Example 5 using appropriate starting materials.

$^1$H-NMR (DMSO-d$_6$) δ ppm: 1.86-2.19 (2H, m), 3.61 (3H, s), 3.71-5.00 (8H, m), 6.62 (1H, d, J=9.5 Hz), 7.09 (1H, dd, J=9.2, 2.8 Hz), 7.20 (1H, d, J=2.8 Hz), 7.44 (1H, d, J=9.2 Hz), 7.84 (1H, d, J=9.5 Hz), 7.80-7.94 (1H, m), 8.02-8.12 (2H, m), 8.52 (1H, d, J=7.3 Hz), 8.73-8.83 (3H, m), 8.93 (1H, s).

EXAMPLE 23

Synthesis of 1-methyl-6-[4-(pyridin-4-ylmethylpyridin-3-ylmethylamino)butoxy]-1H-quinolin-2-one trihydrochloride The synthesis of the title compound was performed in the same manner as in Example 5 using appropriate starting materials.

$^1$H-NMR (DMSO-d$_6$) δ ppm: 1.61-1.98 (4H, m), 2.60-3.00 (2H, m), 3.60 (3H, s), 3.23-5.11 (6H, m), 6.61 (1H, d, J=9.5 Hz), 7.18 (1H, dd, J=9.2, 2.9 Hz), 7.24 (1H, d, J=2.9 Hz), 7.46 (1H, d, J=9.2 Hz), 7.84 (1H, d, J=9.5 Hz), 7.89-8.00 (1H, m), 8.11-8.26 (2H, m), 8.64 (1H, d, J=7.8 Hz), 8.84 (1H, d, J=4.5 Hz), 8.88 (2H, d, J=6.4 Hz), 9.02 (1H, s).

EXAMPLE 24

Synthesis of 1-methyl-6-{3-[(2-pyridin-3-ylethyl)pyridin-4-ylmethylamino]propoxy}-1H-quinolin-2-one The synthesis of the title compound was performed in the same manner as in Example 16 using appropriate starting materials.

¹H-NMR (CDCl₃) δ ppm: 1.88-1.96 (2H, m), 2.68-2.81 (6H, m), 3.66 (2H, s), 3.71 (3H, s), 3.93 (2H, t, J=6.0 Hz), 6.73 (1H, d, J=9.5 Hz), 6.92 (1H, d, J=2.8 Hz), 7.09-7.16 (4H, m), 7.28-7.31 (1H, m), 7.39-7.46 (1H, m), 7.62 (1H, d, J=9.5 Hz), 8.41-8.46 (4H, m).

EXAMPLE 25

Synthesis of 1-Methyl-6-{3-[(2-pyridin-3-ylethyl) pyridin-4-ylmethylamino]propoxy}-3,4-dihydro-1H-quinolin-2-one The synthesis of the title compound was performed in the same manner as in Example 16 using appropriate starting materials.

¹H-NMR (CDCl₃) δ ppm: 1.85-1.91 (2H, m), 2.60-2.88 (10H, m), 3.33 (3H, s), 3.64 (2H, s), 3.88 (2H, t, J=6.0 Hz), 6.64-6.71 (2H, m), 6.89 (1H, d, J=8.7 Hz), 7.13-7.19 (2H, m), 7.30-7.33 (1H, m), 7.35-7.46 (1H, m), 8.40-8.52 (3H, m), 8.53 (1H, d, J=1.2 Hz).

EXAMPLE 26

Synthesis of (2-pyridin-3-ylethyl)pyridin-4-ylmethyl-[3-(quinolin-6-yloxy)propyl]amine The synthesis of the title compound was performed in the same manner as in Example 16 using appropriate starting materials.

¹H-NMR (CDCl₃) δ ppm: 1.93-2.02 (2H, m), 2.71-2.80 (6H, m), 3.66 (2H, s), 4.02 (2H, t, J=6.1 Hz), 6.989 (1H, d, J=2.8 Hz), 7.09-7.18 (3H, m), 7.28-7.39 (3H, m), 7.98-8.06 (2H, m), 8.43-8.45 (4H, m), 8.77-8.78 (1H, m).

EXAMPLE 27

Synthesis of 1-methyl-5-{3-[(2-pyridin-3-ylethyl) pyridin-4-ylmethylamino]propoxy}-1H-quinolin-2-one trihydrochloride (2-Pyridin-3-ylethyl)pyridin-4-ylmethylamine(128 mg), and N-ethyldiisopropylamine(0.13 ml) were added to a DMF solution(5 ml) of 5-(3-iodopropoxy)-1-methyl-1H-quinolin-2-one(172 mg). The mixture was stirred at 60° C. for 3.5 hours. The reaction mixture was added to ice water, followed by extraction using ethyl acetate. The organic layer was washed with water and then saturated saline, dried with anhydrous sodium sulfate, and condensed under reduced pressure. The residue was purified by silica gel column chromatography (ethyl acetate: methanol=10:1→1:1).

The purified product was condensed under reduced pressure. A 4N-hydrogen chloride ethyl acetate solution was added to an ethyl acetate solution of the residue, which was stirred at room temperature. The generated insoluble matter was separated by filtration and dried to give the title compound(21 mg) as a white powder.

¹H-NMR (DMSO-d₆) δ ppm: 2.26-2.54 (2H, m), 3.00-5.29 (10H, m), 3.60 (3H, s), 6.56 (1H, d, J=9.7 Hz), 6.83 (1H, d, J=8.2 Hz), 7.12 (1H, d, J=8.6 Hz), 7.51-7.60 (1H, m), 7.92 (1H, d, J=9.7 Hz), 8.02 (1H, dd, J=8.0, 5.5 Hz), 8.24-8.40 (2H, m), 8.54 (1H, d, J=8.0 Hz), 8.84 (1H, d, J=5.5 Hz), 8.92 (2H, d, J=5.6 Hz), 8.95 (1H, s).

EXAMPLE 28

Synthesis of 1-methyl-7-{3-[(2-pyridin-3-ylethyl) pyridin-4-ylmethylamino]propoxy}-1H-quinolin-2-one trihydrochloride The synthesis of the title compound was performed in the same manner as in Example 27 using appropriate starting materials.

¹H-NMR (DMSO-d₆) δ ppm: 2.14-2.43 (2H, m), 2.88-4.95 (10H, m), 3.59 (3H, s), 6.44 (1H, d, J=9.4 Hz), 6.85 (1H, d, J=8.6 Hz), 6.89 (1H, s), 7.65 (1H, d, J=8.6 Hz), 7.83 (1H, d, J=9.4 Hz), 7.97 (1H, dd, J=8.0, 5.6 Hz), 8.07-8.24 (2H, m), 8.47 (1H, d, J=8.0 Hz), 8.81 (1H, d, J=5.6 Hz), 8.86 (2H, d, J=5.6 Hz), 8.90 (1H, s).

EXAMPLE 29

Synthesis of 1-methyl-8-{3-[(2-pyridin-3-ylethyl) pyridin-4-ylmethylamino]propoxy}-1H-quinolin-2-one trihydrochloride The synthesis of the title compound was performed in the same manner as in Example 27 using appropriate starting materials.

¹H-NMR (DMSO-d₆) δ ppm: 2.30-2.55 (2H, m), 3.25-3.60 (6H, m), 3.77 (3H, s), 4.09-4.29 (2H, m), 4.54-5.00 (2H, m), 6.60 (1H, d, J=9.4 Hz), 7.16-7.28 (2H, m), 7.31 (1H, dd, J=6.8, 2.3 Hz), 7.84 (1H, d, J=9.4 Hz), 8.04 (1H, dd, J=8.1, 5.4 Hz), 8.32-8.46 (2H, m), 8.56 (1H, d, J=8.1 Hz), 8.85 (1H, d, J=5.4 Hz), 8.91-9.02 (3H, m).

EXAMPLE 30

Synthesis of 6-{3-[(2-pyridin-3-ylethyl)pyridin-4-ylmethylamino]propoxy}-1H-quinolin-2-one trihydrochloride The synthesis of the title compound was performed in the same manner as in Example 27 using appropriate starting materials.

¹H-NMR (DMSO-d₆) δ ppm: 2.18-2.40 (2H, m), 3.15-3.56 (6H, m), 3.95-4.16 (2H, m), 4.59-4.87 (2H, m), 6.51 (1H, d, J=9.5 Hz), 7.12 (1H, dd, J=8.9, 2.7 Hz), 7.20 (1H, d, J=2.7 Hz), 7.28 (1H, d, J=8.9 Hz), 7.86 (1H, d, J=9.5 Hz), 8.03 (1H, dd, J=8.1, 5.4 Hz), 8.31-8.44 (2H, m), 8.55 (1H, d, J=8.1 Hz), 8.84 (1H, d, J=5.4 Hz), 8.93-9.03 (3H, m).

EXAMPLE 31

Synthesis of 1-methyl-4-{3-[(2-pyridin-3-ylethyl) pyridin-4-ylmethylamino]propoxy}-1H-quinolin-2-one trihydrochloride Triphenyl phosphine(102 mg) and diethyl azodicarboxylate(68 mg) were added to a tetrahydrofuran (THF) solution(5 ml) of 4-hydroxy-1-methyl-1H-quinolin-2-one(63 mg), and 3-[(2-pyridin-3-ylethyl)pyridin-4-ylmethylamino]propane-1-ol(81.4 mg). The mixture was stirred overnight. After the reaction mixture was condensed under reduced pressure, the residue was purified by silica gel column chromatography (dichloromethane: methanol=20:1→10:1). The purified product was condensed under reduced pressure. A 4N-hydrogen chloride ethyl acetate solution(0.29 ml) was added to an ethyl acetate solution of the residue, which was stirred at room temperature for 30 minutes. The generated insoluble matter was separated by filtration, and dried to give the title compound(126.8 mg) as a white powder.

$^1$H-NMR (DMSO-d$_6$) δ ppm: 2.29-2.56 (2H, m), 3.11-3.61 (6H, m), 3.56 (3H, s), 4.11-4.30 (2H, m), 4.50-4.94 (2H, m), 6.03 (1H, s), 7.32-7.41 (1H, m), 7.52 (1H, d, J=8.4 Hz), 7.62-7.76 (2H, m), 8.10 (1H, dd, J=8.0, 5.3 Hz), 8.21-8.34 (2H, m), 8.53 (1H, d, J=8.0 Hz), 8.83 (1H, d, J=5.3 Hz), 8.90 (2H, d, J=5.7 Hz), 8.94 (1H, s).

EXAMPLE 32

Synthesis of 6-{3-[(2-pyridin-3-ylethyl)pyridin-4-ylmethylamino]propoxy}-2H-isoquinolin-1-one trihydrochloride Triphenyl phosphine(51 mg) and di-tert-butyl azodicarboxylate (45 mg) were added to a tetrahydrofuran (THF) solution(1.5 ml) of 6-hydroxy-2H-isoquinolin-1-one(29 mg), and 3-[(2-pyridin-3-ylethyl)pyridin-4-ylmethylamino]propan-1-ol(40 mg). The mixture was stirred overnight. After the reaction mixture was condensed under reduced pressure, the residue was purified by NH silica gel column chromatography (ethyl acetate: methanol=1:0→4:1). The purified product was condensed under reduced pressure. A 4N-hydrogen chloride ethyl acetate solution(0.06 ml) was added to an ethyl acetate solution of the residue, which was stirred at room temperature for 30 minutes. The generated insoluble matter was separated by filtration, and was dried to produce the title compound(31.4 mg) as a white powder.

$^1$H-NMR (DMSO-d$_6$) δ ppm: 2.14-2.45 (2H, m), 2.91-3.78 (6H, m), 4.08-4.25 (2H, m), 4.37-4.81 (2H, m), 6.46 (1H, d, J=7.1 Hz), 6.99 (1H, dd, J=8.8, 2.2 Hz), 7.08 (1H, d, J=2.2 Hz), 7.10-7.18 (1H, m), 7.92 (1H, dd, J=8.0, 5.5 Hz), 7.99-8.14 (2H, m), 8.08 (1H, d, J=8.8 Hz), 8.41 (1H, d, J=8.0 Hz), 8.78 (1H, d, J=5.5 Hz), 8.83 (2H, d, J=5.8 Hz), 8.87 (1H, s), 10.98-11.17 (1H, m).

EXAMPLE 33

Synthesis of 2-methyl-6-{3-[(2-pyridin-3-ylethyl)pyridin-4-ylmethylamino]propoxy}-2H-isoquinolin-1-one trihydrochloride The synthesis of the title compound was performed in the same manner as in Example 32 using appropriate starting materials.

$^1$H-NMR (DMSO-d$_6$) δ ppm: 2.09-2.41 (2H, m), 2.85-3.44 (6H, m), 3.47 (3H, s), 4.08-4.26 (2H, m), 4.26-4.66 (2H, m), 6.52 (1H, d, J=7.3 Hz), 6.99 (1H, dd, J=8.9, 2.3 Hz), 7.07 (1H, d, J=2.3 Hz), 7.44 (1H, d, J=7.3 Hz), 7.72 (1H, dd, J=7.6, 5.3 Hz), 7.81-7.92 (2H, m), 8.11 (1H, d, J=8.9 Hz), 8.11-8.19 (1H, m), 8.67 (1H, dd, J=5.3, 1.2 Hz), 8.69-8.76 (3H, m).

EXAMPLE 34

Synthesis of 1,3-dimethyl-6-{3-[(2-pyridin-3-ylethyl)pyridin-4-ylmethylamino]propoxy}-3,4-dihydro-1H-quinazolin-2-one trihydrochloride The synthesis of the title compound was performed in the same manner as in Example 32 using appropriate starting materials.

$^1$H-NMR (DMSO-d$_6$) δ ppm: 2.08-2.38 (2H, m), 2.88 (3H, s), 3.16 (3H, s), 3.08-3.56 (6H, m), 3.92-4.05 (2H, m), 4.32 (2H, s), 4.42-4.85 (2H, m), 6.73 (1H, br-s), 6.70-6.90 (2H, m), 7.98 (1H, d-d, J=5.5, 8.1 Hz), 8.04-8.28 (2H, m), 8.46 (1H, d, J=8.1 Hz), 8.81 (1H, d, J=5.5 Hz), 8.81-8.98 (3H, m).

EXAMPLE 35

Synthesis of 6-{3-[(2-pyridin-3-ylethyl)pyridin-4-ylmethylamino]propoxy}-3,4-dihydro-2H-isoquinolin-1-one trihydrochloride The synthesis of the title compound was performed in the same manner as in Example 32 using appropriate starting materials.

$^1$H-NMR (DMSO-d$_6$) δ ppm: 2.13-2.40 (2H, m), 2.86 (2H, t, J=6.5 Hz), 3.10-3.57 (8H, m), 4.00-4.15 (2H, m), 4.55-4.81 (2H, m), 6.74-6.88 (2H, m), 7.66-7.80 (2H, m), 8.01 (1H, d-d, J=5.0, 8.0 Hz), 8.19-8.40 (2H, m), 8.52 (1H, d, J=8.0 Hz), 8.83 (1H, d, J=5.0 Hz), 8.85-9.00 (3H, m).

EXAMPLE 36

Synthesis of 5-{3-[(2-pyridin-3-ylethyl)pyridin-4-ylmethylamino]propoxy}-2,3-dihydro-isoindol-1-one trihydrochloride The synthesis of the title compound was performed in the same manner as in Example 32 using appropriate starting materials.

$^1$H-NMR (DMSO-d$_6$) δ ppm: 2.15-2.43 (2H, m), 3.00-3.58 (6H, m), 3.96-4.16 (2H, m), 4.32 (2H, s), 4.44-4.83 (2H, m), 6.96 (1H, d-d, J=1.9, 8.3 Hz), 7.07 (1H, s), 7.57 (1H, d, J=8.3 Hz), 7.92-8.05 (1H, m), 8.10-8.40 (3H, m), 8.41-8.55 (1H, m), 8.78-9.00 (4H, m).

EXAMPLE 37

Synthesis of N-ethyl-4-{3-[(2-pyridin-3-ylethyl)pyridin-4-ylmethylamino]propoxy}benzamide trihydrochloride 1-(3-Dimethylaminopropyl)-3-ethylcarbodiimide hydrochloride (WSC) (95 mg), and 1-hydroxy benzotriazole (HOBt) (66 mg) were added to a DMF solution(4 ml) of 4-{3-[(2-pyridin-3-ylethyl)pyridin-4-ylmethylamino] propoxy}benzoic acid(149 mg), ethyl amine hydrochloride (38 mg), and triethylamine (0.08 ml). The mixture was stirred at room temperature overnight. The reaction mixture was added to ice water. A 1N-sodium hydroxide aqueous solution was added thereto, followed by extraction using ethyl acetate. The organic layer was washed with water and then was dried with anhydrous sodium sulfate, followed by condensation under reduced pressure. The residue was purified by silica gel column chromatography (ethyl acetate: methanol=10:1→4:1). The purified product was condensed under reduced pressure. A 4N-hydrogen chloride ethyl acetate solution(0.16 ml) was added to an ethyl acetate solution of the residue. The precipitated insoluble matter was separated, washed with ethyl acetate, and dried to give the title compound(80 mg) as a white powder.

$^1$H-NMR (DMSO-d$_6$) δ ppm: 1.11 (3H, t, J=7.2 Hz), 2.10-2.38 (2H, m), 2.89-3.57 (8H, m), 3.95-4.20 (2H, m), 4.28-4.69 (2H, m), 6.92 (2H, d, J=8.8 Hz), 7.75 (1H, dd, J=7.8, 5.2 Hz), 7.82 (2H, d, J=8.8 Hz), 7.83-7.94 (2H, m), 8.18 (1H, d, J=7.8 Hz), 8.35 (1H, t, J=5.4 Hz), 8.68 (1H, dd, J=5.2, 1.3 Hz), 8.71-8.79 (3H, m).

EXAMPLE 38

Synthesis of 2-methyl-6-{3-[(2-pyridin-3-ylethyl)pyridin-4-ylmethylamino]propoxy}-3,4-dihydro-2H-isoquinolin-1-one trihydrochloride The synthesis of the title compound was performed in the same manner as in Example 32 using appropriate starting materials.

$^1$H-NMR (DMSO-d$_6$) δ ppm: 2.10-2.40 (2H, m), 2.74-3.62 (10H, m), 2.99 (3H, s), 3.74-4.20 (2H, m), 4.39-4.82 (2H, m), 6.77 (1H, s), 6.82 (1H, d, J=8.6 Hz), 7.79 (1H, d, J=8.6 Hz), 7.87-8.00 (1H, m), 8.05-8.22 (2H, m), 8.46 (1H, d, J=8.2 Hz), 8.71-8.92 (4H, m).

EXAMPLE 39

Synthesis of [3-(2-methyl-1,1-dioxo-2,3-dihydrobenzo[d]isothiazol-5-yloxy)propyl]-(2-pyridin-3-ylethyl)pyridin-4-ylmethylamine trihydrochloride The synthesis of the title compound was performed in the same manner as in Example 32 using appropriate starting materials.

$^1$H-NMR (DMSO-d$_6$) δ ppm: 2.08-2.39 (2H, m), 2.79 (3H, s), 2.88-3.58 (6H, m), 4.00-4.20 (2H, m), 4.29-4.65 (2H, m), 4.35 (2H, s), 7.02-7.11 (2H, m), 7.70-7.81 (2H, m), 7.81-7.93 (2H, m), 8.18 (1H, d, J=8.1 Hz), 8.68 (1H, dd, J=5.2, 1.2 Hz), 8.70-8.79 (3H, m).

EXAMPLE 40

Synthesis of 1-methyl-6-[3-(phenethylpyridin-4-ylmethylamino)propoxy]-1H-quinolin-2-one dihydrochloride The synthesis of the title compound was performed in the same manner as in Example 5 using appropriate starting materials.

$^1$H-NMR (DMSO-d$_6$) δ ppm: 2.10-2.40 (2H, m), 2.79-3.70 (6H, m), 3.60 (3H, s), 3.99-4.19 (2H, m), 4.30-4.61 (2H, m), 6.62 (1H, d, J=9.5 Hz), 7.15-7.36 (7H, m), 7.47 (1H, d, J=9.2 Hz), 7.68-7.80 (2H, m), 7.84 (1H, d, J=9.5 Hz), 8.67 (2H, d, J=4.9 Hz).

EXAMPLE 41

Synthesis of 1-methyl-6-{3-[(2-pyridin-2-ylethyl)pyridin-4-ylmethylamino]propoxy}-1H-quinolin-2-one trihydrochloride The synthesis of the title compound was performed in the same manner as in Example 5 using appropriate starting materials.

$^1$H-NMR (DMSO-d$_6$) δ ppm: 2.12-2.31 (2H, m), 3.07-3.29 (2H, m), 3.33-3.59 (4H, m), 3.60 (3H, s), 3.95-4.19 (2H, m), 4.53 (2H, s), 6.62 (1H, d, J=9.5 Hz), 7.17 (1H, dd, J=9.2, 2.7 Hz), 7.25 (1H, d, J=2.7 Hz), 7.46 (1H, d, J=9.2 Hz), 7.58-7.67 (1H, m), 7.72 (1H, d, J=7.9 Hz), 7.85 (1H, d, J=9.5 Hz), 8.04 (2H, d, J=6.2 Hz), 8.11-8.21 (1H, m), 8.67 (1H, d, J=4.7 Hz), 8.80 (2H, d, J=6.2 Hz).

EXAMPLE 42

Synthesis of N-methyl-N-(2-{[3-(1-methyl-2-oxo-1,2-dihydroquinolin-6-yloxy)propyl]pyridin-4-ylmethylamino}ethyl)benzamide dihydrochloride The synthesis of the title compound was performed in the same manner as in Example 5 using appropriate starting materials.

$^1$H-NMR (DMSO-d$_6$) δ ppm: 2.15-2.41 (2H, m), 2.95 (3H, s), 3.01-3.51 (4H, m), 3.60 (3H, s), 3.70-4.24 (4H, m), 4.33-4.72 (2H, m), 6.61 (1H, d, J=9.5 Hz), 7.18 (1H, d, J=8.4 Hz), 7.25 (1H, s), 7.33-7.54 (6H, m), 7.82 (1H, d, J=9.5 Hz), 7.92-8.08 (2H, m), 8.67-8.82 (2H, m).

EXAMPLE 43

Synthesis of 1-ethyl-6-{3-[(2-pyridin-3-ylethyl)pyridin-4-ylmethylamino]propoxy}-1H-quinolin-2-one trihydrochloride The synthesis of the title compound was performed in the same manner as in Example 32 using appropriate starting materials.

$^1$H-NMR (DMSO-d$_6$) δ ppm: 1.19 (3H, t, J=7.0 Hz), 2.18-2.41 (2H, m), 2.94-3.59 (6H, m), 3.96-4.18 (2H, m), 4.25 (2H, q, J=7.0 Hz), 4.35-4.63 (2H, m), 6.61 (1H, d, J=9.5 Hz), 7.18 (1H, dd, J=9.3, 2.8 Hz), 7.27 (1H, d, J=2.8 Hz), 7.52 (1H, d, J=9.3 Hz), 7.61-7.76 (1H, m), 7.85 (1H, d, J=9.5 Hz), 7.85-8.00 (2H, m), 8.09-8.20 (1H, m), 8.67 (1H, dd, J=5.3, 1.4 Hz), 8.69-8.80 (3H, m).

EXAMPLE 44

Synthesis of 1-benzyl-6-{3-[(2-pyridin-3-ylethyl)pyridin-4-ylmethylamino]propoxy}-1H-quinolin-2-one trihydrochloride The synthesis of the title compound was performed in the same manner as in Example 32 using appropriate starting materials.

$^1$H-NMR (DMSO-d$_6$) δ ppm: 1.80-2.00 (2H, m), 2.52-2.82 (6H, m), 3.63 (2H, s), 3.78-3.98 (2H, m), 5.54 (2H, s), 6.82 (1H, d, J=9.5 Hz), 6.84-6.99 (2H, m), 7.05-7.44 (10H, m), 7.67 (1H, d, J=9.5 Hz), 8.30-8.52 (4H, m).

EXAMPLE 45

Synthesis of N-methyl-N-(2-{[3-(1-oxo-1,2,3,4-tetrahydroisoquinolin-6-yloxy)propyl]pyridin-4-ylmethylamino}ethyl)benzamide dihydrochloride Benzoyl chloride(0.14 ml) was added to a dichloromethane solution (10 ml) of 6-{3-[(2-methylaminoethyl)pyridin-4-ylmethylamino]propoxy}-3,4-dihydro-2H-isoquinolin-1-one trihydrochloride(382 mg), and triethylamine(0.56 ml) under ice cooling. The mixture was stirred at room temperature overnight. Water was added to the reaction mixture, followed by extraction using dichloromethane. The organic layer was dried with anhydrous sodium sulfate, and condensed under reduced pressure. The residue was purified by silica gel column chromatography (ethyl acetate: methanol=10:1→4:1). The purified product was condensed under reduced pressure. A 4N-hydrogen chloride ethyl acetate solution(0.28 ml) was added to an ethyl acetate solution (10 ml) of the residue. The precipitated insoluble matter was separated, washed with ethyl acetate, and dried to give the title compound(242 mg) as a white powder.

$^1$H-NMR (DMSO-$d_6$) δ ppm: 2.04-2.36 (2H, m), 2.78-2.92 (2H, m), 2.95 (3H, s), 3.00-3.46 (6H, m), 3.64-3.94 (2H, m), 3.94-4.21 (2H, m), 4.31-4.61 (2H, m), 6.77 (1H, s), 6.81 (1H, d, J=8.5 Hz), 7.29-7.59 (6H, m), 7.78 (1H, d, J=8.5 Hz), 7.91-8.18 (2H, m), 8.78 (2H, d, J=4.9 Hz).

EXAMPLE 46

Synthesis of 2,3-dihydrobenzofuran-7-carboxylic acid methyl-(2-{[3-(1-methyl-2-oxo-1,2-dihydro-quinolin-6-yloxy)propyl]pyridin-4-ylmethylamino}ethyl)amide dihydrochloride PS-Carbodiimide resin(1.3 g) and 1-hydroxy benzotriazole (HOBt) (230 mg) were added to acetonitrile and THF solution (4 ml+6 ml) of 1-methyl-6-{3-[(2-methylamino ethyl)pyridin-4-ylmethylamino]propoxy}-1H-quinolin-2-one(304 mg) and 2,3-dihydrobenzofuran-7-carboxylic acid (164 mg). The mixture was stirred at room temperature overnight. After the reaction mixture was filtrated and condensed under reduced pressure, the residue was purified by silica gel column chromatography (ethyl acetate: methanol=1:0→10:1). The purified product was condensed under reduced pressure. A 4N-hydrogen chloride ethyl acetate solution(0.35 ml) was added to an ethyl acetate solution of the residue. The precipitated insoluble matter was separated, washed with ethyl acetate, and dried to give the title compound(324.2 mg) as a white powder.

$^1$H-NMR (DMSO-$d_6$) δ ppm: 2.10-2.44 (2H, m), 2.88-3.45 (6H, m), 2.91 (3H, s), 3.59 (3H, s), 3.70-4.25 (4H, m), 4.31-4.72 (4H, m), 6.58 (1H, d, J=9.5 Hz), 6.75-6.91 (1H, m), 6.91-7.12 (1H, m), 7.12-7.32 (3H, m), 7.43 (1H, d, J=9.0 Hz), 7.78 (1H, d, J=9.5 Hz), 7.98-8.30 (2H, m), 8.69-8.94 (2H, m).

EXAMPLE 47

Synthesis of 3-{3-[(2-pyridin-3-ylethyl)pyridin-4-ylmethylamino]propoxy}-7,8-dihydro-6H-5-thia-8-aza-benzocyclohepten-9-one trihydrochloride The synthesis of the title compound was performed in the same manner as in Example 32 using appropriate starting materials.

$^1$H-NMR (DMSO-$d_6$) δ ppm: 2.10-2.41 (2H, m), 3.00-3.60 (10H, m), 3.99-4.19 (2H, m), 4.43-4.84 (2H, m), 6.89-7.01 (2H, m), 7.48 (1H, d, J=8.6 Hz), 7.98 (1H, dd, J=8.0, 5.3 Hz), 8.04-8.21 (2H, m), 8.27 (1H, t, J=6.5 Hz), 8.46 (1H, d, J=8.0 Hz), 8.81 (1H, d, J=5.3 Hz), 8.81-8.98 (3H, m).

EXAMPLE 48

Synthesis of 1-methyl-3-{3-[(2-pyridin-3-ylethyl)pyridin-4-ylmethylamino]propoxy}-1H-quinolin-2-one trihydrochloride The synthesis of the title compound was performed in the same manner as in Example 31 using appropriate starting materials.

$^1$H-NMR (DMSO-$d_6$) δ ppm: 2.20-2.42 (2H, m), 3.10-3.33 (2H, m), 3.34-3.60 (4H, m), 3.67 (3H, s), 4.00-4.20 (2H, m), 4.55-4.82 (2H, m), 7.20-7.35 (2H, m), 7.40-7.53 (2H, m), 7.65 (1H, d, J=7.7 Hz), 7.93-8.08 (1H, m), 8.18-8.35 (2H, m), 8.53 (1H, d, J=8.1 Hz), 8.82 (1H, d, J=5.1 Hz), 8.90-9.05 (3H, m).

EXAMPLE 49

Synthesis of 1-(6-{3-[(2-pyridin-3-ylethyl)pyridin-4-ylmethylamino]propoxy}-3,4-dihydro-2H-quinolin-1-yl)ethanone trihydrochloride The synthesis of the title compound was performed in the same manner as in Example 32 using appropriate starting materials.

$^1$H-NMR (DMSO-$d_6$) δ ppm: 1.71-1.92 (2H, m), 2.11 (3H, s), 2.01-2.39 (2H, m), 2.58-2.79 (2H, m), 3.00-3.48 (6H, m), 3.51-3.71 (2H, m), 3.89-4.10 (2H, m), 4.50 (2H, s), 6.59-6.79 (2H, m), 7.04-7.56 (1H, m), 7.78 (1H, dd, J=7.8, 5.3 Hz), 7.94 (2H, d, J=4.4 Hz), 8.23 (1H, d, J=7.8 Hz), 8.63-8.82 (4H, m).

EXAMPLE 50

Synthesis of 2,3-dihydrobenzofuran-7-carboxylic acid methyl-(2-{[3-(1-oxo-1,2,3,4-tetrahydroiso-quinolin-6-yloxy)propyl]pyridin-4-ylmethylamino}ethyl)amide dihydrochloride 1-(3-Dimethylaminopropyl)-3-ethylcarbodiimide hydrochloride (WSC) (144 mg), and 1-hydroxy benzotriazole (HOBt) (115 mg) were added to a DMF solution(5 ml) of 6-{3-[(2-methylaminoethyl)pyridin-4-ylmethylamino]propoxy}-3,4-dihydro-2H-isoquinolin-1-one trihydrochloride (234 mg), and 2,3-dihydrobenzofuran-7-carboxylic acid(123 mg). The mixture was stirred at room temperature overnight. Water was added to the reaction mixture, followed by extraction using ethyl acetate. The organic layer was washed with water, and dried with anhydrous sodium sulfate. After condensation under reduced pressure, the residue was purified by NH silica gel column chromatography (ethyl acetate: methanol=1:0→10:1). The purified product was condensed under reduced pressure. A 4N-hydrogen chloride ethyl acetate solution(0.19 ml) was added to an ethyl acetate solution of the residue. The precipitated insoluble matter was separated, washed with ethyl acetate, and dried to give the title compound(164.6 mg) as a white powder.

$^1$H-NMR (DMSO-$d_6$) δ ppm: 2.04-2.35 (2H, m), 2.65-3.41 (10H, m), 2.90 (3H, s), 3.69-4.66 (8H, m), 6.65-6.90 (3H, m), 6.90-7.14 (1H, m), 7.27 (1H, d, J=5.2 Hz), 7.35-7.61 (1H, m), 7.77 (1H, d, J=8.5 Hz), 7.86-8.19 (2H, m), 8.64-8.90 (2H, m).

EXAMPLE 51

Synthesis of 1-methyl-6-(3-{[2-(1-oxo-3,4-dihydro-1H-isoquinolin-2-yl)ethyl]pyridin-4-ylmethylamino}-propoxy)-1H-quinolin-2-one The synthesis of the title compound was performed in the same manner as in Example 16 using appropriate starting materials.

$^1$H-NMR (CDCl$_3$) δ ppm: 1.90-2.09 (2H, m), 2.65-2.81 (4H, m), 2.91 (2H, t, J=6.6 Hz), 3.48 (2H, t, J=6.6 Hz), 3.62-3.78 (4H, m), 3.70 (3H, s), 4.01 (2H, t, J=6.1 Hz), 6.71 (1H, d, J=9.5 Hz), 6.88 (1H, d, J=2.8 Hz), 7.00-7.48 (7H, m), 7.54 (1H, d, J=9.5 Hz), 8.02-8.11 (1H, m), 8.39-8.50 (2H, m).

EXAMPLE 52

Synthesis of 2-fluoro-N-methyl-N-(2-{[3-(1-methyl-2-oxo-1,2-dihydroquinolin-6-yloxy)propyl]pyridin-4-ylmethylamino}ethyl)benzamide tris(phosphate)

The synthesis of the title compound was performed in the same manner as in Example 50 using appropriate starting materials.

Colorless Solid (Ethanol)

mp: 190-191° C.

EXAMPLE 53

Synthesis of 1,3-dimethyl-5-{3-[(2-pyridin-3-yl-ethyl)pyridin-4-ylmethylamino]propoxy}-1,3-dihydrobenzoimidazol-2-one trihydrochloride The synthesis of the title compound was performed in the same manner as in Example 5 using appropriate starting materials.

$^1$H-NMR (DMSO-$d_6$) δ ppm: 2.06-2.42 (2H, brs), 2.97-3.73(m, 12H), 4.04 (2H, t, J=7.0 Hz), 4.42-4.95 (2H, brs), 6.60 (1H, dd, J=2.0, 8.5 Hz), 6.78 (1H, d, J=2.0 Hz), 7.02 (1H, d, J=8.5 Hz), 8.00 (1H, dd, J=5.6, 7.9 Hz), 8.15-8.40 (2H, brs), 8.51 (1H, d, J=7.9 Hz), 8.83 (1H, d, J=5.6 Hz), 8.92 (3H, m), 12.45 (1H, Brs).

EXAMPLE 54

Synthesis of 1,3-dimethyl-5-{3-[(2-pyridin-3-yl-ethyl)pyridin-3-ylmethylamino]propoxy}-1,3-dihydrobenzoimidazol-2-one trihydrochloride The synthesis of the title compound was performed in the same manner as in Example 5 using appropriate starting materials.

$^1$H-NMR (DMSO-$d_6$) δ ppm: 2.17-2.43 (2H, brs), 3.09-3.64(m, 12H), 3.95-4.18 (2H, m), 4.49-4.84 (2H, brs), 6.63 (1H, dd, J=2.2 and 8.5 Hz), 6.81 (1H, d, J=2.2 Hz), 7.03 (1H, d, J=8.5 Hz), 7.89 (1H, dd, J=7.9 and 5.6 Hz), 8.01 (1H, dd, J=7.9 and 5.6 Hz), 8.26 (1H, d, J=8.0 Hz), 8.71 (1H, d, J=8.0 Hz), 8.77-8.92 (2H, m), 8.96 (1H, s), 9.16 (1H, s), 12.18 (1H, brs).

EXAMPLE 55

Synthesis of 2-[2-({3-[4-(2-oxopyrrolidin-1-yl)phenoxy]propyl}pyridin-4-ylmethylamino)ethyl]-2H-isoquinolin-1-one dihydrochloride 2-(2-{[3-(4-Bromophenoxy)propyl]pyridin-4-ylmethylamino}ethyl)-2H-isoquinolin-1-one(500 mg), 2-pyrrolidone(0.228 ml), potassium carbonate(415 mg), copper iodide (I) (190 mg), and N,N'-dimethyl ethylenediamine (0.39 ml) were added to toluene(5 ml). The mixture was stirred at 100° C. for 12 hours under nitrogen atmosphere. The reaction mixture was cooled to room temperature. After adding aqueous ammonia, extraction was performed using ethyl acetate. The organic layer was washed with saturated saline, and dried with sodium sulfate. After the organic layer was condensed under reduced pressure, the residue was purified by silica gel column chromatography (ethyl acetate: methanol=100:0→70:30). The purified product was condensed under reduced pressure. A condensed hydrochloric acid(0.3 ml) was added to an ethanol solution of the residue, followed by condensation under reduced pressure. The residue was recrystallized from isopropyl alcohol/water to give the title compound(350 mg) as a white powder.

mp: 210 to 214° C. (dec.)

EXAMPLE 56

Synthesis of N-methyl-N-[4-(3-{[2-(1-oxo-2H-isoquinolin-2-yl)ethyl]pyridin-4-ylmethylamino}-propoxy)phenyl]acetamide dihydrochloride The synthesis of the title compound was performed in the same manner as in Example 55 using appropriate starting materials.

$^1$H-NMR (CD$_3$OD) δ ppm: 1.82 (3H, s), 2.35-2.54 (2H, m), 3.21 (3H, s), 3.56-3.73 (2H, m), 3.75-3.90 (2H, m), 4.16 (2H, t, J=5.7 Hz), 4.53-4.75 (2H, m), 5.05 (2H, brs), 6.71-6.92 (2H, m), 6.98 (2H, d, J=8.9 Hz), 7.20 (2H, d, J=8.9 Hz), 7.49 (1H, d, J=7.4 Hz), 7.57 (1H, d, J=8.2 Hz), 7.68 (1H, d, J=7.4 Hz), 7.76 (1H, d, J=8.2 Hz), 8.31 (1H, d, J=8.0 Hz), 8.54 (1H, d, J=6.7 Hz), 8.99 (1H, d, J=6.7 Hz).

EXAMPLE 57

Synthesis of 2-[2-({3-[4-(2-oxopiperidin-1-yl)phenoxy]propyl}-pyridin-4-ylmethylamino)ethyl]-2H-isoquinolin-1-one dihydrochloride The synthesis of the title compound was performed in the same manner as in Example 55 using appropriate starting materials.

$^1$H-NMR (CD$_3$OD) δ ppm: 1.94-2.11 (4H, m), 2.22-2.42 (2H, m), 2.56-2.77 (2H, m), 3.59 (2H, t, J=7.3 Hz), 3.64-3.77 (2H, m), 3.78-3.92 (2H, m), 4.08 (2H, t, J=5.5 Hz), 4.67 (2H, brs), 5.04 (2H, brs), 6.80 (1H, d, J=7.4 Hz), 6.90 (2H, d, J=8.9 Hz), 7.24 (2H, d, J=8.9 Hz), 7.51 (1H, d, J=7.4 Hz), 7.55-7.63 (1H, m), 7.68 (1H, d, J=7.5 Hz), 7.72-7.84 (1H, m), 8.32 (1H, d, J=7.8 Hz), 8.49 (2H, d, J=6.7 Hz), 8.88 (2H, d, J=6.7 Hz).

EXAMPLE 58

Synthesis of 2-[2-({3-[4-(2-oxo-2H-pyridin-1-yl)phenoxy]propyl}-pyridin-4-ylmethylamino)ethyl]-2H-isoquinolin-1-one dihydrochloride The synthesis of the title compound was performed in the same manner as in Example 55 using appropriate starting materials.

$^1$H-NMR (CD$_3$OD) δ ppm: 2.25-2.54 (2H, m), 3.50-3.73 (2H, m), 3.76-3.93 (2H, m), 4.16 (2H, t, J=5.6 Hz), 4.67 (2H, brs), 4.84-5.21 (2H, m), 6.79 (1H, d, J=7.4 Hz), 6.86 (1H, dt, J=1.2 and 6.8 Hz), 6.96 (1H, d, J=8.9 Hz), 7.03 (2H, d, J=8.9 Hz), 7.39 (2H, d, J=8.9 Hz), 7.52 (1H, d, 7.4 Hz), 7.57 (1H, dt, J=1.2 and 8.2 Hz), 7.67 (1H, d, J=7.4 Hz), 7.75 (1H, dt, J=1.2 and 8.2 Hz), 7.82-7.99 (2H, m), 8.32 (1H, d, J=8.1 Hz), 8.53 (1H, d, J=6.6 Hz), 8.94 (1H, d, J=6.6 Hz).

EXAMPLE 59

Synthesis of 2-[2-({3-[4-(morpholine-4-carbonyl)phenoxy]propyl}-pyridin-4-ylmethylamino)ethyl]-2H-isoquinolin-1-one dihydrochloride 2-(2-{[3-(4-Bromophenoxy)propyl]pyridin-4-ylmethylamino}ethyl)-2H-isoquinolin-1-one(500 mg), hexacarbonyl molybdenum(264 mg), trans-di-µ-acetatobis[2-(di-o-tolylphosphino)benzyl]dipalladium (II) (Herrmann's palladacycle) (23 mg), sodium carbonate(318 mg), and morpholine(0.26 ml) were added to THF(5 ml). The mixture was heated at 170° C. for 10 minutes (microwave reactor). The reaction mixture was cooled to room temperature. Water and ethyl acetate were added thereto, followed by celite filtration. The organic layer was dried with sodium sulfate, and condensed under reduced pressure. The residue was purified by NH silica gel column chromatography (ethyl acetate: methanol=1:0→7:3). The purified product was condensed under reduced pressure. A 4N-hydrogen chloride ethyl acetate solution was added to an ethyl acetate solution of the residue. The precipitated insoluble matter was separated, washed with ethyl acetate, and dried to give the title compound(150 mg) as a white powder.

$^1$H-NMR (CD$_3$OD) δ ppm: 2.17-2.41 (2H, m), 3.37-3.90 (10H, m), 3.99-4.15 2H, m), 4.50-4.64 (2H, m), 4.67-5.00 (2H, m), 6.81 (1H, d, J=7.4 Hz), 6.88 (2H, d, J=6.2 Hz), 7.38 (2H, d, J=8.5 Hz), 7.45 (1H, d, J=7.4 Hz), 7.60 (1H, t, J=8.2 Hz), 7.71 (1H, d, J=7.4 Hz), 7.79 (1H, t, J=8.2 Hz), 8.32 (1H, d, J=7.9 Hz), 8.38 (2H, brs), 8.83 (2H, brs).

EXAMPLE 60

Synthesis of 1,3-dimethyl-6-{3-[(2-pyridin-3-yl-ethyl)pyridin-4-ylmethylamino]propoxy}-1H-quinazoline-2,4-dione trihydrochloride The synthesis of the title compound was performed in the same manner as in Example 32 using appropriate starting materials.

$^1$H-NMR (DMSO-d$_6$) δ ppm: 2.11-2.39 (2H, m), 3.00-5.03 (16H, m), 7.25-7.37 (1H, m), 7.37-7.54 (2H, m), 7.94-8.05 (1H, m), 8.05-8.35 (2H, m), 8.49 (1H, d, J=8.2 Hz), 8.73-8.99 (4H, m), 12.24 (1H, brs).

EXAMPLE 61

Synthesis of 2-[2-(pyridin-4-ylmethyl-{3-[4-(pyrrolidine-1-carbonyl)phenoxy]propyl}amino)ethyl]-2H-isoquinolin-1-one dihydrochloride The synthesis of the title compound was performed in the same manner as in Example 59 using appropriate starting materials.

$^1$H-NMR (DMSO-d$_6$, 80° C.) δ ppm: 1.75-1.89 (4H, m), 1.92-2.08 (2H, m), 2.78-2.97 (2H, m), 2.99-3.16 (2H, m), 3.35-3.58 (4H, m), 3.91-4.00 (2H, m), 4.07-4.17 (2H, m), 4.17-4.30 (2H, m), 6.57 (1H, d, J=7.3 Hz), 6.79 (2H, d, J=8.8 Hz), 7.41 (2H, d, J=8.8 Hz), 7.34-7.54 (2H, m), 7.56-7.79 (4H, m), 8.20 (1H, d, J=8.7 Hz), 8.53 (2H, d, J=6.2 Hz).

EXAMPLE 62

Synthesis of N-tert-butyl-4-(3-{[2-(1-oxo-2H-iso-quinolin-2-yl)ethyl]pyridin-4-ylmethylamino}propoxy)benzamide dihydrochloride The synthesis of the title compound was performed in the same manner as in Example 59 using appropriate starting materials.

$^1$H-NMR (DMSO-d$_6$, 80° C.) δ ppm: 1.38 (9H, s), 1.92-2.08 (2H, m), 2.83-3.00 (2H, m), 3.04-3.22 (2H, m), 3.96 (2H, d, J=6.2 Hz), 4.10-4.21 (2H, m), 4.21-4.31 (2H, m), 6.59 (1H, d, J=7.3 Hz), 6.77 (2H, d, J=8.8 Hz), 7.23 (1H, brs), 7.42 (1H, d, J=7.3 Hz), 7.49 (1H, m), 7.67 (2H, t, J=7.0 Hz), 7.71 (2H, d, J=8.8 Hz), 7.81 (2H, d, J=6.3), 8.20 (1H, d, J=2.0), 8.56 (2H, d, J=6.3 Hz).

EXAMPLE 63

Synthesis of N-isobutyl-4-(3-{[2-(1-oxo-2H-iso-quinolin-2-yl)ethyl]pyridin-4-ylmethylamino}propoxy)benzamide dihydrochloride The synthesis of the title compound was performed in the same manner as in Example 59 using appropriate starting materials.

$^1$H-NMR (DMSO-d$_6$, 80° C.) δ ppm: 0.90 (6H, d, J=6.5 Hz), 1.75-1.93 (1H, m), 1.93-2.14 (2H, m), 2.85-3.03 (2H, m), 3.03-3.26 (4H, m), 3.90-4.02 (2H, m), 4.15-4.35 (4H, m), 6.59 (1H, d, J=7.4 Hz), 6.80 (2H, d, J=8.8 Hz), 7.31-7.54 (2H, m), 7.61-7.74 (2H, m), 7.76 (2H. d, J=8.8 Hz), 7.86 (2H, d, J=6.3 Hz), 7.98 (1H, brs), 8.20 (1H, d, J=7.4 Hz), 8.59 (2H, d, J=6.3 Hz).

EXAMPLE 64

Synthesis of N-cyclohexyl-4-(3-{[2-(1-oxo-2H-iso-quinolin-2-yl)ethyl]pyridin-4-ylmethylamino}propoxy)benzamide dihydrochloride The synthesis of the title compound was performed in the same manner as in Example 59 using appropriate starting materials.

$^1$H-NMR (DMSO-d$_6$, 80° C.) δ ppm: 1.00-1.45 (4H, m), 1.53-1.66 (1H, m), 1.66-1.88 (4H, m), 1.92-2.08 (2H, m), 2.82-3.01 (2H, m), 3.04-3.22 (2H, m), 3.65-3.84 (2H, m), 3.88-4.01 (2H, m), 4.21-4.30 (4H, m), 6.58 (1H, d, J=7.3 Hz), 6.79 (2H, d, J=8.8 Hz), 7.42 (1H, d, J=7.3 Hz), 7.46-7.53(1H, m), 7.57-7.84 (7H, m), 8.20 (1H, d, J=7.3 Hz), 8.56 (2H, d, J=6.4 Hz).

EXAMPLE 65

1-methyl-6-(3-{[2-(1-oxo-2H-isoquinolin-2-yl)ethyl]pyridin-4-ylmethylamino}propoxy)-1H-quinolin-2-one dihydrochloride The synthesis of the title compound was performed in the same manner as in Example 5 using appropriate starting materials.

Colorless Solid (Isopropyl Alcohol/Water)

mp: 171 to 174° C.

EXAMPLE 66

Synthesis of 2-[2-({3-[4-(2-oxo-oxazolidin-3-yl)phenoxy]propyl}pyridin-4-ylmethylamino)ethyl]-2H-isoquinolin-1-one dihydrochloride The synthesis of the title compound was performed in the same manner as in Example 55 using appropriate starting materials.

$^1$H-NMR (DMSO-d$_6$, 80° C.) δ ppm: 1.87-2.08 (2H, m), 2.79-3.00 (2H, m), 3.01-3.21 (2H, m), 3.86-3.96 (2H, m), 3.96-4.05 (2H, m), 4.11-4.33 (4H, m), 4.34-4.49 (2H, m), 6.58 (1H, d, J=7.4 Hz), 6.79 (2H, d, J=9.1 Hz), 7.39 (2H, d, J=9.1 Hz), 7.33-7.44 (1H, m), 7.44-7.55 (2H, m), 7.57-7.73 (2H, m), 7.77-7.87 (2H, m), 8.20 (1H, d, J=8.0 Hz), 8.50-8.64 (2H, m).

EXAMPLE 67

Synthesis of 2-[2-({3-[3-(2-oxopyrrolidin-1-yl)phenoxy]propyl}pyridin-4-ylmethylamino)ethyl]-2H-isoquinolin-1-one dihydrochloride The synthesis of the title compound was performed in the same manner as in Example 55 using appropriate starting materials.

$^1$H-NMR (DMSO-$d_6$, 80° C.) δ ppm: 1.85-2.16 (4H, m), 2.35-2.55 (2H, m), 2.79-3.01 (2H, m), 3.01-3.21 (2H, m), 3.73-4.26 (8H, m), 6.49-6.63 (2H, m), 7.04-7.14 (1H, m), 7.14-7.28 (2H, m), 7.35-7.54 (2H, m), 7.55-7.72 (2H, m), 7.72-7.92 (2H, m), 8.19 (1H, dd, J=8.1 and 0.6 Hz), 8.47-8.66 (2H, m).

EXAMPLE 68

Synthesis of 2-[2-(pyridin-4-ylmethyl-{3-[3-(pyrrolidine-1-carbonyl)phenoxy]propyl}amino)ethyl]-2H-isoquinolin-1-one dihydrochloride The synthesis of the title compound was performed in the same manner as in Example 59 using appropriate starting materials.

$^1$H-NMR (DMSO-$d_6$, 80° C.) δ ppm: 1.72-1.90 (4H, m), 1.94-2.14 (2H, m), 2.86-3.05 (2H, m), 3.05-3.22 (2H, m), 3.25-3.50 (4H, m), 3.70-4.36 (6H, m), 6.58 (1H, d, J=7.4 Hz), 6.78-6.95 (2H, m), 7.01 (1H, d, J=7.7 Hz), 7.28 (1H, t, J=7.9 Hz), 7.42(1H, d, J=7.4 Hz), 7.44-7.51 (1H, m), 7.55-7.74 (2H, m), 7.83 (2H, d, J=4.9 Hz), 8.20 (1H, d, J=8.1 Hz), 8.58 (2H, d, J=5.6 Hz).

EXAMPLE 69

Synthesis of 5-{2-[[3-(1,3-dimethyl-2-oxo-2,3-dihydro-1H-benzoimidazol-5-yloxy)propyl]-(2-methylpyridin-3-ylmethyl)amino]ethyl}-2-methyl-5H-furo[3,2-c]pyridin-4-one The synthesis of the title compound was performed in the same manner as in Example 5 using appropriate starting materials.

$^1$H-NMR (CDCl$_3$) δ ppm: 1.92-1.95 (2H, m), 2.40 (3H, s), 2.48 (3H, s), 2.76 (2H, t, J=6.9 Hz), 2.86 (2H, t, J=6.2 Hz), 3.39 (3H, s), 3.40 (3H, s), 3.63 (2H, s), 3.90 (2H, t, J=6.0 Hz), 4.01 (2H, t, J=6.2 Hz), 6.31 (1H, dd, J=7.3, 0.6 Hz), 6.49-6.51 (2H, m), 6.54 (1H, dd, J=8.5, 2.3 Hz), 6.83 (1H, d, J=8.4 Hz), 6.86 (1H, dd, J=7.7, 4.9 Hz), 6.93 (1H, d, J=7.3 Hz), 7.42-7.44 (1H, m), 8.28-8.30 (1H, m).

EXAMPLE 70

Synthesis of 2-{2-[[3-(1,3-dimethyl-2-oxo-2,3-dihydro-1H-benzoimidazol-5-yloxy)propyl]-(2-methylpyridin-3-ylmethyl)amino]ethyl}-2H-isoquinolin-1-one The synthesis of the title compound was performed in the same manner as in Example 5 using appropriate starting materials.

$^1$H NMR (CDCl$_3$), δ ppm: 1.92-1.96 (2H, m), 2.48 (3H, s), 2.76 (2H, t, J=6.9 Hz), 2.88 (2H, t, J=6.2 Hz), 3.38 (3H, s), 3.39 (3H, s), 3.63 (2H, s), 3.91 (2H, t, J=6.0 Hz), 4.01 (2H, t, J=6.2 Hz), 6.35 (1H, d, J=7.3 Hz), 6.47 (1H, d, J=2.3 Hz), 6.50 (1H, dd, J=8.4, 2.3 Hz), 6.72 (1H, d, J=7.6, 4.8 Hz), 6.81 (1H, d, J=8.4 Hz), 6.90 (1H, d, J=7.3 Hz), 7.41 (1H, dd, J=7.6, 1.5 Hz), 7.44-7.49 (2H, m), 7.60-7.65 (1H, m), 8.20-8.22 (1H, m), 8.34-8.36 (1H, m).

EXAMPLE 71

Synthesis of 1-methyl-6-{2-[(2-pyridin-3-ylethyl)pyridin-3-ylmethylamino]ethoxy}-1H-quinolin-2-one trihydrochloride A 1N-hydrogen chloride ethanol solution(1.7 ml) was added to an ethanol solution (10 ml) of 1-Methyl-6-{2-[(2-pyridin-3-ylethyl)pyridin-3-ylmethylamino]ethoxy}-1H-quinolin-2-one(195 mg), which was stirred at room temperature. The reaction mixture was condensed under reduced pressure and ethyl acetate was added to the residue. The precipitated insoluble matter was separated, washed with ethyl acetate, and dried to give the title compound(199 mg) as a pale yellow powder.

$^1$H-NMR (DMSO-$d_6$), δ ppm: 3.08-5.02 (10H, m), 3.61 (3H, s), 6.64 (1H, d, J=9.5 Hz), 7.26-7.38 (2H, m), 7.49 (1H, d, J=9.3 Hz), 7.75-7.83 (1H, m), 7.86 (1H, d, J=9.5 Hz), 7.92 (1H, dd, J=8.0, 5.6 Hz), 8.41 (1H, d, J=8.0 Hz), 8.42-8.53 (1H, m), 8.73-8.81 (2H, m), 8.87 (1H, s), 8.92-9.05 (1H, m).

EXAMPLE 72

Synthesis of 1-methyl-6-{2-[(2-pyridin-3-ylethyl)pyridin-4-ylmethylamino]ethoxy}-1H-quinolin-2-one trihydrochloride The synthesis of the title compound was performed in the same manner as in Example 71 using appropriate starting materials.

$^1$H-NMR (DMSO-$d_6$) δ ppm: 3.02-5.62 (10H, m), 3.61 (3H, s), 6.63 (1H, d, J=9.5 Hz), 7.21-7.34 (2H, m), 7.47 (1H, d, J=9.1 Hz), 7.85 (1H, d, J=9.5 Hz), 7.92-8.01 (1H, m), 8.02-8.21 (2H, m), 8.49 (1H, d, J=8.0 Hz), 8.77 (1H, d, J=5.3 Hz), 8.82-8.92 (3H, m).

EXAMPLE 73

Synthesis of 1-methyl-6-{3-[(2-pyridin-3-ylethyl)pyridin-4-ylmethylamino]propoxy}-1H-quinolin-2-one trihydrochloride The synthesis of the title compound was performed in the same manner as in Example 71 using appropriate starting materials.

$^1$H-NMR (DMSO-$d_6$) δ ppm: 2.18-2.43 (2H, m), 3.07-3.49 (4H, m), 3.60 (3H, s), 4.05-4.18 (2H, m), 4.50-4.88 (4H, m), 6.62 (1H, d, J=9.5 Hz), 7.19 (1H, dd, J=9.1, 2.7 Hz), 7.27 (1H, d, J=2.7 Hz), 7.47 (1H, d, J=9.1 Hz), 7.84 (1H, d, J=9.5 Hz), 7.94-8.05 (1H, m), 8.08-8.36 (2H, m), 8.49 (1H, d, J=7.6 Hz), 8.82 (1H, d, J=4.9 Hz), 8.83-8.99 (3H, m).

EXAMPLE 74

Synthesis of 1-methyl-6-{3-[(2-pyridin-3-ylethyl)pyridin-4-ylmethylamino]propoxy}-3,4-dihydro-1H-quinolin-2-one trihydrochloride The synthesis of the title compound was performed in the same manner as in Example 71 using appropriate starting materials.

$^1$H-NMR (DMSO-d$_6$) δ ppm: 2.14-2.38 (2H, m), 2.77-4.95 (14H, m), 3.22 (3H, s), 6.73-6.82 (2H, m), 6.99 (1H, d, J=9.2 Hz), 7.99 (1H, d, J=5.7 Hz), 8.22-8.34 (2H, m), 8.52 (1H, d, J=8.1 Hz), 8.81-8.98 (4H, m).

EXAMPLE 75

Synthesis of (2-pyridin-3-ylethyl)pyridin-4-ylmethyl-[3-(quinolin-6-yloxy)prop yl]amine tetrahydrochloride The synthesis of the title compound was performed in the same manner as in Example 71 using appropriate starting materials.

$^1$H-NMR (DMSO-d$_6$) δ ppm: 2.22-4.78 (12H, m), 7.51-7.61 (2H, m), 7.73-7.97 (4H, m), 8.15 (1H, d, J=9.1 Hz), 8.20-8.33 (1H, m), 8.62-8.81 (5H, m), 8.98 (1H, d, J=4.9 Hz).

EXAMPLE 76

Synthesis of 6-{5-[benzo[1,3]dioxol-5-ylmethyl-(2-pyridin-3-ylethyl)amino]pentyloxy}-1-methyl-1H-quinolin-2-one dihydrochloride The synthesis of the title compound was performed in the same manner as in Example 5 using appropriate starting materials.

1H-NMR (DMSO-D6) δ ppm: 1.31-1.50 (2H, m), 1.68-1.93 (4H, m), 2.95-3.12 (2H, m), 3.12-3.40 (4H, m), 3.58 (3H, s), 3.91-4.38 (4H, m), 6.05 (2H, s), 6.59 (1H, d, J=9.5 Hz), 6.96 (1H, d, J=8.0 Hz), 7.10 (1H, dd, J=8.0, 1.5 Hz), 7.23 (1H, dd, J=9.1, 2.9 Hz), 7.27 (1H, d, J=2.9 Hz), 7.30 (1H, d, J=1.5 Hz), 7.44 (1H, d, J=9.1 Hz), 7.78-7.87 (2H, m), 8.26 (1H, d, J=8.0 Hz), 8.73 (1H, d, J=5.4 Hz), 8.79 (1H, s).

EXAMPLE 77

Synthesis of 6-{5-[benzofuran-2-ylmethyl-(2-pyridin-3-ylethyl)amino]pentyloxy}-1-methyl-1H-quinolin-2-one dihydrochloride The synthesis of the title compound was performed in the same manner as in Example 5 using appropriate starting materials.

1H-NMR (DMSO-D6) δ ppm: 1.40-1.59 (2H, m), 1.68-1.83 (2H, m), 1.83-2.00 (2H, m), 3.04-3.24 (2H, m), 3.24-3.50 (4H, m), 3.58 (3H, s), 3.92-4.11 (2H, m), 4.70 (2H, s), 6.59 (1H, d, J=9.5 Hz), 7.19-7.41 (5H, m), 7.44 (1H, d, J=9.2 Hz), 7.60 (1H, d, J=8.4 Hz), 7.70 (1H, d, J=7.3 Hz), 7.82 (1H, d, J=9.5 Hz), 7.96 (1H, dd, J=8.0, 5.2 Hz), 8.46 (1H, d, J=8.0 Hz), 8.79 (1H, d, J=5.2 Hz), 8.90 (1H, s).

EXAMPLE 78

Synthesis of 6-{5-[benzo[b]thiophen-3-ylmethyl-(2-pyridin-3-ylethyl)amino]pentyloxy}-1-methyl-1H-quinolin-2-one dihydrochloride The synthesis of the title compound was performed in the same manner as in Example 5 using appropriate starting materials.

1H-NMR (DMSO-D6) δ ppm: 1.30-1.49 (2H, m), 1.60-1.98 (4H, m), 3.08-3.28 (2H, m), 3.28-3.51 (4H, m), 3.58 (3H, s), 3.90-4.08 (2H, m), 4.72 (2H, s), 6.59 (1H, d, J=9.5 Hz), 7.20 (1H, dd, J=9.1, 2.8 Hz), 7.26 (1H, d, J=2.8 Hz), 7.39-7.52 (3H, m), 7.82 (1H, d, J=9.5 Hz), 7.90 (1H, dd, J=7.9, 5.4 Hz), 8.06 (1H, d, J=8.7 Hz), 8.14 (1H, d, J=7.3 Hz), 8.30-8.40 (2H, m), 8.76 (1H, d, J=5.4 Hz), 8.85 (1H, s).

EXAMPLE 79

Synthesis of 1-methyl-6-{5-[N-(2-pyridin-3-ylethyl)-N-(pyridin-2-ylmethyl)amino]pentyloxy}-1H-quinolin-2-one trihydrochloride The synthesis of the title compound was performed in the same manner as in Example 5 using appropriate starting materials.

1H-NMR (DMSO-D6) δ ppm: 1.39-1.55 (2H, m), 1.69-1.82 (2H, m), 1.69-2.01 (2H, m), 3.11-3.31 (2H, m), 3.39-3.57 (4H, m), 3.60 (3H, s), 3.96-4.11 (2H, m), 4.67 (2H, s), 6.61 (1H, d, J=9.5 Hz), 7.25 (1H, dd, J=9.2, 2.8 Hz), 7.31 (1H, d, J=2.8 Hz), 7.47 (1H, d, J=9.2 Hz), 7.59 (1H, dd, J=6.8, 5.4 Hz), 7.86 (1H, d, J=9.5 Hz), 7.94 (1H, d, J=7.8 Hz), 8.02-8.12 (2H, m), 8.60 (1H, d, J=8.1 Hz), 8.73 (1H, d, J=4.7 Hz), 8.87 (1H, d, J=5.4 Hz), 8.87 (1H, s).

EXAMPLE 80

Synthesis of 1-methyl-6-{5-[N-(2-pyridin-3-ylethyl)-N-(pyridin-3-ylmethyl)amino]pentyloxy}-1H-quinolin-2-one trihydrochloride The synthesis of the title compound was performed in the same manner as in Example 5 using appropriate starting materials.

1H-NMR (DMSO-D6) δ ppm: 1.40-1.58 (2H, m), 1.71-1.88 (2H, m), 1.88-2.09 (2H, m), 3.08-3.32 (2H, m), 3.32-3.56 (4H, m), 3.60 (3H, s), 3.96-4.10 (2H, m), 4.79 (2H, s), 6.62 (1H, d, J=9.5 Hz), 7.26 (1H, dd, J=9.2, 2.8 Hz), 7.33 (1H, d, J=2.8 Hz), 7.47 (1H, d, J=9.2 Hz), 7.87 (1H, d, J=9.5 Hz), 8.08 (1H, dd, J=8.1, 5.7 Hz), 8.16 (1H, dd, J=8.1, 5.8 Hz), 8.65 (1H, d, J=8.1 Hz), 8.87 (1H, d, J=5.7 Hz), 9.02 (1H, d, J=5.8 Hz), 9.04 (1H, s), 9.08 (1H, d, J=8.1 Hz), 9.39 (1H, s).

EXAMPLE 81

Synthesis of N-[5-(1-methyl-2-oxo-1,2-dihydroquinolin-6-yloxy)pentyl]-N-(2-pyridin-3-ylethyl)benzenesulfonamide hydrochloride Triethylamine (0.35 ml) was added to a dichloromethane solution (5 ml) of 1-methyl-6-[5-(2-pyridin-3-ylethylamino)pentyloxy]-1H-quinolin-2-one (219 mg) and ice-cooled. Benzenesulfonyl chloride (0.096 ml) was added to the resulting mixture, and stirred at room temperature overnight. Water was added to the reaction mixture, and extraction with dichloromethane was performed. The organic layer was washed with water and a saturated sodium chloride aqueous solution, in this order, then dried over anhydrous sodium sulfate, and concentrated under reduced pressure. The residue was purified by NH silica gel column chromatography (ethyl acetate). The purified product was concentrated under reduced pressure. A 1N-hydrogen chloride ethanol solution (0.16 ml) was added to the solution of the residue in ethanol, and stirred for 30 minutes at room temperature. The precipitated insoluble matter was collected by filtration, washed with ethyl acetate, and dried to give the title compound (68 mg) as a yellow powder.

1H-NMR (DMSO-D6) δ ppm: 1.19-1.39 (2H, m), 1.39-1.55 (2H, m), 1.55-1.78 (2H, m), 2.92-3.20 (4H, m), 3.31-3.50 (2H, m), 3.58 (3H, s), 3.86-4.07 (2H, m), 6.59 (1H, d, J=9.5 Hz), 7.21 (1H, dd, J=9.2, 2.8 Hz), 7.27 (1H, d, J=2.8

Hz), 7.44 (1H, d, J=9.2 Hz), 7.51-7.71 (3H, m), 7.71-7.89 (3H, m), 7.99 (1H, dd, J=8.0, 5.7 Hz), 8.49 (1H, d, J=8.0 Hz), 8.79 (1H, d, J=5.7 Hz), 8.87 (1H, s).

EXAMPLE 82

Synthesis of N-[3-(1-methyl-2-oxo-1,2-dihydro-quinolin-6-yloxy)propyl]-2-nitro-N-(2-pyridin-3-ylethyl)benzenesulfonamide The synthesis of the title compound was performed in the same manner as in Example 4 using appropriate starting materials.

1H-NMR (CDCl3) δ ppm: 2.00-2.19 (2H, m), 2.92 (2H, t, J=7.6 Hz), 3.50-3.66 (4H, m), 3.71 (3H, s), 4.01 (2H, t, J=5.8 Hz), 6.72 (1H, d, J=9.5 Hz), 6.93 (1H, d, J=2.8 Hz), 7.13 (1H, dd, J=9.2, 2.8 Hz), 7.19 (1H, dd, J=7.8, 5.4 Hz), 7.29 (1H, d, J=9.2 Hz), 7.50-7.64 (5H, m), 7.96-8.02 (1H, m), 8.42 (1H, d, J=1.7 Hz), 8.46 (1H, dd, J=4.8, 1.7 Hz).

EXAMPLE 83

Synthesis of N-[4-(1-methyl-2-oxo-1,2-dihydro-quinolin-6-yloxy)butyl]-2-nitro-N-(2-pyridin-3-yl-ethyl)benzenesulfonamide The synthesis of the title compound was performed in the same manner as in Example 4 using appropriate starting materials.

1H-NMR (CDCl3) δ ppm: 1.70-1.89 (4H, m), 2.89 (2H, t, J=7.5 Hz), 3.40-3.60 (4H, m), 3.68 (3H, s), 4.01 (2H, t, J=5.1 Hz), 6.71 (1H, d, J=9.5 Hz), 6.98 (1H, d, J=2.8 Hz), 7.13-7.22 (2H, m), 7.29 (1H, d, J=9.2 Hz), 7.49-7.72 (5H, m), 7.95-8.01 (1H, m), 8.40 (1H, d, J=1.7 Hz), 8.44 (1H, dd, J=4.9, 1.7 Hz).

EXAMPLE 84

Synthesis of 1-methyl-6-{3-[N-(2-methylbenzyl)-N-(2-pyridin-3-ylethyl)amino]propoxy}-1H-quinolin-2-one dihydrochloride The synthesis of the title compound was performed in the same manner as in Example 5 using appropriate starting materials.

1H-NMR (DMSO-D6) δ ppm: 2.20-2.45 (2H, m), 2.48 (3H, s), 3.60 (3H, s), 3.10-4.65 (10H, m), 6.63 (1H, d, J=9.5 Hz), 7.20 (1H, dd, J=9.2, 2.8 Hz), 7.24-7.41 (4H, m), 7.48 (1H, d, J=9.2 Hz), 7.73 (1H, d, J=7.0 Hz), 7.84 (1H, d, J=9.5 Hz), 7.96 (1H, dd, J=7.8, 5.5 Hz), 8.43 (1H, d, J=7.8 Hz), 8.80 (1H, d, J=5.5 Hz), 8.90 (1H, s).

EXAMPLE 85

Synthesis of 1-methyl-6-{4-[N-(2-methylbenzyl)-N-(2-pyridin-3-ylethyl)amino]butoxy}-1H-quinolin-2-one dihydrochloride The synthesis of the title compound was performed in the same manner as in Example 5 using appropriate starting materials.

1H-NMR (DMSO-D6) δ ppm: 1.61-1.86 (2H, m), 1.86-2.14 (2H, m), 2.48 (3H, s), 3.10-3.33 (2H, m), 3.33-3.58 (4H, m), 3.60 (3H, s), 3.90-4.80 (4H, m), 6.61 (1H, d, J=9.5 Hz), 7.18-7.37 (5H, m), 7.47 (1H, d, J=9.2 Hz), 7.75 (1H, d, J=7.4 Hz), 7.85 (1H, d, J=9.5 Hz), 8.05 (1H, dd, J=8.0, 5.5 Hz), 8.56 (1H, d, J=8.0 Hz), 8.85 (1H, d, J=5.5 Hz), 8.98 (1H, s).

EXAMPLE 86

Synthesis of 1-methyl-6-{3-[N-(3-phenylpropyl)-N-(2-pyridin-3-ylethyl)amino]propoxy}-1H-quinolin-2-one dihydrochloride The synthesis of the title compound was performed in the same manner as in Example 5 using appropriate starting materials.

1H-NMR (DMSO-D6) δ ppm: 1.91-2.12 (2H, m), 2.12-2.31 (2H, m), 2.59-2.78 (2H, m), 3.58 (3H, s), 3.05-4.39 (10H, m), 6.60 (1H, d, J=9.5 Hz), 7.13-7.34 (7H, m), 7.45 (1H, d, J=9.2 Hz), 7.82 (1H, d, J=9.5 Hz), 7.98 (1H, dd, J=7.9, 5.5 Hz), 8.51 (1H, d, J=7.9 Hz), 8.80 (1H, d, J=5.5 Hz), 8.92 (1H, s).

EXAMPLE 87

Synthesis of 1-methyl-6-{4-[N-(3-phenylpropyl)-N-(2-pyridin-3-ylethyl)amino]butoxy}-1H-quinolin-2-one dihydrochloride The synthesis of the title compound was performed in the same manner as in Example 5 using appropriate starting materials.

1H-NMR (DMSO-D6) δ ppm: 1.71-2.15 (6H, m), 2.55-2.75 (2H, m), 3.57 (3H, s), 3.00-4.34 (10H, m), 6.59 (1H, d, J=9.5 Hz), 7.14-7.32 (7H, m), 7.44 (1H, d, J=9.2 Hz), 7.81 (1H, d, J=9.5 Hz), 7.99 (1H, dd, J=7.9, 5.5 Hz), 8.53 (1H, d, J=7.9 Hz), 8.81 (1H, d, J=5.5 Hz), 8.93 (1H, s).

EXAMPLE 88

Synthesis of 1-methyl-6-{5-[N-((E)-3-phenylallyl)-N-(2-pyridin-3-ylethyl)amino]pentyloxy}-1H-quinolin-2-one dihydrochloride The synthesis of the title compound was performed in the same manner as in Example 5 using appropriate starting materials.

1H-NMR (DMSO-D6) δ ppm: 1.40-1.60 (2H, m), 1.71-2.00 (4H, m), 3.59 (3H, s), 2.97-4.20 (10H, m), 6.51 (1H, dt, J=15.9, 7.0 Hz), 6.61 (1H, d, J=9.5 Hz), 6.95 (1H, d, J=15.9 Hz), 7.20-7.54 (8H, m), 7.83 (1H, d, J=9.5 Hz), 8.00 (1H, dd, J=8.0, 5.5 Hz), 8.53 (1H, d, J=8.0 Hz), 8.82 (1H, d, J=5.5 Hz), 8.96 (1H, s).

EXAMPLE 89

Synthesis of N-methyl-4-{[N-[5-(1-methyl-2-oxo-1,2-dihydroquinolin-6-yloxy)pentyl]-N-(2-pyridin-3-ylethyl)amino]methyl}benzamide dihydrochloride Diethyl phosphorocyanidate (39.1 mg) was added to a DMF solution (1 ml) of 4-{[N-[5-(1-methyl-2-oxo-1,2-dihydroquinolin-6-yloxy)pentyl]-N-(2-pyridin-3-ylethyl)amino]methyl}benzoic acid (0.10 g), methylamine hydrochloride (27 mg), and triethylamine (0.07 ml), and the mixture was stirred at room temperature overnight. Ice water was added to the reaction mixture, and extraction with ethyl acetate was performed. The organic layer was washed with water and a saturated sodium chloride aqueous solution, in this order, then dried over anhydrous sodium sulfate, and concentrated under reduced pressure. The residue was purified by silica gel column chromatography (ethyl acetate:methanol=10:1). The purified product was concentrated under reduced pressure. A 1N-hydrogen chloride ethanol solution (0.16 ml) was added to the solution of the residue in ethanol, and stirred for 30 minutes at room temperature. The precipitated insoluble matter was collected by filtration, washed with ethyl acetate, and dried to give the title compound (81.3 mg) as a white powder.

1H-NMR (CDCl3) δ ppm: 1.40-1.89 (6H, m), 2.54 (2H, t, J=6.2 Hz), 2.71-2.76 (4H, m), 3.03 (3H, d, J=4.9 Hz), 3.66 (2H, s), 3.73 (3H, s), 3.98 (2H, t, J=6.4 Hz), 6.22-6.31 (1H, m), 6.74 (1H, d, J=9.5 Hz), 7.01 (1H, d, J=2.8 Hz), 7.16-7.20 (2H, m), 7.28-7.33 (3H, m), 7.42-7.68 (4H, m), 8.41-7.46 (2H, m).

EXAMPLE 90

Synthesis of N-ethyl-4-{[N-[5-(1-methyl-2-oxo-1,2-dihydroquinolin-6-yloxy)pentyl]-N-(2-pyridin-3-ylethyl)amino]methyl}benzamide dihydrochloride The synthesis of the title compound was performed in the same manner as in Example 89 using appropriate starting materials.

1H-NMR (DMSO-D6) δ ppm: 1.11 (3H, t, J=7.2 Hz), 1.34-1.50 (2H, m), 1.70-1.96 (4H, m), 3.60 (3H, s), 3.00-4.60 (12H, m), 6.62 (1H, d, J=9.5 Hz), 7.24 (1H, dd, J=9.2, 2.8 Hz), 7.30 (1H, d, J=2.8 Hz), 7.47 (1H, d, J=9.2 Hz), 7.78 (2H, d, J=8.2 Hz), 7.85 (1H, d, J=9.5 Hz), 7.86-7.96 (3H, m), 8.31 (1H, d, J=8.0 Hz), 8.55-8.64 (1H, m), 8.76 (1H, d, J=5.2 Hz), 8.80-8.85 (1H, m).

EXAMPLE 91

Synthesis of N,N-dimethyl-4-{[[5-(1-methyl-2-oxo-1,2-dihydroquinolin-6-yloxy)pentyl](2-pyridin-3-ylethyl)amino]methyl}benzamide dihydrochloride The synthesis of the title compound was performed in the same manner as in Example 89 using appropriate starting materials.

1H-NMR (DMSO-D6) δ ppm: 1.35-1.51 (2H, m), 1.68-1.92 (4H, m), 2.89 (3H, s), 3.00 (3H, s), 3.60 (3H, s), 3.04-4.59 (10H, m), 6.62 (1H, d, J=9.5 Hz), 7.25 (1H, dd, J=9.2, 2.8 Hz), 7.30 (1H, d, J=2.8 Hz), 7.43-7.52 (3H, m), 7.75 (2H, d, J=8.1 Hz), 7.85 (1H, d, J=9.5 Hz), 7.81-7.89 (1H, m), 8.29 (1H, d, J=8.0 Hz), 8.75 (1H, d, J=5.4 Hz), 8.81 (1H, s).

EXAMPLE 92

Synthesis of 1-methyl-6-{5-[N-(2-pyridin-3-ylethyl)-N-(quinolin-2-ylmethyl)amino]pentyloxy}-1H-quinolin-2-one trihydrochloride The synthesis of the title compound was performed in the same manner as in Example 5 using appropriate starting materials.

1H-NMR (DMSO-D6) δ ppm: 1.41-1.60 (2H, m), 1.69-1.88 (2H, m), 1.88-2.06 (2H, m), 3.60 (3H, s), 3.21-4.26 (8H, m), 4.85 (2H, s), 6.61 (1H, d, J=9.5 Hz), 7.22 (1H, dd, J=9.2, 2.8 Hz), 7.29 (1H, d, J=2.8 Hz), 7.45 (1H, d, J=9.2 Hz), 7.65-7.74 (1H, m), 7.79-7.91 (3H, m), 8.02-8.13 (3H, m), 8.53 (1H, d, J=8.5 Hz), 8.59 (1H, d, J=8.2 Hz), 8.86 (1H, d, J=5.4 Hz), 9.00 (1H, s).

EXAMPLE 93

Synthesis of 1-methyl-6-{5-[N-(2-pyridin-3-ylethyl)-N-(quinolin-3-ylmethyl)amino]pentyloxy}-1H-quinolin-2-one trihydrochloride The synthesis of the title compound was performed in the same manner as in Example 5 using appropriate starting materials.

1H-NMR (DMSO-D6) δ ppm: 1.42-1.60 (2H, m), 1.72-1.90 (2H, m), 1.90-2.10 (2H, m), 3.60 (3H, s), 3.14-4.36 (8H, m), 4.76 (2H, s), 6.61 (1H, d, J=9.5 Hz), 7.24 (1H, dd, J=9.2, 2.8 Hz), 7.30 (1H, d, J=2.8 Hz), 7.46 (1H, d, J=9.2 Hz), 7.79-7.90 (2H, m), 7.97-8.08 (2H, m), 8.17 (1H, d, J=7.9 Hz), 8.27 (1H, d, J=8.6 Hz), 8.57 (1H, d, J=8.1 Hz), 8.83 (1H, d, J=5.3 Hz), 8.99 (1H, s), 9.13 (1H, s), 9.45 (1H, d, J=1.7 Hz).

EXAMPLE 94

Synthesis of 1-methyl-6-{5-[N-(2-pyridin-3-ylethyl)-N-(quinolin-4-ylmethyl)amino]pentyloxy}-1H-quinolin-2-one trihydrochloride The synthesis of the title compound was performed in the same manner as in Example 5 using appropriate starting materials.

1H-NMR (DMSO-D6) δ ppm: 1.33-1.52 (2H, m), 1.63-1.82 (2H, m), 1.82-2.04 (2H, m), 3.60 (3H, s), 2.99-4.26 (8H, m), 5.00-5.30 (2H, m), 6.61 (1H, d, J=9.5 Hz), 7.22 (1H, dd, J=9.2, 2.7 Hz), 7.28 (1H, d, J=2.7 Hz), 7.46 (1H, d, J=9.2 Hz), 7.84 (1H, d, J=9.5 Hz), 7.87-7.96 (1H, m), 7.96-8.12 (2H, m), 8.37 (1H, d, J=8.5 Hz), 8.42-8.66 (3H, m), 8.83 (1H, d, J=5.5 Hz), 8.94 (1H, s), 9.25 (1H, d, J=5.1 Hz).

EXAMPLE 95

Synthesis of 1-methyl-6-{5-[N-(naphthalen-2-ylmethyl)-N-(2-pyridin-3-ylethyl)amino]pentyloxy}-1H-quinolin-2-one dihydrochloride The synthesis of the title compound was performed in the same manner as in Example 5 using appropriate starting materials.

1H-NMR (DMSO-D6) δ ppm: 1.31-1.56 (2H, m), 1.67-1.82 (2H, m), 1.82-2.05 (2H, m), 3.05-3.25 (2H, m), 3.60 (3H, s), 3.36-4.20 (6H, m), 4.49-4.75 (2H, m), 6.62 (1H, d, J=9.5 Hz), 7.22 (1H, dd, J=9.2, 2.7 Hz), 7.28 (1H, d, J=2.7 Hz), 7.46 (1H, d, J=9.2 Hz), 7.53-7.65 (2H, m), 7.81-8.08 (6H, m), 8.24 (1H, s), 8.55 (1H, d, J=8.2 Hz), 8.83 (1H, d, J=5.4 Hz), 8.98 (1H, s).

EXAMPLE 96

Synthesis of 1-methyl-6-{5-[N-(pyridin-2-yl)-N-(2-pyridin-3-ylethyl)amino]pentyloxy}-1H-quinolin-2-one trihydrochloride 1-methyl-6-[5-(2-pyridin-3-ylethylamino)pentyloxy]-1H-quinolin-2-one(182 mg), 2-bromopyridine(0.060 ml), palladium acetate (II) (11.2 mg), xantphos (32 mg), and sodium-butoxide(68 mg) were added to toluene(2 ml). The mixture was heated at 80° C. for 10 hours under nitrogen atmosphere. The reaction liquid was cooled to room temperature. Water was added to the reaction mixture, followed by extraction with dichloromethane. The organic layer was dried over anhydrous sodium sulfate. The filtrate was condensed under reduced pressure, and the residue was purified by silica gel column chromatography (ethyl acetate). The purified product was condensed under reduced pressure. A 1N-hydrogen chloride in ethanol solution(0.58 ml) was added to a ethanol solution (5 ml) of the residue, and the liquid was stirred at room temperature, and concentrated under reduced pressure. Ethanol and diethyl ether were added to the residue. The precipitated insoluble matter was separated, washed with diethyl ether, and dried to give the title compound(72 mg) as a yellow powder.

1H-NMR (DMSO-D6) δ ppm: 1.42-1.91 (6H, m), 3.60 (3H, s), 3.09-4.36 (8H, m), 6.62 (1H, d, J=9.5 Hz), 6.98 (1H, t, J=6.6 Hz), 7.24 (1H, dd, J=9.2, 2.8 Hz), 7.29 (1H, d, J=2.8 Hz), 7.38 (1H, d, J=9.1 Hz), 7.46 (1H, d, J=9.2 Hz), 7.85 (1H, d, J=9.5 Hz), 7.98-8.11 (3H, m), 8.76-8.88 (2H, m), 9.16 (1H, s).

EXAMPLE 97

Synthesis of N-[4-(1-methyl-2-oxo-1,2-dihydro-quinolin-6-yloxy)butyl]-N-(2-pyridin-3-ylethyl)benzenesulfonamide hydrochloride The synthesis of the title compound was performed in the same manner as in Example 81 using appropriate starting materials.

1H-NMR (DMSO-D6) δ ppm: 1.50-1.76 (4H, m), 3.00-3.15 (2H, m), 3.15-3.29 (2H, m), 3.40-3.55 (2H, m), 3.60 (3H, s), 3.91-4.01 (2H, m), 6.62 (1H, d, J=9.5 Hz), 7.23 (1H, dd, J=9.1, 2.8 Hz), 7.29 (1H, d, J=2.8 Hz), 7.47 (1H, d, J=9.1 Hz), 7.54-7.73 (3H, m), 7.77-7.89 (3H, m), 8.02 (1H, dd, J=8.0, 5.6 Hz), 8.52 (1H, d, J=8.0 Hz), 8.81 (1H, d, J=5.6 Hz), 8.90 (1H, s).

EXAMPLE 98

Synthesis of N-[5-(1-methyl-2-oxo-1,2-dihydro-quinolin-6-yloxy)pentyl]-N-(2-pyridin-3-ylethyl) phenylmethanesulfonamide hydrochloride The synthesis of the title compound was performed in the same manner as in Example 81 using appropriate starting materials.

1H-NMR (DMSO-D6) δ ppm: 1.21-1.41 (2H, m), 1.41-1.59 (2H, m), 1.59-1.79 (2H, m), 2.91-3.18 (4H, m), 3.30-3.48 (2H, m), 3.59 (3H, s), 3.90-4.08 (2H, m), 4.44 (2H, s), 6.60 (1H, d, J=9.5 Hz), 7.23 (1H, dd, J=9.1, 2.8 Hz), 7.29 (1H, d, J=2.8 Hz), 7.32-7.43 (5H, m), 7.45 (1H, d, J=9.1 Hz), 7.83 (1H, d, J=9.5 Hz), 8.01 (1H, dd, J=8.0, 5.5 Hz), 8.47 (1H, d, J=8.0 Hz), 8.81 (1H, d, J=5.5 Hz), 8.87 (1H, s).

EXAMPLE 99

Synthesis of 2,4,6-trimethyl-N-[5-(1-methyl-2-oxo-1,2-dihydroquinolin-6-yloxy)pentyl]-N-(2-pyridin-3-ylethyl)benzenesulfonamide hydrochloride The synthesis of the title compound was performed in the same manner as in Example 81 using appropriate starting materials.

1H-NMR (DMSO-D6) δ ppm: 1.21-1.41 (2H, m), 1.41-1.75 (4H, m), 2.22 (3H, s), 2.37 (6H, s), 2.93-3.08 (2H, m), 3.26-3.38 (2H, m), 3.45-3.59 (2H, m), 3.60 (3H, s), 3.89-4.02 (2H, m), 6.61 (1H, d, J=9.5 Hz), 6.87 (2H, s), 7.23 (1H, dd, J=9.1, 2.8 Hz), 7.27 (1H, d, J=2.8 Hz), 7.47 (1H, d, J=9.1 Hz), 7.79-7.88 (2H, m), 8.32 (1H, d, J=8.0 Hz), 8.71-8.79 (2H, m).

EXAMPLE 100

Synthesis of N-[5-(1-methyl-2-oxo-1,2-dihydro-quinolin-6-yloxy)pentyl]-N-(2-pyridin-3-ylethyl) biphenyl-4-sulfonamide hydrochloride The synthesis of the title compound was performed in the same manner as in Example 81 using appropriate starting materials.

1H-NMR (DMSO-D6) δ ppm: 1.25-1.45 (2H, m), 1.45-1.63 (2H, m), 1.62-1.81 (2H, m), 3.00-3.18 (2H, m), 3.18-3.30 (2H, m), 3.41-3.57 (2H, m), 3.58 (3H, s), 3.90-4.10 (2H, m), 6.60 (1H, d, J=9.5 Hz), 7.21 (1H, dd, J=9.1, 2.8 Hz), 7.27 (1H, d, J=2.8 Hz), 7.41-7.51 (4H, m), 7.69-7.72 (2H, m), 7.81 (1H, d, J=9.5 Hz), 7.85-7.90 (4H, m), 8.00-8.05 (1H, m), 8.53 (1H, d, J=5.5 Hz), 8.82 (1H, d, J=5.5 Hz), 8.92 (1H, s).

EXAMPLE 101

Synthesis of 6-{3-[N,N-bis(pyridin-3-ylmethyl) amino]propoxy}-1-methyl-1H-quinolin-2-one trihydrochloride The synthesis of the title compound was performed in the same manner as in Example 5 using appropriate starting materials.

1H-NMR (DMSO-D6) δ ppm: 2.05-2.36 (2H, m), 2.84-3.19 (2H, m), 3.60 (3H, s), 3.94-4.12 (2H, m), 4.40-4.71 (4H, m), 6.62 (1H, d, J=9.5 Hz), 7.16 (1H, dd, J=9.2, 2.6 Hz), 7.24 (1H, d, J=2.6 Hz), 7.45 (1H, d, J=9.2 Hz), 7.85 (1H, d, J=9.5 Hz), 8.00 (2H, dd, J=7.7, 5.4 Hz), 8.77 (2H, d, J=7.7 Hz), 8.90 (2H, dd, J=5.4 Hz), 9.14 (2H, s).

EXAMPLE 102

Synthesis of N-[5-(1-methyl-2-oxo-1,2-dihydro-quinolin-6-yloxy)pentyl]-N-(2-pyridin-3-ylethyl) benzamide hydrochloride The synthesis of the title compound was performed in the same manner as in Example 45 using appropriate starting materials.

1H-NMR (DMSO-D6) δ ppm: 1.21-1.44 (2H, m), 1.51-1.75 (4H, m), 2.98-3.19 (2H, m), 3.19-3.40 (2H, m), 3.59 (3H, s), 3.59-3.78 (2H, m), 3.89-4.08 (2H, m), 6.58 (1H, d, J=9.5 Hz), 7.14-7.28 (4H, m), 7.33-7.47 (4H, m), 7.79 (1H, d, J=9.5 Hz), 7.87-7.99 (1H, m), 8.25-8.45 (1H, m), 8.74 (1H, d, J=5.4 Hz), 8.69-8.85 (1H, m).

EXAMPLE 103

Synthesis of 2-methyl-N-[5-(1-methyl-2-oxo-1,2-dihydroquinolin-6-yloxy)pentyl]-N-(2-pyridin-3-ylethyl)benzamide hydrochloride The synthesis of the title compound was performed in the same manner as in Example 45 using appropriate starting materials.

1H-NMR (DMSO-D6) δ ppm: 1.21-1.49 (2H, m), 1.49-1.80 (4H, m), 2.13 (3H, s), 2.89-3.77 (6H, m), 3.58 (3H, s), 3.86-4.10 (2H, m), 6.55 (1H, d, J=9.5 Hz), 7.00 (1H, d, J=7.4 Hz), 7.10-7.28 (5H, m), 7.35-7.43 (1H, m), 7.59-7.73 (1H, m), 7.74 (1H, d, J=9.5 Hz), 7.89-8.23 (1H, m), 8.46-8.69 (1H, m), 8.59 (1H, d, J=5.9 Hz).

EXAMPLE 104

Synthesis of N-[5-(1-methyl-2-oxo-1,2-dihydro-quinolin-6-yloxy)pentyl]-N-(2-pyridin-3-ylethyl)-nicotinamide dihydrochloride The synthesis of the title compound was performed in the same manner as in Example 45 using appropriate starting materials.

1H-NMR (DMSO-D6) δ ppm: 1.28-1.48 (2H, m), 1.52-1.79 (4H, m), 2.78-3.00 (2H, m), 3.22-3.51 (2H, m), 3.58 (3H, s), 3.51-3.67 (2H, m), 3.91-4.06 (2H, m), 6.55 (1H, d, J=9.5 Hz), 7.15-7.28 (3H, m), 7.33-7.42 (2H, m), 7.47-7.55 (1H, m), 7.55-7.63 (1H, m), 7.74 (1H, d, J=9.5 Hz), 8.32-8.44 (3H, m), 8.57 (1H, dd, J=4.8, 1.7 Hz).

EXAMPLE 105

Synthesis of 1-methyl-6-{5-[N-(2-pyridin-3-ylethyl)-N-(thiophen-2-ylmethyl)amino]pentyloxy}-1H-quinolin-2-one dihydrochloride The synthesis of the title compound was performed in the same manner as in Example 5 using appropriate starting materials.

1H-NMR (DMSO-D6) δ ppm: 1.38-1.56 (2H, m), 1.68-2.00 (4H, m), 3.00-3.19 (2H, m), 3.27-3.49 (4H, m), 3.60 (3H, s), 3.92-4.10 (2H, m), 4.67 (2H, s), 6.61 (1H, d, J=9.5 Hz), 7.14 (1H, dd, J=5.1, 3.5 Hz), 7.25 (1H, dd, J=9.1, 2.8 Hz), 7.31 (1H, d, J=2.8 Hz), 7.46 (1H, d, J=9.1 Hz), 7.49-7.54 (1H, m), 7.72 (1H, dd, J=5.1, 1.1 Hz), 7.85 (1H, d, J=9.5 Hz), 8.02 (1H, dd, J=8.0, 5.6 Hz), 8.50 (1H, d, J=8.0 Hz), 8.83 (1H, d, J=5.6 Hz), 8.93 (1H, s).

EXAMPLE 106

Synthesis of 1-methyl-6-{5-[N-(2-pyridin-3-ylethyl)-N-(thiophen-3-ylmethyl)amino]pentyloxy}-1H-quinolin-2-one dihydrochloride The synthesis of the title compound was performed in the same manner as in Example 5 using appropriate starting materials.

1H-NMR (DMSO-D6) δ ppm: 1.35-1.55 (2H, m), 1.69-2.00 (4H, m), 2.95-3.14 (2H, m), 3.29-3.51 (4H, m), 3.60 (3H, s), 3.97-4.10 (2H, m), 4.43 (2H, s), 6.61 (1H, d, J=9.5 Hz), 7.25 (1H, dd, J=9.1, 2.7 Hz), 7.31 (1H, d, J=2.7 Hz), 7.44-7.52 (2H, m), 7.63-7.69 (1H, m), 7.85 (1H, d, J=9.5 Hz), 7.95 (1H, d, J=1.8 Hz), 8.05 (1H, dd, J=8.1, 5.6 Hz), 8.54 (1H, d, J=8.1 Hz), 8.85 (1H, d, J=5.6 Hz), 8.96 (1H, s).

EXAMPLE 107

Synthesis of 1-methyl-6-{5-[N-(pyridin-3-yl)-N-(2-pyridin-3-ylethyl)amino]pentyloxy}-1H-quinolin-2-one trihydrochloride The synthesis of the title compound was performed in the same manner as in Example 96 using appropriate starting materials.

1H-NMR (DMSO-D6) δ ppm: 1.40-1.55 (4H, m), 1.66-1.87 (2H, m), 2.98-3.15 (2H, m), 3.32-4.10 (6H, m), 3.59 (3H, s), 6.61 (1H, d, J=9.5 Hz), 7.22 (1H, dd, J=9.1, 2.9 Hz), 7.28 (1H, d, J=2.9 Hz), 7.45 (1H, d, J=9.1 Hz), 7.77 (1H, dd, J=9.0, 5.0 Hz), 7.83 (1H, d, J=9.5 Hz), 7.88-8.09 (3H, m), 8.35 (1H, d, J=2.6 Hz), 8.61 (1H, d, J=8.1 Hz), 8.81 (1H, d, J=5.5 Hz), 9.01 (1H, s).

EXAMPLE 108

Synthesis of N-[3-(1-methyl-2-oxo-1,2-dihydro-quinolin-6-yloxy)propyl]-N-(pyridin-3-ylmethyl) benzamide hydrochloride The synthesis of the title compound was performed in the same manner as in Example 45 using appropriate starting materials.

1H-NMR (DMSO-D6) δ ppm: 1.95-2.10 (2H, m), 3.50 (2H, t, J=7.2 Hz), 3.58 (3H, s), 3.75-4.18 (2H, m), 4.77 (2H, s), 6.57 (1H, d, J=9.5 Hz), 7.08 (1H, dd, J=9.1, 2.7 Hz), 7.12 (1H, d, J=2.7 Hz), 7.35-7.45 (6H, m), 7.70-7.79 (1H, m), 7.75 (1H, d, J=9.5 Hz), 8.18 (1H, d, J=6.9 Hz), 8.67 (1H, d, J=5.2 Hz), 8.71 (1H, s).

EXAMPLE 109

Synthesis of N-[3-(1-methyl-2-oxo-1,2-dihydro-quinolin-6-yloxy)propyl]-N-(2-pyridin-3-ylethyl) benzenesulfonamide hydrochloride The synthesis of the title compound was performed in the same manner as in Example 81 using appropriate starting materials.

1H-NMR (DMSO-D6) δ ppm: 1.82-2.00 (2H, m), 3.02-3.15 (2H, m), 3.29-3.39 (2H, m), 3.45-3.54 (2H, m), 3.60 (3H, s), 3.97 (2H, t, J=6.0 Hz), 6.62 (1H, d, J=9.5 Hz), 7.19-7.27 (2H, m), 7.47 (1H, d, J=9.1 Hz), 7.53-7.71 (3H, m), 7.77-7.83 (2H, m), 7.85 (1H, d, J=9.5 Hz), 8.02 (1H, dd, J=8.0, 5.5 Hz), 8.53 (1H, d, J=8.0 Hz), 8.82 (1H, d, J=5.5 Hz), 8.91 (1H, s).

EXAMPLE 110

Synthesis of 1-methyl-6-{3-[N-(2-pyridin-3-ylethyl)-N-(pyridin-3-ylmethyl)amino]propoxy}-1H-quinolin-2-one trihydrochloride The synthesis of the title compound was performed in the same manner as in Example 5 using appropriate starting materials.

1H-NMR (DMSO-D6) δ ppm: 2.20-2.45 (2H, m), 3.18-3.35 (2H, m), 3.35-3.53 (4H, m), 3.60 (3H, s), 4.01-4.20 (2H, m), 4.50-4.78 (2H, m), 6.63 (1H, d, J=9.5 Hz), 7.23 (1H, dd, J=9.1, 2.8 Hz), 7.30 (1H, d, J=2.8 Hz), 7.48 (1H, d, J=9.1 Hz), 7.82-7.93 (1H, m), 7.85 (1H, d, J=9.5 Hz), 8.01 (1H, dd, J=8.2, 5.8 Hz), 8.52 (1H, d, J=8.2 Hz), 8.67 (1H, d, J=7.0 Hz), 8.80-8.90 (2H, m), 8.95 (1H, s), 9.14 (1H, s).

EXAMPLE 111

Synthesis of N-[5-(1-methyl-2-oxo-1,2-dihydro-quinolin-6-yloxy)pentyl]-N-(2-pyridin-3-ylethyl) ethanesulfonamide hydrochloride The synthesis of the title compound was performed in the same manner as in Example 81 using appropriate starting materials.

1H-NMR (DMSO-D6) δ ppm: 1.15 (3H, t, J=7.4 Hz), 1.30-1.49 (2H, m), 1.49-1.65 (2H, m), 1.65-1.82 (2H, m), 2.80-2.93 (2H, m), 3.14-3.50 (6H, m), 3.59 (3H, s), 4.02 (2H, t, J=6.4 Hz), 6.60 (1H, d, J=9.5 Hz), 7.23 (1H, dd, J=9.2, 2.8 Hz), 7.29 (1H, d, J=2.8 Hz), 7.45 (1H, d, J=9.2 Hz), 7.39-7.48 (1H, m), 7.83 (1H, d, J=9.5 Hz), 7.78-7.85 (1H, m), 8.48 (1H, d, J=5.2 Hz), 8.54 (1H, s).

EXAMPLE 112

Synthesis of N-[5-(1-methyl-2-oxo-1,2-dihydro-quinolin-6-yloxy)pentyl]-N-(2-pyridin-3-ylethyl) cyclohexylmethanesulfonamide hydrochloride The synthesis of the title compound was performed in the same manner as in Example 81 using appropriate starting materials.

1H-NMR (DMSO-D6) δ ppm: 0.90-1.89 (17H, m), 2.75-2.95 (4H, m), 3.08-3.49 (4H, m), 3.59 (3H, s), 4.02 (2H, t, J=6.5 Hz), 6.60 (1H, d, J=9.5 Hz), 7.24 (1H, dd, J=9.0, 2.8 Hz), 7.29 (1H, d, J=2.8 Hz), 7.42 (1H, dd, J=7.9, 4.9 Hz), 7.45 (1H, d, J=9.0 Hz), 7.77-7.82 (1H, m), 7.83 (1H, d, J=9.5 Hz), 8.48 (1H, dd, J=4.9, 1.6 Hz), 8.53 (1H, d, J=1.6 Hz).

EXAMPLE 113

Synthesis of N-[3-(1-methyl-2-oxo-1,2-dihydro-quinolin-6-yloxy)propyl]-N-(pyridin-3-ylmethyl)benzenesulfonamide The synthesis of the title compound was performed in the same manner as in Example 81 using appropriate starting materials.

1H-NMR (DMSO-D6) δ ppm: 1.70-1.91 (2H, m), 3.36 (2H, t, J=7.7 Hz), 3.60 (3H, s), 3.89 (2H, t, J=6.0 Hz), 4.60 (2H, s), 6.62 (1H, d, J=9.5 Hz), 7.11-7.19 (2H, m), 7.44 (1H, d, J=8.8 Hz), 7.60-7.77 (3H, m), 7.83 (1H, d, J=9.5 Hz), 7.92 (2H, d, J=7.2 Hz), 8.03 (1H, dd, J=8.0, 5.6 Hz), 8.55 (1H, d, J=8.0 Hz), 8.83 (1H, d, J=5.6 Hz), 8.89 (1H, s).

EXAMPLE 114

Synthesis of N-[2-(1-methyl-2-oxo-1,2-dihydro-quinolin-6-yloxy)ethyl]-2-nitro-N-(2-pyridin-3-yl-ethyl)benzenesulfonamide hydrochloride The synthesis of the title compound was performed in the same manner as in Example 2 using appropriate starting materials.

1H-NMR (DMSO-D6) δ ppm: 3.10-3.25 (2H, m), 3.60 (3H, s), 3.70-3.90 (4H, m), 4.11-4.28 (2H, m), 6.62 (1H, d, J=9.5 Hz), 7.10 (1H, dd, J=9.2, 2.9 Hz), 7.23 (1H, d, J=2.9 Hz), 7.44 (1H, d, J=9.2 Hz), 7.74-7.91 (3H, m), 7.93-8.09 (3H, m), 8.53 (1H, d, J=8.1 Hz), 8.79 (1H, d, J=5.5 Hz), 8.93 (1H, s).

EXAMPLE 115

Synthesis of N-[3-(1-methyl-2-oxo-1,2-dihydro-quinolin-6-yloxy)propyl]-N-(2-pyridin-3-ylethyl)phenylmethanesulfonamide hydrochloride The synthesis of the title compound was performed in the same manner as in Example 81 using appropriate starting materials.

1H-NMR (DMSO-D6) δ ppm: 1.88-2.04 (2H, m), 3.00-3.14 (2H, m), 3.23-3.39 (2H, m), 3.39-3.51 (2H, m), 3.60 (3H, s), 3.89-4.09 (2H, m), 4.47 (2H, s), 6.62 (1H, d, J=9.5 Hz), 7.21-7.30 (2H, m), 7.33-7.44 (5H, m), 7.48 (1H, d, J=9.0 Hz), 7.86 (1H, d, J=9.5 Hz), 8.02 (1H, dd, J=8.0, 5.5 Hz), 8.47 (1H, d, J=8.0 Hz), 8.81 (1H, d, J=5.5 Hz), 8.87 (1H, s).

EXAMPLE 116

Synthesis of N-[3-(1-methyl-2-oxo-1,2-dihydro-quinolin-6-yloxy)propyl]-N-(pyridin-3-ylmethyl)phenylmethanesulfonamide hydrochloride The synthesis of the title compound was performed in the same manner as in Example 81 using appropriate starting materials.

1H-NMR (DMSO-D6) δ ppm: 1.71-1.89 (2H, m), 3.24-3.41 (2H, m), 3.59 (3H, s), 3.88 (2H, t, J=6.0 Hz), 4.55 (2H, s), 4.67 (2H, s), 6.61 (1H, d, J=9.5 Hz), 7.09-7.21 (2H, m), 7.34-7.51 (6H, m), 7.83 (1H, d, J=9.5 Hz), 7.94-8.06 (1H, m), 8.50 (1H, d, J=7.9 Hz), 8.81 (1H, d, J=5.1 Hz), 8.85 (1H, s).

EXAMPLE 117

Synthesis of N-[2-(1-methyl-2-oxo-1,2-dihydro-quinolin-6-yloxy)ethyl]-N-(2-pyridin-3-ylethyl)phenylmethanesulfonamide hydrochloride The synthesis of the title compound was performed in the same manner as in Example 81 using appropriate starting materials.

1H-NMR (DMSO-D6) δ ppm: 3.01-3.19 (2H, m), 3.40-3.61 (4H, m), 3.60 (3H, s), 4.00-4.15 (2H, m), 4.54 (2H, s), 6.63 (1H, d, J=9.5 Hz), 7.26 (1H, dd, J=9.0, 2.8 Hz), 7.30 (1H, d, J=2.8 Hz), 7.32-7.44 (5H, m), 7.48 (1H, d, J=9.0 Hz), 7.86 (1H, d, J=9.5 Hz), 8.02 (1H, dd, J=8.1, 5.6 Hz), 8.49 (1H, d, J=8.1 Hz), 8.80 (1H, d, J=5.6 Hz), 8.87 (1H, s).

EXAMPLE 118

Synthesis of 1-methyl-6-{2-[N-(2-methylbenzyl)-N-(2-pyridin-3-ylethyl)amino]ethoxy}-1H-quinolin-2-one dihydrochloride The synthesis of the title compound was performed in the same manner as in Example 5 using appropriate starting materials.

1H-NMR (DMSO-D6) δ ppm: 2.48 (3H, s), 3.35-3.84 (6H, m), 3.61 (3H, s), 4.59 (4H, s), 6.64 (1H, d, J=9.5 Hz), 7.23-7.41 (5H, m), 7.50 (1H, d, J=9.2 Hz), 7.80 (1H, d, J=7.4 Hz), 7.86 (1H, d, J=9.5 Hz), 8.03 (1H, dd, J=8.0, 5.5 Hz), 8.53 (1H, d, J=8.0 Hz), 8.85 (1H, d, J=5.5 Hz), 8.96 (1H, s).

EXAMPLE 119

Synthesis of 2-methyl-N-[3-(1-methyl-2-oxo-1,2-dihydroquinolin-6-yloxy)propyl]-N-(pyridin-3-ylmethyl)benzamide hydrochloride The synthesis of the title compound was performed in the same manner as in Example 45 using appropriate starting materials.

1H-NMR (DMSO-D6) δ ppm: 1.80-2.06 (2H, m), 2.17 (3H, s), 3.26-3.49 (2H, m), 3.59 (3H, s), 3.78-4.00 (2H, m), 4.80-5.01 (2H, m), 6.58 (1H, d, J=9.5 Hz), 6.91-7.51 (7H, m), 7.77 (1H, d, J=9.5 Hz), 7.89-8.11 (1H, m), 8.44-8.65 (1H, m), 8.73-8.90 (1H, m), 8.90-9.03 (1H, m).

EXAMPLE 120

Synthesis of 6-{2-[N,N-bis-(pyridin-3-ylmethyl)amino]ethoxy}-1-methyl-1H-quinolin-2-one trihydrochloride The synthesis of the title compound was performed in the same manner as in Example 5 using appropriate starting materials.

1H-NMR (DMSO-D6) δ ppm: 2.85-3.15 (2H, m), 3.61 (3H, s), 3.89-4.41 (6H, m), 6.62 (1H, d, J=9.5 Hz), 7.25-7.34 (2H, m), 7.46 (1H, d, J=8.8 Hz), 7.83 (1H, d, J=9.5 Hz), 7.89-8.01 (2H, m), 8.50-8.60 (2H, m), 8.80 (2H, d, J=5.2 Hz), 8.95 (2H, s).

EXAMPLE 121

Synthesis of 6-{2-[N,N-bis-(pyridin-4-ylmethyl) amino]ethoxy}-1-methyl-1H-quinolin-2-one trihydrochloride The synthesis of the title compound was performed in the same manner as in Example 5 using appropriate starting materials.

1H-NMR (DMSO-D6) δ ppm: 2.91-3.05 (2H, m), 3.60 (3H, s), 4.14 (4H, s), 4.12-4.29 (2H, m), 6.62 (1H, d, J=9.5 Hz), 7.21-7.27 (2H, m), 7.41-7.48 (1H, m), 7.80 (1H, d, J=9.5 Hz), 8.09 (4H, d, J=6.5 Hz), 8.84 (4H, d, J=6.5 Hz).

EXAMPLE 122

Synthesis of 6-[3-[N,N-bis-(pyridin-4-ylmethyl) amino]propoxy]-1-methyl-1H-quinolin-2-one trihydrochloride The synthesis of the title compound was performed in the same manner as in Example 5 using appropriate starting materials.

1H-NMR (DMSO-D6) δ ppm: 1.96-2.19 (2H, m), 2.70-2.98 (2H, m), 3.60 (3H, s), 3.92-4.10 (2H, m), 4.10-4.43 (4H, m), 6.62 (1H, d, J=9.5 Hz), 7.08 (1H, dd, J=9.2, 2.8 Hz), 7.23 (1H, d, J=2.8 Hz), 7.44 (1H, d, J=9.2 Hz), 7.86 (1H, d, J=9.5 Hz), 8.23 (4H, d, J=6.0 Hz), 8.88 (4H, d, J=6.0 Hz).

EXAMPLE 123

Synthesis of N-[2-(1-methyl-2-oxo-1,2-dihydro-quinolin-6-yloxy)ethyl]-N-(2-pyridin-3-ylethyl)benzenesulfonamide hydrochloride The synthesis of the title compound was performed in the same manner as in Example 81 using appropriate starting materials.

1H-NMR (DMSO-D6) δ ppm: 3.07-3.21 (2H, m), 3.49-3.69 (4H, m), 3.60 (3H, s), 4.05-4.23 (2H, m), 6.63 (1H, d, J=9.5 Hz), 7.17 (1H, dd, J=9.1, 2.9 Hz), 7.25 (1H, d, J=2.9 Hz), 7.46 (1H, d, J=9.1 Hz), 7.53-7.72 (3H, m), 7.79-7.89 (3H, m), 8.01 (1H, dd, J=8.1, 5.6 Hz), 8.53 (1H, d, J=8.1 Hz), 8.79 (1H, d, J=5.6 Hz), 8.89 (1H, s).

EXAMPLE 124

Synthesis of 2-methyl-N-[3-(1-methyl-2-oxo-1,2-dihydroquinolin-6-yloxy)propyl]-N-(2-pyridin-3-ylethyl)benzamide hydrochloride The synthesis of the title compound was performed in the same manner as in Example 45 using appropriate starting materials.

1H-NMR (DMSO-D6) δ ppm: 1.82-2.00 (2H, m), 2.12 (3H, s), 2.88-3.50 (6H, m), 3.59 (3H, s), 4.04-4.30 (2H, m), 6.59 (1H, d, J=9.5 Hz), 6.96-7.33 (6H, m), 7.33-7.50 (1H, m), 7.69-7.97 (2H, m), 8.41-8.52 (1H, m), 8.62-8.78 (1H, m), 8.85-8.93 (1H, m).

EXAMPLE 125

Synthesis of N-[3-(1-methyl-2-oxo-1,2-dihydro-quinolin-6-yloxy)propyl]-2-nitro-N-{2-[4-(pyridin-3-ylmethoxy)piperidin-1-yl]ethyl}benzenesulfonamide Sodium iodide (2.93 g) was added to a acetonitrile solution (20 ml) of methanesulfonic acid 2-[[3-(1-methyl-2-oxo-1,2-dihydro-quinolin-6-yloxy)propyl]-(2-nitro-benzenesulfonyl)amino]-ethyl ester (4.37 g), and stirred at 60° C. for 1 hours. The reaction mixture was cooled to room temperature. 4-(pyridin-3-ylmethoxy)piperidine (1.87 g) and N-ethyl diisopropylamine (4.23 ml) were then added to the reaction mixture and stirred at 60° C. for 5 hours. The reaction mixture was cooled to room temperature, and concentrated under reduced pressure. Water was added to the residue, and extraction with dichloromethane was performed. The organic layer was washed with water, and a saturated sodium chloride aqueous solution, in this order. The organic layer was dried over anhydrous sodium sulfate, and concentrated under reduced pressure. The residue was purified by silica gel column chromatography (ethyl acetate:methanol=1:0→10:1). The purified product was concentrated under reduced pressure to give the title compound (3.48 g) as a yellow solid.

1H-NMR (CDCl3) δ ppm: 1.55-1.74 (2H, m), 1.82-1.99 (2H, m), 2.04-2.29 (4H, m), 2.50-2.61 (2H, m), 2.69-2.82 (2H, m), 3.35-3.52 (3H, m), 3.52-3.68 (2H, m), 3.70 (3H, s), 4.01 (2H, t, J=5.9 Hz), 4.54 (2H, s), 6.72 (1H, d, J=9.5 Hz), 6.93 (1H, d, J=2.8 Hz), 7.12 (1H, dd, J=9.2, 2.8 Hz), 7.24-7.32 (2H, m), 7.55-7.70 (5H, m), 8.04-8.13 (1H, m), 8.53 (1H, dd, J=4.8, 1.7 Hz), 8.57 (1H, d, J=1.7 Hz).

EXAMPLE 126

Synthesis of 1-methyl-6-{5-[N-(3-methylbenzyl)-N-(2-pyridin-3-ylethyl)amino]pentyloxy}-1H-quinolin-2-one dihydrochloride The synthesis of the title compound was performed in the same manner as in Example 5 using appropriate starting materials.

1H-NMR (DMSO-D6) δ ppm: 1.33-1.51 (2H, m), 1.69-1.99 (4H, m), 2.32 (3H, s), 2.96-3.15 (2H, m), 3.29-3.50 (4H, m), 3.60 (3H, s), 3.95-4.10 (2H, m), 4.26-4.50 (2H, m), 6.61 (1H, d, J=9.5 Hz), 7.21-7.38 (4H, m), 7.43-7.55 (3H, m), 7.85 (1H, d, J=9.5 Hz), 8.01 (1H, dd, J=8.0, 5.6 Hz), 8.48 (1H, d, J=8.0 Hz), 8.83 (1H, d, J=5.6 Hz), 8.93 (1H, s).

EXAMPLE 127

Synthesis of 1-methyl-6-{5-[N-(4-methylbenzyl)-N-(2-pyridin-3-ylethyl)amino]pentyloxy}-1H-quinolin-2-one dihydrochloride The synthesis of the title compound was performed in the same manner as in Example 5 using appropriate starting materials.

1H-NMR (DMSO-D6) δ ppm: 1.35-1.54 (2H, m), 1.66-2.00 (4H, m), 2.32 (3H, s), 2.94-3.11 (2H, m), 3.28-3.51 (4H, m), 3.60 (3H, s), 4.03 (2H, t, J=6.3 Hz), 4.24-4.50 (2H, m), 6.61 (1H, d, J=9.5 Hz), 7.19-7.34 (4H, m), 7.46 (1H, d, J=9.1 Hz), 7.59 (2H, d, J=8.0 Hz), 7.85 (1H, d, J=9.5 Hz), 8.04 (1H, dd, J=8.1, 5.5 Hz), 8.53 (1H, d, J=8.1 Hz), 8.85 (1H, d, J=5.5 Hz), 8.95 (1H, s).

EXAMPLE 128

Synthesis of 6-{5-[N-(2-methoxybenzyl)-N-(2-pyridin-3-ylethyl)amino]pentyloxy}-1-methyl-1H-quinolin-2-one dihydrochloride The synthesis of the title compound was performed in the same manner as in Example 5 using appropriate starting materials.

1H-NMR (DMSO-D6) δ ppm: 1.33-1.51 (2H, m), 1.68-1.97 (4H, m), 2.96-3.20 (2H, m), 3.28-3.49 (2H, m), 3.59 (3H, s), 3.85 (3H, s), 3.95-4.09 (2H, m), 4.25-4.50 (2H, m), 6.61 (1H, d, J=9.5 Hz), 6.98-7.06 (1H, m), 7.09-7.16 (1H, m), 7.24 (1H, dd, J=9.1, 2.8 Hz), 7.30 (1H, d, J=2.8 Hz), 7.42-7.50 (2H, m), 7.61-7.69 (1H, m), 7.84 (1H, d, J=9.5 Hz), 7.97-8.06 (1H, m), 8.42 (1H, d, J=8.1 Hz), 8.83 (1H, d, J=5.3 Hz), 8.93 (1H, s).

EXAMPLE 129

Synthesis of 6-{5-[N-(2-chlorobenzyl)-N-(2-pyridin-3-ylethyl)amino]pentyloxy}-1-methyl-1H-quinolin-2-one dihydrochloride The synthesis of the title compound was performed in the same manner as in Example 5 using appropriate starting materials.
1H-NMR (DMSO-D6) δ ppm: 1.36-1.55 (2H, m), 1.69-2.00 (4H, m), 3.05-3.22 (2H, m), 3.34-3.64 (4H, m), 3.59 (3H, s), 4.03 (2H, t, J=6.3 Hz), 4.46-4.72 (2H, m), 6.61 (1H, d, J=9.5 Hz), 7.24 (1H, dd, J=9.1, 2.8 Hz), 7.29 (1H, d, J=2.8 Hz), 7.40-7.55 (3H, m), 7.55-7.64 (1H, m), 7.84 (1H, d, J=9.5 Hz), 7.96-8.09 (2H, m), 8.49 (1H, d, J=8.0 Hz), 8.83 (1H, d, J=5.6 Hz), 8.93 (1H, s).

EXAMPLE 130

Synthesis of 1-methyl-6-{3-[N-(2-pyridin-3-ylethyl)-N-(quinolin-4-ylmethyl)amino]propoxy}-1H-quinolin-2-one trihydrochloride The synthesis of the title compound was performed in the same manner as in Example 5 using appropriate starting materials.
1H-NMR (CDCl3) δ ppm: 1.84-2.00 (2H, m), 2.79 (2H, t, J=6.7 Hz), 2.84-2.96 (4H, m), 3.71 (3H, s), 3.85 (2H, t, J=6.0 Hz), 4.10 (2H, s), 6.72 (1H, d, J=9.5 Hz), 6.77 (1H, d, J=2.8 Hz), 6.98 (1H, dd, J=9.2, 2.8 Hz), 7.09-7.16 (1H, m), 7.24 (1H, d, J=9.2 Hz), 7.33 (1H, d, J=4.4 Hz), 7.35-7.45 (2H, m), 7.57 (1H, d, J=9.5 Hz), 7.57-7.66 (1H, m), 8.00-8.11 (2H, m), 8.41-8.47 (2H, m), 8.74 (1H, d, J=4.4 Hz).

EXAMPLE 131

Synthesis of 1-methyl-6-{2-[N-(2-pyridin-3-ylethyl)-N-(quinolin-4-ylmethyl)amino]ethoxy}-1H-quinolin-2-one trihydrochloride The synthesis of the title compound was performed in the same manner as in Example 5 using appropriate starting materials.
1H-NMR (CDCl3) δ ppm: 2.72-2.86 (2H, m), 2.86-3.01 (2H, m), 3.01-3.15 (2H, m), 3.69 (3H, s), 4.00-4.14 (2H, m), 4.22 (2H, s), 6.70 (1H, d, J=9.5 Hz), 6.89 (1H, d, J=2.8 Hz), 7.03-7.13 (2H, m), 7.26 (1H, d, J=9.2 Hz), 7.33-7.48 (3H, m), 7.55 (1H, d, J=9.5 Hz), 7.64-7.72 (1H, m), 8.05-8.15 (2H, m), 8.38 (1H, dd, J=4.7, 1.8 Hz), 8.43 (1H, d, J=1.8 Hz), 8.79 (1H, d, J=4.4 Hz).

EXAMPLE 132

Synthesis of 1-methyl-6-[3-N-(pyridin-3-ylmethyl)-N-(quinolin-4-ylmethyl)amino]propoxy]-1H-quinolin-2-one trihydrochloride The synthesis of the title compound was performed in the same manner as in Example 5 using appropriate starting materials.

1H-NMR (DMSO-D6) δ ppm: 1.93-2.25 (2H, m), 2.63-3.08 (2H, m), 3.62 (3H, s), 3.85-4.79 (6H, m), 6.61 (1H, d, J=9.5 Hz), 6.99 (1H, dd, J=9.2, 2.5 Hz), 7.07 (1H, d, J=2.5 Hz), 7.40 (1H, d, J=9.2 Hz), 7.79 (1H, d, J=9.5 Hz), 7.85-8.08 (3H, m), 8.19-8.36 (1H, m), 8.33 (1H, d, J=8.4 Hz), 8.41-8.52 (1H, m), 8.58-8.71 (1H, m), 8.83 (1H, d, J=5.4 Hz), 8.95-9.07 (1H, m), 9.16 (1H, d, J=5.4 Hz).

EXAMPLE 133

Synthesis of N-[2-(1-methyl-2-oxo-1,2-dihydroquinolin-6-yloxy)ethyl]-2-nitro-N-{2-[4-(pyridin-3-ylmethoxy)piperidin-1-yl]ethyl}benzenesulfonamide The synthesis of the title compound was performed in the same manner as in Example 2 using appropriate starting materials.
1H-NMR (CDCl3) δ ppm: 1.52-1.79 (2H, m), 1.79-1.98 (2H, m), 2.11-2.29 (2H, m), 2.59 (2H, t, J=6.8 Hz), 2.67-2.81 (2H, m), 3.35-3.49 (1H, m), 3.57 (2H, t, J=6.8 Hz), 3.70 (3H, s), 3.81 (2H, t, J=5.5 Hz), 4.21 (2H, t, J=5.5 Hz), 4.53 (2H, s), 6.72 (1H, d, J=9.5 Hz), 6.96 (1H, d, J=2.8 Hz), 7.09 (1H, dd, J=9.1, 2.8 Hz), 7.25-7.32 (2H, m), 7.58 (1H, d, J=9.5 Hz), 7.62-7.72 (4H, m), 8.10-8.16 (1H, m), 8.53 (1H, dd, J=4.8, 1.6 Hz), 8.57 (1H, d, J=1.6 Hz).

EXAMPLE 134

Synthesis of 1-methyl-6-[3-[N-(2-methylbenzyl)-N-{2-[4-(pyridin-3-ylmethoxy)piperidin-1-yl]ethyl}amino]propoxy]-1H-quinolin-2-one trihydrochloride The synthesis of the title compound was performed in the same manner as in Example 5 using appropriate starting materials.
1H-NMR (DMSO-D6) δ ppm: 1.70-2.40 (6H, m), 2.45 (3H, s), 2.78-3.95 (11H, m), 3.60 (3H, s), 4.01-4.19 (2H, m), 4.38-4.60 (2H, m), 4.71 (2H, s), 6.62 (1H, d, J=9.5 Hz), 7.18 (1H, dd, J=9.3, 2.8 Hz), 7.26 (1H, d, J=2.8 Hz), 7.21-7.39 (3H, m), 7.47 (1H, d, J=9.3 Hz), 7.61-7.78 (1H, m), 7.84 (1H, d, J=9.5 Hz), 7.85-7.99 (1H, m), 8.30-8.48 (1H, m), 8.80 (1H, d, J=4.7 Hz), 8.76-8.94 (1H, m).

EXAMPLE 135

Synthesis of 1-methyl-6-[3-[N-{2-[4-(pyridin-3-ylmethoxy)piperidin-1-yl]ethyl}-N-(pyridin-3-ylmethyl)amino]propoxy]-1H-quinolin-2-one tetrahydrochloride The synthesis of the title compound was performed in the same manner as in Example 5 using appropriate starting materials.
1H-NMR (DMSO-D6) δ ppm: 1.79-2.47 (6H, m), 3.01-3.98 (11H, m), 3.60 (3H, s), 3.98-4.21 (2H, m), 4.73 (2H, s), 4.78 (2H, s), 6.62 (1H, d, J=9.5 Hz), 7.24 (1H, dd, J=9.2, 2.9 Hz), 7.32 (1H, d, J=2.9 Hz), 7.48 (1H, d, J=9.2 Hz), 7.87 (1H, d, J=9.5 Hz), 8.04-8.14 (2H, m), 8.55-8.70 (1H, m), 8.87-9.04 (4H, m), 9.30 (1H, s).

EXAMPLE 136

Synthesis of 1-methyl-6-[3-[N-{2-[4-(pyridin-3-ylmethoxy)piperidin-1-yl]ethyl}-N-(pyridin-4-ylmethyl)amino]propoxy]-1H-quinolin-2-one tetrahydrochloride The synthesis of the title compound was performed in the same manner as in Example 5 using appropriate starting materials.

1H-NMR (DMSO-D6) δ ppm: 1.79-2.35 (6H, m), 2.90-3.95 (11H, m), 3.60 (3H, s), 3.95-4.15 (2H, m), 4.40-4.69 (2H, m), 4.76 (2H, s), 6.62 (1H, d, J=9.5 Hz), 7.19 (1H, dd, J=9.1, 2.5 Hz), 7.28 (1H, d, J=2.5 Hz), 7.46 (1H, d, J=9.1 Hz), 7.86 (1H, d, J=9.5 Hz), 7.96-8.12 (1H, m), 8.33 (2H, s), 8.60 (1H, d, J=7.1 Hz), 8.83-9.01 (4H, m).

EXAMPLE 137

Synthesis of 1-methyl-6-[2-(N-(2-methylbenzyl)-N-{2-[4-(pyridin-3-ylmethoxy)piperidin-1-yl]ethyl}amino)ethoxy]-1H-quinolin-2-one trihydrochloride The synthesis of the title compound was performed in the same manner as in Example 5 using appropriate starting materials.

1H-NMR (DMSO-D6) δ ppm: 1.75-2.29 (4H, m), 2.46 (3H, s), 2.92-3.95 (11H, m), 3.61 (3H, s), 4.38-4.69 (4H, m), 4.75 (2H, s), 6.63 (1H, d, J=9.5 Hz), 7.23-7.42 (5H, m), 7.50 (1H, d, J=9.0 Hz), 7.73-7.85 (1H, m), 7.84 (1H, d, J=9.5 Hz), 8.06 (1H, dd, J=7.5, 5.6 Hz), 8.56 (1H, d, J=7.5 Hz), 8.87 (1H, d, J=5.6 Hz), 8.94 (1H, s).

EXAMPLE 138

Synthesis of 1-methyl-6-[2-(N-{2-[4-(pyridin-3-ylmethoxy)piperidin-1-yl]ethyl}-N-(pyridin-3-ylmethyl)amino)ethoxy]-1H-quinolin-2-one tetrahydrochloride The synthesis of the title compound was performed in the same manner as in Example 5 using appropriate starting materials.

1H-NMR (CDCl3) δ ppm: 1.59-1.74 (2H, m), 1.83-1.99 (2H, m), 2.09-2.25 (2H, m), 2.46-2.60 (2H, m), 2.70-2.85 (4H, m), 2.94-3.06 (2H, m), 3.39-3.50 (1H, m), 3.69 (3H, s), 3.78 (2H, s), 4.08 (2H, t, J=5.7 Hz), 4.54 (2H, s), 6.70 (1H, d, J=9.5 Hz), 6.96 (1H, d, J=2.8 Hz), 7.15 (1H, dd, J=9.2, 2.8 Hz), 7.20-7.31 (3H, m), 7.58 (1H, d, J=9.5 Hz), 7.65-7.76 (2H, m), 8.49 (1H, dd, J=4.8, 1.7 Hz), 8.52 (1H, dd, J=4.8, 1.7 Hz), 8.57 (1H, d, J=1.7 Hz), 8.60 (1H, d, J=1.7 Hz).

EXAMPLE 139

Synthesis of 1-methyl-6-[2-(N-{2-[4-(pyridin-3-ylmethoxy)piperidin-1-yl]ethyl}-N-(pyridin-4-ylmethyl)amino)ethoxy]-1H-quinolin-2-one tetrahydrochloride The synthesis of the title compound was performed in the same manner as in Example 5 using appropriate starting materials.

1H-NMR (CDCl3) δ ppm: 1.55-1.74 (2H, m), 1.82-1.96 (2H, m), 2.08-2.22 (2H, m), 2.45-2.57 (2H, m), 2.65-2.89 (4H, m), 2.98 (2H, t, J=5.7 Hz), 3.35-3.49 (1H, m), 3.69 (3H, s), 3.79 (2H, s), 4.09 (2H, t, J=5.7 Hz), 4.54 (2H, s), 6.70 (1H, d, J=9.5 Hz), 6.95 (1H, d, J=2.8 Hz), 7.14 (1H, dd, J=9.2, 2.8 Hz), 7.24-7.36 (4H, m), 7.58 (1H, d, J=9.5 Hz), 7.68 (1H, dt, J=7.8, 1.7 Hz), 8.48-8.55 (3H, m), 8.57 (1H, d, J=1.7 Hz).

EXAMPLE 140

Synthesis of 6-[4-(N,N-bis-(pyridin-3-ylmethyl)amino)butoxy]-1-methyl-1H-quinolin-2-one trihydrochloride The synthesis of the title compound was performed in the same manner as in Example 5 using appropriate starting materials.

1H-NMR (DMSO-D6) δ ppm: 1.60-1.80 (2H, m), 1.80-2.05 (2H, m), 2.80-3.18 (2H, m), 3.60 (3H, s), 3.69-4.71 (6H, m), 6.62 (1H, d, J=9.5 Hz), 7.20 (1H, dd, J=9.1, 2.8 Hz), 7.25 (1H, d, J=2.8 Hz), 7.47 (1H, d, J=9.1 Hz), 7.79-7.91 (2H, m), 7.85 (1H, d, J=9.5 Hz), 8.58 (2H, d, J=8.0 Hz), 8.82 (2H, d, J=4.4 Hz), 9.03 (2H, s).

EXAMPLE 141

Synthesis of 6-[4-(N,N-bis-(pyridin-4-ylmethyl)amino)butoxy]-1-methyl-1H-quinolin-2-one trihydrochloride The synthesis of the title compound was performed in the same manner as in Example 5 using appropriate starting materials.

1H-NMR (DMSO-D6) δ ppm: 1.64-1.88 (4H, m), 2.58-2.82 (2H, m), 3.60 (3H, s), 3.88-4.05 (2H, m), 4.19 (4H, s), 6.61 (1H, d, J=9.5 Hz), 7.16 (1H, dd, J=9.2, 2.8 Hz), 7.24 (1H, d, J=2.8 Hz), 7.46 (1H, d, J=9.2 Hz), 7.84 (1H, d, J=9.5 Hz), 8.19 (4H, d, J=5.6 Hz), 8.90 (4H, d, J=5.6 Hz).

EXAMPLE 142

Synthesis of 1-methyl-6-{4-[N-(2-methylbenzyl)-N-(pyridin-3-ylmethyl)amino]butoxy}-1H-quinolin-2-one dihydrochloride The synthesis of the title compound was performed in the same manner as in Example 5 using appropriate starting materials.

1H-NMR (DMSO-D6) δ ppm: 1.62-1.80 (2H, m), 1.92-2.14 (2H, m), 2.33 (3H, s), 3.00-3.25 (2H, m), 3.60 (3H, s), 3.90-4.78 (6H, m), 6.62 (1H, d, J=9.5 Hz), 7.13-7.35 (5H, m), 7.48 (1H, d, J=9.2 Hz), 7.63-7.79 (1H, m), 7.85 (1H, d, J=9.5 Hz), 7.79-7.92 (1H, m), 8.59-8.75 (1H, m), 8.83 (1H, s), 9.02-9.20 (1H, m).

EXAMPLE 143

Synthesis of 1-methyl-6-{4-[N-(2-methylbenzyl)-N-(pyridin-4-ylmethyl)amino]butoxy}-1H-quinolin-2-one dihydrochloride The synthesis of the title compound was performed in the same manner as in Example 5 using appropriate starting materials.

1H-NMR (DMSO-D6) δ ppm: 1.60-1.80 (2H, m), 1.89-2.15 (2H, m), 2.36 (3H, s), 3.00-3.30 (2H, m), 3.60 (3H, s), 3.82-4.82 (6H, m), 6.62 (1H, d, J=9.5 Hz), 7.06-7.31 (5H, m), 7.47 (1H, d, J=9.1 Hz), 7.61-7.79 (1H, m), 7.84 (1H, d, J=9.5 Hz), 8.11-8.40 (2H, m), 8.86 (2H, d, J=3.5 Hz).

EXAMPLE 144

Synthesis of N-[3-(1-methyl-2-oxo-1,2-dihydroquinolin-6-yloxy)propyl]-2-nitro-N-{2-[4-(pyridin-4-ylmethoxy)piperidin-1-yl]ethyl}benzenesulfonamide The synthesis of the title compound was performed in the same manner as in Example 125 using appropriate starting materials.

1H-NMR (CDCl3) δ ppm: 1.55-1.78 (2H, m), 1.78-1.95 (2H, m), 1.95-2.25 (4H, m), 2.55 (2H, t, J=6.8 Hz), 2.65-2.81 (2H, m), 3.32-3.51 (3H, m), 3.58 (2H, t, J=7.2 Hz), 3.71 (3H, s), 4.01 (2H, t, J=5.8 Hz), 4.53 (2H, s), 6.72 (1H, d, J=9.5 Hz), 6.93 (1H, d, J=2.8 Hz), 7.12 (1H, dd, J=9.2, 2.8 Hz), 7.23-7.30 (3H, m), 7.54-7.64 (4H, m), 8.50-8.61 (1H, m), 8.56 (2H, d, J=6.0 Hz).

EXAMPLE 145

Synthesis of N-[3-(1-methyl-2-oxo-1,2-dihydroquinolin-6-yloxy)propyl]-N-{2-[4-(pyridin-3-ylmethoxy)piperidin-1-yl]ethyl}benzenesulfonamide dihydrochloride The synthesis of the title compound was performed in the same manner as in Example 81 using appropriate starting materials.
1H-NMR (CDCl3) δ ppm: 1.51-1.74 (2H, m), 1.74-1.97 (2H, m), 2.05-2.29 (4H, m), 2.52 (2H, t, J=6.9 Hz), 2.64-2.78 (2H, m), 3.28 (2H, t, J=7.1 Hz), 3.36-3.50 (3H, m), 3.70 (3H, s), 4.06 (2H, t, J=6.0 Hz), 4.53 (2H, s), 6.71 (1H, d, J=9.5 Hz), 6.99 (1H, d, J=2.8 Hz), 7.16 (1H, dd, J=9.2, 2.8 Hz), 7.24-7.31 (2H, m), 7.45-7.62 (4H, m), 7.62-7.70 (1H, m), 7.81-7.88 (2H, m), 8.52 (1H, dd, J=4.8, 1.6 Hz), 8.57 (1H, d, J=1.6 Hz).

EXAMPLE 146

Synthesis of N-[3-(1-Methyl-2-oxo-1,2-dihydroquinolin-6-yloxy)propyl]-N-{2-[4-(pyridin-3-ylmethoxy)piperidin-1-yl]ethyl}phenylmethanesulfonamide dihydrochloride The synthesis of the title compound was performed in the same manner as in Example 81 using appropriate starting materials.
1H-NMR (CDCl3) δ ppm: 1.55-1.74 (2H, m), 1.85-2.08 (2H, m), 2.08-2.29 (4H, m), 2.46 (2H, t, J=6.5 Hz), 2.69-2.83 (2H, m), 3.19 (2H, t, J=7.3 Hz), 3.27 (2H, t, J=6.5 Hz), 3.38-3.52 (1H, m), 3.69 (3H, s), 3.97 (2H, t, J=6.1 Hz), 4.39 (2H, s), 4.54 (2H, s), 6.70 (1H, d, J=9.5 Hz), 6.97 (1H, d, J=2.8 Hz), 7.14 (1H, dd, J=9.2, 2.8 Hz), 7.24-7.31 (2H, m), 7.34-7.46 (5H, m), 7.58 (1H, d, J=9.5 Hz), 7.67 (1H, dt, J=7.8, 1.8 Hz), 8.52 (1H, dd, J=4.8, 1.7 Hz), 8.57 (1H, d, J=1.7 Hz).

EXAMPLE 147

Synthesis of 2-methyl-N-[3-(1-methyl-2-oxo-1,2-dihydroquinolin-6-yloxy)propyl]-N-{2-[4-(pyridin-3-ylmethoxy)piperidin-1-yl]ethyl}benzamide The synthesis of the title compound was performed in the same manner as in Example 45 using appropriate starting materials.
1H-NMR (DMSO-D6) δ ppm: 1.31-2.81 (10H, m), 2.21 (3H, s), 3.04-4.16 (9H, m), 3.58 (3H, s), 4.40-4.60 (2H, m), 6.57 (1H, d, J=9.5 Hz), 6.95-7.50 (8H, m), 7.61-7.88 (2H, m), 8.47 (1H, d, J=3.5 Hz), 8.51 (1H, s).

EXAMPLE 148

Synthesis of N-[3-(1-methyl-2-oxo-1,2,3,4-tetrahydroquinolin-6-yloxy)propyl]-2-nitro-N-(2-pyridin-3-ylethyl)benzenesulfonamide The synthesis of the title compound was performed in the same manner as in Example 2 using appropriate starting materials.
1H-NMR (CDCl3) δ ppm: 2.00-2.14 (2H, m), 2.55-2.68 (2H, m), 2.80-3.00 (4H, m), 3.33 (3H, m), 3.50-3.65 (4H, m), 3.94 (2H, t, J=5.8 Hz), 6.66-6.75 (2H, m), 6.87 (1H, d, J=8.6 Hz), 7.20 (1H, dd, J=7.8, 4.8 Hz), 7.50-7.68 (4H, m), 7.97-8.02 (1H, m), 8.41 (1H, d, J=1.6 Hz), 8.46 (1H, dd, J=4.8, 1.6 Hz).

EXAMPLE 149

Synthesis of 1-methyl-6-[3-(N-(2-methylbenzyl)-N-{2-[4-(pyridin-4-ylmethoxy)piperidin-1-yl]ethyl}amino)propoxy]-1H-quinolin-2-one trihydrochloride The synthesis of the title compound was performed in the same manner as in Example 5 using appropriate starting materials.
1H-NMR (DMSO-D6) δ ppm: 1.81-2.39 (6H, m), 2.46 (3H, s), 3.01-3.51 (7H, m), 3.60 (3H, s), 3.63-3.91 (4H, m), 4.01-4.18 (2H, m), 4.30-4.52 (2H, m), 4.84 (2H, s), 6.62 (1H, d, J=9.5 Hz), 7.18 (1H, dd, J=9.2, 2.8 Hz), 7.21-7.38 (4H, m), 7.47 (1H, d, J=9.2 Hz), 7.73 (1H, d, J=6.0 Hz), 7.84 (1H, d, J=9.5 Hz), 7.92 (2H, d, J=5.7 Hz), 8.84 (2H, d, J=5.7 Hz).

EXAMPLE 150

Synthesis of 1-methyl-6-[3-(N-{2-[4-(pyridin-4-ylmethoxy)piperidin-1-yl]ethyl}-N-(pyridin-3-ylmethyl)amino)propoxy]-1H-quinolin-2-one tetrahydrochloride The synthesis of the title compound was performed in the same manner as in Example 5 using appropriate starting materials.
1H-NMR (DMSO-D6) δ ppm: 1.95-2.33 (6H, m), 3.00-3.90 (13H, m), 3.60 (3H, s), 4.00-4.12 (2H, m), 4.87 (2H, s), 6.62 (1H, d, J=9.5 Hz), 7.21 (1H, dd, J=9.1, 2.9 Hz), 7.28 (1H, d, J=2.9 Hz), 7.47 (1H, d, J=9.1 Hz), 7.79-7.89 (1H, m), 7.85 (1H, d, J=9.5 Hz), 7.96-8.05 (2H, m), 8.56 (1H, d, J=7.9 Hz), 8.82 (1H, d, J=4.0 Hz), 8.89 (2H, d, J=6.6 Hz), 9.05 (1H, s).

EXAMPLE 151

Synthesis of 1-methyl-6-[3-(N-{2-[4-(pyridin-4-ylmethoxy)piperidin-1-yl]ethyl}-N-(pyridin-4-ylmethyl)amino)propoxy]-1H-quinolin-2-one tetrahydrochloride The synthesis of the title compound was performed in the same manner as in Example 5 using appropriate starting materials.
1H-NMR (DMSO-D6) δ ppm: 1.82-2.30 (6H, m), 2.78-3.90 (13H, m), 3.60 (3H, s), 4.00-4.18 (2H, m), 4.87 (2H, s), 6.62 (1H, d, J=9.5 Hz), 7.17 (1H, dd, J=9.2, 2.9 Hz), 7.27 (1H, d, J=2.9 Hz), 7.45 (1H, d, J=9.2 Hz), 7.85 (1H, d, J=9.5 Hz), 8.02 (2H, d, J=6.4 Hz), 8.15 (2H, d, J=5.3 Hz), 8.86 (2H, d, J=5.3 Hz), 8.89 (2H, d, J=6.4 Hz).

EXAMPLE 152

Synthesis of 1-methyl-6-{3-[N-(2-methylbenzyl)-N-(2-pyridin-3-ylethyl)amino]propoxy}-3,4-dihydro-1H-quinolin-2-one dihydrochloride The synthesis of the title compound was performed in the same manner as in Example 5 using appropriate starting materials.
1H-NMR (DMSO-D6) δ ppm: 2.14-2.41 (2H, m), 2.41-2.57 (2H, m), 2.70-2.85 (2H, m), 2.47 (3H, s), 3.21 (3H, s), 3.20-3.39 (2H, m), 3.39-3.62 (4H, m), 3.92-4.08 (2H, m), 4.48 (2H, s), 6.75-6.82 (2H, m), 6.99 (1H, d, J=9.4 Hz), 7.09-7.40 (3H, m), 7.76 (1H, d, J=7.3 Hz), 8.00 (1H, dd, J=8.0, 5.3 Hz), 8.50 (1H, d, J=8.0 Hz), 8.83 (1H, d, J=5.3 Hz), 8.95 (1H, s).

EXAMPLE 153

Synthesis of 1-methyl-6-{3-[N-(2-pyridin-3-ylethyl)-N-(pyridin-3-ylmethyl)amino]propoxy}-3,4-dihydro-1H-quinolin-2-one trihydrochloride The synthesis of the title compound was performed in the same manner as in Example 5 using appropriate starting materials.
1H-NMR (DMSO-D6) δ ppm: 2.19-2.40 (2H, m), 2.40-2.61 (2H, m), 2.83 (2H, t, J=6.8 Hz), 3.22 (3H, s), 3.19-3.38 (2H, m), 3.38-3.60 (4H, m), 3.98-4.10 (2H, m), 4.67 (2H, s), 6.76-6.86 (2H, m), 7.00 (1H, d, J=8.8 Hz), 7.92 (1H, dd, J=8.0, 4.9 Hz), 8.02 (1H, dd, J=8.1, 5.4 Hz), 8.54 (1H, d, J=8.1 Hz), 8.74 (1H, d, J=8.0 Hz), 8.83 (1H, d, J=5.4 Hz), 8.88 (1H, d, J=4.9 Hz), 8.96 (1H, s), 9.18 (1H, s).

EXAMPLE 154

Synthesis of N-[3-(1-methyl-2-oxo-1,2,3,4-tetrahydroquinolin-6-yloxy)propyl]-N-(2-pyridin-3-ylethyl)benzenesulfonamide hydrochloride The synthesis of the title compound was performed in the same manner as in Example 81 using appropriate starting materials.
1H-NMR (DMSO-D6) δ ppm: 1.76-1.95 (2H, m), 2.41-2.58 (2H, m), 2.83 (2H, t, J=7.8 Hz), 3.07 (2H, t, J=7.2 Hz), 3.22 (3H, s), 3.32 (2H, t, J=7.5 Hz), 3.49 (2H, t, J=7.2 Hz), 3.87 (2H, t, J=6.0 Hz), 6.73-6.82 (2H, m), 6.99 (1H, d, J=8.4 Hz), 7.52-7.87 (5H, m), 7.97 (1H, dd, J=8.1, 5.5 Hz), 8.46 (1H, d, J=8.1 Hz), 8.79 (1H, d, J=5.5 Hz), 8.86 (1H, s).

EXAMPLE 155

Synthesis of 3-{[N-[5-(1-methyl-2-oxo-1,2-dihydroquinolin-6-yloxy)pentyl]-N-(2-pyridin-3-ylethyl)amino]methyl}benzoic acid methyl ester dihydrochloride The synthesis of the title compound was performed in the same manner as in Example 5 using appropriate starting materials.
1H-NMR (DMSO-D6) δ ppm: 1.30-1.52 (2H, m), 1.66-2.00 (4H, m), 2.98-3.19 (2H, m), 3.30-3.50 (4H, m), 3.60 (3H, s), 3.87 (3H, s), 3.95-4.11 (2H, m), 4.43-4.66 (2H, m), 6.61 (1H, d, J=9.5 Hz), 7.24 (1H, dd, J=9.1, 2.8 Hz), 7.29 (1H, d, J=2.8 Hz), 7.46 (1H, d, J=9.1 Hz), 7.61 (1H, dd, J=7.8, 7.7 Hz), 7.84 (1H, d, J=9.5 Hz), 7.95-8.05 (2H, m), 8.08 (1H, d, J=7.8 Hz), 8.27 (1H, s), 8.48 (1H, d, J=8.1 Hz), 8.83 (1H, d, J=5.2 Hz), 8.94 (1H, s).

EXAMPLE 156

Synthesis of 3-{[N-[3-(1-methyl-2-oxo-1,2-dihydroquinolin-6-yloxy)propyl]-N-(2-pyridin-3-ylethyl)amino]methyl}benzoic acid methyl ester dihydrochloride The synthesis of the title compound was performed in the same manner as in Example 5 using appropriate starting materials.
1H-NMR (DMSO-D6) δ ppm: 2.20-2.45 (2H, m), 3.28 (2H, t, J=6.9 Hz), 3.37-3.58 (4H, m), 3.60 (3H, s), 3.87 (3H, s), 4.11 (2H, t, J=6.0 Hz), 4.48-4.72 (2H, m), 6.62 (1H, d, J=9.5 Hz), 7.17 (1H, dd, J=9.2, 2.8 Hz), 7.25 (1H, d, J=2.8 Hz), 7.46 (1H, d, J=9.2 Hz), 7.62 (1H, dd, J=8.0, 7.7 Hz), 7.83 (1H, d, J=9.5 Hz), 8.02 (1H, d, J=8.0 Hz), 8.05 (1H, dd, J=8.1, 5.5 Hz), 8.13 (1H, d, J=7.7 Hz), 8.29 (1H, s), 8.57 (1H, d, J=8.1 Hz), 8.86 (1H, d, J=5.5 Hz), 8.99 (1H, s).

EXAMPLE 157

Synthesis of 6-{3-[N-(1H-imidazol-4-ylmethyl)-N-(2-pyridin-3-ylethyl)amino]propoxy}-1-methyl-1H-quinolin-2-one trihydrochloride The synthesis of the title compound was performed in the same manner as in Example 5 using appropriate starting materials.
1H-NMR (DMSO-D6) δ ppm: 2.21-2.49 (2H, m), 3.20-3.55 (6H, m), 3.60 (3H, s), 4.15 (2H, t, J=6.0 Hz), 4.64 (2H, s), 6.63 (1H, d, J=9.5 Hz), 7.26 (1H, dd, J=9.2, 2.9 Hz), 7.32 (1H, d, J=2.9 Hz), 7.48 (1H, d, J=9.2 Hz), 7.86 (1H, d, J=9.5 Hz), 8.00 (1H, dd, J=8.0, 5.3 Hz), 8.01 (1H, s), 8.56 (1H, d, J=8.0 Hz), 8.83 (1H, d, J=5.3 Hz), 8.99 (1H, s), 9.19 (1H, s).

EXAMPLE 158

Synthesis of 1-methyl-6-{3-[N-(3-methylbenzyl)-N-(2-pyridin-3-ylethyl)amino]propoxy}-1H-quinolin-2-one dihydrochloride The synthesis of the title compound was performed in the same manner as in Example 5 using appropriate starting materials.
1H-NMR (DMSO-D6) δ ppm: 2.20-2.40 (2H, m), 2.32 (3H, s), 3.12-3.30 (2H, m), 3.30-3.50 (4H, m), 3.60 (3H, s), 4.11 (2H, t, J=5.9 Hz), 4.29-4.57 (2H, m), 6.62 (1H, d, J=9.5 Hz), 7.20 (1H, dd, J=9.2, 2.9 Hz), 7.23-7.30 (2H, m), 7.34 (1H, dd, J=7.8, 7.6 Hz), 7.47 (1H, d, J=9.2 Hz), 7.49-7.56 (2H, m), 7.84 (1H, d, J=9.5 Hz), 7.99 (1H, dd, J=8.0, 5.5 Hz), 8.47 (1H, d, J=8.0 Hz), 8.82 (1H, d, J=5.5 Hz), 8.92 (1H, s).

EXAMPLE 159

Synthesis of N-(3-imidazol-1-ylpropyl)-N-[3-(1-methyl-2-oxo-1,2-dihydroquinolin-6-yloxy)propyl]-2-nitrobenzenesulfonamide The synthesis of the title compound was performed in the same manner as in Example 2 using appropriate starting materials.
1H-NMR (CDCl3) δ ppm: 1.98-2.20 (4H, m), 3.35 (2H, t, J=6.4 Hz), 3.52 (2H, t, J=7.1 Hz), 3.71 (3H, s), 3.91-4.08 (4H, m), 6.73 (1H, d, J=9.5 Hz), 6.88-6.93 (2H, m), 7.05-7.09 (1H, m), 7.10 (1H, dd, J=9.1, 2.8 Hz), 7.24-7.31 (1H, m), 7.47 (1H, s), 7.55-7.65 (4H, m), 7.93-7.99 (1H, m).

EXAMPLE 160

Synthesis of 1-methyl-6-{3-[N-(2-methylbenzyl)-N-(2-pyridin-4-ylethyl)amino]propoxy}-1H-quinolin-2-one dihydrochloride The synthesis of the title compound was performed in the same manner as in Example 5 using appropriate starting materials.

1H-NMR (DMSO-D6) δ ppm: 2.14-2.40 (2H, m), 2.48 (3H, s), 3.14-3.40 (2H, m), 3.40-4.30 (6H, m), 3.60 (3H, s), 4.30-4.60 (2H, m), 6.62 (1H, d, J=9.5 Hz), 7.06-7.39 (5H, m), 7.47 (1H, d, J=9.1 Hz), 7.74 (1H, d, J=8.0 Hz), 7.84 (1H, d, J=9.5 Hz), 7.98 (2H, d, J=5.6 Hz), 8.87 (2H, d, J=5.6 Hz).

EXAMPLE 161

Synthesis of 1-methyl-6-{3-[N-(2-pyridin-4-ylethyl)-N-(pyridin-3-ylmethyl)amino]propoxy}-1H-quinolin-2-one trihydrochloride The synthesis of the title compound was performed in the same manner as in Example 5 using appropriate starting materials.
1H-NMR (DMSO-D6) δ ppm: 2.21-2.42 (2H, m), 3.19-3.39 (2H, m), 3.39-3.60 (4H, m), 3.60 (3H, s), 4.01-4.19 (2H, m), 4.50-4.79 (2H, m), 6.62 (1H, d, J=9.5 Hz), 7.23 (1H, d, J=9.0 Hz), 7.28 (1H, s), 7.48 (1H, d, J=9.0 Hz), 7.85 (1H, d, J=9.5 Hz), 7.85-7.95 (1H, m), 8.05 (2H, d, J=5.5 Hz), 8.69 (1H, d, J=6.7 Hz), 8.82-8.93 (3H, m), 9.15 (1H, s).

EXAMPLE 162

Synthesis of 1-methyl-6-{3-[N-(2-pyridin-4-ylethyl)-N-(pyridin-4-ylmethyl)amino]propoxy}-1H-quinolin-2-one trihydrochloride The synthesis of the title compound was performed in the same manner as in Example 5 using appropriate starting materials.
1H-NMR (DMSO-D6) δ ppm: 2.16-2.40 (2H, m), 3.13-3.40 (2H, m), 3.40-3.61 (4H, m), 3.60 (3H, s), 4.00-4.18 (2H, m), 4.58-4.88 (2H, m), 6.62 (1H, d, J=9.5 Hz), 7.19 (1H, dd, J=9.2, 2.8 Hz), 7.26 (1H, d, J=2.8 Hz), 7.47 (1H, d, J=9.2 Hz), 7.85 (1H, d, J=9.5 Hz), 8.05 (2H, d, J=6.5 Hz), 8.34 (2H, d, J=5.5 Hz), 8.89 (2H, d, J=6.5 Hz), 8.95 (2H, d, J=5.5 Hz).

EXAMPLE 163

Synthesis of N-(2-methylbenzyl)-N-(2-pyridin-3-ylethyl)-N-[3-(quinolin-6-yloxy)propyl]amine trihydrochloride Sodium iodide (113 mg) was added to a DMF solution (5 ml) of N-(3-chloropropyl)-N-(2-methylbenzyl)-N-(2-pyridin-3-ylethyl)amine (151 mg), and stirred at 60° C. for 1 hours. The reaction mixture was cooled to room temperature. Potassium carbonate (104 mg) and 6-hydroxyquinoline (87 mg) were then added to the reaction mixture and stirred at 60° C. for 24 hours. The reaction mixture was added to ice water, and the extraction with ethyl acetate was performed. The organic layer was washed with a saturated sodium chloride aqueous solution, dried over anhydrous sodium sulfate, and concentrated under reduced pressure. The residue was purified by silica gel column chromatography (n-hexane:ethyl acetate=1:1→0:1). The purified product was condensed under reduced pressure. A 4N-hydrogen chloride in ethyl acetate solution(0.014 ml) was added to a ethyl acetate solution (1 ml) of the residue, and the liquid was stirred at room temperature. The precipitated insoluble product was separated, washed with ether, and dried to give the title compound (7.6 mg) as a brown powder.
1H-NMR (DMSO-D6) δ ppm: 2.28-2.60 (2H, m), 2.49 (3H, s), 3.20-4.11 (6H, m), 4.27 (2H, t, J=5.6 Hz), 4.36-4.61 (2H, m), 7.22-7.38 (3H, m), 7.63 (1H, dd, J=9.2, 2.5 Hz), 7.68 (1H, d, J=2.5 Hz), 7.74 (1H, d, J=7.9 Hz), 7.87-7.96 (2H, m), 8.26 (1H, d, J=9.2 Hz), 8.39 (1H, d, J=7.9 Hz), 8.78 (1H, d, J=4.3 Hz), 8.84 (1H, d, J=8.8 Hz), 8.88 (1H, s), 9.05 (1H, d, J=5.0 Hz).

EXAMPLE 164

Synthesis of N-(2-methylbenzyl)-N-(2-pyridin-3-ylethyl)-N-[3-(pyridin-3-yloxy)propyl]amine trihydrochloride The synthesis of the title compound was performed in the same manner as in Example 163 using appropriate starting materials.
1H-NMR (DMSO-D6) δ ppm: 2.24-2.45 (2H, m), 2.49 (3H, s), 3.18-3.41 (2H, m), 3.41-3.68 (4H, m), 4.32 (2H, t, J=5.8 Hz), 4.37-4.62 (2H, m), 7.20-7.38 (3H, m), 7.78 (1H, d, J=7.4 Hz), 7.94 (1H, dd, J=8.7, 5.4 Hz), 8.04 (1H, dd, J=8.2, 5.7 Hz), 8.07 (1H, dd, J=8.7, 2.3 Hz), 8.52 (1H, d, J=5.4 Hz), 8.55 (1H, d, J=8.2 Hz), 8.62 (1H, d, J=2.3 Hz), 8.85 (1H, d, J=5.5 Hz), 8.97 (1H, s).

EXAMPLE 165

Synthesis of 1-methyl-6-{3-[N-(3-methylpyridin-4-ylmethyl)-N-(2-pyridin-3-ylethyl)amino]propoxy}-1H-quinolin-2-one trihydrochloride The synthesis of the title compound was performed in the same manner as in Example 5 using appropriate starting materials.
1H-NMR (DMSO-D6) δ ppm: 2.20-2.46 (2H, m), 2.58 (3H, s), 3.20-3.62 (6H, m), 3.61 (3H, s), 4.05-4.20 (2H, m), 4.76 (2H, s), 6.62 (1H, d, J=9.5 Hz), 7.21 (1H, dd, J=9.2, 2.8 Hz), 7.29 (1H, d, J=2.8 Hz), 7.47 (1H, d, J=9.2 Hz), 7.86 (1H, d, J=9.5 Hz), 8.05 (1H, dd, J=8.0, 5.6 Hz), 8.60 (1H, d, J=8.0 Hz), 8.51-8.67 (1H, m), 8.86 (1H, d, J=5.6 Hz), 8.82-8.92 (2H, m), 9.00 (1H, s).

EXAMPLE 166

Synthesis of 1-methyl-6-{3-[N-(3-methylpyridin-4-ylmethyl)-N-(2-pyridin-3-ylethyl)amino]propoxy}-3,4-dihydro-1H-quinolin-2-one trihydrochloride The synthesis of the title compound was performed in the same manner as in Example 5 using appropriate starting materials.
1H-NMR (DMSO-D6) δ ppm: 2.04-2.36 (2H, m), 2.52 (3H, s), 2.83 (2H, t, J=7.9 Hz), 3.10-3.60 (6H, m), 3.22 (3H, s), 3.64-4.85 (6H, m), 6.72-6.81 (2H, m), 6.99 (1H, d, J=9.2 Hz), 8.00 (1H, dd, J=8.1, 5.5 Hz), 8.51 (1H, d, J=8.1 Hz), 8.69-8.84 (3H, m), 8.82 (1H, d, J=5.5 Hz), 8.92 (1H, s).

EXAMPLE 167

Synthesis of 6-{3-[N-(3-imidazol-1-ylpropyl)-N-(pyridin-4-ylmethyl)amino]propoxy}-1-methyl-1H-quinolin-2-one trihydrochloride The synthesis of the title compound was performed in the same manner as in Example 5 using appropriate starting materials.
1H-NMR (DMSO-D6) δ ppm: 2.17-2.60 (4H, m), 2.98-3.35 (4H, m), 3.60 (3H, s), 4.09 (2H, t, J=6.4 Hz), 4.32 (2H, t, J=7.2 Hz), 4.59 (2H, s), 6.63 (1H, d, J=9.5 Hz), 7.19 (1H, dd, J=9.1, 2.8 Hz), 7.27 (1H, d, J=2.8 Hz), 7.47 (1H, d, J=9.1

Hz), 7.71 (1H, s), 7.78-7.89 (2H, m), 8.15 (2H, d, J=5.9 Hz), 8.86 (2H, d, J=5.9 Hz), 9.23 (1H, s).

EXAMPLE 169

Synthesis of N-(2-pyridin-3-ylethyl)-N-(pyridin-4-ylmethyl)-N-[3-(pyridin-3-yloxy)propyl]amine tetrahydrochloride The synthesis of the title compound was performed in the same manner as in Example 163 using appropriate starting materials.

1H-NMR (DMSO-D6) δ ppm: 2.19-2.40 (2H, m), 3.06-4.10 (6H, m), 4.28 (2H, t, J=5.8 Hz), 4.74 (2H, s), 7.89 (1H, dd, J=8.7, 5.2 Hz), 7.96-8.06 (2H, m), 8.17 (2H, d, J=5.4 Hz), 8.46-8.52 (2H, m), 8.60 (1H, d, J=2.6 Hz), 8.82 (1H, d, J=5.6 Hz), 8.88 (2H, d, J=5.4 Hz), 8.91 (1H, s).

EXAMPLE 170

Synthesis of 6-{3-[N-(3-hydroxybenzyl)-N-(2-pyridin-3-ylethyl)amino]propoxy}-1-methyl-1H-quinolin-2-one hydrochloride The synthesis of the title compound was performed in the same manner as in Example 5 using appropriate starting materials.

1H-NMR (DMSO-D6) δ ppm: 2.20-2.41 (2H, m), 3.18-3.50 (6H, m), 3.60 (3H, s), 4.11 (2H, t, J=5.9 Hz), 4.24-4.51 (2H, m), 6.62 (1H, d, J=9.5 Hz), 6.88 (1H, dd, J=8.3, 1.1 Hz), 7.07-7.15 (2H, m), 7.19-7.25 (2H, m), 7.28 (1H, d, J=2.9 Hz), 7.47 (1H, d, J=9.2 Hz), 7.80-7.89 (2H, m), 8.30 (1H, d, J=8.0 Hz), 8.74 (1H, dd, J=5.4, 1.4 Hz), 8.83 (1H, d, J=1.4 Hz).

Example 171

Synthesis of 6-{3-[N-(3-hydroxymethylbenzyl)-N-(2-pyridin-3-ylethyl)amino]propoxy}-1-methyl-1H-quinolin-2-one dihydrochloride Sodium borohydride (16.5 mg) was added to a THF solution (4 ml) of 3-{[N-[3-(1-methyl-2-oxo-1,2-dihydroquinolin-6-yloxy)propyl]-N-(2-pyridin-3-ylethyl)amino]methyl}benzoic acid methyl ester (192 mg). Methanol (1 ml) was added to the mixture and stirred for 1.5 hour while heated under reflux. The reaction liquid was cooled to room temperature. Water was added to the reaction mixture, followed by extraction with dichloromethane. The organic layer was dried over anhydrous sodium sulfate. The filtrate was condensed under reduced pressure, and the residue was purified by silica gel column chromatography (ethyl acetate: methanol=10:1→4:1). The purified product was condensed under reduced pressure. A 4N-hydrogen chloride in ethyl acetate solution(0.082 ml) was added to a ethyl acetate solution (1 ml) of the residue, and the liquid was stirred at room temperature. The precipitated insoluble matter was separated, washed with ether, and dried to give the title compound(53.4 mg) as a white powder.

1H-NMR (DMSO-D6) δ ppm: 2.20-2.41 (2H, m), 3.14-3.47 (6H, m), 3.60 (3H, s), 4.11 (2H, t, J=5.9 Hz), 4.30-4.60 (2H, m), 4.53 (2H, s), 6.62 (1H, d, J=9.5 Hz), 7.21 (1H, dd, J=9.2, 2.9 Hz), 7.28 (1H, d, J=2.9 Hz), 7.38-7.45 (2H, m), 7.47 (1H, d, J=9.2 Hz), 7.56-7.66 (2H, m), 7.71 (1H, dd, J=8.0, 5.2 Hz), 7.84 (1H, d, J=9.5 Hz), 8.13 (1H, d, J=8.0 Hz), 8.67 (1H, dd, J=5.2, 1.5 Hz), 8.73 (1H, d, J=1.5 Hz).

Example 172

Synthesis of N-[3-(1-methyl-2-oxo-1,2-dihydroquinolin-6-yloxy)propyl]-2-nitro-N-(2-piperidin-1-ylethyl)benzenesulfonamide The synthesis of the title compound was performed in the same manner as in Example 125 using appropriate starting materials.

1H-NMR (CDCl3) δ ppm: 1.33-1.50 (2H, m), 1.50-1.61 (4H, m), 2.08-2.19 (2H, m), 2.30-2.46 (4H, m), 2.52 (2H, t, J=6.9 Hz), 3.50 (2H, t, J=6.9 Hz), 3.59 (2H, t, J=7.0 Hz), 3.70 (3H, s), 4.02 (2H, t, J=5.9 Hz), 6.71 (1H, d, J=9.5 Hz), 6.94 (1H, d, J=2.8 Hz), 7.12 (1H, dd, J=9.2, 2.8 Hz), 7.28 (1H, d, J=9.2 Hz), 7.55-7.66 (4H, m), 8.06-8.14 (1H, m).

Example 173

Synthesis of N-(2-diethylaminoethyl)-N-[3-(1-methyl-2-oxo-1,2-dihydroquinolin-6-yloxy)propyl]-2-nitrobenzenesulfonamide The synthesis of the title compound was performed in the same manner as in Example 125 using appropriate starting materials.

1H-NMR (CDCl3) δ ppm: 0.99 (6H, t, J=7.1 Hz), 2.00-2.19 (2H, m), 2.53 (4H, q, J=7.1 Hz), 2.65 (2H, t, J=7.1 Hz), 3.44 (2H, t, J=7.1 Hz), 3.60 (2H, t, J=7.0 Hz), 3.69 (3H, s), 4.02 (2H, t, J=5.9 Hz), 6.70 (1H, d, J=9.5 Hz), 6.94 (1H, d, J=2.8 Hz), 7.12 (1H, dd, J=9.2, 2.8 Hz), 7.27 (1H, d, J=9.2 Hz), 7.54-7.66 (4H, m), 8.02-8.09 (1H, m).

Example 174

Synthesis of N-[3-(1-methyl-2-oxo-1,2-dihydroquinolin-6-yloxy)propyl]-N-[2-(4-methylpiperazin-1-yl)ethyl]-2-nitrobenzenesulfonamide The synthesis of the title compound was performed in the same manner as in Example 125 using appropriate starting materials.

1H-NMR (CDCl3) δ ppm: 2.01-2.19 (2H, m), 2.47 (3H, s), 2.28-2.56 (8H, m), 2.55 (2H, t, J=6.8 Hz), 3.48 (2H, t, J=6.8 Hz), 3.58 (2H, t, J=7.1 Hz), 3.69 (3H, s), 4.02 (2H, t, J=5.9 Hz), 6.69 (1H, d, J=9.5 Hz), 6.93 (1H, d, J=2.7 Hz), 7.11 (1H, dd, J=9.2, 2.7 Hz), 7.27 (1H, d, J=9.2 Hz), 7.54-7.66 (4H, m), 8.04-8.12 (1H, m).

Example 175

Synthesis of 1-methyl-6-{3-[N-(2-piperidin-1-ylethyl)-N-(pyridin-4-ylmethyl)amino]propoxy}-1H-quinolin-2-one trihydrochloride The synthesis of the title compound was performed in the same manner as in Example 5 using appropriate starting materials.

1H-NMR (DMSO-D6) δ ppm: 1.67-2.26 (8H, m), 2.71-3.60 (10H, m), 3.60 (3H, s), 3.98-4.14 (2H, m), 4.19-5.00 (2H, m), 6.62 (1H, d, J=9.5 Hz), 7.17 (1H, dd, J=9.2, 2.8 Hz), 7.27 (1H, d, J=2.8 Hz), 7.46 (1H, d, J=9.2 Hz), 7.85 (1H, d, J=9.5 Hz), 8.13 (2H, d, J=5.4 Hz), 8.86 (2H, d, J=5.4 Hz).

Example 176

Synthesis of 6-{3-[N-(2-diethylaminoethyl)-N-(pyridin-4-ylmethyl)amino]propoxy}-1-methyl-1H-quinolin-2-one trihydrochloride The synthesis of the title compound was performed in the same manner as in Example 5 using appropriate starting materials.

1H-NMR (DMSO-D6) δ ppm: 1.19 (6H, t, J=7.2 Hz), 1.90-2.10 (2H, m), 2.58-2.82 (2H, m), 2.90-3.30 (4H, m), 3.10 (4H, q, J=7.2 Hz), 3.60 (3H, s), 3.79-4.14 (4H, m), 6.62 (1H, d, J=9.5 Hz), 7.16 (1H, dd, J=9.2, 2.9 Hz), 7.26 (1H, d, J=2.9 Hz), 7.45 (1H, d, J=9.2 Hz), 7.67 (2H, d, J=5.8 Hz), 7.84 (1H, d, J=9.5 Hz), 8.62 (2H, d, J=5.8 Hz).

Example 177

Synthesis of 1-methyl-6-(3-{N-[2-(4-methylpiperazin-1-yl)ethyl]N-(pyridin-4-ylmethyl)amino}propoxy)-1H-quinolin-2-one tetrahydrochloride The synthesis of the title compound was performed in the same manner as in Example 5 using appropriate starting materials.

1H-NMR (DMSO-D6) δ ppm: 2.01-2.21 (2H, m), 2.79 (3H, s), 2.87-3.02 (2H, m), 3.11-3.42 (8H, m), 3.42-3.70 (4H, m), 3.60 (3H, s), 4.00-4.14 (2H, m), 4.31 (2H, s), 6.62 (1H, d, J=9.5 Hz), 7.17 (1H, dd, J=9.3, 2.8 Hz), 7.27 (1H, d, J=2.8 Hz), 7.46 (1H, d, J=9.3 Hz), 7.85 (1H, d, J=9.5 Hz), 8.14 (2H, d, J=6.3 Hz), 8.83 (2H, d, J=6.3 Hz).

Example 178

Synthesis of 1-methyl-5-{3-[N-(2-pyridin-3-ylethyl)-N-(pyridin-4-ylmethyl)amino]propoxy}-3,4-dihydro-1H-quinolin-2-one trihydrochloride The synthesis of the title compound was performed in the same manner as in Example 4 using appropriate starting materials.

1H-NMR (DMSO-D6) δ ppm: 2.10-2.40 (2H, m), 2.40-2.68 (4H, m), 2.95-4.82 (10H, m), 3.23 (3H, s), 6.66-6.77 (2H, m), 7.21 (1H, dd, J=8.3, 8.2 Hz), 7.91 (1H, dd, J=8.0, 5.5 Hz), 7.97-8.08 (2H, m), 8.38 (1H, d, J=8.0 Hz), 8.73-8.82 (3H, m), 8.85 (1H, s).

Example 179

Synthesis of 1-methyl-7-{3-[N-(2-pyridin-3-ylethyl)-N-(pyridin-4-ylmethyl)amino]propoxy}-3,4-dihydro-1H-quinolin-2-one trihydrochloride The synthesis of the title compound was performed in the same manner as in Example 4 using appropriate starting materials.

1H-NMR (DMSO-D6) δ ppm: 2.08-2.36 (2H, m), 2.78 (2H, t, J=7.9 Hz), 2.97-4.81 (12H, m), 3.22 (3H, s), 6.50-6.58 (2H, m), 7.11 (1H, d, J=8.9 Hz), 7.88 (1H, dd, J=7.9, 5.4 Hz), 7.92-8.04 (2H, m), 8.35 (1H, d, J=7.9 Hz), 8.72-8.86 (4H, m).

Example 180

Synthesis of N-(4-{3-[N'-(2-pyridin-3-ylethyl)-N'-(pyridin-4-ylmethyl)amino]propoxy}phenyl)acetamide trihydrochloride The synthesis of the title compound was performed in the same manner as in Example 31 using appropriate starting materials.

1H-NMR (DMSO-D6) δ ppm: 2.01 (3H, s), 2.13-2.40 (2H, m), 3.08-3.52 (6H, m), 3.90-4.10 (2H, m), 4.70 (2H, s), 6.83 (2H, d, J=9.0 Hz), 7.49 (2H, d, J=9.0 Hz), 8.01 (1H, dd, J=8.1, 2.6 Hz), 8.24-8.34 (2H, m), 8.52 (1H, d, J=8.1 Hz), 8.83 (1H, d, J=2.6 Hz), 8.89-8.98 (3H, m).

Example 181

Synthesis of N-[4-(1,7-naphthyridin-2-yloxy)butyl]-N-(2-pyridin-3-ylethyl)-N-(pyridin-4-ylmethyl)amine dihydrochloride The synthesis of the title compound was performed in the same manner as in Example 5 using appropriate starting materials.

1H-NMR (DMSO-D6) δ ppm: 1.70-2.06 (4H, m), 2.99-3.20 (2H, m), 3.20-3.43 (4H, m), 4.33-4.71 (4H, m), 7.29 (1H, d, J=9.0 Hz), 7.64-7.72 (1H, m), 7.89 (2H, d, J=5.8 Hz), 7.94 (1H, d, J=5.5 Hz), 8.10 (1H, d, J=8.0 Hz), 8.36 (1H, d, J=9.0 Hz), 8.51 (1H, d, J=5.5 Hz), 8.63 (1H, d, J=5.1 Hz), 8.68 (2H, d, J=5.8 Hz), 8.70 (1H, s), 9.16 (1H, s).

Example 182

Synthesis of 7-{4-[N-(2-pyridin-3-ylethyl)-N-(pyridin-4-ylmethyl)amino]butoxy}-3,4-dihydro-1H-1,8-naphthyridin-2-one dihydrochloride The synthesis of the title compound was performed in the same manner as in Example 5 using appropriate starting materials.

1H-NMR (DMSO-D6) δ ppm: 1.59-1.80 (2H, m), 1.80-2.04 (2H, m), 2.39-2.58 (2H, m), 2.78 (2H, t, J=8.0 Hz), 2.95-3.20 (2H, m), 3.20-3.45 (4H, m), 4.16 (2H, t, J=6.1 Hz), 4.51 (2H, s), 6.33 (1H, d, J=8.0 Hz), 7.50 (1H, d, J=8.0 Hz), 7.80 (1H, dd, J=7.9, 5.0 Hz), 7.96 (2H, d, J=5.8 Hz), 8.24 (1H, d, J=7.9 Hz), 8.71 (1H, d, J=5.0 Hz), 8.75 (2H, d, J=5.8 Hz), 8.78 (1H, s), 10.24 (1H, s).

Example 183

Synthesis of N-(2-{N'-[3-(1-methyl-2-oxo-1,2-dihydroquinolin-6-yloxy)propyl]-N'-(pyridin-4-ylmethyl)amino}ethyl)benzamide dihydrochloride The synthesis of the title compound was performed in the same manner as in Example 5 using appropriate starting materials.

1H-NMR (DMSO-D6) δ ppm: 2.21-2.42 (2H, m), 3.14-3.45 (4H, m), 3.60 (3H, s), 3.58-4.20 (4H, m), 4.58-4.75 (2H, m), 6.62 (1H, d, J=9.5 Hz), 7.18 (1H, d, J=9.4 Hz), 7.24 (1H, s), 7.41-7.59 (4H, m), 7.82 (1H, d, J=9.5 Hz), 7.85-7.94 (2H, m), 8.04 (2H, d, J=5.5 Hz), 8.80 (2H, d, J=5.5 Hz), 8.93 (1H, s).

Example 184

Synthesis of N-(2-{N'-[3-(1-methyl-2-oxo-1,2-dihydroquinolin-6-yloxy)propyl]-N'-(pyridin-4-ylmethyl)amino}ethyl)isobutyramide dihydrochloride The synthesis of the title compound was performed in the same manner as in Example 5 using appropriate starting materials.

1H-NMR (DMSO-D6) δ ppm: 0.98 (6H, d, J=6.9 Hz), 1.94-2.20 (2H, m), 2.29-2.41 (1H, m), 2.59-3.09 (4H, m), 3.09-3.54 (4H, m), 3.60 (3H, s), 3.92-4.19 (2H, m), 6.62 (1H, d, J=9.5 Hz), 7.18 (1H, dd, J=9.2, 2.8 Hz), 7.25 (1H, d, J=2.8 Hz), 7.46 (1H, d, J=9.2 Hz), 7.56 (2H, d, J=4.2 Hz), 7.83 (1H, d, J=9.5 Hz), 7.92 (1H, s), 8.57 (2H, d, J=4.2 Hz).

Example 185

Synthesis of N-(2-{N'-[3-(1-methyl-2-oxo-1,2-dihydroquinolin-6-yloxy)propyl]-N'-(pyridin-4-ylmethyl)amino}ethyl)nicotinamide trihydrochloride The synthesis of the title compound was performed in the same manner as in Example 5 using appropriate starting materials.

1H-NMR (DMSO-D6) δ ppm: 2.16-2.43 (2H, m), 3.20-3.51 (4H, m), 3.60 (3H, s), 3.69-3.94 (2H, m), 3.94-4.21 (2H, m), 4.76 (2H, s), 6.62 (1H, d, J=9.5 Hz), 7.18 (1H, dd, J=9.0, 2.7 Hz), 7.25 (1H, d, J=2.7 Hz), 7.46 (1H, d, J=9.0 Hz), 7.77-7.89 (2H, m), 8.31 (2H, d, J=5.5 Hz), 8.65 (1H, d, J=8.0 Hz), 8.83-8.98 (3H, m), 9.25 (1H, s), 9.56 (1H, s).

Example 186

Synthesis of {N-[3-(1-methyl-2-oxo-1,2-dihydroquinolin-6-yloxy)propyl]-N-(pyridin-4-ylmethyl)carbamoyloxy}acetic acid ethyl ester Potassium carbonate (1.66 g) was added to a DMF solution (50 ml) of 1-methyl-6-{3-[(pyridin-4-ylmethyl)amino]propoxy}-1H-quinolin-2-one (1.5 g). The mixture was cooled to 0° C., and ethyl bromoacetate (1.16 ml) was added to the mixture and stirred at room temperature overnight. The reaction mixture was added to ice water, and extraction with ethyl acetate was performed. The organic layer was washed with a saturated sodium chloride aqueous solution, dried over anhydrous sodium sulfate, and concentrated under reduced pressure. The residue was purified by silica gel column chromatography (ethyl acetate: methanol=20:1→10:1). The purified product was condensed under reduced pressure. The residue was recrystallized from ether, and dried to give the title compound(0.55 g) as a white powder.

1H-NMR (CDCl3) δ ppm: 1.29 (3H, t, J=7.2 Hz), 2.00-2.19 (2H, m), 3.53 (2H, t, J=5.9 Hz), 3.71 (3H, s), 3.95-4.11 (2H, m), 4.23 (2H, q, J=7.2 Hz), 4.46-4.59 (2H, m), 4.63 (2H, s), 6.72 (1H, d, J=9.5 Hz), 6.99 (1H, s), 7.10-7.35 (4H, m), 7.59 (1H, d, J=9.5 Hz), 8.58 (2H, s).

Example 187

Synthesis of {N-[3-(1-methyl-2-oxo-1,2-dihydroquinolin-6-yloxy)propyl]-N-(pyridin-4-ylmethyl)amino}acetic acid ethyl ester Potassium carbonate (1.66 g) and ethyl bromoacetate (1.16 ml) were added to a DMF solution (50 ml) of 1-methyl-6-{3-[(pyridin-4-ylmethyl)amino]propoxy}-1H-quinolin-2-one (1.5 g), and stirred at room temperature overnight. The reaction mixture was added to ice water, and extraction with ethyl acetate was performed. The organic layer was washed with a saturated sodium chloride aqueous solution, dried over anhydrous sodium sulfate, and concentrated under reduced pressure. The residue was purified by silica gel column chromatography (ethyl acetate: methanol=100:0→85:15). The purified product was condensed under reduced pressure to give the title compound (1.28 g) as a orange oil.

1H-NMR (CDCl3) δ ppm: 1.27 (3H, t, J=7.1 Hz), 1.89-2.04 (2H, m), 2.86 (2H, t, J=6.8 Hz), 3.38 (2H, s), 3.71 (3H, s), 3.84 (2H, s), 4.07 (2H, t, J=6.2 Hz), 4.17 (2H, q, J=7.1 Hz), 6.72 (1H, d, J=9.5 Hz), 6.96 (1H, d, J=2.8 Hz), 7.11 (1H, dd, J=9.2, 2.8 Hz), 7.25-7.35 (3H, m), 7.59 (1H, d, J=9.5 Hz), 8.48 (2H, d, J=6.0 Hz).

Example 188

Synthesis of 2-methyl-N-(2-{N-[3-(1-methyl-2-oxo-1,2-dihydroquinolin-6-yloxy)propyl]-N-(pyridin-4-ylmethyl)amino}ethyl)benzamide dihydrochloride The synthesis of the title compound was performed in the same manner as in Example 5 using appropriate starting materials.

1H-NMR (DMSO-D6) δ ppm: 2.19-2.40 (2H, m), 2.33 (3H, s), 3.07-3.45 (4H, m), 3.60 (3H, s), 3.63-3.84 (2H, m), 4.12 (2H, t, J=5.9 Hz), 4.58 (2H, s), 6.62 (1H, d, J=9.5 Hz), 7.16-7.29 (4H, m), 7.29-7.41 (2H, m), 7.46 (1H, d, J=9.2 Hz), 7.82 (1H, d, J=9.5 Hz), 7.99 (2H, d, J=6.0 Hz), 8.57 (1H, s), 8.78 (2H, d, J=6.0 Hz).

Example 189

Synthesis of N-(2-{N'-[3-(1-methyl-2-oxo-1,2-dihydroquinolin-6-yloxy)propyl]-N'-(pyridin-4-ylmethyl)amino}ethyl)benzenesulfonamide The synthesis of the title compound was performed in the same manner as in Example 5 using appropriate starting materials.

1H-NMR (CDCl3) δ ppm: 1.81-1.98 (2H, m), 2.51-2.66 (4H, m), 2.98-3.10 (2H, m), 3.50 (2H, s), 3.72 (3H, s), 4.01 (2H, t, J=5.9 Hz), 5.03 (1H, t, J=5.4 Hz), 6.73 (1H, d, J=9.5 Hz), 7.00 (1H, d, J=2.8 Hz), 7.10-7.18 (3H, m), 7.30 (1H, d, J=9.2 Hz), 7.42-7.47 (2H, m), 7.48-7.55 (1H, m), 7.62 (1H, d, J=9.5 Hz), 7.74-7.94 (2H, m), 8.47 (2H, d, J=5.9 Hz).

Example 190

Synthesis of N-ethyl-2-{N-[3-(1-methyl-2-oxo-1,2-dihydroquinolin-6-yloxy)propyl]-N-(pyridin-4-ylmethyl)amino}acetamide dihydrochloride The synthesis of the title compound was performed in the same manner as in Example 50 using appropriate starting materials.

1H-NMR (DMSO-D6) δ ppm: 1.00 (3H, t, J=7.2 Hz), 2.09-2.40 (2H, m), 3.00-3.17 (2H, m), 3.17-3.35 (2H, m), 3.60 (3H, s), 3.73 (2H, s), 4.10 (2H, t, J=5.9 Hz), 4.53 (2H, s), 6.62 (1H, d, J=9.5 Hz), 7.20 (1H, dd, J=9.2, 2.8 Hz), 7.28 (1H, d, J=2.8 Hz), 7.47 (1H, d, J=9.2 Hz), 7.84 (1H, d, J=9.5 Hz), 8.07 (2H, d, J=6.2 Hz), 8.53 (1H, s), 8.85 (2H, d, J=6.2 Hz).

Example 191

Synthesis of N,N-diethyl-2-{N'-[3-(1-methyl-2-oxo-1,2-dihydroquinolin-6-yloxy)propyl]-N'-(pyridin-4-ylmethyl)amino}acetamide dihydrochloride The synthesis of the title compound was performed in the same manner as in Example 50 using appropriate starting materials.
1H-NMR (DMSO-D6) δ ppm: 0.97 (3H, t, J=7.1 Hz), 1.06 (3H, t, J=7.1 Hz), 2.17-2.35 (2H, m), 3.12-3.30 (4H, m), 3.30-3.45 (2H, m), 3.60 (3H, s), 4.11 (2H, t, J=5.8 Hz), 4.29 (2H, s), 4.61 (2H, s), 6.62 (1H, d, J=9.5 Hz), 7.22 (1H, dd, J=9.2, 2.8 Hz), 7.30 (1H, d, J=2.8 Hz), 7.48 (1H, d, J=9.2 Hz), 7.85 (1H, d, J=9.5 Hz), 8.06 (2H, d, J=5.9 Hz), 8.87 (2H, d, J=5.9 Hz).

Example 192

Synthesis of 2-{N'-[3-(1-methyl-2-oxo-1,2-dihydroquinolin-6-yloxy)propyl]-N'-(pyridin-4-ylmethyl)amino}-N-phenylacetamide dihydrochloride The synthesis of the title compound was performed in the same manner as in Example 50 using appropriate starting materials.
1H-NMR (DMSO-D6) δ ppm: 2.07-2.32 (2H, m), 3.12-3.40 (2H, m), 3.61 (3H, s), 3.90-4.08 (2H, m), 4.08-4.21 (2H, m), 4.60 (2H, s), 6.61 (1H, d, J=9.5 Hz), 7.09 (1H, t, J=7.4 Hz), 7.18 (1H, dd, J=9.2, 2.8 Hz), 7.26 (1H, d, J=2.8 Hz), 7.28-7.37 (2H, m), 7.44 (1H, d, J=9.2 Hz), 7.59 (2H, d, J=7.7 Hz), 7.82 (1H, d, J=9.5 Hz), 8.16 (2H, d, J=6.2 Hz), 8.88 (2H, d, J=6.2 Hz).

Example 193

Synthesis of N-(2-{N'-[3-(1-methyl-2-oxo-1,2-dihydroquinolin-6-yloxy)propyl]-N'-(pyridin-4-ylmethyl)amino}ethyl)phenylmethanesulfonamide dihydrochloride The synthesis of the title compound was performed in the same manner as in Example 81 using appropriate starting materials.
1H-NMR (DMSO-D6) δ ppm: 2.02-2.38 (2H, m), 2.79-3.56 (6H, m), 3.60 (3H, s), 3.96-4.16 (2H, m), 4.40-4.72 (2H, m), 4.41 (2H, s), 6.62 (1H, d, J=9.5 Hz), 7.20 (1H, dd, J=9.1, 2.7 Hz), 7.27 (1H, d, J=2.7 Hz), 7.31-7.41 (5H, m), 7.47 (1H, d, J=9.1 Hz), 7.83 (1H, d, J=9.5 Hz), 8.01 (2H, d, J=5.8 Hz), 8.81 (2H, d, J=5.8 Hz).

Example 194

Synthesis of 1-methyl-6-{3-[N-(pyridin-4-ylmethyl)-N-(3-pyridin-3-ylpropyl)amino]propoxy}-1H-quinolin-2-one trihydrochloride The synthesis of the title compound was performed in the same manner as in Example 5 using appropriate starting materials.
1H-NMR (DMSO-D6) δ ppm: 2.10-2.40 (4H, m), 2.75-2.92 (2H, m), 3.00-3.16 (2H, m), 3.16-3.31 (2H, m), 3.60 (3H, s), 4.10 (2H, t, J=5.8 Hz), 4.50 (2H, s), 6.62 (1H, d, J=9.5 Hz), 7.19 (1H, dd, J=9.1, 2.8 Hz), 7.27 (1H, d, J=2.8 Hz), 7.47 (1H, d, J=9.1 Hz), 7.84 (1H, d, J=9.5 Hz), 7.83-8.09 (3H, m), 8.34 (1H, d, J=7.9 Hz), 8.64-9.02 (4H, m).

Example 195

Synthesis of 2-methyl-6-{3-[N-(2-pyridin-3-ylethyl)-N-(pyridin-4-ylmethyl)amino]propoxy}-2,3-dihydroisoindol-1-one trihydrochloride The synthesis of the title compound was performed in the same manner as in Example 32 using appropriate starting materials.
1H-NMR (DMSO-D6) δ ppm: 2.19-2.40 (2H, m), 3.07 (3H, s), 3.13-3.33 (2H, m), 3.33-3.53 (4H, m), 4.12 (2H, t, J=5.8 Hz), 4.39 (2H, s), 4.66 (2H, s), 7.09 (1H, dd, J=8.2, 2.3 Hz), 7.14 (1H, d, J=2.3 Hz), 7.48 (1H, d, J=8.2 Hz), 7.99 (1H, dd, J=8.1, 5.2 Hz), 8.22 (2H, d, J=5.0 Hz), 8.50 (1H, d, J=8.1 Hz), 8.82 (1H, d, J=5.2 Hz), 8.89 (2H, d, J=5.0 Hz), 8.92 (1H, s).

Example 196

Synthesis of 7-{3-[N-(2-pyridin-3-ylethyl)-N-(pyridin-4-ylmethyl)amino]propoxy}-2H-isoquinolin-1-one trihydrochloride The synthesis of the title compound was performed in the same manner as in Example 32 using appropriate starting materials.
1H-NMR (CDCl3) δ ppm: 1.80-2.04 (2H, m), 2.63-2.86 (6H, m), 3.66 (2H, s), 4.08 (2H, t, J=6.0 Hz), 6.54 (1H, d, J=7.1 Hz), 7.07 (1H, d, J=6.5 Hz), 7.15 (2H, d, J=5.9 Hz), 7.15-7.24 (2H, m), 7.39-7.46 (1H, m), 7.49 (1H, d, J=8.7 Hz), 7.77 (1H, d, J=2.6 Hz), 8.39-8.45 (3H, m), 8.47 (1H, dd, J=4.8, 1.6 Hz), 10.96 (1H, s).

Example 197

Synthesis of 2-methyl-7-{3-[N-(2-pyridin-3-ylethyl)-N-(pyridin-4-ylmethyl)amino]propoxy}-2H-isoquinolin-1-one trihydrochloride The synthesis of the title compound was performed in the same manner as in Example 32 using appropriate starting materials.
1H-NMR (DMSO-D6) δ ppm: 2.13-2.40 (2H, m), 3.00-3.40 (6H, m), 3.51 (3H, s), 4.13 (2H, t, J=5.6 Hz), 4.48 (2H, s), 6.58 (1H, d, J=7.3 Hz), 7.25 (1H, dd, J=8.7, 2.6 Hz), 7.35 (1H, d, J=7.3 Hz), 7.56-7.65 (2H, m), 7.75 (1H, dd, J=7.9, 5.3 Hz), 7.90 (2H, d, J=5.2 Hz), 8.20 (1H, d, J=7.9 Hz), 8.68 (1H, d, J=5.3 Hz), 8.70-8.78 (3H, m).

Example 198

Synthesis of 3-methyl-6-{3-[N-(2-pyridin-3-ylethyl)-N-(pyridin-4-ylmethyl)amino]propoxy}-3H-quinazolin-4-one trihydrochloride The synthesis of the title compound was performed in the same manner as in Example 32 using appropriate starting materials.
1H-NMR (DMSO-D6) δ ppm: 2.20-2.43 (2H, m), 3.05-3.60 (6H, m), 3.52 (3H, s), 4.10-4.30 (2H, m), 4.65 (2H, s), 7.40 (1H, dd, J=8.9, 2.8 Hz), 7.52 (1H, d, J=2.8 Hz), 7.67 (1H, d, J=8.9 Hz), 7.99 (1H, dd, J=8.0, 5.3 Hz), 8.21 (2H, d, J=5.8

Hz), 8.43 (1H, s), 8.49 (1H, d, J=8.0 Hz), 8.82 (1H, d, J=5.3 Hz), 8.89 (2H, d, J=5.8 Hz), 8.92 (1H, s).

Example 199

Synthesis of 2-methyl-7-{3-[N-(2-pyridin-3-ylethyl)-N-(pyridin-4-ylmethyl)amino]propoxy}-3,4-dihydro-2H-isoquinolin-1-one trihydrochloride The synthesis of the title compound was performed in the same manner as in Example 32 using appropriate starting materials.
1H-NMR (DMSO-D6) δ ppm: 2.16-2.39 (2H, m), 2.90 (2H, t, J=6.6 Hz), 3.02 (3H, s), 3.10-3.46 (6H, m), 3.52 (2H, t, J=6.6 Hz), 3.97-4.12 (2H, m), 4.59 (2H, s), 6.98 (1H, dd, J=8.3, 2.7 Hz), 7.21 (1H, d, J=8.3 Hz), 7.35 (1H, d, J=2.7 Hz), 7.92 (1H, dd, J=8.0, 5.5 Hz), 8.07 (2H, d, J=6.1 Hz), 8.40 (1H, d, J=8.0 Hz), 8.77 (1H, d, J=5.5 Hz), 8.81 (2H, d, J=6.1 Hz), 8.86 (1H, s).

Example 200

Synthesis of 7-{3-[N-(2-pyridin-3-ylethyl)-N-(pyridin-4-ylmethyl)amino]propoxy}-3,4-dihydro-2H-isoquinolin-1-one trihydrochloride The synthesis of the title compound was performed in the same manner as in Example 32 using appropriate starting materials.
1H-NMR (DMSO-D6) δ ppm: 2.18-2.41 (2H, m), 2.82 (2H, t, J=6.6 Hz), 3.12-3.60 (8H, m), 4.00-4.18 (2H, m), 4.72 (2H, s), 7.00 (1H, dd, J=8.4, 2.7 Hz), 7.23 (1H, d, J=8.4 Hz), 7.34 (1H, d, J=2.7 Hz), 7.96 (1H, s), 8.02 (1H, dd, J=8.0, 5.7 Hz), 8.23-8.38 (2H, m), 8.53 (1H, d, J=8.0 Hz), 8.83 (1H, d, J=5.7 Hz), 8.89-8.99 (3H, m).

Example 201

Synthesis of 2-{3-[N-(2-pyridin-3-ylethyl)-N-(pyridin-4-ylmethyl)amino]propoxy}benzoic acid ethyl ester dihydrochloride The synthesis of the title compound was performed in the same manner as in Example 32 using appropriate starting materials.
1H-NMR (DMSO-D6) δ ppm: 1.23 (3H, t, J=7.1 Hz), 2.05-2.39 (2H, m), 2.91-3.52 (6H, m), 3.97-4.21 (2H, m), 4.17 (2H, q, J=7.1 Hz), 4.46 (2H, s), 6.99-7.07 (1H, m), 7.11 (1H, d, J=8.4 Hz), 7.49-7.58 (1H, m), 7.65 (1H, dd, J=7.7, 1.7 Hz), 7.71 (1H, dd, J=7.5, 5.6 Hz), 7.79-7.93 (2H, m), 8.14 (1H, d, J=7.5 Hz), 8.62-8.76 (4H, m).

Example 202

Synthesis of 3-{3-[N-(2-pyridin-3-ylethyl)-N-(pyridin-4-ylmethyl)amino]propoxy}benzoic acid ethyl ester dihydrochloride The synthesis of the title compound was performed in the same manner as in Example 32 using appropriate starting materials.
1H-NMR (DMSO-D6) δ ppm: 1.32 (3H, t, J=7.1 Hz), 2.10-2.40 (2H, m), 2.94-3.60 (6H, m), 4.00-4.18 (2H, m), 4.32 (2H, q, J=7.1 Hz), 4.50 (2H, s), 7.11-7.24 (1H, m), 7.40 (1H, s), 7.37-7.49 (1H, m), 7.56 (1H, d, J=7.7 Hz), 7.81 (1H, dd, J=7.8, 5.4 Hz), 7.83-8.00 (2H, m), 8.25 (1H, d, J=7.8 Hz), 8.64-8.84 (4H, m).

Example 203

Synthesis of 4-{3-[N-(2-pyridin-3-ylethyl)-N-(pyridin-4-ylmethyl)amino]propoxy}benzoic acid ethyl ester dihydrochloride The synthesis of the title compound was performed in the same manner as in Example 32 using appropriate starting materials.
1H-NMR (DMSO-D6) δ ppm: 1.31 (3H, t, J=7.1 Hz), 2.12-2.41 (2H, m), 3.02-3.60 (6H, m), 4.00-4.20 (2H, m), 4.28 (2H, q, J=7.1 Hz), 4.41-4.74 (2H, m), 6.99 (2H, d, J=8.8 Hz), 7.89 (1H, dd, J=7.7, 5.8 Hz), 7.91 (2H, d, J=8.8 Hz), 7.99 (2H, d, J=5.8 Hz), 8.36 (1H, d, J=7.7 Hz), 8.76 (1H, d, J=5.8 Hz), 8.79 (2H, d, J=5.8 Hz), 8.84 (1H, s).

Example 204

Synthesis of N-ethyl-2-{3-[N'-(2-pyridin-3-ylethyl)-N'-(pyridin-4-ylmethyl)amino]propoxy}benzamide trihydrochloride The synthesis of the title compound was performed in the same manner as in Example 50 using appropriate starting materials.
1H-NMR (DMSO-D6) δ ppm: 1.05 (3H, t, J=7.2 Hz), 2.20-2.42 (2H, m), 3.08-3.60 (8H, m), 4.07-4.26 (2H, m), 4.52-4.82 (2H, m), 7.02 (1H, dd, J=7.6, 7.5 Hz), 7.09 (1H, d, J=8.2 Hz), 7.39-7.48 (1H, m), 7.59 (1H, dd, J=7.6, 1.7 Hz), 7.99 (1H, dd, J=8.0, 5.2 Hz), 8.07 (1H, s), 8.22 (2H, d, J=5.0 Hz), 8.49 (1H, d, J=8.0 Hz), 8.82 (1H, d, J=5.2 Hz), 8.88 (2H, d, J=5.0 Hz), 8.92 (1H, s).

Example 205

Synthesis of N,N-diethyl-2-{3-[N'-(2-pyridin-3-ylethyl)-N'-(pyridin-4-ylmethyl)amino]propoxy}benzamide trihydrochloride The synthesis of the title compound was performed in the same manner as in Example 50 using appropriate starting materials.
1H-NMR (DMSO-D6) δ ppm: 0.91 (3H, t, J=7.1 Hz), 1.06 (3H, t, J=7.1 Hz), 2.01-2.41 (2H, m), 3.01 (4H, q, J=7.1 Hz), 2.97-3.59 (6H, m), 3.94-4.19 (2H, m), 4.38-4.74 (2H, m), 6.99 (1H, dd, J=7.4, 7.3 Hz), 7.05 (1H, d, J=8.3 Hz), 7.12 (1H, dd, J=7.4, 1.7 Hz), 7.31-7.40 (1H, m), 7.91 (1H, dd, J=8.0, 5.5 Hz), 8.05 (2H, d, J=5.9 Hz), 8.37 (1H, d, J=8.0 Hz), 8.78 (1H, d, J=5.5 Hz), 8.81 (2H, d, J=5.9 Hz), 8.84 (1H, s).

Example 206

Synthesis of N-ethyl-3-{3-[N'-(2-pyridin-3-ylethyl)-N'-(pyridin-4-ylmethyl)amino]propoxy}benzamide trihydrochloride The synthesis of the title compound was performed in the same manner as in Example 50 using appropriate starting materials.
1H-NMR (DMSO-D6) δ ppm: 1.12 (3H, t, J=7.2 Hz), 2.10-2.38 (2H, m), 3.00-3.41 (8H, m), 3.99-4.20 (2H, m), 4.42 (2H, s), 7.01 (1H, dd, J=8.0, 2.3 Hz), 7.31-7.49 (3H, m), 7.58 (1H, dd, J=7.7, 5.1 Hz), 7.79 (2H, d, J=5.8 Hz), 7.98 (1H, d, J=7.7 Hz), 8.51 (1H, t, J=5.2 Hz), 8.59 (1H, dd, J=5.1, 1.6 Hz), 8.63 (1H, d, J=1.6 Hz), 8.69 (2H, d, J=5.8 Hz).

Example 207

Synthesis of N,N-diethyl-3-{3-[N'-(2-pyridin-3-yl-ethyl)-N'-(pyridin-4-ylmethyl)amino]propoxy}benzamide trihydrochloride The synthesis of the title compound was performed in the same manner as in Example 50 using appropriate starting materials.

1H-NMR (DMSO-D6) δ ppm: 0.90-1.25 (6H, m), 2.09-2.38 (2H, m), 2.92-3.59 (10H, m), 3.98-4.16 (2H, m), 4.52 (2H, s), 6.82 (1H, d, J=1.7 Hz), 6.89 (1H, d, J=7.5 Hz), 6.94 (1H, dd, J=8.2, 1.7 Hz), 7.34 (1H, dd, J=8.2, 7.5 Hz), 7.85 (1H, dd, J=8.0, 5.2 Hz), 7.99 (2H, d, J=5.4 Hz), 8.31 (1H, d, J=8.0 Hz), 8.74 (1H, dd, J=5.2, 1.5 Hz), 8.78 (2H, d, J=5.4 Hz), 8.82 (1H, d, J=1.5 Hz).

Example 208

Synthesis of N,N-diethyl-4-{3-[N'-(2-pyridin-3-yl-ethyl)-N'-(pyridin-4-ylmethyl)amino]propoxy}benzamide trihydrochloride The synthesis of the title compound was performed in the same manner as in Example 50 using appropriate starting materials.

1H-NMR (DMSO-D6) δ ppm: 1.09 (6H, t, J=6.8 Hz), 2.12-2.40 (2H, m), 2.95-3.59 (10H, m), 3.95-4.15 (2H, m), 4.56 (2H, s), 6.92 (2H, d, J=8.6 Hz), 7.30 (2H, d, J=8.6 Hz), 7.91 (1H, dd, J=8.0, 5.3 Hz), 8.06 (2H, d, J=6.0 Hz), 8.38 (1H, d, J=8.0 Hz), 8.77 (1H, d, J=5.3 Hz), 8.82 (2H, d, J=6.0 Hz), 8.86 (1H, s).

Example 209

Synthesis of 2-methyl-8-{3-[N-(2-pyridin-3-ylethyl)-N-(pyridin-4-ylmethyl)amino]propoxy}-3,4-dihydro-2H-isoquinolin-1-one The synthesis of the title compound was performed in the same manner as in Example 32 using appropriate starting materials.

1H-NMR (CDCl3) δ ppm: 1.92-2.10 (2H, m), 2.67-3.00 (6H, m), 2.91 (2H, t, J=6.4 Hz), 3.09 (3H, s), 3.46 (2H, t, J=6.4 Hz), 3.69 (2H, s), 4.00 (2H, t, J=5.9 Hz), 6.75 (1H, d, J=7.3 Hz), 6.79 (1H, d, J=8.5 Hz), 7.09-7.19 (3H, m), 7.31 (1H, dd, J=8.5, 7.3 Hz), 7.44 (1H, d, J=7.6 Hz), 8.35-8.46 (4H, m).

Example 210

Synthesis of N,N-dimethyl-2-(4-{3-[N'-(2-pyridin-3-ylethyl)-N'-(pyridin-4-ylmethyl)amino]propoxy}phenyl)propionamide trihydrochloride The synthesis of the title compound was performed in the same manner as in Example 32 using appropriate starting materials.

1H-NMR (DMSO-D6) δ ppm: 1.23 (3H, d, J=6.8 Hz), 2.12-2.35 (2H, m), 2.80 (3H, s), 2.87 (3H, s), 3.00-3.49 (6H, m), 3.90-4.10 (3H, m), 4.56 (2H, s), 6.82 (2H, d, J=8.6 Hz), 7.16 (2H, d, J=8.6 Hz), 7.90 (1H, dd, J=8.0, 5.5 Hz), 8.05 (2H, d, J=5.5 Hz), 8.37 (1H, d, J=8.0 Hz), 8.76 (1H, d, J=5.5 Hz), 8.81 (2H, d, J=5.5 Hz), 8.85 (1H, s).

Example 211

Synthesis of 2-methyl-5-{3-[N-(2-pyridin-3-ylethyl)-N-(pyridin-4-ylmethyl)amino]propoxy}-3,4-dihydro-2H-isoquinolin-1-one trihydrochloride The synthesis of the title compound was performed in the same manner as in Example 32 using appropriate starting materials.

1H-NMR (DMSO-D6) δ ppm: 2.06-2.40 (2H, m), 2.67 (2H, t, J=6.7 Hz), 3.00 (3H, s), 3.06-3.42 (6H, m), 3.47 (2H, t, J=6.7 Hz), 3.92-4.16 (2H, m), 4.16-4.78 (2H, m), 7.08 (1H, d, J=8.0 Hz), 7.29 (1H, dd, J=8.2, 8.0 Hz), 7.48 (1H, d, J=8.2 Hz), 7.68 (1H, dd, J=7.7, 5.2 Hz), 7.77-7.89 (2H, m), 8.10 (1H, d, J=7.7 Hz), 8.65 (1H, dd, J=5.2, 1.3 Hz), 8.66-8.75 (3H, m).

Example 212

Synthesis of 1,4-dimethyl-6-{3-[N-(2-pyridin-3-ylethyl)-N-(pyridin-4-ylmethyl)amino]propoxy}-1H-quinolin-2-one trihydrochloride The synthesis of the title compound was performed in the same manner as in Example 32 using appropriate starting materials.

1H-NMR (DMSO-D6) δ ppm: 2.14-2.41 (2H, m), 2.42 (3H, s), 2.96-3.50 (6H, m), 3.58 (3H, s), 4.01-4.22 (2H, m), 4.52 (2H, s), 6.54 (1H, s), 7.16 (1H, d, J=2.5 Hz), 7.21 (1H, dd, J=9.2, 2.5 Hz), 7.47 (1H, d, J=9.2 Hz), 7.82 (1H, dd, J=7.9, 5.6 Hz), 7.96 (2H, d, J=4.8 Hz), 8.29 (1H, d, J=7.9 Hz), 8.72 (1H, d, J=5.6 Hz), 8.76 (2H, d, J=4.8 Hz), 8.81 (1H, s).

Example 213

Synthesis of 1-methyl-6-{3-[N-(2-pyridin-2-ylethyl)-N-(pyridin-3-ylmethyl)amino]propoxy}-1H-quinolin-2-one trihydrochloride The synthesis of the title compound was performed in the same manner as in Example 5 using appropriate starting materials.

1H-NMR (DMSO-D6) δ ppm: 2.22-2.40 (2H, m), 3.20-3.38 (2H, m), 3.46-3.62 (4H, m), 3.60 (3H, s), 4.11 (2H, t, J=5.9 Hz), 4.62 (2H, s), 6.62 (1H, d, J=9.5 Hz), 7.22 (1H, dd, J=9.1, 2.8 Hz), 7.29 (1H, d, J=2.8 Hz), 7.47 (1H, d, J=9.1 Hz), 7.60-7.69 (1H, m), 7.74 (1H, d, J=7.9 Hz), 7.81 (1H, dd, J=7.9, 5.0 Hz), 7.85 (1H, d, J=9.5 Hz), 8.14-8.23 (1H, m), 8.58 (1H, d, J=7.9 Hz), 8.69 (1H, d, J=5.0 Hz), 8.82 (1H, dd, J=5.2, 1.3 Hz), 9.08 (1H, d, J=1.3 Hz).

Example 214

Synthesis of N-benzyl-N-(2-{N'-[3-(1-methyl-2-oxo-1,2-dihydroquinolin-6-yloxy)propyl]-N'-(pyridin-4-ylmethyl)amino}ethyl)acetamide dihydrochloride The synthesis of the title compound was performed in the same manner as in Example 5 using appropriate starting materials.

1H-NMR (DMSO-D6) δ ppm: 1.99 (3H, s), 2.02-2.31 (2H, m), 2.90-3.45 (4H, m), 3.60 (3H, s), 3.50-3.89 (2H, m), 3.98-4.15 (2H, m), 4.25-4.65 (2H, m), 4.60 (2H, s), 6.62 (1H, d, J=9.5 Hz), 7.12-7.42 (7H, m), 7.46 (1H, d, J=9.2 Hz), 7.83 (1H, d, J=9.5 Hz), 7.87 (2H, d, J=5.8 Hz), 8.75 (2H, d, J=5.8 Hz).

Example 215

Synthesis of 1-methyl-6-{3-[N-(pyridin-4-ylmethyl)-N-(quinolin-6-yl)amino]propoxy}-1H-quinolin-2-one trihydrochloride The synthesis of the title compound was performed in the same manner as in Example 5 using appropriate starting materials.
1H-NMR (DMSO-D6) δ ppm: 2.10-2.27 (2H, m), 3.60 (3H, s), 3.87 (2H, t, J=7.4 Hz), 4.16 (2H, t, J=5.8 Hz), 5.07 (2H, s), 6.61 (1H, d, J=9.5 Hz), 7.24-7.32 (3H, m), 7.47 (1H, d, J=10.1 Hz), 7.69-7.79 (4H, m), 7.81 (1H, d, J=9.5 Hz), 8.11 (1H, d, J=9.5 Hz), 8.61 (1H, d, J=8.4 Hz), 8.75 (2H, d, J=6.4 Hz), 8.82 (1H, d, J=5.1 Hz).

Example 216

Synthesis of 6-(3-{N-[2-(7-bromo-1-oxo-1H-isoquinolin-2-yl)ethyl]-N-(pyridin-4-ylmethyl)amino}propoxy)-1-methyl-1H-quinolin-2-one dihydrochloride The synthesis of the title compound was performed in the same manner as in Example 5 using appropriate starting materials.
1H-NMR (DMSO-D6) δ ppm: 1.93-2.38 (2H, m), 2.74-3.54 (6H, m), 3.61 (3H, s), 3.79-4.15 (2H, m), 4.39 (2H, s), 6.62 (1H, d, J=9.5 Hz), 6.70 (1H, d, J=7.4 Hz), 6.98-7.25 (2H, m), 7.42 (1H, d, J=9.2 Hz), 7.60 (1H, d, J=7.4 Hz), 7.65 (1H, d, J=8.5 Hz), 7.80 (1H, d, J=9.5 Hz), 7.87 (1H, dd, J=8.5, 1.8 Hz), 8.00-8.23 (2H, m), 8.27 (1H, d, J=1.8 Hz), 8.65-8.98 (2H, m).

Example 217

Synthesis of N-methyl-N-(2-{N'-[3-(1-methyl-2-oxo-1,2-dihydroquinolin-6-yloxy)propyl]-N'-(pyridin-4-ylmethyl)amino}ethyl)phenylmethanesulfonamide dihydrochloride The synthesis of the title compound was performed in the same manner as in Example 81 using appropriate starting materials.
1H-NMR (CDCl3) δ ppm: 1.82-2.02 (2H, m), 2.54 (2H, t, J=6.7 Hz), 2.62 (2H, t, J=6.7 Hz), 2.67 (3H, s), 2.99 (2H, t, J=6.7 Hz), 3.58 (2H, s), 3.71 (3H, s), 4.04 (2H, t, J=6.2 Hz), 4.22 (2H, s), 6.72 (1H, d, J=9.5 Hz), 7.01 (1H, d, J=2.8 Hz), 7.11 (1H, dd, J=9.2, 2.8 Hz), 7.22 (2H, d, J=5.9 Hz), 7.23-7.40 (6H, m), 7.61 (1H, d, J=9.5 Hz), 8.46 (2H, d, J=5.9 Hz).

Example 218

Synthesis of 2,4,6,N-tetramethyl-N-(2-{N'-[3-(1-methyl-2-oxo-1,2-dihydroquinolin-6-yloxy)propyl]-N'-(pyridin-4-ylmethyl)amino}ethyl)benzenesulfonamide dihydrochloride The synthesis of the title compound was performed in the same manner as in Example 81 using appropriate starting materials.
1H-NMR (CDCl3) δ ppm: 1.82-2.01 (2H, m), 2.28 (3H, s), 2.56 (6H, s), 2.65 (3H, s), 2.61-2.79 (4H, m), 3.29 (2H, t, J=7.2 Hz), 3.60 (2H, s), 3.71 (3H, s), 4.04 (2H, t, J=6.1 Hz), 6.72 (1H, d, J=9.5 Hz), 6.92 (2H, s), 6.99 (1H, d, J=2.8 Hz), 7.11 (1H, dd, J=9.2, 2.8 Hz), 7.19-7.35 (3H, m), 7.60 (1H, d, J=9.5 Hz), 8.47 (2H, d, J=5.9 Hz).

Example 219

Synthesis of N-methyl-N-(2-{N'-[3-(1-methyl-2-oxo-1,2-dihydroquinolin-6-yloxy)propyl]-N'-(pyridin-4-ylmethyl)amino}ethyl)benzenesulfonamide dihydrochloride The synthesis of the title compound was performed in the same manner as in Example 81 using appropriate starting materials.
1H-NMR (CDCl3) δ ppm: 1.92-2.08 (2H, m), 2.67 (3H, s), 2.61-2.80 (4H, m), 3.12 (2H, t, J=6.5 Hz), 3.66 (2H, s), 3.71 (3H, s), 4.11 (2H, t, J=6.2 Hz), 6.72 (1H, d, J=9.5 Hz), 7.04 (1H, d, J=2.8 Hz), 7.14 (1H, dd, J=9.2, 2.8 Hz), 7.24-7.35 (3H, m), 7.43-7.61 (3H, m), 7.63 (1H, d, J=9.5 Hz), 7.74 (2H, d, J=6.0 Hz), 8.48 (2H, d, J=6.0 Hz).

Example 220

Synthesis of 4-methoxy-N-methyl-N-(2-{N'-[3-(1-methyl-2-oxo-1,2-dihydroquinolin-6-yloxy)propyl]-N'-(pyridin-4-ylmethyl)amino}ethyl)benzenesulfonamide dihydrochloride The synthesis of the title compound was performed in the same manner as in Example 81 using appropriate starting materials.
1H-NMR (CDCl3) δ ppm: 1.85-2.08 (2H, m), 2.64 (3H, s), 2.60-2.79 (4H, m), 3.09 (2H, t, J=6.6 Hz), 3.66 (2H, s), 3.71 (3H, s), 3.85 (3H, s), 4.11 (2H, t, J=6.2 Hz), 6.71 (1H, d, J=9.5 Hz), 6.94 (2H, d, J=8.9 Hz), 7.04 (1H, d, J=2.8 Hz), 7.13 (1H, dd, J=9.1, 2.8 Hz), 7.20-7.32 (3H, m), 7.56-7.73 (3H, m), 8.47 (2H, d, J=6.0 Hz).

Example 221

Synthesis of 2-nitro-N-[3-(1-oxo-1,2,3,4-tetrahydroisoquinolin-6-yloxy)propyl]-N-(2-pyridin-3-ylethyl)benzenesulfonamide The synthesis of the title compound was performed in the same manner as in Example 2 using appropriate starting materials.
1H-NMR (CDCl3) δ ppm: 1.96-2.20 (2H, m), 2.82-3.04 (4H, m), 3.47-3.69 (6H, m), 3.99 (2H, t, J=5.8 Hz), 5.97 (1H, s), 6.62 (1H, d, J=2.4 Hz), 6.74 (1H, dd, J=8.6, 2.4 Hz), 7.20 (1H, dd, J=7.8, 4.8 Hz), 7.49-7.64 (4H, m), 7.94-8.01 (2H, m), 8.42 (1H, d, J=1.7 Hz), 8.46 (1H, dd, J=7.8, 1.7 Hz).

Example 222

Synthesis of 6-{3-[N-(2-methylbenzyl)-N-(2-pyridin-3-ylethyl)amino]propoxy}-3,4-dihydro-2H-isoquinolin-1-one dihydrochloride The synthesis of the title compound was performed in the same manner as in Example 5 using appropriate starting materials.
1H-NMR (DMSO-D6) δ ppm: 2.15-2.42 (2H, m), 2.51 (3H, s), 2.86 (2H, t, J=6.5 Hz), 3.19-3.65 (8H, m), 4.11 (2H, t, J=6.0 Hz), 4.33-4.62 (2H, m), 6.78-6.91 (2H, m), 7.22-7.40

Example 223

Synthesis of 6-{3-[N-(2-pyridin-3-ylethyl)-N-(quinolin-4-ylmethyl)amino]propoxy}-3,4-dihydro-2H-isoquinolin-1-one trihydrochloride The synthesis of the title compound was performed in the same manner as in Example 5 using appropriate starting materials.

1H-NMR (DMSO-D6) δ ppm: 2.10-2.45 (2H, m), 2.84 (2H, t, J=6.4 Hz), 3.10-3.73 (8H, m), 3.95-4.10 (2H, m), 4.91-5.41 (2H, m), 6.70 (1H, s), 6.74 (1H, d, J=8.4 Hz), 7.64-7.80 (2H, m), 7.86-7.98 (1H, m), 7.98-8.12 (2H, m), 8.38 (1H, d, J=8.4 Hz), 8.43-8.69 (2H, m), 8.53 (1H, d, J=8.2 Hz), 8.82 (1H, d, J=5.2 Hz), 8.94 (1H, s), 9.23 (1H, d, J=1.7 Hz).

Example 224

Synthesis of 2-methyl-N-[3-(1-oxo-1,2,3,4-tetrahydroisoquinolin-6-yloxy)propyl]-N-(2-pyridin-3-ylethyl)benzamide hydrochloride The synthesis of the title compound was performed in the same manner as in Example 45 using appropriate starting materials.

1H-NMR (DMSO-D6) δ ppm: 1.82-2.24 (2H, m), 2.08 (3H, s), 2.85 (2H, t, J=6.1 Hz), 2.90-3.51 (6H, m), 3.36 (2H, t, J=6.6 Hz), 3.51-4.04 (2H, m), 6.46-7.30 (7H, m), 7.60-8.08 (2H, s), 8.35-9.00 (2H, m).

Example 225

Synthesis of N-[3-(1-oxo-1,2,3,4-tetrahydroisoquinolin-6-yloxy)propyl]-N-(2-pyridin-3-ylethyl)benzenesulfonamide hydrochloride The synthesis of the title compound was performed in the same manner as in Example 81 using appropriate starting materials.

1H-NMR (CDCl3) δ ppm: 1.89-2.09 (2H, m), 2.80-3.04 (4H, m), 3.24-3.45 (4H, m), 3.45-3.60 (2H, m), 3.98 (2H, t, J=5.9 Hz), 5.92 (1H, s), 6.66 (1H, d, J=2.4 Hz), 6.82 (1H, dd, J=8.6, 2.4 Hz), 7.12-7.39 (1H, m), 7.43-7.63 (4H, m), 7.74-7.89 (2H, m), 8.00 (1H, d, J=8.6 Hz), 8.40 (1H, d, J=1.7 Hz), 8.46 (1H, dd, J=7.8, 1.7 Hz).

Example 226

Synthesis of 4-methoxy-N-methyl-N-(2-{N'-[3-(1-methyl-2-oxo-1,2-dihydroquinolin-6-yloxy)propyl]-N'-(pyridin-4-ylmethyl)amino}ethyl)benzamide dihydrochloride The synthesis of the title compound was performed in the same manner as in Example 46 using appropriate starting materials.

1H-NMR (DMSO-D6) δ ppm: 2.10-2.46 (2H, m), 2.99 (3H, s), 3.08-3.49 (4H, m), 3.60 (3H, s), 3.78 (3H, s), 3.74-3.98 (2H, m), 3.98-4.20 (2H, m), 4.62 (2H, s), 6.62 (1H, d, J=9.5 Hz), 6.96 (2H, d, J=8.9 Hz), 7.18 (1H, dd, J=8.9, 2.6 Hz), 7.25 (1H, d, J=2.6 Hz), 7.31-7.54 (3H, m), 7.82 (1H, d, J=9.5 Hz), 8.14 (2H, d, J=5.7 Hz), 8.85 (2H, d, J=5.7 Hz).

Example 227

Synthesis of thiophene-3-carboxylic acid methyl-(2-{N-[3-(1-methyl-2-oxo-1,2-dihydroquinolin-6-yloxy)propyl]-N-(pyridin-4-ylmethyl)amino}ethyl) amide dihydrochloride The synthesis of the title compound was performed in the same manner as in Example 46 using appropriate starting materials.

1H-NMR (DMSO-D6) δ ppm: 2.11-2.38 (2H, m), 3.05 (3H, s), 3.02-3.47 (4H, m), 3.60 (3H, s), 3.47-4.21 (4H, m), 4.56 (2H, s), 6.62 (1H, d, J=9.5 Hz), 7.17 (1H, dd, J=9.1, 2.6 Hz), 7.25 (1H, d, J=2.6 Hz), 7.20-7.36 (1H, m), 7.46 (1H, d, J=9.1 Hz), 7.60 (1H, dd, J=4.9, 2.9 Hz), 7.82 (1H, d, J=9.5 Hz), 7.80-7.96 (1H, m), 8.03 (2H, d, J=5.2 Hz), 8.80 (2H, d, J=5.2 Hz).

Example 228

Synthesis of N-methyl-N-(2-{N'-[3-(1-methyl-2-oxo-1,2-dihydroquinolin-6-yloxy)propyl]-N'-(pyridin-4-ylmethyl)amino}ethyl)isobutyramide dihydrochloride The synthesis of the title compound was performed in the same manner as in Example 46 using appropriate starting materials.

1H-NMR (DMSO-D6) δ ppm: 0.99 (6H, d, J=6.7 Hz), 2.11-2.41 (2H, m), 2.75-2.89 (1H, m), 3.05 (3H, s), 3.05-3.41 (4H, m), 3.60 (3H, s), 3.68-3.84 (2H, m), 4.00-4.21 (2H, m), 4.63 (2H, s), 6.62 (1H, d, J=9.5 Hz), 7.20 (1H, dd, J=9.1, 2.6 Hz), 7.27 (1H, d, J=2.6 Hz), 7.47 (1H, d, J=9.1 Hz), 7.83 (1H, d, J=9.5 Hz), 8.19 (2H, d, J=5.4 Hz), 8.90 (2H, d, J=5.4 Hz).

Example 229

Synthesis of 2-methoxy-N-methyl-N-(2-{N'-[3-(1-methyl-2-oxo-1,2-dihydroquinolin-6-yloxy)propyl]-N'-(pyridin-4-ylmethyl)amino}ethyl)benzamide dihydrochloride The synthesis of the title compound was performed in the same manner as in Example 46 using appropriate starting materials.

1H-NMR (DMSO-D6) δ ppm: 2.12-2.40 (2H, m), 2.79 (3H, s), 2.71-3.02 (2H, m), 3.10-3.33 (2H, m), 3.59 (3H, s), 3.76 (3H, s), 3.81-4.25 (4H, m), 4.55 (2H, s), 6.58 (1H, d, J=9.5 Hz), 6.90-7.27 (5H, m), 7.27-7.50 (2H, m), 7.78 (1H, d, J=9.5 Hz), 8.12 (2H, d, J=5.0 Hz), 8.81 (2H, d, J=5.0 Hz).

Example 230

Synthesis of 2-fluoro-N-methyl-N-(2-{N'-[3-(1-methyl-2-oxo-1,2-dihydroquinolin-6-yloxy)propyl]-N'-(pyridin-4-ylmethyl)amino}ethyl)benzamide dihydrochloride The synthesis of the title compound was performed in the same manner as in Example 46 using appropriate starting materials.

1H-NMR (DMSO-D6) δ ppm: 2.13-2.41 (2H, m), 2.88 (3H, s), 2.76-3.10 (2H, m), 3.10-3.48 (2H, m), 3.59 (3H, s), 3.80-4.05 (2H, m), 4.05-4.21 (2H, m), 4.62 (2H, s), 6.59 (1H, d, J=9.5 Hz), 7.08-7.58 (7H, m), 7.79 (1H, d, J=9.5 Hz), 8.25 (2H, s), 8.86 (2H, s).

(3H, m), 7.70-7.82 (3H, m), 8.04 (1H, dd, J=8.0, 5.3 Hz), 8.54 (1H, d, J=8.1 Hz), 8.85 (1H, d, J=5.3 Hz), 8.97 (1H, s).

Example 231

Synthesis of 3,N-dimethyl-N-(2-{N'-[3-(1-methyl-2-oxo-1,2-dihydroquinolin-6-yloxy)propyl]-N'-(pyridin-4-ylmethyl)amino}ethyl)benzamide dihydrochloride The synthesis of the title compound was performed in the same manner as in Example 46 using appropriate starting materials.

1H-NMR (DMSO-D6) δ ppm: 2.31 (3H, s), 2.21-2.45 (2H, m), 2.95 (3H, s), 3.12-3.49 (4H, m), 3.60 (3H, s), 3.79-4.21 (4H, m), 4.65 (2H, s), 6.62 (1H, d, J=9.5 Hz), 7.11-7.40 (6H, m), 7.46 (1H, d, J=9.2 Hz), 7.82 (1H, d, J=9.5 Hz), 8.18 (2H, s), 8.86 (2H, s).

Example 232

Synthesis of benzo[1,3]dioxole-5-carboxylic acid N-methyl-(2-{N'-[3-(1-methyl-2-oxo-1,2-dihydroquinolin-6-yloxy)propyl]-N'-(pyridin-4-ylmethyl)amino}ethyl)amide hydrochloride The synthesis of the title compound was performed in the same manner as in Example 46 using appropriate starting materials.

1H-NMR (DMSO-D6) δ ppm: 2.19-2.46 (2H, m), 2.97 (3H, s), 3.05-3.49 (4H, m), 3.60 (3H, s), 3.71-3.94 (2H, m), 3.94-4.20 (2H, m), 4.66 (2H, s), 6.06 (2H, s), 6.62 (1H, d, J=9.5 Hz), 6.87-7.12 (3H, m), 7.19 (1H, dd, J=9.1, 2.7 Hz), 7.25 (1H, d, J=2.7 Hz), 7.46 (1H, d, J=9.1 Hz), 7.82 (1H, d, J=9.5 Hz), 8.21 (2H, d, J=5.6 Hz), 8.89 (2H, d, J=5.6 Hz).

Example 233

Synthesis of 2-(3-methoxyphenyl)-N-methyl-N-(2-{N'-[3-(1-methyl-2-oxo-1,2-dihydroquinolin-6-yloxy)propyl]-N'-(pyridin-4-ylmethyl)amino}ethyl) acetamide dihydrochloride The synthesis of the title compound was performed in the same manner as in Example 46 using appropriate starting materials.

1H-NMR (DMSO-D6) δ ppm: 2.09-2.31 (2H, m), 2.78-3.30 (4H, m), 3.03 (3H, s), 3.59 (3H, s), 3.68 (2H, s), 3.72 (3H, s), 3.53-3.89 (2H, m), 3.96-4.19 (2H, m), 4.44 (2H, s), 6.58 (1H, d, J=9.5 Hz), 6.70-6.90 (3H, m), 7.10-7.29 (3H, m), 7.43 (1H, d, J=9.0 Hz), 7.78 (1H, d, J=9.5 Hz), 8.00 (2H, d, J=5.3 Hz), 8.76 (2H, d, J=5.3 Hz).

Example 234

Synthesis of 4,5-dimethylfuran-2-carboxylic acid N-methyl-N-(2-{N'-[3-(1-methyl-2-oxo-1,2-dihydroquinolin-6-yloxy)propyl]-N'-(pyridin-4-ylmethyl)amino}ethyl)amide hydrochloride The synthesis of the title compound was performed in the same manner as in Example 46 using appropriate starting materials.

1H-NMR (DMSO-D6) δ ppm: 1.91 (3H, s), 2.23 (3H, s), 2.13-2.42 (2H, m), 3.04-3.46 (4H, m), 3.17 (3H, s), 3.60 (3H, s), 3.81-4.21 (4H, m), 4.68 (2H, s), 6.62 (1H, d, J=9.5 Hz), 6.89 (1H, s), 7.18 (1H, dd, J=9.1, 2.8 Hz), 7.25 (1H, d, J=2.8 Hz), 7.46 (1H, d, J=9.1 Hz), 7.83 (1H, d, J=9.5 Hz), 8.26 (2H, d, J=5.1 Hz), 8.92 (2H, d, J=5.1 Hz).

Example 235

Synthesis of 2-{3-[N-(2-pyridin-3-ylethyl)-N-(pyridin-4-ylmethyl)amino]propoxy}-7,8-dihydro-6H-5-thia-8-aza-benzocyclohepten-9-one trihydrochloride The synthesis of the title compound was performed in the same manner as in Example 32 using appropriate starting materials.

1H-NMR (DMSO-D6) δ ppm: 2.10-2.40 (2H, m), 2.93-3.57 (10H, m), 3.95-4.15 (2H, m), 4.61 (2H, s), 6.97 (1H, dd, J=8.4, 2.7 Hz), 7.03 (1H, d, J=2.7 Hz), 7.40 (1H, d, J=8.4 Hz), 7.96 (1H, dd, J=8.1, 5.4 Hz), 8.11 (2H, s), 8.36 (1H, t, J=6.7 Hz), 8.44 (1H, d, J=8.1 Hz), 8.80 (1H, d, J=5.4 Hz), 8.81-8.96 (3H, m).

Example 236

Synthesis of 1-ethyl-6-{3-[N-(2-pyridin-3-ylethyl)-N-(pyridin-4-ylmethyl)amino]propoxy}-3,4-dihydro-1H-quinolin-2-one trihydrochloride The synthesis of the title compound was performed in the same manner as in Example 32 using appropriate starting materials.

1H-NMR (DMSO-D6) δ ppm: 1.10 (3H, t, J=7.0 Hz), 2.08-2.30 (2H, m), 2.40-2.54 (2H, m), 2.80 (2H, t, J=7.9 Hz), 3.00-3.45 (6H, m), 3.87 (2H, q, J=7.0 Hz), 3.94-4.11 (2H, m), 4.49 (2H, s), 6.69-6.80 (2H, m), 7.03 (1H, d, J=9.0 Hz), 7.79 (1H, dd, J=8.0, 5.4 Hz), 7.93 (2H, d, J=4.9 Hz), 8.24 (1H, d, J=8.0 Hz), 8.70 (1H, d, J=5.4 Hz), 8.70-8.82 (3H, m).

Example 237

Synthesis of 1-methyl-6-{2-[N-((E)-3-pyridin-4-ylallyl)-N-(pyridin-3-ylmethyl)amino]ethoxy}-1H-quinolin-2-one trihydrochloride The synthesis of the title compound was performed in the same manner as in Example 5 using appropriate starting materials.

1H-NMR (CDCl3) δ ppm: 3.00 (2H, t, J=5.6 Hz), 3.43 (2H, d, J=2.1 Hz), 3.70 (3H, s), 3.81 (2H, s), 4.13 (2H, t, J=5.6 Hz), 6.46-6.55 (1H, m), 6.53 (1H, d, J=2.1 Hz), 6.72 (1H, d, J=9.5 Hz), 6.96 (1H, d, J=2.8 Hz), 7.10-7.35 (5H, m), 7.57 (1H, d, J=9.5 Hz), 7.73 (1H, d, J=5.3 Hz), 8.42-8.58 (3H, m), 8.63 (1H, s).

Example 238

Synthesis of 1-methyl-6-{2-[N-(pyridin-3-ylmethyl)-N-(3-pyridin-3-ylpropyl)amino]ethoxy}-1H-quinolin-2-one trihydrochloride The synthesis of the title compound was performed in the same manner as in Example 5 using appropriate starting materials.

1H-NMR (DMSO-D6) δ ppm: 2.07-2.31 (2H, m), 2.70-2.95 (2H, m), 3.03-3.25 (2H, m), 3.40-3.69 (2H, m), 3.61 (3H, s), 4.37-4.68 (4H, m), 6.64 (1H, d, J=9.5 Hz), 7.20-7.42 (2H, m), 7.51 (1H, d, J=9.2 Hz), 7.58-7.72 (1H, m), 7.78-7.99 (2H, m), 8.30-8.50 (2H, m), 8.68-8.80 (2H, m), 8.85 (1H, s), 8.98 (1H, s).

Example 239

Synthesis of 1-methyl-6-{2-[N-(pyridin-4-ylmethyl)-N-(3-pyridin-3-ylpropyl)amino]ethoxy}-1H-quinolin-2-one trihydrochloride The synthesis of the title compound was performed in the same manner as in Example 5 using appropriate starting materials.
1H-NMR (DMSO-D6) δ ppm: 2.01-2.31 (2H, m), 2.69-2.90 (2H, m), 2.90-3.22 (2H, m), 3.22-3.55 (2H, m), 3.61 (3H, s), 4.30-4.66 (4H, m), 6.63 (1H, d, J=9.5 Hz), 7.26 (1H, dd, J=9.2, 2.7 Hz), 7.33 (1H, d, J=2.7 Hz), 7.50 (1H, d, J=9.2 Hz), 7.76-7.92 (2H, m), 7.98 (2H, d, J=6.1 Hz), 8.33 (1H, d, J=7.9 Hz), 8.72 (1H, d, J=6.5 Hz), 8.73-8.88 (3H, m).

Example 240

Synthesis of 1-methyl-6-{2-[N-((E)-3-pyridin-3-ylallyl)-N-(pyridin-3-ylmethyl)amino]ethoxy}-1H-quinolin-2-one trihydrochloride The synthesis of the title compound was performed in the same manner as in Example 5 using appropriate starting materials.
1H-NMR (DMSO-D6) δ ppm: 3.47-3.68 (2H, m), 3.60 (3H, s), 3.94-4.12 (2H, m), 4.46-4.70 (2H, m), 4.70 (2H, s), 6.62 (1H, d, J=9.5 Hz), 6.87-7.08 (2H, m), 7.29-7.54 (3H, m), 7.78-7.94 (3H, m), 8.49 (1H, d, J=8.0 Hz), 8.66 (1H, d, J=8.0 Hz), 8.75 (1H, d, J=5.4 Hz), 8.82 (1H, d, J=5.4 Hz), 9.01 (1H, s), 9.12 (1H, s).

Example 241

Synthesis of 1-methyl-6-{2-[N-((E)-3-pyridin-3-ylallyl)-N-(pyridin-4-ylmethyl)amino]ethoxy}-1H-quinolin-2-one trihydrochloride The synthesis of the title compound was performed in the same manner as in Example 5 using appropriate starting materials.
1H-NMR (DMSO-D6) δ ppm: 3.21-3.48 (2H, m), 3.59 (3H, s), 3.70-3.98 (2H, m), 4.28-4.59 (4H, m), 6.62 (1H, d, J=9.5 Hz), 6.68-6.94 (2H, m), 7.18-7.38 (2H, m), 7.46 (1H, d, J=9.0 Hz), 7.57-7.71 (1H, m), 7.82 (1H, d, J=9.5 Hz), 8.02 (2H, d, J=5.1 Hz), 8.23 (1H, d, J=7.1 Hz), 8.62 (1H, d, J=5.1 Hz), 8.66-8.91 (3H, m).

Example 242

Synthesis of N-methyl-3-{N'-[3-(1-methyl-2-oxo-1,2-dihydroquinolin-6-yloxy)propyl]-N'-(pyridin-4-ylmethyl)amino}-N-phenylpropionamide Sodium ethoxide (34 mg) and 3-chloro-N-methyl-N-phenylpropionamide (148 mg) were added to a ethanol solution (5 ml) of 1-methyl-6-{3-[(pyridin-4-ylmethyl)amino]propoxy}-1H-quinolin-2-one (161 mg), and stirred at 60° C. for 8.5 hours. The reaction mixture was concentrated under reduced pressure. The residue was purified by silica gel column chromatography (ethyl acetate: methanol=10:0→4:1). The purified product was condensed under reduced pressure to give the title compound (5.6 mg) as a colorless oil.
1H-NMR (CDCl3) δ ppm: 1.80-1.98 (2H, m), 2.26 (2H, t, J=7.3 Hz), 2.53 (2H, t, J=6.5 Hz), 2.81 (2H, t, J=7.3 Hz), 3.24 (3H, s), 3.44 (2H, s), 3.72 (3H, s), 3.98 (2H, t, J=6.0 Hz), 6.73 (1H, d, J=9.5 Hz), 6.93 (1H, d, J=2.7 Hz), 7.00-7.19 (5H, m), 7.24-7.41 (4H, m), 7.60 (1H, d, J=9.5 Hz), 8.42 (2H, d, J=5.4 Hz).

Example 243

Synthesis of 3-{N'-[3-(1-methyl-2-oxo-1,2-dihydroquinolin-6-yloxy)propyl]-N'-(pyridin-4-ylmethyl)amino}-N-o-tolylpropionamide dihydrochloride The synthesis of the title compound was performed in the same manner as in Example 5 using appropriate starting materials.
1H-NMR (DMSO-D6) δ ppm: 2.30 (3H, s), 2.20-2.40 (2H, m), 2.91-3.18 (2H, m), 3.18-3.37 (2H, m), 3.37-3.55 (2H, m), 3.60 (3H, s), 3.93-4.20 (2H, m), 4.66 (2H, s), 6.62 (1H, d, J=9.5 Hz), 7.00-7.31 (5H, m), 7.36 (1H, d, J=7.3 Hz), 7.46 (1H, d, J=9.2 Hz), 7.82 (1H, d, J=9.5 Hz), 8.20 (2H, d, J=5.2 Hz), 8.90 (2H, d, J=5.2 Hz), 9.72 (1H, s).

Example 244

Synthesis of N-methyl-3-{N'-[3-(1-methyl-2-oxo-1,2-dihydroquinolin-6-yloxy)propyl]-N'-(pyridin-4-ylmethyl)amino}-N-o-tolylpropionamide dihydrochloride The synthesis of the title compound was performed in the same manner as in Example 5 using appropriate starting materials.
1H-NMR (DMSO-D6) δ ppm: 2.18 (3H, s), 2.08-2.42 (2H, m), 2.95-3.19 (2H, m), 3.06 (3H, s), 3.19-3.49 (4H, m), 3.60 (3H, s), 3.93-4.13 (2H, m), 4.48 (2H, s), 6.62 (1H, d, J=9.5 Hz), 7.15 (1H, dd, J=9.2, 2.8 Hz), 7.19-7.41 (5H, m), 7.48 (1H, d, J=9.2 Hz), 7.84 (1H, d, J=9.5 Hz), 7.97 (2H, d, J=6.0 Hz), 8.80 (2H, d, J=6.0 Hz).

Example 245

Synthesis of furan-3-carboxylic acid methyl-(2-{N-[3-(1-methyl-2-oxo-1,2-dihydroquinolin-6-yloxy)propyl]-N-(pyridin-4-ylmethyl)amino}ethyl)amide hydrochloride The synthesis of the title compound was performed in the same manner as in Example 46 using appropriate starting materials.
1H-NMR (DMSO-D6) δ ppm: 2.13-2.41 (2H, m), 2.98-3.48 (4H, m), 3.15 (3H, s), 3.60 (3H, s), 3.78-3.98 (2H, m), 3.98-4.20 (2H, m), 4.65 (2H, s), 6.62 (1H, d, J=9.5 Hz), 6.74 (1H, s), 7.18 (1H, dd, J=9.1, 2.6 Hz), 7.26 (1H, d, J=2.6 Hz), 7.46 (1H, d, J=9.1 Hz), 7.75 (1H, s), 7.83 (1H, d, J=9.5 Hz), 8.15 (1H, s), 8.20 (2H, d, J=5.2 Hz), 8.89 (2H, d, J=5.2 Hz).

Example 246

Synthesis of N-methyl-N-(2-{N'-[3-(1-methyl-2-oxo-1,2-dihydroquinolin-6-yloxy)propyl]-N'-(pyridin-4-ylmethyl)amino}ethyl)-2-thiophen-2-ylacetamide dihydrochloride The synthesis of the title compound was performed in the same manner as in Example 46 using appropriate starting materials.
1H-NMR (DMSO-D6) δ ppm: 2.12-2.49 (2H, m), 3.08 (3H, s), 3.12-3.41 (4H, m), 3.60 (3H, s), 3.65-3.88 (2H, m), 3.97 (2H, s), 4.00-4.16 (2H, m), 4.44-4.93 (2H, m), 6.62 (1H, d, J=9.5 Hz), 6.87-7.02 (2H, m), 7.19 (1H, dd, J=9.2, 2.7 Hz), 7.26 (1H, d, J=2.7 Hz), 7.37 (1H, dd, J=5.0, 1.3 Hz), 7.46 (1H, d, J=9.2 Hz), 7.83 (1H, d, J=9.5 Hz), 8.24 (2H, d, J=5.4 Hz), 8.91 (2H, d, J=5.4 Hz).

Example 247

Synthesis of cyclohexanecarboxylic acid N-methyl-(2-{N'-[3-(1-methyl-2-oxo-1,2-dihydroquinolin-6-yloxy)propyl]-N'-(pyridin-4-ylmethyl)amino}ethyl) amide dihydrochloride The synthesis of the title compound was performed in the same manner as in Example 46 using appropriate starting materials.

1H-NMR (DMSO-D6) δ ppm: 1.03-1.45 (6H, m), 1.45-1.80 (4H, m), 2.17-2.41 (2H, m), 2.41-2.65 (1H, m), 3.05 (3H, s), 3.08-3.40 (4H, m), 3.60 (3H, s), 3.66-3.82 (2H, m), 4.00-4.20 (2H, m), 4.68 (2H, s), 6.62 (1H, d, J=9.5 Hz), 7.20 (1H, dd, J=9.2, 2.8 Hz), 7.27 (1H, d, J=2.8 Hz), 7.47 (1H, d, J=9.2 Hz), 7.84 (1H, d, J=9.5 Hz), 8.26 (2H, d, J=5.5 Hz), 8.94 (2H, d, J=5.5 Hz).

Example 248

Synthesis of 3-methoxy-N-methyl-N-(2-{N'-[3-(1-methyl-2-oxo-1,2-dihydroquinolin-6-yloxy)propyl]-N'-(pyridin-4-ylmethyl)amino}ethyl)benzamide dihydrochloride The synthesis of the title compound was performed in the same manner as in Example 46 using appropriate starting materials.

1H-NMR (DMSO-D6) δ ppm: 2.20-2.48 (2H, m), 2.95 (3H, s), 3.13-3.51 (4H, m), 3.60 (3H, s), 3.77 (3H, s), 3.82-4.01 (2H, m), 4.01-4.22 (2H, m), 4.76 (2H, s), 6.62 (1H, d, J=9.5 Hz), 6.82-7.09 (3H, m), 7.09-7.40 (3H, m), 7.46 (1H, d, J=9.2 Hz), 7.83 (1H, d, J=9.5 Hz), 8.32 (2H, s), 8.94 (2H, s).

Example 249

Synthesis of 5-methylisoxazole-3-carboxylic acid N-methyl-(2-{N'-[3-(1-methyl-2-oxo-1,2-dihydroquinolin-6-yloxy)propyl]-N-(pyridin-4-ylmethyl) amino}ethyl)amide dihydrochloride The synthesis of the title compound was performed in the same manner as in Example 46 using appropriate starting materials.

1H-NMR (CDCl3) δ ppm: 1.85-2.09 (2H, m), 2.66 (3H, s), 2.59-2.82 (4H, m), 2.98-3.30 (2H, m), 3.20 (3H, s), 3.64 (2H, s), 3.71 (3H, s), 3.98-4.15 (2H, m), 6.25 (1H, s), 6.71 (1H, d, J=9.5 Hz), 6.99 (1H, d, J=7.4 Hz), 7.03-7.16 (1H, m), 7.16-7.35 (3H, m), 7.62 (1H, d, J=9.5 Hz), 8.36-8.51 (2H, m).

Example 250

Synthesis of benzo[b]thiophene-3-carboxylic acid N-methyl-(2-{N'-[3-(1-methyl-2-oxo-1,2-dihydroquinolin-6-yloxy)propyl]-N-(pyridin-4-ylmethyl) amino}ethyl)amide dihydrochloride The synthesis of the title compound was performed in the same manner as in Example 46 using appropriate starting materials.

1H-NMR (DMSO-D6) δ ppm: 2.15-2.41 (2H, m), 3.03 (3H, s), 3.11-3.51 (4H, m), 3.59 (3H, s), 3.75-4.88 (6H, m), 6.61 (1H, d, J=9.5 Hz), 7.09-7.35 (2H, m), 7.35-7.54 (3H, m), 7.67-7.87 (2H, m), 7.87-8.32 (4H, m), 8.88 (2H, s).

Example 251

Synthesis of 2,4-dimethoxy-N-methyl-N-(2-{N'-[3-(1-methyl-2-oxo-1,2-dihydroquinolin-6-yloxy)propyl]-N'-(pyridin-4-ylmethyl)amino}ethyl)benzamide dihydrochloride The synthesis of the title compound was performed in the same manner as in Example 46 using appropriate starting materials.

1H-NMR (DMSO-D6) δ ppm: 2.08-2.32 (2H, m), 2.68-3.00 (2H, m), 2.84 (3H, s), 3.00-3.34 (2H, m), 3.59 (3H, s), 3.75 (3H, s), 3.77 (3H, s), 3.65-4.58 (6H, m), 6.45-6.62 (3H, m), 6.98-7.22 (3H, m), 7.41 (1H, d, J=9.0 Hz), 7.78 (1H, d, J=9.5 Hz), 7.94 (2H, s), 8.71 (2H, s).

Example 252

Synthesis of 2,3-dimethoxy-N-methyl-N-(2-{N'-[3-(1-methyl-2-oxo-1,2-dihydroquinolin-6-yloxy)propyl]-N'-(pyridin-4-ylmethyl)amino}ethyl)benzamide dihydrochloride The synthesis of the title compound was performed in the same manner as in Example 46 using appropriate starting materials.

1H-NMR (DMSO-D6) δ ppm: 2.16-2.40 (2H, m), 2.80 (3H, s), 2.80-3.11 (2H, m), 3.11-3.40 (2H, m), 3.59 (3H, s), 3.70 (3H, s), 3.82 (3H, s), 3.85-4.05 (2H, m), 4.05-4.21 (2H, m), 4.59 (2H, s), 6.58 (1H, d, J=9.5 Hz), 6.64-6.87 (2H, m), 7.00-7.29 (3H, m), 7.43 (1H, d, J=9.0 Hz), 7.78 (1H, d, J=9.5 Hz), 8.20 (2H, s), 8.82 (2H, s).

Example 253

Synthesis of 6-{3-[N-(1-benzoylpiperidin-4-yl)-N-(pyridin-4-ylmethyl)amino]propoxy}-1-methyl-1H-quinolin-2-one dihydrochloride The synthesis of the title compound was performed in the same manner as in Example 50 using appropriate starting materials.

1H-NMR (DMSO-D6) δ ppm: 1.78-2.02 (2H, m), 2.02-2.42 (4H, m), 2.63-3.50 (5H, m), 3.59 (3H, s), 3.50-4.90 (6H, m), 6.62 (1H, d, J=9.5 Hz), 7.17 (1H, dd, J=9.0, 2.6 Hz), 7.22 (1H, d, J=2.6 Hz), 7.35-7.56 (6H, m), 7.82 (1H, d, J=9.5 Hz), 8.27 (2H, s), 8.89 (2H, s).

Example 254

Synthesis of 6-(3-{N-[1-(2,3-dihydrobenzofuran-7-carbonyl)piperidin-4-yl]-N-(pyridin-4-ylmethyl) amino}propoxy)-1-methyl-1H-quinolin-2-one dihydrochloride The synthesis of the title compound was performed in the same manner as in Example 50 using appropriate starting materials.

1H-NMR (DMSO-D6) δ ppm: 1.68-1.93 (2H, m), 2.03-2.41 (4H, m), 2.60-3.36 (5H, m), 3.59 (3H, s), 3.62-4.79 (6H, m), 4.04 (2H, t, J=7.1 Hz), 4.56 (2H, t, J=8.6 Hz), 6.62 (1H, d, J=9.5 Hz), 6.89 (1H, dd, J=7.2, 7.1 Hz), 7.09 (1H, d, J=7.2 Hz), 7.16 (1H, dd, J=9.2, 2.7 Hz), 7.22 (1H, d, J=2.7 Hz), 7.31

(1H, d, J=7.1 Hz), 7.45 (1H, d, J=9.2 Hz), 7.82 (1H, d, J=9.5 Hz), 8.28 (2H, s), 8.89 (2H, s).

Example 255

Synthesis of 1-methyl-6-{3-[N-(1-phenylpiperidin-4-yl)-N-(pyridin-4-ylmethyl)amino]propoxy}-1H-quinolin-2-one trihydrochloride The synthesis of the title compound was performed in the same manner as in Example 96 using appropriate starting materials.

1H-NMR (DMSO-D6) δ ppm: 1.91-2.43 (6H, m), 2.63-4.31 (9H, m), 3.60 (3H, s), 4.31-4.83 (2H, m), 6.62 (1H, d, J=9.5 Hz), 6.79-7.39 (7H, m), 7.45 (1H, d, J=9.2 Hz), 7.83 (1H, d, J=9.5 Hz), 8.09 (2H, d, J=5.0 Hz), 8.79 (2H, d, J=5.0 Hz).

Example 256

Synthesis of 1-Methyl-6-(3-{N-[2-(N'-methyl-N'-phenylamino)ethyl]-N-(pyridin-4-ylmethyl)amino}propoxy)-1H-quinolin-2-one trihydrochloride The synthesis of the title compound was performed in the same manner as in Example 96 using appropriate starting materials.

1H-NMR (DMSO-D6) δ ppm: 2.12-2.33 (2H, m), 2.90 (3H, s), 3.07-3.34 (4H, m), 3.60 (3H, s), 3.34-4.00 (2H, m), 4.00-4.16 (2H, m), 4.57 (2H, s), 6.62 (1H, d, J=9.5 Hz), 6.68 (1H, t, J=7.3 Hz), 6.79 (2H, d, J=7.3 Hz), 7.11-7.23 (3H, m), 7.24 (1H, d, J=2.8 Hz), 7.46 (1H, d, J=9.0 Hz), 7.83 (1H, d, J=9.5 Hz), 8.04 (2H, d, J=4.9 Hz), 8.81 (2H, d, J=4.9 Hz).

Example 257

Synthesis of 6-{3-[N-(1-methoxyisoquinolin-4-yl)-N-(pyridin-4-ylmethyl)amino]propoxy}-1-methyl-1H-quinolin-2-one The synthesis of the title compound was performed in the same manner as in Example 5 using appropriate starting materials.

1H-NMR (CDCl3) δ ppm: 1.92-2.17 (2H, m), 3.34 (2H, t, J=6.9 Hz), 3.70 (3H, s), 3.99 (2H, t, J=5.9 Hz), 4.09 (3H, s), 4.26 (2H, s), 6.70 (1H, d, J=9.5 Hz), 6.85 (1H, d, J=2.8 Hz), 7.04 (1H, dd, J=9.1, 2.8 Hz), 7.19-7.35 (3H, m), 7.52 (1H, d, J=9.5 Hz), 7.51-7.62 (1H, m), 7.62-7.74 (1H, m), 7.80 (1H, s), 8.18 (1H, d, J=8.2 Hz), 8.26 (1H, d, J=7.6 Hz), 8.48 (2H, d, J=5.9 Hz).

Example 258

Synthesis of 1-methyl-6-{3-[N-(1-oxo-1,2-dihydroisoquinolin-4-yl)-N-(pyridin-4-ylmethyl)amino]propoxy}-1H-quinolin-2-one 6-{3-[N-(1-Methoxyisoquinolin-4-yl)-N-(pyridin-4-ylmethyl)amino]propoxy}-1-methyl-1H-quinolin-2-one (55 mg) was added to a 1N-hydrogen chloride in ethanol solution(5 ml), and stirred at 75° C. for 2 hours. The reaction mixture was cooled to room temperature. 1N-Sodium hydroxide aqueous solution(5 ml) was added to the reaction mixture, followed by extraction with dichloromethane. The organic layer was dried over anhydrous sodium sulfate. The filtrate was condensed under reduced pressure, and the residue was purified by silica gel column chromatography (ethyl acetate: methanol=10:0→4:1). The purified product was condensed under reduced pressure to give the title compound(20.6 mg) as a colorless oil.

1H-NMR (CDCl3) δ ppm: 1.92-2.14 (2H, m), 3.22 (2H, t, J=6.8 Hz), 3.70 (3H, s), 4.02 (2H, t, J=5.9 Hz), 4.16 (2H, s), 6.71 (1H, d, J=9.5 Hz), 6.89 (1H, d, J=2.8 Hz), 7.01 (1H, s), 7.09 (1H, dd, J=9.1, 2.8 Hz), 7.20-7.33 (3H, m), 7.54 (1H, d, J=9.5 Hz), 7.52-7.67 (1H, m), 7.67-7.80 (1H, m), 8.08 (1H, d, J=8.2 Hz), 8.46 (1H, d, J=7.2 Hz), 8.51 (2H, d, J=5.9 Hz).

Example 259

Synthesis of 1-Methyl-6-(3-{N-[2-(7-oxo-7H-furo[2,3-c]pyridin-6-yl)ethyl]-N-(pyridin-4-ylmethyl)amino}propoxy)-1H-quinolin-2-one dihydrochloride The synthesis of the title compound was performed in the same manner as in Example 5 using appropriate starting materials.

1H-NMR (DMSO-D6) δ ppm: 1.79-2.09 (2H, m), 2.60-4.15 (8H, m), 3.61 (3H, s), 4.76 (2H, s), 6.58 (1H, d, J=7.0 Hz), 6.63 (1H, d, J=9.5 Hz), 6.90 (1H, d, J=1.8 Hz), 6.99-7.19 (2H, m), 7.44 (1H, d, J=9.1 Hz), 7.51 (1H, d, J=7.0 Hz), 7.68 (2H, d, J=4.6 Hz), 7.83 (1H, d, J=9.5 Hz), 8.13 (1H, d, J=1.8 Hz), 8.53 (2H, d, J=4.6 Hz).

Example 260

Synthesis of 1-methyl-6-[3-(2-pyridin-3-ylethylamino)propoxy]-1H-quinolin-2-one

The synthesis of the title compound was performed in the same manner as in Example 3 using appropriate starting materials.

1H-NMR (CDCl3) δ ppm: 1.90-2.06 (2H, m), 2.76-3.00 (6H, m), 3.72 (3H, s), 4.08 (2H, t, J=6.1 Hz), 6.73 (1H, d, J=9.5 Hz), 6.99 (1H, d, J=2.8 Hz), 7.15 (1H, dd, J=9.2, 2.8 Hz), 7.21 (1H, ddd, J=7.7, 4.8, 0.6 Hz), 7.29 (1H, d, J=9.2 Hz), 7.51-7.57 (1H, m), 7.60 (1H, d, J=9.5 Hz), 8.47 (1H, dd, J=4.8, 1.7 Hz), 8.51 (1H, d, J=1.7 Hz).

Example 261

Synthesis of 1-methyl-6-[4-(2-pyridin-3-ylethylamino)butoxy]-1H-quinolin-2-one

The synthesis of the title compound was performed in the same manner as in Example 3 using appropriate starting materials.

1H-NMR (CDCl3) δ ppm: 1.58-1.76 (2H, m), 1.76-1.92 (2H, m), 2.71 (2H, t, J=7.2 Hz), 2.78-3.00 (4H, m), 3.70 (3H, s), 4.00 (2H, t, J=6.2 Hz), 6.70 (1H, d, J=9.5 Hz), 6.98 (1H, d, J=2.8 Hz), 7.15 (1H, dd, J=9.2, 2.8 Hz), 7.22 (1H, dd, J=7.7, 4.8 Hz), 7.28 (1H, d, J=9.2 Hz), 7.49-7.56 (1H, m), 7.59 (1H, d, J=9.5 Hz), 8.46 (1H, dd, J=4.8, 1.8 Hz), 8.48 (1H, d, J=1.8 Hz).

Example 262

Synthesis of 1-methyl-6-{3-[(pyridin-3-ylmethyl)amino]propoxy}-1H-quinolin-2-one 3N-Hydrochloric acid(5 ml) was added to a ethanol solution(5 ml) of N-[3-(1-Methyl-2-oxo-1,2-dihydroquinolin-6-yloxy)propyl]-N-(pyridin-3-ylmethyl)benzamide(250.1 mg), and stirred for 60 hours while heated under reflux. The reaction mixture was cooled to room temperature. Water was added thereto, washed with ethyl acetate. A saturated sodium hydrogencarbonate aqueous solution was added to the aqueous layer, followed by extraction using dichloromethane. The organic layer was dried with anhydrous sodium sulfate, and condensed under reduced pressure to give the title compound (168 mg) as a colorless oil.

1H-NMR (CDCl3) δ ppm: 1.93-2.10 (2H, m), 2.86 (2H, t, J=6.8 Hz), 3.71 (3H, s), 3.84 (2H, s), 4.11 (2H, t, J=6.2 Hz), 6.71 (1H, d, J=9.5 Hz), 7.00 (1H, d, J=2.8 Hz), 7.16 (1H, dd, J=9.2, 2.8 Hz), 7.22-7.33 (2H, m), 7.59 (1H, d, J=9.5 Hz), 7.65-7.72 (1H, m), 8.50 (1H, dd, J=4.8, 1.7 Hz), 8.58 (1H, d, J=1.7 Hz).

Example 263

Synthesis of 1-methyl-6-[2-(2-pyridin-3-ylethylamino)ethoxy]-1H-quinolin-2-one

The synthesis of the title compound was performed in the same manner as in Example 3 using appropriate starting materials.

1H-NMR (CDCl3) δ ppm: 2.76-2.90 (2H, m), 2.90-3.04 (2H, m), 3.07 (2H, t, J=5.2 Hz), 3.71 (3H, s), 4.12 (2H, t, J=5.2 Hz), 6.72 (1H, d, J=9.5 Hz), 7.00 (1H, d, J=2.8 Hz), 7.16 (1H, dd, J=9.2, 2.8 Hz), 7.23 (1H, dd, J=7.7, 4.8 Hz), 7.30 (1H, d, J=9.2 Hz), 7.52-7.59 (1H, m), 7.59 (1H, d, J=9.5 Hz), 8.48 (1H, dd, J=4.8, 1.7 Hz), 8.51 (1H, d, J=1.7 Hz).

Example 264

Synthesis of 1-methyl-6-{2-[N-(pyridin-3-ylmethyl)amino]ethoxy}-1H-quinolin-2-one 3-Pyridine carbaldyde(0.99 ml) and 6-(2-Aminoethoxy)-1-methyl-1H-quinolin-2-one(2.18 g) were added to methanol (50 ml). The mixture was stirred at room temperature for 7 hours. The mixture was cooled to 0° C., and sodium borohydride(0.757 g) was added thereto. The mixture was further stirred at room temperature overnight. Water was added to the reaction mixture and methanol was distilled off under reduced pressure. The residue was subjected to extraction using dichloromethane. The organic layer was washed with saturated saline, dried with anhydrous sodium sulfate, and was condensed under reduced pressure. The residue was purified by basic silica gel column chromatography (ethyl acetate). The purified product was condensed under reduced pressure to give the title compound(3.063 g) as a yellow oil.

1H-NMR (CDCl3) δ ppm: 3.06 (2H, t, J=5.0 Hz), 3.71 (3H, s), 3.91 (2H, s), 4.14 (2H, t, J=5.0 Hz), 6.72 (1H, d, J=9.5 Hz), 7.01 (1H, d, J=2.8 Hz), 7.19 (1H, dd, J=9.2, 2.8 Hz), 7.24-7.33 (2H, m), 7.59 (1H, d, J=9.5 Hz), 7.68-7.75 (1H, m), 8.52 (1H, dd, J=4.8, 1.7 Hz), 8.61 (1H, d, J=1.7 Hz).

Example 265

Synthesis of methanesulfonic acid 2-[N-[3-(1-methyl-2-oxo-1,2-dihydroquinolin-6-yloxy)propyl]-N-(2-nitro-benzenesulfonyl)amino]ethyl ester Methane sulfonyl chloride(1.14 ml) was added to a dichloromethane solution(50 ml) of N-(2-hydroxy-thyl)-N-[3-(1-methyl-2-oxo-1,2-dihydroquinolin-6-yloxy)propyl]-2-nitrobenzenesulfonamide(4.52 g) and triethylamine(2.73 ml). The mixture was stirred at room temperature overnight. 1N-Sodium hydroxide aqueous solution was added to the reaction mixture, followed by extraction using dichloromethane. The organic layer was washed with saturated saline, and dried with sodium sulfate. After the organic layer was condensed under reduced pressure, the residue was purified by silica gel column chromatography (ethyl acetate). The purified product was condensed under reduced pressure to give the title compound(4.37 g) as a yellow solid.

1H-NMR (CDCl3) δ ppm: 2.00-2.21 (2H, m), 3.03 (3H, s), 3.63 (2H, t, J=7.6 Hz), 3.71 (3H, s), 3.75 (2H, t, J=5.5 Hz), 4.01 (2H, t, J=6.0 Hz), 4.40 (2H, t, J=5.5 Hz), 6.72 (1H, d, J=9.5 Hz), 6.92 (1H, d, J=2.8 Hz), 7.11 (1H, dd, J=9.2, 2.8 Hz), 7.28 (1H, d, J=9.2 Hz), 7.56-7.67 (4H, m), 8.02-8.08 (1H, m).

Example 266

Synthesis of 1-methyl-6-(3-{2-[4-(pyridin-3-ylmethoxy)piperidin-1-yl]ethylamino}propoxy)-1H-quinolin-2-one The synthesis of the title compound was performed in the same manner as in Example 3 using appropriate starting materials.

1H-NMR (CDCl3) δ ppm: 1.54-2.24 (8H, m), 2.49 (2H, t, J=6.1 Hz), 2.66-2.90 (6H, m), 3.33-3.50 (1H, m), 3.70 (3H, s), 4.00-4.18 (2H, m), 4.54 (2H, s), 6.71 (1H, d, J=9.5 Hz), 7.02 (1H, d, J=2.8 Hz), 7.19 (1H, dd, J=9.2, 2.8 Hz), 7.23-7.32 (2H, m), 7.59 (1H, d, J=9.5 Hz), 7.63-7.71 (1H, m), 8.53 (1H, dd, J=4.7, 1.5 Hz), 8.57 (1H, d, J=1.5 Hz).

Example 267

Synthesis of 1-methyl-6-(2-{2-[4-(pyridin-3-ylmethoxy)piperidin-1-yl]ethylamino}ethoxy)-1H-quinolin-2-one The synthesis of the title compound was performed in the same manner as in Example 3 using appropriate starting materials.

1H-NMR (CDCl3) δ ppm: 1.58-1.85 (2H, m), 1.85-2.02 (2H, m), 2.10-2.25 (2H, m), 2.51 (2H, t, J=6.1 Hz), 2.70-2.85 (4H, m), 3.05 (2H, t, J=5.5 Hz), 3.36-3.50 (1H, m), 3.71 (3H, s), 4.13 (2H, t, J=5.5 Hz), 4.56 (2H, s), 6.72 (1H, d, J=9.5 Hz), 7.02 (1H, d, J=2.8 Hz), 7.20 (1H, dd, J=9.2, 2.8 Hz), 7.25-7.33 (2H, m), 7.60 (1H, d, J=9.5 Hz), 7.65-7.72 (1H, m), 8.53 (1H, dd, J=4.8, 1.6 Hz), 8.58 (1H, d, J=1.6 Hz).

Example 268

Synthesis of 1-methyl-6-{4-[(pyridin-4-ylmethyl)amino]butoxy}-1H-quinolin-2-one

The synthesis of the title compound was performed in the same manner as in Example 264 using appropriate starting materials.

1H-NMR (CDCl3) δ ppm: 1.62-1.80 (2H, m), 1.80-2.00 (2H, m), 2.72 (2H, t, J=7.0 Hz), 3.71 (3H, s), 3.83 (2H, s), 4.03 (2H, t, J=6.2 Hz), 6.71 (1H, d, J=9.5 Hz), 6.98 (1H, d, J=2.8 Hz), 7.16 (1H, dd, J=9.2, 2.8 Hz), 7.22-7.32 (3H, m), 7.59 (1H, d, J=9.5 Hz), 8.54 (2H, d, J=5.9 Hz).

Example 269

Synthesis of 1-methyl-6-{4-[(pyridin-3-ylmethyl)amino]butoxy}-1H-quinolin-2-one

The synthesis of the title compound was performed in the same manner as in Example 264 using appropriate starting materials.

1H-NMR (CDCl3) δ ppm: 1.60-1.80 (2H, m), 1.80-1.98 (2H, m), 2.72 (2H, t, J=7.0 Hz), 3.71 (3H, s), 3.83 (2H, s), 4.02 (2H, t, J=6.2 Hz), 6.71 (1H, d, J=9.5 Hz), 6.98 (1H, d, J=2.8 Hz), 7.16 (1H, dd, J=9.2, 2.8 Hz), 7.22-7.33 (2H, m), 7.59 (1H, d, J=9.5 Hz), 7.63-7.71 (1H, m), 8.51 (1H, dd, J=4.7, 1.5 Hz), 8.57 (1H, d, J=1.5 Hz).

Example 270

Synthesis of 1-methyl-6-(3-{2-[4-(pyridin-4-yl-methoxy)piperidin-1-yl]ethylamino}propoxy)-1H-quinolin-2-one The synthesis of the title compound was performed in the same manner as in Example 3 using appropriate starting materials.
1H-NMR (CDCl3) δ ppm: 1.54-2.24 (8H, m), 2.49 (2H, t, J=6.0 Hz), 2.62-2.90 (6H, m), 3.30-3.49 (1H, m), 3.70 (3H, s), 4.10 (2H, t, J=6.2 Hz), 4.54 (2H, s), 6.71 (1H, d, J=9.5 Hz), 7.02 (1H, d, J=2.7 Hz), 7.19 (1H, dd, J=9.2, 2.7 Hz), 7.20-7.32 (3H, m), 7.59 (1H, d, J=9.5 Hz), 8.56 (2H, d, J=5.9 Hz).

Example 272

Synthesis of 1-methyl-6-[3-(2-pyridin-3-ylethylamino)propoxy]-3,4-dihydro-1H-quinolin-2-one The synthesis of the title compound was performed in the same manner as in Example 3 using appropriate starting materials.
1H-NMR (CDCl3) δ ppm: 1.82-2.02 (2H, m), 2.55-2.68 (2H, m), 2.78-2.99 (8H, m), 3.33 (3H, s), 3.99 (2H, t, J=6.1 Hz), 6.70 (1H, d, J=2.7 Hz), 6.74 (1H, dd, J=8.6, 2.7 Hz), 6.88 (1H, d, J=8.6 Hz), 7.21 (1H, dd, J=7.8, 4.8 Hz), 7.50-7.57 (1H, m), 8.46 (1H, dd, J=4.8, 1.8 Hz), 8.49 (1H, d, J=1.8 Hz).

Example 273

Synthesis of 1-methyl-6-[3-(2-pyridin-4-ylethylamino)propoxy]-1H-quinolin-2-one

The synthesis of the title compound was performed in the same manner as in Example 3 using appropriate starting materials.
1H-NMR (CDCl3) δ ppm: 1.92-2.08 (2H, m), 2.77-2.90 (4H, m), 2.90-3.01 (2H, m), 3.71 (3H, s), 4.07 (2H, t, J=6.1 Hz), 6.72 (1H, d, J=9.5 Hz), 6.96 (1H, d, J=2.8 Hz), 7.09-7.19 (3H, m), 7.29 (1H, d, J=9.3 Hz), 7.59 (1H, d, J=9.5 Hz), 8.50 (2H, d, J=6.0 Hz).

Example 274

Synthesis of 6-[3-(3-imidazol-1-yl-propylamino)propoxy]-1-methyl-1H-quinolin-2-one 3-(1-Methyl-2-oxo-1,2-dihydroquinolin-6-yloxy)propionaldehyde (127.5 mg) prepared from 6-hydroxy-1-methylquinolin-2(1H)-one and N-(3-aminopropyl)imidazole (82.9 mg) were added to methanol (10 ml). The mixture was stirred at room temperature for 7 hours. The mixture was cooled to 0° C., and sodium borohydride(31.4 mg) was added thereto. The mixture was further stirred at room temperature overnight. Water was added to the reaction mixture and methanol was distilled off under reduced pressure. The residue was subjected to extraction using dichloromethane. The organic layer was washed with saturated saline, dried with anhydrous sodium sulfate, and was condensed under reduced pressure. The residue was purified by NH silica gel column chromatography (ethyl acetate: methanol=10:0→4:1). The purified product was condensed under reduced pressure to give the title compound(21 mg) as a yellow oil.
1H-NMR (CDCl3) δ ppm: 1.81-2.02 (4H, m), 2.49-2.58 (2H, m), 2.80 (2H, t, J=6.9 Hz), 3.70 (3H, s), 3.93-4.15 (4H, m), 6.71 (1H, d, J=9.5 Hz), 6.91 (1H, s), 7.01 (1H, d, J=2.8 Hz), 7.05 (1H, s), 7.18 (1H, dd, J=9.2, 2.8 Hz), 7.29 (1H, d, J=9.2 Hz), 7.47 (1H, s), 7.60 (1H, d, J=9.5 Hz).

Example 275

Synthesis of 1-methyl-6-[3-(2-piperidin-1-ylethylamino)propoxy]-1H-quinolin-2-one The synthesis of the title compound was performed in the same manner as in Example 3 using appropriate starting materials.
1H-NMR (CDCl3) δ ppm: 1.32-1.49 (2H, m), 1.49-1.63 (4H, m), 1.94-2.08 (2H, m), 2.28-2.41 (4H, m), 2.45 (2H, t, J=6.2 Hz), 2.73 (2H, t, J=6.2 Hz), 2.83 (2H, t, J=6.9 Hz), 3.70 (3H, s), 4.10 (2H, t, J=6.2 Hz), 6.70 (1H, d, J=9.5 Hz), 7.01 (1H, d, J=2.8 Hz), 7.18 (1H, dd, J=9.2, 2.8 Hz), 7.28 (1H, d, J=9.2 Hz), 7.59 (1H, d, J=9.5 Hz).

Example 276

Synthesis of 6-[3-(2-diethylaminoethylamino)propoxy]-1-methyl-1H-quinolin-2-one

The synthesis of the title compound was performed in the same manner as in Example 3 using appropriate starting materials.
1H-NMR (CDCl3) δ ppm: 1.00 (6H, t, J=7.1 Hz), 1.90-2.08 (2H, m), 2.41-2.60 (6H, m), 2.69 (2H, t, J=5.7 Hz), 2.83 (2H, t, J=6.9 Hz), 3.71 (3H, s), 4.10 (2H, t, J=6.3 Hz), 6.71 (1H, d, J=9.5 Hz), 7.02 (1H, d, J=2.8 Hz), 7.19 (1H, dd, J=9.2, 2.8 Hz), 7.29 (1H, d, J=9.2 Hz), 7.59 (1H, d, J=9.5 Hz).

Example 277

Synthesis of 1-methyl-6-{3-[2-(4-methylpiperazin-1-yl)ethylamino]propoxy}-1H-quinolin-2-one The synthesis of the title compound was performed in the same manner as in Example 3 using appropriate starting materials.
1H-NMR (CDCl3) δ ppm: 1.91-2.08 (2H, m), 2.26 (3H, s), 2.31-2.63 (10H, m), 2.73 (2H, t, J=6.1 Hz), 2.83 (2H, t, J=6.8 Hz), 3.70 (3H, s), 4.10 (2H, t, J=6.2 Hz), 6.71 (1H, d, J=9.5 Hz), 7.02 (1H, d, J=2.6 Hz), 7.19 (1H, dd, J=9.2, 2.6 Hz), 7.29 (1H, d, J=9.2 Hz), 7.59 (1H, d, J=9.5 Hz).

Example 278

Synthesis of N-{2-[3-(1-methyl-2-oxo-1,2-dihydroquinolin-6-yloxy)propylamino]ethyl}benzamide The synthesis of the title compound was performed in the same manner as in Example 3 using appropriate starting materials.
1H-NMR (CDCl3) δ ppm: 1.92-2.10 (2H, m), 2.82-3.00 (4H, m), 3.49-3.61 (2H, m), 3.68 (3H, s), 4.11 (2H, t, J=6.1 Hz), 6.70 (1H, d, J=9.5 Hz), 6.81 (1H, s), 6.97 (1H, d, J=2.8 Hz), 7.14 (1H, dd, J=9.2, 2.8 Hz), 7.23 (1H, d, J=9.2 Hz), 7.31-7.39 (2H, m), 7.41-7.48 (1H, m), 7.54 (1H, d, J=9.5 Hz), 7.70-7.77 (2H, m).

Example 279

Synthesis of N-{2-[3-(1-methyl-2-oxo-1,2-dihydro-quinolin-6-yloxy)propylamino]ethyl}isobutyramide The synthesis of the title compound was performed in the same manner as in Example 3 using appropriate starting materials.
1H-NMR (CDCl3) δ ppm: 1.13 (6H, d, J=6.9 Hz), 1.90-2.08 (2H, m), 2.25-2.41 (1H, m), 2.75-2.90 (4H, m), 3.30-3.42 (2H, m), 3.70 (3H, s), 4.09 (2H, t, J=6.1 Hz), 6.09 (1H, s), 6.71 (1H, d, J=9.5 Hz), 7.00 (1H, d, J=2.8 Hz), 7.17 (1H, dd, J=9.2, 2.8 Hz), 7.29 (1H, d, J=9.2 Hz), 7.59 (1H, d, J=9.5 Hz).

Example 280

Synthesis of N-{2-[3-(1-methyl-2-oxo-1,2-dihydro-quinolin-6-yloxy)propylamino]ethyl}nicotinamide The synthesis of the title compound was performed in the same manner as in Example 3 using appropriate starting materials.
1H-NMR (CDCl3) δ ppm: 1.90-2.10 (2H, m), 2.80-3.00 (4H, m), 3.49-3.62 (2H, m), 3.68 (3H, s), 4.11 (2H, t, J=6.2 Hz), 6.69 (1H, d, J=9.5 Hz), 6.96 (1H, d, J=2.7 Hz), 7.02 (1H, s), 7.14 (1H, dd, J=9.1, 2.7 Hz), 7.24 (1H, d, J=9.1 Hz), 7.31 (1H, dd, J=7.9, 4.8 Hz), 7.56 (1H, d, J=9.5 Hz), 8.03-8.11 (1H, m), 8.67 (1H, dd, J=4.8, 1.9 Hz), 8.95 (1H, d, J=1.9 Hz).

Example 281

Synthesis of N-{2-[3-(1-methyl-2-oxo-1,2-dihydro-quinolin-6-yloxy)propylamino]ethyl}benzenesulfonamide The synthesis of the title compound was performed in the same manner as in Example 3 using appropriate starting materials.
1H-NMR (CDCl3) δ ppm: 1.80-1.99 (2H, m), 2.65-2.81 (4H, m), 2.99-3.12 (2H, m), 3.70 (3H, s), 4.05 (2H, t, J=6.1 Hz), 6.71 (1H, d, J=9.5 Hz), 6.99 (1H, d, J=2.7 Hz), 7.16 (1H, dd, J=9.1, 2.7 Hz), 7.28 (1H, d, J=9.1 Hz), 7.45-7.63 (4H, m), 7.82-7.90 (2H, m).

Example 282

Synthesis of {N-[3-(1-methyl-2-oxo-1,2-dihydro-quinolin-6-yloxy)propyl]-N-(pyridin-4-ylmethyl)amino}acetic acid A 1N-sodium hydroxide aqueous solution(3 ml) was added to a methanol solution (15 ml) of {N-[3-(1-methyl-2-oxo-1,2-dihydroquinolin-6-yloxy)propyl]-N-(pyridin-4-ylmethyl)amino}acetic acid ethyl ester (614 mg). The mixture was stirred at room temperature overnight. 1N-Hydrochloric acid(3 ml) was added to the reaction mixture and condensed under reduced pressure. Methanol was added to the residue, and the generated insoluble matter was separated by filtration. The filtrate was condensed under reduced pressure to give the title compound(468 mg) as a white amorphous solid.
1H-NMR (DMSO-D6) δ ppm: 1.75-1.94 (2H, m), 2.73 (2H, t, J=6.8 Hz), 3.03 (2H, s), 3.59 (3H, s), 3.82 (2H, s), 4.04 (2H, t, J=6.4 Hz), 6.59 (1H, d, J=9.5 Hz), 7.17 (1H, dd, J=9.1, 2.9 Hz), 7.23 (1H, d, J=2.9 Hz), 7.32 (2H, d, J=5.9 Hz), 7.44 (1H, d, J=9.1 Hz), 7.83 (1H, d, J=9.5 Hz), 8.40 (2H, d, J=5.9 Hz).

Example 283

Synthesis of 1-methyl-6-{3-[(pyridin-4-ylmethyl)amino]propoxy}-1H-quinolin-2-one The synthesis of the title compound was performed in the same manner as in Example 264 using appropriate starting materials.
1H-NMR (CDCl3) δ ppm: 1.86-2.10 (2H, m), 2.70-2.92 (2H, m), 3.71 (3H, s), 3.85 (2H, s), 4.12 (2H, t, J=6.0 Hz), 6.72 (1H, d, J=9.5 Hz), 7.00 (1H, d, J=2.8 Hz), 7.08-7.38 (4H, m), 7.59 (1H, d, J=9.5 Hz), 8.53 (2H, d, J=5.9 Hz).

Example 284

Synthesis of 6-{3-[(2-aminoethyl)-N-(pyridin-4-ylmethyl)amino]propoxy}-1-methyl-1H-quinolin-2-one A 4N-hydrogen chloride ethyl acetate solution(0.22 ml) was added to an ethyl acetate solution (3 ml) of (2-{[3-(1-Methyl-2-oxo-1,2-dihydro-quinolin-6-yloxy)-propyl]-pyridin-4-ylmethyl-amino}-ethyl)-carbamic acid tert-butyl ester (137 mg), and the mixture was stirred at room temperature overnight. 5N-Ammoia methanol solution(1 ml) was added to the reaction mixture, and the generated insoluble matter was separated by filtration. The filtrate was condensed under reduced pressure to give the title compound(85.7 mg) as an colorless oil.
1H-NMR (CDCl3) δ ppm: 1.88-2.08 (2H, m), 2.57 (2H, t, J=6.0 Hz), 2.67 (2H, t, J=6.9 Hz), 2.80 (2H, t, J=6.0 Hz), 3.62 (2H, s), 3.71 (3H, s), 4.05 (2H, t, J=6.0 Hz), 6.71 (1H, d, J=9.5 Hz), 6.95 (1H, d, J=2.8 Hz), 7.10 (1H, dd, J=9.2, 2.8 Hz), 7.22-7.32 (3H, m), 7.59 (1H, d, J=9.5 Hz), 8.49 (2H, d, J=6.0 Hz).

Example 285

Synthesis of 2-{3-[N-(2-pyridin-3-ylethyl)-N-(pyridin-4-ylmethyl)amino]propoxy}benzoic acid A 1N-sodium hydroxide aqueous solution(1.8 ml) was added to a methanol solution (3 ml) of 2-{3-[N-(2-pyridin-3-ylethyl)-N-(pyridin-4-ylmethyl)amino]propoxy}benzoic acid ethyl ester(372 mg). The mixture was stirred at room temperature overnight. 6N-Hydrochloric acid(0.3 ml) was added to the reaction mixture and condensed under reduced pressure. Methanol was added to the residue, and the generated insoluble matter was separated by filtration. The filtrate was condensed under reduced pressure to give the title compound(458 mg) as a colorless oil.
1H-NMR (DMSO-D6) δ ppm: 2.12-2.38 (2H, m), 3.09-3.48 (6H, m), 4.01-4.19 (2H, m), 4.46 (2H, s), 6.92-7.08 (1H, m), 7.10 (1H, d, J=6.9 Hz), 7.41-7.56 (1H, m), 7.64-7.77 (2H, m), 7.85 (2H, s), 8.13 (1H, d, J=7.6 Hz), 8.65 (1H, dd, J=5.2, 1.2 Hz), 8.68-8.80 (3H, m).

Example 286

Synthesis of 3-{3-[N-(2-pyridin-3-yl-ethyl)-N-(pyridin-4-ylmethyl)amino]propoxy}benzoic acid The synthesis of the title compound was performed in the same manner as in Example 285 using appropriate starting materials.
1H-NMR (DMSO-D6) δ ppm: 2.10-2.41 (2H, m), 3.02-3.59 (6H, m), 3.98-4.22 (2H, m), 4.43-4.72 (2H, m), 7.19 (1H, d, J=8.3 Hz), 7.31-7.46 (2H, m), 7.54 (1H, d, J=7.7 Hz), 7.63-7.77 (1H, m), 7.83 (2H, s), 8.04-8.20 (1H, m), 8.65 (1H, d, J=5.3 Hz), 8.66-8.79 (3H, m).

Example 287

Synthesis of 4-{3-[N-(2-pyridin-3-ylethyl)-N-(pyridin-4-ylmethyl)amino]propoxy}benzoic acid The synthesis of the title compound was performed in the same manner as in Example 285 using appropriate starting materials.

1H-NMR (DMSO-D6) δ ppm: 2.16-2.38 (2H, m), 3.00-3.99 (6H, m), 3.99-4.16 (2H, m), 4.35-4.69 (2H, m), 6.96 (2H, d, J=8.8 Hz), 7.62-7.80 (1H, m), 7.80-7.99 (4H, m), 8.19 (1H, d, J=6.7 Hz), 8.60-8.80 (4H, m).

Example 288

Synthesis of 1-methyl-6-[3-(2-pyridin-2-ylethylamino)propoxy]-1H-quinolin-2-one

The synthesis of the title compound was performed in the same manner as in Example 3 using appropriate starting materials.

1H-NMR (CDCl3) δ ppm: 1.91-2.12 (2H, m), 2.86 (2H, t, J=6.8 Hz), 2.92-3.14 (4H, m), 3.71 (3H, s), 4.07 (2H, t, J=6.2 Hz), 6.71 (1H, d, J=9.5 Hz), 6.99 (1H, d, J=2.8 Hz), 7.07-7.25 (3H, m), 7.28 (1H, d, J=9.5 Hz), 7.51-7.68 (2H, m), 8.51 (1H, dd, J=4.8, 0.8 Hz).

Example 289

Synthesis of 1-methyl-6-[3-(quinolin-6-ylamino)propoxy]-1H-quinolin-2-one

6-Aminoquinoline(360 mg) was added to the methanol solution(10 ml) of 6-(3-iodopropoxy)-1-methyl-1H-quinolin-2-one(172 mg) and stirred at 60° C. for 17 hours. The reaction mixture was added to ice water, and extraction with dichloromethane was performed. The organic layer was dried over anhydrous sodium sulfate and concentrated under reduced pressure. The residue was purified by silica gel column chromatography (ethyl acetate: methanol=10:0→4:1). The purified product was condensed under reduced pressure to give the title compound(86.4 mg) as a yellow amorphous solid.

1H-NMR (CDCl3) δ ppm: 2.13-2.29 (2H, m), 3.50 (2H, t, J=6.6 Hz), 3.70 (3H, s), 4.18 (2H, t, J=5.8 Hz), 6.67-6.77 (2H, m), 7.01 (1H, d, J=2.7 Hz), 7.11 (1H, dd, J=9.1, 2.7 Hz), 7.18-7.27 (2H, m), 7.29 (1H, d, J=9.1 Hz), 7.56 (1H, d, J=9.5 Hz), 7.86 (1H, s), 7.89 (1H, s), 8.61 (1H, dd, J=4.2, 1.6 Hz).

Example 290

Synthesis of N-benzyl-N-{2-[3-(1-methyl-2-oxo-1,2-dihydroquinolin-6-yloxy)propylamino]ethyl}acetamide The synthesis of the title compound was performed in the same manner as in Example 3 using appropriate starting materials.

1H-NMR (CDCl3) δ ppm: 1.87-2.06 (2H, m), 2.12 (3H, s), 2.70-2.90 (4H, m), 3.51 (2H, t, J=6.5 Hz), 3.71 (3H, s), 3.98-4.15 (2H, m), 4.58 (2H, s), 6.71 (1H, d, J=9.5 Hz), 6.98-7.03 (1H, m), 7.13-7.21 (2H, m), 7.21-7.40 (5H, m), 7.59 (1H, d, J=9.5 Hz).

Example 291

Synthesis of 6-{3-[2-(7-bromo-1-oxo-1H-isoquinolin-2-yl)ethylamino]propoxy}-1-methyl-1H-quinolin-2-one The synthesis of the title compound was performed in the same manner as in Example 3 using appropriate starting materials.

1H-NMR (CDCl3) δ ppm: 1.88-2.05 (2H, m), 2.87 (2H, t, J=6.6 Hz), 3.06 (2H, t, J=6.1 Hz), 3.70 (3H, s), 4.04 (2H, t, J=6.1 Hz), 4.12 (2H, t, J=6.1 Hz), 6.37 (1H, d, J=7.3 Hz), 6.71 (1H, d, J=9.5 Hz), 6.93 (1H, d, J=2.8 Hz), 7.09 (1H, dd, J=9.2, 2.8 Hz), 7.12 (1H, d, J=7.3 Hz), 7.23 (1H, d, J=9.2 Hz), 7.32 (1H, d, J=8.5 Hz), 7.55 (1H, d, J=9.5 Hz), 7.67 (1H, dd, J=8.5, 2.1 Hz), 8.52 (1H, d, J=2.1 Hz).

Example 292

Synthesis of 1-Methyl-6-{3-[(2-methylamino-ethyl)-pyridin-4-ylmethyl-amino]-propoxy}-1H-quinolin-2-one trihydrochloride A 4N-hydrogen chloride ethyl acetate solution(4.2 ml) was added to an ethyl acetate solution (30 ml) of methyl-(2-{[3-(1-methyl-2-oxo-1,2-dihydro-quinolin-6-yloxy)-propyl]-pyridin-4-ylmethyl-amino}-ethyl)-carbamic acid tert-butyl ester (1.0 g), and the mixture was stirred for 30 minutes at room temperature. The reaction mixture was condensed under reduced pressure to give the title compound(1.0 g) as a white powder.

1H-NMR (DMSO-D6) δ ppm: 1.95-2.22 (2H, m), 2.52 (3H, s), 2.56 (2H, t, J=5.4 Hz), 2.77-3.40 (4H, m), 3.61 (3H, s), 3.99-4.16 (2H, m), 4.16-5.10 (2H, m), 6.62 (1H, d, J=9.5 Hz), 7.16 (1H, dd, J=9.2, 2.8 Hz), 7.28 (1H, d, J=2.8 Hz), 7.45 (1H, d, J=9.2 Hz), 7.84 (1H, d, J=9.5 Hz), 8.17 (2H, d, J=5.0 Hz), 8.83 (2H, d, J=5.0 Hz).

Example 293

Synthesis of 1-Methyl-6-{3-[(2-methylamino-ethyl)-pyridin-4-ylmethyl-amino]-propoxy}-1H-quinolin-2-one A 4N-hydrogen chloride ethyl acetate solution(48 ml) was added to an ethyl acetate solution (300 ml) of methyl-(2-{[3-(1-methyl-2-oxo-1,2-dihydro-quinolin-6-yloxy)-propyl]-pyridin-4-ylmethyl-amino}-ethyl)-carbamic acid tert-butyl ester (11.5 g), and the mixture was stirred at room temperature overnight. The reaction mixture was condensed under reduced pressure. PL-HCO3(40 g) was added to the methanol solution of the residue and followed by celite filtration. The filtrate was condensed under reduced pressure to give the title compound(9.96 g) as a brown oil.

1H-NMR (CDCl3) δ ppm: 1.88-2.07 (2H, m), 2.43 (3H, s), 2.68 (2H, t, J=6.9 Hz), 2.70-2.88 (4H, m), 3.64 (2H, s), 3.70 (3H, s), 4.04 (2H, t, J=5.9 Hz), 6.71 (1H, d, J=9.5 Hz), 6.97 (1H, d, J=2.8 Hz), 7.10 (1H, dd, J=9.1, 2.8 Hz), 7.20-7.36 (3H, m), 7.59 (1H, d, J=9.5 Hz), 8.49 (2H, d, J=6.0 Hz).

Example 294

Synthesis of 6-[3-(2-Pyridin-3-yl-ethylamino)-propoxy]-3,4-dihydro-2H-isoquinolin-1-one The synthesis of the title compound was performed in the same manner as in Example 3 using appropriate starting materials.

1H-NMR (CDCl3) δ ppm: 1.84-2.02 (2H, m), 2.74-2.87 (4H, m), 2.87-3.02 (4H, m), 3.48-3.61 (2H, m), 4.06 (2H, t, J=6.1 Hz), 5.88 (1H, s), 6.66 (1H, d, J=2.4 Hz), 6.81 (1H, dd, J=8.6, 2.4 Hz), 7.20 (1H, dd, J=7.7, 4.8 Hz), 7.47-7.60 (1H, m), 8.00 (1H, d, J=8.6 Hz), 8.46 (1H, dd, J=4.8, 1.8 Hz), 8.49 (1H, d, J=1.8 Hz).

Example 295

Synthesis of 1-Methyl-6-{2-[(pyridin-4-ylmethyl)-amino]-ethoxy}-1H-quinolin-2-one The synthesis of the title compound was performed in the same manner as in Example 264 using appropriate starting materials.

1H-NMR (CDCl3) δ ppm: 3.05 (2H, t, J=5.2 Hz), 3.71 (3H, s), 3.92 (2H, s), 4.15 (2H, t, J=5.2 Hz), 6.72 (1H, d, J=9.5 Hz), 7.02 (1H, d, J=2.8 Hz), 7.19 (1H, dd, J=9.2, 2.8 Hz), 7.23-7.46 (3H, m), 7.59 (1H, d, J=9.5 Hz), 8.56 (2H, d, J=6.0 Hz).

Example 296

Synthesis of 3-[3-(1-Methyl-2-oxo-1,2-dihydro-quinolin-6-yloxy)-propylamino]-N-o-tolyl-propionamide Sodium ethoxide(34 mg) was added to an ethanol solution (5 ml) of 6-(3-amino-propoxy)-1-methyl-1H-quinolin-2-one (116 mg) and 3-chloro-N-o-tolyl-propionamide(148 mg). The mixture was stirred at 60° C. for 5 hours. The reaction mixture was condensed under reduced pressure. The residue was purified by silica gel column chromatography (dichloromethane: methanol=20:1→10:1). The purified product was condensed under reduced pressure to give the title compound (115 mg) as a white powder.

1H-NMR (CDCl3) δ ppm: 2.15-2.36 (2H, m), 2.26 (3H, s), 2.99-3.56 (6H, m), 3.63 (3H, s), 4.11 (2H, t, J=5.6 Hz), 6.66 (1H, d, J=9.5 Hz), 6.92-7.29 (6H, m), 7.47 (1H, d, J=9.5 Hz), 7.59 (1H, d, J=6.9 Hz), 9.25 (1H, s).

Example 297

Synthesis of N-Methyl-3-[3-(1-methyl-2-oxo-1,2-dihydro-quinolin-6-yloxy)-propylamino]-N-o-tolyl-propionamide 6-(3-Amino-propoxy)-1-methyl-1H-quinolin-2-one(194 mg) was added to an ethanol solution (5 ml) of N-methyl-N-o-tolyl-acrylamide(146 mg). The mixture was stirred at room temperature overnight. The reaction mixture was condensed under reduced pressure. The residue was purified by silica gel column chromatography (dichloromethane: methanol=20:1→10:1). The purified product was condensed under reduced pressure to give the title compound(172.6 mg) as a colorless oil.

1H-NMR (CDCl3) δ ppm: 2.06-2.25 (2H, m), 2.24 (3H, s), 2.25-2.50 (2H, m), 2.86-3.03 (4H, m), 3.20 (3H, s), 3.70 (3H, s), 4.12 (2H, t, J=6.0 Hz), 6.71 (1H, d, J=9.5 Hz), 7.07 (1H, d, J=2.3 Hz), 7.13 (1H, dd, J=8.3, 2.3 Hz), 7.19-7.38 (5H, m), 7.60 (1H, d, J=9.5 Hz).

Example 298

Synthesis of 1-Methyl-6-[3-(piperidin-4-yl-pyridin-4-ylmethyl-amino)-propoxy]-1H-quinolin-2-one Trifluoroacetic acid (30 ml) was added to a dichloromethane solution (10 ml) of 4-{[3-(1-methyl-2-oxo-1,2-dihydro-quinolin-6-yloxy)-propyl]-pyridin-4-ylmethyl-amino}-piperidine-1-carboxylic acid tert-butyl ester (1.08 g), and the mixture was stirred at room temperature overnight. The reaction mixture was condensed under reduced pressure. PL-HCO3(40 g) was added to the dichloromethane solution of the residue and followed by celite filtration. The filtrate was condensed under reduced pressure. The residue was purified by NH silica gel column chromatography (ethyl acetate:methanol=4:1). The purified product was condensed under reduced pressure to give the title compound(758 mg) as an orange oil.

1H-NMR (CDCl3) δ ppm: 1.45-1.65 (2H, m), 1.70-1.99 (4H, m), 2.50-2.69 (3H, m), 2.74 (2H, t, J=6.7 Hz), 3.11-3.25 (2H, m), 3.68 (2H, s), 3.71 (3H, s), 4.00 (2H, t, J=6.0 Hz), 6.72 (1H, d, J=9.5 Hz), 6.93 (1H, d, J=2.8 Hz), 7.10 (1H, dd, J=9.2, 2.8 Hz), 7.23-7.35 (3H, m), 7.60 (1H, d, J=9.5 Hz), 8.47 (2H, d, J=6.0 Hz).

Example 299

Synthesis of 6-[3-(1-Methoxy-isoquinolin-4-ylamino)-propoxy]-1-methyl-1H-quinolin-2-one 6-(3-Amino-propoxy)-1-methyl-1H-quinolin-2-one(232 mg), 4-bromo-1-methoxy-isoquinoline(286 mg), palladium acetate (II) (22 mg), xantphos (558 mg), and sodium t-butoxide(192 mg) were added to dioxane(10 ml). The mixture was heated at 80° C. for overnight under argon atmosphere. The reaction liquid was cooled to room temperature. Water was added to the reaction mixture, and followed by celite filtration. The filtrate was extracted with dichloromethane. The organic layer was dried over anhydrous sodium sulfate. The filtrate was condensed under reduced pressure, and the residue was purified by silica gel column chromatography (ethyl acetate: hexane=2:1→1:0). The purified product was condensed under reduced pressure to give the title compound(99 mg) as a brown amorphous solid.

1H-NMR (CDCl3) δ ppm: 2.20-2.37 (2H, m), 3.48 (2H, t, J=6.5 Hz), 3.68 (3H, s), 4.06 (3H, s), 4.22 (2H, t, J=5.9 Hz), 6.69 (1H, d, J=9.5 Hz), 7.00 (1H, d, J=2.7 Hz), 7.13-7.31 (2H, m), 7.39 (1H, s), 7.51-7.62 (2H, m), 7.62-7.73 (1H, m), 7.79 (1H, d, J=8.3 Hz), 8.25 (1H, dd, J=8.3, 0.5 Hz).

Example 300

Synthesis of 1-Methyl-6-{3-[2-(7-oxo-7H-furo[2,3-c]pyridin-6-yl)-ethylamino]-propoxy}-1H-quinolin-2-one The synthesis of the title compound was performed in the same manner as in Example 3 using appropriate starting materials.

1H-NMR (CDCl3) δ ppm: 1.87-2.03 (2H, m), 2.86 (2H, t, J=6.7 Hz), 3.06 (2H, t, J=6.2 Hz), 3.70 (3H, s), 4.06 (2H, t, J=6.1 Hz), 4.18 (2H, t, J=6.2 Hz), 6.39 (1H, d, J=7.0 Hz), 6.61 (1H, d, J=2.1 Hz), 6.71 (1H, d, J=9.5 Hz), 6.97 (1H, d, J=2.8 Hz), 7.08-7.19 (2H, m), 7.21-7.32 (1H, m), 7.59 (1H, d, J=9.5 Hz), 7.71 (1H, d, J=2.1 Hz).

Example 301

Synthesis of 1-Methyl-6-[5-(2-pyridin-3-yl-ethylamino)-pentyloxy]-1H-quinolin-2-one The synthesis of the title compound was performed in the same manner as in Example 3 using appropriate starting materials.

1H-NMR (CDCl3) δ ppm: 1.44-1.72 (4H, m), 1.72-1.90 (2H, m), 2.67 (2H, t, J=6.9 Hz), 2.74-2.97 (4H, m), 3.71 (3H, s), 4.00 (2H, t, J=6.4 Hz), 6.71 (1H, d, J=9.5 Hz), 6.99 (1H, d, J=2.8 Hz), 7.17 (1H, dd, J=9.2, 2.8 Hz), 7.22 (1H, dd, J=7.8, 4.8 Hz), 7.29 (1H, d, J=9.2 Hz), 7.50-7.56 (1H, m), 7.59 (1H, d, J=9.5 Hz), 8.47 (1H, dd, J=4.8, 1.8 Hz), 8.49 (1H, d, J=1.8 Hz).

Example 302

N-(2-Methyl-benzyl)-4-(1-methyl-2-oxo-1,2-dihydro-quinolin-6-yloxy)-N-{2-[4-(pyridin-3-yl-methoxy)-piperidin-1-yl]-ethyl}-butyramide dihydrochloride To a DMF solution (3 ml) of 4-(1-Methyl-2-oxo-1,2-dihydro-quinolin-6-yloxy)-butyric acid (100 mg) were sequentially added (2-methyl-benzyl)-{2-[4-(pyridin-3-yl-methoxy)-piperidin-1-yl]-ethyl}-amine (143 mg), triethylamine (47 mg), diethylphosphorocyanidate (DEPC, 84 mg) while ice-cooling, followed by stirring at room temperature overnight. Water was added to the reaction mixture and then subjected to extraction using ethyl acetate. The thus-obtained organic layer was washed with an aqueous saturated sodium chloride solution twice, dried over anhydrous sodium sulfate and then concentrated under reduced pressure. The residue was purified using silica gel column chromatography (dichloromethane:ethyl acetate:methanol: 28% ammonia solution=70:20:10:1). The purified product was concentrated under reduced pressure. A 4N-hydrogen chloride in ethyl acetate solution was added to a ethyl acetate solution of the residue. The mixture was condensed under reduced pressure to give the title compound (165 mg) as a pale yellow amorphous solid.

1H-NMR (DMSO-d6) δ ppm: 1.79-2.60 (8H, m), 2.24, 2.28 (total 3H, each-s), 2.68-4.28 (11H, m), 3.58 (3H, s), 4.45-4.76 (4H, m), 6.59, 6.60 (total 1H, each-d, J=9.5 Hz), 6.82-7.50 (7H, m), 7.75-7.88 (1H, m), 7.88-8.00 (1H, m), 8.35-8.50 (1H, m), 8.72-8.95 (2H, m).

Example 303

N-(2-Methyl-benzyl)-4-(1-methyl-2-oxo-1,2-dihydro-quinolin-6-yloxy)-N-(2-pyridin-3-yl-ethyl)-butyramide hydrochloride The synthesis of the title compound was performed in the same manner as in Example 302 using appropriate starting materials.

1H-NMR (DMSO-d6) δ ppm: 1.80-2.08 (2H, m), 2.23, 2.27 (total 3H, each-s), 2.29-2.63 (2H, m), 2.96-3.14 (2H, m), 3.59 (3H, s), 3.48-3.70 (2H, m), 3.93, 4.04 (total 2H, each-t, J=6.3 Hz), 4.57, 4.61 (total 2H, each-s), 6.60, 6.61 (total 1H, each-d, J=9.5 Hz), 6.85-7.33 (6H, m), 7.38-7.50 (1H, m), 7.78-7.89 (1H, m), 7.89-8.00 (1H, m), 8.82-8.47 (1H, m), 8.70-8.80 (1H, m), 8.80-8.92 (1H, m).

Example 304

1-[5-(1-Methyl-2-oxo-1,2-dihydro-quinolin-6-yloxy)-pentyl]-3-phenyl-1-(2-pyridin-3-yl-ethyl)-urea hydrochloride N-Ethyldiisopropylamine (0.192 ml) was added to a dichloromethane solution(5 ml) of 1-methyl-6-[5-(2-pyridin-3-ylethylamino)pentyloxy]-1H-quinolin-2-one dihydrochloride (219 mg). The mixture was stirred at room temperature for 5 minutes. The reaction mixture was condensed under reduced pressure. Phenylisocyanate(0.065 ml) and toluene(2 ml) were added to the residue. The mixture was stirred at 100° C. for 1 hour. The reaction mixture was purified by NH silica gel column chromatography (ethyl acetate: hexane=1:1→1: 0). The purified product was concentrated under reduced pressure. A 1N-hydrogen chloride ethanol solution was added to the solution of the residue in ethanol, and stirred for 30 minutes at room temperature. The precipitated insoluble matter was collected by filtration, washed with ethyl acetate, and dried to give the title compound (147 mg) as a pale yellow flakes.

1H-NMR (DMSO-d6) δ ppm: 1.38-1.83 (6H, m), 3.04 (2H, t, J=7.0 Hz), 3.36 (2H, t, J=7.1 Hz), 3.59 (3H, s), 3.65 (2H, t, J=7.1 Hz), 4.03 (2H, t, J=6.4 Hz), 6.60 (1H, d, J=9.5 Hz), 6.93 (1H, t, J=7.3 Hz), 7.18-7.28 (4H, m), 7.38-7.45 (3H, m), 7.81 (1H, d, J=9.5 Hz), 7.89-7.94 (1H, m), 8.26 (1H, s), 8.42 (1H, d, J=8.1 Hz), 8.73 (1H, d, J=5.5 Hz), 8.86 (1H, s)

Example 305

2-Methyl-N-[3-(1-methyl-2-oxo-1,2,3,4-tetrahydro-quinolin-6-yloxy)-propyl]-N-(2-pyridin-3-yl-ethyl)-benzamide hydrochloride The synthesis of the title compound was performed in the same manner as in Example 45 using appropriate starting materials.

1H-NMR (DMSO-D6, 100° C.) δ ppm: 1.81-2.08 (2H, m), 2.14 (3H, s), 2.40-2.60 (2H, m), 2.70-2.84 (2H, m), 2.85-3.03 (2H, m), 3.21 (3H, s), 3.38-3.73 (4H, m), 3.78-4.00 (2H, m), 6.56-6.82 (2H, m), 6.85-7.04 (2H, m), 7.08-7.31 (3H, m), 7.32-7.48 (1H, m), 7.54-7.84 (1H, m), 8.28-8.60 (2H, m).

Example 306

4-Methyl-N-[3-(1-methyl-2-oxo-1,2,3,4-tetrahydro-quinolin-6-yloxy)-propyl]-N-(2-pyridin-3-yl-ethyl)-benzamide hydrochloride The synthesis of the title compound was performed in the same manner as in Example 45 using appropriate starting materials.

1H-NMR (DMSO-D6, 100° C.) δ ppm: 1.86-2.02 (2H, m), 2.32 (3H, s), 2.40-2.60 (2H, m), 2.73-2.88 (2H, m), 2.89-3.02 (2H, m), 3.21 (3H, s), 3.40-3.52 (2H, m), 3.56-3.69 (2H, m), 3.87-3.96 (2H, m), 6.70 (1H, s), 6.62-6.78 (1H, m), 6.93 (1H, d, J=9.0 Hz), 7.10 (2H, d, J=8.0 Hz), 7.17 (2H, d, J=8.0 Hz), 7.41-7.58 (1H, m), 7.73-7.93 (1H, m), 8.38-8.58 (2H, m).

Example 307

N-[3-(1-Methyl-2-oxo-1,2,3,4-tetrahydro-quinolin-6-yloxy)-propyl]-N-(2-pyridin-3-yl-ethyl)-isobutyramide hydrochloride The synthesis of the title compound was performed in the same manner as in Example 45 using appropriate starting materials.

1H-NMR (DMSO-D6, 100° C.) δ ppm: 0.94 (6H, d, J=6.6 Hz), 1.86-2.00 (2H, m), 2.43-2.53 (2H, m), 2.65-2.89 (3H, m), 2.89-3.02 (2H, m), 3.21 (3H, s), 3.34-3.50 (2H, m), 3.52-3.66 (2H, m), 3.90-4.04 (2H, m), 6.70-6.84 (2H, m), 6.89-7.01 (1H, m), 7.56-7.70 (1H, m), 7.98-8.12 (1H, m), 8.50-8.67 (2H, m).

Example 308

N-[3-(1-Methyl-2-oxo-1,2,3,4-tetrahydro-quinolin-6-yloxy)-propyl]-N-(2-pyridin-3-yl-ethyl)-isonicotinamide dihydrochloride The synthesis of the title compound was performed in the same manner as in Example 45 using appropriate starting materials.

1H-NMR (DMSO-D6, 100° C.) δ ppm: 1.90-2.05 (2H, m), 2.49-2.53 (2H, m), 2.74-2.88 (2H, m), 2.91-3.12 (2H, m), 3.21 (3H, s), 3.32-3.54 (2H, m), 3.54-3.75 (2H, m), 3.81-4.02 (2H, m), 6.60-6.81 (2H, m), 6.94 (1H, d, J=8.7 Hz), 7.23 (2H, d, J=5.1 Hz), 7.43-7.68 (1H, m), 7.76-8.09 (1H, m), 8.42-8.70 (4H, m).

Examples 310 to 986

The following compounds were obtained in the same manner as in Examples above using appropriate starting materials.

TABLE A

| Example No. | R1 | MS(M + 1) |
|---|---|---|
| 310 | —OCH$_3$ | 492 |
| 311 | —O(CH$_2$)$_2$C$_6$H$_5$ | 582 |
| 312 | —N(CH$_3$)(CH$_2$)$_2$N(CH$_3$)C$_6$H$_5$ | 624 |
| 313 | —OCH(C$_6$H$_5$)$_2$ | 644 |
| 314 | —N(CH$_3$)(CH$_2$)$_2$C$_6$H$_5$ | 595 |
| 315 | —N(CH$_3$)(CH$_2$)$_2$N(C$_2$H$_5$)$_2$ | 590 |
| 316 | —OC$_6$H$_5$ | 554 |
| 317 | —C$_6$H$_5$ | 538 |
| 318 | —CH$_2$CONHC$_2$H$_5$ | 547 |

TABLE B

| Example No. | R1 | MS(M + 1) |
|---|---|---|
| 319 | 2-Cl-C$_6$H$_4$-CH$_2$-O-CH$_2$- | 602 |
| 320 | 2-CF$_3$-C$_6$H$_4$-CH$_2$-O-CH$_2$- | 636 |
| 321 | pyridin-4-yl-CH$_2$-O-CH$_2$- | 569 |
| 322 | (CH$_3$)$_2$N-CH$_2$-CH$_2$-(4-CH$_3$-C$_6$H$_4$)- | 609 |
| 323 | 2-phenyl-4-methylmorpholinyl | 623 |

TABLE B-continued
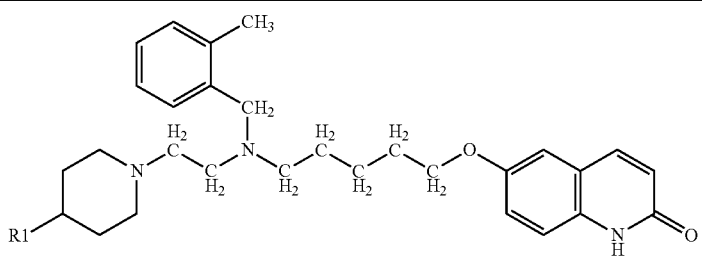
| Example No. | R1 | MS(M + 1) |
|---|---|---|
| 324 | N,N-dimethyl-5-methoxy-indan-2-amine | 637 |
| 325 | 1-methyl-4-phenyl-imidazole | 604 |
| 326 | N,N-dimethyl-2-cyclohexyl-ethylamine | 601 |
| 327 | 1-ethyl-imidazole | 542 |
| 328 | N,N-dimethyl-cyclopropylmethylamine | 545 |
| 329 | 4-methyl-morpholine | 547 |
| 330 | 2-fluorobenzyl methyl ether | 586 |
| 331 | N,N-dimethyl-4-(4-methoxyphenyl)butylamine | 653 |
| 332 | 1,2-dimethyl-benzimidazole | 592 |
| 333 | N,N-dimethyl-cyclohexylmethylamine | 587 |

TABLE B-continued

[Structure: piperidine-R1 linked via CH2CH2-N(CH2-o-tolyl)-CH2CH2CH2CH2-O-quinolin-2(1H)-one]

| Example No. | R1 | MS(M + 1) |
|---|---|---|
| 334 | 3,4-dichloro-benzyl methoxymethyl (–OCH2-C6H3(Cl)2) | 636 |
| 335 | 4-(trifluoromethoxy)benzyl methoxymethyl | 652 |
| 336 | N-methyl-N-(phenylacetyl)amino (–N(CH3)C(O)CH2Ph) | 609 |
| 337 | 2-(4-chlorophenyl)ethyl | 586 |
| 338 | 2-(4-methylphenyl)ethyl | 566 |
| 339 | N-methyl-N-benzylamino | 581 |
| 340 | cyclohexyl | 544 |
| 341 | –CH(N(CH3))CH2-O-C6H4-CH3 | 625 |
| 342 | 3-(4-methoxyphenyl)propyl | 596 |
| 343 | (4-chlorophenyl)methyl | 572 |
| 344 | (4-(trifluoromethoxy)phenoxy)methoxy | 638 |

TABLE B-continued

[Structure: piperidine-R1 / CH2 / N / CH2CH2 / N(2-methylbenzyl) / CH2CH2CH2CH2 / O / quinolin-2(1H)-one]

| Example No. | R1 | MS(M + 1) |
|---|---|---|
| 345 | 4-(trifluoromethoxy)phenyl-N(H)(CH3)- | 637 |
| 346 | 2-aminophenyl acetyl | 581 |
| 347 | 4-methoxyphenyl acetyl | 596 |
| 348 | 4-chlorophenyl acetyl | 600 |
| 349 | 4-chloro-N,N-dimethylaniline | 601 |
| 350 | 1,6-dimethyl-3,4-dihydroquinolin-2(1H)-on-7-yl | 621 |
| 351 | 4-fluoro-N,N-dimethylaniline | 585 |

TABLE C

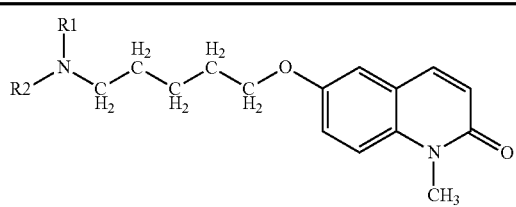

| Example No. | R1 | R2 | MS(M + 1) |
|---|---|---|---|
| 352 | —(CH2)3CH3 | —(CH2)3CH3 | 373 |
| 353 | —CH2C6H5 | —(CH2)3N(CH3)2 | 436 |
| 354 | —CH3 | —(CH2)3N(CH3)CH2C6H5 | 436 |
| 355 | —H | —(CH2)3N(CH3)2 | 346 |
| 356 | —CH3 | —CH3 | 289 |

TABLE D

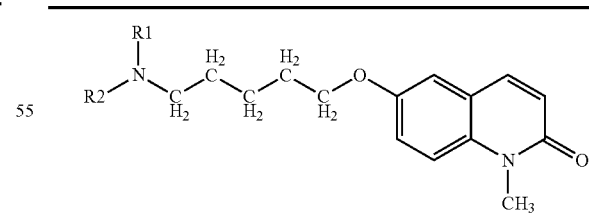

| Example No. | R1 | R2 | MS(M + 1) |
|---|---|---|---|
| 357 | —CH3 | cyclohexylmethyl | 357 |

439
TABLE D-continued

Structure: R1R2N-CH2-CH2-CH2-CH2-CH2-O-(6-position of 1-methyl-quinolin-2(1H)-one)

| Example No. | R1 | R2 | MS(M + 1) |
|---|---|---|---|
| 358 | —CH₃ | (2-pyridyl)propyl | 380 |
| 359 | —C₂H₅ | 4-chlorophenyl-pentyl | 455 |
| 360 | —CH₃ | 4-(4-chlorophenyl)piperidinylmethyl | 468 |
| 361 | —CH₃ | 4-chlorophenyl-ethyl | 399 |
| 362 | —H | 2,5-dimethylphenyl | 351 |
| 363 | —H | 4-methylpyridyl | 338 |
| 364 | —C₂H₅ | 4-biphenyl-ethyl | 455 |
| 365 | —H | 3-fluorophenyl-propyl | 383 |
| 366 | —H | 1-pyrrolidinyl-propyl | 358 |
| 367 | —CH₃ | 4-methyl-1-benzyl-piperidinyl | 448 |
| 368 | —CH₃ | 4-methyl-1-(4-chlorobenzoyl)-piperidinyl | 496 |
| 369 | —H | (S)-2-methyl-3-(diethylamino)propyl | 374 |

440
TABLE E

Structure: R1-CH2-CH2-N(CH2-(2-methylphenyl))-CH2-CH2-CH2-CH2-CH2-O-(6-position of quinolin-2(1H)-one)

| Example No. | R1 | MS (M + 1) |
|---|---|---|
| 370 | 1-methyl-3-[2-(4-methoxyphenyl)ethyl]piperidinyl | 596 |
| 371 | 4-methyl-1-phenyl-piperazin-2-one | 553 |
| 372 | 4-methyl-1-(4-trifluoromethylbenzyl)piperazin-2-one | 635 |
| 373 | 1-methyl-4-(4-methoxybenzylidene)piperidinyl | 580 |
| 374 | N-methyl-tropanyl | 488 |
| 375 | N-methyl-spiro[5.5]piperidinyl | 530 |
| 376 | 2-methyl-1,2,3,4-tetrahydroisoquinolinyl | 510 |
| 377 | 2-methyl-2,3,4,9-tetrahydro-1H-β-carbolinyl | 549 |
| 378 | 6-methyl-4,5,6,7-tetrahydrothieno[2,3-c]pyridinyl | 516 |
| 379 | N-methyl-decahydroquinolinyl | 516 |
| 380 | 1,4-dimethyl-1,4-diazepanyl | 491 |

TABLE E-continued

Structure: Quinolin-2(1H)-one with 6-O-(CH₂)₃-CH(N(CH₂-2-methylphenyl)(CH₂CH₂-R1))-

| Example No. | R1 | MS (M + 1) |
|---|---|---|
| 381 | 4-(4-methyl-1,4-diazepan-1-yl)pyridine | 554 |
| 382 | 1-methyl-4-(3-morpholinopropyl)-1,4-diazepane | 604 |
| 383 | N,N-dimethyl-1-((4-methylmorpholin-2-yl)methyl)piperidin-4-amine | 604 |
| 384 | 1-methyl-1H-indazol-3-yl | 495 |
| 385 | 1-methyl-1H-benzo[d][1,2,3]triazol-5-yl | 496 |
| 386 | 1-methyl-5-phenyl-1H-imidazol-2-yl | 521 |
| 387 | 1,5,6-trimethyl-1H-benzo[d]imidazol-2-yl | 523 |
| 388 | 1-methyl-5-phenyl-1H-tetrazol-2-yl | 523 |
| 389 | 2-cyclohexyl-1-methyl-1H-imidazol-5-yl | 527 |
| 390 | 1-methyl-3-(2-(piperazin-1-yl)acetamido)pyridinium | 597 |

TABLE E-continued

| Example No. | R1 | MS (M + 1) |
|---|---|---|
| 391 | 2-methyl-2H-benzo[d][1,2,3]triazol-4-yl | 496 |
| 392 | 2-methyl-5-phenyl-2H-tetrazol-3-yl | 523 |
| 393 | 3-methyl-3H-imidazo[4,5-c]pyridin-2-yl | 496 |

TABLE F

Structure: R2-N(R1)-CH₂CH₂-N(CH₂-2-methylphenyl)-(CH₂)₃-CH₂-O-quinolin-2(1H)-one (6-position)

| Example No. | R1 | R2 | MS(M + 1) |
|---|---|---|---|
| 394 | —(CH₂)₂CH₃ | —(CH₂)₃C₆H₅ | 554 |
| 395 | —(CH₂)₂N(CH₃)₂ | —CH₂C₆H₅ | 555 |
| 396 | —H | —CH₂C(CH₃)₃ | 464 |
| 397 | —CH₃ | —(CH₂)₂N(C₂H₅)₂ | 507 |
| 398 | —H | —(CH₂)₂SCH₃ | 468 |

TABLE G

Structure: R2-N(R1)-CH₂CH₂-N(CH₂-2-methylphenyl)-(CH₂)₃-CH₂-O-quinolin-2(1H)-one

| Example No. | R1 | R2 | MS (M + 1) |
|---|---|---|---|
| 399 | —C₂H₅ | —(CH₂)₂-O-(4-methoxyphenyl) | 572 |

TABLE G-continued

| Example No. | R1 | R2 | MS (M + 1) |
|---|---|---|---|
| 400 | —CH₃ | cyclohexyl-methyl | 490 |
| 401 | —H | (1-methylpiperidin-4-yl)(1-methylbenzimidazol-2-yl) | 607 |
| 402 | —CH₃ | 4-chlorobenzyl | 518 |
| 403 | —CH₃ | 2-(pyridin-2-yl)ethyl | 513 |
| 404 | —CH₃ | (1-methylpiperidin-4-yl)methyl | 505 |
| 405 | —H | cyclooctylmethyl | 504 |
| 406 | —H | 2-(pyridin-2-yl)ethyl | 485 |
| 407 | —H | 2-(pyridin-3-yl)ethyl | 485 |
| 408 | —H | 2-(pyridin-4-yl)ethyl | 485 |
| 409 | —H | 2-(furan-2-yl)ethyl | 474 |
| 410 | —CH₃ | 3-(N-methyl-N-(4-fluorophenyl)amino)propyl | 559 |
| 411 | —CH₃ | (1-acetylpiperidin-4-yl)methyl | 533 |
| 412 | —C₂H₅ | (benzo[d][1,3]dioxol-5-yl)ethyl | 556 |
| 413 | —C₂H₅ | cyclohexylethyl | 518 |
| 414 | —CH₃ | (1-(4-chlorophenyl)piperidin-4-yl)methyl | 601 |
| 415 | —H | (benzo[d][1,3]dioxol-5-yl)ethyl | 528 |
| 416 | —H | cyclopentylmethyl | 462 |
| 417 | —H | 4-(1H-imidazol-1-yl)butyl | 502 |
| 418 | —H | (quinolin-3-yl)methyl | 521 |
| 419 | —H | (4-phenoxyphenyl)methyl | 562 |
| 420 | —H | 4-morpholinobutyl | 521 |
| 421 | —CH₂C₆H₅ | (1-benzylpiperidin-4-yl)methyl | 657 |
| 422 | —CH₃ | (1-(tert-butoxycarbonyl)piperidin-4-yl)methyl | 591 |
| 423 | —H | 2-(thiophen-2-yl)ethyl | 490 |
| 424 | —H | (5-methyl-1,3,4-thiadiazol-2-yl)methyl | 478 |

TABLE G-continued
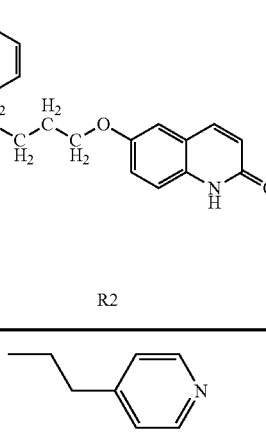
| Example No. | R1 | R2 | MS (M + 1) |
|---|---|---|---|
| 425 | —H | 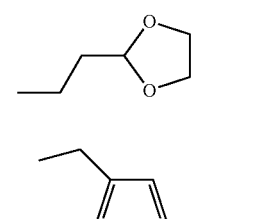 | 499 |
| 426 | —H | 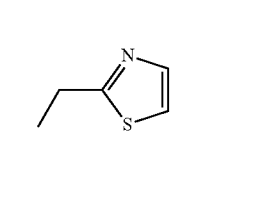 | 494 |
| 427 | —H | 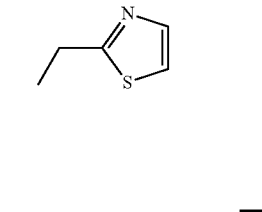 | 474 |
| 428 | —H | 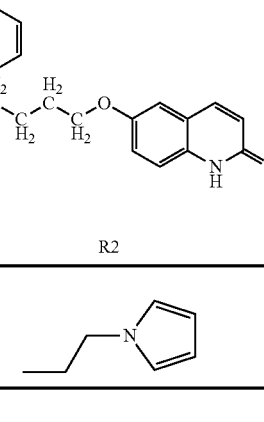 | 491 |
| 429 | —H | 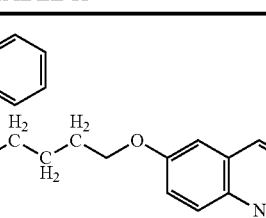 | 487 |
TABLE H
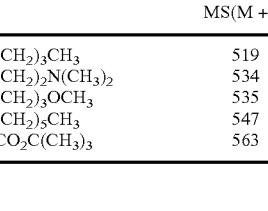
| Example No. | R1 | MS(M + 1) |
|---|---|---|
| 432 | —(CH$_2$)$_3$CH$_3$ | 519 |
| 433 | —(CH$_2$)$_2$N(CH$_3$)$_2$ | 534 |
| 434 | —(CH$_2$)$_3$OCH$_3$ | 535 |
| 435 | —(CH$_2$)$_5$CH$_3$ | 547 |
| 436 | —CO$_2$C(CH$_3$)$_3$ | 563 |
TABLE I
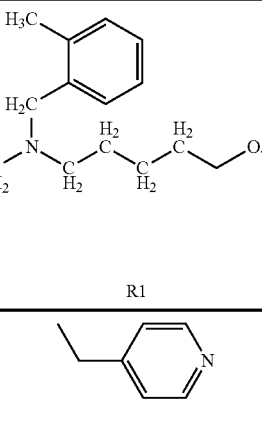
| Example No. | R1 | MS(M + 1) |
|---|---|---|
| 437 | 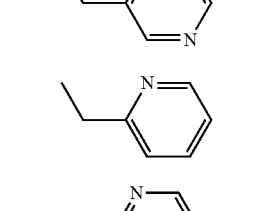 | 554 |
| 438 | 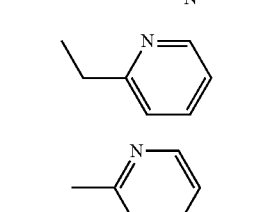 | 554 |
| 439 | 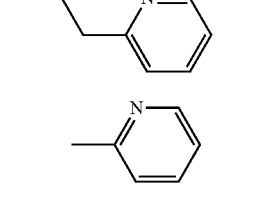 | 554 |
| 440 | | 540 |

TABLE I-continued

[Structure: piperazine-R1 connected via -CH2CH2-N(CH2-(2-methylphenyl))-CH2CH2CH2-CH(CH2-O-)- linked to 6-position of quinolin-2(1H)-one]

| Example No. | R1 | MS(M + 1) |
|---|---|---|
| 441 | 2-pyrimidinyl-methyl | 541 |
| 442 | (benzo[1,3]dioxol-5-yl)ethyl | 597 |
| 443 | 4-pyridinyl-methyl | 540 |
| 444 | 1-(4-methoxyphenyl)-1-phenylethyl | 659 |
| 445 | 1,1-bis(4-fluorophenyl)ethyl | 665 |
| 446 | 1-phenyl-1-(4-pyridinyl)ethyl | 630 |
| 447 | 7-methylbenzofuran-? | 579 |
| 448 | 3-methylbenzo[d]isothiazol-? | 596 |
| 449 | 5-chloro-7-methylbenzofuran-? | 613 |

TABLE I-continued
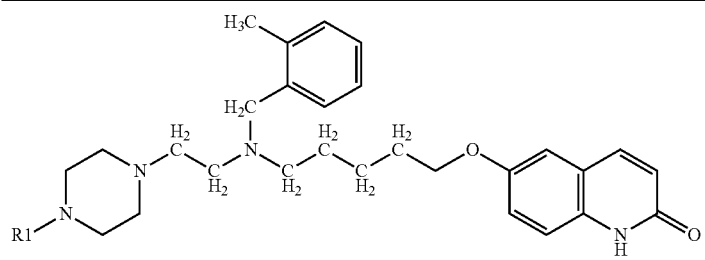
| Example No. | R1 | MS(M + 1) |
|---|---|---|
| 450 | 4-benzofuranyl | 579 |
| 451 | 2-methylbenzoxazolyl | 580 |
| 452 | 2-methylbenzyl (ethyl linker) | 567 |
| 453 | 2,3-dimethylphenyl | 553 |
| 454 | cyclopentyl | 531 |
| 455 | cycloheptyl | 559 |
| 456 | 2-(pyrrolidin-1-yl)ethyl | 560 |
| 457 | 2-methoxy-6-methylphenyl | 569 |
| 458 | 2-(trifluoromethoxy)benzyl | 637 |
| 459 | 2-quinolinylmethyl | 604 |

TABLE I-continued
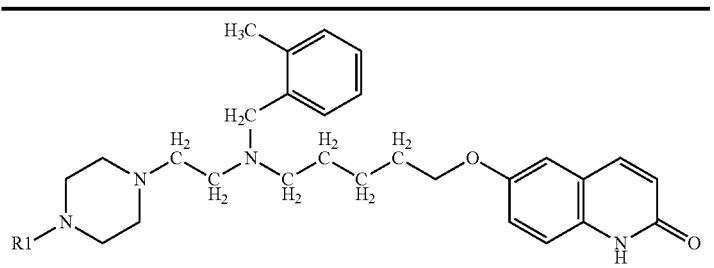
| Example No. | R1 | MS(M + 1) |
|---|---|---|
| 460 | 5-ethyl-1-benzyl-tetrazole | 635 |
| 461 | 5-ethyl-1-ethyl-tetrazole | 573 |
| 462 | 5-ethyl-1-phenethyl-tetrazole | 649 |
| 463 | 4-ethyl-2-phenyl-thiazole | 636 |
| 464 | 5-methyl-7-methyl-benzofuran | 593 |
| 465 | 4-(trifluoromethoxy)phenyl-methyl | 623 |
| 466 | 2-(trifluoromethyl)phenyl-methyl | 607 |
| 467 | 3-methyl-quinolin-2(1H)-one | 606 |

TABLE I-continued
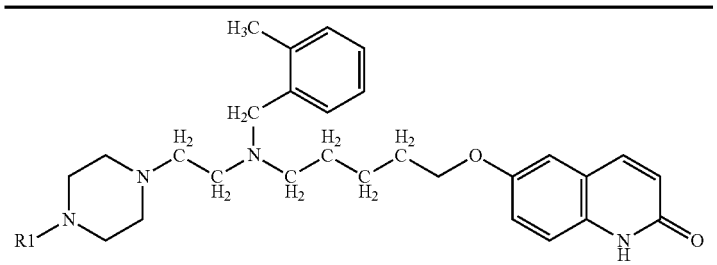
| Example No. | R1 | MS(M + 1) |
|---|---|---|
| 468 | (N-phenyl propanamide) | 596 |
| 469 | (3-(4-methoxyphenyl)propyl) | 597 |
| 470 | (2-methylbenzothiazole) | 596 |
| 471 | (1-(benzo[d][1,3]dioxol-5-yl)ethanone) | 611 |
| 472 | (2-ethyl-1,3-dioxolane) | 549 |
| 473 | (4-ethyl-1-methylpiperidine) | 574 |
| 474 | (3-ethylfuran) | 543 |
| 475 | (3-methylpyridine) | 540 |
| 476 | (1-propyl-1H-imidazole) | 557 |
| 477 | (2,4-dimethylpyridine) | 554 |
| 478 | (N-(pyridin-3-yl)propanamide) | 597 |

TABLE I-continued

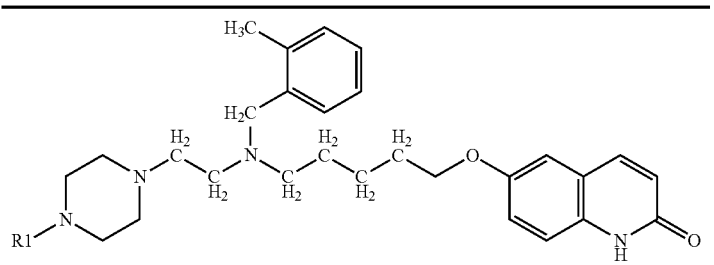

| Example No. | R1 | MS(M + 1) |
|---|---|---|
| 479 | [2-propyl-pyridine] | 568 |
| 480 | [N-methyl-4-(trifluoromethyl)aniline] | 622 |
| 481 | [4-methyl-2,3-dihydro-1H-indene] | 579 |
| 482 | [2-methyl-N,N-dimethyl-benzothiazol-6-amine] | 639 |
| 483 | [5-fluoro-6-methyl-benzofuran] | 597 |

TABLE J

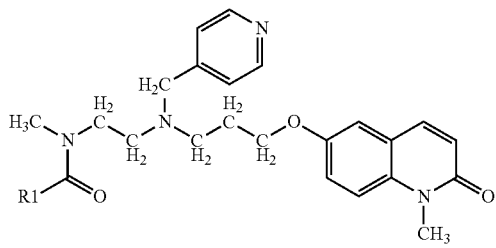

| Example No. | R1 | MS(M + 1) |
|---|---|---|
| 484 | —CH$_2$OC$_6$H$_5$ | 515 |
| 485 | —(CH$_2$)$_2$C$_6$H$_5$ | 513 |
| 486 | —CH=CHC$_6$H$_5$ | 511 |
| 487 | —(CH$_2$)$_2$OC$_6$H$_5$ | 529 |
| 488 | —(CH$_2$)$_3$C$_6$H$_5$ | 527 |
| 489 | —CH(CH$_3$)$_2$ | 451 |
| 490 | —(CH$_2$)$_2$N(COCH$_3$)C$_6$H$_5$ | 570 |

TABLE K

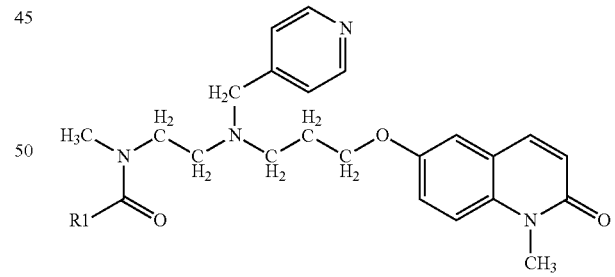

| Example No. | R1 | MS(M + 1) |
|---|---|---|
| 491 | [2-(pyridin-3-yl)ethyl] | 514 |
| 492 | [2-methylpyridine] | 486 |

TABLE K-continued

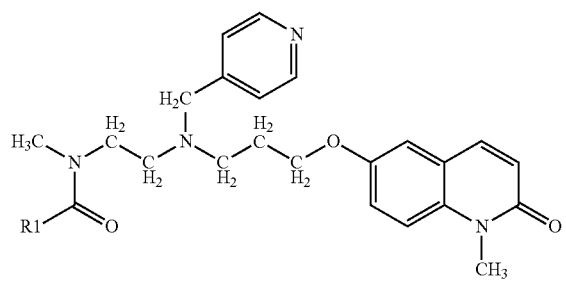

| Example No. | R1 | MS(M + 1) |
|---|---|---|
| 493 | 3-pyridyl | 486 |
| 494 | 4-pyridyl | 486 |
| 495 | 3-pyridyl-ethyl | 500 |
| 496 | 2-furyl | 475 |
| 497 | 2-thienyl | 491 |
| 498 | 3-furyl | 475 |
| 499 | 3-thienyl | 491 |
| 500 | 2-ethylthienyl | 505 |
| 501 | 3-ethylthienyl | 505 |
| 502 | methylcyclohexyl | 491 |
| 503 | ethylcyclohexyl | 505 |

TABLE K-continued

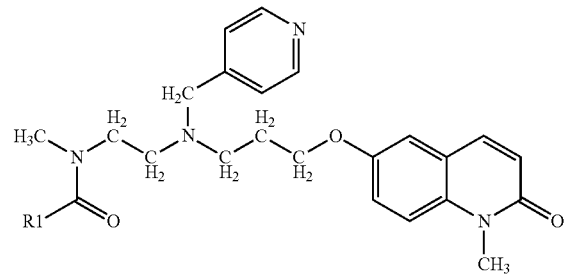

| Example No. | R1 | MS(M + 1) |
|---|---|---|
| 504 | 4-methylpiperidinyl-benzoyl | 596 |
| 505 | 2-methylchroman | 541 |
| 506 | 6-methylnaphthyl | 535 |
| 507 | 8-methylnaphthyl | 535 |
| 508 | methylbenzodioxole | 529 |
| 509 | 2-methyl-6-ethylphenyl | 513 |
| 510 | 3-methoxy-ethylphenyl | 529 |
| 511 | 4-methoxy-propenylphenyl | 541 |
| 512 | 3-propenylpyridyl | 512 |
| 513 | 4-propenylpyridyl | 512 |

TABLE K-continued

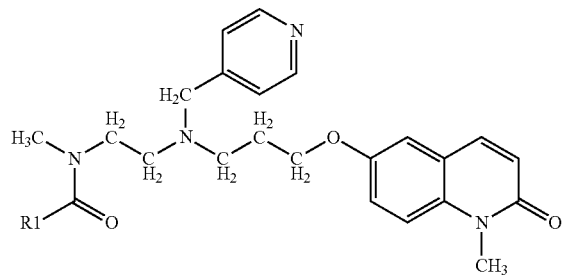

| Example No. | R1 | MS(M + 1) |
|---|---|---|
| 514 | 1-methyl-1-phenylcyclopropyl | 525 |
| 515 | 2-methyl-1H-indol-yl | 524 |
| 516 | 3-methyl-1H-indol-yl | 524 |
| 517 | 2-methyl-1H-pyrrol-yl | 474 |
| 518 | 2-methylbenzofuran-yl | 525 |
| 519 | 3-ethyl-methylphenyl | 513 |
| 520 | phenylthioethyl | 531 |
| 521 | 3-ethyl-1H-indol-yl | 538 |
| 522 | 1,2-dimethyl-1H-indol-yl | 538 |
| 523 | 2-methylbenzothiophen-yl | 541 |

TABLE K-continued

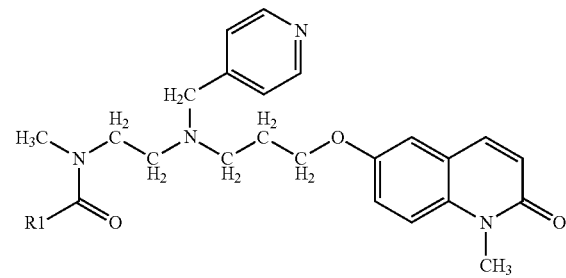

| Example No. | R1 | MS(M + 1) |
|---|---|---|
| 524 | 1-(pyridin-2-yl)propenyl | 512 |
| 525 | 4-methyl-3,4-dihydroquinolin-2(1H)-one-yl | 554 |
| 526 | 3-ethyl-1-methyl-1H-indol-yl | 552 |
| 527 | N-ethylaniline | 514 |
| 528 | 1-ethyl-1H-tetrazol-yl | 491 |
| 529 | 3-methyl-1H-indazol-yl | 525 |
| 530 | 3-methyltetrahydrofuran-yl | 479 |
| 531 | 4-methyltetrahydropyran-yl | 493 |
| 532 | 4-ethyltetrahydropyran-yl | 507 |
| 533 | 4-methylthiazol-yl | 492 |

TABLE K-continued

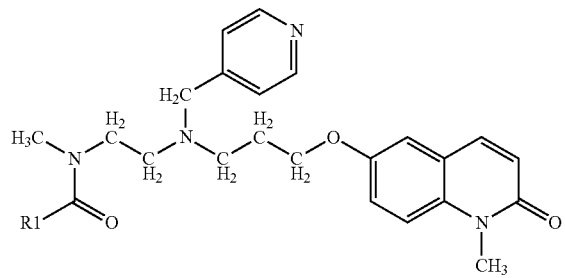

| Example No. | R1 | MS(M + 1) |
|---|---|---|
| 534 | 2,5-dimethylfuran-3-yl (3,5-dimethylfuran-2-yl) | 503 |
| 535 | (E)-1-(furan-2-yl)propenyl | 501 |
| 536 | 5-ethyl-2-methoxy-3-hydroxyphenyl | 545 |
| 537 | 5-methyl-2,3-dihydrobenzofuran-2-yl | 527 |
| 538 | 7-methyl-2,3-dihydrobenzofuran-2-yl | 527 |
| 539 | 1-(p-tolyl)cyclopropyl | 539 |
| 540 | 5-methyl-2,3-dihydrobenzo[1,4]dioxin-2-yl | 543 |
| 541 | 1,5-dimethyl-1H-benzotriazol-? | 540 |
| 542 | 2,4-dimethyloxazol-5-yl | 490 |
| 543 | 5-methylthiazol-2-yl | 492 |

TABLE K-continued

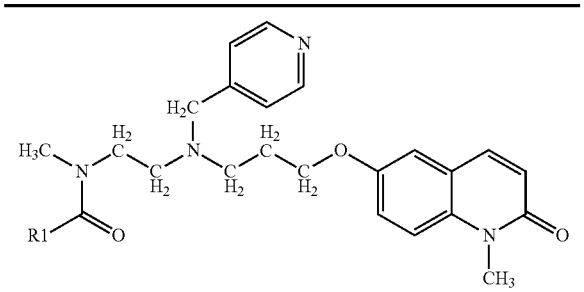

| Example No. | R1 | MS(M + 1) |
|---|---|---|
| 544 | 2,4,5-trimethyloxazol-? | 504 |
| 545 | 6-methyl-2,3-dihydrobenzo[1,4]dioxin-2-yl | 543 |
| 546 | 4,7-dimethyl-3,4-dihydro-2H-benzo[1,4]oxazin-? | 556 |
| 547 | 5-methyl-6-phenylpyridin-? | 562 |
| 548 | 4,5-dimethyl-4H-furo[3,2-b]pyrrol-? | 528 |
| 549 | 6-methylthieno[2,3-b]pyrazin-? | 543 |
| 550 | 6-methyl-1-oxo-indan-? | 539 |
| 551 | 1-(3-methylisoxazol-5-yl)ethyl | 518 |
| 552 | 5-methylisoxazol-3-yl | 476 |

TABLE K-continued

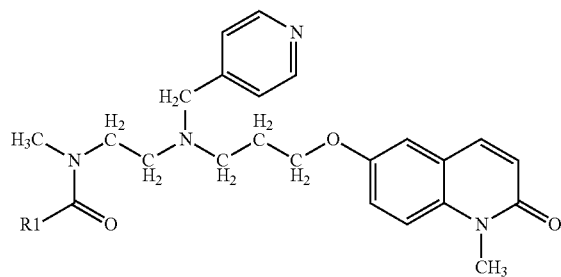

| Example No. | R1 | MS(M + 1) |
|---|---|---|
| 553 | 1,5-dimethylimidazol-4-yl | 489 |
| 554 | 1,4-dimethylimidazol-5-yl | 489 |
| 555 | 1,2-dimethylimidazol-5-yl | 489 |
| 556 | 3,5-dimethylisoxazol-4-yl | 490 |

TABLE L

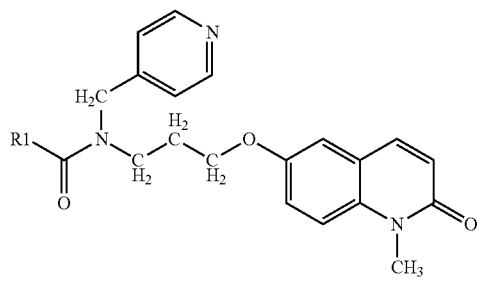

| Example No. | R1 | MS(M + 1) |
|---|---|---|
| 557 | 6-methylbenzo[1,3]dioxol-5-yl | 472 |
| 558 | 5-methyl-1H-indazol-6-yl | 468 |

TABLE L-continued

| Example No. | R1 | MS(M + 1) |
|---|---|---|
| 559 | 4-methyl-1H-indazol-5-yl | 468 |
| 560 | 5-methyl-2,3-dihydrobenzofuran-6-yl | 470 |
| 561 | 7-methyl-2,3-dihydrobenzofuran-4-yl | 470 |
| 562 | benzofuran-5-yl-X1 | 468 |
| 563 | 4-methyl-1H-indol-5-yl | 467 |
| 564 | 1,5-dimethyl-1H-benzotriazol-6-yl | 483 |
| 565 | 6-methylquinoxalin-7-yl | 480 |
| 566 | 2,3,6-trimethylquinoxalin-7-yl | 508 |
| 567 | 6-methyl-2,3-dihydrobenzo[1,4]dioxin-7-yl | 486 |

TABLE L-continued

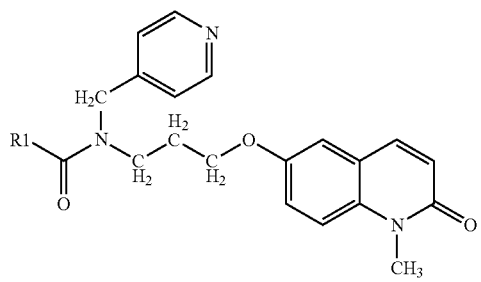

| Example No. | R1 | MS(M + 1) |
|---|---|---|
| 568 | (4-methyl-3,4-dihydro-2H-benzo[b][1,4]oxazin-7-yl) | 499 |
| 569 | (7-methyl-2H-benzo[b][1,4]oxazin-3(4H)-on-yl) | 499 |
| 570 | (2,5-dimethyl-1H-benzo[d]imidazol-yl) | 482 |

TABLE L-continued

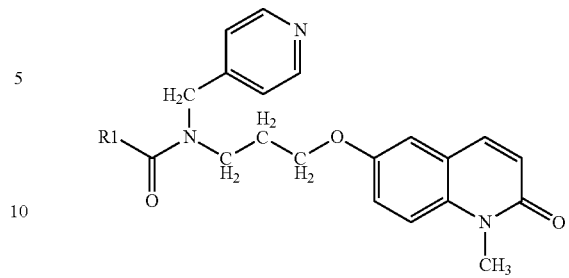

| Example No. | R1 | MS(M + 1) |
|---|---|---|
| 571 | (6-methyl-2,3-dihydro-1H-inden-1-on-yl) | 482 |
| 572 | (5-methylbenzo[b]thiophen-yl) | 484 |
| 573 | (1,5-dimethyl-1H-indol-yl) | 481 |

TABLE M

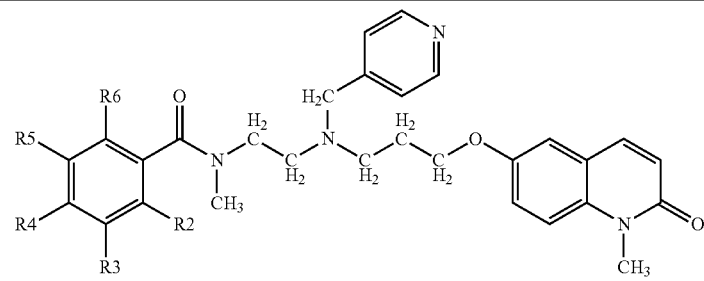

| Example No. | R2 | R3 | R4 | R5 | R6 | MS(M + 1) |
|---|---|---|---|---|---|---|
| 574 | —H | —H | —OCH₃ | —H | —H | 515 |
| 575 | —H | —H | —NHCOCH₃ | —H | —H | 542 |
| 576 | —H | —H | —H | —NHCOCH₃ | —H | 542 |
| 577 | —H | —H | —CF₃ | —H | —H | 553 |
| 578 | —H | —H | —H | —H | —OCH₃ | 515 |
| 579 | —H | —H | —H | —H | —CH₃ | 499 |
| 580 | —H | —H | —H | —H | —F | 503 |
| 581 | —H | —H | —H | —H | —N(CH₃)₂ | 528 |
| 582 | —H | —H | —H | —OCH₃ | —H | 515 |
| 583 | —H | —H | —H | —CH₃ | —H | 499 |
| 584 | —H | —H | —COCH₃ | —H | —H | 527 |
| 585 | —H | —H | —C₆H₅ | —H | —H | 561 |
| 586 | —H | —H | —SO₂NH₂ | —H | —H | 564 |
| 587 | —H | —H | (1H-pyrrol-1-yl) | —H | —H | 550 |
| 588 | —H | —H | (pyridin-3-yl) | —H | —H | 562 |

TABLE M-continued

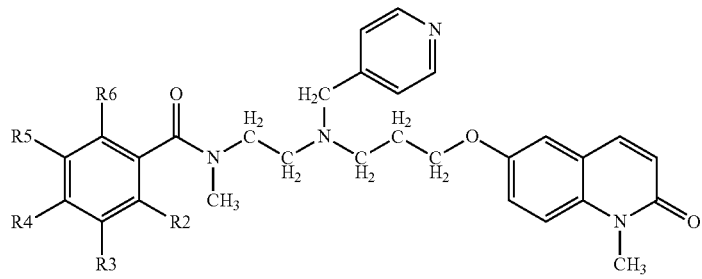

| Example No. | R2 | R3 | R4 | R5 | R6 | MS(M + 1) |
|---|---|---|---|---|---|---|

TABLE N

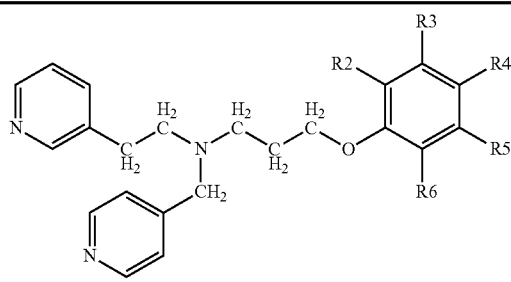

| Example No. | R2 | R3 | R4 | R5 | R6 | MS(M + 1) |
|---|---|---|---|---|---|---|
| 589 | —H | —H | —H | —H | —OCH₃ | 378 |
| 590 | —H | —H | —H | —OCH₃ | —H | 378 |
| 591 | —H | —H | —OCH₃ | —H | —H | 378 |
| 592 | —H | —H | —H | —H | —H | 348 |
| 593 | —H | —H | —H | —H | —CN | 373 |
| 594 | —H | —H | —H | —CN | —H | 373 |
| 595 | —H | —H | —CN | —H | —H | 373 |
| 596 | —H | —H | —H | —H | —CF₃ | 416 |
| 597 | —H | —H | —H | —CF₃ | —H | 416 |
| 598 | —H | —H | —CF₃ | —H | —H | 416 |
| 599 | —H | —H | —H | —H | —OCF₃ | 432 |
| 600 | —H | —H | —H | —OCF₃ | —H | 432 |
| 601 | —H | —H | —OCF₃ | —H | —H | 432 |
| 602 | —H | —H | —H | —C₆H₅ | —H | 424 |
| 603 | —H | —H | —H | —N(C₂H₅)₂ | —H | 419 |
| 604 | —H | —H | —(CH₂)₂COCH₃ | —H | —H | 418 |
| 605 | —H | —H | —COC₂H₅ | —H | —H | 404 |
| 606 | —H | —OH | —COCH₃ | —H | —H | 406 |
| 607 | —H | —H | —SCH₃ | —H | —H | 394 |
| 608 | —H | —H | —C₆H₅ | —H | —H | 424 |
| 609 | —H | —H | —H | —H | —C₆H₅ | 424 |
| 610 | —H | —H | —H | —OC₆H₅ | —H | 440 |
| 611 | —H | —H | —COCH₃ | —H | —H | 390 |
| 612 | —H | —H | 1-methyl-1,2,4-triazol-3-yl | —H | —H | 415 |
| 613 | —H | —H | —H | —H | 5-methylisoxazol-3-yl | 415 |
| 614 | —H | —H | 1-methylimidazol-2-yl | —H | —H | 414 |

TABLE N-continued
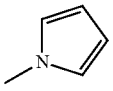
| Example No. | R2 | R3 | R4 | R5 | R6 | MS(M + 1) |
|---|---|---|---|---|---|---|
| 615 | —H | —H | 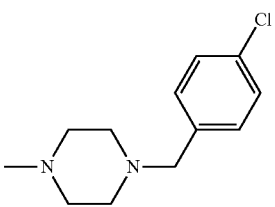 | —H | —H | 413 |
| 616 | —H | —H | 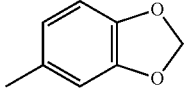 | —H | —H | 556 |
TABLE O
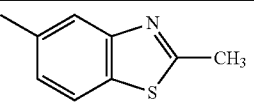
| Example No. | R1 | MS(M + 1) |
|---|---|---|
| 617 | 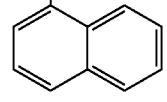 | 392 |
| 618 | 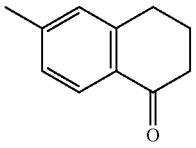 | 398 |
| 619 | 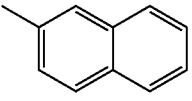 | 398 |
| 620 | 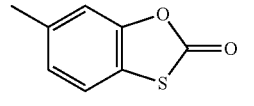 | 405 |
TABLE O-continued
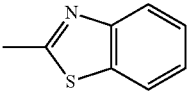
| Example No. | R1 | MS(M + 1) |
|---|---|---|
| 621 | 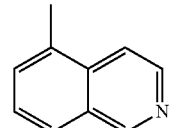 | 419 |
| 622 | | 416 |
| 623 | | 422 |
| 624 | | 399 |

TABLE O-continued
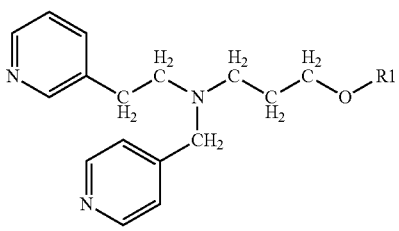
| Example No. | R1 | MS(M + 1) |
|---|---|---|
| 625 | 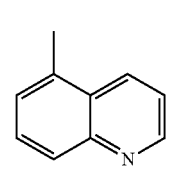 | 349 |
| 626 | 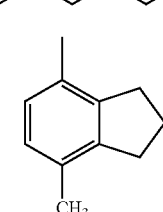 | 399 |
| 627 | 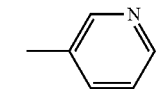 | 349 |
| 628 | 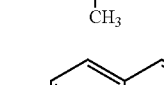 | 416 |
| 629 | 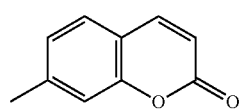 | 399 |
| 630 | 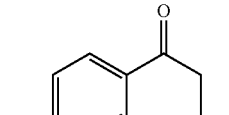 | 413 |
| 631 | 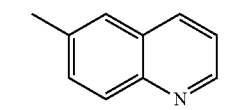 | 400 |
| 632 | 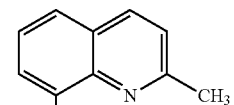 | 402 |
| 633 | 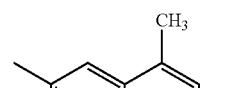 | 363 |
| 634 | 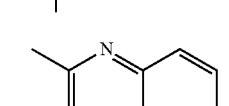 | 380 |
TABLE O-continued
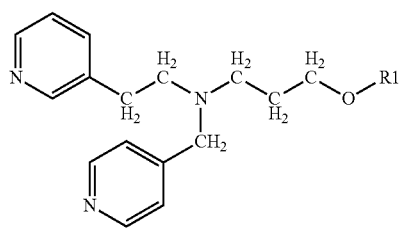
| Example No. | R1 | MS(M + 1) |
|---|---|---|
| 635 | 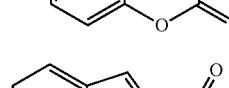 | 399 |
| 636 | 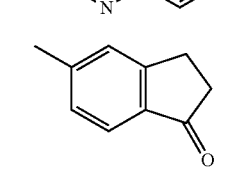 | 402 |
| 637 | 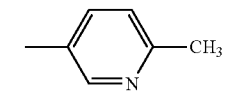 | 416 |
| 638 | 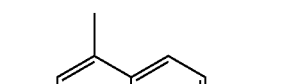 | 416 |
| 639 | 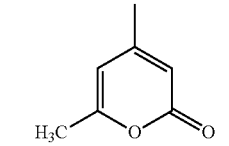 | 430 |
| 640 | 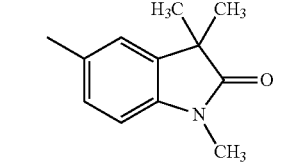 | 430 |
| 641 | 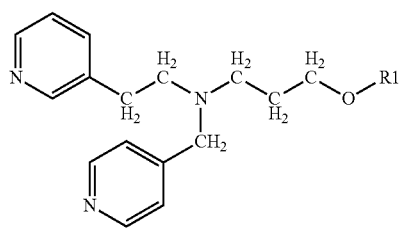 | 446 |
| 642 | 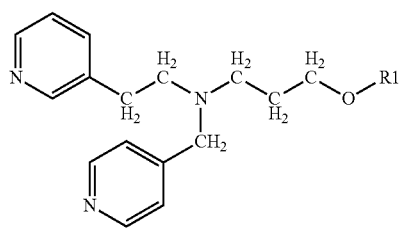 | 445 |

TABLE O-continued

Common structure (Examples 643–649): 3-pyridyl-CH₂-CH₂-N(CH₂-4-pyridyl)-CH₂-CH₂-O-R1

| Example No. | R1 | MS(M + 1) |
|---|---|---|
| 643 | 2-methyl-6-methylbenzothiazol-yl | 419 |
| 644 | 1,3-dimethyl-5-methyl-2-oxo-benzimidazol-yl | 432 |
| 645 | 6-methyl-3-oxo-3,4-dihydro-2H-1,4-benzothiazin-yl | 435 |
| 646 | 1,4-dimethyl-6-methyl-2,3-dioxo-1,2,3,4-tetrahydroquinoxalin-yl | 460 |
| 647 | 1,3-dimethyl-6-methyl-2,4-dioxo-quinazolin-yl | 460 |
| 648 | 4-methyl-7-methyl-2,5-dioxo-2,3,4,5-tetrahydro-1H-benzo[e][1,4]diazepin-yl | 460 |
| 649 | 1,3-dimethyl-7-methyl-2,5-dioxo-2,3,4,5-tetrahydro-1H-benzo[e][1,4]diazepin-yl | 474 |

TABLE O-continued

Common structure (Examples 650–657): 3-pyridyl-CH₂-CH₂-N(CH₂-4-pyridyl)-CH₂-CH₂-O-R1

| Example No. | R1 | MS(M + 1) |
|---|---|---|
| 650 | 7-methyl-2-oxo-2,3,4,5-tetrahydro-1H-benzo[b]azocin-yl | 445 |
| 651 | 3,3-dimethyl-6-methyl-2-oxoindolin-yl | 431 |
| 652 | 6-methyl-2-oxo-1,2,3,4-tetrahydroquinolin-yl | 417 |
| 653 | 6-methyl-2-oxo-2,3-dihydrobenzothiazol-yl | 421 |
| 654 | 1-methyl-6-methyl-2-oxo-1,2,3,4-tetrahydroquinolin-yl | 431 |
| 655 | 7-methyl-2-oxo-1,2,3,4-tetrahydroquinolin-yl | 417 |
| 656 | 7-methyl-2-oxo-2,3,4,5-tetrahydro-1H-benzo[b]azepin-yl | 431 |
| 657 | 1-methyl-7-methyl-2-oxo-2,3,4,5-tetrahydro-1H-benzo[b]azepin-yl | 445 |

TABLE O-continued

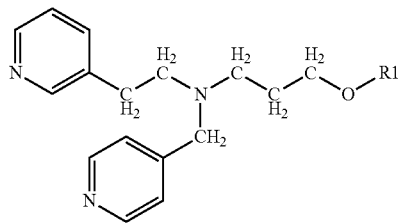

| Example No. | R1 | MS(M + 1) |
|---|---|---|
| 658 | 6-methyl-2,3,4,5-tetrahydro-1H-benzo[b]azepin-2-one | 431 |
| 659 | 3,3,5-trimethyl-1,3-dihydro-2H-indol-2-one | 431 |
| 660 | 6-methylbenzo[d]oxazol-2(3H)-one | 405 |
| 661 | 3,6-dimethylbenzo[d]oxazol-2(3H)-one | 419 |
| 662 | 1,3,6-trimethyl-3,4-dihydroquinazolin-2(1H)-one | 446 |
| 663 | 3,6-dimethyl-3,4-dihydroquinazolin-2(1H)-one | 432 |
| 664 | 6-methyl-3,4-dihydroisoquinolin-1(2H)-one | 417 |
| 665 | 7-methyl-2,3,4,5-tetrahydro-1H-benzo[b]azepin-2-one | 431 |

TABLE O-continued

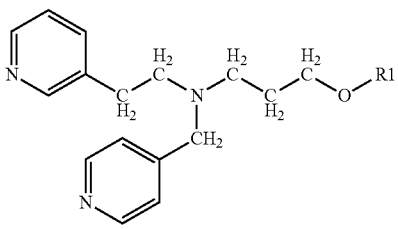

| Example No. | R1 | MS(M + 1) |
|---|---|---|
| 666 | 6-methylisoindolin-1-one | 403 |
| 667 | 7-methyl-2,3-dihydrobenzo[b][1,4]thiazepin-4(5H)-one | 449 |
| 668 | 8-methyl-2,3-dihydrobenzo[b][1,4]thiazepin-4(5H)-one | 449 |
| 669 | 6-methyl-2H-benzo[b][1,4]thiazin-3(4H)-one | 435 |
| 670 | 1-acetyl-6-methyl-1,2,3,4-tetrahydroquinoline | 445 |
| 671 | 6-methyl-2-phenylbenzo[d]oxazole | 465 |

TABLE P
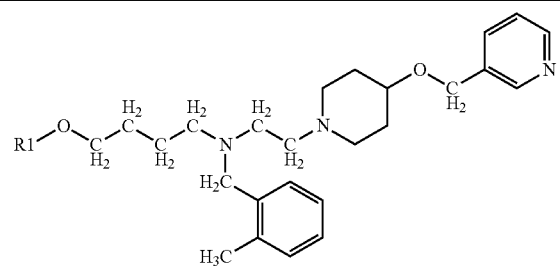
| Example No. | R1 | MS(M + 1) |
|---|---|---|
| 672 | | 557 |
| 673 | | 545 |
| 674 | | 571 |
| 675 | | 647 |
| 676 | | 555 |
| 677 | | 555 |
| 678 | | 556 |
| 679 | | 578 |
| 680 | | 538 |
TABLE P-continued
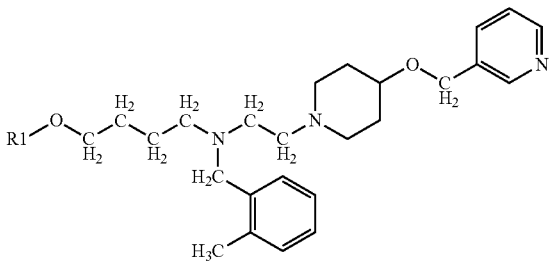
| Example No. | R1 | MS(M + 1) |
|---|---|---|
| 681 | | 577 |
| 682 | | 530 |
| 683 | | 571 |
| 684 | | 531 |
| 685 | | 571 |
| 686 | | 585 |
| 687 | | 583 |
| 688 | | 575 |
| 689 | | 575 |

TABLE P-continued

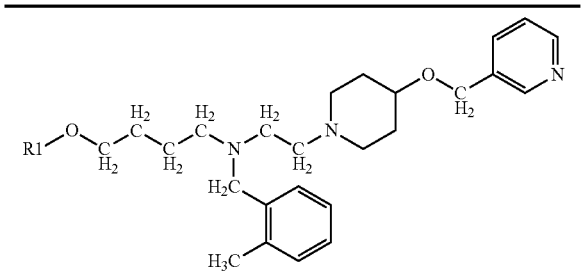

| Example No. | R1 | MS(M + 1) |
|---|---|---|
| 690 | (8-methyl-3,4-dihydroquinolin-2(1H)-one) | 557 |
| 691 | (4-methyl-2H-chromen-2-one) | 556 |

TABLE P-continued

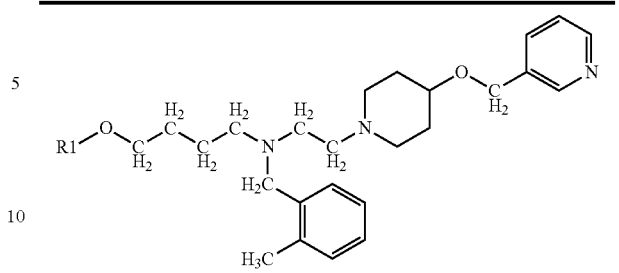

| Example No. | R1 | MS(M + 1) |
|---|---|---|
| 692 | (6-methyl-2-phenylbenzothiazole) | 621 |
| 693 | (2-(o-tolyl)benzoxazole) | 605 |

TABLE Q

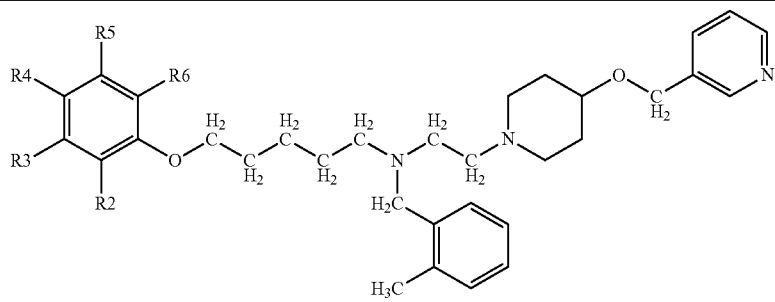

| Example No. | R2 | R3 | R4 | R5 | R6 | MS(M + 1) |
|---|---|---|---|---|---|---|
| 694 | —H | —H | —OCH$_3$ | —H | —H | 532 |
| 695 | —H | —OCH$_3$ | —OCH$_3$ | —H | —H | 562 |
| 696 | —Cl | —H | —H | —H | —H | 536 |
| 697 | —H | —Cl | —H | —H | —H | 536 |
| 698 | —H | —H | —Cl | —H | —H | 536 |
| 699 | —H | —Cl | —Cl | —H | —H | 570 |
| 700 | —H | —H | —CH$_3$ | —H | —H | 516 |
| 701 | —H | —CH$_3$ | —CH$_3$ | —H | —H | 530 |
| 702 | —H | —H | —CO$_2$C$_2$H$_5$ | —H | —H | 574 |
| 703 | —H | —H | —CN | —H | —H | 527 |
| 704 | —H | —H | —CF$_3$ | —H | —H | 570 |
| 705 | —H | —H | —OCF$_3$ | —H | —H | 586 |
| 706 | —H | —H | —(CH$_2$)$_2$CH$_3$ | —H | —H | 544 |
| 707 | —H | —F | —Cl | —H | —H | 554 |
| 708 | —OCH$_3$ | —H | —CH$_2$CH=CH$_2$ | —H | —H | 572 |
| 709 | —H | —N(C$_2$H$_5$)$_2$ | —H | —H | —H | 573 |
| 710 | —H | —H | —CH(CH$_3$)$_2$ | —H | —H | 544 |
| 711 | —H | —H | —(CH$_2$)$_2$COCH$_3$ | —H | —H | 572 |
| 712 | —H | —NHC$_6$H$_5$ | —H | —H | —H | 593 |
| 713 | —H | —H | —SCH$_3$ | —H | —H | 548 |
| 714 | (2-methylbenzothiazol-6-yl) | —H | —H | —H | —H | 635 |

TABLE Q-continued

| Example No. | R2 | R3 | R4 | R5 | R6 | MS(M + 1) |
|---|---|---|---|---|---|---|
| 715 | —H | —H | —C$_6$H$_5$ | —H | —H | 578 |
| 716 | —H | —H | —OCH$_2$C$_6$H$_5$ | —H | —H | 608 |
| 717 | —H | —H | —CH$_2$C$_6$H$_5$ | —H | —H | 592 |
| 718 | —H | —H | —O(CH$_2$)$_7$CH$_3$ | —H | —H | 630 |
| 719 | —H | —OC$_6$H$_5$ | —H | —H | —H | 594 |
| 720 | —H | —H | —(CH$_2$)$_5$CH$_3$ | —H | —H | 586 |
| 721 | —H | —H | —NO$_2$ | —H | —H | 547 |
| 722 | —H | —H | —COCH$_3$ | —H | —H | 544 |
| 723 | —H | —H | —H | —H | —H | 502 |
| 724 | —H | —H | —NHCOCH$_3$ | —H | —H | 559 |
| 725 | —H | —H | 1-(1,2,4-triazolyl) | —H | —H | 569 |
| 726 | —H | —H | 1-imidazolyl | —H | —H | 568 |
| 727 | —H | —H | 1-pyrrolyl | —H | —H | 567 |
| 728 | —H | —H | N-methyl-N-(4-chlorophenyl)-1-methylpiperidin-4-ylamino | —H | —H | 724 |
| 729 | —H | —H | cyclohexyl | —H | —H | 584 |
| 730 | —H | —H | N-methyl-N-(4-chlorophenyl)-1-methylpiperidin-4-ylamino | —H | —H | 724 |
| 731 | —H | —H | 2-oxopyrrolidin-1-yl | —H | —H | 585 |

TABLE R

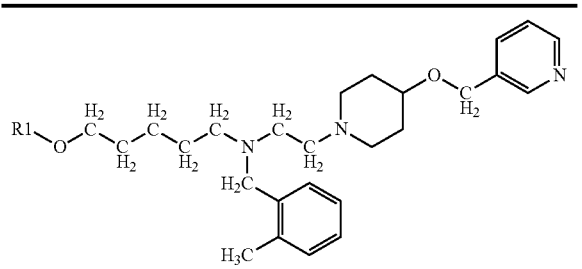

| Example No. | R1 | MS(M + 1) |
|---|---|---|
| 732 | benzo[d][1,3]dioxol-5-yl-methyl | 546 |
| 733 | naphthalen-1-yl-methyl | 552 |
| 734 | naphthalen-2-yl-methyl | 552 |
| 735 | benzo[d]thiazol-2-yl-methyl | 559 |
| 736 | 6-methyl-3,4-dihydronaphthalen-1(2H)-one | 570 |
| 737 | 2-oxobenzo[d][1,3]oxathiol-6-yl-methyl | 576 |
| 738 | isoquinolin-5-yl-methyl | 553 |
| 739 | pyridin-2-yl-methyl | 503 |
| 740 | quinolin-5-yl-methyl | 553 |
| 741 | pyridin-3-yl-methyl | 503 |

TABLE R-continued

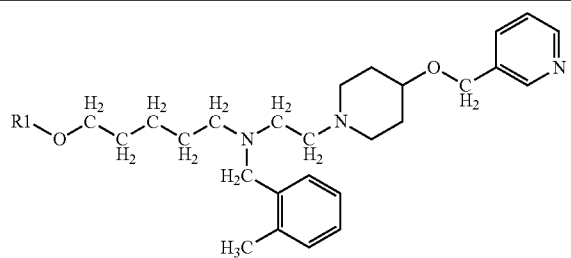

| Example No. | R1 | MS(M + 1) |
|---|---|---|
| 742 | 7-methyl-2H-chromen-2-one | 570 |
| 743 | quinolin-6-yl-methyl | 553 |
| 744 | benzo[d]isoxazol-3-yl-methyl | 543 |
| 745 | benzo[c][1,2,5]oxadiazol-5-yl-methyl | 544 |
| 746 | quinoxalin-2-yl-methyl | 554 |
| 747 | 2,3-dihydro-1H-inden-5-yl-methyl | 542 |
| 748 | 6-methylpyridin-3-yl-methyl | 517 |
| 749 | 6-methyl-2H-pyran-2-one | 534 |
| 750 | isoquinolin-7-yl-methyl | 553 |
| 751 | 4,7-dimethyl-2,3-dihydro-1H-inden-5-yl-methyl | 556 |

TABLE R-continued

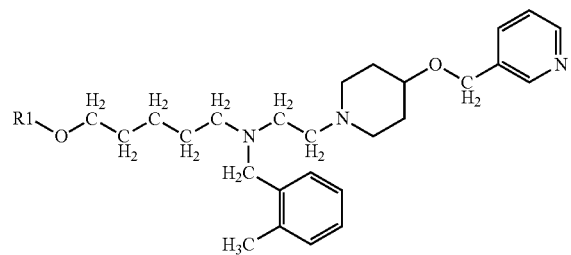

| Example No. | R1 | MS(M + 1) |
|---|---|---|
| 752 | 6-cyano-2-naphthyl | 577 |
| 753 | 4-methyl-6-yl-2H-chromen-2-one | 584 |
| 754 | 2-acetyl-7-methylbenzofuran-yl | 584 |
| 755 | 6-methoxy-7-methyl-3,4-dihydroisoquinolin-yl | 585 |
| 756 | 1,7-dimethyl-6-methoxy-3,4-dihydroisoquinolin-yl | 599 |
| 757 | 1,3,3-trimethyl-5-yl-2-oxoindolin-yl | 599 |
| 758 | 1,3,6-trimethyl-2-oxo-2,3-dihydro-1H-benzimidazol-5-yl | 586 |
| 759 | 4,7-dimethyl-2,5-dioxo-2,3,4,5-tetrahydro-1H-benzo[e][1,4]diazepin-yl | 614 |

TABLE R-continued

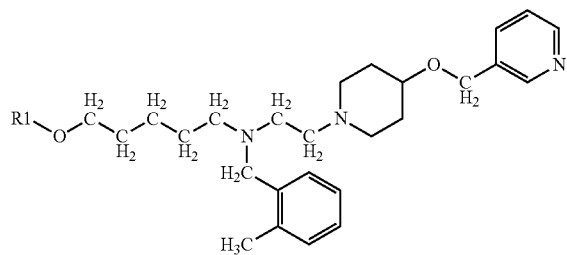

| Example No. | R1 | MS(M + 1) |
|---|---|---|
| 760 | 6-methyl-3,4-dihydroquinolin-2(1H)-one | 571 |
| 761 | 2,6-dimethylbenzo[d]thiazol-yl | 573 |
| 762 | 6-methyl-benzo[d]thiazol-2(3H)-one | 575 |
| 763 | 1,6-dimethyl-3,4-dihydroquinolin-2(1H)-one | 585 |
| 764 | 7-methyl-3,4-dihydroquinolin-2(1H)-one | 571 |
| 765 | 7-methyl-4,5-dihydro-1H-benzo[b]azepin-2(3H)-one | 585 |
| 766 | 1,7-dimethyl-4,5-dihydro-1H-benzo[b]azepin-2(3H)-one | 599 |
| 767 | 8-methyl-4,5-dihydro-1H-benzo[b]azepin-2(3H)-one | 585 |
| 768 | 8-methyl-3,4-dihydrobenzo[b][1,4]oxazepin-5(2H)-one | 587 |

TABLE R-continued
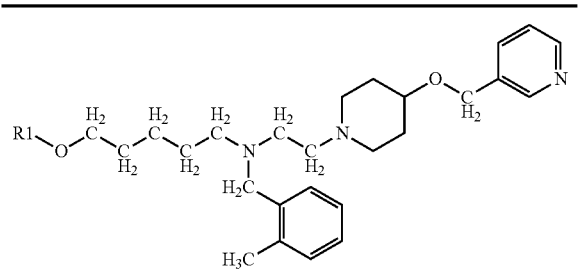
| Example No. | R1 | MS(M + 1) |
|---|---|---|
| 769 | 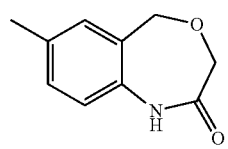 | 587 |
| 770 | 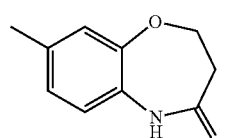 | 587 |
| 771 | 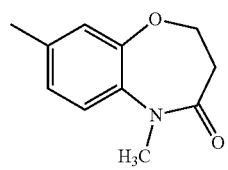 | 601 |
| 772 | 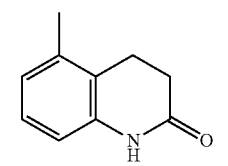 | 571 |
TABLE R-continued
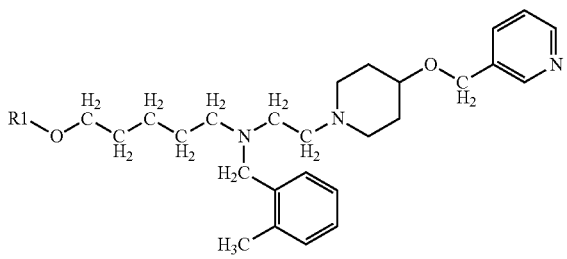
| Example No. | R1 | MS(M + 1) |
|---|---|---|
| 773 | 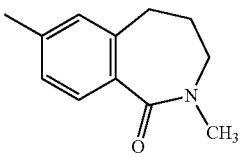 | 599 |
| 774 | 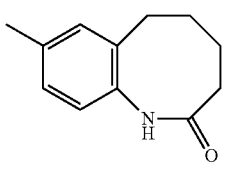 | 599 |
| 775 | 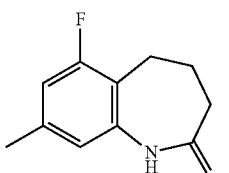 | 603 |
| 776 | 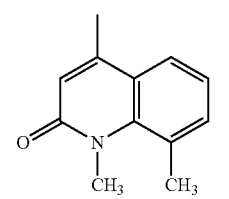 | 597 |
TABLE S
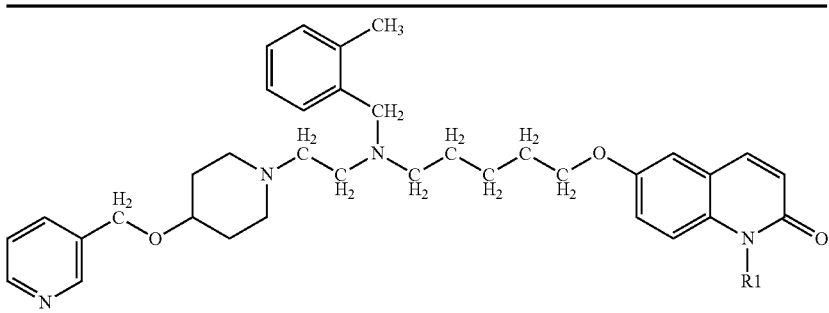
| Example No. | R1 | MS(M + 1) |
|---|---|---|
| 777 | —CH$_2$C$_6$H$_5$ | 659 |
| 778 | —CH$_2$CH=CH$_2$ | 609 |
| 779 | —CH$_2$CH=CHC$_6$H$_5$ | 685 |
| 780 | —(CH$_2$)$_3$C$_6$H$_5$ | 687 |
| 781 | —CH$_2$COC$_6$H$_5$ | 687 |
| 782 | —CH$_3$ | 583 |
| 783 | —C$_2$H$_5$ | 597 |

TABLE S-continued
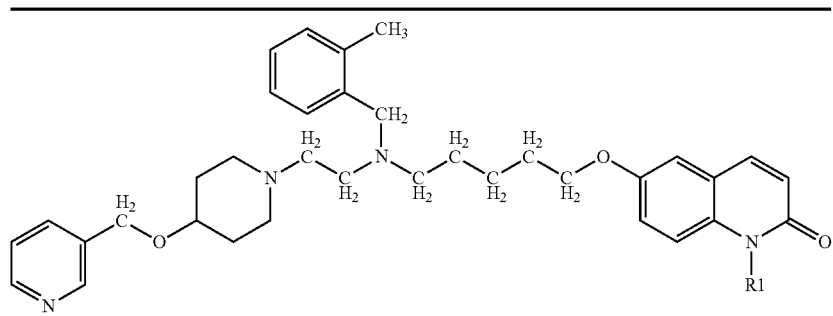
| Example No. | R1 | MS(M + 1) |
|---|---|---|
| 784 | —(CH$_2$)$_2$CH$_3$ | 611 |
| 785 | —CH$_2$CH(CH$_3$)$_2$ | 625 |
| 786 | —(CH$_2$)$_2$N(CH$_3$)$_2$ | 640 |
| 787 | —(CH$_2$)$_3$CH$_2$CH=CH$_2$ | 651 |
| 788 | —(CH$_2$)$_3$OH | 627 |
TABLE T
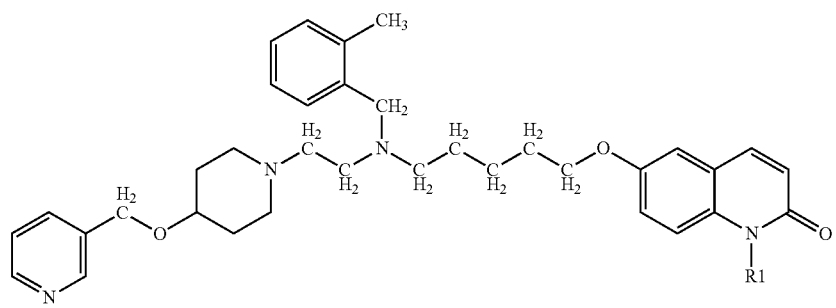
| Example No. | R1 | MS(M + 1) |
|---|---|---|
| 789 | | 693 |
| 790 | | 727 |
| 791 | | 673 |
| 792 | | 735 |
| 793 | | 665 |
| 794 | | 660 |

TABLE T-continued
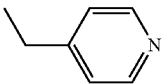
| Example No. | R1 | MS(M + 1) |
|---|---|---|
| 795 | 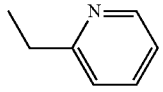 | 660 |
| 796 | 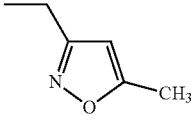 | 660 |
| 797 | 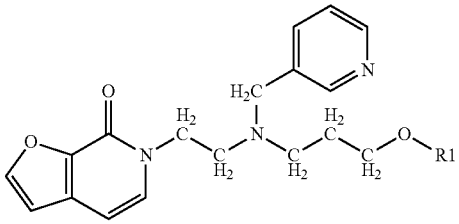 | 664 |
TABLE U
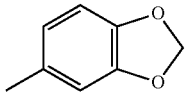
| Example No. | R1 | MS(M + 1) |
|---|---|---|
| 798 | 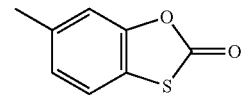 | 448 |
| 799 | 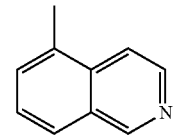 | 478 |
| 800 | 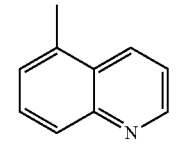 | 455 |
| 801 | 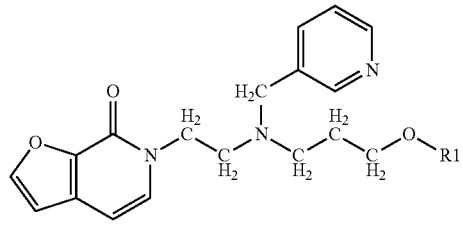 | 455 |
TABLE U-continued
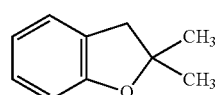
| Example No. | R1 | MS(M + 1) |
|---|---|---|
| 802 | 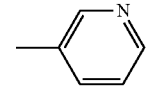 | 474 |
| 803 | 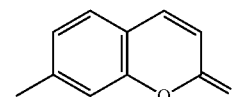 | 405 |
| 804 | 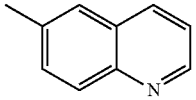 | 472 |
| 805 | 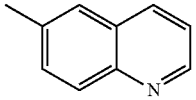 | 455 |

TABLE U-continued

[Structure: furopyridinone-CH2CH2-N(CH2-pyridin-3-yl)-CH2-CH(CH2-O-R1)]

| Example No. | R1 | MS(M + 1) |
|---|---|---|
| 806 | 8-methyl-2-methylquinolin-yl | 469 |
| 807 | 3-methylquinoxalin-yl | 456 |
| 808 | 7-methylisoquinolin-yl | 455 |
| 809 | 5,7,8-trimethylquinolin-yl | 483 |
| 810 | 1,3,3,5-tetramethyl-2-oxoindolin-yl | 501 |
| 811 | 2,6-dimethylbenzothiazol-yl | 475 |
| 812 | 1,3,5-trimethyl-2-oxobenzimidazol-yl | 488 |
| 813 | 1,4-dimethyl-7-methyl-2,3-dioxoquinoxalin-yl | 516 |
| 814 | 1,3,6-trimethyl-2,4-dioxoquinazolin-yl | 516 |
| 815 | 3,3,6-trimethyl-2-oxoindolin-yl | 487 |
| 816 | 6-methyl-2-oxobenzothiazol-yl | 477 |
| 817 | 1,6-dimethyl-2-oxo-tetrahydroquinolin-yl | 487 |
| 818 | 7-methyl-2-oxo-tetrahydrobenzazepin-yl | 487 |
| 819 | 1,7-dimethyl-2-oxo-tetrahydrobenzazepin-yl | 501 |
| 820 | 8-methyl-2-oxo-tetrahydrobenzazepin-yl | 487 |
| 821 | 8-methyl-4-oxo-benzoxazepin-yl | 489 |

TABLE U-continued
| Example No. | R1 | MS(M + 1) |
|---|---|---|
| 822 | 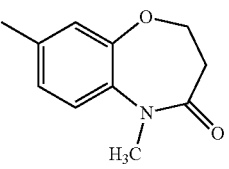 | 503 |
| 823 | 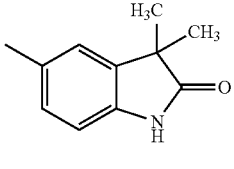 | 487 |
| 824 | 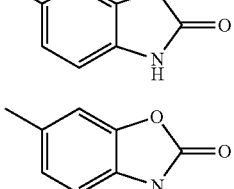 | 461 |
| 825 | 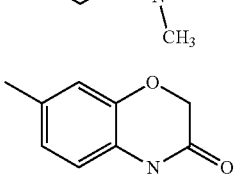 | 475 |
| 826 | 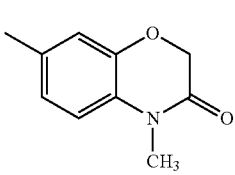 | 475 |
| 827 | 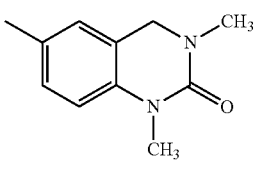 | 489 |
| 828 | 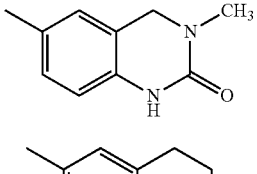 | 502 |
| 829 | 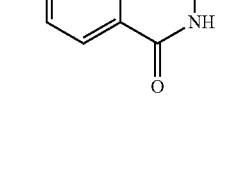 | 488 |
| 830 |  | 473 |
TABLE U-continued
| Example No. | R1 | MS(M + 1) |
|---|---|---|
| 831 | 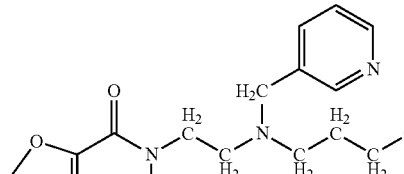 | 487 |
| 832 | 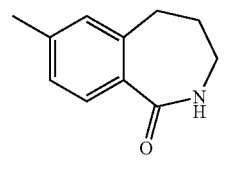 | 459 |
| 833 | 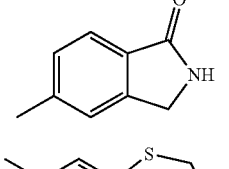 | 505 |
| 834 | 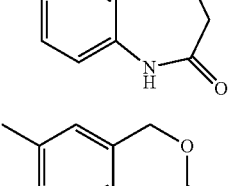 | 475 |
| 835 | 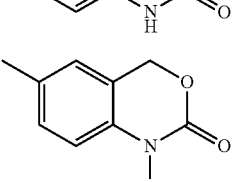 | 489 |
| 836 | 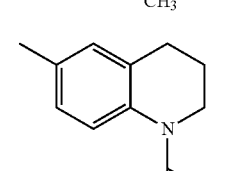 | 501 |
| 837 | 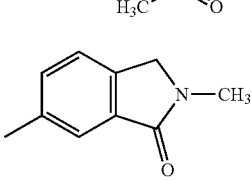 | 473 |
| 838 | 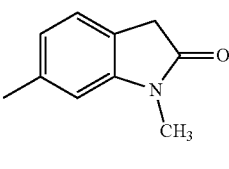 | 473 |
| 839 |  | 474 |

TABLE U-continued
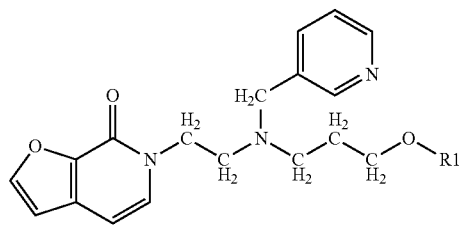
| Example No. | R1 | MS(M + 1) |
|---|---|---|
| 840 | | 455 |
| 841 | | 469 |
| 842 | | 443 |
| 843 | | 485 |
| 844 | | 499 |
| 845 | | 487 |
| 846 | | 458 |
| 847 | | 484 |
TABLE U-continued
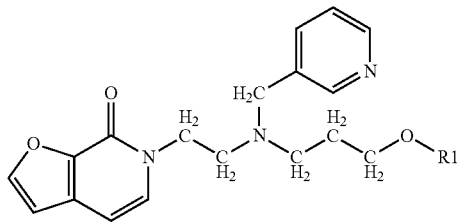
| Example No. | R1 | MS(M + 1) |
|---|---|---|
| 848 | | 455 |
| 849 | | 485 |
| 850 | | 469 |
| 851 | | 473 |
| 852 | | 473 |
| 853 | | 456 |
| 854 | | 461 |
| 855 | | 455 |
| 856 | | 455 |

TABLE U-continued

Structure: furopyridinone-CH₂CH₂-N(CH₂-3-pyridyl)-CH₂CH₂-O-R1

| Example No. | R1 | MS(M + 1) |
|---|---|---|
| 857 | 8-methylisoquinolin-5-yl | 455 |
| 858 | 6-methylbenzofuran-? | 444 |
| 859 | 4-(2-oxopyrrolidin-1-yl)phenyl-methyl | 487 |
| 860 | 5-methyl-1,2,3,4-tetrahydroisoquinolin-1-one | 473 |
| 861 | 5-methyl-2-methyl-3,4-dihydroisoquinolin-1(2H)-one | 487 |
| 862 | 6-methyl-2-methyl-3,4-dihydroisoquinolin-1(2H)-one | 487 |
| 863 | 7-methyl-2-methyl-3,4-dihydroisoquinolin-1(2H)-one | 487 |

TABLE V

| Example No. | R2 | R3 | R4 | R5 | R6 | MS (M + 1) |
|---|---|---|---|---|---|---|
| 864 | —H | —H | —H | —H | —H | 428 |
| 865 | —H | —H | —OCH₃ | —H | —H | 458 |
| 866 | —H | —N(CH₃)₂ | —H | —H | —H | 471 |
| 867 | —H | —H | —N(CH₃)₂ | —H | —H | 471 |
| 868 | —H | —H | —CN | —H | —H | 453 |
| 869 | —COCH₃ | —H | —H | —H | —H | 470 |
| 870 | —H | —H | —COCH₃ | —H | —H | 470 |
| 871 | —OC₆H₅ | —H | —H | —H | —H | 520 |
| 872 | —H | —H | —OC₆H₅ | —H | —H | 520 |
| 873 | —CN | —H | —H | —H | —H | 453 |
| 874 | —H | —H | —C₆H₅ | —H | —H | 504 |
| 875 | —H | —H | —SO₂CH₃ | —H | —H | 506 |
| 876 | —H | —H | —N(C₂H₅)₂ | —H | —H | 499 |
| 877 | —H | —C₆H₅ | —H | —H | —H | 504 |
| 878 | —H | —H | 1-methyl-2-oxopyrrolidin-yl | —H | —H | 511 |
| 879 | —H | —H | 1-methylpyrrol-yl | —H | —H | 493 |
| 880 | —H | —H | 1-methylpyrazol-yl | —H | —H | 494 |
| 881 | —H | 1-ethyl-1,2,4-triazol-yl | —H | —H | —H | 509 |
| 882 | —H | 1-methyl-1,2,4-triazol-yl | —H | —H | —H | 495 |

TABLE W
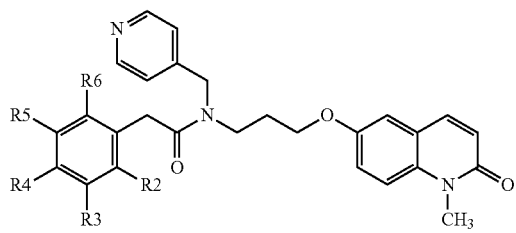
| Example No. | R2 | R3 | R4 | R5 | R6 | MS (M + 1) |
|---|---|---|---|---|---|---|
| 883 | —H | —H | —CH₃ | —H | —H | 456 |
| 884 | —H | —H | —F | —H | —H | 460 |
| 885 | —H | —H | —OCH₃ | —H | —H | 472 |
| 886 | —H | —H | —H | —H | —CH₃ | 456 |
| 887 | —H | —H | —H | —OCH₃ | —H | 472 |
| 888 | —H | —H | —H | —H | —OCH₃ | 472 |
| 889 | —H | —H | —OCH₃ | —OH | —H | 488 |
TABLE X
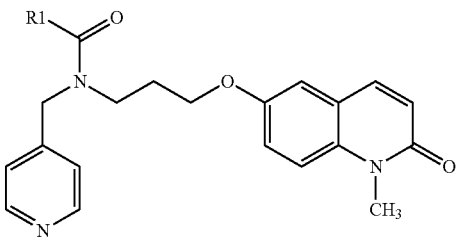
| Example No. | R1 | MS(M + 1) |
|---|---|---|
| 890 | —CH₂OC₆H₅ | 458 |
| 891 | —(CH₂)₂C₆H₅ | 456 |
| 892 | —CH=CHC₆H₅ | 454 |
| 893 | —(CH₂)₂OC₆H₅ | 472 |
| 894 | —(CH₂)₃C₆H₅ | 470 |
| 895 | —(CH₂)₄C₆H₅ | 484 |
| 896 | —CH₂SC₆H₅ | 474 |
| 897 | —(CH₂)₂COC₆H₅ | 484 |
TABLE Y
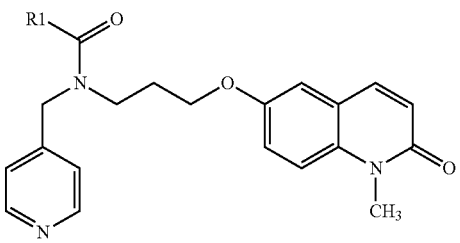
| Example No. | R1 | MS(M + 1) |
|---|---|---|
| 898 |  | 457 |
| 899 |  | 476 |
TABLE Y-continued
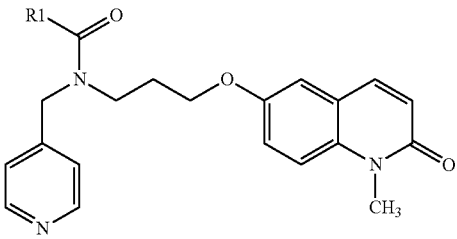
| Example No. | R1 | MS(M + 1) |
|---|---|---|
| 900 | 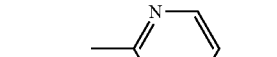 | 488 |
| 901 | 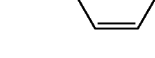 | 429 |
| 902 | 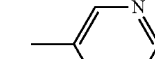 | 429 |
| 903 | 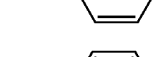 | 429 |
| 904 | 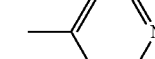 | 418 |
| 905 | 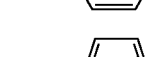 | 434 |
| 906 | 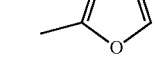 | 418 |
| 907 |  | 434 |
| 908 | 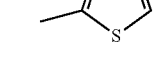 | 448 |
| 909 | 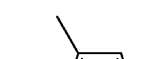 | 448 |
| 910 | 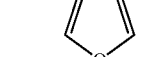 | 434 |
| 911 | 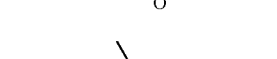 | 484 |

TABLE Y-continued
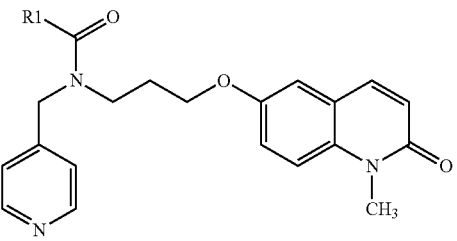
| Example No. | R1 | MS(M + 1) |
|---|---|---|
| 912 | 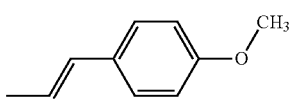 | 484 |
| 913 | 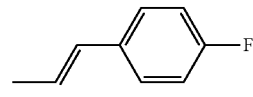 | 472 |
| 914 | 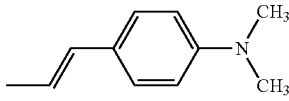 | 497 |
| 915 | 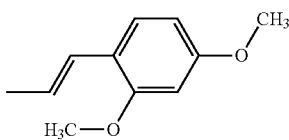 | 514 |
| 916 | 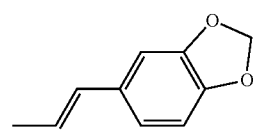 | 498 |
| 917 | 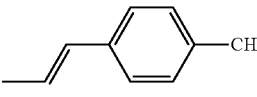 | 468 |
| 918 | 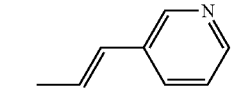 | 455 |
| 919 | 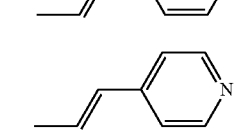 | 455 |
| 920 | 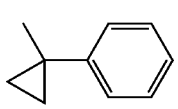 | 468 |
| 921 | 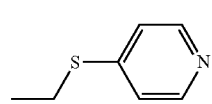 | 475 |
| 922 | 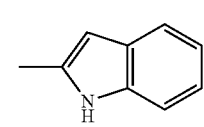 | 467 |
TABLE Y-continued
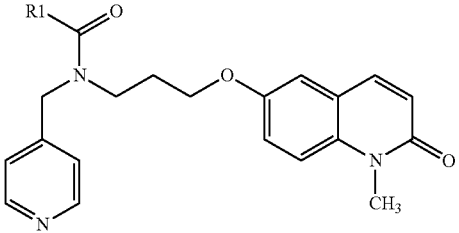
| Example No. | R1 | MS(M + 1) |
|---|---|---|
| 923 | 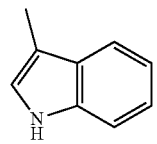 | 467 |
| 924 | 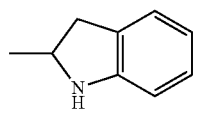 | 469 |
| 925 | 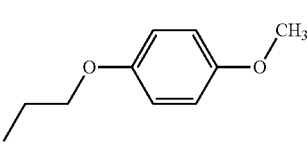 | 502 |
| 926 | 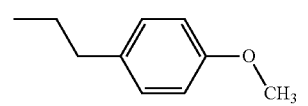 | 486 |
| 927 | 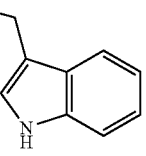 | 481 |
| 928 | 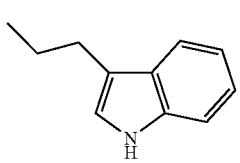 | 495 |
| 929 | 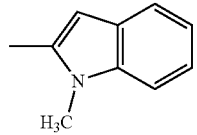 | 481 |
| 930 | 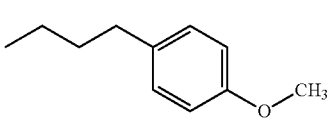 | 500 |
| 931 | 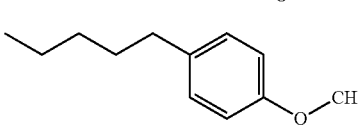 | 514 |
| 932 | 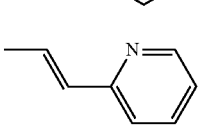 | 455 |

TABLE Y-continued

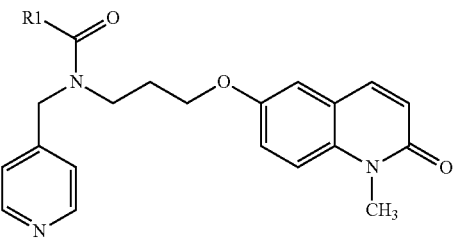

| Example No. | R1 | MS(M + 1) |
|---|---|---|
| 933 | 5-ethoxy-3,4-dihydroquinolin-2(1H)-one | 527 |
| 934 | 7-ethoxy-3,4-dihydroquinolin-2(1H)-one | 527 |
| 935 | 8-ethoxy-3,4-dihydroquinolin-2(1H)-one | 527 |
| 936 | 1-butyl-3,4-dihydroquinolin-2(1H)-one | 539 |
| 937 | 3,5-diethyl-2-methyl-1H-indole | 523 |
| 938 | 3-ethyl-5-methoxy-1H-indole | 511 |
| 939 | 3-ethyl-7-methyl-1H-indole | 495 |
| 940 | N-ethylaniline | 457 |

TABLE Y-continued

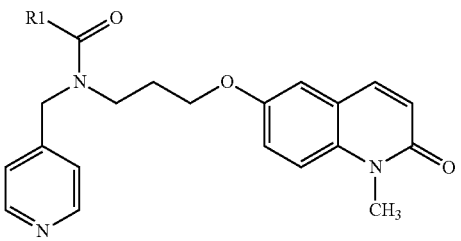

| Example No. | R1 | MS(M + 1) |
|---|---|---|
| 941 | 1,2-dimethyl-1H-pyrrole | 431 |
| 942 | 4-propenyl-1H-imidazole | 444 |
| 943 | 4-methylcinnoline | 480 |
| 944 | 3-methyl-1H-indazole | 468 |
| 945 | 4-methyltetrahydro-2H-pyran | 436 |
| 946 | 4-ethyltetrahydro-2H-pyran | 450 |
| 947 | 4-methylthiazole | 435 |
| 948 | 2,5-dimethyl-3-methylfuran | 446 |
| 949 | 2-chloro-4-methylthiophene | 468 |
| 950 | 2-propenylfuran | 444 |

TABLE Y-continued

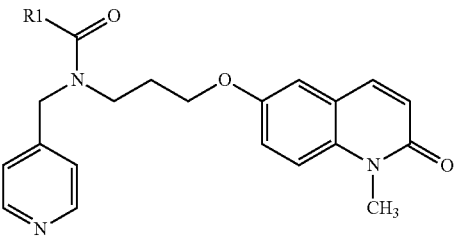

| Example No. | R1 | MS(M + 1) |
|---|---|---|
| 951 | 2-methoxyphenylpropyl | 486 |
| 952 | 1-(4-methylphenyl)cyclopropyl | 482 |
| 953 | 4-phenylcyclohexylmethyl | 510 |
| 954 | 2-methyl-oxazol-4-yl | 433 |
| 955 | 5-methylthiazol-2-yl | 435 |
| 956 | 4-methyl-5-phenyloxazol-2-yl | 495 |
| 957 | 2,4,5-trimethyloxazol-2-yl | 447 |
| 958 | 3-methyl-2-oxo-1H-quinolin-4-yl | 495 |
| 959 | N-ethyl-N-methyl-3-fluoroaniline | 489 |
| 960 | N-butyl-N-methyl-3-fluoroaniline | 517 |

TABLE Y-continued

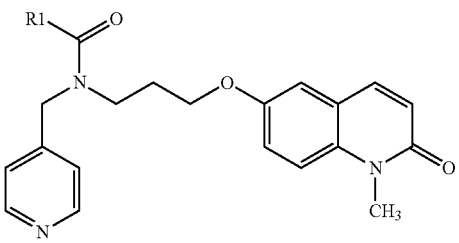

| Example No. | R1 | MS(M + 1) |
|---|---|---|
| 961 | N-ethyl-N-methyl-3-methoxyaniline | 501 |
| 962 | 2-methylindanyl | 468 |
| 963 | N-propyl-N-acetylaniline | 513 |
| 964 | 6-methyl-2-phenylpyridin-3-yl | 505 |
| 965 | 5-methyl-2-phenylpyridin-3-yl | 505 |
| 966 | 5-methyl-3-phenylpyridin-2-yl | 505 |
| 967 | 2-methylthieno[3,2-b]pyrazin-6-yl | 486 |
| 968 | 4-chlorophenylpropyl | 490 |
| 969 | 5-methylisoxazol-3-yl | 419 |
| 970 | benzo[1,3]dioxol-5-ylpropyl | 500 |

TABLE Y-continued
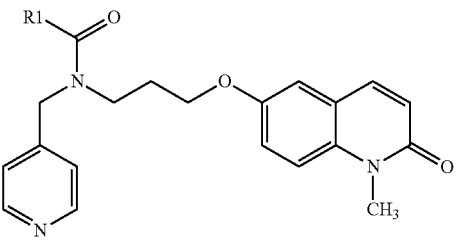
| Example No. | R1 | MS(M + 1) |
|---|---|---|
| 971 | 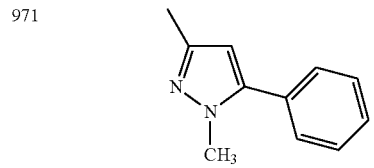 | 508 |
| 972 | 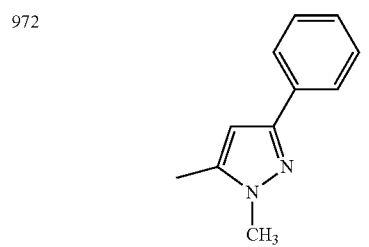 | 508 |
| 973 | 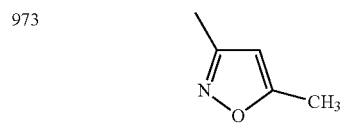 | 433 |
| 974 | 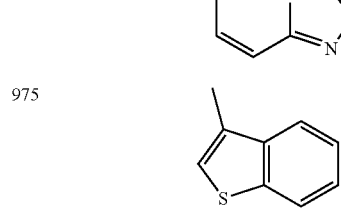 | 468 |
| 975 | 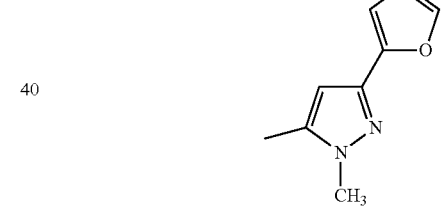 | 484 |
TABLE Y-continued
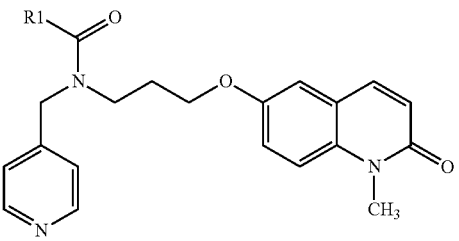
| Example No. | R1 | MS(M + 1) |
|---|---|---|
| 976 | 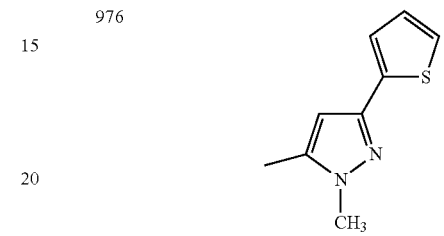 | 514 |
| 977 | 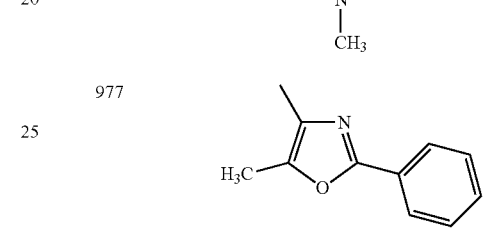 | 509 |
| 978 |  | 482 |
| 979 | 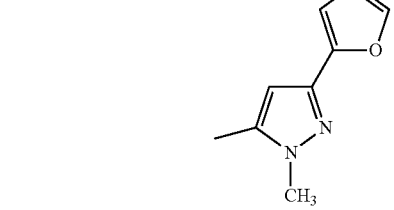 | 498 |
TABLE Z
| Example No. | structure | MS(M + 1) |
|---|---|---|
| 981 | 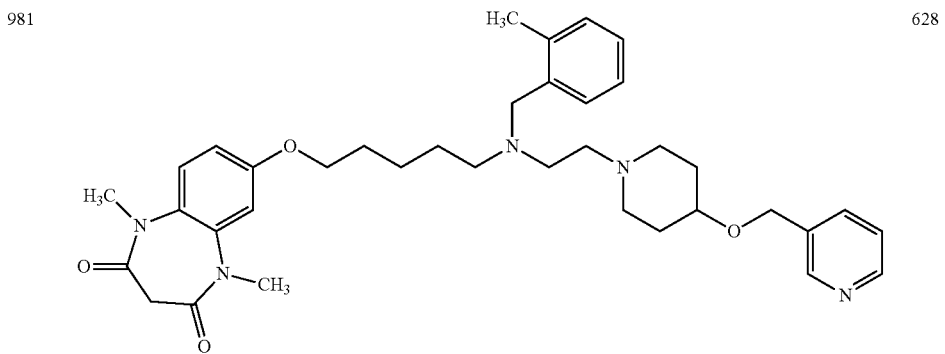 | 628 |

TABLE Z-continued

| Example No. | structure | MS(M + 1) |
| --- | --- | --- |
| 982 | 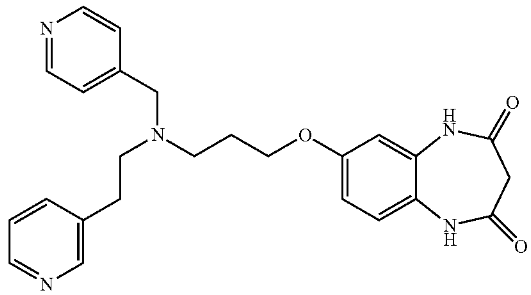 [SMILES: O=C1CC(=O)Nc2cc(OCCCN(CCc3cccnc3)Cc3ccncc3)ccc2N1] | 446 |
| 983 | 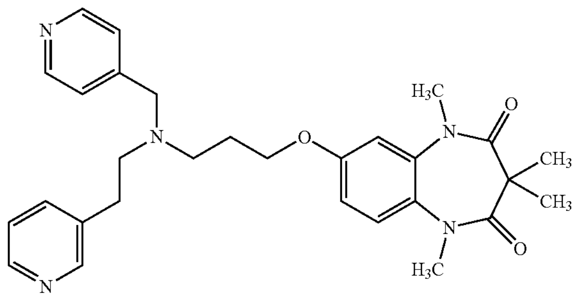 [SMILES: CN1C(=O)C(C)(C)C(=O)N(C)c2cc(OCCCN(CCc3cccnc3)Cc3ccncc3)ccc21] | 502 |
| 984 | 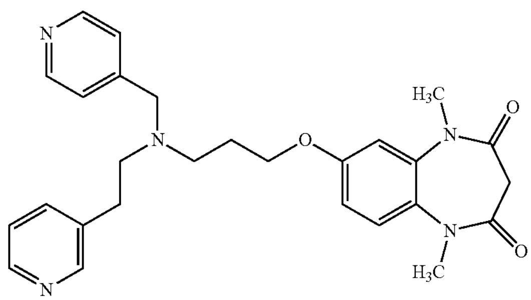 [SMILES: CN1C(=O)CC(=O)N(C)c2cc(OCCCN(CCc3cccnc3)Cc3ccncc3)ccc21] | 474 |
| 985 | 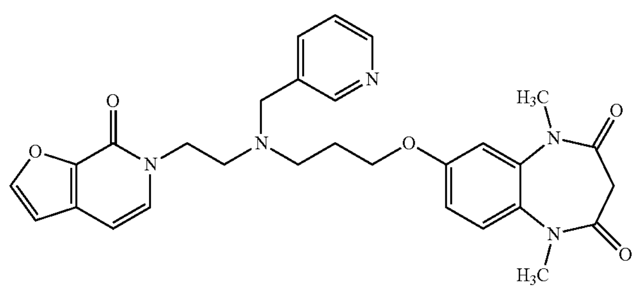 [SMILES: CN1C(=O)CC(=O)N(C)c2cc(OCCCN(CCn3ccc4ccoc4c3=O)Cc3cccnc3)ccc21] | 530 |
| 986 | 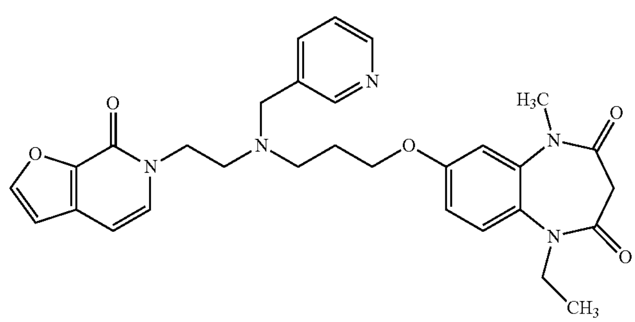 [SMILES: CCN1C(=O)CC(=O)N(C)c2cc(OCCCN(CCn3ccc4ccoc4c3=O)Cc3cccnc3)ccc21] | 544 |

Pharmacological Test 1
(1) Production of Human Kv1.5-expressing CHO-K1 Cell Lines CHO-K1 cell lines stably expressing human Kv1.5 channels were prepared in the following manner.

Full-length human Kv1.5 cDNA was cloned from a human heart cDNA library (produced by Stratagene). The obtained human Kv1.5 sequence corresponds to the sequence described in FASEB J. 5, 331-337 (1991).

The obtained human Kv1.5 cDNA was inserted into a plasmid encoding a CMV promoter and a G418 resistance marker to produce a Kv1.5 expression vector. The human Kv1.5 expression vector was transfected into CHO-K1 cells by the lipofectamine method. After culturing the cells in an F-12 medium (produced by Invitrogen Corp.) containing 10% FBS (produced by Invitrogen Corp.) for 3 or 4 days, the medium was replaced with a FBS-containing F-12 medium that included 1,000 μg/ml of G418 (produced by Invitrogen Corp.), and single colonies were isolated. The amount of Kv1.5 channel expression in the single colonies was quantified at the mRNA level by RT-PCR and then quantified at the protein level by western blotting. Finally, the expressed current was analyzed by patch clamp method. Cell lines expressing a current of 200 pA or more per cell were selected as channel-expressing cell lines for activity measurement by patch clamp method.

(2) Production of CHO Cell Line Expressing Human GIRK1/4

CHO cell lines stably expressing human GIRK1/4 channels were prepared in the following manner.

Full-length human GIRK1 cDNA was cloned from HuH cell- and HeLa cell-derived cDNA libraries. Full-length GIRK4 cDNA was amplified from a human heart cDNA library (produced by Clontech Laboratories, Inc.) by PCR using synthetic primers shown in Table 1, and cloned into the Eco-RI restriction enzyme site of pCR-Blunt (produced by Invitrogen Corporation) or into the HincII site of pUC118 (produced by Takara Bio, Inc.).

TABLE 1

| Primer | Sequence | |
|---|---|---|
| hGIRK1-S | 5'-ATGTCTGCACTCCGAAG GAAATTTG-3' | SEQ ID No. 1 |
| hGIRK1-A | 5'-TTATGTGAAGCGATCAG AGTTC-3' | SEQ ID No. 2 |
| hGIRK1-F2 | 5'-GCAGGGTACCCCTTCGT ATTATGTCTGCACTCC-3' | SEQ ID No. 3 |
| hGIRK1-A3 | 5'-GGTGTCTGCCGAGATTT GA-3' | SEQ ID No. 4 |
| hGIRK1-A4 | 5'-CCGAGTGTAGGCGATCA CCC-3' | SEQ ID No. 5 |
| hGIRK4-S | 5'-ATGGCTGGCGATTCTAG GAATGCC-3' | SEQ ID No. 6 |
| hGIRK4-A | 5'-TCTCACCGAGCCCCTGG CCTCCC-3' | SEQ ID No. 7 |
| hGIRK4-S2 | 5'-AACCAGGACATGGAGAT TGG-3' | SEQ ID No. 8 |
| hGIRK4-A2 | 5'-GAGAACAGGAAAGCGGA CAC-3' | SEQ ID No. 9 |

The obtained human GIRK1 and GIRK4 cDNA sequences correspond to known sequences (NCBI database: GIRK1 (NM_002239) and GIRK4 (NM_000890) respectively). The obtained GIRK1 and GIRK4 cDNA sequences were cloned into the Eco-RI restriction enzyme site of pCR-Blunt (available from Invitrogen Corporation) or into the HincII site of pUC118 (available from Takara Bio, Inc.). A GIRK4 expression vector was constructed by insertion into the BamHI-XhoI site of pcDNA5/FRT. A GIRK1 expression vector was constructed by insertion into the KpnI-XhoI site of pcDNA3.1(+) or pCAG_neo. FLP-IN-CHO cells (produced by Invitrogen Corporation) were transfected with human GIRK1 and GIRK4 expression vectors by using Lipofectamine 2000 (produced by Invitrogen Corporation) according to the protocol enclosed with the reagent or using an electronic induction method ("Nucleofector Kit-T", produced by Amaxa). First, the cells transfected with the GIRK4 expression vector were cultured in a 10% serum-containing F12 medium (produced by Sigma) supplemented with 600 μg/ml of hygromycin in an incubator with 5% carbon dioxide at 37° C. Then the cells expressing GIRK4 were transfected with the GIRK1 expression vector and were cultured in 10% serum-containing F12 medium supplemented with 350 μg/ml of G418 and 600 μg/ml of hygromycin in an incubator with 5% carbon dioxide at 37° C. to select GIRK1/4 expressing cell lines. Cell populations whose growth was observed after about 2 weeks were isolated using cloning rings, and the obtained single colonies were proliferated. RNA was extracted from single colonies, and single-stranded cDNA was synthesized by a cDNA synthesis kit (produced by Invitrogen Corporation), and the amount of expression was quantified at the mRNA level by real-time PCR (Applied Biosystems, Ltd.). Finally, the expressed current was analyzed by patch clamp method described below. The cell lines expressing a current of 500 pA or more per cell were selected as channel-expressing cell lines for activity measurement by patch clamping method.

(3) Measurement of Ion Channel Current by Patch Clamp Method (Human Kv1.5-expressing CHO-K1 Cell Line)

An experiment was carried out using a patch clamp setup at room temperature (20 to 26° C.). A perfusion chamber having a diameter of 20 mm (flow rate: about 5 ml/min) was mounted on the stage of a phase-contrast inverted microscope (produced by Nikon Corporation) placed on a vibration isolated table. A poly-L-lysine (produced by Sigma)-coated coverslip (diameter: 15 mm, produced by Matsunami Glass Ind., Ltd.) on which human Kv1.5-expressing cells were cultured was placed in the perfusion chamber.

Depolarizing stimulation pulses were applied and ionic current was recorded by using a patch clamp amplifier (EPC-7 or EPC-7 PLUS, produced by HEKA) and a personal computer (manufactured by IBM Corp.) in which software for data acquisition and analysis of ion channel current (PULSE 8.77, produced by HEKA) was installed. The current was measured in the whole-cell configuration of the patch-clamp technique. The tip (resistance: 2 to 4 MΩ) of a borosilicate glass pipette (produced by Sutter Instrument Co.) was gently placed on the cell membrane by using a three-dimensional mechanical micromanipulator (produced by Shoshin EM Corporation). Weak suction resulted in giga seal formation (the pipette resistance increased to more than 1 GΩ). Subsequently, stronger suction was applied to break the cell membrane. The capacitative current derived from the cell membrane was corrected using a patch clamp amplifier. Subsequently, the series resistance (Rs) between the pipette and the interior of the cell was measured and corrected.

The composition of the extracellular solution used is shown below. Unless otherwise specified, these components were obtained from Wako Pure Chemical Industries, Ltd.

| | |
|---|---|
| NaCl | 140 mM, |
| KCl | 40 mM, |
| CaCl$_2$ | 1.8 mM, |
| MgCl$_2$ | 1 mM, |
| NaH$_2$PO$_4$ | 0.33 mM, |
| HEPES | 5 mM |
| Glucose | 5.5 mM |
| | (pH = 7.4) |

Each test compound was prepared as a 1000-fold concentrated stock solution that was dissolved in DMSO and then diluted in the extracellular solution.

The composition of the electrode internal solution used is shown below. Unless otherwise specified, these components were obtained from Wako Pure Chemical Industries, Ltd.

| | |
|---|---|
| KOH | 100 mM, |
| KCl | 40 mM, |
| Aspartic acid | 70 mM, |
| MgCl$_2$ | 1 mM, |
| MgATP | 5 mM, |
| K$_2$ creatine phosphate | 5 mM, |
| HEPES | 5 mM |
| EGTA | 5 mM |
| | (pH = 7.2) |

(4) Measurement of Ion Channel Current by Patch Clamp Method (Human GIRK1/4-expressing CHO-K1 Cell Line)

An experiment was carried out using a patch clamp setup at room temperature (20 to 26° C.). A perfusion chamber having a diameter of 20 mm (flow rate: about 5 ml/min) was mounted on the stage of a phase-contrast inverted microscope (produced by Nikon Corporation) placed on a vibration isolation table. A poly-L-lysine (produced by Sigma)-coated coverslip (diameter: 15 mm, produced by Matsunami Glass Ind., Ltd.) on which human GIRK1/4-expressing cells were cultured was placed in the perfusion chamber.

Hyperpolarizing stimulation pulses were applied and ionic current was recorded using a patch clamp amplifier (EPC-7 or EPC-7 PLUS, manufactured by HEKA) and a personal computer (manufactured by IBM Corp.) in which software for data acquisition and analysis of ion channel current (PULSE 8.77, manufactured by HEKA) was installed. The current was measured in the whole-cell configuration of the patch-clamp technique. The tip (resistance: 2 to 4 MΩ) of a borosilicate glass pipette (produced by Sutter Instrument Co.) was gently placed on the cell membrane by using a three-dimensional mechanical micromanipulator (produced by Shoshin EM Corporation). Weak suction resulted in giga seal formation (the pipette resistance increased to more than 1 GΩ). Subsequently, stronger suction was applied to break the cell membrane. The capacitative current derived from the cell membrane was corrected using a patch clamp amplifier. Subsequently, the series resistance (Rs) between the pipette and the interior of the cell was measured and corrected.

The composition of the extracellular solution used is shown below. Unless otherwise specified, these components were obtained from Wako Pure Chemical Industries, Ltd.

| | |
|---|---|
| NaCl | 140 mM, |
| KCl | 4 mM, |
| CaCl$_2$ | 1.8 mM, |
| MgCl$_2$ | 1 mM, |
| NaH$_2$PO$_4$ | 0.33 mM, |
| HEPES | 5 mM |
| Glucose | 5.5 mM |
| | (pH = 7.4) |

Each test compound was prepared as a 1000-fold concentrated stock solution that was dissolved in DMSO and then diluted in the extracellular solution.

The composition of the electrode internal solution used is shown below. Unless otherwise specified, these components were obtained from Wako Pure Chemical Industries, Ltd.

| | |
|---|---|
| KOH | 100 mM, |
| KCl | 40 mM, |
| Aspartic acid | 70 mM, |
| MgCl$_2$ | 1 mM, |
| MgATP | 5 mM, |
| K$_2$ creatine phosphate | 5 mM, |
| HEPES | 5 mM |
| EGTA | 5 mM |
| | (pH = 7.2) |

(5) Measurement of Human Kv1.5 Current

While the membrane potential was held at −80 mV, depolarizing pulses (−80 mV for 0.05 seconds→☐☐+40 mV for 0.2 seconds →☐☐−40 mV for 0.2 seconds→☐☐−80 mV for 0.05 seconds) were applied at a stimulation frequency of 1 Hz to measure Kv1.5 channel current. More specifically, first, while perfusing an extracellular solution containing 0.1% DMSO and holding the membrane potential at −80 mV, depolarizing pulses were applied. The current obtained during the pulse application was recorded as a current in the absence of the test compounds. Subsequently, while perfusing an extracellular solution containing 0.1 μM of a test compound and holding the membrane potential at −80 mV, depolarizing pulses were applied. After the inhibitory effect of the test compound had been stabilized, the current was recorded. The same procedure was repeated using an extracellular solution containing 1 μM of the test compound and then using an extracellular solution containing 10 μM of the test compound. The current obtained using the solution containing the test compound at each concentration was recorded.

The data was analyzed by using the step end current recorded during the +40 mV depolarizing stimulation. The "step end current" refers to the average current flowing for a period of 195 to 199 milliseconds from the start of the +40 mV depolarizing pulse stimulation.

Using the step end current in the presence of the test compound and the step end current in the absence of the test compound, the relative current in the solution containing the test compound at each concentration was calculated according to the following formula:

Relative current=(Step end current in the presence of the test compound)/(Step end current in the absence of the test compound)

(6) Measurement of Human GIRK1/4 Current

While the membrane potential was held at −80 mV, hyperpolarizing pulses (−80 mV for 0.05 seconds→☐☐−120 mV for 0.2 seconds→☐☐−80 mV for 0.05 seconds) were applied at a stimulation frequency of 1 Hz to measure GIRK1/4 channel current. More specifically, first, while perfusing an extracellular solution containing 0.1% DMSO and maintaining the membrane potential at −80 mV, hyperpolarizing pulses were applied. The current obtained during the pulse application was recorded as the current in the absence of the test compounds. Subsequently, while perfusing an extracellular solution containing 0.1 μM of a test compound and maintaining the membrane potential at −80 mV, hyperpolarizing pulses were applied. After the inhibitory effect of the test compound had been stabilized, the current was recorded. The same procedure was repeated using an extracellular solution containing 1 μM of the test compound and then using an extracellular solution containing 10 μM of the test compound. The current obtained using the solution containing the test compound at each concentration were recorded.

The data was analyzed by using the step end current recorded during the −120 mV depolarizing stimulation. The "step end current" refers to the average current flowing for a period of 195 to 199 milliseconds from the start of the −120 mV depolarizing pulse stimulation.

Using the step end current in the presence of the test compound and the step end current in the absence of the test compound, the relative current in the solution containing the test compound at each concentration was calculated according to the following formula:

Relative current=(Step end current in the presence of the test compound)/(Step end current in the absence of the test compound)

(7) Calculation of Inhibitory Activity on Kv1.5 Channel Ionic Current and GIRK1/4 Channel Current The concentration for 50% inhibition of Kv1.5 channel current or GIRK1/4 channel current ($IC_{50}$ value) was calculated according to the following nonlinear regression equation:

Relative current=1/(1+[Concentration of the compound]/$IC_{50}$)$^{nH}$ wherein nH is the Hill coefficient.
Table 2 shows the test results.

TABLE 2

| Test Compound | KV1.5 $IC_{50}$ (μM) |
| --- | --- |
| Compound of Example 14 | 0.23 |
| Compound of Example 18 | 0.39 |
| Compound of Example 24 | 0.32 |
| Compound of Example 26 | 0.30 |
| Compound of Example 34 | 0.33 |
| Compound of Example 38 | 0.38 |
| Compound of Example 40 | 0.86 |
| Compound of Example 42 | 0.77 |
| Compound of Example 46 | 0.42 |
| Compound of Example 62 | 0.12 |

3. Third Invention

REFERENCE EXAMPLE 1

Synthesis of ethyl N-(5-methoxy-2-nitrophenyl)-N-methyl malonamate

Sodium hydride (60% in oil, 96 mg) was suspended in 10 ml of dimethylformamide (DMF). N-Methyl-5-methoxy-2-nitroaniline (364 mg) was added thereto at 0° C., and stirring was conducted at room temperature for 30 minutes. Ethyl malonyl chloride (0.38 ml) was added at 0° C. to the stirred mixture, and the reaction mixture was stirred at room temperature overnight. Water was added thereto, and extraction with ethyl acetate was performed. The organic layer was dried over sodium sulfate, and concentrated under reduced pressure. The residue was purified by silica gel column chromatography (n-hexane:ethyl acetate=2:1→1:2). The purified product was concentrated under reduced pressure to give the title compound(554 mg) as a yellow oil.
$^1$H-NMR (CDCl$_3$) δppm: 1.24 (3H, t, J=7.1 Hz), 3.15-3.17 (2H, m), 3.25 (3H, s), 3.92 (3H, s), 4.13 (2H, q, J=7.1 Hz), 6.93 (1H, d, J=2.8 Hz), 7.02 (1H, dd, J=2.8 and 9.2 Hz), 8.15 (1H, d, J=9.2 Hz).

REFERENCE EXAMPLE 2

Synthesis of ethyl N-(2-amino-5-methoxyphenyl)-N-methyl malonamate

Palladium on carbon (10%, 0.5 g) was added to an ethanol solution (150 ml) of ethyl N-(5-methoxy-2-nitrophenyl)-N-methyl malonamate (3.0 g), and catalytic reduction was conducted at room temperature and normal pressure. The reaction mixture was filtered through Celite to remove the catalyst. The filtrate was concentrated under reduced pressure to give the title compound(2.68 g) as a yellow oil.
$^1$H-NMR (CDCl$_3$) δppm: 1.22 (3H, t, J=7.1 Hz), 3.19-3.27 (5H, m), 3.52-3.68 (2H, br), 3.74 (3H, s), 4.11 (2H, q, J=7.1 Hz), 6.62 (1H, d, J=2.7 Hz), 6.73 (1H, d, J=8.7 Hz), 6.79 (1H, dd, J=2.7 and 8.7 Hz).

REFERENCE EXAMPLE 3

Synthesis of 8-methoxy-1-methyl-1,5-dihydrobenzo [b][1,4]diazepine-2,4-dione

Sodium ethoxide (204 mg) was added to an ethanol solution (15 ml) of ethyl N-(2-amino-5-methoxyphenyl)-N-methyl malonamate (266 mg), and stirred at 65° C. for 2.5 hours. The reaction mixture was cooled to room temperature, and concentrated under reduced pressure. The residue was purified by silica gel column chromatography (dichloromethane:methanol=1:0→10:1). The purified product was concentrated to dryness under reduced pressure to give the title compound(176.3 mg) as a white powder.
$^1$H-NMR (CDCl$_3$) δppm: 3.36 (2H, s), 3.43 (3H, s), 3.84 (3H, s), 6.79-6.83 (1H, m), 7.06-7.09 (1H, m), 8.72 (1H, br-s).

REFERENCE EXAMPLE 4

Synthesis of 1-ethyl-7-methoxy-5-methyl-1,5-dihydrobenzo[b][1,4]diazepine-2,4-dione Sodium hydride (60% in oil, 44 mg) was suspended in dimethylformamide (DMF) (8 ml), and cooled in an ice water bath to 0° C.
8-Methoxy-1-methyl-1,5-dihydrobenzo[b][1,4]diazepine-2,4-dione (220 mg) was added to the suspension at the same temperature, and stirred at 0° C. for 1 hour. Ethyl iodide (187 mg) was added to the mixture and stirred at room temperature overnight. Water was added to the reaction mixture, and extraction with ethyl acetate was performed. The organic layer was dried over sodium sulfate, and concentrated under reduced pressure. The residue was purified by silica gel column chromatography (n-hexane:ethyl acetate=4:1→1:1). The purified product was concentrated to dryness under reduced pressure to give the title compound(190.2 mg) as a yellow solid.
$^1$H-NMR (CDCl$_3$) δppm: 1.11 (3H, t, J=7.1 Hz), 3.31-3.32 (2H, m), 3.40 (3H, s), 3.59-3.68 (1H, m), 3.85 (3H, s), 4.18-4.30 (1H, m), 6.78 (1H, d, J=2.8 Hz), 6.84 (1H, dd, J=9.0 and 2.8 Hz), 7.26 (1H, d, J=9.0 Hz).

REFREENCE EXAMPLE 5

Synthesis of 1-ethyl-7-methoxy-3,3,5-trimethyl-1,5-dihydrobenzo[b][1,4]diazepine-2,4-dione Sodium hydride (60% in oil, 76 mg) was suspended in DMF (8 ml). 1-Ethyl-7-methoxy-5-methyl-1,5-dihydrobenzo[b][1,4]diazepine-2,4-dione (190 mg) was added thereto at 0° C., and stirring was conducted at the same temperature for 1 hour. Methyl iodide (0.19 ml) was added to the mixture, and stirred at room temperature for 3 days. Water was added to the reaction mixture, and extraction with ethyl acetate was performed. The organic layer was dried over sodium sulfate, and concentrated under reduced pressure. The residue was purified by silica gel column chromatography (ethyl acetate). The purified product was concentrated to dryness under reduced pressure to give the title compound (169 mg) as a yellow powder.

$^1$H-NMR (CDCl$_3$) δppm: 0.86 (3H, s), 1.15 (3H, t, J=7.1 Hz), 1.53 (3H, s), 3.40 (3H, s), 3.65-3.76 (1H, m), 3.85 (3H, s), 4.12-4.24 (1H, m), 6.73 (1H, d, J=2.8 Hz), 6.83 (1H, dd, J=9.0 and 2.8 Hz), 7.22 (1H, d, J=9.0 Hz).

REFERENCE EXAMPLE 6

Synthesis of 1-ethyl-7-hydroxy-3,3,5-trimethyl-1,5-dihydrobenzo[b][1,4]diazepine-2,4-dione A 1.0 M boron tribromide/dichloromethane solution (1.22 ml) was added to a dichloromethane solution (3 ml) of 1-ethyl-7-methoxy-3,3,5-trimethyl-1,5-dihydrobenzo[b][1,4]diazepine-2,4-dione (169 mg) at 0° C., and stirred at room temperature overnight. Water and methanol were added to the reaction mixture and extraction with the mixture solvent (dichloromethane:methanol=10:1) was performed. The organic layer was dried over anhydrous sodium sulfate, and concentrated to dryness under reduced pressure to give the title compound(156.4 mg) as a white powder.

$^1$H-NMR (CDCl$_3$) δppm: 0.90 (3H, s), 1.16 (3H, t, J=7.0 Hz), 1.55 (3H, s), 3.41 (3H, s), 3.66-3.78 (1H, m), 4.12-4.23 (1H, m), 6.79 (1H, d, J=2.7 Hz), 6.84 (1H, dd, J=8.8 and 2.7 Hz), 6.88 (1H, d, J=2.7 Hz), 7.18 (1H, d, J=8.8 Hz).

REFERENCE EXAMPLE 7

Synthesis of 7-(3-chloropropoxy)-1-ethyl-3,3,5-trimethyl-1,5-dihydrobenzo[b][1,4]diazepine-2,4-dione 1-Ethyl-7-hydroxy-3,3,5-trimethyl-1,5-dihydrobenzo[b][1,4]diazepine-2,4-dione (1.85 g) and potassium carbonate (1.2 g) were added to 50% water-containing acetonitrile (40 ml), and dissolved by heating to 70° C. 1-Bromo-3-chloropropane (2.1 ml) was added thereto, and heating was conducted under reflux for 6 hours. The reaction mixture was cooled to room temperature. Water was added, and extraction with ethyl acetate was performed. The organic layer was dried over sodium sulfate, and concentrated under reduced pressure. The residue was purified by silica gel column chromatography (n-hexane:ethyl acetate=2:1→1:1). The purified product was concentrated to dryness under reduced pressure to give the title compound(2.18 g) as a colorless oil.

$^1$H-NMR (CDCl$_3$) δppm: 0.86 (3H, s), 1.15 (3H, t, J=7.1 Hz), 1.53 (3H, s), 2.21-2.38 (2H, m), 3.40 (3H, s), 3.63-3.89 (4H, m), 4.10-4.26 (2H, m), 6.74 (1H, d, J=2.8 Hz), 6.83 (1H, dd, J=2.8 and 9.0 Hz), 7.21 (1H, d, J=9.0 Hz).

REFERENCE EXAMPLE 8

Synthesis of 1-ethyl-7-(3-iodopropoxy)-3,3,5-trimethyl-1,5-dihydrobenzo[b][1,4]diazepine-2,4-dione 7-(3-Chloropropoxy)-1-ethyl-3,3,5-trimethyl-1,5-dihydro-benzo[b][1,4]diazepine-2,4-dione (2.18 g) and sodium iodide (4.8 g) were added to acetone (50 ml), and heated under reflux for 8.5 hours. The reaction mixture was cooled to room temperature, water was added, and extraction with ethyl acetate was performed. The organic layer was dried over sodium sulfate, and concentrated under reduced pressure. The residue was purified by silica gel column chromatography (n-hexane:ethyl acetate=1:1). The purified product was concentrated under reduced pressure to give the title compound(2.76 g) as a colorless oil.

$^1$H-NMR (CDCl$_3$) δppm: 0.87 (3H, s), 1.15 (3H, t, J=7.1 Hz), 1.53 (3H, s), 2.26-2.34 (2H, m), 3.39 (2H, t, J=6.6 Hz), 3.65-3.76 (1H, m), 3.41 (3H, s), 4.07 (2H, t, J=5.8 Hz), 4.12-4.24 (1H, m), 6.74 (1H, d, J=2.8 Hz), 6.83 (1H, dd, J=9.0 and 2.8 Hz), 7.22 (1H, d, J=9.0 Hz).

REFERENCE EXAMPLE 9

Synthesis of 3-iodoquinolin-4-ol

Potassium carbonate(5.2 g) was added to a DMF solution (50 ml) of 4-hydroxy quinoline(5.0 g) and the mixture was stirred. Iodine (9.6 g) was added to the mixture, followed by stirring at room temperature for 3 hours. A saturated sodium hydrogencarbonate aqueous solution (73 ml) of 25% sodium sulfite, and water(50 ml) were added to the reaction mixture. The mixture was stirred and the precipitated insoluble matter was separated. The filtrate was washed with water and dried to give the title compound (9.0 g) as a white powder.

mp: 288 to 294° C. (dec.)

REFERENCE EXAMPLE 10

Synthesis of 3-bromoquinolin-4-ol

N-Bromosuccinimide(1.3 g) was added to a DMF solution (15 ml) of 4-hydroxy quinoline(1.0 g) and the mixture was stirred at room temperature for 15 hours. A sodium hydrogencarbonate aqueous solution of 25% sodium sulfite was added to the mixture. The mixture was stirred and the precipitated insoluble matter was separated. The filtrate was dissolved in a mixture of ethyl acetate and methanol, and an insoluble matter was removed by filtration. The filtrate was condensed under reduced pressure, and the residue was washed with ethyl acetate and dried to give the title compound (1.1 g) as a white powder.

mp: 286 to 287° C.

REFERENCE EXAMPLE 11

Synthesis of 3-bromo-1H-quinolin-2-one

Hydrogen peroxide solution(5.9 ml) was added to a THF solution (16 ml) of methyltrioxorhenium (VII) (24 mg). The mixture was stirred for 10 minutes at room temperature. 3-Bromoquinoline(4.0 g) was added thereto, and the mixture was stirred at room temperature for four days. Ethyl acetate (20 ml) was added to the reaction mixture. 20% Sodium sulfite aqueous solution(30 ml) was added slowly to the mixture under ice cooling. The mixture was stirred at room temperature. The organic layer was condensed to a half volume under reduced pressure. Ethyl acetate(20 ml) and 15% potassium carbonate aqueous solution(19 ml) were added thereto, and the organic layer was extracted. 15% Potassium carbonate aqueous solution(19 ml) of p-toluenesulfonyl chloride(4 g) were added thereto. The mixture was stirred for 10 minutes at room temperature. The generated insoluble matter was separated, washed with ethyl acetate, water, and then with ether, and dried to give the title compound(3.2 g) as a white powder.

mp: 263 to 265° C.

REFERENCE EXAMPLE 12

Synthesis of 1-(pyridin-3-yl)-2,3-dihydrobenzoimidazol-2-one

N,N'-Carbonyldiimidazole(0.57 g) was added to a DMF solution (5 ml) of N-pyridine-3-ylbenzene-1,2-diamine(0.5 g). The mixture was stirred at room temperature for 1.5 hours. Water was added to the reaction mixture and the precipitated insoluble matter was separated, washed with water, and dried to give the title compound(0.5 g) as a pale whitish purple powder.

mp: 232 to 233° C. (dec.).

REFERENCE EXAMPLE 13

Synthesis of 5-(2,2-dihydroxyethyl)-2-methyl-5H-furo[3,2-c]pyridin-4-one

Sodium hydride (60% in oil, 0.32 g) was suspended in DMF(10 ml), and was cooled to 0° C. in an ice water bath. 2-Methyl-5H-furo[3,2-c]pyridin-4-one (0.57 g) was added thereto at the same temperature, and the mixture was stirred at 0° C. for an hour. Bromoacetaldehyde dimethylacetal(2.3 ml) was added thereto, and the mixture was stirred at 80° C. for 5 hours. Water was added to the reaction liquid, followed by extraction by ethyl acetate. The organic layer was dried over sodium sulfate, and condensed under reduced pressure. A 3N-hydrochloric acid(2 ml) was added to an acetone solution (10 ml) of the residue, and the liquid was stirred at 70° C. for 10 hours. Water was added to the reaction liquid and stirred at room temperature. The precipitated insoluble matter was separated, washed with water, and dried to give the title compound(0.56 g) as a white solid.

$^1$H-NMR (DMSO-D$_6$), δppm: 2.36 (s, 3H), 3.86 (d, J=5.4 Hz, 2H), 4.94-4.98 (m, 1H), 6.04 (d, J=6.4 Hz, 2H), 6.52 (s, 1H), 6.59 (d, J=7.4 Hz, 1H), 7.41 (d, J=7.4H, 1H).

REFERENCE EXAMPLE 14

Synthesis of 5-(1H-benzoimidazol-2-ylmethyl)-2-methyl-5H-furo[3,2-c]pyridin-4-one 5-(2,2-Dihydroxyethyl)-2-methyl-5H-furo[3,2-c]pyridine-4-one (2.1 g) and o-phenylenediamine(1.1 g) were suspended in ethanol(20 ml). Sodium hydrogensulfite(5.2 g) was added, and the mixture was heated and stirred overnight under reflux. The reaction mixture was cooled to room temperature. Water was added thereto and the precipitated insoluble matter was separated, washed with water, and dried to give the title compound(2.25 g).

$^1$H NMR (CDCl$_3$), δ ppm: 2.36 (3H, s), 5.44 (2H, s), 6.55 (1H, s), 6.73 (1H, d, J=7.4 Hz), 7.05-7.15 (2H, m), 7.43 (1H, d, J=7.0 Hz), 7.50 (1H, d, J=8.3 Hz), 7.70 (1H, d, J=7.4 Hz).

REFERENCE EXAMPLE 15

Synthesis of 3-(pyridin-3-yl)-1H-quinolin-4-one

2N Hydrochloric acid(10 ml) was added to a DMF solution(5 ml) of 4-chloro-(3-pyridin-3-yl)quinoline(0.51 g), and the mixture was stirred at 80° C. for 1 hour. After the reaction mixture was cooled to room temperature, 2N sodium hydroxide aqueous solution(10 ml) was added dropwise under ice cooling. The mixture was stirred. The precipitated insoluble matter was separated, washed with water and ether, and dried to give the title compound(0.35 g) as a pale whitish purple powder.

mp: 240 to 242° C. (dec.)

REFERENCE EXAMPLE 16

Synthesis of 5-[{1-(3-chloropropyl)-1H-benzoimidazol-2-yl}methyl]-2-methyl-5H-furo[3,2-c]pyridin-4-one 5-(1H-Benzimidazol-2-ylmethyl)-2-methyl-5H-furo[3,2-c]pyridine-4-one(0.75 g), 1-bromo-3-chloropropane(1.3 ml), and potassium carbonate(0.95 g) were added to 50% hydrous acetonitrile(16 ml). The mixture was heated overnight under reflux. The reaction mixture was cooled to room temperature. Water was added thereto, followed by extraction by ethyl acetate. The organic layer was dried over sodium sulfate, and condensed under reduced pressure. The residue was purified by silica gel column chromatography (hexane: ethyl acetate=1:1→0:1). The purified product was condensed to dryness under reduced pressure to give the title compound (0.18 g) as a colorless oily matter.

$^1$H NMR (CDCl$_3$), δ ppm: 2.02-2.09 (2H, m), 2.41 (3H, s), 3.54 (2H, t, J=6.1 Hz), 4.55-4.61 (2H, m), 5.56 (2H, s), 6.51-6.53 (2H, m), 7.24-7.32 (2H, m), 7.40-7.46 (1H, m), 7.54 (1H, d, J=5.9 Hz), 7.73-7.79 (1H, m).

REFERENCE EXAMPLE 17

Synthesis of 5-(3-chloropropyl)-2-methyl-5H-furo[3,2-c]pyridin-4-one

Methane sulfonyl chloride(0.24 ml) was added to a dichloromethane solution(10 ml) of 5-(3-hydroxypropyl)-2-methyl-5H-furo[3,2-c]pyridine-4-one (0.28 g) and triethylamine(0.45 ml). The mixture was stirred at room temperature for two days. The reaction liquid was condensed under reduced pressure. The residue was purified by silica gel column chromatography (ethyl acetate: hexane=1:4→1:1). The purified product was condensed to dryness under reduced pressure to give the title compound(0.16 g) as a white amorphous solid.

$^1$H NMR (CDCl$_3$), δ ppm: 2.25-2.41 (2H, m), 2.41 (3H, s), 3.56 (2H, t, J=6.1 Hz), 4.18 (2H, t, 6.6 Hz), 6.48 (1H, d, J=7.4 Hz), 6.55 (1H, s), 7.17 (1H, d, J=7.4 Hz).

REFERENCE EXAMPLE 18

Synthesis of 7-(2-chloroethoxy)-1-ethyl-3,3,5-trimethyl-1,5-dihydrobenzo[b][1,4]diazepine-2,4-dione 1-Ethyl-7-hydroxy-3,3,5-trimethyl-1,5-dihydrobenzo[b][1,4]diazepine-2,4-dione(1.2 g) and potassium carbonate (0.95 g) were added to 50% hydrous acetonitrile(24 ml). The mixture was heated to 70° C. to be dissolved. 1-Bromo-2-chloroethane(1.9 ml) was added, and the mixture was heated under reflux for 7 hours. The reaction mixture was cooled to room temperature. Water was added thereto, followed by extraction by ethyl acetate. The organic layer was dried by sodium sulfate, and condensed under reduced pressure. The residue was purified by silica gel column chromatography (hexane: ethyl acetate=2:1→1:1). The purified product was condensed to dryness under reduced pressure to give the title compound(1.4 g) as a colorless oily matter.

$^1$H NMR (CDCl$_3$), δ ppm: 0.86 (3H, s), 1.15 (3H, t, J=7.1 Hz), 1.53 (3H, s), 3.40 (3H, s), 3.64-3.77 (1H, m), 3.85 (2H, t, J=5.7 Hz), 4.03-4.15 (1H, m), 4.26 (2H, t, J=5.7 Hz), 6.77 (1H, d, J=2.8 Hz), 6.83 (1H, dd, J=9.0, 2.8 Hz), 7.23 (1H, d, J=9.0 Hz).

REFERENCE EXAMPLE 19

Synthesis of 7-[3-(3-aminopyridin-4-ylamino)propoxy]-1-ethyl-3,3,5-trimethyl-1,5-dihydrobenzo[b][1,4]diazepine-2,4-dione 10% Palladium on carbon(0.7 g) was added to a methanol solution (30 ml) of 1-ethyl-3,3,5-trimethyl-7-[3-(3-nitropyridin-4-ylamino)propoxy]-1,5-dihydrobenzo[b][1,4]diazepine-2,4-dione(1.8 g). The mixture was subjected to catalytic reduction at room temperature under normal pressure. The reaction mixture was subjected to celite filtration to remove the catalyst. The filtrate was condensed under reduced pressure to give the title compound(1.4 g) as an orange amorphous solid.

$^1$H NMR (CDCl$_3$), δ ppm: 0.86 (3H, s), 1.14 (3H, t, J=7.1 Hz), 1.53 (3H, s), 2.12-2.24 (2H, m), 3.40 (3H, m), 3.40-3.52 (2H, m), 3.63-3.74 (1H, m), 4.03-4.14 (3H, m), 6.51 (1H, d, J=5.4 Hz), 6.75-6.76 (1H, m), 6.84 (1H, dd, J=9.0, 2.8 Hz), 7.22 (1H, d, J=9.0 Hz), 7.93 (1H, s), 7.98 (1H, d, J=5.4 Hz).

EXAMPLE 1

Synthesis of 1-ethyl-3,3,5-trimethyl-7-[3-(2-phenylpiperidin-1-yl)propoxy]-1,5-dihydrobenzo[b][1,4]diazepine-2,4-dione hydrochloride Potassium carbonate(0.54 g), sodium iodide(0.21 g), and 2-phenyl piperidine(0.23 g) were added to a DMF solution(15 ml) of 7-(3-chloropropoxy)-1-ethyl-3,3,5-trimethyl-1,5-dihydrobenzo[b][1,4]diazepine-2,4-dione(0.44 g). The mixture was stirred at 70° C. for 5 hours. The reaction mixture was cooled to room temperature. Water was added thereto, followed by extraction by ethyl acetate. The organic layer was washed with water and then with saturated saline, and dried with anhydrous magnesium sulfate. After condensation under reduced pressure, the residue was purified by silica gel column chromatography (hexane: ethyl acetate=2:1→1:1). The purified product was condensed under reduced pressure. A 4N-Hydrogen chloride ethyl acetate solution(0.2 ml) was added to an ethyl acetate solution (10 ml) of the residue, which was stirred at room temperature. The liquid was condensed to dryness under reduced pressure to give the title compound(0.18 g) as a white amorphous solid.

$^1$H NMR (CDCl$_3$), δ ppm: 0.82(3H, s), 1.12 (3H, t, J=7.0 Hz), 1.51 (3H, s), 1.89-3.22(11H, m), 3.36(3H, s), 3.62-3.97 (5H, m), 4.09-4.18 (1H, m), 6.53-6.54 (1H, m), 6.62-6.67 (1H, m), 7.16 (1H, d, J=9.0 Hz), 7.36-7.47 (3H, m), 7.61-7.90 (2H, m), 12.40 (1H, brs).

EXAMPLE 2

Synthesis of 7-[3-((R)-2,4-dibenzylpiperazin-1-yl)propoxy]-1-ethyl-3,3,5-trimethyl-1,5-dihydrobenzo[b][1,4]diazepine-2,4-dione dihydrochloride The synthesis of the title compound was performed in the same manner as in Example 1 using appropriate starting materials.

$^1$H NMR (DMSO-d$_6$), δ ppm: 0.75(3H, s), 1.01 (3H, t, J=6.8 Hz), 1.33 (3H, s), 2.15-2.40(2H, m), 2.83-3.90 (13H, m), 3.97-4.61 (7H, m), 6.96-7.01 (2H, m), 7.28-7.44 (9H, m), 7.59 (2H, br).

EXAMPLE 3

Synthesis of 1-ethyl-3,3,5-trimethyl-7-{3-[2-(2-methyl-4-oxo-4H-furo[3,2-c]pyridin-5-ylmethyl)benzimidazol-1-yl]propoxy}-1,5-dihydrobenzo[b][1,4]diazepine-2,4-dione 5-(1H-Benzimidazol-2-ylmethyl)-2-methyl-5H-furo[3,2-c]pyridine-4-one(0.28 g) and potassium carbonate(0.9 g) were added to a DMF solution(2 ml) of 1-ethyl-7-(3-iodopropoxy)-3,3,5-trimethyl-1,5-dihydrobenzo[b][1,4]diazepine-2,4-dione (0.43 g). The mixture was stirred at 60° C. overnight. After the reaction liquid was condensed under reduced pressure, the residue was purified by silica gel column chromatography (ethyl acetate: methanol=20:1→4:1). The purified product was condensed to dryness under reduced pressure to give the title compound(0.43 g) as a white amorphous solid.

$^1$H NMR (CDCl$_3$), δ ppm: 0.85 (3H, s), 1.15 (3H, t, J=7.1 Hz), 1.53 (3H, s), 2.12-2.23 (2H, m), 2.40 (3H, s), 3.38 (3H, s), 3.61-3.72 (1H, m), 3.95 (2H, t, J=5.7 Hz), 4.05-4.15 (1H, m), 4.65 (2H, t, J=6.5 Hz), 5.53 (2H, s), 6.49-6.55 (2H, m), 6.70-6.71 (1H, m), 6.74-6.80 (1H, m), 7.19 (1H, d, J=9.0 Hz), 7.24-7.27 (2H, m), 7.33-7.38 (1H, m), 7.54 (1H, d, J=7.5 Hz), 7.75-7.79 (1H, m).

EXAMPLE 4

Synthesis of 1-ethyl-3,3,5-trimethyl-7-{2-[2-(2-methyl-4-oxo-4H-furo[3,2-c]pyridin-5-ylmethyl)benzimidazol-1-yl]ethoxy}-1,5-dihydrobenzo[b][1,4]diazepine-2,4-dione Potassium carbonate(0.58 g), sodium iodide(0.21 g), and 5-(1H-benzimidazol-2-ylmethyl)-2-methyl-5H-furo[3,2-c]pyridine-4-one(0.39 g) were added to a DMF solution(30 ml) of 7-(2-chloroethoxy)-1-ethyl-3,3,5-trimethyl-1,5-dihydrobenzo[b][1,4]diazepine-2,4-dione(0.47 g). The mixture was stirred at 65° C. overnight. The mixture was further stirred at 100° C. overnight. After the reaction mixture was condensed under reduced pressure, the residue was purified by silica gel column chromatography (ethyl acetate: methanol=95:5→85:15). The purified product was condensed to dryness under reduced pressure to give the title compound (0.44 g) as a white amorphous solid.

$^1$H NMR (CDCl$_3$), δ ppm: 0.77 (3H, s), 1.09 (3H, t, J=7.1 Hz), 1.49 (3H, s), 2.40 (3H, s), 3.26 (3H, s), 3.61-3.74 (1H, m), 4.05-4.18 (1H, m), 4.24 (2H, t, J=5.0 Hz), 4.93 (2H, t, J=5.0 Hz), 5.55-5.66 (2H, m), 6.44-6.45 (1H, m), 6.51-6.54 (2H, m), 6.57-6.64 (1H, m), 7.00 (1H, d, J=9.0 Hz), 7.25-7.36 (2H, m), 7.58-7.62 (1H, m), 7.63 (1H, d, 7.6 Hz), 7.77-7.80 (1H, m).

EXAMPLE 5

Synthesis of 1-ethyl-3,3,5-trimethyl-7-[3-(2-phenylbenzoimidazol-1-yl)propoxy]-1,5-dihydrobenzo[b][1,4]diazepine-2,4-dione hydrochloride 2-Phenyl-1H-benzimidazole(0.2 g) and potassium carbonate(0.29 g) were added to a DMF solution(5 ml) of 1-ethyl-7-(3-iodopropoxy)-3,3,5-trimethyl-1,5-dihydrobenzo[b][1, 4]diazepine-2,4-dione(0.49 g). The mixture was stirred at 60° C. for 7 hours. The reaction mixture was poured to ice water (50 ml), and the generated insoluble matter was separated. The insoluble matter was dissolved in ethyl acetate. The liquid was dried over sodium sulfate and condensed under reduced pressure. The residue was purified by silica gel column chromatography (hexane: ethyl acetate=1:3). The purified product was condensed under reduced pressure. A 1N-hydrogen chloride ethanol solution(1.0 ml) was added to an isopropyl alcohol solution of the residue. The mixture was condensed under reduced pressure. Ether was added to the residue. The generated insoluble matter was separated by filtration and dried to give the title compound(0.32 g) as a white powder.

mp: 132 to 134° C.

EXAMPLE 6

Synthesis of 7-[3-(4-chloro-2-oxo-3-phenyl-2H-quinolin-1-yl)propoxy]-1-ethyl-3,3,5-trimethyl-1,5-dihydrobenzo[b][1,4]diazepine-2,4-dione 4-Chloro-3-phenyl-1H-quinoline-2-one(0.3 g) was suspended in DMF(6 ml). Sodium hydride (60% in oil) (51 mg) was added, and the mixture was stirred for 15 minutes at room temperature. 1-Ethyl-7-(3-iodopropoxy)-3,3,5-trimethyl-1,5-dihydrobenzo[b][1,4]diazepine-2,4-dione(0.55 g) was added thereto and the mixture was stirred at room temperature for 7 days. The reaction mixture was poured to ice water(50 ml), and the generated insoluble matter was separated. The insoluble matter was dissolved in ethyl acetate. The liquid was dried over sodium sulfate and condensed under reduced pressure. The residue was purified by silica gel column chromatography (hexane: ethyl acetate=1:1→1:3). The purified product was condensed under reduced pressure, and the residue was recrystallized from ether, thereby obtaining the title compound(0.28 g) as a white powder.

mp: 122 to 128° C.

EXAMPLE 7

Synthesis of 1-ethyl-3,3,5-trimethyl-7-{3-[2-(2-methyl-4-oxo-4H-furo[3,2-c]pyridin-5-ylmethyl)imidazo[4,5-c]pyridin-1-yl]propoxy}-1,5-dihydrobenzo[b][1,4]diazepine-2,4-dione dihydrochloride A DMF solution(4 ml) of 5-(2,2-dihydroxyethyl)-2-methyl-5H-furo[3,2-c]pyridine-4-one(0.20 g), 7-[3-(3-aminopyridin-4-ylamino)propoxy]-1-ethyl-3,3,5-trimethyl-1,5-dihydrobenzo[b][1,4]diazepine-2,4-dione(0.37 g), and sodium hydrogensulfite(0.47 g) were heated at 180° C. for 10 minutes (microwave reactor). After the reaction liquid was condensed under reduced pressure, the residue was purified by silica gel column chromatography (ethyl acetate: methanol=95:5→60:40). The purified product was condensed under reduced pressure. A 4N-hydrogen chloride ethyl acetate solution was added to an ethyl acetate solution of the residue, which was stirred at room temperature. The generated insoluble matter was separated by filtration, and dried to give the title compound(0.47 g) as a white amorphous solid.

$^1$H NMR (DMSO-$d_6$), δ ppm: 0.70 (3H, s), 0.95 (3H, t, J=7.1 Hz), 1.30 (3H, s), 2.31-2.41 (2H, m), 2.40 (3H, s), 3.29 (3H, s), 3.60-3.70 (1H, m), 3.98-4.09 (1H, m), 4.16 (2H, t, J=6.0 Hz), 4.79 (2H, t, J=6.6 Hz), 5.67 (2H, s), 6.54 (1H, s), 6.80-6.85 (3H, m), 7.33 (1H, d, J=6.5 Hz), 7.76 (1H, d, J=7.5 Hz), 8.33 (1H, d, J=6.5 Hz), 8.60 (1H, d, J=6.5 Hz), 9.36 (1H, s).

EXAMPLE 8

Synthesis of 7-[3-(3-bromo-2-oxo-2H-quinolin-1-yl)propoxy]-1-ethyl-3,3,5-trimethyl-1,5-dihydrobenzo[b][1,4]diazepine-2,4-dione Under ice cooling, sodium hydride (60% in oil, 0.2 g) was added to a DMF solution(10 ml) of 3-bromo-1H-quinoline-2-one(1.0 g). The mixture was stirred at the same temperature for 15 minutes. Lithium bromide(0.76 g) was added to the mixture, and the liquid was stirred at the same temperature for another 15 minutes, and then at room temperature for an hour. The reaction mixture was cooled to 0° C., and 1-ethyl-7-(3-iodopropoxy)-3,3,5-trimethyl-1,5-dihydrobenzo[b][1,4]diazepine-2,4-dione(2.1 g) was added thereto. The mixture was stirred at room temperature for 2 hours, and at 50° C. for 8 hours. The reaction mixture was poured to ice water, and the generated insoluble matter was separated. The insoluble matter was dissolved in a mixed solvent of ethyl acetate and dichloromethane. The liquid was dried with sodium sulfate and condensed under reduced pressure. Ethyl acetate was added to the residue. The generated insoluble matter was separated and dried to give the title compound(1.2 g) as a white powder.

mp: 168 to 169° C.

EXAMPLE 9

Synthesis of 1-ethyl-3,3,5-trimethyl-7-[3-(2-oxo-2H-quinolin-1-yl)propoxy]-1,5-dihydrobenzo[b][1,4]diazepine-2,4-dione The synthesis of the title compound was performed in the same manner as in Example 8 using appropriate starting materials.

White Powder mp: 134 to 135° C.

EXAMPLE 10

Synthesis of 1-ethyl-7-[3-(3-iodo-4-oxo-4H-quinolin-1-yl)propoxy]-3,3,5-trimethyl-1,5-dihydrobenzo[b][1,4]diazepine-2,4-dione The synthesis of the title compound was performed in the same manner as in Example 8 using appropriate starting materials.

White Powder mp: 97 to 106° C.

EXAMPLE 11

Synthesis of 1-ethyl-3,3,5-trimethyl-7-[3-(4-oxo-3-(pyridin-3-yl)-4H-quinolin-1-yl)propoxy]-1,5-dihydrobenzo[b][1,4]diazepine-2,4-dione The synthesis of the title compound was performed in the same manner as in Example 8 using appropriate starting materials.

White Powder mp: 199 to 201° C.

EXAMPLE 12

Synthesis of 1-ethyl-3,3,5-trimethyl-7-[3-(4-oxo-4H-quinolin-1-yl)propoxy]-1,5-dihydrobenzo[b][1,4]diazepine-2,4-dione The synthesis of the title compound was performed in the same manner as in Example 8 using appropriate starting materials.
White Powder
mp: 174 to 177° C.

EXAMPLE 13

Synthesis of 7-[3-(3-bromo-4-oxo-4H-quinolin-1-yl)propoxy]-1-ethyl-3,3,5-trimethyl-1,5-dihydrobenzo[b][1,4]diazepine-2,4-dione The synthesis of the title compound was performed in the same manner as in Example 8 using appropriate starting materials.
White Powder
mp: 180 to 183° C.

EXAMPLE 14

Synthesis of 1-ethyl-3,3,5-trimethyl-7-[3-(2-oxo-3-phenyl-2,3-dihydrobenzimidazol-1-yl)propoxy]-1,5-dihydrobenzo[b][1,4]diazepine-2,4-dione The synthesis of the title compound was performed in the same manner as in Example 6 using appropriate starting materials.
$^1$H NMR (CDCl$_3$), δ ppm: 0.84(3H, s), 1.14 (3H, t, J=7.1 Hz), 1.52 (3H, s), 2.27-2.41 (2H, m), 3.36(3H, s), 3.6-3.78 (1H, m), 4.09(2H, t, J=5.9 Hz), 4.11-4.26 (1H, m), 4.20(2H, t, J=6.6 Hz), 6.68 (1H, d, J=2.8 Hz), 6.80 (1H, dd, J=2.8, 9.0 Hz), 6.99-7.14 (4H, m), 7.19 (1H, d, J=9.0 Hz), 7.33-7.47 (1H, m), 7.47-7.58 (4H, m).

EXAMPLE 15

Synthesis of 1-ethyl-7-[3-(3-hydroxy-2-oxo-3-phenyl-2,3-dihydroindol-1-yl)propoxy]-3,3,5-trimethyl-1,5-dihydrobenzo[b][1,4]diazepine-2,4-dione The synthesis of the title compound was performed in the same manner as in Example 6 using appropriate starting materials.
White Powder
mp: 153 to 156° C.

EXAMPLE 16

Synthesis of 1-ethyl-3,3,5-trimethyl-7-[3-(2-oxo-3-(pyridin-3-yl)-2,3-dihydrobenzimidazol-1-yl)propoxy]-1,5-dihydrobenzo[b][1,4]diazepine-2,4-dione hydrochloride 1-(Pyridin-3-yl)-1,3-dihydrobenzimidazole-2-one(0.2 g) was suspended in DMF(6 ml). Sodium hydride (55% in oil, 48 mg) was added under ice cooling, and the mixture was stirred at room temperature for 30 minutes. 1-Ethyl-7-(3-iodopropoxy)-3,3,5-trimethyl-1,5-dihydrobenzo[b][1,4]diazepine-2,4-dione(0.45 g) was added to the mixture. The mixture was stirred at room temperature for 3 hours. The reaction mixture was poured to ice water(100 ml), followed by extraction with ethyl acetate. The organic layer was dried over sodium sulfate and condensed under reduced pressure. The residue was purified by silica gel column chromatography (ethyl acetate). The purified product was condensed under reduced pressure. A 0.5N-hydrogen chloride ethanol solution(1.9 ml) was added to an isopropyl alcohol solution of the residue. The mixture was condensed under reduced pressure. Ether was added to the residue. The generated insoluble matter was separated by filtration and dried to give the title compound(0.38 g) as a white powder.
White Powder
mp: 119 to 125° C.

EXAMPLE 17

Synthesis of 1-ethyl-3,3,5-trimethyl-7-[3-(2'-oxospiro[[1,3]dioxolane-2,3'-indoline]-1'-yl)propoxy]-1,5-dihydrobenzo[b][1,4]diazepine-2,4-dione The synthesis of the title compound was performed in the same manner as in Example 6 using appropriate starting materials.
White Powder
mp: 143 to 147° C.

EXAMPLE 18

Synthesis of 1-ethyl-3,3,5-trimethyl-7-[3-(2-phenylindol-1-yl)propoxy]-1,5-dihydrobenzo[b][1,4]diazepine-2,4-dione The synthesis of the title compound was performed in the same manner as in Example 6 using appropriate starting materials.
White Powder
mp: 140 to 142° C.

EXAMPLE 19

Synthesis of 1-ethyl-3,3,5-trimethyl-7-[3-(2-oxo-3-phenyl-2H-quinolin-1-yl)propoxy]-1,5-dihydrobenzo[b][1,4]diazepine-2,4-dione 7-[3-(3-Bromo-2-oxo-2H-quinolin-1-yl)propoxy]-1-ethyl-3,3,5-trimethyl-1,5-dihydrobenzo[b][1,4]diazepine-2,4-dione(0.5 g), phenylboronic acid(0.12 g), tetrakis(triphenyl phosphine)palladium (0) (0.11 g), and potassium carbonate (0.39 g) were added to dioxane(5 ml). The mixture was heated under reflux for 2 hours under nitrogen atmosphere. The reaction mixture was cooled to room temperature. Water was added thereto, followed by extraction by ethyl acetate. The organic layer was dried over sodium sulfate, and condensed under reduced pressure. The residue was purified by silica gel column chromatography (ethyl acetate: hexane=1:1→3:1). The purified product was condensed to dryness under reduced pressure, thereby obtaining the title compound(0.34 g) as a white amorphous solid.
$^1$H NMR (CDCl$_3$), δ ppm: 0.84(3H, s), 1.14 (3H, t, J=7.1 Hz), 1.52 (3H, s), 2.27-2.42(2H, m), 3.37(3H, s), 3.62-3.80 (1H, m), 4.05-4.28 (3H, m), 4.62(2H, t, J=7.2 Hz), 6.72 (1H, d, J=2.7 Hz), 6.83 (1H, dd, J=2.7, 9.0 Hz), 7.19 (1H, d, J=9.0

Hz), 7.20-7.30 (1H, m), 7.32-7.58 (5H, m), 7.60-7.67 (1H, m), 7.67-7.74 (2H, m), 7.84(1H, s).

EXAMPLE 20

Synthesis of 1-ethyl-3,3,5-trimethyl-7-[3-(4-oxo-3-phenyl-4H-quinolin-1-yl)propoxy]-1,5-dihydrobenzo[b][1,4]diazepine-2,4-dione The synthesis of the title compound was performed in the same manner as in Example 19 using appropriate starting materials.
White Powder
mp: 150 to 152° C.

EXAMPLE 21

Synthesis of 1-ethyl-7-{3-[3-(6-methoxypyridin-3-yl)-4-oxo-4H-quinolin-1-yl]propoxy}-3,3,5-trimethyl-1,5-dihydrobenzo[b][1,4]diazepine-2,4-dione The synthesis of the title compound was performed in the same manner as in Example 19 using appropriate starting materials.
White Powder
mp: 159 to 161° C.

EXAMPLE 22

Synthesis of 1-ethyl-7-{3-[3-(6-methoxypyridin-3-yl)-4-oxo-4H-quinoline-1-yl]propoxy}-3,3,5-trimethyl-1,5-dihydrobenzo[b][1,4]diazepine-2,4-dione mesylate Methanesulfonic acid(0.024 ml) was added to an ethyl acetate/isopropyl alcohol solution(1:1, 8 ml) of 1-ethyl-7-{3-[3-(6-methoxypyridin-3-yl)-4-oxo-4H-quinoline-1-yl]propoxy}-3,3,5-trimethyl-1,5-dihydrobenzo[b][1,4]diazepine-2,4-dione(0.2 g) at 0° C., which was stirred at the same temperature for 2 hours. The precipitated insoluble matter was separated, washed with isopropyl alcohol, and dried to give the title compound(0.19 g) as a white powder.
White Powder
mp: 188 to 189° C.

EXAMPLE 23

Synthesis of 1-ethyl-3,3,5-trimethyl-7-[3-(2-oxo-3-phenyl-3,4-dihydro-2H-quinolin-1-yl)propoxy]-1,5-dihydrobenzo[b][1,4]diazepine-2,4-dione 10% Palladium on carbon(20 mg) was added to an ethanol/ethyl acetate solution (1:1, 4 ml) of 7-[3-(4-chloro-2-oxo-3-phenyl-2H-quinoline-1-yl)propoxy]-1-ethyl-3,3,5-trimethyl-1,5-dihydrobenzo[b][1,4]diazepine-2,4-dione(0.19 g). The mixture was subjected to catalytic reduction at 50° C. under normal pressure for 6 hours. The reaction mixture was subjected to celite filtration to remove the catalyst. The filtrate was condensed under reduced pressure. The residue was purified by silica gel column chromatography (hexane: ethyl acetate=1:1). The purified product was condensed under reduced pressure, and the residue was recrystallized from ether/hexane, thereby obtaining the title compound(0.1 g) as a white powder.
mp: 100 to 105° C.

EXAMPLE 24

Synthesis of 7-[3-(2,3-dioxo-2,3-dihydroindol-1-yl)propoxy]-1-ethyl-3,3,5-trimethyl-1,5-dihydrobenzo[b][1,4]diazepine-2,4-dione The synthesis of the title compound was performed in the same manner as in Example 6 using appropriate starting materials.
Orange Powder
mp: 162 to 163° C.

EXAMPLE 25

Synthesis of 1-ethyl-3,3,5-trimethyl-7-[3-(2-oxo-2,3-dihydroindol-1-yl)propoxy]-1,5-dihydrobenzo[b][1,4]diazepine-2,4-dione 7-[3-(2,3-Dioxo-2,3-dihydroindol-1-yl)propoxy]-1-ethyl-3,3,5-trimethyl-1,5-dihydrobenzo[b][1,4]diazepine-2,4-dione(0.3 g) was suspended in hydrazine hydrate(3 ml), and the liquid was stirred for two hours while heated under reflux. The reaction mixture was cooled to room temperature. Water was added thereto, followed by extraction by ethyl acetate. The organic layer was dried by anhydrous sodium sulfate, and condensed under reduced pressure. The residue was purified by silica gel column chromatography (ethyl acetate: hexane=85:15). The purified product was condensed under reduced pressure, and the residue was recrystallized from ether/hexane, thereby obtaining the title compound(0.18 g) as a pale brownish white powder.
mp: 146 to 149° C.

EXAMPLE 26

Synthesis of 1-ethyl-3,3,5-trimethyl-7-(3-((3-(1-oxoisoquinolin-2(2H)-yl)propyl)(pyridin-4-ylmethyl)amino)propoxy)-1H-benzo[b][1,4]diazepine-2,4(3H,5H)-dione The synthesis of the title compound was performed in the same manner as in Example 6 using appropriate starting materials.
$^{1}$H-NMR (CDCl$_3$) δppm: 0.84 (s, 3H), 1.14 (t, J=7.1 Hz, 3H), 1.51 (s, 3H), 1.90-2.00 (m, 4H), 2.58 (t, J=6.8 Hz, 2H), 2.68 (t, J=6.8 Hz, 2H), 3.38 (s, 3H), 3.61 (s, 2H), 3.62-3.72 (m, 1H), 3.95-4.00 (m, 4H), 4.08-4.22 (m, 1H), 6.44 (d, J=7.3 Hz, 1H), 6.68 (d, J=2.7 Hz, 1H), 6.75 (dd, J=9.0 and 2.7 Hz, 1H), 6.95 (d, J=7.3 Hz, 1H), 7.17 (d, J=9.0 Hz, 1H), 7.25-7.27 (m, 2H), 7.45-7.52 (m, 2H), 7.60-7.70 (m, 1H), 8.40 (d, J=7.9 Hz, 1H), 8.48 (d, J=1.5 Hz, 2H).

EXAMPLE 27

Synthesis of 1-ethyl-3,3,5-trimethyl-7-(3-((3-(1-oxoisoquinolin-2(2H)-yl)propyl)(pyridin-4-ylmethyl)amino)propoxy)-1H-benzo[b][1,4]diazepine-2,4(3H,5H)-dione dihydrochloride A 4N-hydrogen chloride in ethyl acetate solution(0.3 ml) was added to an ethyl acetate solution (3 ml) of 1-ethyl-3,3,5-trimethyl-7-(3-((3-(1-oxoisoquinolin-2(2H)-yl)propyl)(pyridin-4-ylmethyl)amino)propoxy)-1H-benzo[b][1,4]diazepine-2,4(3H,5H)-dione (159 mg), and the mixture was stirred at room temperature for two hours. The reaction mixture was condensed under reduced pressure to give the title compound(178 mg) as a amorphous solid.

$^1$H-NMR (DMSO-$d_6$) δppm: 0.74 (s, 3H), 1.00 (t, J=7.0 Hz, 3H), 1.32 (s, 3H), 2.25 (br, 4H), 3.01-3.31 (m, 4H), 3.31 (s, 3H), 3.61-3.70 (m, 1H), 4.00-4.12 (m, 5H), 4.61 (br, 2H), 6.65 (d, J=7.4 Hz, 1H), 6.86-6.91 (m, 2H), 7.39 (d, J=8.9 Hz, 1H), 7.47-7.53 (m, 2H), 7.65-7.74 (m, 2H), 8.08 (br, 2H), 8.21 (d, J=8.0 Hz, 1H), 8.80 (br, 2H).

Pharmacological Test 1

(1) Production of Human Kv1.5-expressing CHO-K1 Cell Lines

CHO-K1 cell lines stably expressing human Kv1.5 channels were prepared in the following manner.

Full-length human Kv1.5 cDNA was cloned from a human heart cDNA library (produced by Stratagene). The obtained human Kv1.5 sequence corresponds to the sequence described in FASEB J. 5, 331-337 (1991).

The obtained human Kv1.5 cDNA was inserted into a plasmid encoding a CMV promoter and a G418 resistance marker to produce a Kv1.5 expression vector. The human Kv1.5 expression vector was transfected into CHO-K1 cells by the lipofectamine method. After culturing the cells in an F-12 medium (produced by Invitrogen Corp.) containing 10% FBS (produced by Invitrogen Corp.) for 3 or 4 days, the medium was replaced with a FBS-containing F-12 medium that included 1,000 μg/ml of G418 (produced by Invitrogen Corp.), and single colonies were isolated. The amount of Kv1.5 channel expression in the single colonies was quantified at the mRNA level by RT-PCR and then quantified at the protein level by western blotting. Finally, the expressed current was analyzed by patch clamp method. Cell lines expressing a current of 200 pA or more per cell were selected as channel-expressing cell lines for activity measurement by patch clamp method.

(2) Production of CHO Cell Line Expressing Human GIRK1/4

CHO cell lines stably expressing human GIRK1/4 channels were prepared in the following manner.

Full-length human GIRK1 cDNA was cloned from HuH cell- and HeLa cell-derived cDNA libraries. Full-length GIRK4 cDNA was amplified from a human heart cDNA library (produced by Clontech Laboratories, Inc.) by PCR using synthetic primers shown in Table 1, and cloned into the Eco-RI restriction enzyme site of pCR-Blunt (produced by Invitrogen Corporation) or into the HincII site of pUC118 (produced by Takara Bio, Inc.).

TABLE 1

| Primer | Sequence | |
|---|---|---|
| hGIRK1-S | 5'-ATGTCTGCACTCCGAAG GAAATTTG-3' | SEQ ID No. 1 |
| hGIRK1-A | 5'-TTATGTGAAGCGATCAG AGTTC-3' | SEQ ID No. 2 |
| hGIRK1-F2 | 5'-GCAGGGTACCCCTTCGT ATTATGTCTGCACTCC-3' | SEQ ID No. 3 |
| hGIRK1-A3 | 5'-GGTGTCTGCCGAGATTT GA-3' | SEQ ID No. 4 |
| hGIRK1-A4 | 5'-CCGAGTGTAGGCGATCA CCC-3' | SEQ ID No. 5 |
| hGIRK4-S | 5'-ATGGCTGGCGATTCTAG GAATGCC-3' | SEQ ID No. 6 |
| hGIRK4-A | 5'-TCTCACCGAGCCCCTGG CCTCCC-3' | SEQ ID No. 7 |
| hGIRK4-S2 | 5'-AACCAGGACATGGAGAT TGG-3' | SEQ ID No. 8 |
| hGIRK4-A2 | 5'-GAGAACAGGAAAGCGGA CAC-3' | SEQ ID No. 9 |

The obtained human GIRK1 and GIRK4 cDNA sequences correspond to known sequences (NCBI database: GIRK1 (NM_002239) and GIRK4 (NM_000890) respectively). The obtained GIRK1 and GIRK4 cDNA sequences were cloned into the Eco-RI restriction enzyme site of pCR-Blunt (available from Invitrogen Corporation) or into the HincII site of pUC118 (available from Takara Bio, Inc.). A GIRK4 expression vector was constructed by insertion into the BamHI-XhoI site of pcDNA5/FRT. A GIRK1 expression vector was constructed by insertion into the KpnI-XhoI site of pcDNA3.1(+) or pCAG_neo. FLP-IN-CHO cells (produced by Invitrogen Corporation) were transfected with human GIRK1 and GIRK4 expression vectors by using Lipofectamine 2000 (produced by Invitrogen Corporation) according to the protocol enclosed with the reagent or using an electronic induction method ("Nucleofector Kit-T", produced by Amaxa). First, the cells transfected with the GIRK4 expression vector were cultured in a 10% serum-containing F12 medium (produced by Sigma) supplemented with 600 μg/ml of hygromycin in an incubator with 5% carbon dioxide at 37° C. Then the cells expressing GIRK4 were transfected with the GIRK1 expression vector and were cultured in 10% serum-containing F12 medium supplemented with 350 μg/ml of G418 and 600 μg/ml of hygromycin in an incubator with 5% carbon dioxide at 37° C. to select GIRK1/4 expressing cell lines. Cell populations whose growth was observed after about 2 weeks were isolated using cloning rings, and the obtained single colonies were proliferated. RNA was extracted from single colonies, and single-stranded cDNA was synthesized by a cDNA synthesis kit (produced by Invitrogen Corporation), and the amount of expression was quantified at the mRNA level by real-time PCR (Applied Biosystems, Ltd.). Finally, the expressed current was analyzed by patch clamp method described below. The cell lines expressing a current of 500 pA or more per cell were selected as channel-expressing cell lines for activity measurement by patch clamping method.

(3) Measurement of Ion Channel Current by Patch Clamp Method (Human Kv1.5-expressing CHO-K1 Cell Line)

An experiment was carried out using a patch clamp setup at room temperature (20 to 26° C.). A perfusion chamber having a diameter of 20 mm (flow rate: about 5 ml/min) was mounted on the stage of a phase-contrast inverted microscope (produced by Nikon Corporation) placed on a vibration isolated table. A poly-L-lysine (produced by Sigma)-coated coverslip (diameter: 15 mm, produced by Matsunami Glass Ind., Ltd.) on which human Kv1.5-expressing cells were cultured was placed in the perfusion chamber.

Depolarizing stimulation pulses were applied and ionic current was recorded by using a patch clamp amplifier (EPC-7 or EPC-7 PLUS, produced by HEKA) and a personal computer (manufactured by IBM Corp.) in which software for data acquisition and analysis of ion channel current (PULSE 8.77, produced by HEKA) was installed. The current was measured in the whole-cell configuration of the patch-clamp technique. The tip (resistance: 2 to 4 MΩ) of a borosilicate glass pipette (produced by Sutter Instrument Co.) was gently placed on the cell membrane by using a three-dimensional mechanical micromanipulator (produced by Shoshin EM Corporation). Weak suction resulted in giga seal formation (the pipette resistance increased to more than 1 GΩ). Subsequently, stronger suction was applied to break the cell membrane. The capacitative current derived from the cell membrane was corrected using a patch clamp amplifier. Subsequently, the series resistance (Rs) between the pipette and the interior of the cell was measured and corrected.

The composition of the extracellular solution used is shown below. Unless otherwise specified, these components were obtained from Wako Pure Chemical Industries, Ltd.

| | |
|---|---|
| NaCl | 140 mM, |
| KCl | 40 mM, |
| $CaCl_2$ | 1.8 mM, |
| $MgCl_2$ | 1 mM, |
| $NaH_2PO_4$ | 0.33 mM, |
| HEPES | 5 mM |
| Glucose | 5.5 mM |
| | (pH = 7.4) |

Each test compound was prepared as a 1000-fold concentrated stock solution that was dissolved in DMSO and then diluted in the extracellular solution.

The composition of the electrode internal solution used is shown below. Unless otherwise specified, these components were obtained from Wako Pure Chemical Industries, Ltd.

| | |
|---|---|
| KOH | 100 mM, |
| KCl | 40 mM, |
| Aspartic acid | 70 mM, |
| $MgCl_2$ | 1 mM, |
| MgATP | 5 mM, |
| $K_2$ creatine phosphate | 5 mM, |
| HEPES | 5 mM |
| EGTA | 5 mM |
| | (pH = 7.2) |

(4) Measurement of Ion Channel Current by Patch Clamp Method (Human GIRK1/4-expressing CHO-K1 Cell Line)

An experiment was carried out using a patch clamp setup at room temperature (20 to 26° C.). A perfusion chamber having a diameter of 20 mm (flow rate: about 5 ml/min) was mounted on the stage of a phase-contrast inverted microscope (produced by Nikon Corporation) placed on a vibration isolation table. A poly-L-lysine (produced by Sigma)-coated coverslip (diameter: 15 mm, produced by Matsunami Glass Ind., Ltd.) on which human GIRK1/4-expressing cells were cultured was placed in the perfusion chamber.

Hyperpolarizing stimulation pulses were applied and ionic current was recorded using a patch clamp amplifier (EPC-7 or EPC-7 PLUS, manufactured by HEKA) and a personal computer (manufactured by IBM Corp.) in which software for data acquisition and analysis of ion channel current (PULSE 8.77, manufactured by HEKA) was installed. The current was measured in the whole-cell configuration of the patch-clamp technique. The tip (resistance: 2 to 4 MΩ) of a borosilicate glass pipette (produced by Sutter Instrument Co.) was gently placed on the cell membrane by using a three-dimensional mechanical micromanipulator (produced by Shoshin EM Corporation). Weak suction resulted in giga seal formation (the pipette resistance increased to more than 1 GΩ). Subsequently, stronger suction was applied to break the cell membrane. The capacitative current derived from the cell membrane was corrected using a patch clamp amplifier. Subsequently, the series resistance (Rs) between the pipette and the interior of the cell was measured and corrected.

The composition of the extracellular solution used is shown below. Unless otherwise specified, these components were obtained from Wako Pure Chemical Industries, Ltd.

| | |
|---|---|
| NaCl | 140 mM, |
| KCl | 4 mM, |
| $CaCl_2$ | 1.8 mM, |
| $MgCl_2$ | 1 mM, |
| $NaH_2PO_4$ | 0.33 mM, |
| HEPES | 5 mM |
| Glucose | 5.5 mM |
| | (pH = 7.4) |

Each test compound was prepared as a 1000-fold concentrated stock solution that was dissolved in DMSO and then diluted in the extracellular solution.

The composition of the electrode internal solution used is shown below. Unless otherwise specified, these components were obtained from Wako Pure Chemical Industries, Ltd.

| | |
|---|---|
| KOH | 100 mM, |
| KCl | 40 mM, |
| Aspartic acid | 70 mM, |
| $MgCl_2$ | 1 mM, |
| MgATP | 5 mM, |
| $K_2$ creatine phosphate | 5 mM, |
| HEPES | 5 mM |
| EGTA | 5 mM |
| | (pH = 7.2) |

(5) Measurement of human Kv1.5 current

While the membrane potential was holded at −80 mV, depolarizing pulses (−80 mV for 0.05 seconds→□□+40 mV for 0.2 seconds→□□−40 mV for 0.2 seconds→□□−80 mV for 0.05 seconds) were applied at a stimulation frequency of 1 Hz to measure Kv1.5 channel current. More specifically, first, while perfusing an extracellular solution containing 0.1% DMSO and holding the membrane potential at −80 mV, depolarizing pulses were applied. The current obtained during the pulse application was recorded as a current in the absence of the test compounds. Subsequently, while perfusing an extracellular solution containing 0.1 μM of a test compound and holding the membrane potential at −80 mV, depolarizing pulses were applied. After the inhibitory effect of the test compound had been stabilized, the current was recorded. The same procedure was repeated using an extracellular solution containing 1 μM of the test compound and then using an extracellular solution containing 10 μM of the test compound. The current obtained using the solution containing the test compound at each concentration was recorded.

The data was analyzed by using the step end current recorded during the +40 mV depolarizing stimulation. The "step end current" refers to the average current flowing for a period of 195 to 199 milliseconds from the start of the +40 mV depolarizing pulse stimulation.

Using the step end current in the presence of the test compound and the step end current in the absence of the test compound, the relative current in the solution containing the test compound at each concentration was calculated according to the following formula:

Relative current=(Step end current in the presence of the test compound)/(Step end current in the absence of the test compound)

(6) Measurement of Human GIRK1/4 Current

While the membrane potential was held at −80 mV, hyperpolarizing pulses (−80 mV for 0.05 seconds→□□−120 mV for 0.2 seconds→□□−80 mV for 0.05 seconds) were applied at a stimulation frequency of 1 Hz to measure GIRK1/4 channel current. More specifically, first, while perfusing an extracellular solution containing 0.1% DMSO and maintaining the membrane potential at −80 mV, hyperpolarizing pulses were applied. The current obtained during the pulse application was recorded as the current in the absence of the test compounds. Subsequently, while perfusing an extracellular solution containing 0.1 μM of a test compound and maintaining the membrane potential at −80 mV, hyperpolarizing pulses were applied. After the inhibitory effect of the test compound had been stabilized, the current was recorded. The same procedure was repeated using an extracellular solution containing 1 μM of the test compound and then using an extracellular solution containing 10 μM of the test compound. The current obtained using the solution containing the test compound at each concentration were recorded.

The data was analyzed by using the step end current recorded during the −120 mV depolarizing stimulation. The "step end current" refers to the average current flowing for a period of 195 to 199 milliseconds from the start of the −120 mV depolarizing pulse stimulation.

Using the step end current in the presence of the test compound and the step end current in the absence of the test compound, the relative current in the solution containing the test compound at each concentration was calculated according to the following formula:

Relative current=(Step end current in the presence of the test compound)/(Step end current in the absence of the test compound)

(7) Calculation of Inhibitory Activity on Kv1.5 Channel Ionic Current and GIRK1/4 Channel Current The concentration for 50% inhibition of Kv1.5 channel current or GIRK1/4 channel current ($IC_{50}$ value) was calculated according to the following nonlinear regression equation:

Relative current=$1/(1+[\text{Concentration of the compound}]/IC_{50})^{nH}$ wherein nH is the Hill coefficient.

Table 2 shows the test results.

TABLE 2

| Test Compound | KV1.5 $IC_{50}$ (μM) |
| --- | --- |
| Compound of Example 2 | 1.10 |
| Compound of Example 5 | 0.87 |
| Compound of Example 6 | 0.60 |
| Compound of Example 14 | 0.40 |
| Compound of Example 20 | 0.34 |
| Compound of Example 21 | 0.84 |
| Compound of Example 22 | 1.50 |

The invention claimed is:
1. A compound represented by Formula (1):

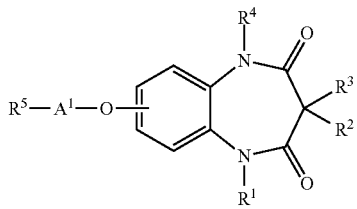

(1)

or a pharmaceutically acceptable salt thereof,
wherein $R^1$, $R^2$, $R^3$, and $R^4$ are each independently hydrogen or $C_{1-6}$ alkyl; $R^2$ and $R^3$ may be linked to form $C_{1-6}$ alkylene;
$A^1$ is $C_{1-6}$ alkylene optionally substituted with one or more hydroxyls; and
$R^5$ is an aryl or heterocyclic group, each of which is optionally substituted,
wherein the heterocyclic group is one member selected from the group consisting of the following groups (a) to (m):
(a) unsaturated 3- to 8-membered heteromonocyclic group containing 1 to 4 nitrogen atom(s),
(b) saturated 3- to 8-membered heteromonocyclic group containing 1 to 4 nitrogen atom(s),
(c) unsaturated condensed 7- to 12-membered heterocyclic group containing 1 to 5 nitrogen atom(s),
(d) unsaturated 3- to 8-membered heteromonocyclic group containing 1 to 2 oxygen atom(s),
(e) unsaturated condensed 7- to 12-membered heterocyclic group containing 1 to 3 oxygen atom(s),
(f) unsaturated 3- to 8-membered heteromonocyclic group containing 1 to 2 oxygen atom(s) and 1 to 3 nitrogen atom(s),
(g) saturated 3- to 8-membered heteromonocyclic group containing 1 to 2 oxygen atom(s) and 1 to 3 nitrogen atom(s),
(h) unsaturated condensed 7 to 12-membered heterocyclic group containing 1 to 2 oxygen atom(s) and 1 to 3 nitrogen atom(s),
(i) unsaturated 3- to 8-membered heteromonocyclic group containing 1 to 2 sulfur atom(s) and 1 to 3 nitrogen atom(s),
(j) saturated 3- to 8-membered heteromonocyclic group containing 1 to 2 sulfur atom(s) and 1 to 3 nitrogen atom(s),
(k) unsaturated 3- to 8-membered heteromonocyclic group containing a sulfur atom,
(l) unsaturated condensed 7- to 12-membered heterocyclic groups containing 1 to 3 sulfur atom(s), and
(m) unsaturated condensed 7- to 12-membered heterocyclic group containing 1 to 2 sulfur atom(s) and 1 to 3 nitrogen atom(s),
wherein the substituents of aryl and heterocyclic group are each independently one or more substituents selected from the group consisting of:
(1) oxo;
(2) $C_{1-6}$ alkyl optionally substituted with one or more halogens or heterocyclic groups optionally substituted with one or more substituents selected from the group consisting of $C_{1-6}$ alkyl; $C_{1-6}$ alkoxy; $C_{1-6}$ alkanoyl; $C_{1-6}$ alkylsulfonyl; hydroxyl; halogen; carboxy; $C_{1-6}$ alkoxycarbonyl; amino optionally substituted with one or more substituents selected from the group consisting of $C_{1-6}$ alkyl, $C_{1-6}$ alkanoyl, and $C_{1-6}$ alkylsulfonyl; $C_{1-6}$ alkyl thio; cyano; and oxo;
(3) cyclo $C_{3-6}$ alkyl;
(4) $C_{1-6}$ alkoxy;
(5) aryl optionally substituted with one or more substituents selected from the group consisting of $C_{1-6}$ alkyl; $C_{1-6}$ alkoxy; $C_{1-6}$ alkanoyl; $C_{1-6}$ alkylsulfonyl; hydroxyl; halogen; carboxy; $C_{1-6}$ alkoxycarbonyl; amino optionally substituted with one or more substituents selected from the group consisting of $C_{1-6}$ alkyl, $C_{1-6}$ alkanoyl, and $C_{1-6}$ alkylsulfonyl; $C_{1-6}$ alkyl thio; and cyano;
(6) aralkyl optionally substituted with one or more substituents selected from the group consisting of $C_{1-6}$ alkyl; $C_{1-6}$ alkoxy; $C_{1-6}$ alkanoyl; $C_{1-6}$ alkylsulfonyl; hydroxyl; halogen; carboxy; $C_{1-6}$ alkoxycarbonyl; amino optionally substituted with one or more substituents selected from the group consisting of $C_{1-6}$ alkyl, $C_{1-6}$ alkanoyl, and $C_{1-6}$ alkylsulfonyl; $C_{1-6}$ alkyl thio; cyano; and oxo;
(7) a heterocyclic group optionally substituted with one or more substituents selected from the group consisting of $C_{1-6}$ alkyl; $C_{1-6}$ alkoxy; $C_{1-6}$ alkanoyl; $C_{1-6}$ alkylsulfonyl; hydroxyl; halogen; carboxy; $C_{1-6}$ alkoxycarbonyl; amino optionally substituted with one or more substituents selected from the group consisting of $C_{1-6}$ alkyl, $C_{1-6}$ alkanoyl, and $C_{1-6}$ alkylsulfonyl; $C_{1-6}$ alkyl thio; cyano; and oxo;
(8) hydroxyl;
(9) halogen;
(10) carboxy;
(11) $C_{1-6}$ alkanoyl;
(12) $C_{1-6}$ alkoxycarbonyl;
(13) $C_{1-4}$ alkylenedioxy;
(14) cyano;
(15) nitro;
(16) sulfo;
(17) amino optionally substituted with one or more substituents selected from the group consisting of $C_{1-6}$ alkyl, $C_{1-6}$ alkanoyl, and $C_{1-6}$ alkylsulfonyl;
(18) $C_{1-6}$ alkylsulfonyl; and
(19) $C_{1-6}$ alkyl thio,
wherein the heterocyclic group of the group (7) is at least one member selected from the group consisting of the following groups (a) to (m):
(a) unsaturated 3- to 8-membered heteromonocyclic group containing 1 to 4 nitrogen atom(s),
(b) saturated 3- to 8-membered heteromonocyclic group containing 1 to 4 nitrogen atom(s),
(c) unsaturated condensed 7- to 12-membered heterocyclic group containing 1 to 5 nitrogen atom(s),
(d) unsaturated 3- to 8-membered heteromonocyclic group containing 1 to 2 oxygen atom(s),
(e) unsaturated condensed 7- to 12-membered heterocyclic group containing 1 to 3 oxygen atom(s),
(f) unsaturated 3- to 8-membered heteromonocyclic group containing 1 to 2 oxygen atom(s) and 1 to 3 nitrogen atom(s),
(g) saturated 3- to 8-membered heteromonocyclic group containing 1 to 2 oxygen atom(s) and 1 to 3 nitrogen atom(s),
(h) unsaturated condensed 7 to 12-membered heterocyclic group containing 1 to 2 oxygen atom(s) and 1 to 3 nitrogen atom(s), (i) unsaturated 3- to 8-membered heteromonocyclic group containing 1 to 2 sulfur atom(s) and 1 to 3 nitrogen atom(s),
(j) saturated 3- to 8-membered heteromonocyclic group containing 1 to 2 sulfur atom(s) and 1 to 3 nitrogen atom(s),
(k) unsaturated 3- to 8-membered heteromonocyclic group containing a sulfur atom, and
(m) unsaturated condensed 7- to 12-membered heterocyclic group containing 1 to 2 sulfur atom(s) and 1 to 3 nitrogen atom(s).

2. The compound represented by Formula (1) or a pharmaceutically acceptable salt thereof according to claim 1, wherein $R^1$, $R^2$, $R^3$, and $R^4$ are each independently $C_{1-6}$ alkyl;
$A^1$ is $C_{1-6}$ alkylene; and
$R^5$ is piperidyl, piperazinyl, indolyl, benzimidazolyl, 2,3-dihydrobenzimidazolyl, 2,3-dihydroindolyl, furo[2,3-c]pyridyl, 6,7-dihydrofuro[2,3-c]pyridyl, furo[3,2-c]pyridyl, 4,5-dihydrofuro[3,2-c]pyridyl, furo[2,3-b]pyridyl, 6,7-dihydrofuro[2,3-b]pyridyl, thieno[2,3-c]pyridyl, 6,7-dihydrothieno[2,3-c]pyridyl, 1,2,3,4-tetrahydro-1H-isoquinolyl, carbostyril, 3,4-dihydrocarbostyril, quinolyl, 1,4-dihydroquinolyl, 1,2,3,4-tetrahydroquinolyl, pyrido[3,4-d]imidazolyl, or pyrido[2,3-d]imidazolyl, each of which is optionally substituted with one or more substituents selected from the group consisting of:

(1) oxo;
(2a) $C_{1-3}$ alkyl optionally substituted with 6,7-dihydrofuro[2,3-c]pyridyl or 4,5-dihydrofuro[3,2-c]pyridyl, each of which is optionally substituted with one or more substituents selected from the group consisting of oxo and $C_{1-6}$ alkyl;
(4a) $C_{1-3}$ alkoxy;
(5a) phenyl;
(6a) benzyl;
(7a) pyridyl optionally substituted with one or more substituents selected from the group consisting of $C_{1-6}$ alkyl and $C_{1-6}$ alkoxy;
(9) halogen;
(10) carboxy;
(12a) $C_{1-3}$ alkoxycarbonyl; and
(13a) $C_{1-4}$ alkylenedioxy.

3. A pharmaceutical composition comprising a compound represented by Formula (1) or a pharmaceutically acceptable salt thereof according to claim 1, and a pharmacologically acceptable carrier.

4. A method of treating arrhythmia, comprising administering to a patient a compound represented by Formula (1) or a pharmaceutically acceptable salt thereof according to claim 1.

* * * * *